United States Patent
Barney et al.

(12)

(10) Patent No.: US 6,258,782 B1
(45) Date of Patent: Jul. 10, 2001

(54) HYBRID POLYPEPTIDES WITH ENHANCED PHARMACOKINETIC PROPERTIES

(75) Inventors: Shawn Barney, Apex; Kelly I. Guthrie, Graham; Gene Merutka, Hillsborough, all of NC (US); Mohmed K. Anwer, Foster City, CA (US); Dennis M. Lambert, Cary, NC (US)

(73) Assignee: Trimeris, Inc., Durham, NC (US)

( * ) Notice: Subject to any disclaimer, the term of this patent is extended or adjusted under 35 U.S.C. 154(b) by 0 days.

(21) Appl. No.: 09/082,279

(22) Filed: May 20, 1998

(51) Int. Cl.[7] .......................... A61K 38/16; C07K 14/00; C07K 14/155
(52) U.S. Cl. .................... 514/13; 514/2; 514/12; 514/15; 530/300; 530/313; 530/324; 530/328; 530/350
(58) Field of Search ..................... 530/300, 313, 530/324, 326, 328, 350, 397, 398, 399; 514/2, 12, 13, 15

(56) References Cited

U.S. PATENT DOCUMENTS

| | | | |
|---|---|---|---|
| 5,357,041 | * 10/1994 | Roberts et al. | 530/326 |
| 5,358,934 | * 10/1994 | Borovsky et al. | 514/17 |
| 5,464,933 | 11/1995 | Bolognesi et al. | 530/324 |
| 5,656,480 | 8/1997 | Wild et al. | 435/325 |
| 5,723,129 | * 3/1998 | Potter et al. | 424/200.1 |
| 5,763,160 | * 6/1998 | Wang | 435/5 |
| 5,843,913 | * 12/1998 | Li et al. | 514/44 |
| 5,968,776 | 10/1999 | Klein et al. | 435/69.3 |
| 6,080,724 | * 6/2000 | Chassaing et al. | 514/13 |

FOREIGN PATENT DOCUMENTS

| | | |
|---|---|---|
| 272858 | * 6/1988 | (EP). |
| 306912 | * 3/1989 | (EP). |
| 578293 | * 1/1994 | (EP). |
| 91/07664 | * 5/1991 | (WO). |
| 91/09872 | * 7/1991 | (WO). |
| 93/14207 | * 7/1993 | (WO). |
| WO 96/19495 | 6/1996 | (WO). |
| WO 99/59615 | 11/1999 | (WO). |

OTHER PUBLICATIONS

Adams et al., 1985, "The c–myc oncogene driven by immunoglobulin enhancers induces lymphoid malignancy in transgenic mice", Nature 318:533–538.

Alexander et al., 1987, "Expression of the c–myc oncogene under control of an immunoglobulin enhancer in E$\mu$–myc transgenic mice", Mol. Cell. Biol. 5:1436–1444.

Fingl & Woodbury, 1975, in "The Pharmacological Basis of Therapeutics", Ch.1 p. 1.

Goff et al., 1981, "Isolation properties of Moloney Murine Leukemia virus mutants: use of rapid assay for release of virion reverse transcriptase", J. Virol. 62:139–147.

(List continued on next page.)

Primary Examiner—Jeffrey E. Russel
(74) Attorney, Agent, or Firm—Pennie & Edmonds LLP

(57) ABSTRACT

The present invention relates to enhancer peptide sequences originally derived from various retroviral envelope (gp41) protein sequences that enhance the pharmacokinetic properties of any core polypeptide to which they are linked. The invention is based on the discovery that hybrid polypeptides comprising the enhancer peptide sequences linked to a core polypeptide possess enhanced pharmacokinetic properties such as increased half life. The invention further relates to methods for enhancing the pharmacokinetic properties of any core polypeptide through linkage of the enhancer peptide sequences to the core polypeptide. The core polypeptides to be used in the practice of the invention can include any pharmacologically useful peptide that can be used, for example, as a therapeutic or prophylactic reagent.

15 Claims, 21 Drawing Sheets

OTHER PUBLICATIONS

Figure 3:
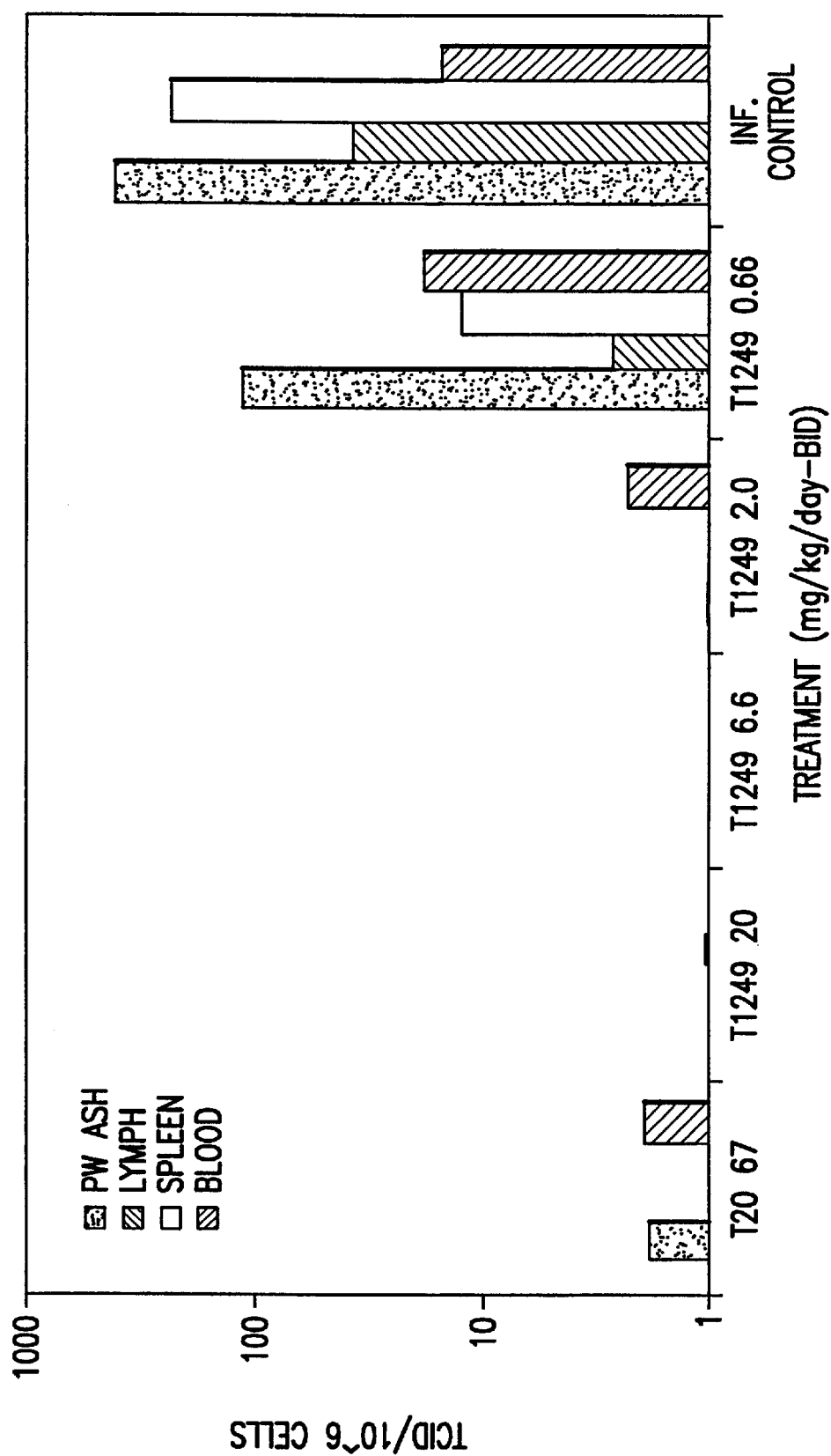

Grosschedl et al., 1984, "Introduction of a μ immunoglobulin gene into the mouse germline: specific expression in lymphoid cells and synthesis of functional antibody", Cell 38:647–658.

Hammer et al., 1987, "Diversity of Alpha–protein gene expression in mice is generated by a combination of separate enhancer elements", Science 235:53–58.

Hanahan, 1985, "Heritable formation of pancreatic β–cell tumors in transgenic mice expressing recombinant insulin/simian virus 40 oncogenes", Nature 315:115–122.

Kelsey et al., 1987, "Species– and tissue–specific expression of human $\alpha_1$–antitrypsin in transgenic mice", Genes and Dev. 1:161–171.

Kollias et al., 1986, "Regulated expression of Human $^A\gamma$–, β–, and hybrid γβ–globin genes in transgenic mice: manipulation of the developmental expression patterns", Cell 46:89–94.

Krumlauf et al., 1985, "Developmental regulation of α–fetoprotein genes in transgenic mice", Mol. Cell. Biol. 5:1639–1648.

Macdonald, 1987, "Expression of the pancreatic elastase I genes in transgenic mice", Hepatology 7:42S–51S.

Magram et al., 1985, "Developmental regulation of a clothed adult β–globulin gene in transgenic mice", Nature 315:338–340.

Mason et al., 1986, "The hypogonadal mouse: reproductive functions restored by gene therapy", Science 234:1372–1378.

Matthews et al., 1987, "Interaction between the human T–cell lymphotropic virus type $III_B$ envelope glycoprotein gp120 and the surface antigen CD4:role of carbohydrate in binding and cell fusion", PNAS 84:5424–5428.

Olson et al., 1993, "Concepts and progress in the development of mimetics", J. Me. Chem. 36:3049.

Ornitz et al., 1986, "Elastase I promoter directs expression of human growth hormone and SV40 T antigen genes to pancreatic acinar cells in transgenic mice", Cold Spring Harbor Symp. Quant. Biol. 50:399–409.

Pinkert al., 1987, "An albumin enhancer located 10Kb upstream functions along with it promoter to direct efficient, liver–specific expression in transgenic mice", Genes and Dev. 1:268–276.

Popovic et al., 1984, "Detection, Isolation, and continuous production of cytopathic retrovirus (HTLV–III) from patients with AIDS and Pre–AIDS", Science 224:497–508.

Readhead et al., 1987, "Expression of a myelin basic protein gene in transgenic shiverer mice: correction of the dysmyelinating phenotype", Cell 48:703–712.

Rimsky & Matthews, 1998, "Determinants of human Immunodeficiency virus type 1 resistance to gp41–derived inhibitory peptides", J. Virol. 72:986–993.

Shani M., 1985, "Tissue–specific expression of rat myosin light chain 2 gene in transgenic mice", Nature, 314:283–286.

Swift et al., 1984, "Tissue–specific expression of the rat pancreatic elastase I gene in transgenic mice", Cell 38:639–646.

Weislow et al., 1989, "New Soluble–formazan assay for HIV–1 cytopathic effects: application to high–flux screening of synthetic and natural products for AIDS–antiviral activity", J. Natl. Cancer Inst. 81:577–586.

Willey, 1988, "In vitro mutagenesis identifies a region within the envelope gene of the human immunodeficiency virus that is critical for infectivity", J. Virol. 62:139–147.

Sigma Chemical Company, Biochemicals Organic Compounds For Research And Diagnostic Reagents. p. 1864, 1994.*

* cited by examiner

FIG. 1

FIG.2A

| SIV AND HIV-2 SEQUENCES | | | | | HIV-1 SEQUENCES | | | | | HIV-1 SEQUENCES | | | | |
|---|---|---|---|---|---|---|---|---|---|---|---|---|---|---|
| SIV | W | Q | E | W | E | Q | K | I | I | W | I | Q | W | D | K | E | I | I | W | M | Q | W | K | R | E | I | I |
| | W | L | E | W | E | R | Q | I | I | W | L | Q | W | D | R | E | I | I | W | M | E | W | N | R | E | I | I |
| | W | L | E | W | E | K | Q | I | I | W | M | D | W | E | K | E | I | I | W | R | E | W | D | R | E | I | I |
| | W | Q | Q | W | E | Q | Q | I | I | W | M | Q | W | D | R | E | I | I | W | T | E | W | E | R | E | I | I |
| | W | Q | Q | W | E | K | Q | I | I | W | M | E | W | E | R | E | I | I | W | L | E | W | E | R | E | I | I |
| HIV-2 | W | Q | E | W | E | H | K | I | I | W | M | E | W | E | R | E | I | I | W | M | G | W | E | R | E | I | I |
| | W | Q | Q | W | E | G | K | I | I | W | I | E | W | D | R | E | I | I | W | Q | E | W | D | Q | Q | I | I |
| | W | Q | Q | W | E | Q | Q | I | I | W | M | Q | W | D | R | E | I | I | W | M | K | W | E | R | E | I | I |
| | W | Q | K | W | E | Q | Q | I | I | W | I | Q | W | E | R | E | I | I | | | | | | | | | |
| | W | Q | E | W | E | Q | R | I | I | W | G | I | W | R | W | G | I | I | W | X | X | W | X | X | E | I | I |

FIG.2B

| SIV SEQUENCES | | | | | HIV-2 SEQUENCES | | | | | HIV-1 SEQUENCES | | | | | HIV-1 SEQUENCES | | | | |
|---|---|---|---|---|---|---|---|---|---|---|---|---|---|---|---|---|---|---

| PHARMACOKINETIC PARAMETERS | T20BQ1 | T1249A1 |
|---|---|---|
| DOSE (mg/kg IV) | 2.5 | 2.5 |
| DETECTION METHOD | FLUORESCENCE HPLC | FLUORESCENCE HPLC |
| $T_{1/2\beta}$ (h) | 1.6 | 4.71 |
| $Cl_\beta$ (ml/h) | 27.94 | 9.62 |
| $AUC_{[0-8]}$ (ug/h/ml) | 26.12 | 71.43 |

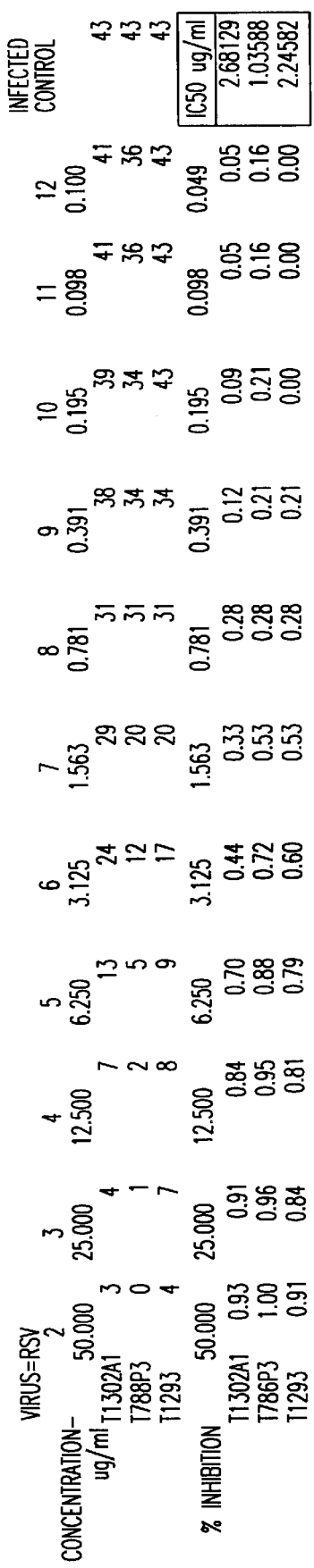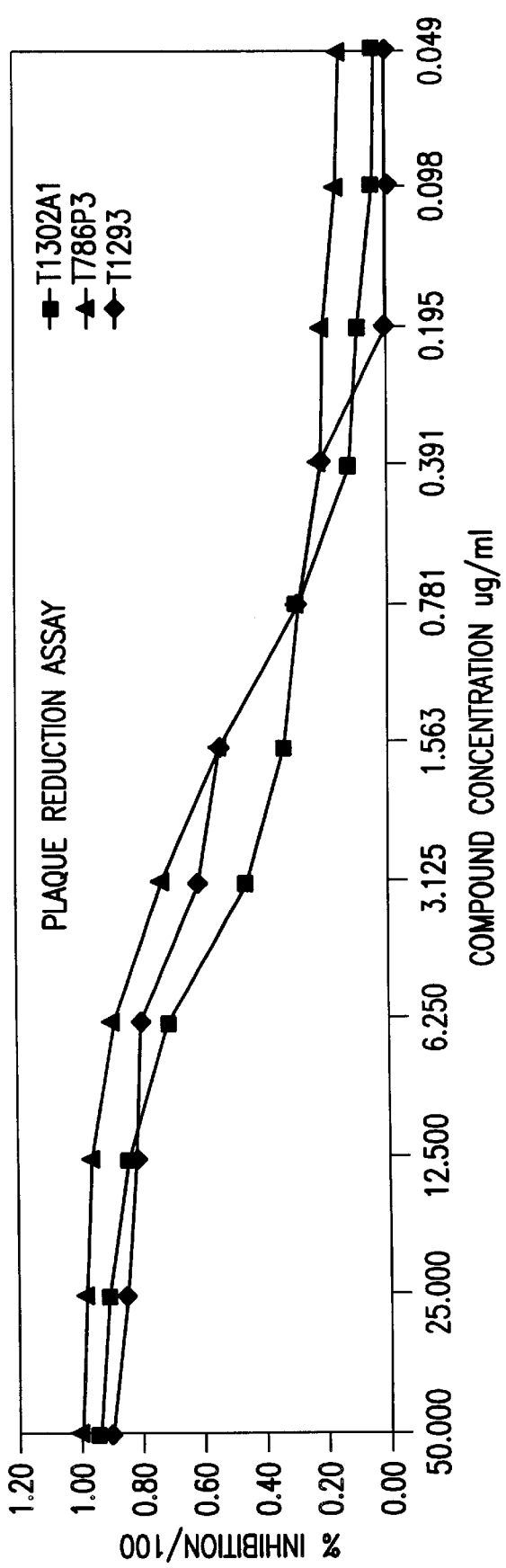
FIG. 11A

| Trimeris No. | | | Peptide | IP t1/2 | Peptide | HIV-1 Fusion EC-50 ng/ml | RSV Fusion EC-50 ng/ml |
|---|---|---|---|---|---|---|---|
| HIV-1 T20 Ac- | N N M T W M E W D R E I N N Y T S L I H S L I E E S Q N Q Q E K N E Q E L L E L D K W A S L W N W F | Y T S L I H S L I E E S Q N Q Q E K N E Q E L L E L D K W A S L W N W F | -NH2 | 1.5h | HIV-1 T20 | 3 | >20000 |
| HIV-1 T379 Ac- | | Y T S L I H S L I E E S Q N Q Q E K N E Q E L L E L D K W A S L F N F F | -NH2 | 20m | HIV-1 T379 | 3 | |
| SIV T402 Ac- | | L E E N I T A L L E E A Q I Q Q E K N M Y E L Q K L N S W D V F G N W F | -NH2 | 20m | SIV T402 | 3 | |
| HIV-2 T698 Ac- | | L E A N I S Q S L E Q A Q I Q Q E K N M Y E L Q K L N S W D V F I T N W L | -NH2 | <20m | HIV-2 T698 | 50 | |
| HIV-1 T649 Ac- | W M E W D R E I N N Y T S L I H S L I E E S Q N Q Q E K N E Q E L L E L | | -NH2 | 20m | HIV-1 T649 | 7 | |
| SIV T391 Ac- | Q E W E R K V D F L E E N I T A L L E E A Q I Q Q E K N M Y E L Q K L | | -NH2 | 20m | SIV T391 | 15 | |
| HIV-2 T856 Ac- | W Q E W E Q K V R Y L E A N I S Q S L E Q A Q I Q Q E K N M Y E L Q K L | | -NH2 | 20m | HIV-2 T856 | 7 | |
| HYBRID T1052 Ac- | W Q E W E Q K V R Y L E A N I T A L L E Q A Q I Q Q E K N E Y E L Q K L | | -NH2 | 20m | HYBRID T1052 | 9 | |
| | | | | IV t1/2 | | | |
| HIV-1 T625 Ac- | M T W M E W D R E I N N Y T S L I H S L I E E S Q N Q Q E K N E Q E L L E L D K W A S L W N W F | | -NH2 | >4h | HIV-1 T625 | 7 | |
| HIV-1 T866 Ac- | D R E I N N Y T S L I H S L I E E S Q N Q Q E K N E Q E L L E L D K | | -NH2 | >4h | HIV-1 T866 | 5 | |
| HIV-1 T867 Ac- | N N M T W M E W D R E I N N Y T S L I H S L I E E S Q N Q Q E K N E Q E L L E L D K | | -NH2 | 20m | HIV-1 T867 | 6 | |

FIG.13A

FIG. 13B

| HIV-1/SIV/HIV-2 HYBRIDS | | N-terminal | Hybrid (T1052-like) Core Sequence | C-terminal | | IV t1/2 | | |
|---|---|---|---|---|---|---|---|---|
| HYBRID T1387 | Ac- | | TALLEQAQIQQEKNEYELQKLDK | WASLWNWF | -NH2 | <5m | HYBRID T1387 | >10000 |
| HYBRID T1388 | Ac- | WQEWEQKVRYLEAN | TALLEQAQIQQEKNEYELQKLDK | WASLWNWF | -NH2 | <5m | HYBRID T1388 | >10000 |
| HYBRID T1226 | Ac- | NNWTWQEWEQKVRYLEAN | ITALLEQAQIQQEKNEYELQKLDK | WASLWNWF | -NH2 | | HYBRID T1226 | 4 |
| HYBRID T1227 | Ac- | | ITALLEQAQIQQEKNEYELQKLDK | WASLWNWF | -NH2 | | HYBRID T1227 | 7 |
| HYBRID T1248 | Ac- | WNWF | ITALLEQAQIQQEKNEYELQKLDK | WASLWNWF | -NH2 | | HYBRID T1248 | 6 |
| HYBRID T1267 | Ac- | WQEWDREI | TALLEQAQIQQEKNEYELQKLDK | WASLWNWF | -NH2 | | HYBRID T1267 | 3 |
| HYBRID T1269 | Ac- | WQEWDREISNYTSL | ITALLEQAQIQQEKNEYELQKLDE | WASLWNWF | -NH2 | | HYBRID T1269 | 3 |
| HYBRID T1311 | Ac- | WQEWEREISNYTSL | ITALLEQAQIQQEKNEYELQKLDE | WASLWNWF | -NH2 | | HYBRID T1311 | 53 |
| HYBRID T1314 | Ac- | WQEWEREISAYTSL | ITALLEQAQIQQEKTEYELQKLIE | WEWF | -NH2 | | HYBRID T1314 | 30 |
| HYBRID T1312 | Ac- | WQEWEREISAYTSL | ITALLEQAQIQQEKIIEYELQKLIE | WEWF | -NH2 | | HYBRID T1312 | 12 |
| HYBRID T1313 | Ac- | WQEWEREISAYTSL | ITALLEQAQIQQEKIIEYELQKLE | WEWF | -NH2 | | HYBRID T1313 | 5 |
| HYBRID T1275 | Ac- | WQEWDREI | TALLEQAQIQQEKNEYELQKLDE | WASLWNWF | -NH2 | | HYBRID T1275 | 6 |
| HYBRID T1276 | Ac- | WQEWEREI | TALLEQAQIQQEKNEYELQKLDE | WASLWNWF | -NH2 | | HYBRID T1276 | 7 |
| HYBRID T1277 | Ac- | WQEWEREI | TALLEQAQIQQEKTEYELQKLIE | WEWF | -NH2 | 1h | HYBRID T1277 | 3 |
| HYBRID T1278 | Ac- | WQEWEREI | TALLEQAQIQQEKIIEYELQKLIE | WEWF | -NH2 | 2.5h | HYBRID T1278 | 6 |
| HYBRID T1279 | Ac- | WQEWEREI | TALLEQAQIQQEKIIEYELQKLE | WEWF | -NH2 | | HYBRID T1279 | 3 |
| HYBRID T1280 | Ac- | WQEWEQKI | TALLEQAQIQQEKNEYELQKLDE | WASLWNWF | -NH2 | | HYBRID T1280 | 7 |
| HYBRID T1247 | Ac- | WQEWEQKI | TALLEQAQIQQEKNEYELQKLDK | WASLWNWF | -NH2 | | HYBRID T1247 | 1 |
| HYBRID T1249 | Ac- | WQEWEQKI | TALLEQAQIQQEKNEYELQKLDK | WASLWEWF | -NH2 | 4.7h | HYBRID T1249 | 2 |
| HYBRID T1353 | Ac- | WQEWEQKI | TALLEQAQIQQEKTEYELQKLDK | WASLWEWF | -NH2 | | HYBRID T1353 | 2 |
| HYBRID T1330 | Ac- | WQEWEQKI | TALLEQAQIQQEKIIEYELQKLAK | WASLWEWF | -NH2 | | HYBRID T1330 | 28  3544 |
| HYBRID T1331 | Ac- | WQEWEQKI | TALLEQAQIQQEKIIEYELQKLAE | WASLWEWF | -NH2 | | HYBRID T1331 | 30  11136 |
| HYBRID T1332 | Ac- | WQEWEQKI | TALLEQAQIQQEKAEYELQKLAE | WASLWEWF | -NH2 | | HYBRID T1332 | 18 |
| HYBRID T1333 | Ac- | WQEWEQKI | TALLEQAQIQQEKAEYELQKLAK | WASLWEWF | -NH2 | | HYBRID T1333 | 33 |
| HYBRID T1334 | Ac- | WQEWEQKI | TALLEQAQIQQEKNEYELQKLAE | WASLWEWF | -NH2 | | HYBRID T1334 | 35 |
| HYBRID T1347 | Ac- | WQEWEQKI | TALLEQAQIQQEKNEYELQKLAE | WAGLWEWF | -NH2 | | HYBRID T1347 | 8  3819 |
| HYBRID T1350 | Ac- | WQEWEQKI | TALLEQAQIQQEKNEYELQKLAE | WAWAWF | -NH2 | | HYBRID T1350 | 6  4516 |
| HYBRID T1348 | Ac- | WQEWEQKI | TALLEQAQIQQEKNEYELQKLAE | WASLWAW | -NH2 | | HYBRID T1348 | 7  5255 |

| Peptide | N-term | Sequence | C-term | IV t1/2 | Peptide | RSV Fusion EC-50 ng/ml | RSV Fusion EC-50 ng/ml |
|---|---|---|---|---|---|---|---|
| HYBRID T1351 | Ac- | WQEWEQKI TALLEQAQIQQEKNEYELQKLAEWAGLWAW | -NH2 | | HYBRID T1351 | 8 | 20897 |
| HYBRID T1349 | Ac- | WQEWEQKI TALLEQAQIQQEKAEYELQKLAEWASLWAW | -NH2 | | HYBRID T1349 | 86 | 15326 |
| HYBRID T1352 | Ac- | WQEWEQKI TALLEQAQIQQEKAEYELQKLAEWAGLWAW | -NH2 | | HYBRID T1352 | 193 | 14358 |
| HYBRID T1339 | Ac- | WQEWEQKI TALLEQAQIQQEKIEYELQKLDK WEWF | -NH2 | 45m | HYBRID T1339 | 13 | 367 |
| HYBRID T1293 | Ac- | WQEWEQKI TALLEQAQIQQEKIEYELQKLIE WEWF | -NH2 | 2.6h | HYBRID T1293 | 11 | 3085 |
| HYBRID T1337 | Ac- | WQEWEQKI TALLEQAQIQQEKNEYELQKLIE WEWF | -NH2 | | HYBRID T1337 | 4 | 21618 |
| HYBRID T1338 | Ac- | WQEWEQKI TALLEQAQIQQEKGEYELQKLIE WEWF | -NH2 | | HYBRID T1338 | 234 | 579 |
| HYBRID T1294 | Ac- | WQEWEQKI TALLEQAQIQQEKIEYELQKLIEWASLWEWF | -NH2 | | HYBRID T1294 | 32 | 7774 |
| HYBRID T1309 | Ac- | WQEWEQKI TALLEQAQIQQEKIEYELQKLIKWASLWEWF | -NH2 | | HYBRID T1309 | 153 | >50000 |
| HYBRID T1281 | Ac- | WQEWE I TALLEQAQIQQEKNEYELQKLDE WEWF | -NH2 | | HYBRID T1281 | 3 | 34597 |
| HYBRID T1282 | Ac- | WQEWE I TALLEQAQIQQEKNEYELQKLIE WEWF | -NH2 | | HYBRID T1282 | 4 | 3090 |
| HYBRID T1283 | Ac- | WQEWE I TALLEQAQIQQEKIEYELQKLDE WEWF | -NH2 | | HYBRID T1283 | 33 | 2393 |
| HYBRID T1284 | Ac- | WQEWE I TALLEQAQIQQEKIEYELQKLIE WEWF | -NH2 | | HYBRID T1284 | 31 | 21022 |
| HYBRID T1295 | Ac- | WQEWE I TALLEQAQIQQEKIEYELQKLIEWASLWEWF | -NH2 | | HYBRID T1295 | 60 | >50000 |

Biological Activity

| | | | | IV t1/2 | Peptide | RSV Fusion EC-50 ng/ml | RSV Fusion EC-50 ng/ml |
|---|---|---|---|---|---|---|---|
| RSV T67 | Ac- | DEFDASISQVNEKINQSLAFIRKSDELL | -NH2 | <5m | RSVT67 | 500 | |
| RSV T786 | Ac- | VYPSDEYDASISQVNEEINQALAYIRKADELLENV | -NH2 | <8m | RSVT786 | 1200 | 3085 |

HIV-1/HIV-2/RSV HYBRIDS

T67 Active Core Sequence

| | | | | | |
|---|---|---|---|---|---|
| HYBRID T1138 | Ac- | YTSLIHSLGG DEFDESISQVNEKIEESLAFIRKSDELLGGWASLWNWF | -NH2 | HYBRID T1138 | 1000 |
| HYBRID T1155 | Ac- | YTSLIHSLGG DEFDESISQVNEKIEESLAFIRKSDELL | -NH2 | HYBRID T1155 | 200 |
| HYBRID T1137 | Ac- | YTSLGG DEFDESISQVNEKIEESLAFIRKSDELL GGWNWF | -NH2 | HYBRID T1137 | |
| HYBRID T1156 | Ac- | YTSLGG DEFDESISQVNEKIEESLAFIRKSDELL | -NH2 | HYBRID T1156 | 750 |
| HYBRID T1157 | Ac- | DEFDESISQVNEKIEESLAFIRKSDELLGGWASLWNWF | -NH2 | HYBRID T1157 | 3000 |
| HYBRID T1158 | Ac- | DEFDESISQVNEKIEESLAFIRKSDELL GGWNWF | -NH2 | HYBRID T1158 | |
| HYBRID T1170 | Ac- | WNWF DEFDESISQVNEKIEESLAFIRKSDELL WNWF | -NH2 | HYBRID T1170 | 2900 |

FIG.13C

| | | | | | | | | |
|---|---|---|---|---|---|---|---|---|
| HIV-1/HIV-2/RSV HYBRIDS | | | T786 Active Core Sequence | | | | | |
| T1475 | Ac- | | DEYDASISQVNEKINQALAYIREADEL | | -NH2 | | T1475 | |
| T1474 | Ac- | | DEYDASISQVNEEINQALAYIREADEL | | -NH2 | | T1474 | |
| HYBRID T1285 | Ac- | WQEWDREI | DEYDASISQVNEKINQALAYIREADEL | WEWF | -NH2 | | HYBRID T1285 | 1800 |
| HYBRID T1288 | Ac- | WQEWDREI | DEYDASISQVNEEINQALAYIREADEL | WEWF | -NH2 | | HYBRID T1288 | |
| HYBRID T1286 | Ac- | WQEWEREI | DEYDASISQVNEKINQALAYIREADEL | WEWF | -NH2 | | HYBRID T1286 | |
| HYBRID T1289 | Ac- | WQEWEREI | DEYDASISQVNEEINQALAYIREADEL | WEWF | -NH2 | | HYBRID T1289 | |
| HYBRID T1287 | Ac- | WQEWE I | DEYDASISQVNEKINQALAYIREADEL | WEWF | -NH2 | | HYBRID T1287 | 1900 |
| HYBRID T1290 | Ac- | WQEWE I | DEYDASISQVNEEINQALAYIREADEL | WEWF | -NH2 | | HYBRID T1290 | 3200 |
| HYBRID T1291 | Ac- | WQEW | DEYDASISQVNEKINQALAYIREADEL | WEWF | -NH2 | | HYBRID T1291 | 2000 |
| HYBRID T1292 | Ac- | WQEW | DEYDASISQVNEEINQALAYIREADEL | WEWF | -NH2 | | HYBRID T1292 | 3900 |
| HYBRID T1301 | Ac- | WQEW | DEYDASISQVNEKINQALAYIREADEL | WAWF | -NH2 | 2.2h | HYBRID T1301 | 1200 |
| HYBRID T1302 | Ac- | WQAW | DEYDASISQVNEKINQALAYIREADEL | WAWF | -NH2 | 2.6h | HYBRID T1302 | 2000 |
| HYBRID T1303 | Ac- | WQAW | DEYDASISQVNEKINQALAYIREADEL | WEWF | -NH2 | | HYBRID T1303 | 1200 |
| LH-RH T1323 | Ac- | | QHWSYGLRPG | | -NH2 | 7m | LH-RH T1323 | N/A |
| HIV-1/HIV-2/LH-RH HYBRIDS | | | LH-RH Core Sequence | | | | | |
| HYBRID T1326 | Ac- | WNWF | QHWSYGLRPG | WNWF | -NH2 | | HYBRID T1326 | N/A |
| HYBRID T1327 | Ac- | FNFF | QHWSYGLRPG | FNFF | -NH2 | | HYBRID T1327 | N/A |
| HYBRID T1328 | Ac- | GAGA | QHWSYGLRPG | AGAG | -NH2 | | HYBRID T1328 | N/A |
| HYBRID T1324 | Ac- | WQEWEQKI | QHWSYGLRPG | WASLWEWF | -NH2 | 35m | HYBRID T1324 | N/A |
| HYBRID T1325 | Ac- | WQEWEQKI | QHWSYGLRPG | WEWF | -NH2 | | HYBRID T1325 | N/A |
| HYBRID T1354 | Ac- | WQEW | QHWSYGLRPG | WEWF | -NH2 | | HYBRID T1354 | N/A |
| HYBRID T1355 | Ac- | WQAW | QHWSYGLRPG | WAWF | -NH2 | | HYBRID T1355 | N/A |

FIG. 13D

SEQUENCE LISTING

<160> NUMBER OF SEQ ID NOS: 1515

<210> SEQ ID NO 1
<211> LENGTH: 19
<212> TYPE: PRT
<213> ORGANISM: Artificial Sequence
<220> FEATURE:
<223> OTHER INFORMATION: Core polypeptide

<400> SEQUENCE: 1

Gly Ile Lys Gln Leu Gln Ala Arg Ile Leu Ala Val Glu Arg Tyr Leu

-continued

```
                1               5                  10                 15
Lys Asp Gln

<210> SEQ ID NO 2
<211> LENGTH: 19
<212> TYPE: PRT
<213> ORGANISM: Artificial Sequence
<220> FEATURE:
<223> OTHER INFORMATION: Core polypeptide

<400> SEQUENCE: 2

Asn Asn Leu Leu Arg Ala Ile Glu Ala Gln Gln His Leu Leu Gln Leu
 1               5                  10                 15

Thr Val Trp

<210> SEQ ID NO 3
<211> LENGTH: 18
<212> TYPE: PRT
<213> ORGANISM: Artificial Sequence
<220> FEATURE:
<223> OTHER INFORMATION: Core polypeptide

<400> SEQUENCE: 3

Asn Glu Gln Glu Leu Leu Glu Leu Asp Lys Trp Ala Ser Leu Trp Asn
 1               5                  10                 15

Trp Phe

<210> SEQ ID NO 4
<211> LENGTH: 18
<212> TYPE: PRT
<213> ORGANISM: Artificial Sequence
<220> FEATURE:
<223> OTHER INFORMATION: Core polypeptide

<400> SEQUENCE: 4

Tyr Thr Ser Leu Ile His Ser Leu Ile Glu Glu Ser Gln Asn Gln Gln
 1               5                  10                 15

Glu Lys

<210> SEQ ID NO 5
<211> LENGTH: 28
<212> TYPE: PRT
<213> ORGANISM: Artificial Sequence
<220> FEATURE:
<223> OTHER INFORMATION: Core polypeptide

<400> SEQUENCE: 5

Val Trp Gly Ile Lys Gln Leu Gln Ala Arg Ile Leu Ala Val Glu Arg
 1               5                  10                 15

Tyr Leu Lys Asp Gln Gln Leu Leu Gly Ile Trp Gly
                20                  25

<210> SEQ ID NO 6
<211> LENGTH: 28
<212> TYPE: PRT
<213> ORGANISM: Artificial Sequence
<220> FEATURE:
<223> OTHER INFORMATION: Core polypeptide

<400> SEQUENCE: 6

Gln His Leu Leu Gln Leu Thr Val Trp Gly Ile Lys Gln Leu Gln Ala
 1               5                  10                 15

Arg Ile Leu Ala Val Glu Arg Tyr Leu Lys Asp Gln
```

```
            20                  25

<210> SEQ ID NO 7
<211> LENGTH: 28
<212> TYPE: PRT
<213> ORGANISM: Artificial Sequence
<220> FEATURE:
<223> OTHER INFORMATION: Core polypeptide

<400> SEQUENCE: 7

Leu Arg Ala Ile Glu Ala Gln Gln His Leu Leu Gln Leu Thr Val Trp
  1               5                  10                  15

Gly Ile Lys Gln Leu Gln Ala Arg Ile Leu Ala Val
            20                  25

<210> SEQ ID NO 8
<211> LENGTH: 28
<212> TYPE: PRT
<213> ORGANISM: Artificial Sequence
<220> FEATURE:
<223> OTHER INFORMATION: Core polypeptide

<400> SEQUENCE: 8

Val Gln Gln Gln Asn Asn Leu Leu Ala Arg Ile Glu Ala Gln Gln His
  1               5                  10                  15

Leu Leu Gln Leu Thr Val Trp Gly Ile Lys Gln Leu
            20                  25

<210> SEQ ID NO 9
<211> LENGTH: 28
<212> TYPE: PRT
<213> ORGANISM: Artificial Sequence
<220> FEATURE:
<223> OTHER INFORMATION: Core polypeptide

<400> SEQUENCE: 9

Arg Gln Leu Leu Ser Gly Ile Val Gln Gln Asn Asn Leu Leu Arg
  1               5                  10                  15

Ala Ile Glu Ala Gln Gln His Leu Leu Gln Leu Thr
            20                  25

<210> SEQ ID NO 10
<211> LENGTH: 28
<212> TYPE: PRT
<213> ORGANISM: Artificial Sequence
<220> FEATURE:
<223> OTHER INFORMATION: Core polypeptide

<400> SEQUENCE: 10

Met Thr Leu Thr Val Gln Ala Arg Gln Leu Leu Ser Gly Ile Val Gln
  1               5                  10                  15

Gln Gln Asn Asn Leu Leu Arg Ala Ile Glu Ala Gln
            20                  25

<210> SEQ ID NO 11
<211> LENGTH: 27
<212> TYPE: PRT
<213> ORGANISM: Artificial Sequence
<220> FEATURE:
<223> OTHER INFORMATION: Core polypeptide

<400> SEQUENCE: 11

Val Val Ser Leu Ser Asn Gly Val Ser Val Leu Thr Ser Lys Val Leu
  1               5                  10                  15
```

Asp Leu Lys Asn Tyr Ile Asp Lys Gln Leu Leu
            20                  25

<210> SEQ ID NO 12
<211> LENGTH: 28
<212> TYPE: PRT
<213> ORGANISM: Artificial Sequence
<220> FEATURE:
<223> OTHER INFORMATION: Core polypeptide

<400> SEQUENCE: 12

Leu Leu Ser Thr Asn Lys Ala Val Val Ser Leu Ser Asn Gly Val Ser
1               5                   10                  15

Val Leu Thr Ser Lys Val Leu Asp Leu Lys Asn Tyr
            20                  25

<210> SEQ ID NO 13
<211> LENGTH: 28
<212> TYPE: PRT
<213> ORGANISM: Artificial Sequence
<220> FEATURE:
<223> OTHER INFORMATION: Core polypeptide

<400> SEQUENCE: 13

Val Leu His Leu Glu Gly Glu Val Asn Lys Ile Lys Ser Ala Leu Leu
1               5                   10                  15

Ser Thr Asn Lys Ala Val Val Ser Leu Ser Asn Gly
            20                  25

<210> SEQ ID NO 14
<211> LENGTH: 28
<212> TYPE: PRT
<213> ORGANISM: Artificial Sequence
<220> FEATURE:
<223> OTHER INFORMATION: Core polypeptide

<400> SEQUENCE: 14

Leu Leu Ser Thr Asn Lys Ala Val Val Ser Leu Ser Asn Gly Val Ser
1               5                   10                  15

Val Leu Thr Ser Lys Val Leu Asp Leu Lys Asn Tyr
            20                  25

<210> SEQ ID NO 15
<211> LENGTH: 36
<212> TYPE: PRT
<213> ORGANISM: Artificial Sequence
<220> FEATURE:
<223> OTHER INFORMATION: Core polypeptide

<400> SEQUENCE: 15

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 16
<211> LENGTH: 38
<212> TYPE: PRT
<213> ORGANISM: Artificial Sequence
<220> FEATURE:
<223> OTHER INFORMATION: Core polypeptide

<400> SEQUENCE: 16

```
Asn Asn Leu Leu Arg Ala Ile Glu Ala Gln Gln His Leu Leu Gln Leu
 1               5                  10                  15

Thr Val Trp Gly Ile Lys Gln Leu Gln Ala Arg Ile Leu Ala Val Glu
            20                  25                  30

Arg Tyr Leu Lys Asp Gln
        35
```

```
<210> SEQ ID NO 17
<211> LENGTH: 42
<212> TYPE: PRT
<213> ORGANISM: Artificial Sequence
<220> FEATURE:
<223> OTHER INFORMATION: Core polypeptide

<400> SEQUENCE: 17
```

```
Ile Glu Leu Ser Asn Ile Lys Glu Asn Lys Cys Asn Gly Thr Asp Ala
 1               5                  10                  15

Lys Val Lys Leu Ile Lys Gln Glu Leu Asp Lys Tyr Lys Asn Ala Val
            20                  25                  30

Thr Glu Leu Gln Leu Leu Met Gln Ser Thr
        35                  40
```

```
<210> SEQ ID NO 18
<211> LENGTH: 28
<212> TYPE: PRT
<213> ORGANISM: Artificial Sequence
<220> FEATURE:
<223> OTHER INFORMATION: Core polypeptide

<400> SEQUENCE: 18
```

```
Ile Glu Leu Ser Asn Ile Lys Glu Asn Lys Cys Asn Gly Thr Asp Ala
 1               5                  10                  15

Lys Val Lys Leu Ile Lys Gln Glu Leu Asp Lys Tyr
            20                  25
```

```
<210> SEQ ID NO 19
<211> LENGTH: 28
<212> TYPE: PRT
<213> ORGANISM: Artificial Sequence
<220> FEATURE:
<223> OTHER INFORMATION: Core polypeptide

<400> SEQUENCE: 19
```

```
Glu Asn Lys Cys Asn Gly Thr Asp Ala Lys Val Lys Leu Ile Lys Gln
 1               5                  10                  15

Glu Leu Asp Lys Tyr Lys Asn Ala Val Thr Glu Leu
            20                  25
```

```
<210> SEQ ID NO 20
<211> LENGTH: 28
<212> TYPE: PRT
<213> ORGANISM: Artificial Sequence
<220> FEATURE:
<223> OTHER INFORMATION: Core polypeptide

<400> SEQUENCE: 20
```

```
Asp Ala Lys Val Lys Leu Ile Lys Gln Glu Leu Asp Lys Tyr Lys Asn
 1               5                  10                  15

Ala Val Thr Glu Leu Gln Leu Leu Met Gln Ser Thr
            20                  25
```

```
<210> SEQ ID NO 21
```

```
<211> LENGTH: 28
<212> TYPE: PRT
<213> ORGANISM: Artificial Sequence
<220> FEATURE:
<223> OTHER INFORMATION: Core polypeptide

<400> SEQUENCE: 21

Cys Asn Gly Thr Asp Ala Lys Val Lys Leu Ile Lys Gln Glu Leu Asp
  1               5                  10                  15

Lys Tyr Lys Asn Ala Val Thr Glu Leu Gln Leu Leu
             20                  25

<210> SEQ ID NO 22
<211> LENGTH: 35
<212> TYPE: PRT
<213> ORGANISM: Artificial Sequence
<220> FEATURE:
<223> OTHER INFORMATION: Core polypeptide

<400> SEQUENCE: 22

Ser Asn Ile Lys Glu Asn Lys Cys Asn Gly Thr Asp Ala Lys Val Lys
  1               5                  10                  15

Leu Ile Lys Gln Glu Leu Asp Lys Tyr Lys Asn Ala Val Thr Glu Leu
             20                  25                  30

Gln Leu Leu
         35

<210> SEQ ID NO 23
<211> LENGTH: 37
<212> TYPE: PRT
<213> ORGANISM: Artificial Sequence
<220> FEATURE:
<223> OTHER INFORMATION: Core polypeptide

<400> SEQUENCE: 23

Ala Ser Gly Val Ala Val Ser Lys Val Leu His Leu Glu Gly Glu Val
  1               5                  10                  15

Asn Lys Ile Lys Ser Ala Leu Leu Ser Thr Asn Lys Ala Val Val Ser
             20                  25                  30

Leu Ser Asn Gly Val
         35

<210> SEQ ID NO 24
<211> LENGTH: 35
<212> TYPE: PRT
<213> ORGANISM: Artificial Sequence
<220> FEATURE:
<223> OTHER INFORMATION: Core polypeptide

<400> SEQUENCE: 24

Ser Gly Val Ala Val Ser Lys Val Leu His Leu Glu Gly Glu Val Asn
  1               5                  10                  15

Lys Ile Lys Ser Ala Leu Leu Ser Thr Asn Lys Ala Val Val Ser Leu
             20                  25                  30

Ser Asn Gly
         35

<210> SEQ ID NO 25
<211> LENGTH: 35
<212> TYPE: PRT
<213> ORGANISM: Artificial Sequence
<220> FEATURE:
<223> OTHER INFORMATION: Core polypeptide
```

```
<400> SEQUENCE: 25

Val Leu His Leu Glu Gly Glu Val Asn Lys Ile Lys Ser Ala Leu Leu
 1               5                   10                  15

Ser Thr His Lys Ala Val Val Ser Leu Ser Asn Gly Val Ser Val Leu
            20                  25                  30

Thr Ser Lys
        35

<210> SEQ ID NO 26
<211> LENGTH: 36
<212> TYPE: PRT
<213> ORGANISM: Artificial Sequence
<220> FEATURE:
<223> OTHER INFORMATION: Core polypeptide

<400> SEQUENCE: 26

Ala Arg Lys Leu Gln Arg Met Lys Gln Leu Glu Asp Lys Val Glu Glu
 1               5                   10                  15

Leu Leu Ser Lys Asn Tyr His Tyr Leu Glu Asn Glu Val Ala Arg Leu
            20                  25                  30

Lys Lys Leu Val
        35

<210> SEQ ID NO 27
<211> LENGTH: 34
<212> TYPE: PRT
<213> ORGANISM: Artificial Sequence
<220> FEATURE:
<223> OTHER INFORMATION: Core polypeptide

<400> SEQUENCE: 27

Arg Met Lys Gln Leu Glu Asp Lys Val Glu Glu Leu Leu Ser Lys Asn
 1               5                   10                  15

Tyr His Tyr Leu Glu Asn Glu Val Ala Arg Leu Lys Lys Leu Val Gly
            20                  25                  30

Glu Arg

<210> SEQ ID NO 28
<211> LENGTH: 28
<212> TYPE: PRT
<213> ORGANISM: Artificial Sequence
<220> FEATURE:
<223> OTHER INFORMATION: Core polypeptide

<400> SEQUENCE: 28

Val Gln Gln Gln Asn Asn Leu Leu Arg Ala Ile Glu Ala Gln Gln His
 1               5                   10                  15

Leu Leu Gln Leu Thr Val Trp Gly Ile Lys Gln Leu
            20                  25

<210> SEQ ID NO 29
<211> LENGTH: 28
<212> TYPE: PRT
<213> ORGANISM: Artificial Sequence
<220> FEATURE:
<223> OTHER INFORMATION: Core polypeptide

<400> SEQUENCE: 29

Leu Arg Ala Ile Glu Ala Gln Gln His Leu Leu Gln Leu Thr Val Trp
 1               5                   10                  15

Gly Ile Lys Gln Leu Gln Ala Arg Ile Leu Ala Val
            20                  25
```

<210> SEQ ID NO 30
<211> LENGTH: 28
<212> TYPE: PRT
<213> ORGANISM: Artificial Sequence
<220> FEATURE:
<223> OTHER INFORMATION: Core polypeptide

<400> SEQUENCE: 30

Gln His Leu Leu Gln Leu Thr Val Trp Gly Ile Lys Gln Leu Gln Ala
1               5                   10                  15

Arg Ile Leu Ala Val Glu Arg Tyr Leu Lys Asp Gln
            20                  25

<210> SEQ ID NO 31
<211> LENGTH: 28
<212> TYPE: PRT
<213> ORGANISM: Artificial Sequence
<220> FEATURE:
<223> OTHER INFORMATION: Core polypeptide

<400> SEQUENCE: 31

Arg Gln Leu Leu Ser Gly Ile Val Gln Gln Gln Asn Asn Leu Leu Arg
1               5                   10                  15

Ala Ile Glu Ala Gln Gln His Leu Leu Gln Leu Thr
            20                  25

<210> SEQ ID NO 32
<211> LENGTH: 28
<212> TYPE: PRT
<213> ORGANISM: Artificial Sequence
<220> FEATURE:
<223> OTHER INFORMATION: Core polypeptide

<400> SEQUENCE: 32

Met Thr Leu Thr Val Gln Ala Arg Gln Leu Leu Ser Gly Ile Val Gln
1               5                   10                  15

Gln Gln Asn Asn Leu Leu Arg Ala Ile Glu Ala Gln
            20                  25

<210> SEQ ID NO 33
<211> LENGTH: 28
<212> TYPE: PRT
<213> ORGANISM: Artificial Sequence
<220> FEATURE:
<223> OTHER INFORMATION: Core polypeptide

<400> SEQUENCE: 33

Ala Lys Gln Ala Arg Ser Asp Ile Glu Lys Leu Lys Glu Ala Ile Arg
1               5                   10                  15

Asp Thr Asn Lys Ala Val Gln Ser Val Gln Ser Ser
            20                  25

<210> SEQ ID NO 34
<211> LENGTH: 35
<212> TYPE: PRT
<213> ORGANISM: Artificial Sequence
<220> FEATURE:
<223> OTHER INFORMATION: Core polypeptide

<400> SEQUENCE: 34

Ala Ala Val Ala Leu Val Glu Ala Lys Gln Ala Arg Ser Asp Ile Glu
1               5                   10                  15

Lys Leu Lys Glu Ala Ile Arg Asp Thr Asn Lys Ala Val Gln Ser Val 20                  25                  30
Gln Ser Ser
        35

<210> SEQ ID NO 35
<211> LENGTH: 35
<212> TYPE: PRT
<213> ORGANISM: Artificial Sequence
<220> FEATURE:
<223> OTHER INFORMATION: Core polypeptide

<400> SEQUENCE: 35

Ala Lys Gln Ala Arg Ser Asp Ile Glu Lys Leu Lys Glu Ala Ile Arg
 1               5                  10                  15

Asp Thr Asn Lys Ala Val Gln Ser Val Gln Ser Ser Ile Gly Asn Leu
                20                  25                  30

Ile Val Ala
        35

<210> SEQ ID NO 36
<211> LENGTH: 28
<212> TYPE: PRT
<213> ORGANISM: Artificial Sequence
<220> FEATURE:
<223> OTHER INFORMATION: Core polypeptide

<400> SEQUENCE: 36

Gly Thr Ile Ala Leu Gly Val Ala Thr Ser Ala Gln Ile Thr Ala Ala
 1               5                  10                  15

Val Ala Leu Val Glu Ala Lys Gln Ala Arg Ser Asp
                20                  25

<210> SEQ ID NO 37
<211> LENGTH: 28
<212> TYPE: PRT
<213> ORGANISM: Artificial Sequence
<220> FEATURE:
<223> OTHER INFORMATION: Core polypeptide

<400> SEQUENCE: 37

Ala Thr Ser Ala Gln Ile Thr Ala Ala Val Ala Leu Val Glu Ala Lys
 1               5                  10                  15

Gln Ala Arg Ser Asp Ile Glu Lys Leu Lys Glu Ala
                20                  25

<210> SEQ ID NO 38
<211> LENGTH: 28
<212> TYPE: PRT
<213> ORGANISM: Artificial Sequence
<220> FEATURE:
<223> OTHER INFORMATION: Core polypeptide

<400> SEQUENCE: 38

Ala Ala Val Ala Leu Val Glu Ala Lys Gln Ala Arg Ser Asp Ile Glu
 1               5                  10                  15

Lys Leu Lys Glu Ala Ile Arg Asp Thr Asn Lys Ala
                20                  25

<210> SEQ ID NO 39
<211> LENGTH: 35
<212> TYPE: PRT
<213> ORGANISM: Artificial Sequence
<220> FEATURE:
<223> OTHER INFORMATION: Core polypeptide

```
<400> SEQUENCE: 39

Ile Asp Ile Ser Ile Glu Leu Asn Lys Ala Lys Ser Asp Leu Glu Glu
 1               5                  10                  15

Ser Lys Glu Trp Ile Glu Lys Ser Asn Gln Glu Leu Asp Ser Ile Gly
                20                  25                  30

Asn Trp Glu
        35

<210> SEQ ID NO 40
<211> LENGTH: 28
<212> TYPE: PRT
<213> ORGANISM: Artificial Sequence
<220> FEATURE:
<223> OTHER INFORMATION: Core polypeptide

<400> SEQUENCE: 40

Ile Glu Lys Leu Lys Glu Ala Ile Arg Asp Thr Asn Lys Ala Val Gln
 1               5                  10                  15

Ser Val Gln Ser Ser Ile Gly Asn Leu Ile Val Ala
                20                  25

<210> SEQ ID NO 41
<211> LENGTH: 28
<212> TYPE: PRT
<213> ORGANISM: Artificial Sequence
<220> FEATURE:
<223> OTHER INFORMATION: Core polypeptide

<400> SEQUENCE: 41

Ile Arg Asp Thr Asn Lys Ala Val Gln Ser Val Gln Ser Ser Ile Gly
 1               5                  10                  15

Asn Leu Ile Val Ala Ile Lys Ser Val Gln Asp Tyr
                20                  25

<210> SEQ ID NO 42
<211> LENGTH: 28
<212> TYPE: PRT
<213> ORGANISM: Artificial Sequence
<220> FEATURE:
<223> OTHER INFORMATION: Core polypeptide

<400> SEQUENCE: 42

Ala Val Gln Ser Val Gln Ser Ser Ile Gly Asn Leu Ile Val Ala Ile
 1               5                  10                  15

Lys Ser Val Gln Asp Tyr Val Asn Lys Glu Ile Val
                20                  25

<210> SEQ ID NO 43
<211> LENGTH: 50
<212> TYPE: PRT
<213> ORGANISM: Artificial Sequence
<220> FEATURE:
<223> OTHER INFORMATION: Core polypeptide

<400> SEQUENCE: 43

Gln Ala Arg Gln Leu Leu Ser Gly Ile Val Gln Gln Gln Asn Asn Leu
 1               5                  10                  15

Leu Arg Ala Ile Glu Ala Gln Gln His Leu Leu Gln Leu Thr Val Trp
                20                  25                  30

Gly Ile Lys Gln Leu Ala Arg Ile Leu Ala Val Glu Arg Tyr Leu Lys
                35                  40                  45
```

```
Asp Gln
    50

<210> SEQ ID NO 44
<211> LENGTH: 28
<212> TYPE: PRT
<213> ORGANISM: Artificial Sequence
<220> FEATURE:
<223> OTHER INFORMATION: Core polypeptide

<400> SEQUENCE: 44

Gln Ala Arg Gln Leu Leu Ser Gly Ile Val Gln Gln Asn Asn Leu
1               5                   10                  15

Leu Arg Ala Ile Glu Ala Gln Gln His Leu Leu Gln
            20                  25

<210> SEQ ID NO 45
<211> LENGTH: 48
<212> TYPE: PRT
<213> ORGANISM: Artificial Sequence
<220> FEATURE:
<223> OTHER INFORMATION: Core polypeptide

<400> SEQUENCE: 45

Met Thr Trp Met Glu Met Asp Arg Glu Ile Asn Asn Tyr Thr Ser Leu
1               5                   10                  15

Ile Gly Ser Leu Ile Glu Glu Ser Gln Asn Gln Gln Glu Lys Asn Glu
            20                  25                  30

Gln Glu Leu Leu Glu Leu Asp Lys Trp Ala Ser Leu Trp Asn Trp Phe
        35                  40                  45

<210> SEQ ID NO 46
<211> LENGTH: 35
<212> TYPE: PRT
<213> ORGANISM: Artificial Sequence
<220> FEATURE:
<223> OTHER INFORMATION: Core polypeptide

<400> SEQUENCE: 46

Trp Met Glu Trp Asp Arg Glu Ile Asn Asn Tyr Thr Ser Leu Ile Gly
1               5                   10                  15

Ser Leu Ile Glu Glu Ser Gln Asn Gln Gln Glu Lys Asn Glu Gln Glu
            20                  25                  30

Leu Leu Glu
        35

<210> SEQ ID NO 47
<211> LENGTH: 28
<212> TYPE: PRT
<213> ORGANISM: Artificial Sequence
<220> FEATURE:
<223> OTHER INFORMATION: Core polypeptide

<400> SEQUENCE: 47

Ile Asn Asn Tyr Thr Ser Leu Ile Gly Ser Leu Ile Glu Glu Ser Gln
1               5                   10                  15

Asn Gln Gln Glu Lys Asn Glu Gln Glu Leu Leu Glu
            20                  25

<210> SEQ ID NO 48
<211> LENGTH: 35
<212> TYPE: PRT
<213> ORGANISM: Artificial Sequence
<220> FEATURE:
```

<223> OTHER INFORMATION: Core polypeptide

<400> SEQUENCE: 48

Ile Asn Asn Tyr Thr Ser Leu Ile Gly Ser Leu Ile Glu Glu Ser Gln
1               5                   10                  15

Asn Gln Gln Glu Lys Asn Glu Gln Glu Leu Leu Glu Leu Asp Lys Trp
            20                  25                  30

Ala Ser Leu
        35

<210> SEQ ID NO 49
<211> LENGTH: 33
<212> TYPE: PRT
<213> ORGANISM: Artificial Sequence
<220> FEATURE:
<223> OTHER INFORMATION: Core polypeptide

<400> SEQUENCE: 49

Glu Trp Asp Arg Glu Ile Asn Asn Tyr Thr Ser Leu Ile Gly Ser Leu
1               5                   10                  15

Ile Glu Glu Ser Gln Asn Gln Gln Glu Lys Asn Glu Gln Glu Gly Gly
            20                  25                  30

Cys

<210> SEQ ID NO 50
<211> LENGTH: 28
<212> TYPE: PRT
<213> ORGANISM: Artificial Sequence
<220> FEATURE:
<223> OTHER INFORMATION: Core polypeptide

<400> SEQUENCE: 50

Gln Ser Arg Thr Leu Leu Ala Gly Ile Val Gln Gln Gln Gln Gln Leu
1               5                   10                  15

Leu Asp Val Val Lys Arg Gln Gln Glu Leu Leu Arg
            20                  25

<210> SEQ ID NO 51
<211> LENGTH: 44
<212> TYPE: PRT
<213> ORGANISM: Artificial Sequence
<220> FEATURE:
<223> OTHER INFORMATION: Core polypeptide

<400> SEQUENCE: 51

Asn Asn Asp Thr Trp Gln Glu Trp Glu Arg Lys Val Asp Phe Leu Glu
1               5                   10                  15

Glu Asn Ile Thr Ala Leu Leu Glu Glu Ala Gln Ile Gln Gln Glu Lys
            20                  25                  30

Asn Met Tyr Glu Leu Gln Lys Leu Asn Ser Trp Asp
        35                  40

<210> SEQ ID NO 52
<211> LENGTH: 28
<212> TYPE: PRT
<213> ORGANISM: Artificial Sequence
<220> FEATURE:
<223> OTHER INFORMATION: Core polypeptide

<400> SEQUENCE: 52

Trp Gln Glu Trp Glu Arg Lys Val Asp Phe Leu Glu Glu Asn Ile Thr
1               5                   10                  15

Ala Leu Leu Glu Glu Ala Gln Ile Gln Gln Glu Lys
            20                  25

<210> SEQ ID NO 53
<211> LENGTH: 28
<212> TYPE: PRT
<213> ORGANISM: Artificial Sequence
<220> FEATURE:
<223> OTHER INFORMATION: Core polypeptide

<400> SEQUENCE: 53

Val Asp Phe Leu Glu Glu Asn Ile Thr Ala Leu Leu Glu Glu Ala Gln
1               5                   10                  15

Ile Gln Gln Glu Lys Asn Met Tyr Glu Leu Gln Lys
            20                  25

<210> SEQ ID NO 54
<211> LENGTH: 28
<212> TYPE: PRT
<213> ORGANISM: Artificial Sequence
<220> FEATURE:
<223> OTHER INFORMATION: Core polypeptide

<400> SEQUENCE: 54

Ile Thr Ala Leu Leu Glu Glu Ala Gln Ile Gln Gln Glu Lys Asn Met
1               5                   10                  15

Tyr Glu Leu Gln Lys Leu Asn Ser Trp Asp Val Phe
            20                  25

<210> SEQ ID NO 55
<211> LENGTH: 36
<212> TYPE: PRT
<213> ORGANISM: Artificial Sequence
<220> FEATURE:
<223> OTHER INFORMATION: Core polypeptide

<400> SEQUENCE: 55

Ser Ser Glu Ser Phe Thr Leu Leu Glu Gln Trp Asn Asn Trp Lys Leu
1               5                   10                  15

Gln Leu Ala Glu Gln Trp Leu Glu Gln Ile Asn Glu Lys His Tyr Leu
            20                  25                  30

Glu Asp Ile Ser
        35

<210> SEQ ID NO 56
<211> LENGTH: 10
<212> TYPE: PRT
<213> ORGANISM: Artificial Sequence
<220> FEATURE:
<223> OTHER INFORMATION: Core polypeptide

<400> SEQUENCE: 56

Asp Lys Trp Ala Ser Leu Trp Asn Trp Phe
1               5                   10

<210> SEQ ID NO 57
<211> LENGTH: 18
<212> TYPE: PRT
<213> ORGANISM: Artificial Sequence
<220> FEATURE:
<223> OTHER INFORMATION: Core polypeptide

<400> SEQUENCE: 57

Asn Glu Gln Glu Leu Leu Glu Leu Asp Lys Trp Ala Ser Leu Trp Asn
1               5                   10                  15

Trp Phe

<210> SEQ ID NO 58
<211> LENGTH: 20
<212> TYPE: PRT
<213> ORGANISM: Artificial Sequence
<220> FEATURE:
<223> OTHER INFORMATION: Core polypeptide

<400> SEQUENCE: 58

Glu Lys Asn Glu Gln Glu Leu Leu Glu Leu Asp Lys Trp Ala Ser Leu
 1               5                  10                  15

Trp Asn Trp Phe
            20

<210> SEQ ID NO 59
<211> LENGTH: 23
<212> TYPE: PRT
<213> ORGANISM: Artificial Sequence
<220> FEATURE:
<223> OTHER INFORMATION: Core polypeptide

<400> SEQUENCE: 59

Asn Gln Gln Glu Lys Asn Glu Gln Glu Leu Leu Glu Leu Asp Lys Trp
 1               5                  10                  15

Ala Ser Leu Trp Asn Trp Phe
            20

<210> SEQ ID NO 60
<211> LENGTH: 26
<212> TYPE: PRT
<213> ORGANISM: Artificial Sequence
<220> FEATURE:
<223> OTHER INFORMATION: Core polypeptide

<400> SEQUENCE: 60

Glu Ser Gln Asn Gln Gln Glu Lys Asn Glu Gln Glu Leu Leu Glu Leu
 1               5                  10                  15

Asp Lys Trp Ala Ser Leu Trp Asn Trp Phe
            20                  25

<210> SEQ ID NO 61
<211> LENGTH: 33
<212> TYPE: PRT
<213> ORGANISM: Artificial Sequence
<220> FEATURE:
<223> OTHER INFORMATION: Core polypeptide

<400> SEQUENCE: 61

Leu Ile His Ser Leu Ile Glu Glu Ser Gln Asn Gln Gln Glu Lys Asn
 1               5                  10                  15

Glu Gln Glu Leu Leu Glu Leu Asp Lys Trp Ala Ser Leu Trp Asn Trp
                20                  25                  30

Phe

<210> SEQ ID NO 62
<211> LENGTH: 28
<212> TYPE: PRT
<213> ORGANISM: Artificial Sequence
<220> FEATURE:
<223> OTHER INFORMATION: Core polypeptide

<400> SEQUENCE: 62

-continued

Asn Asp Gln Lys Lys Leu Met Ser Asn Val Gln Ile Val Arg Gln
1               5                   10                  15

Gln Ser Tyr Ser Ile Met Ser Ile Ile Lys Glu Glu
            20                  25

<210> SEQ ID NO 63
<211> LENGTH: 28
<212> TYPE: PRT
<213> ORGANISM: Artificial Sequence
<220> FEATURE:
<223> OTHER INFORMATION: Core polypeptide

<400> SEQUENCE: 63

Asp Glu Phe Asp Ala Ser Ile Ser Gln Val Asn Glu Lys Ile Asn Gln
1               5                   10                  15

Ser Leu Ala Phe Ile Arg Lys Ser Asp Glu Leu Leu
            20                  25

<210> SEQ ID NO 64
<211> LENGTH: 27
<212> TYPE: PRT
<213> ORGANISM: Artificial Sequence
<220> FEATURE:
<223> OTHER INFORMATION: Core polypeptide

<400> SEQUENCE: 64

Val Ser Lys Gly Tyr Ser Ala Leu Arg Thr Gly Trp Tyr Thr Ser Val
1               5                   10                  15

Ile Thr Ile Glu Leu Ser Asn Ile Lys Glu Asn
            20                  25

<210> SEQ ID NO 65
<211> LENGTH: 27
<212> TYPE: PRT
<213> ORGANISM: Artificial Sequence
<220> FEATURE:
<223> OTHER INFORMATION: Core polypeptide

<400> SEQUENCE: 65

Val Val Ser Leu Ser Asn Gly Val Ser Val Leu Thr Ser Lys Val Leu
1               5                   10                  15

Asp Leu Lys Asn Tyr Ile Asp Lys Gln Leu Leu
            20                  25

<210> SEQ ID NO 66
<211> LENGTH: 28
<212> TYPE: PRT
<213> ORGANISM: Artificial Sequence
<220> FEATURE:
<223> OTHER INFORMATION: Core polypeptide

<400> SEQUENCE: 66

Val Asn Lys Ile Lys Ser Ala Leu Leu Ser Thr Asn Lys Ala Val Val
1               5                   10                  15

Ser Leu Ser Asn Gly Val Ser Val Leu Thr Ser Lys
            20                  25

<210> SEQ ID NO 67
<211> LENGTH: 35
<212> TYPE: PRT
<213> ORGANISM: Artificial Sequence
<220> FEATURE:
<223> OTHER INFORMATION: Core polypeptide

<400> SEQUENCE: 67

-continued

Pro Ile Ile Asn Phe Tyr Asp Pro Leu Val Phe Pro Ser Asp Glu Phe
1               5                   10                  15

Asp Ala Ser Ile Ser Gln Val Asn Glu Lys Ile Asn Gln Ser Leu Ala
            20                  25                  30

Phe Ile Arg
        35

<210> SEQ ID NO 68
<211> LENGTH: 28
<212> TYPE: PRT
<213> ORGANISM: Artificial Sequence
<220> FEATURE:
<223> OTHER INFORMATION: Core polypeptide

<400> SEQUENCE: 68

Asn Leu Val Tyr Ala Gln Leu Gln Phe Thr Tyr Asp Thr Leu Arg Gly
1               5                   10                  15

Tyr Ile Asn Arg Ala Leu Ala Gln Ile Ala Glu Ala
            20                  25

<210> SEQ ID NO 69
<211> LENGTH: 31
<212> TYPE: PRT
<213> ORGANISM: Artificial Sequence
<220> FEATURE:
<223> OTHER INFORMATION: Core polypeptide

<400> SEQUENCE: 69

Leu Asn Gln Val Asp Leu Thr Glu Thr Leu Glu Arg Tyr Gln Gln Arg
1               5                   10                  15

Leu Asn Thr Tyr Ala Leu Val Ser Lys Asp Ala Ser Tyr Arg Ser
            20                  25                  30

<210> SEQ ID NO 70
<211> LENGTH: 27
<212> TYPE: PRT
<213> ORGANISM: Artificial Sequence
<220> FEATURE:
<223> OTHER INFORMATION: Core polypeptide

<400> SEQUENCE: 70

Glu Leu Leu Val Leu Lys Lys Ala Gln Leu Asn Arg His Ser Tyr Leu
1               5                   10                  15

Lys Asp Ser Asp Phe Leu Asp Ala Ala Leu Asp
            20                  25

<210> SEQ ID NO 71
<211> LENGTH: 27
<212> TYPE: PRT
<213> ORGANISM: Artificial Sequence
<220> FEATURE:
<223> OTHER INFORMATION: Core polypeptide

<400> SEQUENCE: 71

Leu Ala Glu Ala Gly Glu Glu Ser Val Thr Glu Asp Thr Glu Arg Glu
1               5                   10                  15

Asp Thr Glu Glu Glu Arg Glu Asp Glu Glu Glu
            20                  25

<210> SEQ ID NO 72
<211> LENGTH: 35
<212> TYPE: PRT
<213> ORGANISM: Artificial Sequence

```
<220> FEATURE:
<223> OTHER INFORMATION: Core polypeptide

<400> SEQUENCE: 72

Ala Leu Leu Ala Glu Ala Gly Glu Glu Ser Val Thr Glu Asp Thr Glu
 1               5                  10                  15

Arg Glu Asp Thr Glu Glu Glu Arg Glu Asp Glu Glu Glu Glu Asn Glu
            20                  25                  30

Ala Arg Thr
        35

<210> SEQ ID NO 73
<211> LENGTH: 35
<212> TYPE: PRT
<213> ORGANISM: Artificial Sequence
<220> FEATURE:
<223> OTHER INFORMATION: Core polypeptide

<400> SEQUENCE: 73

Glu Thr Glu Arg Ser Val Asp Leu Val Ala Ala Leu Leu Ala Glu Ala
 1               5                  10                  15

Gly Glu Glu Ser Val Thr Glu Asp Thr Glu Arg Glu Asp Thr Glu Glu
            20                  25                  30

Glu Arg Glu
        35

<210> SEQ ID NO 74
<211> LENGTH: 28
<212> TYPE: PRT
<213> ORGANISM: Artificial Sequence
<220> FEATURE:
<223> OTHER INFORMATION: Core polypeptide

<400> SEQUENCE: 74

Glu Glu Ser Val Thr Glu Asp Thr Glu Arg Glu Asp Thr Glu Glu Glu
 1               5                  10                  15

Arg Glu Asp Glu Glu Glu Glu Asn Glu Ala Arg Thr
            20                  25

<210> SEQ ID NO 75
<211> LENGTH: 28
<212> TYPE: PRT
<213> ORGANISM: Artificial Sequence
<220> FEATURE:
<223> OTHER INFORMATION: Core polypeptide

<400> SEQUENCE: 75

Val Asp Leu Val Ala Ala Leu Leu Ala Glu Ala Gly Glu Glu Ser Val
 1               5                  10                  15

Thr Glu Asp Thr Glu Arg Glu Asp Thr Glu Glu Glu
            20                  25

<210> SEQ ID NO 76
<211> LENGTH: 25
<212> TYPE: PRT
<213> ORGANISM: Artificial Sequence
<220> FEATURE:
<223> OTHER INFORMATION: Core polypeptide

<400> SEQUENCE: 76

Asn Ser Glu Thr Glu Arg Ser Val Asp Leu Val Ala Ala Leu Leu Ala
 1               5                  10                  15

Glu Ala Gly Glu Glu Ser Val Thr Glu
```

```
            20                  25

<210> SEQ ID NO 77
<211> LENGTH: 28
<212> TYPE: PRT
<213> ORGANISM: Artificial Sequence
<220> FEATURE:
<223> OTHER INFORMATION: Core polypeptide

<400> SEQUENCE: 77

Asp Ile Ser Tyr Ala Gln Leu Gln Phe Thr Tyr Asp Val Leu Lys Asp
 1               5                  10                  15

Tyr Ile Asn Asp Ala Leu Arg Asn Ile Met Asp Ala
            20                  25

<210> SEQ ID NO 78
<211> LENGTH: 30
<212> TYPE: PRT
<213> ORGANISM: Artificial Sequence
<220> FEATURE:
<223> OTHER INFORMATION: Core polypeptide

<400> SEQUENCE: 78

Ser Asn Val Phe Ser Lys Asp Glu Ile Met Arg Glu Tyr Asn Ser Gln
 1               5                  10                  15

Lys Gln His Ile Arg Thr Leu Ser Ala Lys Val Asn Asp Asn
            20                  25                  30

<210> SEQ ID NO 79
<211> LENGTH: 35
<212> TYPE: PRT
<213> ORGANISM: Artificial Sequence
<220> FEATURE:
<223> OTHER INFORMATION: Core polypeptide

<400> SEQUENCE: 79

Ile Asp Ile Ser Ile Glu Leu Asn Lys Ala Lys Ser Asp Leu Glu Glu
 1               5                  10                  15

Ala Lys Glu Trp Ile Lys Lys Ala Asn Gln Lys Leu Asp Ser Ile Gly
            20                  25                  30

Asn Trp His
        35

<210> SEQ ID NO 80
<211> LENGTH: 35
<212> TYPE: PRT
<213> ORGANISM: Artificial Sequence
<220> FEATURE:
<223> OTHER INFORMATION: Core polypeptide

<400> SEQUENCE: 80

Ile Asp Ile Ser Ile Glu Leu Asn Lys Ala Lys Ser Asp Leu Glu Glu
 1               5                  10                  15

Ser Lys Glu Trp Ile Lys Lys Ala Asn Gln Lys Leu Asp Ser Ile Gly
            20                  25                  30

Asn Trp His
        35

<210> SEQ ID NO 81
<211> LENGTH: 39
<212> TYPE: PRT
<213> ORGANISM: Artificial Sequence
<220> FEATURE:
<223> OTHER INFORMATION: Core polypeptide
```

<400> SEQUENCE: 81

Tyr Glu Ser Thr Gln Lys Ala Phe Asp Gly Ile Thr Asn Lys Val Asn
1               5                   10                  15

Ser Val Ile Glu Lys Thr Asn Thr Gln Phe Glu Ala Val Gly Lys Glu
            20                  25                  30

Phe Gly Asn Leu Glu Lys Arg
            35

<210> SEQ ID NO 82
<211> LENGTH: 28
<212> TYPE: PRT
<213> ORGANISM: Artificial Sequence
<220> FEATURE:
<223> OTHER INFORMATION: Core polypeptide

<400> SEQUENCE: 82

Asp Glu Tyr Asp Ala Ser Ile Ser Gln Val Asn Glu Lys Ile Asn Gln
1               5                   10                  15

Ser Leu Ala Phe Ile Arg Lys Ser Asp Glu Leu Leu
            20                  25

<210> SEQ ID NO 83
<211> LENGTH: 38
<212> TYPE: PRT
<213> ORGANISM: Artificial Sequence
<220> FEATURE:
<223> OTHER INFORMATION: Core polypeptide

<400> SEQUENCE: 83

Val Leu His Gln Leu Asn Ile Gln Leu Lys Gln Tyr Leu Glu Thr Gln
1               5                   10                  15

Glu Arg Leu Leu Ala Gly Asn Arg Ile Ala Ala Arg Gln Leu Leu Gln
            20                  25                  30

Ile Trp Lys Asp Val Ala
            35

<210> SEQ ID NO 84
<211> LENGTH: 38
<212> TYPE: PRT
<213> ORGANISM: Artificial Sequence
<220> FEATURE:
<223> OTHER INFORMATION: Core polypeptide

<400> SEQUENCE: 84

Leu Trp His Glu Gln Leu Leu Asn Thr Ala Gln Arg Ala Gly Leu Gln
1               5                   10                  15

Leu Gln Leu Ile Asn Gln Ala Leu Ala Val Arg Glu Lys Val Leu Ile
            20                  25                  30

Arg Tyr Asp Ile Gln Lys
            35

<210> SEQ ID NO 85
<211> LENGTH: 35
<212> TYPE: PRT
<213> ORGANISM: Artificial Sequence
<220> FEATURE:
<223> OTHER INFORMATION: Core polypeptide

<400> SEQUENCE: 85

Leu Leu Asp Asn Phe Glu Ser Thr Trp Glu Gln Ser Lys Glu Leu Trp
1               5                   10                  15

```
Glu Gln Gln Glu Ile Ser Ile Gln Asn Leu His Lys Ser Ala Leu Gln
            20                  25                  30

Glu Tyr Trp
        35

<210> SEQ ID NO 86
<211> LENGTH: 36
<212> TYPE: PRT
<213> ORGANISM: Artificial Sequence
<220> FEATURE:
<223> OTHER INFORMATION: Core polypeptide

<400> SEQUENCE: 86

Leu Ser Asn Leu Leu Gln Ile Ser Asn Asn Ser Asp Glu Trp Leu Glu
1               5                   10                  15

Ala Leu Glu Ile Glu His Glu Lys Trp Lys Leu Thr Gln Trp Gln Ser
            20                  25                  30

Tyr Glu Gln Phe
        35

<210> SEQ ID NO 87
<211> LENGTH: 36
<212> TYPE: PRT
<213> ORGANISM: Artificial Sequence
<220> FEATURE:
<223> OTHER INFORMATION: Core polypeptide

<400> SEQUENCE: 87

Lys Leu Glu Ala Leu Glu Gly Lys Leu Glu Ala Leu Glu Gly Lys Leu
1               5                   10                  15

Glu Ala Leu Glu Gly Lys Leu Glu Ala Leu Glu Gly Lys Leu Glu Ala
            20                  25                  30

Leu Glu Gly Lys
        35

<210> SEQ ID NO 88
<211> LENGTH: 29
<212> TYPE: PRT
<213> ORGANISM: Artificial Sequence
<220> FEATURE:
<223> OTHER INFORMATION: Core polypeptide

<400> SEQUENCE: 88

Glu Leu Arg Ala Leu Arg Gly Glu Leu Arg Ala Leu Arg Gly Glu Leu
1               5                   10                  15

Arg Ala Leu Arg Gly Glu Leu Arg Ala Leu Arg Gly Lys
            20                  25

<210> SEQ ID NO 89
<211> LENGTH: 36
<212> TYPE: PRT
<213> ORGANISM: Artificial Sequence
<220> FEATURE:
<223> OTHER INFORMATION: Core polypeptide

<400> SEQUENCE: 89

Glu Leu Lys Ala Lys Glu Leu Glu Gly Glu Gly Leu Ala Glu Gly Glu
1               5                   10                  15

Glu Ala Leu Lys Gly Leu Leu Glu Lys Ala Ala Lys Leu Glu Gly Leu
            20                  25                  30

Glu Leu Leu Lys
        35
```

<210> SEQ ID NO 90
<211> LENGTH: 33
<212> TYPE: PRT
<213> ORGANISM: Artificial Sequence
<220> FEATURE:
<223> OTHER INFORMATION: Core polypeptide

<400> SEQUENCE: 90

Met Glu Trp Asp Arg Glu Ile Asn Asn Tyr Thr Ser Leu Ile His Ser
1               5                   10                  15

Leu Ile Glu Glu Ser Gln Asn Gln Gln Glu Lys Asn Glu Gln Glu Leu
            20                  25                  30

Leu

<210> SEQ ID NO 91
<211> LENGTH: 36
<212> TYPE: PRT
<213> ORGANISM: Artificial Sequence
<220> FEATURE:
<223> OTHER INFORMATION: Core polypeptide

<400> SEQUENCE: 91

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Ala Phe
        35

<210> SEQ ID NO 92
<211> LENGTH: 36
<212> TYPE: PRT
<213> ORGANISM: Artificial Sequence
<220> FEATURE:
<223> OTHER INFORMATION: Core polypeptide

<400> SEQUENCE: 92

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Ala Asn Trp Phe
        35

<210> SEQ ID NO 93
<211> LENGTH: 36
<212> TYPE: PRT
<213> ORGANISM: Artificial Sequence
<220> FEATURE:
<223> OTHER INFORMATION: Core polypeptide

<400> SEQUENCE: 93

Tyr Thr Ser Leu Ile His Ser Leu Ile Glu Glu Ser Gln Asn Gln Gln
1               5                   10                  15

Glu Lys Asn Gln Gln Glu Leu Leu Glu Leu Asp Lys Trp Ala Ser Leu
            20                  25                  30

Trp Asn Trp Phe
        35

<210> SEQ ID NO 94
<211> LENGTH: 36
<212> TYPE: PRT

```
<213> ORGANISM: Artificial Sequence
<220> FEATURE:
<223> OTHER INFORMATION: Core polypeptide

<400> SEQUENCE: 94

Tyr Thr Ser Leu Ile His Ser Leu Ile Glu Glu Ser Gln Asn Gln Gln
 1               5                  10                  15

Glu Lys Asn Glu Gln Glu Leu Leu Gln Leu Asp Lys Trp Ala Ser Leu
            20                  25                  30

Trp Asn Trp Phe
        35

<210> SEQ ID NO 95
<211> LENGTH: 36
<212> TYPE: PRT
<213> ORGANISM: Artificial Sequence
<220> FEATURE:
<223> OTHER INFORMATION: Core polypeptide

<400> SEQUENCE: 95

Tyr Thr Ser Leu Ile His Ser Leu Ile Glu Glu Ser Gln Asn Gln Gln
 1               5                  10                  15

Glu Lys Asn Gln Gln Glu Leu Leu Gln Leu Asp Lys Trp Ala Ser Leu
            20                  25                  30

Trp Asn Trp Phe
        35

<210> SEQ ID NO 96
<211> LENGTH: 33
<212> TYPE: PRT
<213> ORGANISM: Artificial Sequence
<220> FEATURE:
<223> OTHER INFORMATION: Core polypeptide

<400> SEQUENCE: 96

Arg Met Lys Gln Leu Glu Asp Lys Val Glu Glu Leu Leu Ser Lys Asn
 1               5                  10                  15

Tyr His Leu Glu Asn Glu Val Ala Arg Leu Lys Lys Leu Val Gly Glu
            20                  25                  30

Arg

<210> SEQ ID NO 97
<211> LENGTH: 28
<212> TYPE: PRT
<213> ORGANISM: Artificial Sequence
<220> FEATURE:
<223> OTHER INFORMATION: Core polypeptide

<400> SEQUENCE: 97

Gln Gln Leu Leu Gln Leu Thr Val Trp Gly Ile Lys Gln Leu Gln Ala
 1               5                  10                  15

Arg Ile Leu Ala Val Glu Arg Tyr Leu Lys Asn Gln
            20                  25

<210> SEQ ID NO 98
<211> LENGTH: 18
<212> TYPE: PRT
<213> ORGANISM: Artificial Sequence
<220> FEATURE:
<223> OTHER INFORMATION: Core polypeptide

<400> SEQUENCE: 98

Asn Glu Gln Glu Leu Leu Glu Leu Asp Lys Trp Ala Ser Leu Trp Asn
```

```
                1               5              10              15
Trp Phe

<210> SEQ ID NO 99
<211> LENGTH: 36
<212> TYPE: PRT
<213> ORGANISM: Artificial Sequence
<220> FEATURE:
<223> OTHER INFORMATION: Core polypeptide

<400> SEQUENCE: 99

Tyr Thr Ser Leu Ile Gln Ser Leu Ile Glu Glu Ser Gln Asn Gln Gln
  1               5                  10                  15

Glu Lys Asn Glu Gln Glu Leu Leu Glu Leu Asp Lys Trp Ala Ser Leu
             20                  25                  30

Trp Asn Trp Phe
         35

<210> SEQ ID NO 100
<211> LENGTH: 35
<212> TYPE: PRT
<213> ORGANISM: Artificial Sequence
<220> FEATURE:
<223> OTHER INFORMATION: Core polypeptide

<400> SEQUENCE: 100

Ile Ile Asn Phe Tyr Asp Pro Leu Val Phe Pro Ser Asp Glu Phe Asp
  1               5                  10                  15

Ala Ser Ile Ser Gln Val Asn Glu Lys Ile Asn Gln Ser Leu Ala Phe
             20                  25                  30

Ile Arg Lys
         35

<210> SEQ ID NO 101
<211> LENGTH: 35
<212> TYPE: PRT
<213> ORGANISM: Artificial Sequence
<220> FEATURE:
<223> OTHER INFORMATION: Core polypeptide

<400> SEQUENCE: 101

Ile Asn Phe Tyr Asp Pro Leu Val Phe Pro Ser Asp Glu Phe Asp Ala
  1               5                  10                  15

Ser Ile Ser Gln Val Asn Glu Lys Ile Asn Gln Ser Leu Ala Phe Ile
             20                  25                  30

Arg Lys Ser
         35

<210> SEQ ID NO 102
<211> LENGTH: 35
<212> TYPE: PRT
<213> ORGANISM: Artificial Sequence
<220> FEATURE:
<223> OTHER INFORMATION: Core polypeptide

<400> SEQUENCE: 102

Asn Phe Tyr Asp Pro Leu Val Phe Pro Ser Asp Glu Phe Asp Ala Ser
  1               5                  10                  15

Ile Ser Gln Val Asn Glu Lys Ile Asn Gln Ser Leu Ala Phe Ile Arg
             20                  25                  30

Lys Ser Asp
         35
```

<210> SEQ ID NO 103
<211> LENGTH: 35
<212> TYPE: PRT
<213> ORGANISM: Artificial Sequence
<220> FEATURE:
<223> OTHER INFORMATION: Core polypeptide

<400> SEQUENCE: 103

```
Phe Tyr Asp Pro Leu Val Phe Pro Ser Asp Glu Phe Asp Ala Ser Ile
  1               5                  10                  15

Ser Gln Val Asn Glu Lys Ile Asn Gln Ser Leu Ala Phe Ile Arg Lys
             20                  25                  30

Ser Asp Glu
        35
```

<210> SEQ ID NO 104
<211> LENGTH: 35
<212> TYPE: PRT
<213> ORGANISM: Artificial Sequence
<220> FEATURE:
<223> OTHER INFORMATION: Core polypeptide

<400> SEQUENCE: 104

```
Tyr Asp Pro Leu Val Phe Pro Ser Asp Glu Phe Asp Ala Ser Ile Ser
  1               5                  10                  15

Gln Val Asn Glu Lys Ile Asn Gln Ser Leu Ala Phe Ile Arg Lys Ser
             20                  25                  30

Asp Glu Leu
        35
```

<210> SEQ ID NO 105
<211> LENGTH: 35
<212> TYPE: PRT
<213> ORGANISM: Artificial Sequence
<220> FEATURE:
<223> OTHER INFORMATION: Core polypeptide

<400> SEQUENCE: 105

```
Asp Pro Leu Val Phe Pro Ser Asp Glu Phe Asp Ala Ser Ile Ser Gln
  1               5                  10                  15

Val Asn Glu Lys Ile Asn Gln Ser Leu Ala Phe Ile Arg Lys Ser Asp
             20                  25                  30

Glu Leu Leu
        35
```

<210> SEQ ID NO 106
<211> LENGTH: 35
<212> TYPE: PRT
<213> ORGANISM: Artificial Sequence
<220> FEATURE:
<223> OTHER INFORMATION: Core polypeptide

<400> SEQUENCE: 106

```
Pro Leu Val Phe Pro Ser Asp Glu Phe Asp Ala Ser Ile Ser Gln Val
  1               5                  10                  15

Asn Glu Lys Ile Asn Gln Ser Leu Ala Phe Ile Arg Lys Ser Asp Glu
             20                  25                  30

Leu Leu His
        35
```

<210> SEQ ID NO 107

```
<211> LENGTH: 35
<212> TYPE: PRT
<213> ORGANISM: Artificial Sequence
<220> FEATURE:
<223> OTHER INFORMATION: Core polypeptide

<400> SEQUENCE: 107

Leu Val Phe Pro Ser Asp Glu Phe Asp Ala Ser Ile Ser Gln Val Asn
 1               5                  10                  15

Glu Lys Ile Asn Gln Ser Leu Ala Phe Ile Arg Lys Ser Asp Glu Leu
             20                  25                  30

Leu His Asn
         35

<210> SEQ ID NO 108
<211> LENGTH: 35
<212> TYPE: PRT
<213> ORGANISM: Artificial Sequence
<220> FEATURE:
<223> OTHER INFORMATION: Core polypeptide

<400> SEQUENCE: 108

Val Phe Pro Ser Asp Glu Phe Asp Ala Ser Ile Ser Gln Val Asn Glu
 1               5                  10                  15

Lys Ile Asn Gln Ser Leu Ala Phe Ile Arg Lys Ser Asp Glu Leu Leu
             20                  25                  30

His Asn Val
         35

<210> SEQ ID NO 109
<211> LENGTH: 35
<212> TYPE: PRT
<213> ORGANISM: Artificial Sequence
<220> FEATURE:
<223> OTHER INFORMATION: Core polypeptide

<400> SEQUENCE: 109

Phe Pro Ser Asp Glu Phe Asp Ala Ser Ile Ser Gln Val Asn Glu Lys
 1               5                  10                  15

Ile Asn Gln Ser Leu Ala Phe Ile Arg Lys Ser Asp Glu Leu Leu His
             20                  25                  30

Asn Val Asn
         35

<210> SEQ ID NO 110
<211> LENGTH: 35
<212> TYPE: PRT
<213> ORGANISM: Artificial Sequence
<220> FEATURE:
<223> OTHER INFORMATION: Core polypeptide

<400> SEQUENCE: 110

Pro Ser Asp Glu Phe Asp Ala Ser Ile Ser Gln Val Asn Glu Lys Ile
 1               5                  10                  15

Asn Gln Ser Leu Ala Phe Ile Arg Lys Ser Asp Glu Leu Leu His Asn
             20                  25                  30

Val Asn Ala
         35

<210> SEQ ID NO 111
<211> LENGTH: 35
<212> TYPE: PRT
<213> ORGANISM: Artificial Sequence
```

```
<220> FEATURE:
<223> OTHER INFORMATION: Core polypeptide

<400> SEQUENCE: 111

Ser Asp Glu Phe Asp Ala Ser Ile Ser Gln Val Asn Glu Lys Ile Asn
 1               5                  10                  15

Gln Ser Leu Ala Phe Ile Arg Lys Ser Asp Glu Leu Leu His Asn Val
            20                  25                  30

Asn Ala Gly
        35

<210> SEQ ID NO 112
<211> LENGTH: 35
<212> TYPE: PRT
<213> ORGANISM: Artificial Sequence
<220> FEATURE:
<223> OTHER INFORMATION: Core polypeptide

<400> SEQUENCE: 112

Asp Glu Phe Asp Ala Ser Ile Ser Gln Val Asn Glu Lys Ile Asn Gln
 1               5                  10                  15

Ser Leu Ala Phe Ile Arg Lys Ser Asp Glu Leu Leu His Asn Val Asn
            20                  25                  30

Ala Gly Lys
        35

<210> SEQ ID NO 113
<211> LENGTH: 35
<212> TYPE: PRT
<213> ORGANISM: Artificial Sequence
<220> FEATURE:
<223> OTHER INFORMATION: Core polypeptide

<400> SEQUENCE: 113

Glu Phe Asp Ala Ser Ile Ser Gln Val Asn Glu Lys Ile Asn Gln Ser
 1               5                  10                  15

Leu Ala Phe Ile Arg Lys Ser Asp Glu Leu Leu His Asn Val Asn Ala
            20                  25                  30

Gly Lys Ser
        35

<210> SEQ ID NO 114
<211> LENGTH: 35
<212> TYPE: PRT
<213> ORGANISM: Artificial Sequence
<220> FEATURE:
<223> OTHER INFORMATION: Core polypeptide

<400> SEQUENCE: 114

Phe Asp Ala Ser Ile Ser Gln Val Asn Glu Lys Ile Asn Gln Ser Leu
 1               5                  10                  15

Ala Phe Ile Arg Lys Ser Asp Glu Leu Leu His Asn Val Asn Ala Gly
            20                  25                  30

Lys Ser Thr
        35

<210> SEQ ID NO 115
<211> LENGTH: 35
<212> TYPE: PRT
<213> ORGANISM: Artificial Sequence
<220> FEATURE:
<223> OTHER INFORMATION: Core polypeptide
```

```
<400> SEQUENCE: 115

Asp Ala Ser Ile Ser Gln Val Asn Glu Lys Ile Asn Gln Ser Leu Ala
 1               5                  10                  15

Phe Ile Arg Lys Ser Asp Glu Leu Leu His Asn Val Asn Ala Gly Lys
             20                  25                  30

Ser Thr Thr
        35

<210> SEQ ID NO 116
<211> LENGTH: 35
<212> TYPE: PRT
<213> ORGANISM: Artificial Sequence
<220> FEATURE:
<223> OTHER INFORMATION: Core polypeptide

<400> SEQUENCE: 116

Ala Ser Gly Val Ala Val Ser Lys Val Leu His Leu Glu Gly Glu Val
 1               5                  10                  15

Asn Lys Ile Lys Ser Ala Leu Leu Ser Thr Asn Lys Ala Val Val Ser
             20                  25                  30

Leu Ser Asn
        35

<210> SEQ ID NO 117
<211> LENGTH: 35
<212> TYPE: PRT
<213> ORGANISM: Artificial Sequence
<220> FEATURE:
<223> OTHER INFORMATION: Core polypeptide

<400> SEQUENCE: 117

Ser Gly Val Ala Val Ser Lys Val Leu His Leu Glu Gly Glu Val Asn
 1               5                  10                  15

Lys Ile Lys Ser Ala Leu Leu Ser Thr Asn Lys Ala Val Val Ser Leu
             20                  25                  30

Ser Asn Gly
        35

<210> SEQ ID NO 118
<211> LENGTH: 35
<212> TYPE: PRT
<213> ORGANISM: Artificial Sequence
<220> FEATURE:
<223> OTHER INFORMATION: Core polypeptide

<400> SEQUENCE: 118

Gly Val Ala Val Ser Lys Val Leu His Leu Glu Gly Glu Val Asn Lys
 1               5                  10                  15

Ile Lys Ser Ala Leu Leu Ser Thr Asn Lys Ala Val Val Ser Leu Ser
             20                  25                  30

Asn Gly Val
        35

<210> SEQ ID NO 119
<211> LENGTH: 35
<212> TYPE: PRT
<213> ORGANISM: Artificial Sequence
<220> FEATURE:
<223> OTHER INFORMATION: Core polypeptide

<400> SEQUENCE: 119

Val Ala Val Ser Lys Val Leu His Leu Glu Gly Glu Val Asn Lys Ile
```

```
           1               5              10              15
Lys Ser Ala Leu Leu Ser Thr Asn Lys Ala Val Val Ser Leu Ser Asn
                        20              25              30

Gly Val Ser
        35
```

<210> SEQ ID NO 120
<211> LENGTH: 35
<212> TYPE: PRT
<213> ORGANISM: Artificial Sequence
<220> FEATURE:
<223> OTHER INFORMATION: Core polypeptide

<400> SEQUENCE: 120

```
Ala Val Ser Lys Val Leu His Leu Glu Gly Glu Val Asn Lys Ile Lys
 1               5              10              15

Ser Ala Leu Leu Ser Thr Asn Lys Ala Val Val Ser Leu Ser Asn Gly
                20              25              30

Val Ser Val
        35
```

<210> SEQ ID NO 121
<211> LENGTH: 35
<212> TYPE: PRT
<213> ORGANISM: Artificial Sequence
<220> FEATURE:
<223> OTHER INFORMATION: Core polypeptide

<400> SEQUENCE: 121

```
Val Ser Lys Val Leu His Leu Glu Gly Glu Val Asn Lys Ile Lys Ser
 1               5              10              15

Ala Leu Leu Ser Thr Asn Lys Ala Val Val Ser Leu Ser Asn Gly Val
                20              25              30

Ser Val Leu
        35
```

<210> SEQ ID NO 122
<211> LENGTH: 35
<212> TYPE: PRT
<213> ORGANISM: Artificial Sequence
<220> FEATURE:
<223> OTHER INFORMATION: Core polypeptide

<400> SEQUENCE: 122

```
Ser Lys Val Leu His Leu Glu Gly Glu Val Asn Lys Ile Lys Ser Ala
 1               5              10              15

Leu Leu Ser Thr Asn Lys Ala Val Val Ser Leu Ser Asn Gly Val Ser
                20              25              30

Val Leu Thr
        35
```

<210> SEQ ID NO 123
<211> LENGTH: 35
<212> TYPE: PRT
<213> ORGANISM: Artificial Sequence
<220> FEATURE:
<223> OTHER INFORMATION: Core polypeptide

<400> SEQUENCE: 123

```
Lys Val Leu His Leu Glu Gly Glu Val Asn Lys Ile Lys Ser Ala Leu
 1               5              10              15

Leu Ser Thr Asn Lys Ala Val Val Ser Leu Ser Asn Gly Val Ser Val
```

-continued

```
                    20                  25                  30

Leu Thr Ser
        35

<210> SEQ ID NO 124
<211> LENGTH: 35
<212> TYPE: PRT
<213> ORGANISM: Artificial Sequence
<220> FEATURE:
<223> OTHER INFORMATION: Core polypeptide

<400> SEQUENCE: 124

Val Leu His Leu Glu Gly Glu Val Asn Lys Ile Lys Ser Ala Leu Leu
 1               5                  10                  15

Ser Thr Asn Lys Ala Val Val Ser Leu Ser Asn Gly Val Ser Val Leu
                20                  25                  30

Thr Ser Lys
        35

<210> SEQ ID NO 125
<211> LENGTH: 35
<212> TYPE: PRT
<213> ORGANISM: Artificial Sequence
<220> FEATURE:
<223> OTHER INFORMATION: Core polypeptide

<400> SEQUENCE: 125

Leu His Leu Glu Gly Glu Val Asn Lys Ile Lys Ser Ala Leu Leu Ser
 1               5                  10                  15

Thr Asn Lys Ala Val Val Ser Leu Ser Asn Gly Val Ser Val Leu Thr
                20                  25                  30

Ser Lys Val
        35

<210> SEQ ID NO 126
<211> LENGTH: 35
<212> TYPE: PRT
<213> ORGANISM: Artificial Sequence
<220> FEATURE:
<223> OTHER INFORMATION: Core polypeptide

<400> SEQUENCE: 126

His Leu Glu Gly Glu Val Asn Lys Ile Lys Ser Ala Leu Leu Ser Thr
 1               5                  10                  15

Asn Lys Ala Val Val Ser Leu Ser Asn Gly Val Ser Val Leu Thr Ser
                20                  25                  30

Lys Val Leu
        35

<210> SEQ ID NO 127
<211> LENGTH: 35
<212> TYPE: PRT
<213> ORGANISM: Artificial Sequence
<220> FEATURE:
<223> OTHER INFORMATION: Core polypeptide

<400> SEQUENCE: 127

Leu Glu Gly Glu Val Asn Lys Ile Lys Ser Ala Leu Leu Ser Thr Asn
 1               5                  10                  15

Lys Ala Val Val Ser Leu Ser Asn Gly Val Ser Val Leu Thr Ser Lys
                20                  25                  30

Val Leu Asp
```

35

<210> SEQ ID NO 128
<211> LENGTH: 35
<212> TYPE: PRT
<213> ORGANISM: Artificial Sequence
<220> FEATURE:
<223> OTHER INFORMATION: Core polypeptide

<400> SEQUENCE: 128

Glu Gly Glu Val Asn Lys Ile Lys Ser Ala Leu Leu Ser Thr Asn Lys
 1               5                  10                  15

Ala Val Val Ser Leu Ser Asn Gly Val Ser Val Leu Thr Ser Lys Val
            20                  25                  30

Leu Asp Leu
        35

<210> SEQ ID NO 129
<211> LENGTH: 35
<212> TYPE: PRT
<213> ORGANISM: Artificial Sequence
<220> FEATURE:
<223> OTHER INFORMATION: Core polypeptide

<400> SEQUENCE: 129

Gly Glu Val Asn Lys Ile Lys Ser Ala Leu Leu Ser Thr Asn Lys Ala
 1               5                  10                  15

Val Val Ser Leu Ser Asn Gly Val Ser Val Leu Thr Ser Lys Val Leu
            20                  25                  30

Asp Leu Lys
        35

<210> SEQ ID NO 130
<211> LENGTH: 35
<212> TYPE: PRT
<213> ORGANISM: Artificial Sequence
<220> FEATURE:
<223> OTHER INFORMATION: Core polypeptide

<400> SEQUENCE: 130

Glu Val Asn Lys Ile Lys Ser Ala Leu Leu Ser Thr Asn Lys Ala Val
 1               5                  10                  15

Val Ser Leu Ser Asn Gly Val Ser Val Leu Thr Ser Lys Val Leu Asp
            20                  25                  30

Leu Lys Asn
        35

<210> SEQ ID NO 131
<211> LENGTH: 35
<212> TYPE: PRT
<213> ORGANISM: Artificial Sequence
<220> FEATURE:
<223> OTHER INFORMATION: Core polypeptide

<400> SEQUENCE: 131

Val Asn Lys Ile Lys Ser Ala Leu Leu Ser Thr Asn Lys Ala Val Val
 1               5                  10                  15

Ser Leu Ser Asn Gly Val Ser Val Leu Thr Ser Lys Val Leu Asp Leu
            20                  25                  30

Lys Asn Tyr
        35

```
<210> SEQ ID NO 132
<211> LENGTH: 35
<212> TYPE: PRT
<213> ORGANISM: Artificial Sequence
<220> FEATURE:
<223> OTHER INFORMATION: Core polypeptide

<400> SEQUENCE: 132

Asn Lys Ile Lys Ser Ala Leu Leu Ser Thr Asn Lys Ala Val Val Ser
 1               5                  10                  15

Leu Ser Asn Gly Val Ser Val Leu Thr Ser Lys Val Leu Asp Leu Lys
            20                  25                  30

Asn Tyr Ile
        35

<210> SEQ ID NO 133
<211> LENGTH: 35
<212> TYPE: PRT
<213> ORGANISM: Artificial Sequence
<220> FEATURE:
<223> OTHER INFORMATION: Core polypeptide

<400> SEQUENCE: 133

Lys Ile Lys Ser Ala Leu Leu Ser Thr Asn Lys Ala Val Val Ser Leu
 1               5                  10                  15

Ser Asn Gly Val Ser Val Leu Thr Ser Lys Val Leu Asp Leu Lys Asn
            20                  25                  30

Tyr Ile Asp
        35

<210> SEQ ID NO 134
<211> LENGTH: 35
<212> TYPE: PRT
<213> ORGANISM: Artificial Sequence
<220> FEATURE:
<223> OTHER INFORMATION: Core polypeptide

<400> SEQUENCE: 134

Ile Lys Ser Ala Leu Leu Ser Thr Asn Lys Ala Val Val Ser Leu Ser
 1               5                  10                  15

Asn Gly Val Ser Val Leu Thr Ser Lys Val Leu Asp Leu Lys Asn Tyr
            20                  25                  30

Ile Asp Lys
        35

<210> SEQ ID NO 135
<211> LENGTH: 35
<212> TYPE: PRT
<213> ORGANISM: Artificial Sequence
<220> FEATURE:
<223> OTHER INFORMATION: Core polypeptide

<400> SEQUENCE: 135

Lys Ser Ala Leu Leu Ser Thr Asn Lys Ala Val Val Ser Leu Ser Asn
 1               5                  10                  15

Gly Val Ser Val Leu Thr Ser Lys Val Leu Asp Leu Lys Asn Tyr Ile
            20                  25                  30

Asp Lys Gln
        35

<210> SEQ ID NO 136
<211> LENGTH: 35
<212> TYPE: PRT
```

```
<213> ORGANISM: Artificial Sequence
<220> FEATURE:
<223> OTHER INFORMATION: Core polypeptide

<400> SEQUENCE: 136

Ser Ala Leu Leu Ser Thr Asn Lys Ala Val Val Ser Leu Ser Asn Gly
1               5                   10                  15

Val Ser Val Leu Thr Ser Lys Val Leu Asp Leu Lys Asn Tyr Ile Asp
            20                  25                  30

Lys Gln Leu
        35

<210> SEQ ID NO 137
<211> LENGTH: 35
<212> TYPE: PRT
<213> ORGANISM: Artificial Sequence
<220> FEATURE:
<223> OTHER INFORMATION: Core polypeptide

<400> SEQUENCE: 137

Ala Leu Leu Ser Thr Asn Lys Ala Val Val Ser Leu Ser Asn Gly Val
1               5                   10                  15

Ser Val Leu Thr Ser Lys Val Leu Asp Leu Lys Asn Tyr Ile Asp Lys
            20                  25                  30

Gln Leu Leu
        35

<210> SEQ ID NO 138
<211> LENGTH: 35
<212> TYPE: PRT
<213> ORGANISM: Artificial Sequence
<220> FEATURE:
<223> OTHER INFORMATION: Core polypeptide

<400> SEQUENCE: 138

Tyr Thr Ser Val Ile Thr Ile Glu Leu Ser Asn Ile Lys Glu Asn Lys
1               5                   10                  15

Cys Asn Gly Thr Asp Ala Lys Val Lys Leu Ile Lys Gln Glu Leu Asp
            20                  25                  30

Lys Tyr Lys
        35

<210> SEQ ID NO 139
<211> LENGTH: 35
<212> TYPE: PRT
<213> ORGANISM: Artificial Sequence
<220> FEATURE:
<223> OTHER INFORMATION: Core polypeptide

<400> SEQUENCE: 139

Thr Ser Val Ile Thr Ile Glu Leu Ser Asn Ile Lys Glu Asn Lys Cys
1               5                   10                  15

Asn Gly Thr Asp Ala Lys Val Lys Leu Ile Lys Gln Glu Leu Asp Lys
            20                  25                  30

Tyr Lys Asn
        35

<210> SEQ ID NO 140
<211> LENGTH: 35
<212> TYPE: PRT
<213> ORGANISM: Artificial Sequence
<220> FEATURE:
<223> OTHER INFORMATION: Core polypeptide
```

-continued

```
<400> SEQUENCE: 140

Ser Val Ile Thr Ile Glu Leu Ser Asn Ile Lys Glu Asn Lys Cys Asn
 1               5                  10                  15

Gly Thr Asp Ala Lys Val Lys Leu Ile Lys Gln Glu Leu Asp Lys Tyr
             20                  25                  30

Lys Asn Ala
         35

<210> SEQ ID NO 141
<211> LENGTH: 35
<212> TYPE: PRT
<213> ORGANISM: Artificial Sequence
<220> FEATURE:
<223> OTHER INFORMATION: Core polypeptide

<400> SEQUENCE: 141

Val Ile Thr Ile Glu Leu Ser Asn Ile Lys Glu Asn Lys Cys Asn Gly
 1               5                  10                  15

Thr Asp Ala Lys Val Lys Leu Ile Lys Gln Glu Leu Asp Lys Tyr Lys
             20                  25                  30

Asn Ala Val
         35

<210> SEQ ID NO 142
<211> LENGTH: 35
<212> TYPE: PRT
<213> ORGANISM: Artificial Sequence
<220> FEATURE:
<223> OTHER INFORMATION: Core polypeptide

<400> SEQUENCE: 142

Ile Thr Ile Glu Leu Ser Asn Ile Lys Glu Asn Lys Cys Asn Gly Thr
 1               5                  10                  15

Asp Ala Lys Val Lys Leu Ile Lys Gln Glu Leu Asp Lys Tyr Lys Asn
             20                  25                  30

Ala Val Thr
         35

<210> SEQ ID NO 143
<211> LENGTH: 35
<212> TYPE: PRT
<213> ORGANISM: Artificial Sequence
<220> FEATURE:
<223> OTHER INFORMATION: Core polypeptide

<400> SEQUENCE: 143

Thr Ile Glu Leu Ser Asn Ile Lys Glu Asn Lys Cys Asn Gly Thr Asp
 1               5                  10                  15

Ala Lys Val Lys Leu Ile Lys Gln Glu Leu Asp Lys Tyr Lys Asn Ala
             20                  25                  30

Val Thr Glu
         35

<210> SEQ ID NO 144
<211> LENGTH: 35
<212> TYPE: PRT
<213> ORGANISM: Artificial Sequence
<220> FEATURE:
<223> OTHER INFORMATION: Core polypeptide

<400> SEQUENCE: 144
```

Ile Glu Leu Ser Asn Ile Lys Glu Asn Lys Cys Asn Gly Thr Asp Ala
1               5                   10                  15

Lys Val Lys Leu Ile Lys Gln Glu Leu Asp Lys Tyr Lys Asn Ala Val
            20                  25                  30

Thr Glu Leu
        35

<210> SEQ ID NO 145
<211> LENGTH: 35
<212> TYPE: PRT
<213> ORGANISM: Artificial Sequence
<220> FEATURE:
<223> OTHER INFORMATION: Core polypeptide

<400> SEQUENCE: 145

Glu Leu Ser Asn Ile Lys Glu Asn Lys Cys Asn Gly Thr Asp Ala Lys
1               5                   10                  15

Val Lys Leu Ile Lys Gln Glu Leu Asp Lys Tyr Lys Asn Ala Val Thr
            20                  25                  30

Glu Leu Gln
        35

<210> SEQ ID NO 146
<211> LENGTH: 35
<212> TYPE: PRT
<213> ORGANISM: Artificial Sequence
<220> FEATURE:
<223> OTHER INFORMATION: Core polypeptide

<400> SEQUENCE: 146

Leu Ser Asn Ile Lys Glu Asn Lys Cys Asn Gly Thr Asp Ala Lys Val
1               5                   10                  15

Lys Leu Ile Lys Gln Glu Leu Asp Lys Tyr Lys Asn Ala Val Thr Glu
            20                  25                  30

Leu Gln Leu
        35

<210> SEQ ID NO 147
<211> LENGTH: 35
<212> TYPE: PRT
<213> ORGANISM: Artificial Sequence
<220> FEATURE:
<223> OTHER INFORMATION: Core polypeptide

<400> SEQUENCE: 147

Ser Asn Ile Lys Glu Asn Lys Cys Asn Gly Thr Asp Ala Lys Val Lys
1               5                   10                  15

Leu Ile Lys Gln Glu Leu Asp Lys Tyr Lys Asn Ala Val Thr Glu Leu
            20                  25                  30

Gln Leu Leu
        35

<210> SEQ ID NO 148
<211> LENGTH: 35
<212> TYPE: PRT
<213> ORGANISM: Artificial Sequence
<220> FEATURE:
<223> OTHER INFORMATION: Core polypeptide

<400> SEQUENCE: 148

Asn Ile Lys Glu Asn Lys Cys Asn Gly Thr Asp Ala Lys Val Lys Leu
1               5                   10                  15

Ile Lys Gln Glu Leu Asp Lys Tyr Lys Asn Ala Val Thr Glu Leu Gln
            20                  25                  30

Leu Leu Met
        35

<210> SEQ ID NO 149
<211> LENGTH: 35
<212> TYPE: PRT
<213> ORGANISM: Artificial Sequence
<220> FEATURE:
<223> OTHER INFORMATION: Core polypeptide

<400> SEQUENCE: 149

Ile Lys Glu Asn Lys Cys Asn Gly Thr Asp Ala Lys Val Lys Leu Ile
 1               5                  10                  15

Lys Gln Glu Leu Asp Lys Tyr Lys Asn Ala Val Thr Glu Leu Gln Leu
            20                  25                  30

Leu Met Gln
        35

<210> SEQ ID NO 150
<211> LENGTH: 35
<212> TYPE: PRT
<213> ORGANISM: Artificial Sequence
<220> FEATURE:
<223> OTHER INFORMATION: Core polypeptide

<400> SEQUENCE: 150

Lys Glu Asn Lys Cys Asn Gly Thr Asp Ala Lys Val Lys Leu Ile Lys
 1               5                  10                  15

Gln Glu Leu Asp Lys Tyr Lys Asn Ala Val Thr Glu Leu Gln Leu Leu
            20                  25                  30

Met Gln Ser
        35

<210> SEQ ID NO 151
<211> LENGTH: 35
<212> TYPE: PRT
<213> ORGANISM: Artificial Sequence
<220> FEATURE:
<223> OTHER INFORMATION: Core polypeptide

<400> SEQUENCE: 151

Glu Asn Lys Cys Asn Gly Thr Asp Ala Lys Val Lys Leu Ile Lys Gln
 1               5                  10                  15

Glu Leu Asp Lys Tyr Lys Asn Ala Val Thr Glu Leu Gln Leu Leu Met
            20                  25                  30

Gln Ser Thr
        35

<210> SEQ ID NO 152
<211> LENGTH: 36
<212> TYPE: PRT
<213> ORGANISM: Artificial Sequence
<220> FEATURE:
<223> OTHER INFORMATION: Core polypeptide

<400> SEQUENCE: 152

Leu Leu Asp Asn Phe Glu Ser Thr Trp Glu Gln Ser Lys Glu Leu Trp
 1               5                  10                  15

Glu Leu Gln Glu Ile Ser Ile Gln Asn Leu His Lys Ser Ala Leu Gln
            20                  25                  30

```
Glu Tyr Trp Asn
        35

<210> SEQ ID NO 153
<211> LENGTH: 35
<212> TYPE: PRT
<213> ORGANISM: Artificial Sequence
<220> FEATURE:
<223> OTHER INFORMATION: Core polypeptide

<400> SEQUENCE: 153

Ala Leu Gly Val Ala Thr Ser Ala Gln Ile Thr Ala Ala Val Ala Leu
 1               5                  10                  15

Val Glu Ala Lys Gln Ala Arg Ser Asp Ile Glu Lys Leu Lys Glu Ala
            20                  25                  30

Ile Arg Asp
        35

<210> SEQ ID NO 154
<211> LENGTH: 35
<212> TYPE: PRT
<213> ORGANISM: Artificial Sequence
<220> FEATURE:
<223> OTHER INFORMATION: Core polypeptide

<400> SEQUENCE: 154

Leu Gly Val Ala Thr Ser Ala Gln Ile Thr Ala Ala Val Ala Leu Val
 1               5                  10                  15

Glu Ala Lys Gln Ala Arg Ser Asp Ile Glu Lys Leu Lys Glu Ala Ile
            20                  25                  30

Arg Asp Thr
        35

<210> SEQ ID NO 155
<211> LENGTH: 35
<212> TYPE: PRT
<213> ORGANISM: Artificial Sequence
<220> FEATURE:
<223> OTHER INFORMATION: Core polypeptide

<400> SEQUENCE: 155

Gly Val Ala Thr Ser Ala Gln Ile Thr Ala Ala Val Ala Leu Val Glu
 1               5                  10                  15

Ala Lys Gln Ala Arg Ser Asp Ile Glu Lys Leu Lys Glu Ala Ile Arg
            20                  25                  30

Asp Thr Asn
        35

<210> SEQ ID NO 156
<211> LENGTH: 35
<212> TYPE: PRT
<213> ORGANISM: Artificial Sequence
<220> FEATURE:
<223> OTHER INFORMATION: Core polypeptide

<400> SEQUENCE: 156

Val Ala Thr Ser Ala Gln Ile Thr Ala Ala Val Ala Leu Val Glu Ala
 1               5                  10                  15

Lys Gln Ala Arg Ser Asp Ile Glu Lys Leu Lys Glu Ala Ile Arg Asp
            20                  25                  30

Thr Asn Lys
        35
```

```
<210> SEQ ID NO 157
<211> LENGTH: 35
<212> TYPE: PRT
<213> ORGANISM: Artificial Sequence
<220> FEATURE:
<223> OTHER INFORMATION: Core polypeptide

<400> SEQUENCE: 157

Ala Thr Ser Ala Gln Ile Thr Ala Ala Val Ala Leu Val Glu Ala Lys
 1               5                  10                  15

Gln Ala Arg Ser Asp Ile Glu Lys Leu Lys Glu Ala Ile Arg Asp Thr
            20                  25                  30

Asn Lys Ala
         35

<210> SEQ ID NO 158
<211> LENGTH: 35
<212> TYPE: PRT
<213> ORGANISM: Artificial Sequence
<220> FEATURE:
<223> OTHER INFORMATION: Core polypeptide

<400> SEQUENCE: 158

Thr Ser Ala Gln Ile Thr Ala Ala Val Ala Leu Val Glu Ala Lys Gln
 1               5                  10                  15

Ala Arg Ser Asp Ile Glu Lys Leu Lys Glu Ala Ile Arg Asp Thr Asn
            20                  25                  30

Lys Ala Val
         35

<210> SEQ ID NO 159
<211> LENGTH: 35
<212> TYPE: PRT
<213> ORGANISM: Artificial Sequence
<220> FEATURE:
<223> OTHER INFORMATION: Core polypeptide

<400> SEQUENCE: 159

Ser Ala Gln Ile Thr Ala Ala Val Ala Leu Val Glu Ala Lys Gln Ala
 1               5                  10                  15

Arg Ser Asp Ile Glu Lys Leu Lys Glu Ala Ile Arg Asp Thr Asn Lys
            20                  25                  30

Ala Val Gln
         35

<210> SEQ ID NO 160
<211> LENGTH: 35
<212> TYPE: PRT
<213> ORGANISM: Artificial Sequence
<220> FEATURE:
<223> OTHER INFORMATION: Core polypeptide

<400> SEQUENCE: 160

Ala Gln Ile Thr Ala Ala Val Ala Leu Val Glu Ala Lys Gln Ala Arg
 1               5                  10                  15

Ser Asp Ile Glu Lys Leu Lys Glu Ala Ile Arg Asp Thr Asn Lys Ala
            20                  25                  30

Val Gln Ser
         35

<210> SEQ ID NO 161
<211> LENGTH: 35
```

```
<212> TYPE: PRT
<213> ORGANISM: Artificial Sequence
<220> FEATURE:
<223> OTHER INFORMATION: Core polypeptide

<400> SEQUENCE: 161

Gln Ile Thr Ala Ala Val Ala Leu Val Glu Ala Lys Gln Ala Arg Ser
 1               5                  10                  15

Asp Ile Glu Lys Leu Lys Glu Ala Ile Arg Asp Thr Asn Lys Ala Val
            20                  25                  30

Gln Ser Val
        35

<210> SEQ ID NO 162
<211> LENGTH: 35
<212> TYPE: PRT
<213> ORGANISM: Artificial Sequence
<220> FEATURE:
<223> OTHER INFORMATION: Core polypeptide

<400> SEQUENCE: 162

Ile Thr Ala Ala Val Ala Leu Val Glu Ala Lys Gln Ala Arg Ser Asp
 1               5                  10                  15

Ile Glu Lys Leu Lys Glu Ala Ile Arg Asp Thr Asn Lys Ala Val Gln
            20                  25                  30

Ser Val Gln
        35

<210> SEQ ID NO 163
<211> LENGTH: 35
<212> TYPE: PRT
<213> ORGANISM: Artificial Sequence
<220> FEATURE:
<223> OTHER INFORMATION: Core polypeptide

<400> SEQUENCE: 163

Thr Ala Ala Val Ala Leu Val Glu Ala Lys Gln Ala Arg Ser Asp Ile
 1               5                  10                  15

Glu Lys Leu Lys Glu Ala Ile Arg Asp Thr Asn Lys Ala Val Gln Ser
            20                  25                  30

Val Gln Ser
        35

<210> SEQ ID NO 164
<211> LENGTH: 35
<212> TYPE: PRT
<213> ORGANISM: Artificial Sequence
<220> FEATURE:
<223> OTHER INFORMATION: Core polypeptide

<400> SEQUENCE: 164

Ala Ala Val Ala Leu Val Glu Ala Lys Gln Ala Arg Ser Asp Ile Glu
 1               5                  10                  15

Lys Leu Lys Glu Ala Ile Arg Asp Thr Asn Lys Ala Val Gln Ser Val
            20                  25                  30

Gln Ser Ser
        35

<210> SEQ ID NO 165
<211> LENGTH: 35
<212> TYPE: PRT
<213> ORGANISM: Artificial Sequence
<220> FEATURE:
```

<223> OTHER INFORMATION: Core polypeptide

<400> SEQUENCE: 165

Ala Val Ala Leu Val Glu Ala Lys Gln Ala Arg Ser Asp Ile Glu Lys
1               5                   10                  15

Leu Lys Glu Ala Ile Arg Asp Thr Asn Lys Ala Val Gln Ser Val Gln
                20                  25                  30

Ser Ser Ile
        35

<210> SEQ ID NO 166
<211> LENGTH: 35
<212> TYPE: PRT
<213> ORGANISM: Artificial Sequence
<220> FEATURE:
<223> OTHER INFORMATION: Core polypeptide

<400> SEQUENCE: 166

Val Ala Leu Val Glu Ala Lys Gln Ala Arg Ser Asp Ile Glu Lys Leu
1               5                   10                  15

Lys Glu Ala Ile Arg Asp Thr Asn Lys Ala Val Gln Ser Val Gln Ser
                20                  25                  30

Ser Ile Gly
        35

<210> SEQ ID NO 167
<211> LENGTH: 35
<212> TYPE: PRT
<213> ORGANISM: Artificial Sequence
<220> FEATURE:
<223> OTHER INFORMATION: Core polypeptide

<400> SEQUENCE: 167

Ala Leu Val Glu Ala Lys Gln Ala Arg Ser Asp Ile Glu Lys Leu Lys
1               5                   10                  15

Glu Ala Ile Arg Asp Thr Asn Lys Ala Val Gln Ser Val Gln Ser Ser
                20                  25                  30

Ile Gly Asn
        35

<210> SEQ ID NO 168
<211> LENGTH: 35
<212> TYPE: PRT
<213> ORGANISM: Artificial Sequence
<220> FEATURE:
<223> OTHER INFORMATION: Core polypeptide

<400> SEQUENCE: 168

Leu Val Glu Ala Lys Gln Ala Arg Ser Asp Ile Glu Lys Leu Lys Glu
1               5                   10                  15

Ala Ile Arg Asp Thr Asn Lys Ala Val Gln Ser Val Gln Ser Ser Ile
                20                  25                  30

Gly Asn Leu
        35

<210> SEQ ID NO 169
<211> LENGTH: 35
<212> TYPE: PRT
<213> ORGANISM: Artificial Sequence
<220> FEATURE:
<223> OTHER INFORMATION: Core polypeptide

<400> SEQUENCE: 169

Val Glu Ala Lys Gln Ala Arg Ser Asp Ile Glu Lys Leu Lys Glu Ala
1               5                   10                  15

Ile Arg Asp Thr Asn Lys Ala Val Gln Ser Val Gln Ser Ser Ile Gly
            20                  25                  30

Asn Leu Ile
        35

<210> SEQ ID NO 170
<211> LENGTH: 35
<212> TYPE: PRT
<213> ORGANISM: Artificial Sequence
<220> FEATURE:
<223> OTHER INFORMATION: Core polypeptide

<400> SEQUENCE: 170

Glu Ala Lys Gln Ala Arg Ser Asp Ile Glu Lys Leu Lys Glu Ala Ile
1               5                   10                  15

Arg Asp Thr Asn Lys Ala Val Gln Ser Val Gln Ser Ser Ile Gly Asn
            20                  25                  30

Leu Ile Val
        35

<210> SEQ ID NO 171
<211> LENGTH: 35
<212> TYPE: PRT
<213> ORGANISM: Artificial Sequence
<220> FEATURE:
<223> OTHER INFORMATION: Core polypeptide

<400> SEQUENCE: 171

Lys Gln Ala Arg Ser Asp Ile Glu Lys Leu Lys Glu Ala Ile Arg Asp
1               5                   10                  15

Thr Asn Lys Ala Val Gln Ser Val Gln Ser Ser Ile Gly Asn Leu Ile
            20                  25                  30

Val Ala Ile
        35

<210> SEQ ID NO 172
<211> LENGTH: 34
<212> TYPE: PRT
<213> ORGANISM: Artificial Sequence
<220> FEATURE:
<223> OTHER INFORMATION: Core polypeptide

<400> SEQUENCE: 172

Gln Ala Arg Ser Asp Glu Lys Leu Lys Glu Ala Ile Arg Asp Thr Asn
1               5                   10                  15

Lys Ala Val Gln Ser Val Gln Ser Ser Ile Gly Asn Leu Ile Val Ala
            20                  25                  30

Ile Lys

<210> SEQ ID NO 173
<211> LENGTH: 35
<212> TYPE: PRT
<213> ORGANISM: Artificial Sequence
<220> FEATURE:
<223> OTHER INFORMATION: Core polypeptide

<400> SEQUENCE: 173

Gln Ala Arg Ser Asp Ile Glu Lys Leu Lys Glu Ala Ile Arg Asp Thr
1               5                   10                  15

```
Asn Lys Ala Val Gln Ser Val Gln Ser Ser Ile Gly Asn Leu Ile Val
         20                  25                  30

Ala Ile Lys
        35

<210> SEQ ID NO 174
<211> LENGTH: 35
<212> TYPE: PRT
<213> ORGANISM: Artificial Sequence
<220> FEATURE:
<223> OTHER INFORMATION: Core polypeptide

<400> SEQUENCE: 174

Ala Arg Ser Asp Ile Glu Lys Leu Lys Glu Ala Ile Arg Asp Thr Asn
  1               5                  10                  15

Lys Ala Val Gln Ser Val Gln Ser Ser Ile Gly Asn Leu Ile Val Ala
             20                  25                  30

Ile Lys Ser
        35

<210> SEQ ID NO 175
<211> LENGTH: 35
<212> TYPE: PRT
<213> ORGANISM: Artificial Sequence
<220> FEATURE:
<223> OTHER INFORMATION: Core polypeptide

<400> SEQUENCE: 175

Arg Ser Asp Ile Glu Lys Leu Lys Glu Ala Ile Arg Asp Thr Asn Lys
  1               5                  10                  15

Ala Val Gln Ser Val Gln Ser Ser Ile Gly Asn Leu Ile Val Ala Ile
             20                  25                  30

Lys Ser Val
        35

<210> SEQ ID NO 176
<211> LENGTH: 35
<212> TYPE: PRT
<213> ORGANISM: Artificial Sequence
<220> FEATURE:
<223> OTHER INFORMATION: Core polypeptide

<400> SEQUENCE: 176

Ser Asp Ile Glu Lys Leu Lys Glu Ala Ile Arg Asp Thr Asn Lys Ala
  1               5                  10                  15

Val Gln Ser Val Gln Ser Ser Ile Gly Asn Leu Ile Val Ala Ile Lys
             20                  25                  30

Ser Val Gln
        35

<210> SEQ ID NO 177
<211> LENGTH: 35
<212> TYPE: PRT
<213> ORGANISM: Artificial Sequence
<220> FEATURE:
<223> OTHER INFORMATION: Core polypeptide

<400> SEQUENCE: 177

Asp Ile Glu Lys Leu Lys Glu Ala Ile Arg Asp Thr Asn Lys Ala Val
  1               5                  10                  15

Gln Ser Val Gln Ser Ser Ile Gly Asn Leu Ile Val Ala Ile Lys Ser
             20                  25                  30
```

-continued

Val Gln Asp
        35

<210> SEQ ID NO 178
<211> LENGTH: 35
<212> TYPE: PRT
<213> ORGANISM: Artificial Sequence
<220> FEATURE:
<223> OTHER INFORMATION: Core polypeptide

<400> SEQUENCE: 178

Ile Glu Lys Leu Lys Glu Ala Ile Arg Asp Thr Asn Lys Ala Val Gln
 1               5                  10                  15

Ser Val Gln Ser Ser Ile Gly Asn Leu Ile Val Ala Ile Lys Ser Val
            20                  25                  30

Gln Asp Tyr
        35

<210> SEQ ID NO 179
<211> LENGTH: 35
<212> TYPE: PRT
<213> ORGANISM: Artificial Sequence
<220> FEATURE:
<223> OTHER INFORMATION: Core polypeptide

<400> SEQUENCE: 179

Glu Lys Leu Lys Glu Ala Ile Arg Asp Thr Asn Lys Ala Val Gln Ser
 1               5                  10                  15

Val Gln Ser Ser Ile Gly Asn Leu Ile Val Ala Ile Lys Ser Val Gln
            20                  25                  30

Asp Tyr Val
        35

<210> SEQ ID NO 180
<211> LENGTH: 35
<212> TYPE: PRT
<213> ORGANISM: Artificial Sequence
<220> FEATURE:
<223> OTHER INFORMATION: Core polypeptide

<400> SEQUENCE: 180

Lys Leu Lys Glu Ala Ile Arg Asp Thr Asn Lys Ala Val Gln Ser Val
 1               5                  10                  15

Gln Ser Ser Ile Gly Asn Leu Ile Val Ala Ile Lys Ser Val Gln Asp
            20                  25                  30

Tyr Val Asn
        35

<210> SEQ ID NO 181
<211> LENGTH: 35
<212> TYPE: PRT
<213> ORGANISM: Artificial Sequence
<220> FEATURE:
<223> OTHER INFORMATION: Core polypeptide

<400> SEQUENCE: 181

Leu Lys Glu Ala Ile Arg Asp Thr Asn Lys Ala Val Gln Ser Val Gln
 1               5                  10                  15

Ser Ser Ile Gly Asn Leu Ile Val Ala Ile Lys Ser Val Gln Asp Tyr
            20                  25                  30

Val Asn Lys
        35

```
<210> SEQ ID NO 182
<211> LENGTH: 35
<212> TYPE: PRT
<213> ORGANISM: Artificial Sequence
<220> FEATURE:
<223> OTHER INFORMATION: Core polypeptide

<400> SEQUENCE: 182

Lys Glu Ala Ile Arg Asp Thr Asn Lys Ala Val Gln Ser Val Gln Ser
1               5                   10                  15

Ser Ile Gly Asn Leu Ile Val Ala Ile Lys Ser Val Gln Asp Tyr Val
            20                  25                  30

Asn Lys Glu
        35

<210> SEQ ID NO 183
<211> LENGTH: 35
<212> TYPE: PRT
<213> ORGANISM: Artificial Sequence
<220> FEATURE:
<223> OTHER INFORMATION: Core polypeptide

<400> SEQUENCE: 183

Glu Ala Ile Arg Asp Thr Asn Lys Ala Val Gln Ser Val Gln Ser Ser
1               5                   10                  15

Ile Gly Asn Leu Ile Val Ala Ile Lys Ser Val Gln Asp Tyr Val Asn
            20                  25                  30

Lys Glu Ile
        35

<210> SEQ ID NO 184
<211> LENGTH: 35
<212> TYPE: PRT
<213> ORGANISM: Artificial Sequence
<220> FEATURE:
<223> OTHER INFORMATION: Core polypeptide

<400> SEQUENCE: 184

Ala Ile Arg Asp Thr Asn Lys Ala Val Gln Ser Val Gln Ser Ser Ile
1               5                   10                  15

Gly Asn Leu Ile Val Ala Ile Lys Ser Val Gln Asp Tyr Val Asn Lys
            20                  25                  30

Glu Ile Val
        35

<210> SEQ ID NO 185
<211> LENGTH: 34
<212> TYPE: PRT
<213> ORGANISM: Artificial Sequence
<220> FEATURE:
<223> OTHER INFORMATION: Core polypeptide

<400> SEQUENCE: 185

Ile Arg Asp Thr Asn Lys Ala Val Gln Ser Val Gln Ser Ser Ile Gly
1               5                   10                  15

Asn Leu Ile Val Ala Ile Lys Ser Val Gln Asp Tyr Val Asn Lys Glu
            20                  25                  30

Ile Val

<210> SEQ ID NO 186
<211> LENGTH: 35
<212> TYPE: PRT
```

<213> ORGANISM: Artificial Sequence
<220> FEATURE:
<223> OTHER INFORMATION: Core polypeptide

<400> SEQUENCE: 186

Tyr Thr Pro Asn Asp Ile Thr Leu Asn Asn Ser Val Ala Leu Asp Pro
1               5                   10                  15

Ile Asp Ile Ser Ile Glu Leu Asn Lys Ala Lys Ser Asp Leu Glu Glu
            20                  25                  30

Ser Lys Glu
        35

<210> SEQ ID NO 187
<211> LENGTH: 35
<212> TYPE: PRT
<213> ORGANISM: Artificial Sequence
<220> FEATURE:
<223> OTHER INFORMATION: Core polypeptide

<400> SEQUENCE: 187

Thr Pro Asn Asp Ile Thr Leu Asn Asn Ser Val Ala Leu Asp Pro Ile
1               5                   10                  15

Asp Ile Ser Ile Glu Leu Asn Lys Ala Lys Ser Asp Leu Glu Glu Ser
            20                  25                  30

Lys Glu Trp
        35

<210> SEQ ID NO 188
<211> LENGTH: 35
<212> TYPE: PRT
<213> ORGANISM: Artificial Sequence
<220> FEATURE:
<223> OTHER INFORMATION: Core polypeptide

<400> SEQUENCE: 188

Pro Asn Asp Ile Thr Leu Asn Asn Ser Val Ala Leu Asp Pro Ile Asp
1               5                   10                  15

Ile Ser Ile Glu Leu Asn Lys Ala Lys Ser Asp Leu Glu Glu Ser Lys
            20                  25                  30

Glu Trp Ile
        35

<210> SEQ ID NO 189
<211> LENGTH: 35
<212> TYPE: PRT
<213> ORGANISM: Artificial Sequence
<220> FEATURE:
<223> OTHER INFORMATION: Core polypeptide

<400> SEQUENCE: 189

Asn Asp Ile Thr Leu Asn Asn Ser Val Ala Leu Asp Pro Ile Asp Ile
1               5                   10                  15

Ser Ile Glu Leu Asn Lys Ala Lys Ser Asp Leu Glu Glu Ser Lys Glu
            20                  25                  30

Trp Ile Arg
        35

<210> SEQ ID NO 190
<211> LENGTH: 35
<212> TYPE: PRT
<213> ORGANISM: Artificial Sequence
<220> FEATURE:
<223> OTHER INFORMATION: Core polypeptide

```
<400> SEQUENCE: 190

Asp Ile Thr Leu Asn Asn Ser Val Ala Leu Asp Pro Ile Asp Ile Ser
 1               5                  10                  15

Ile Glu Leu Asn Lys Ala Lys Ser Asp Leu Glu Glu Ser Lys Glu Trp
            20                  25                  30

Ile Arg Arg
        35

<210> SEQ ID NO 191
<211> LENGTH: 35
<212> TYPE: PRT
<213> ORGANISM: Artificial Sequence
<220> FEATURE:
<223> OTHER INFORMATION: Core polypeptide

<400> SEQUENCE: 191

Ile Thr Leu Asn Asn Ser Val Ala Leu Asp Pro Ile Asp Ile Ser Ile
 1               5                  10                  15

Glu Leu Asn Lys Ala Lys Ser Asp Leu Glu Glu Ser Lys Glu Trp Ile
            20                  25                  30

Arg Arg Ser
        35

<210> SEQ ID NO 192
<211> LENGTH: 35
<212> TYPE: PRT
<213> ORGANISM: Artificial Sequence
<220> FEATURE:
<223> OTHER INFORMATION: Core polypeptide

<400> SEQUENCE: 192

Thr Leu Asn Asn Ser Val Ala Leu Asp Pro Ile Asp Ile Ser Ile Glu
 1               5                  10                  15

Leu Asn Lys Ala Lys Ser Asp Leu Glu Glu Ser Lys Glu Trp Ile Arg
            20                  25                  30

Arg Ser Asn
        35

<210> SEQ ID NO 193
<211> LENGTH: 35
<212> TYPE: PRT
<213> ORGANISM: Artificial Sequence
<220> FEATURE:
<223> OTHER INFORMATION: Core polypeptide

<400> SEQUENCE: 193

Leu Asn Asn Ser Val Ala Leu Asp Pro Ile Asp Ile Ser Ile Glu Leu
 1               5                  10                  15

Asn Lys Ala Lys Ser Asp Leu Glu Glu Ser Lys Glu Trp Ile Arg Arg
            20                  25                  30

Ser Asn Gln
        35

<210> SEQ ID NO 194
<211> LENGTH: 35
<212> TYPE: PRT
<213> ORGANISM: Artificial Sequence
<220> FEATURE:
<223> OTHER INFORMATION: Core polypeptide

<400> SEQUENCE: 194
```

-continued

Asn Asn Ser Val Ala Leu Asp Pro Ile Asp Ile Ser Ile Glu Leu Asn
1               5                   10                  15

Lys Ala Lys Ser Asp Leu Glu Glu Ser Lys Glu Trp Ile Arg Arg Ser
            20                  25                  30

Asn Gln Lys
        35

<210> SEQ ID NO 195
<211> LENGTH: 35
<212> TYPE: PRT
<213> ORGANISM: Artificial Sequence
<220> FEATURE:
<223> OTHER INFORMATION: Core polypeptide

<400> SEQUENCE: 195

Asn Ser Val Ala Leu Asp Pro Ile Asp Ile Ser Ile Glu Leu Asn Lys
1               5                   10                  15

Ala Lys Ser Asp Leu Glu Glu Ser Lys Glu Trp Ile Arg Arg Ser Asn
            20                  25                  30

Gln Lys Leu
        35

<210> SEQ ID NO 196
<211> LENGTH: 35
<212> TYPE: PRT
<213> ORGANISM: Artificial Sequence
<220> FEATURE:
<223> OTHER INFORMATION: Core polypeptide

<400> SEQUENCE: 196

Ser Val Ala Leu Asp Pro Ile Asp Ile Ser Ile Glu Leu Asn Lys Ala
1               5                   10                  15

Lys Ser Asp Leu Glu Glu Ser Lys Glu Trp Ile Arg Arg Ser Asn Gln
            20                  25                  30

Lys Leu Asp
        35

<210> SEQ ID NO 197
<211> LENGTH: 35
<212> TYPE: PRT
<213> ORGANISM: Artificial Sequence
<220> FEATURE:
<223> OTHER INFORMATION: Core polypeptide

<400> SEQUENCE: 197

Val Ala Leu Asp Pro Ile Asp Ile Ser Ile Glu Leu Asn Lys Ala Lys
1               5                   10                  15

Ser Asp Leu Glu Glu Ser Lys Glu Trp Ile Arg Arg Ser Asn Gln Lys
            20                  25                  30

Leu Asp Ser
        35

<210> SEQ ID NO 198
<211> LENGTH: 35
<212> TYPE: PRT
<213> ORGANISM: Artificial Sequence
<220> FEATURE:
<223> OTHER INFORMATION: Core polypeptide

<400> SEQUENCE: 198

Ala Leu Asp Pro Ile Asp Ile Ser Ile Glu Leu Asn Lys Ala Lys Ser
1               5                   10                  15

Asp Leu Glu Glu Ser Lys Glu Trp Ile Arg Arg Ser Asn Gln Lys Leu
            20                  25                  30

Asp Ser Ile
        35

<210> SEQ ID NO 199
<211> LENGTH: 35
<212> TYPE: PRT
<213> ORGANISM: Artificial Sequence
<220> FEATURE:
<223> OTHER INFORMATION: Core polypeptide

<400> SEQUENCE: 199

Leu Asp Pro Ile Asp Ile Ser Ile Glu Leu Asn Lys Ala Lys Ser Asp
 1               5                  10                  15

Leu Glu Glu Ser Lys Glu Trp Ile Arg Arg Ser Asn Gln Lys Leu Asp
            20                  25                  30

Ser Ile Gly
        35

<210> SEQ ID NO 200
<211> LENGTH: 35
<212> TYPE: PRT
<213> ORGANISM: Artificial Sequence
<220> FEATURE:
<223> OTHER INFORMATION: Core polypeptide

<400> SEQUENCE: 200

Asp Pro Ile Asp Ile Ser Ile Glu Leu Asn Lys Ala Lys Ser Asp Leu
 1               5                  10                  15

Glu Glu Ser Lys Glu Trp Ile Arg Arg Ser Asn Gln Lys Leu Asp Ser
            20                  25                  30

Ile Gly Asn
        35

<210> SEQ ID NO 201
<211> LENGTH: 35
<212> TYPE: PRT
<213> ORGANISM: Artificial Sequence
<220> FEATURE:
<223> OTHER INFORMATION: Core polypeptide

<400> SEQUENCE: 201

Pro Ile Asp Ile Ser Ile Glu Leu Asn Lys Ala Lys Ser Asp Leu Glu
 1               5                  10                  15

Glu Ser Lys Glu Trp Ile Arg Arg Ser Asn Gln Lys Leu Asp Ser Ile
            20                  25                  30

Gly Asn Trp
        35

<210> SEQ ID NO 202
<211> LENGTH: 35
<212> TYPE: PRT
<213> ORGANISM: Artificial Sequence
<220> FEATURE:
<223> OTHER INFORMATION: Core polypeptide

<400> SEQUENCE: 202

Ile Asp Ile Ser Ile Glu Leu Asn Lys Ala Lys Ser Asp Leu Glu Glu
 1               5                  10                  15

Ser Lys Glu Trp Ile Arg Arg Ser Asn Gln Lys Leu Asp Ser Ile Gly
            20                  25                  30

Asn Trp His
        35

<210> SEQ ID NO 203
<211> LENGTH: 35
<212> TYPE: PRT
<213> ORGANISM: Artificial Sequence
<220> FEATURE:
<223> OTHER INFORMATION: Core polypeptide

<400> SEQUENCE: 203

Asp Ile Ser Ile Glu Leu Asn Lys Ala Lys Ser Asp Leu Glu Glu Ser
1               5                   10                  15

Lys Glu Trp Ile Arg Arg Ser Asn Gln Lys Leu Asp Ser Ile Gly Asn
            20                  25                  30

Trp His Gln
        35

<210> SEQ ID NO 204
<211> LENGTH: 35
<212> TYPE: PRT
<213> ORGANISM: Artificial Sequence
<220> FEATURE:
<223> OTHER INFORMATION: Core polypeptide

<400> SEQUENCE: 204

Ile Ser Ile Glu Leu Asn Lys Ala Lys Ser Asp Leu Glu Glu Ser Lys
1               5                   10                  15

Glu Trp Ile Arg Arg Ser Asn Gln Lys Leu Asp Ser Ile Gly Asn Trp
            20                  25                  30

His Gln Ser
        35

<210> SEQ ID NO 205
<211> LENGTH: 35
<212> TYPE: PRT
<213> ORGANISM: Artificial Sequence
<220> FEATURE:
<223> OTHER INFORMATION: Core polypeptide

<400> SEQUENCE: 205

Ser Ile Glu Leu Asn Lys Ala Lys Ser Asp Leu Glu Glu Ser Lys Glu
1               5                   10                  15

Trp Ile Arg Arg Ser Asn Gln Lys Leu Asp Ser Ile Gly Asn Trp His
            20                  25                  30

Gln Ser Ser
        35

<210> SEQ ID NO 206
<211> LENGTH: 35
<212> TYPE: PRT
<213> ORGANISM: Artificial Sequence
<220> FEATURE:
<223> OTHER INFORMATION: Core polypeptide

<400> SEQUENCE: 206

Ile Glu Leu Asn Lys Ala Lys Ser Asp Leu Glu Glu Ser Lys Glu Trp
1               5                   10                  15

Ile Arg Arg Ser Asn Gln Lys Leu Asp Ser Ile Gly Asn Trp His Gln
            20                  25                  30

Ser Ser Thr
        35

```
<210> SEQ ID NO 207
<211> LENGTH: 35
<212> TYPE: PRT
<213> ORGANISM: Artificial Sequence
<220> FEATURE:
<223> OTHER INFORMATION: Core polypeptide

<400> SEQUENCE: 207

Glu Leu Asn Lys Ala Lys Ser Asp Leu Glu Ser Lys Glu Trp Ile
1               5                  10                  15

Arg Arg Ser Asn Gln Lys Leu Asp Ser Ile Gly Asn Trp His Gln Ser
            20                  25                  30

Ser Thr Thr
        35

<210> SEQ ID NO 208
<211> LENGTH: 36
<212> TYPE: PRT
<213> ORGANISM: Artificial Sequence
<220> FEATURE:
<223> OTHER INFORMATION: Core polypeptide

<400> SEQUENCE: 208

Glu Leu Arg Ala Leu Arg Gly Glu Leu Arg Ala Leu Arg Gly Glu Leu
1               5                  10                  15

Arg Ala Leu Arg Gly Glu Leu Arg Ala Leu Arg Gly Glu Leu Arg Ala
            20                  25                  30

Leu Arg Gly Lys
        35

<210> SEQ ID NO 209
<211> LENGTH: 36
<212> TYPE: PRT
<213> ORGANISM: Artificial Sequence
<220> FEATURE:
<223> OTHER INFORMATION: Core polypeptide

<400> SEQUENCE: 209

Tyr Thr Ser Leu Ile His Ser Leu Ile Glu Glu Ser Gln Asn Gln Gln
1               5                  10                  15

Gln Lys Asn Glu Gln Glu Leu Leu Glu Leu Asp Lys Trp Ala Ser Leu
            20                  25                  30

Trp Asn Trp Phe
        35

<210> SEQ ID NO 210
<211> LENGTH: 36
<212> TYPE: PRT
<213> ORGANISM: Artificial Sequence
<220> FEATURE:
<223> OTHER INFORMATION: Core polypeptide

<400> SEQUENCE: 210

Tyr Thr Ser Leu Ile His Ser Leu Ile Glu Glu Ser Gln Asn Gln Gln
1               5                  10                  15

Glu Lys Asn Glu Gln Glu Leu Leu Glu Leu Asn Lys Trp Ala Ser Leu
            20                  25                  30

Trp Asn Trp Phe
        35

<210> SEQ ID NO 211
<211> LENGTH: 36
```

```
<212> TYPE: PRT
<213> ORGANISM: Artificial Sequence
<220> FEATURE:
<223> OTHER INFORMATION: Core polypeptide

<400> SEQUENCE: 211

Tyr Thr Ser Leu Ile His Ser Leu Ile Glu Gln Ser Gln Asn Gln Gln
 1               5                  10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 212
<211> LENGTH: 36
<212> TYPE: PRT
<213> ORGANISM: Artificial Sequence
<220> FEATURE:
<223> OTHER INFORMATION: Core polypeptide

<400> SEQUENCE: 212

Tyr Thr Ser Leu Ile His Ser Leu Ile Gln Ser Gln Asn Gln Gln
 1               5                  10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 213
<211> LENGTH: 36
<212> TYPE: PRT
<213> ORGANISM: Artificial Sequence
<220> FEATURE:
<223> OTHER INFORMATION: Core polypeptide

<400> SEQUENCE: 213

Tyr Thr Ser Leu Ile His Ser Leu Ile Gln Gln Ser Gln Asn Gln Gln
 1               5                  10                  15

Gln Lys Asn Gln Gln Gln Leu Leu Gln Leu Asn Lys Trp Ala Ser Leu
            20                  25                  30

Trp Asn Trp Phe
        35

<210> SEQ ID NO 214
<211> LENGTH: 17
<212> TYPE: PRT
<213> ORGANISM: Artificial Sequence
<220> FEATURE:
<223> OTHER INFORMATION: Core polypeptide

<400> SEQUENCE: 214

Glu Gln Glu Leu Leu Glu Leu Asp Lys Trp Ala Ser Leu Trp Asn Trp
 1               5                  10                  15

Phe

<210> SEQ ID NO 215
<211> LENGTH: 16
<212> TYPE: PRT
<213> ORGANISM: Artificial Sequence
<220> FEATURE:
<223> OTHER INFORMATION: Core polypeptide

<400> SEQUENCE: 215
```

Gln Glu Leu Leu Glu Leu Asp Lys Trp Ala Ser Leu Trp Asn Trp Phe
 1               5                  10                  15

<210> SEQ ID NO 216
<211> LENGTH: 15
<212> TYPE: PRT
<213> ORGANISM: Artificial Sequence
<220> FEATURE:
<223> OTHER INFORMATION: Core polypeptide

<400> SEQUENCE: 216

Glu Leu Leu Glu Leu Asp Lys Trp Ala Ser Leu Trp Asn Trp Phe
 1               5                  10                  15

<210> SEQ ID NO 217
<211> LENGTH: 14
<212> TYPE: PRT
<213> ORGANISM: Artificial Sequence
<220> FEATURE:
<223> OTHER INFORMATION: Core polypeptide

<400> SEQUENCE: 217

Leu Leu Glu Leu Asp Lys Trp Ala Ser Leu Trp Asn Trp Phe
 1               5                  10

<210> SEQ ID NO 218
<211> LENGTH: 13
<212> TYPE: PRT
<213> ORGANISM: Artificial Sequence
<220> FEATURE:
<223> OTHER INFORMATION: Core polypeptide

<400> SEQUENCE: 218

Leu Glu Leu Asp Lys Trp Ala Ser Leu Trp Asn Trp Phe
 1               5                  10

<210> SEQ ID NO 219
<211> LENGTH: 12
<212> TYPE: PRT
<213> ORGANISM: Artificial Sequence
<220> FEATURE:
<223> OTHER INFORMATION: Core polypeptide

<400> SEQUENCE: 219

Glu Leu Asp Lys Trp Ala Ser Leu Trp Asn Trp Phe
 1               5                  10

<210> SEQ ID NO 220
<211> LENGTH: 11
<212> TYPE: PRT
<213> ORGANISM: Artificial Sequence
<220> FEATURE:
<223> OTHER INFORMATION: Core polypeptide

<400> SEQUENCE: 220

Leu Asp Lys Trp Ala Ser Leu Trp Asn Trp Phe
 1               5                  10

<210> SEQ ID NO 221
<211> LENGTH: 10
<212> TYPE: PRT
<213> ORGANISM: Artificial Sequence
<220> FEATURE:
<223> OTHER INFORMATION: Core polypeptide

<400> SEQUENCE: 221

Asp Lys Trp Ala Ser Leu Trp Asn Trp Phe 1               5                    10

<210> SEQ ID NO 222
<211> LENGTH: 9
<212> TYPE: PRT
<213> ORGANISM: Artificial Sequence
<220> FEATURE:
<223> OTHER INFORMATION: Core polypeptide

<400> SEQUENCE: 222

Lys Trp Ala Ser Leu Trp Asn Trp Phe
 1               5

<210> SEQ ID NO 223
<211> LENGTH: 8
<212> TYPE: PRT
<213> ORGANISM: Artificial Sequence
<220> FEATURE:
<223> OTHER INFORMATION: Core polypeptide

<400> SEQUENCE: 223

Trp Ala Ser Leu Trp Asn Trp Phe
 1               5

<210> SEQ ID NO 224
<211> LENGTH: 7
<212> TYPE: PRT
<213> ORGANISM: Artificial Sequence
<220> FEATURE:
<223> OTHER INFORMATION: Core polypeptide

<400> SEQUENCE: 224

Ala Ser Leu Trp Asn Trp Phe
 1               5

<210> SEQ ID NO 225
<211> LENGTH: 18
<212> TYPE: PRT
<213> ORGANISM: Artificial Sequence
<220> FEATURE:
<223> OTHER INFORMATION: Core polypeptide

<400> SEQUENCE: 225

Tyr Thr Ser Leu Ile His Ser Leu Ile Glu Glu Ser Gln Asn Gln Gln
 1               5                   10                  15

Glu Lys

<210> SEQ ID NO 226
<211> LENGTH: 36
<212> TYPE: PRT
<213> ORGANISM: Artificial Sequence
<220> FEATURE:
<223> OTHER INFORMATION: Core polypeptide

<400> SEQUENCE: 226

Tyr Thr Ser Leu Ile His Ser Leu Ile Glu Glu Ser Gln Asn Gln Gln
 1               5                   10                  15

Glu Lys Asn Glu Gln Glu Leu Leu Glu Leu Asp Lys Trp Ala Ser Leu
             20                  25                  30

Ala Asn Ala Ala
         35

<210> SEQ ID NO 227
<211> LENGTH: 36
<212> TYPE: PRT

```
<213> ORGANISM: Artificial Sequence
<220> FEATURE:
<223> OTHER INFORMATION: Core polypeptide

<400> SEQUENCE: 227

Tyr Thr Ser Leu Ile His Ser Leu Ile Glu Glu Ser Gln Asn Gln Gln
 1               5                  10                  15

Glu Lys Asn Glu Gln Gln Leu Leu Glu Leu Asp Lys Trp Ala Ser Leu
            20                  25                  30

Trp Asn Trp Phe
         35

<210> SEQ ID NO 228
<211> LENGTH: 36
<212> TYPE: PRT
<213> ORGANISM: Artificial Sequence
<220> FEATURE:
<223> OTHER INFORMATION: Core polypeptide

<400> SEQUENCE: 228

Tyr Thr Ser Leu Ile Gln Ser Leu Ile Glu Glu Ser Gln Asn Gln Gln
 1               5                  10                  15

Glu Lys Asn Gln Gln Glu Leu Leu Glu Leu Asp Lys Trp Ala Ser Leu
            20                  25                  30

Trp Asn Trp Phe
         35

<210> SEQ ID NO 229
<211> LENGTH: 14
<212> TYPE: PRT
<213> ORGANISM: Artificial Sequence
<220> FEATURE:
<223> OTHER INFORMATION: Core polypeptide

<400> SEQUENCE: 229

Cys Leu Glu Leu Asp Lys Trp Ala Ser Leu Trp Asn Trp Phe
 1               5                  10

<210> SEQ ID NO 230
<211> LENGTH: 13
<212> TYPE: PRT
<213> ORGANISM: Artificial Sequence
<220> FEATURE:
<223> OTHER INFORMATION: Core polypeptide

<400> SEQUENCE: 230

Leu Glu Leu Asp Lys Phe Ala Ser Leu Phe Asn Phe
 1               5                  10

<210> SEQ ID NO 231
<211> LENGTH: 28
<212> TYPE: PRT
<213> ORGANISM: Artificial Sequence
<220> FEATURE:
<223> OTHER INFORMATION: Core polypeptide

<400> SEQUENCE: 231

Glu Ala Ala Ala Arg Glu Ala Ala Arg Glu Ala Ala Ala Arg Leu
 1               5                  10                  15

Glu Leu Asp Lys Trp Ala Ser Leu Trp Asn Trp Phe
            20                  25

<210> SEQ ID NO 232
<211> LENGTH: 28
```

<212> TYPE: PRT
<213> ORGANISM: Artificial Sequence
<220> FEATURE:
<223> OTHER INFORMATION: Core polypeptide

<400> SEQUENCE: 232

Arg Met Lys Gln Leu Glu Asp Lys Val Glu Glu Leu Leu Ser Lys Leu
 1               5                  10                  15

Glu Leu Asp Lys Trp Ala Ser Leu Trp Asn Trp Phe
             20                  25

<210> SEQ ID NO 233
<211> LENGTH: 35
<212> TYPE: PRT
<213> ORGANISM: Artificial Sequence
<220> FEATURE:
<223> OTHER INFORMATION: Core polypeptide

<400> SEQUENCE: 233

Pro Ser Leu Arg Asp Pro Ile Ser Ala Glu Ile Ser Ile Gln Ala Leu
 1               5                  10                  15

Ser Tyr Ala Leu Gly Gly Asp Ile Asn Lys Val Leu Glu Lys Leu Gly
             20                  25                  30

Tyr Ser Gly
         35

<210> SEQ ID NO 234
<211> LENGTH: 35
<212> TYPE: PRT
<213> ORGANISM: Artificial Sequence
<220> FEATURE:
<223> OTHER INFORMATION: Core polypeptide

<400> SEQUENCE: 234

Ser Leu Arg Asp Pro Ile Ser Ala Glu Ile Ser Ile Gln Ala Leu Ser
 1               5                  10                  15

Tyr Ala Leu Gly Gly Asp Ile Asn Lys Val Leu Glu Lys Leu Gly Tyr
             20                  25                  30

Ser Gly Gly
         35

<210> SEQ ID NO 235
<211> LENGTH: 35
<212> TYPE: PRT
<213> ORGANISM: Artificial Sequence
<220> FEATURE:
<223> OTHER INFORMATION: Core polypeptide

<400> SEQUENCE: 235

Leu Arg Asp Pro Ile Ser Ala Glu Ile Ser Ile Gln Ala Leu Ser Tyr
 1               5                  10                  15

Ala Leu Gly Gly Asp Ile Asn Lys Val Leu Glu Lys Leu Gly Tyr Ser
             20                  25                  30

Gly Gly Asp
         35

<210> SEQ ID NO 236
<211> LENGTH: 35
<212> TYPE: PRT
<213> ORGANISM: Artificial Sequence
<220> FEATURE:
<223> OTHER INFORMATION: Core polypeptide

<400> SEQUENCE: 236

Arg Asp Pro Ile Ser Ala Glu Ile Ser Ile Gln Ala Leu Ser Tyr Ala
1               5                  10                 15

Leu Gly Gly Asp Ile Asn Lys Val Leu Glu Lys Leu Gly Tyr Ser Gly
             20                  25                 30

Gly Asp Leu
         35

<210> SEQ ID NO 237
<211> LENGTH: 35
<212> TYPE: PRT
<213> ORGANISM: Artificial Sequence
<220> FEATURE:
<223> OTHER INFORMATION: Core polypeptide

<400> SEQUENCE: 237

Asp Pro Ile Ser Ala Glu Ile Ser Ile Gln Ala Leu Ser Tyr Ala Leu
1               5                  10                 15

Gly Gly Asp Ile Asn Lys Val Leu Glu Lys Leu Gly Tyr Ser Gly Gly
             20                  25                 30

Asp Leu Leu
         35

<210> SEQ ID NO 238
<211> LENGTH: 35
<212> TYPE: PRT
<213> ORGANISM: Artificial Sequence
<220> FEATURE:
<223> OTHER INFORMATION: Core polypeptide

<400> SEQUENCE: 238

Pro Ile Ser Ala Glu Ile Ser Ile Gln Ala Leu Ser Tyr Ala Leu Gly
1               5                  10                 15

Gly Asp Ile Asn Lys Val Leu Glu Lys Leu Gly Tyr Ser Gly Gly Asp
             20                  25                 30

Leu Leu Gly
         35

<210> SEQ ID NO 239
<211> LENGTH: 35
<212> TYPE: PRT
<213> ORGANISM: Artificial Sequence
<220> FEATURE:
<223> OTHER INFORMATION: Core polypeptide

<400> SEQUENCE: 239

Ile Ser Ala Glu Ile Ser Ile Gln Ala Leu Ser Tyr Ala Leu Gly Gly
1               5                  10                 15

Asp Ile Asn Lys Val Leu Glu Lys Leu Gly Tyr Ser Gly Gly Asp Leu
             20                  25                 30

Leu Gly Ile
         35

<210> SEQ ID NO 240
<211> LENGTH: 35
<212> TYPE: PRT
<213> ORGANISM: Artificial Sequence
<220> FEATURE:
<223> OTHER INFORMATION: Core polypeptide

<400> SEQUENCE: 240

Ser Ala Glu Ile Ser Ile Gln Ala Leu Ser Tyr Ala Leu Gly Gly Asp
1               5                  10                 15

Ile Asn Lys Val Leu Glu Lys Leu Gly Tyr Ser Gly Gly Asp Leu Leu
            20                  25                  30

Gly Ile Leu
        35

<210> SEQ ID NO 241
<211> LENGTH: 35
<212> TYPE: PRT
<213> ORGANISM: Artificial Sequence
<220> FEATURE:
<223> OTHER INFORMATION: Core polypeptide

<400> SEQUENCE: 241

Ala Glu Ile Ser Ile Gln Ala Leu Ser Tyr Ala Leu Gly Gly Asp Ile
 1               5                  10                  15

Asn Lys Val Leu Glu Lys Leu Gly Tyr Ser Gly Gly Asp Leu Leu Gly
            20                  25                  30

Ile Leu Glu
        35

<210> SEQ ID NO 242
<211> LENGTH: 35
<212> TYPE: PRT
<213> ORGANISM: Artificial Sequence
<220> FEATURE:
<223> OTHER INFORMATION: Core polypeptide

<400> SEQUENCE: 242

Glu Ile Ser Ile Gln Ala Leu Ser Tyr Ala Leu Gly Gly Asp Ile Asn
 1               5                  10                  15

Lys Val Leu Glu Lys Leu Gly Tyr Ser Gly Gly Asp Leu Leu Gly Ile
            20                  25                  30

Leu Glu Ser
        35

<210> SEQ ID NO 243
<211> LENGTH: 35
<212> TYPE: PRT
<213> ORGANISM: Artificial Sequence
<220> FEATURE:
<223> OTHER INFORMATION: Core polypeptide

<400> SEQUENCE: 243

Ile Ser Ile Gln Ala Leu Ser Tyr Ala Leu Gly Gly Asp Ile Asn Lys
 1               5                  10                  15

Val Leu Glu Lys Leu Gly Tyr Ser Gly Gly Asp Leu Leu Gly Ile Leu
            20                  25                  30

Glu Ser Arg
        35

<210> SEQ ID NO 244
<211> LENGTH: 35
<212> TYPE: PRT
<213> ORGANISM: Artificial Sequence
<220> FEATURE:
<223> OTHER INFORMATION: Core polypeptide

<400> SEQUENCE: 244

Ser Ile Gln Ala Leu Ser Tyr Ala Leu Gly Gly Asp Ile Asn Lys Val
 1               5                  10                  15

Leu Glu Lys Leu Gly Tyr Ser Gly Gly Asp Leu Leu Gly Ile Leu Glu
            20                  25                  30

```
Ser Arg Gly
        35

<210> SEQ ID NO 245
<211> LENGTH: 35
<212> TYPE: PRT
<213> ORGANISM: Artificial Sequence
<220> FEATURE:
<223> OTHER INFORMATION: Core polypeptide

<400> SEQUENCE: 245

Ile Gln Ala Leu Ser Tyr Ala Leu Gly Gly Asp Ile Asn Lys Val Leu
 1               5                  10                  15

Glu Lys Leu Gly Tyr Ser Gly Gly Asp Leu Leu Gly Ile Leu Glu Ser
            20                  25                  30

Arg Gly Ile
        35

<210> SEQ ID NO 246
<211> LENGTH: 35
<212> TYPE: PRT
<213> ORGANISM: Artificial Sequence
<220> FEATURE:
<223> OTHER INFORMATION: Core polypeptide

<400> SEQUENCE: 246

Gln Ala Leu Ser Tyr Ala Leu Gly Gly Asp Ile Asn Lys Val Leu Glu
 1               5                  10                  15

Lys Leu Gly Tyr Ser Gly Gly Asp Leu Leu Gly Ile Leu Glu Ser Arg
            20                  25                  30

Gly Ile Lys
        35

<210> SEQ ID NO 247
<211> LENGTH: 35
<212> TYPE: PRT
<213> ORGANISM: Artificial Sequence
<220> FEATURE:
<223> OTHER INFORMATION: Core polypeptide

<400> SEQUENCE: 247

Ala Leu Ser Tyr Ala Leu Gly Gly Asp Ile Asn Lys Val Leu Glu Lys
 1               5                  10                  15

Leu Gly Tyr Ser Gly Gly Asp Leu Leu Gly Ile Leu Glu Ser Arg Gly
            20                  25                  30

Ile Lys Ala
        35

<210> SEQ ID NO 248
<211> LENGTH: 35
<212> TYPE: PRT
<213> ORGANISM: Artificial Sequence
<220> FEATURE:
<223> OTHER INFORMATION: Core polypeptide

<400> SEQUENCE: 248

Leu Ser Tyr Ala Leu Gly Gly Asp Ile Asn Lys Val Leu Glu Lys Leu
 1               5                  10                  15

Gly Tyr Ser Gly Gly Asp Leu Leu Gly Ile Leu Glu Ser Arg Gly Ile
            20                  25                  30

Lys Ala Arg
        35
```

<210> SEQ ID NO 249
<211> LENGTH: 35
<212> TYPE: PRT
<213> ORGANISM: Artificial Sequence
<220> FEATURE:
<223> OTHER INFORMATION: Core polypeptide

<400> SEQUENCE: 249

Pro Asp Ala Val Tyr Leu His Arg Ile Asp Leu Gly Pro Pro Ile Ser
1               5                   10                  15

Leu Glu Arg Leu Asp Val Gly Thr Asn Leu Gly Asn Ala Ile Ala Lys
            20                  25                  30

Leu Glu Asp
        35

<210> SEQ ID NO 250
<211> LENGTH: 35
<212> TYPE: PRT
<213> ORGANISM: Artificial Sequence
<220> FEATURE:
<223> OTHER INFORMATION: Core polypeptide

<400> SEQUENCE: 250

Asp Ala Val Tyr Leu His Arg Ile Asp Leu Gly Pro Pro Ile Ser Leu
1               5                   10                  15

Glu Arg Leu Asp Val Gly Thr Asn Leu Gly Asn Ala Ile Ala Lys Leu
            20                  25                  30

Glu Asp Ala
        35

<210> SEQ ID NO 251
<211> LENGTH: 35
<212> TYPE: PRT
<213> ORGANISM: Artificial Sequence
<220> FEATURE:
<223> OTHER INFORMATION: Core polypeptide

<400> SEQUENCE: 251

Ala Val Tyr Leu His Arg Ile Asp Leu Gly Pro Pro Ile Ser Leu Glu
1               5                   10                  15

Arg Leu Asp Val Gly Thr Asn Leu Gly Asn Ala Ile Ala Lys Leu Glu
            20                  25                  30

Asp Ala Lys
        35

<210> SEQ ID NO 252
<211> LENGTH: 35
<212> TYPE: PRT
<213> ORGANISM: Artificial Sequence
<220> FEATURE:
<223> OTHER INFORMATION: Core polypeptide

<400> SEQUENCE: 252

Val Tyr Leu His Arg Ile Asp Leu Gly Pro Pro Ile Ser Leu Glu Arg
1               5                   10                  15

Leu Asp Val Gly Thr Asn Leu Gly Asn Ala Ile Ala Lys Leu Glu Asp
            20                  25                  30

Ala Lys Glu
        35

<210> SEQ ID NO 253

```
<211> LENGTH: 35
<212> TYPE: PRT
<213> ORGANISM: Artificial Sequence
<220> FEATURE:
<223> OTHER INFORMATION: Core polypeptide

<400> SEQUENCE: 253

Tyr Leu His Arg Ile Asp Leu Gly Pro Pro Ile Ser Leu Glu Arg Leu
 1               5                  10                  15

Asp Val Gly Thr Asn Leu Gly Asn Ala Ile Ala Lys Leu Glu Asp Ala
            20                  25                  30

Lys Glu Leu
        35

<210> SEQ ID NO 254
<211> LENGTH: 35
<212> TYPE: PRT
<213> ORGANISM: Artificial Sequence
<220> FEATURE:
<223> OTHER INFORMATION: Core polypeptide

<400> SEQUENCE: 254

Leu His Arg Ile Asp Leu Gly Pro Pro Ile Ser Leu Glu Arg Leu Asp
 1               5                  10                  15

Val Gly Thr Asn Leu Gly Asn Ala Ile Ala Lys Leu Glu Asp Ala Lys
            20                  25                  30

Glu Leu Leu
        35

<210> SEQ ID NO 255
<211> LENGTH: 35
<212> TYPE: PRT
<213> ORGANISM: Artificial Sequence
<220> FEATURE:
<223> OTHER INFORMATION: Core polypeptide

<400> SEQUENCE: 255

His Arg Ile Asp Leu Gly Pro Pro Ile Ser Leu Glu Arg Leu Asp Val
 1               5                  10                  15

Gly Thr Asn Leu Gly Asn Ala Ile Ala Lys Leu Glu Asp Ala Lys Glu
            20                  25                  30

Leu Leu Glu
        35

<210> SEQ ID NO 256
<211> LENGTH: 35
<212> TYPE: PRT
<213> ORGANISM: Artificial Sequence
<220> FEATURE:
<223> OTHER INFORMATION: Core polypeptide

<400> SEQUENCE: 256

Arg Ile Asp Leu Gly Pro Pro Ile Ser Leu Glu Arg Leu Asp Val Gly
 1               5                  10                  15

Thr Asn Leu Gly Asn Ala Ile Ala Lys Leu Glu Asp Ala Lys Glu Leu
            20                  25                  30

Leu Glu Ser
        35

<210> SEQ ID NO 257
<211> LENGTH: 35
<212> TYPE: PRT
<213> ORGANISM: Artificial Sequence
```

```
<220> FEATURE:
<223> OTHER INFORMATION: Core polypeptide

<400> SEQUENCE: 257

Ile Asp Leu Gly Pro Pro Ile Ser Leu Glu Arg Leu Asp Val Gly Thr
 1               5                  10                  15

Asn Leu Gly Asn Ala Ile Ala Lys Leu Glu Asp Ala Lys Glu Leu Leu
                20                  25                  30

Glu Ser Ser
        35

<210> SEQ ID NO 258
<211> LENGTH: 35
<212> TYPE: PRT
<213> ORGANISM: Artificial Sequence
<220> FEATURE:
<223> OTHER INFORMATION: Core polypeptide

<400> SEQUENCE: 258

Asp Leu Gly Pro Pro Ile Ser Leu Glu Arg Leu Asp Val Gly Thr Asn
 1               5                  10                  15

Leu Gly Asn Ala Ile Ala Lys Leu Glu Asp Ala Lys Glu Leu Leu Glu
                20                  25                  30

Ser Ser Asp
        35

<210> SEQ ID NO 259
<211> LENGTH: 35
<212> TYPE: PRT
<213> ORGANISM: Artificial Sequence
<220> FEATURE:
<223> OTHER INFORMATION: Core polypeptide

<400> SEQUENCE: 259

Leu Gly Pro Pro Ile Ser Leu Glu Arg Leu Asp Val Gly Thr Asn Leu
 1               5                  10                  15

Gly Asn Ala Ile Ala Lys Leu Glu Asp Ala Lys Glu Leu Leu Glu Ser
                20                  25                  30

Ser Asp Gln
        35

<210> SEQ ID NO 260
<211> LENGTH: 35
<212> TYPE: PRT
<213> ORGANISM: Artificial Sequence
<220> FEATURE:
<223> OTHER INFORMATION: Core polypeptide

<400> SEQUENCE: 260

Gly Pro Pro Ile Ser Leu Glu Arg Leu Asp Val Gly Thr Asn Leu Gly
 1               5                  10                  15

Asn Ala Ile Ala Lys Leu Glu Asp Ala Lys Glu Leu Leu Glu Ser Ser
                20                  25                  30

Asp Gln Ile
        35

<210> SEQ ID NO 261
<211> LENGTH: 35
<212> TYPE: PRT
<213> ORGANISM: Artificial Sequence
<220> FEATURE:
<223> OTHER INFORMATION: Core polypeptide
```

-continued

```
<400> SEQUENCE: 261

Pro Pro Ile Ser Leu Glu Arg Leu Asp Val Gly Thr Asn Leu Gly Asn
1               5                   10                  15
Ala Ile Ala Lys Leu Glu Asp Ala Lys Glu Leu Leu Glu Ser Ser Asp
            20                  25                  30
Gln Ile Leu
        35

<210> SEQ ID NO 262
<211> LENGTH: 35
<212> TYPE: PRT
<213> ORGANISM: Artificial Sequence
<220> FEATURE:
<223> OTHER INFORMATION: Core polypeptide

<400> SEQUENCE: 262

Pro Ile Ser Leu Glu Arg Leu Asp Val Gly Thr Asn Leu Gly Asn Ala
1               5                   10                  15
Ile Ala Lys Leu Glu Asp Ala Lys Glu Leu Leu Glu Ser Ser Asp Gln
            20                  25                  30
Ile Leu Arg
        35

<210> SEQ ID NO 263
<211> LENGTH: 34
<212> TYPE: PRT
<213> ORGANISM: Artificial Sequence
<220> FEATURE:
<223> OTHER INFORMATION: Core polypeptide

<400> SEQUENCE: 263

Ile Ser Leu Glu Arg Leu Asp Val Gly Thr Asn Leu Gly Asn Ala Ile
1               5                   10                  15
Ala Lys Leu Glu Asp Ala Lys Glu Leu Leu Glu Ser Ser Asp Gln Ile
            20                  25                  30
Arg Ser

<210> SEQ ID NO 264
<211> LENGTH: 35
<212> TYPE: PRT
<213> ORGANISM: Artificial Sequence
<220> FEATURE:
<223> OTHER INFORMATION: Core polypeptide

<400> SEQUENCE: 264

Ser Leu Glu Arg Leu Asp Val Gly Thr Asn Leu Gly Asn Ala Ile Ala
1               5                   10                  15
Lys Leu Glu Asp Ala Lys Glu Leu Leu Glu Ser Ser Asp Gln Ile Leu
            20                  25                  30
Arg Ser Met
        35

<210> SEQ ID NO 265
<211> LENGTH: 35
<212> TYPE: PRT
<213> ORGANISM: Artificial Sequence
<220> FEATURE:
<223> OTHER INFORMATION: Core polypeptide

<400> SEQUENCE: 265

Leu Glu Arg Leu Asp Val Gly Thr Asn Leu Gly Asn Ala Ile Ala Lys
1               5                   10                  15
```

-continued

Leu Glu Asp Ala Lys Glu Leu Leu Glu Ser Ser Asp Gln Ile Leu Arg
            20                  25                  30

Ser Met Lys
        35

<210> SEQ ID NO 266
<211> LENGTH: 13
<212> TYPE: PRT
<213> ORGANISM: Artificial Sequence
<220> FEATURE:
<223> OTHER INFORMATION: Core polypeptide

<400> SEQUENCE: 266

Glu Trp Ile Arg Arg Ser Asn Gln Lys Leu Asp Ser Ile
1               5                   10

<210> SEQ ID NO 267
<211> LENGTH: 13
<212> TYPE: PRT
<213> ORGANISM: Artificial Sequence
<220> FEATURE:
<223> OTHER INFORMATION: Core polypeptide

<400> SEQUENCE: 267

Leu Glu Leu Asp Lys Trp Ala Ser Leu Ala Asn Ala Phe
1               5                   10

<210> SEQ ID NO 268
<211> LENGTH: 13
<212> TYPE: PRT
<213> ORGANISM: Artificial Sequence
<220> FEATURE:
<223> OTHER INFORMATION: Core polypeptide

<400> SEQUENCE: 268

Leu Glu Leu Asp Lys Trp Ala Ser Leu Phe Asn Phe Phe
1               5                   10

<210> SEQ ID NO 269
<211> LENGTH: 13
<212> TYPE: PRT
<213> ORGANISM: Artificial Sequence
<220> FEATURE:
<223> OTHER INFORMATION: Core polypeptide

<400> SEQUENCE: 269

Leu Glu Leu Asp Lys Trp Ala Ser Leu Ala Asn Trp Phe
1               5                   10

<210> SEQ ID NO 270
<211> LENGTH: 13
<212> TYPE: PRT
<213> ORGANISM: Artificial Sequence
<220> FEATURE:
<223> OTHER INFORMATION: Core polypeptide

<400> SEQUENCE: 270

Leu Glu Leu Asp Lys Trp Ala Ser Leu Trp Asn Ala Phe
1               5                   10

<210> SEQ ID NO 271
<211> LENGTH: 35
<212> TYPE: PRT
<213> ORGANISM: Artificial Sequence
<220> FEATURE:
<223> OTHER INFORMATION: Core polypeptide

```
<400> SEQUENCE: 271

Glu Leu Gly Asn Val Asn Asn Ser Ile Ser Asn Ala Leu Asp Lys Leu
 1               5                  10                  15

Glu Glu Ser Asn Ser Lys Leu Asp Lys Val Asn Val Lys Leu Thr Ser
            20                  25                  30

Thr Ser Ala
        35

<210> SEQ ID NO 272
<211> LENGTH: 35
<212> TYPE: PRT
<213> ORGANISM: Artificial Sequence
<220> FEATURE:
<223> OTHER INFORMATION: Core polypeptide

<400> SEQUENCE: 272

Thr Glu Leu Gly Asn Val Asn Asn Ser Ile Ser Asn Ala Leu Asp Lys
 1               5                  10                  15

Leu Glu Glu Ser Asn Ser Lys Leu Asp Lys Val Asn Val Lys Leu Thr
            20                  25                  30

Ser Thr Ser
        35

<210> SEQ ID NO 273
<211> LENGTH: 35
<212> TYPE: PRT
<213> ORGANISM: Artificial Sequence
<220> FEATURE:
<223> OTHER INFORMATION: Core polypeptide

<400> SEQUENCE: 273

Ser Thr Glu Leu Gly Asn Val Asn Asn Ser Ile Ser Asn Ala Leu Asp
 1               5                  10                  15

Lys Leu Glu Glu Ser Asn Ser Lys Leu Asp Lys Val Asn Val Lys Leu
            20                  25                  30

Thr Ser Thr
        35

<210> SEQ ID NO 274
<211> LENGTH: 35
<212> TYPE: PRT
<213> ORGANISM: Artificial Sequence
<220> FEATURE:
<223> OTHER INFORMATION: Core polypeptide

<400> SEQUENCE: 274

Ile Ser Thr Glu Leu Gly Asn Val Asn Asn Ser Ile Ser Asn Ala Leu
 1               5                  10                  15

Asp Lys Leu Glu Glu Ser Asn Ser Lys Leu Asp Lys Val Asn Val Lys
            20                  25                  30

Leu Thr Ser
        35

<210> SEQ ID NO 275
<211> LENGTH: 35
<212> TYPE: PRT
<213> ORGANISM: Artificial Sequence
<220> FEATURE:
<223> OTHER INFORMATION: Core polypeptide

<400> SEQUENCE: 275
```

```
Asp Ile Ser Thr Glu Leu Gly Asn Val Asn Asn Ser Ile Ser Asn Ala
1               5                   10                  15

Leu Asp Lys Leu Glu Glu Ser Asn Ser Lys Leu Asp Lys Val Asn Val
            20                  25                  30

Lys Leu Thr
        35

<210> SEQ ID NO 276
<211> LENGTH: 35
<212> TYPE: PRT
<213> ORGANISM: Artificial Sequence
<220> FEATURE:
<223> OTHER INFORMATION: Core polypeptide

<400> SEQUENCE: 276

Leu Asp Ile Ser Thr Glu Leu Gly Asn Val Asn Asn Ser Ile Ser Asn
1               5                   10                  15

Ala Leu Asp Lys Leu Glu Glu Ser Asn Ser Lys Leu Asp Lys Val Asn
            20                  25                  30

Val Lys Leu
        35

<210> SEQ ID NO 277
<211> LENGTH: 35
<212> TYPE: PRT
<213> ORGANISM: Artificial Sequence
<220> FEATURE:
<223> OTHER INFORMATION: Core polypeptide

<400> SEQUENCE: 277

Asn Leu Asp Ile Ser Thr Glu Leu Gly Asn Val Asn Asn Ser Ile Ser
1               5                   10                  15

Asn Ala Leu Asp Lys Leu Glu Glu Ser Asn Ser Lys Leu Asp Lys Val
            20                  25                  30

Asn Val Lys
        35

<210> SEQ ID NO 278
<211> LENGTH: 35
<212> TYPE: PRT
<213> ORGANISM: Artificial Sequence
<220> FEATURE:
<223> OTHER INFORMATION: Core polypeptide

<400> SEQUENCE: 278

Gly Asn Leu Asp Ile Ser Thr Glu Leu Gly Asn Val Asn Asn Ser Ile
1               5                   10                  15

Ser Asn Ala Leu Asp Lys Leu Glu Glu Ser Asn Ser Lys Leu Asp Lys
            20                  25                  30

Val Asn Val
        35

<210> SEQ ID NO 279
<211> LENGTH: 35
<212> TYPE: PRT
<213> ORGANISM: Artificial Sequence
<220> FEATURE:
<223> OTHER INFORMATION: Core polypeptide

<400> SEQUENCE: 279

Thr Gly Asn Leu Asp Ile Ser Thr Glu Leu Gly Asn Val Asn Asn Ser
1               5                   10                  15
```

```
Ile Ser Asn Ala Leu Asp Lys Leu Glu Glu Ser Asn Ser Lys Leu Asp
            20                  25                  30

Lys Val Asn
        35
```

<210> SEQ ID NO 280
<211> LENGTH: 35
<212> TYPE: PRT
<213> ORGANISM: Artificial Sequence
<220> FEATURE:
<223> OTHER INFORMATION: Core polypeptide

<400> SEQUENCE: 280

```
Val Thr Gly Asn Leu Asp Ile Ser Thr Glu Leu Gly Asn Val Asn Asn
 1               5                  10                  15

Ser Ile Ser Asn Ala Leu Asp Lys Leu Glu Glu Ser Asn Ser Lys Leu
            20                  25                  30

Asp Lys Val
        35
```

<210> SEQ ID NO 281
<211> LENGTH: 35
<212> TYPE: PRT
<213> ORGANISM: Artificial Sequence
<220> FEATURE:
<223> OTHER INFORMATION: Core polypeptide

<400> SEQUENCE: 281

```
Ile Val Thr Gly Asn Leu Asp Ile Ser Thr Glu Leu Gly Asn Val Asn
 1               5                  10                  15

Asn Ser Ile Ser Asn Ala Leu Asp Lys Leu Glu Glu Ser Asn Ser Lys
            20                  25                  30

Leu Asp Lys
        35
```

<210> SEQ ID NO 282
<211> LENGTH: 35
<212> TYPE: PRT
<213> ORGANISM: Artificial Sequence
<220> FEATURE:
<223> OTHER INFORMATION: Core polypeptide

<400> SEQUENCE: 282

```
Val Ile Val Thr Gly Asn Leu Asp Ile Ser Thr Glu Leu Gly Asn Val
 1               5                  10                  15

Asn Asn Ser Ile Ser Asn Ala Leu Asp Lys Leu Glu Glu Ser Asn Ser
            20                  25                  30

Lys Leu Asp
        35
```

<210> SEQ ID NO 283
<211> LENGTH: 35
<212> TYPE: PRT
<213> ORGANISM: Artificial Sequence
<220> FEATURE:
<223> OTHER INFORMATION: Core polypeptide

<400> SEQUENCE: 283

```
Gln Val Ile Val Thr Gly Asn Leu Asp Ile Ser Thr Glu Leu Gly Asn
 1               5                  10                  15

Val Asn Asn Ser Ile Ser Asn Ala Leu Asp Lys Leu Glu Glu Ser Asn
            20                  25                  30
```

Ser Lys Leu
        35

<210> SEQ ID NO 284
<211> LENGTH: 35
<212> TYPE: PRT
<213> ORGANISM: Artificial Sequence
<220> FEATURE:
<223> OTHER INFORMATION: Core polypeptide

<400> SEQUENCE: 284

Ser Gln Val Ile Val Thr Gly Asn Leu Asp Ile Ser Thr Glu Leu Gly
1               5                   10                  15

Asn Val Asn Asn Ser Ile Ser Asn Ala Leu Asp Lys Leu Glu Glu Ser
            20                  25                  30

Asn Ser Lys
        35

<210> SEQ ID NO 285
<211> LENGTH: 35
<212> TYPE: PRT
<213> ORGANISM: Artificial Sequence
<220> FEATURE:
<223> OTHER INFORMATION: Core polypeptide

<400> SEQUENCE: 285

Asp Ser Gln Val Ile Val Thr Gly Asn Leu Asp Ile Ser Thr Glu Leu
1               5                   10                  15

Gly Asn Val Asn Asn Ser Ile Ser Asn Ala Leu Asp Lys Leu Glu Glu
            20                  25                  30

Ser Asn Ser
        35

<210> SEQ ID NO 286
<211> LENGTH: 35
<212> TYPE: PRT
<213> ORGANISM: Artificial Sequence
<220> FEATURE:
<223> OTHER INFORMATION: Core polypeptide

<400> SEQUENCE: 286

Leu Asp Ser Gln Val Ile Val Thr Gly Asn Leu Asp Ile Ser Thr Glu
1               5                   10                  15

Leu Gly Asn Val Asn Asn Ser Ile Ser Asn Ala Leu Asp Lys Leu Glu
            20                  25                  30

Glu Ser Asn
        35

<210> SEQ ID NO 287
<211> LENGTH: 35
<212> TYPE: PRT
<213> ORGANISM: Artificial Sequence
<220> FEATURE:
<223> OTHER INFORMATION: Core polypeptide

<400> SEQUENCE: 287

Ile Leu Asp Ser Gln Val Ile Val Thr Gly Asn Leu Asp Ile Ser Thr
1               5                   10                  15

Glu Leu Gly Asn Val Asn Asn Ser Ile Ser Asn Ala Leu Asp Lys Leu
            20                  25                  30

Glu Glu Ser
        35

```
<210> SEQ ID NO 288
<211> LENGTH: 35
<212> TYPE: PRT
<213> ORGANISM: Artificial Sequence
<220> FEATURE:
<223> OTHER INFORMATION: Core polypeptide

<400> SEQUENCE: 288

Ser Ile Leu Asp Ser Gln Val Ile Val Thr Gly Asn Leu Asp Ile Ser
 1               5                  10                  15

Thr Glu Leu Gly Asn Val Asn Asn Ser Ile Ser Asn Ala Leu Asp Lys
            20                  25                  30

Leu Glu Glu
        35

<210> SEQ ID NO 289
<211> LENGTH: 35
<212> TYPE: PRT
<213> ORGANISM: Artificial Sequence
<220> FEATURE:
<223> OTHER INFORMATION: Core polypeptide

<400> SEQUENCE: 289

Ile Ser Ile Leu Asp Ser Gln Val Ile Val Thr Gly Asn Leu Asp Ile
 1               5                  10                  15

Ser Thr Glu Leu Gly Asn Val Asn Asn Ser Ile Ser Asn Ala Leu Asp
            20                  25                  30

Lys Leu Glu
        35

<210> SEQ ID NO 290
<211> LENGTH: 35
<212> TYPE: PRT
<213> ORGANISM: Artificial Sequence
<220> FEATURE:
<223> OTHER INFORMATION: Core polypeptide

<400> SEQUENCE: 290

Asn Ile Ser Ile Leu Asp Ser Gln Val Ile Val Thr Gly Asn Leu Asp
 1               5                  10                  15

Ile Ser Thr Glu Leu Gly Asn Val Asn Asn Ser Ile Ser Asn Ala Leu
            20                  25                  30

Asp Lys Leu
        35

<210> SEQ ID NO 291
<211> LENGTH: 35
<212> TYPE: PRT
<213> ORGANISM: Artificial Sequence
<220> FEATURE:
<223> OTHER INFORMATION: Core polypeptide

<400> SEQUENCE: 291

Lys Asn Ile Ser Ile Leu Asp Ser Gln Val Ile Val Thr Gly Asn Leu
 1               5                  10                  15

Asp Ile Ser Thr Glu Leu Gly Asn Val Asn Asn Ser Ile Ser Asn Ala
            20                  25                  30

Leu Asp Lys
        35

<210> SEQ ID NO 292
<211> LENGTH: 35
```

-continued

```
<212> TYPE: PRT
<213> ORGANISM: Artificial Sequence
<220> FEATURE:
<223> OTHER INFORMATION: Core polypeptide

<400> SEQUENCE: 292

Gln Lys Asn Ile Ser Ile Leu Asp Ser Gln Val Ile Val Thr Gly Asn
 1               5                  10                  15

Leu Asp Ile Ser Thr Glu Leu Gly Asn Val Asn Asn Ser Ile Ser Asn
            20                  25                  30

Ala Leu Asp
        35

<210> SEQ ID NO 293
<211> LENGTH: 35
<212> TYPE: PRT
<213> ORGANISM: Artificial Sequence
<220> FEATURE:
<223> OTHER INFORMATION: Core polypeptide

<400> SEQUENCE: 293

Tyr Gln Lys Asn Ile Ser Ile Leu Asp Ser Gln Val Ile Val Thr Gly
 1               5                  10                  15

Asn Leu Asp Ile Ser Thr Glu Leu Gly Asn Val Asn Asn Ser Ile Ser
            20                  25                  30

Asn Ala Leu
        35

<210> SEQ ID NO 294
<211> LENGTH: 35
<212> TYPE: PRT
<213> ORGANISM: Artificial Sequence
<220> FEATURE:
<223> OTHER INFORMATION: Core polypeptide

<400> SEQUENCE: 294

Thr Tyr Gln Lys Asn Ile Ser Ile Leu Asp Ser Gln Val Ile Val Thr
 1               5                  10                  15

Gly Asn Leu Asp Ile Ser Thr Glu Leu Gly Asn Val Asn Asn Ser Ile
            20                  25                  30

Ser Asn Ala
        35

<210> SEQ ID NO 295
<211> LENGTH: 35
<212> TYPE: PRT
<213> ORGANISM: Artificial Sequence
<220> FEATURE:
<223> OTHER INFORMATION: Core polypeptide

<400> SEQUENCE: 295

Ala Thr Tyr Gln Lys Asn Ile Ser Ile Leu Asp Ser Gln Val Ile Val
 1               5                  10                  15

Thr Gly Asn Leu Asp Ile Ser Thr Glu Leu Gly Asn Val Asn Asn Ser
            20                  25                  30

Ile Ser Asn
        35

<210> SEQ ID NO 296
<211> LENGTH: 35
<212> TYPE: PRT
<213> ORGANISM: Artificial Sequence
<220> FEATURE:
```

<223> OTHER INFORMATION: Core polypeptide

<400> SEQUENCE: 296

Asp Ala Thr Tyr Gln Lys Asn Ile Ser Ile Leu Asp Ser Gln Val Ile
1               5                   10                  15

Val Thr Gly Asn Leu Asp Ile Ser Thr Glu Leu Gly Asn Val Asn Asn
            20                  25                  30

Ser Ile Ser
        35

<210> SEQ ID NO 297
<211> LENGTH: 35
<212> TYPE: PRT
<213> ORGANISM: Artificial Sequence
<220> FEATURE:
<223> OTHER INFORMATION: Core polypeptide

<400> SEQUENCE: 297

Phe Asp Ala Thr Tyr Gln Lys Asn Ile Ser Ile Leu Asp Ser Gln Val
1               5                   10                  15

Ile Val Thr Gly Asn Leu Asp Ile Ser Thr Glu Leu Gly Asn Val Asn
            20                  25                  30

Asn Ser Ile
        35

<210> SEQ ID NO 298
<211> LENGTH: 35
<212> TYPE: PRT
<213> ORGANISM: Artificial Sequence
<220> FEATURE:
<223> OTHER INFORMATION: Core polypeptide

<400> SEQUENCE: 298

Glu Phe Asp Ala Thr Tyr Gln Lys Asn Ile Ser Ile Leu Asp Ser Gln
1               5                   10                  15

Val Ile Val Thr Gly Asn Leu Asp Ile Ser Thr Glu Leu Gly Asn Val
            20                  25                  30

Asn Asn Ser
        35

<210> SEQ ID NO 299
<211> LENGTH: 35
<212> TYPE: PRT
<213> ORGANISM: Artificial Sequence
<220> FEATURE:
<223> OTHER INFORMATION: Core polypeptide

<400> SEQUENCE: 299

Gly Glu Phe Asp Ala Thr Tyr Gln Lys Asn Ile Ser Ile Leu Asp Ser
1               5                   10                  15

Gln Val Ile Val Thr Gly Asn Leu Asp Ile Ser Thr Glu Leu Gly Asn
            20                  25                  30

Val Asn Asn
        35

<210> SEQ ID NO 300
<211> LENGTH: 35
<212> TYPE: PRT
<213> ORGANISM: Artificial Sequence
<220> FEATURE:
<223> OTHER INFORMATION: Core polypeptide

<400> SEQUENCE: 300

Ser Gly Glu Phe Asp Ala Thr Tyr Gln Lys Asn Ile Ser Ile Leu Asp
1               5                   10                  15

Ser Gln Val Ile Val Thr Gly Asn Leu Asp Ile Ser Thr Glu Leu Gly
            20                  25                  30

Asn Val Asn
        35

<210> SEQ ID NO 301
<211> LENGTH: 35
<212> TYPE: PRT
<213> ORGANISM: Artificial Sequence
<220> FEATURE:
<223> OTHER INFORMATION: Core polypeptide

<400> SEQUENCE: 301

Leu Ser Gly Glu Phe Asp Ala Thr Tyr Gln Lys Asn Ile Ser Ile Leu
1               5                   10                  15

Asp Ser Gln Val Ile Val Thr Gly Asn Leu Asp Ile Ser Thr Glu Leu
            20                  25                  30

Gly Asn Val
        35

<210> SEQ ID NO 302
<211> LENGTH: 35
<212> TYPE: PRT
<213> ORGANISM: Artificial Sequence
<220> FEATURE:
<223> OTHER INFORMATION: Core polypeptide

<400> SEQUENCE: 302

Arg Leu Ser Gly Glu Phe Asp Ala Thr Tyr Gln Lys Asn Ile Ser Ile
1               5                   10                  15

Leu Asp Ser Gln Val Ile Val Thr Gly Asn Leu Asp Ile Ser Thr Glu
            20                  25                  30

Leu Gly Asn
        35

<210> SEQ ID NO 303
<211> LENGTH: 35
<212> TYPE: PRT
<213> ORGANISM: Artificial Sequence
<220> FEATURE:
<223> OTHER INFORMATION: Core polypeptide

<400> SEQUENCE: 303

Leu Arg Leu Ser Gly Glu Phe Asp Ala Thr Tyr Gln Lys Asn Ile Ser
1               5                   10                  15

Ile Leu Asp Ser Gln Val Ile Val Thr Gly Asn Leu Asp Ile Ser Thr
            20                  25                  30

Glu Leu Gly
        35

<210> SEQ ID NO 304
<211> LENGTH: 35
<212> TYPE: PRT
<213> ORGANISM: Artificial Sequence
<220> FEATURE:
<223> OTHER INFORMATION: Core polypeptide

<400> SEQUENCE: 304

Thr Leu Arg Leu Ser Gly Glu Phe Asp Ala Thr Tyr Gln Lys Asn Ile
1               5                   10                  15

```
Ser Ile Leu Asp Ser Gln Val Ile Val Thr Gly Asn Leu Asp Ile Ser
            20                  25                  30

Thr Glu Leu
        35

<210> SEQ ID NO 305
<211> LENGTH: 35
<212> TYPE: PRT
<213> ORGANISM: Artificial Sequence
<220> FEATURE:
<223> OTHER INFORMATION: Core polypeptide

<400> SEQUENCE: 305

Ile Thr Leu Arg Leu Ser Gly Glu Phe Asp Ala Thr Tyr Gln Lys Asn
1               5                   10                  15

Ile Ser Ile Leu Asp Ser Gln Val Ile Val Thr Gly Asn Leu Asp Ile
            20                  25                  30

Ser Thr Glu
        35

<210> SEQ ID NO 306
<211> LENGTH: 35
<212> TYPE: PRT
<213> ORGANISM: Artificial Sequence
<220> FEATURE:
<223> OTHER INFORMATION: Core polypeptide

<400> SEQUENCE: 306

Gly Ile Thr Leu Arg Leu Ser Gly Glu Phe Asp Ala Thr Tyr Gln Lys
1               5                   10                  15

Asn Ile Ser Ile Leu Asp Ser Gln Val Ile Val Thr Gly Asn Leu Asp
            20                  25                  30

Ile Ser Thr
        35

<210> SEQ ID NO 307
<211> LENGTH: 35
<212> TYPE: PRT
<213> ORGANISM: Artificial Sequence
<220> FEATURE:
<223> OTHER INFORMATION: Core polypeptide

<400> SEQUENCE: 307

Thr Ala Thr Ile Glu Ala Val His Glu Val Thr Asp Gly Leu Ser Gln
1               5                   10                  15

Leu Ala Val Ala Val Gly Lys Met Gln Gln Phe Val Asn Asp Gln Phe
            20                  25                  30

Asn Asn Thr
        35

<210> SEQ ID NO 308
<211> LENGTH: 35
<212> TYPE: PRT
<213> ORGANISM: Artificial Sequence
<220> FEATURE:
<223> OTHER INFORMATION: Core polypeptide

<400> SEQUENCE: 308

Ile Thr Ala Thr Ile Glu Ala Val His Glu Val Thr Asp Gly Leu Ser
1               5                   10                  15

Gln Leu Ala Val Ala Val Gly Lys Met Gln Gln Phe Val Asn Asp Gln
            20                  25                  30
```

Phe Asn Asn
        35

<210> SEQ ID NO 309
<211> LENGTH: 35
<212> TYPE: PRT
<213> ORGANISM: Artificial Sequence
<220> FEATURE:
<223> OTHER INFORMATION: Core polypeptide

<400> SEQUENCE: 309

Ser Ile Thr Ala Thr Ile Glu Ala Val His Glu Val Thr Asp Gly Leu
 1               5                  10                  15

Ser Gln Leu Ala Val Ala Val Gly Lys Met Gln Gln Phe Val Asn Asp
            20                  25                  30

Gln Phe Asn
        35

<210> SEQ ID NO 310
<211> LENGTH: 35
<212> TYPE: PRT
<213> ORGANISM: Artificial Sequence
<220> FEATURE:
<223> OTHER INFORMATION: Core polypeptide

<400> SEQUENCE: 310

Lys Glu Ser Ile Thr Ala Thr Ile Glu Ala Val His Glu Val Thr Asp
 1               5                  10                  15

Gly Leu Ser Gln Leu Ala Val Ala Val Gly Lys Met Gln Gln Phe Val
            20                  25                  30

Asn Asp Gln
        35

<210> SEQ ID NO 311
<211> LENGTH: 35
<212> TYPE: PRT
<213> ORGANISM: Artificial Sequence
<220> FEATURE:
<223> OTHER INFORMATION: Core polypeptide

<400> SEQUENCE: 311

Leu Lys Glu Ser Ile Thr Ala Thr Ile Glu Ala Val His Glu Val Thr
 1               5                  10                  15

Asp Gly Leu Ser Gln Leu Ala Val Ala Val Gly Lys Met Gln Gln Phe
            20                  25                  30

Val Asn Asp
        35

<210> SEQ ID NO 312
<211> LENGTH: 35
<212> TYPE: PRT
<213> ORGANISM: Artificial Sequence
<220> FEATURE:
<223> OTHER INFORMATION: Core polypeptide

<400> SEQUENCE: 312

Arg Leu Lys Glu Ser Ile Thr Ala Thr Ile Glu Ala Val His Glu Val
 1               5                  10                  15

Thr Asp Gly Leu Ser Gln Leu Ala Val Ala Val Gly Lys Met Gln Gln
            20                  25                  30

Phe Val Asn
        35

-continued

<210> SEQ ID NO 313
<211> LENGTH: 35
<212> TYPE: PRT
<213> ORGANISM: Artificial Sequence
<220> FEATURE:
<223> OTHER INFORMATION: Core polypeptide

<400> SEQUENCE: 313

Leu Arg Leu Lys Glu Ser Ile Thr Ala Thr Ile Glu Ala Val His Glu
1               5                   10                  15

Val Thr Asp Gly Leu Ser Gln Leu Ala Val Ala Val Gly Lys Met Gln
            20                  25                  30

Gln Phe Val
        35

<210> SEQ ID NO 314
<211> LENGTH: 35
<212> TYPE: PRT
<213> ORGANISM: Artificial Sequence
<220> FEATURE:
<223> OTHER INFORMATION: Core polypeptide

<400> SEQUENCE: 314

Ile Leu Arg Leu Lys Glu Ser Ile Thr Ala Thr Ile Glu Ala Val His
1               5                   10                  15

Glu Val Thr Asp Gly Leu Ser Gln Leu Ala Val Ala Val Gly Lys Met
            20                  25                  30

Gln Gln Phe
        35

<210> SEQ ID NO 315
<211> LENGTH: 35
<212> TYPE: PRT
<213> ORGANISM: Artificial Sequence
<220> FEATURE:
<223> OTHER INFORMATION: Core polypeptide

<400> SEQUENCE: 315

Asn Ile Leu Arg Leu Lys Glu Ser Ile Thr Ala Thr Ile Glu Ala Val
1               5                   10                  15

His Glu Val Thr Asp Gly Leu Ser Gln Leu Ala Val Ala Val Gly Lys
            20                  25                  30

Met Gln Gln
        35

<210> SEQ ID NO 316
<211> LENGTH: 35
<212> TYPE: PRT
<213> ORGANISM: Artificial Sequence
<220> FEATURE:
<223> OTHER INFORMATION: Core polypeptide

<400> SEQUENCE: 316

Ala Asn Ile Leu Arg Leu Lys Glu Ser Ile Thr Ala Thr Ile Glu Ala
1               5                   10                  15

Val His Glu Val Thr Asp Gly Leu Ser Gln Leu Ala Val Ala Val Gly
            20                  25                  30

Lys Met Gln
        35

<210> SEQ ID NO 317

```
<211> LENGTH: 35
<212> TYPE: PRT
<213> ORGANISM: Artificial Sequence
<220> FEATURE:
<223> OTHER INFORMATION: Core polypeptide

<400> SEQUENCE: 317

Ala Ala Asn Ile Leu Arg Leu Lys Glu Ser Ile Thr Ala Thr Ile Glu
 1               5                  10                  15

Ala Val His Glu Val Thr Asp Gly Leu Ser Gln Leu Ala Val Ala Val
            20                  25                  30

Gly Lys Met
        35

<210> SEQ ID NO 318
<211> LENGTH: 35
<212> TYPE: PRT
<213> ORGANISM: Artificial Sequence
<220> FEATURE:
<223> OTHER INFORMATION: Core polypeptide

<400> SEQUENCE: 318

His Lys Cys Asp Asp Glu Cys Met Asn Ser Val Lys Asn Gly Thr Tyr
 1               5                  10                  15

Asp Tyr Pro Lys Tyr Glu Glu Glu Ser Lys Leu Asn Arg Asn Glu Ile
            20                  25                  30

Lys Gly Val
        35

<210> SEQ ID NO 319
<211> LENGTH: 35
<212> TYPE: PRT
<213> ORGANISM: Artificial Sequence
<220> FEATURE:
<223> OTHER INFORMATION: Core polypeptide

<400> SEQUENCE: 319

Lys Cys Asp Asp Glu Cys Met Asn Ser Val Lys Asn Gly Thr Tyr Asp
 1               5                  10                  15

Tyr Pro Lys Tyr Glu Glu Glu Ser Lys Leu Asn Arg Asn Glu Ile Lys
            20                  25                  30

Gly Val Lys
        35

<210> SEQ ID NO 320
<211> LENGTH: 35
<212> TYPE: PRT
<213> ORGANISM: Artificial Sequence
<220> FEATURE:
<223> OTHER INFORMATION: Core polypeptide

<400> SEQUENCE: 320

Cys Asp Asp Glu Cys Met Asn Ser Val Lys Asn Gly Thr Tyr Asp Tyr
 1               5                  10                  15

Pro Lys Tyr Glu Glu Glu Ser Lys Leu Asn Arg Asn Glu Ile Lys Gly
            20                  25                  30

Val Lys Leu
        35

<210> SEQ ID NO 321
<211> LENGTH: 35
<212> TYPE: PRT
<213> ORGANISM: Artificial Sequence
```

```
<220> FEATURE:
<223> OTHER INFORMATION: Core polypeptide

<400> SEQUENCE: 321

Asp Asp Glu Cys Met Asn Ser Val Lys Asn Gly Thr Tyr Asp Tyr Pro
1               5                   10                  15
Lys Tyr Glu Glu Glu Ser Lys Leu Asn Arg Asn Glu Ile Lys Gly Val
            20                  25                  30
Lys Leu Ser
        35

<210> SEQ ID NO 322
<211> LENGTH: 35
<212> TYPE: PRT
<213> ORGANISM: Artificial Sequence
<220> FEATURE:
<223> OTHER INFORMATION: Core polypeptide

<400> SEQUENCE: 322

Asp Glu Cys Met Asn Ser Val Lys Asn Gly Thr Tyr Asp Tyr Pro Lys
1               5                   10                  15
Tyr Glu Glu Glu Ser Lys Leu Asn Arg Asn Glu Ile Lys Gly Val Lys
            20                  25                  30
Leu Ser Ser
        35

<210> SEQ ID NO 323
<211> LENGTH: 35
<212> TYPE: PRT
<213> ORGANISM: Artificial Sequence
<220> FEATURE:
<223> OTHER INFORMATION: Core polypeptide

<400> SEQUENCE: 323

Glu Cys Met Asn Ser Val Lys Asn Gly Thr Tyr Asp Tyr Pro Lys Tyr
1               5                   10                  15
Glu Glu Glu Ser Lys Leu Asn Arg Asn Glu Ile Lys Gly Val Lys Leu
            20                  25                  30
Ser Ser Met
        35

<210> SEQ ID NO 324
<211> LENGTH: 35
<212> TYPE: PRT
<213> ORGANISM: Artificial Sequence
<220> FEATURE:
<223> OTHER INFORMATION: Core polypeptide

<400> SEQUENCE: 324

Cys Met Asn Ser Val Lys Asn Gly Thr Tyr Asp Tyr Pro Lys Tyr Glu
1               5                   10                  15
Glu Glu Ser Lys Leu Asn Arg Asn Glu Ile Lys Gly Val Lys Leu Ser
            20                  25                  30
Ser Met Gly
        35

<210> SEQ ID NO 325
<211> LENGTH: 35
<212> TYPE: PRT
<213> ORGANISM: Artificial Sequence
<220> FEATURE:
<223> OTHER INFORMATION: Core polypeptide
```

-continued

```
<400> SEQUENCE: 325

Met Asn Ser Val Lys Asn Gly Thr Tyr Asp Tyr Pro Lys Tyr Glu Glu
  1               5                  10                  15

Glu Ser Lys Leu Asn Arg Asn Glu Ile Lys Gly Val Lys Leu Ser Ser
             20                  25                  30

Met Gly Val
        35

<210> SEQ ID NO 326
<211> LENGTH: 35
<212> TYPE: PRT
<213> ORGANISM: Artificial Sequence
<220> FEATURE:
<223> OTHER INFORMATION: Core polypeptide

<400> SEQUENCE: 326

Asn Ser Val Lys Asn Gly Thr Tyr Asp Tyr Pro Lys Tyr Glu Glu Glu
  1               5                  10                  15

Ser Lys Leu Asn Arg Asn Glu Ile Lys Gly Val Lys Leu Ser Ser Met
             20                  25                  30

Gly Val Tyr
        35

<210> SEQ ID NO 327
<211> LENGTH: 35
<212> TYPE: PRT
<213> ORGANISM: Artificial Sequence
<220> FEATURE:
<223> OTHER INFORMATION: Core polypeptide

<400> SEQUENCE: 327

Ser Val Lys Asn Gly Thr Tyr Asp Tyr Pro Lys Tyr Glu Glu Glu Ser
  1               5                  10                  15

Lys Leu Asn Arg Asn Glu Ile Lys Gly Val Lys Leu Ser Ser Met Gly
             20                  25                  30

Val Tyr Gln
        35

<210> SEQ ID NO 328
<211> LENGTH: 35
<212> TYPE: PRT
<213> ORGANISM: Artificial Sequence
<220> FEATURE:
<223> OTHER INFORMATION: Core polypeptide

<400> SEQUENCE: 328

Val Lys Asn Gly Thr Tyr Asp Tyr Pro Lys Tyr Glu Glu Glu Ser Lys
  1               5                  10                  15

Leu Asn Arg Asn Glu Ile Lys Gly Val Lys Leu Ser Ser Met Gly Val
             20                  25                  30

Tyr Gln Ile
        35

<210> SEQ ID NO 329
<211> LENGTH: 35
<212> TYPE: PRT
<213> ORGANISM: Artificial Sequence
<220> FEATURE:
<223> OTHER INFORMATION: Core polypeptide

<400> SEQUENCE: 329

Lys Asn Gly Thr Tyr Asp Tyr Pro Lys Tyr Glu Glu Glu Ser Lys Leu
```

-continued

```
                1               5                  10                15

Asn Arg Asn Glu Ile Lys Gly Val Lys Leu Ser Ser Met Gly Val Tyr
                    20                  25                  30

Gln Ile Leu
        35

<210> SEQ ID NO 330
<211> LENGTH: 13
<212> TYPE: PRT
<213> ORGANISM: Artificial Sequence
<220> FEATURE:
<223> OTHER INFORMATION: Core polypeptide

<400> SEQUENCE: 330

Ala Phe Ile Arg Lys Ser Asp Glu Leu Leu His Asn Val
 1               5                  10

<210> SEQ ID NO 331
<211> LENGTH: 35
<212> TYPE: PRT
<213> ORGANISM: Artificial Sequence
<220> FEATURE:
<223> OTHER INFORMATION: Core polypeptide

<400> SEQUENCE: 331

Val Val Leu Ala Gly Ala Ala Leu Gly Val Ala Thr Ala Ala Gln Ile
 1               5                  10                  15

Thr Ala Gly Ile Ala Leu His Gln Ser Met Leu Asn Ser Gln Ala Ile
                20                  25                  30

Asp Asn Leu
        35

<210> SEQ ID NO 332
<211> LENGTH: 35
<212> TYPE: PRT
<213> ORGANISM: Artificial Sequence
<220> FEATURE:
<223> OTHER INFORMATION: Core polypeptide

<400> SEQUENCE: 332

Val Leu Ala Gly Ala Ala Leu Gly Val Ala Thr Ala Ala Gln Ile Thr
 1               5                  10                  15

Ala Gly Ile Ala Leu His Gln Ser Met Leu Asn Ser Gln Ala Ile Asp
                20                  25                  30

Asn Leu Arg
        35

<210> SEQ ID NO 333
<211> LENGTH: 35
<212> TYPE: PRT
<213> ORGANISM: Artificial Sequence
<220> FEATURE:
<223> OTHER INFORMATION: Core polypeptide

<400> SEQUENCE: 333

Leu Ala Gly Ala Ala Leu Gly Val Ala Thr Ala Ala Gln Ile Thr Ala
 1               5                  10                  15

Gly Ile Ala Leu His Gln Ser Met Leu Asn Ser Gln Ala Ile Asp Asn
                20                  25                  30

Leu Arg Ala
        35
```

<210> SEQ ID NO 334
<211> LENGTH: 35
<212> TYPE: PRT
<213> ORGANISM: Artificial Sequence
<220> FEATURE:
<223> OTHER INFORMATION: Core polypeptide

<400> SEQUENCE: 334

Ala Gly Ala Ala Leu Gly Val Ala Thr Ala Ala Gln Ile Thr Ala Gly
1               5                   10                  15

Ile Ala Leu His Gln Ser Met Leu Asn Ser Gln Ala Ile Asp Asn Leu
            20                  25                  30

Arg Ala Ser
        35

<210> SEQ ID NO 335
<211> LENGTH: 35
<212> TYPE: PRT
<213> ORGANISM: Artificial Sequence
<220> FEATURE:
<223> OTHER INFORMATION: Core polypeptide

<400> SEQUENCE: 335

Gly Ala Ala Leu Gly Val Ala Thr Ala Ala Gln Ile Thr Ala Gly Ile
1               5                   10                  15

Ala Leu His Gln Ser Met Leu Asn Ser Gln Ala Ile Asp Asn Leu Arg
            20                  25                  30

Ala Ser Leu
        35

<210> SEQ ID NO 336
<211> LENGTH: 35
<212> TYPE: PRT
<213> ORGANISM: Artificial Sequence
<220> FEATURE:
<223> OTHER INFORMATION: Core polypeptide

<400> SEQUENCE: 336

Ala Ala Leu Gly Val Ala Thr Ala Ala Gln Ile Thr Ala Gly Ile Ala
1               5                   10                  15

Leu His Gln Ser Met Leu Asn Ser Gln Ala Ile Asp Asn Leu Arg Ala
            20                  25                  30

Ser Leu Glu
        35

<210> SEQ ID NO 337
<211> LENGTH: 35
<212> TYPE: PRT
<213> ORGANISM: Artificial Sequence
<220> FEATURE:
<223> OTHER INFORMATION: Core polypeptide

<400> SEQUENCE: 337

Ala Leu Gly Val Ala Thr Ala Ala Gln Ile Thr Ala Gly Ile Ala Leu
1               5                   10                  15

His Gln Ser Met Leu Asn Ser Gln Ala Ile Asp Asn Leu Arg Ala Ser
            20                  25                  30

Leu Glu Thr
        35

<210> SEQ ID NO 338
<211> LENGTH: 35
<212> TYPE: PRT

<213> ORGANISM: Artificial Sequence
<220> FEATURE:
<223> OTHER INFORMATION: Core polypeptide

<400> SEQUENCE: 338

Leu Gly Val Ala Thr Ala Ala Gln Ile Thr Ala Gly Ile Ala Leu His
1               5                   10                  15

Gln Ser Met Leu Asn Ser Gln Ala Ile Asp Asn Leu Arg Ala Ser Leu
            20                  25                  30

Glu Thr Thr
        35

<210> SEQ ID NO 339
<211> LENGTH: 35
<212> TYPE: PRT
<213> ORGANISM: Artificial Sequence
<220> FEATURE:
<223> OTHER INFORMATION: Core polypeptide

<400> SEQUENCE: 339

Gly Val Ala Thr Ala Ala Gln Ile Thr Ala Gly Ile Ala Leu His Gln
1               5                   10                  15

Ser Met Leu Asn Ser Gln Ala Ile Asp Asn Leu Arg Ala Ser Leu Glu
            20                  25                  30

Thr Thr Asn
        35

<210> SEQ ID NO 340
<211> LENGTH: 35
<212> TYPE: PRT
<213> ORGANISM: Artificial Sequence
<220> FEATURE:
<223> OTHER INFORMATION: Core polypeptide

<400> SEQUENCE: 340

Val Ala Thr Ala Ala Gln Ile Thr Ala Gly Ile Ala Leu His Gln Ser
1               5                   10                  15

Met Leu Asn Ser Gln Ala Ile Asp Asn Leu Arg Ala Ser Leu Glu Thr
            20                  25                  30

Thr Asn Gln
        35

<210> SEQ ID NO 341
<211> LENGTH: 35
<212> TYPE: PRT
<213> ORGANISM: Artificial Sequence
<220> FEATURE:
<223> OTHER INFORMATION: Core polypeptide

<400> SEQUENCE: 341

Ala Thr Ala Ala Gln Ile Thr Ala Gly Ile Ala Leu His Gln Ser Met
1               5                   10                  15

Leu Asn Ser Gln Ala Ile Asp Asn Leu Arg Ala Ser Leu Glu Thr Thr
            20                  25                  30

Asn Gln Ala
        35

<210> SEQ ID NO 342
<211> LENGTH: 35
<212> TYPE: PRT
<213> ORGANISM: Artificial Sequence
<220> FEATURE:
<223> OTHER INFORMATION: Core polypeptide

<400> SEQUENCE: 342

Thr Ala Ala Gln Ile Thr Ala Gly Ile Ala Leu His Gln Ser Met Leu
1               5                   10                  15

Asn Ser Gln Ala Ile Asp Asn Leu Arg Ala Ser Leu Glu Thr Thr Asn
            20                  25                  30

Gln Ala Ile
        35

<210> SEQ ID NO 343
<211> LENGTH: 35
<212> TYPE: PRT
<213> ORGANISM: Artificial Sequence
<220> FEATURE:
<223> OTHER INFORMATION: Core polypeptide

<400> SEQUENCE: 343

Ala Ala Gln Ile Thr Ala Gly Ile Ala Leu His Gln Ser Met Leu Asn
1               5                   10                  15

Ser Gln Ala Ile Asp Asn Leu Arg Ala Ser Leu Glu Thr Thr Asn Gln
            20                  25                  30

Ala Ile Glu
        35

<210> SEQ ID NO 344
<211> LENGTH: 35
<212> TYPE: PRT
<213> ORGANISM: Artificial Sequence
<220> FEATURE:
<223> OTHER INFORMATION: Core polypeptide

<400> SEQUENCE: 344

Ala Gln Ile Thr Ala Gly Ile Ala Leu His Gln Ser Met Leu Asn Ser
1               5                   10                  15

Gln Ala Ile Asp Asn Leu Arg Ala Ser Leu Glu Thr Thr Asn Gln Ala
            20                  25                  30

Ile Glu Ala
        35

<210> SEQ ID NO 345
<211> LENGTH: 35
<212> TYPE: PRT
<213> ORGANISM: Artificial Sequence
<220> FEATURE:
<223> OTHER INFORMATION: Core polypeptide

<400> SEQUENCE: 345

Gln Ile Thr Ala Gly Ile Ala Leu His Gln Ser Met Leu Asn Ser Gln
1               5                   10                  15

Ala Ile Asp Asn Leu Arg Ala Ser Leu Glu Thr Thr Asn Gln Ala Ile
            20                  25                  30

Glu Ala Ile
        35

<210> SEQ ID NO 346
<211> LENGTH: 35
<212> TYPE: PRT
<213> ORGANISM: Artificial Sequence
<220> FEATURE:
<223> OTHER INFORMATION: Core polypeptide

<400> SEQUENCE: 346

```
Ile Thr Ala Gly Ile Ala Leu His Gln Ser Met Leu Asn Ser Gln Ala
 1               5                  10                  15

Ile Asp Asn Leu Arg Ala Ser Leu Glu Thr Thr Asn Gln Ala Ile Glu
                20                  25                  30

Ala Ile Arg
        35

<210> SEQ ID NO 347
<211> LENGTH: 35
<212> TYPE: PRT
<213> ORGANISM: Artificial Sequence
<220> FEATURE:
<223> OTHER INFORMATION: Core polypeptide

<400> SEQUENCE: 347

Thr Ala Gly Ile Ala Leu His Gln Ser Met Leu Asn Ser Gln Ala Ile
 1               5                  10                  15

Asp Asn Leu Arg Ala Ser Leu Glu Thr Thr Asn Gln Ala Ile Glu Ala
                20                  25                  30

Ile Arg Gln
        35

<210> SEQ ID NO 348
<211> LENGTH: 35
<212> TYPE: PRT
<213> ORGANISM: Artificial Sequence
<220> FEATURE:
<223> OTHER INFORMATION: Core polypeptide

<400> SEQUENCE: 348

Ala Gly Ile Ala Leu His Gln Ser Met Leu Asn Ser Gln Ala Ile Asp
 1               5                  10                  15

Asn Leu Arg Ala Ser Leu Glu Thr Thr Asn Gln Ala Ile Glu Ala Ile
                20                  25                  30

Arg Gln Ala
        35

<210> SEQ ID NO 349
<211> LENGTH: 35
<212> TYPE: PRT
<213> ORGANISM: Artificial Sequence
<220> FEATURE:
<223> OTHER INFORMATION: Core polypeptide

<400> SEQUENCE: 349

Gly Ile Ala Leu His Gln Ser Met Leu Asn Ser Gln Ala Ile Asp Asn
 1               5                  10                  15

Leu Arg Ala Ser Leu Glu Thr Thr Asn Gln Ala Ile Glu Ala Ile Arg
                20                  25                  30

Gln Ala Gly
        35

<210> SEQ ID NO 350
<211> LENGTH: 35
<212> TYPE: PRT
<213> ORGANISM: Artificial Sequence
<220> FEATURE:
<223> OTHER INFORMATION: Core polypeptide

<400> SEQUENCE: 350

Ile Ala Leu His Gln Ser Met Leu Asn Ser Gln Ala Ile Asp Asn Leu
 1               5                  10                  15
```

-continued

Arg Ala Ser Leu Glu Thr Thr Asn Gln Ala Ile Glu Ala Ile Arg Gln
                20                  25                  30

Ala Gly Gln
        35

<210> SEQ ID NO 351
<211> LENGTH: 35
<212> TYPE: PRT
<213> ORGANISM: Artificial Sequence
<220> FEATURE:
<223> OTHER INFORMATION: Core polypeptide

<400> SEQUENCE: 351

Ala Leu His Gln Ser Met Leu Asn Ser Gln Ala Ile Asp Asn Leu Arg
1               5                   10                  15

Ala Ser Leu Glu Thr Thr Asn Gln Ala Ile Glu Ala Ile Arg Gln Ala
                20                  25                  30

Gly Gln Glu
        35

<210> SEQ ID NO 352
<211> LENGTH: 35
<212> TYPE: PRT
<213> ORGANISM: Artificial Sequence
<220> FEATURE:
<223> OTHER INFORMATION: Core polypeptide

<400> SEQUENCE: 352

Leu His Gln Ser Met Leu Asn Ser Gln Ala Ile Asp Asn Leu Arg Ala
1               5                   10                  15

Ser Leu Glu Thr Thr Asn Gln Ala Ile Glu Ala Ile Arg Gln Ala Gly
                20                  25                  30

Gln Glu Met
        35

<210> SEQ ID NO 353
<211> LENGTH: 35
<212> TYPE: PRT
<213> ORGANISM: Artificial Sequence
<220> FEATURE:
<223> OTHER INFORMATION: Core polypeptide

<400> SEQUENCE: 353

His Gln Ser Met Leu Asn Ser Gln Ala Ile Asp Asn Leu Arg Ala Ser
1               5                   10                  15

Leu Glu Thr Thr Asn Gln Ala Ile Glu Ala Ile Arg Gln Ala Gly Gln
                20                  25                  30

Glu Met Ile
        35

<210> SEQ ID NO 354
<211> LENGTH: 35
<212> TYPE: PRT
<213> ORGANISM: Artificial Sequence
<220> FEATURE:
<223> OTHER INFORMATION: Core polypeptide

<400> SEQUENCE: 354

Gln Ser Met Leu Asn Ser Gln Ala Ile Asp Asn Leu Arg Ala Ser Leu
1               5                   10                  15

Glu Thr Thr Asn Gln Ala Ile Glu Ala Ile Arg Gln Ala Gly Gln Glu
                20                  25                  30

```
Met Ile Leu
        35

<210> SEQ ID NO 355
<211> LENGTH: 35
<212> TYPE: PRT
<213> ORGANISM: Artificial Sequence
<220> FEATURE:
<223> OTHER INFORMATION: Core polypeptide

<400> SEQUENCE: 355

Ser Met Leu Asn Ser Gln Ala Ile Asp Asn Leu Arg Ala Ser Leu Glu
 1               5                  10                  15

Thr Thr Asn Gln Ala Ile Glu Ala Ile Arg Gln Ala Gly Gln Glu Met
            20                  25                  30

Ile Leu Ala
        35

<210> SEQ ID NO 356
<211> LENGTH: 35
<212> TYPE: PRT
<213> ORGANISM: Artificial Sequence
<220> FEATURE:
<223> OTHER INFORMATION: Core polypeptide

<400> SEQUENCE: 356

Met Leu Asn Ser Gln Ala Ile Asp Asn Leu Arg Ala Ser Leu Glu Thr
 1               5                  10                  15

Thr Asn Gln Ala Ile Glu Ala Ile Arg Gln Ala Gly Gln Glu Met Ile
            20                  25                  30

Leu Ala Val
        35

<210> SEQ ID NO 357
<211> LENGTH: 35
<212> TYPE: PRT
<213> ORGANISM: Artificial Sequence
<220> FEATURE:
<223> OTHER INFORMATION: Core polypeptide

<400> SEQUENCE: 357

Leu Asn Ser Gln Ala Ile Asp Asn Leu Arg Ala Ser Leu Glu Thr Thr
 1               5                  10                  15

Asn Gln Ala Ile Glu Ala Ile Arg Gln Ala Gly Gln Glu Met Ile Leu
            20                  25                  30

Ala Val Gln
        35

<210> SEQ ID NO 358
<211> LENGTH: 35
<212> TYPE: PRT
<213> ORGANISM: Artificial Sequence
<220> FEATURE:
<223> OTHER INFORMATION: Core polypeptide

<400> SEQUENCE: 358

Asn Ser Gln Ala Ile Asp Asn Leu Arg Ala Ser Leu Glu Thr Thr Asn
 1               5                  10                  15

Gln Ala Ile Glu Ala Ile Arg Gln Ala Gly Gln Glu Met Ile Leu Ala
            20                  25                  30

Val Gln Gly
        35
```

<210> SEQ ID NO 359
<211> LENGTH: 35
<212> TYPE: PRT
<213> ORGANISM: Artificial Sequence
<220> FEATURE:
<223> OTHER INFORMATION: Core polypeptide

<400> SEQUENCE: 359

Ser Gln Ala Ile Asp Asn Leu Arg Ala Ser Leu Glu Thr Thr Asn Gln
1               5                   10                  15

Ala Ile Glu Ala Ile Arg Gln Ala Gly Gln Glu Met Ile Leu Ala Val
            20                  25                  30

Gln Gly Val
        35

<210> SEQ ID NO 360
<211> LENGTH: 35
<212> TYPE: PRT
<213> ORGANISM: Artificial Sequence
<220> FEATURE:
<223> OTHER INFORMATION: Core polypeptide

<400> SEQUENCE: 360

Gln Ala Ile Asp Asn Leu Arg Ala Ser Leu Glu Thr Thr Asn Gln Ala
1               5                   10                  15

Ile Glu Ala Ile Arg Gln Ala Gly Gln Glu Met Ile Leu Ala Val Gln
            20                  25                  30

Gly Val Gln
        35

<210> SEQ ID NO 361
<211> LENGTH: 35
<212> TYPE: PRT
<213> ORGANISM: Artificial Sequence
<220> FEATURE:
<223> OTHER INFORMATION: Core polypeptide

<400> SEQUENCE: 361

Ala Ile Asp Asn Leu Arg Ala Ser Leu Glu Thr Thr Asn Gln Ala Ile
1               5                   10                  15

Glu Ala Ile Arg Gln Ala Gly Gln Glu Met Ile Leu Ala Val Gln Gly
            20                  25                  30

Val Gln Asp
        35

<210> SEQ ID NO 362
<211> LENGTH: 35
<212> TYPE: PRT
<213> ORGANISM: Artificial Sequence
<220> FEATURE:
<223> OTHER INFORMATION: Core polypeptide

<400> SEQUENCE: 362

Ile Asp Asn Leu Arg Ala Ser Leu Glu Thr Thr Asn Gln Ala Ile Glu
1               5                   10                  15

Ala Ile Arg Gln Ala Gly Gln Glu Met Ile Leu Ala Val Gln Gly Val
            20                  25                  30

Gln Asp Tyr
        35

<210> SEQ ID NO 363
<211> LENGTH: 35

```
<212> TYPE: PRT
<213> ORGANISM: Artificial Sequence
<220> FEATURE:
<223> OTHER INFORMATION: Core polypeptide

<400> SEQUENCE: 363

Asp Asn Leu Arg Ala Ser Leu Glu Thr Thr Asn Gln Ala Ile Glu Ala
 1               5                  10                  15

Ile Arg Gln Ala Gly Gln Glu Met Ile Leu Ala Val Gln Gly Val Gln
            20                  25                  30

Asp Tyr Ile
        35

<210> SEQ ID NO 364
<211> LENGTH: 35
<212> TYPE: PRT
<213> ORGANISM: Artificial Sequence
<220> FEATURE:
<223> OTHER INFORMATION: Core polypeptide

<400> SEQUENCE: 364

Asn Leu Arg Ala Ser Leu Glu Thr Thr Asn Gln Ala Ile Glu Ala Ile
 1               5                  10                  15

Arg Gln Ala Gly Gln Glu Met Ile Leu Ala Val Gln Gly Val Gln Asp
            20                  25                  30

Tyr Ile Asn
        35

<210> SEQ ID NO 365
<211> LENGTH: 35
<212> TYPE: PRT
<213> ORGANISM: Artificial Sequence
<220> FEATURE:
<223> OTHER INFORMATION: Core polypeptide

<400> SEQUENCE: 365

Leu Arg Ala Ser Leu Glu Thr Thr Asn Gln Ala Ile Glu Ala Ile Arg
 1               5                  10                  15

Gln Ala Gly Gln Glu Met Ile Leu Ala Val Gln Gly Val Gln Asp Tyr
            20                  25                  30

Ile Asn Asn
        35

<210> SEQ ID NO 366
<211> LENGTH: 35
<212> TYPE: PRT
<213> ORGANISM: Artificial Sequence
<220> FEATURE:
<223> OTHER INFORMATION: Core polypeptide

<400> SEQUENCE: 366

Arg Ala Ser Leu Glu Thr Thr Asn Gln Ala Ile Glu Ala Ile Arg Gln
 1               5                  10                  15

Ala Gly Gln Glu Met Ile Leu Ala Val Gln Gly Val Gln Asp Tyr Ile
            20                  25                  30

Asn Asn Glu
        35

<210> SEQ ID NO 367
<211> LENGTH: 33
<212> TYPE: PRT
<213> ORGANISM: Artificial Sequence
<220> FEATURE:
```

<223> OTHER INFORMATION: Core polypeptide

<400> SEQUENCE: 367

Tyr Thr Ser Val Ile Thr Ile Glu Leu Ser Asn Ile Lys Glu Asn Lys
 1               5                  10                  15

Asn Gly Thr Asp Ala Val Lys Leu Ile Lys Gln Glu Leu Asp Lys Tyr
             20                  25                  30

Lys

<210> SEQ ID NO 368
<211> LENGTH: 33
<212> TYPE: PRT
<213> ORGANISM: Artificial Sequence
<220> FEATURE:
<223> OTHER INFORMATION: Core polypeptide

<400> SEQUENCE: 368

Thr Ser Val Ile Thr Ile Glu Leu Ser Asn Ile Lys Glu Asn Lys Asn
 1               5                  10                  15

Gly Thr Asp Ala Val Lys Leu Ile Lys Gln Glu Leu Asp Lys Tyr Lys
             20                  25                  30

Asn

<210> SEQ ID NO 369
<211> LENGTH: 33
<212> TYPE: PRT
<213> ORGANISM: Artificial Sequence
<220> FEATURE:
<223> OTHER INFORMATION: Core polypeptide

<400> SEQUENCE: 369

Ser Val Ile Thr Ile Glu Leu Ser Asn Ile Lys Glu Asn Lys Asn Gly
 1               5                  10                  15

Thr Asp Ala Val Lys Leu Ile Lys Gln Glu Leu Asp Lys Tyr Lys Asn
             20                  25                  30

Ala

<210> SEQ ID NO 370
<211> LENGTH: 34
<212> TYPE: PRT
<213> ORGANISM: Artificial Sequence
<220> FEATURE:
<223> OTHER INFORMATION: Core polypeptide

<400> SEQUENCE: 370

Ser Asn Ile Lys Glu Asn Lys Asn Gly Thr Asp Ala Lys Val Lys Leu
 1               5                  10                  15

Ile Lys Gln Glu Leu Asp Lys Tyr Lys Asn Ala Val Thr Glu Leu Gln
             20                  25                  30

Leu Leu

<210> SEQ ID NO 371
<211> LENGTH: 34
<212> TYPE: PRT
<213> ORGANISM: Artificial Sequence
<220> FEATURE:
<223> OTHER INFORMATION: Core polypeptide

<400> SEQUENCE: 371

Lys Glu Asn Lys Asn Gly Thr Asp Ala Lys Val Lys Leu Ile Lys Gln
 1               5                  10                  15

Glu Leu Asp Lys Tyr Lys Asn Ala Val Thr Glu Leu Gln Leu Leu Met
            20                  25                  30

Gln Ser

<210> SEQ ID NO 372
<211> LENGTH: 15
<212> TYPE: PRT
<213> ORGANISM: Artificial Sequence
<220> FEATURE:
<223> OTHER INFORMATION: Core polypeptide

<400> SEQUENCE: 372

Cys Leu Glu Leu Asp Lys Trp Ala Ser Leu Trp Asn Trp Phe Cys
 1               5                  10                  15

<210> SEQ ID NO 373
<211> LENGTH: 15
<212> TYPE: PRT
<213> ORGANISM: Artificial Sequence
<220> FEATURE:
<223> OTHER INFORMATION: Core polypeptide

<400> SEQUENCE: 373

Cys Leu Glu Leu Asp Lys Trp Ala Ser Leu Ala Asn Trp Phe Cys
 1               5                  10                  15

<210> SEQ ID NO 374
<211> LENGTH: 15
<212> TYPE: PRT
<213> ORGANISM: Artificial Sequence
<220> FEATURE:
<223> OTHER INFORMATION: Core polypeptide

<400> SEQUENCE: 374

Cys Leu Glu Leu Asp Lys Trp Ala Ser Leu Phe Asn Phe Phe Cys
 1               5                  10                  15

<210> SEQ ID NO 375
<211> LENGTH: 36
<212> TYPE: PRT
<213> ORGANISM: Artificial Sequence
<220> FEATURE:
<223> OTHER INFORMATION: Core polypeptide

<400> SEQUENCE: 375

Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser Leu
            20                  25                  30

Phe Asn Phe Phe
         35

<210> SEQ ID NO 376
<211> LENGTH: 35
<212> TYPE: PRT
<213> ORGANISM: Artificial Sequence
<220> FEATURE:
<223> OTHER INFORMATION: Core polypeptide

<400> SEQUENCE: 376

Arg Met Lys Gln Leu Glu Asp Lys Val Glu Glu Leu Leu Ser Lys Asn
 1               5                  10                  15

Tyr His Leu Glu Asn Glu Leu Glu Leu Asp Lys Trp Ala Ser Leu Trp
            20                  25                  30

```
Asn Trp Phe
        35

<210> SEQ ID NO 377
<211> LENGTH: 28
<212> TYPE: PRT
<213> ORGANISM: Artificial Sequence
<220> FEATURE:
<223> OTHER INFORMATION: Core polypeptide

<400> SEQUENCE: 377

Lys Val Glu Glu Leu Leu Ser Lys Asn Tyr His Leu Glu Asn Glu Leu
 1               5                  10                  15

Glu Leu Asp Lys Trp Ala Ser Leu Trp Asn Trp Phe
            20                  25

<210> SEQ ID NO 378
<211> LENGTH: 29
<212> TYPE: PRT
<213> ORGANISM: Artificial Sequence
<220> FEATURE:
<223> OTHER INFORMATION: Core polypeptide

<400> SEQUENCE: 378

Arg Met Lys Gln Leu Glu Asp Lys Val Glu Glu Leu Leu Ser Lys Leu
 1               5                  10                  15

Glu Trp Ile Arg Arg Ser Asn Gln Lys Leu Asp Ser Ile
            20                  25

<210> SEQ ID NO 379
<211> LENGTH: 29
<212> TYPE: PRT
<213> ORGANISM: Artificial Sequence
<220> FEATURE:
<223> OTHER INFORMATION: Core polypeptide

<400> SEQUENCE: 379

Arg Met Lys Gln Leu Glu Asp Lys Val Glu Glu Leu Leu Ser Lys Leu
 1               5                  10                  15

Ala Phe Ile Arg Lys Ser Asp Glu Leu Leu His Asn Val
            20                  25

<210> SEQ ID NO 380
<211> LENGTH: 28
<212> TYPE: PRT
<213> ORGANISM: Artificial Sequence
<220> FEATURE:
<223> OTHER INFORMATION: Core polypeptide

<400> SEQUENCE: 380

Glu Leu Glu Ala Leu Arg Gly Glu Leu Arg Ala Leu Arg Gly Glu Leu
 1               5                  10                  15

Glu Leu Asp Lys Trp Ala Ser Leu Trp Asn Trp Phe
            20                  25

<210> SEQ ID NO 381
<211> LENGTH: 34
<212> TYPE: PRT
<213> ORGANISM: Artificial Sequence
<220> FEATURE:
<223> OTHER INFORMATION: Core polypeptide

<400> SEQUENCE: 381

Leu Asp Pro Ile Asp Ile Ser Ile Glu Leu Asn Lys Ala Lys Ser Asp
 1               5                  10                  15
```

Leu Glu Glu Ser Lys Glu Trp Ile Arg Arg Ser Asn Gln Lys Leu Asp
            20                  25                  30

Ser Ile

<210> SEQ ID NO 382
<211> LENGTH: 16
<212> TYPE: PRT
<213> ORGANISM: Artificial Sequence
<220> FEATURE:
<223> OTHER INFORMATION: Core polypeptide

<400> SEQUENCE: 382

Cys Asn Glu Gln Leu Ser Asp Ser Phe Pro Val Glu Phe Phe Gln Val
 1               5                  10                  15

<210> SEQ ID NO 383
<211> LENGTH: 21
<212> TYPE: PRT
<213> ORGANISM: Artificial Sequence
<220> FEATURE:
<223> OTHER INFORMATION: Core polypeptide

<400> SEQUENCE: 383

Met Ala Glu Asp Asp Pro Tyr Leu Gly Arg Pro Glu Gln Met Phe His
 1               5                  10                  15

Leu Asp Pro Ser Leu
            20

<210> SEQ ID NO 384
<211> LENGTH: 20
<212> TYPE: PRT
<213> ORGANISM: Artificial Sequence
<220> FEATURE:
<223> OTHER INFORMATION: Core polypeptide

<400> SEQUENCE: 384

Glu Asp Phe Ser Ser Ile Ala Asp Met Asp Phe Ser Ala Leu Leu Ser
 1               5                  10                  15

Gln Ile Ser Ser
            20

<210> SEQ ID NO 385
<211> LENGTH: 35
<212> TYPE: PRT
<213> ORGANISM: Artificial Sequence
<220> FEATURE:
<223> OTHER INFORMATION: Core polypeptide

<400> SEQUENCE: 385

Thr Trp Gln Glu Trp Glu Arg Lys Val Asp Phe Leu Glu Glu Asn Ile
 1               5                  10                  15

Thr Ala Leu Leu Glu Glu Ala Gln Ile Gln Gln Glu Lys Asn Met Tyr
            20                  25                  30

Glu Leu Gln
        35

<210> SEQ ID NO 386
<211> LENGTH: 35
<212> TYPE: PRT
<213> ORGANISM: Artificial Sequence
<220> FEATURE:
<223> OTHER INFORMATION: Core polypeptide

<400> SEQUENCE: 386

```
Trp Gln Glu Trp Glu Arg Lys Val Asp Phe Leu Glu Glu Asn Ile Thr
1               5                   10                  15

Ala Leu Leu Glu Glu Ala Gln Ile Gln Gln Glu Lys Asn Met Tyr Glu
            20                  25                  30

Leu Gln Lys
        35

<210> SEQ ID NO 387
<211> LENGTH: 35
<212> TYPE: PRT
<213> ORGANISM: Artificial Sequence
<220> FEATURE:
<223> OTHER INFORMATION: Core polypeptide

<400> SEQUENCE: 387

Gln Glu Trp Glu Arg Lys Val Asp Phe Leu Glu Glu Asn Ile Thr Ala
1               5                   10                  15

Leu Leu Glu Glu Ala Gln Ile Gln Gln Glu Lys Asn Met Tyr Glu Leu
            20                  25                  30

Gln Lys Leu
        35

<210> SEQ ID NO 388
<211> LENGTH: 35
<212> TYPE: PRT
<213> ORGANISM: Artificial Sequence
<220> FEATURE:
<223> OTHER INFORMATION: Core polypeptide

<400> SEQUENCE: 388

Glu Trp Glu Arg Lys Val Asp Phe Leu Glu Glu Asn Ile Thr Ala Leu
1               5                   10                  15

Leu Glu Glu Ala Gln Ile Gln Gln Glu Lys Asn Met Tyr Glu Leu Gln
            20                  25                  30

Lys Leu Asn
        35

<210> SEQ ID NO 389
<211> LENGTH: 35
<212> TYPE: PRT
<213> ORGANISM: Artificial Sequence
<220> FEATURE:
<223> OTHER INFORMATION: Core polypeptide

<400> SEQUENCE: 389

Trp Glu Arg Lys Val Asp Phe Leu Glu Glu Asn Ile Thr Ala Leu Leu
1               5                   10                  15

Glu Glu Ala Gln Ile Gln Gln Glu Lys Asn Met Tyr Glu Leu Gln Lys
            20                  25                  30

Leu Asn Ser
        35

<210> SEQ ID NO 390
<211> LENGTH: 35
<212> TYPE: PRT
<213> ORGANISM: Artificial Sequence
<220> FEATURE:
<223> OTHER INFORMATION: Core polypeptide

<400> SEQUENCE: 390

Glu Arg Lys Val Asp Phe Leu Glu Glu Asn Ile Thr Ala Leu Leu Glu
1               5                   10                  15
```

Glu Ala Gln Ile Gln Gln Glu Lys Asn Met Tyr Glu Leu Gln Lys Leu
            20                  25                  30

Asn Ser Trp
        35

<210> SEQ ID NO 391
<211> LENGTH: 35
<212> TYPE: PRT
<213> ORGANISM: Artificial Sequence
<220> FEATURE:
<223> OTHER INFORMATION: Core polypeptide

<400> SEQUENCE: 391

Arg Lys Val Asp Phe Leu Glu Glu Asn Ile Thr Ala Leu Leu Glu Glu
 1               5                  10                  15

Ala Gln Ile Gln Gln Glu Lys Asn Met Tyr Glu Leu Gln Lys Leu Asn
            20                  25                  30

Ser Trp Asp
        35

<210> SEQ ID NO 392
<211> LENGTH: 35
<212> TYPE: PRT
<213> ORGANISM: Artificial Sequence
<220> FEATURE:
<223> OTHER INFORMATION: Core polypeptide

<400> SEQUENCE: 392

Lys Val Asp Phe Leu Glu Glu Asn Ile Thr Ala Leu Leu Glu Glu Ala
 1               5                  10                  15

Gln Ile Gln Gln Glu Lys Asn Met Tyr Glu Leu Gln Lys Leu Asn Ser
            20                  25                  30

Trp Asp Val
        35

<210> SEQ ID NO 393
<211> LENGTH: 35
<212> TYPE: PRT
<213> ORGANISM: Artificial Sequence
<220> FEATURE:
<223> OTHER INFORMATION: Core polypeptide

<400> SEQUENCE: 393

Val Asp Phe Leu Glu Glu Asn Ile Thr Ala Leu Leu Glu Glu Ala Gln
 1               5                  10                  15

Ile Gln Gln Glu Lys Asn Met Tyr Glu Leu Gln Lys Leu Asn Ser Trp
            20                  25                  30

Asp Val Phe
        35

<210> SEQ ID NO 394
<211> LENGTH: 35
<212> TYPE: PRT
<213> ORGANISM: Artificial Sequence
<220> FEATURE:
<223> OTHER INFORMATION: Core polypeptide

<400> SEQUENCE: 394

Asp Phe Leu Glu Glu Asn Ile Thr Ala Leu Leu Glu Glu Ala Gln Ile
 1               5                  10                  15

Gln Gln Glu Lys Asn Met Tyr Glu Leu Gln Lys Leu Asn Ser Trp Asp
            20                  25                  30

Val Phe Gly
        35

<210> SEQ ID NO 395
<211> LENGTH: 35
<212> TYPE: PRT
<213> ORGANISM: Artificial Sequence
<220> FEATURE:
<223> OTHER INFORMATION: Core polypeptide

<400> SEQUENCE: 395

Phe Leu Glu Glu Asn Ile Thr Ala Leu Leu Glu Glu Ala Gln Ile Gln
 1               5                  10                  15

Gln Glu Lys Asn Met Tyr Glu Leu Gln Lys Leu Asn Ser Trp Asp Val
            20                  25                  30

Phe Gly Asn
        35

<210> SEQ ID NO 396
<211> LENGTH: 35
<212> TYPE: PRT
<213> ORGANISM: Artificial Sequence
<220> FEATURE:
<223> OTHER INFORMATION: Core polypeptide

<400> SEQUENCE: 396

Leu Glu Glu Asn Ile Thr Ala Leu Leu Glu Glu Ala Gln Ile Gln Gln
 1               5                  10                  15

Glu Lys Asn Met Tyr Glu Leu Gln Lys Leu Asn Ser Trp Asp Val Phe
            20                  25                  30

Gly Asn Trp
        35

<210> SEQ ID NO 397
<211> LENGTH: 36
<212> TYPE: PRT
<213> ORGANISM: Artificial Sequence
<220> FEATURE:
<223> OTHER INFORMATION: Core polypeptide

<400> SEQUENCE: 397

Leu Glu Glu Asn Ile Thr Ala Leu Leu Glu Glu Ala Gln Ile Gln Gln
 1               5                  10                  15

Glu Lys Asn Met Tyr Glu Leu Gln Lys Leu Asn Ser Trp Asp Val Phe
            20                  25                  30

Gly Asn Trp Phe
        35

<210> SEQ ID NO 398
<211> LENGTH: 36
<212> TYPE: PRT
<213> ORGANISM: Artificial Sequence
<220> FEATURE:
<223> OTHER INFORMATION: Core polypeptide

<400> SEQUENCE: 398

Asn Glu Gln Ser Glu Glu Lys Gly Asn Glu Leu Tyr Trp Ala Lys Glu
 1               5                  10                  15

Gln Leu Leu Asp Leu Leu Phe Asn Ile Phe Asn Gln Thr Val Gly Ala
            20                  25                  30

Trp Ile Met Gln
        35

```
<210> SEQ ID NO 399
<211> LENGTH: 33
<212> TYPE: PRT
<213> ORGANISM: Artificial Sequence
<220> FEATURE:
<223> OTHER INFORMATION: Core polypeptide

<400> SEQUENCE: 399

Glu Trp Glu Arg Lys Val Asp Phe Leu Glu Glu Asn Ile Thr Ala Leu
 1               5                  10                  15

Leu Glu Glu Ala Gln Ile Gln Gln Glu Lys Asn Met Tyr Glu Gly Gly
            20                  25                  30

Cys

<210> SEQ ID NO 400
<211> LENGTH: 38
<212> TYPE: PRT
<213> ORGANISM: Artificial Sequence
<220> FEATURE:
<223> OTHER INFORMATION: Core polypeptide

<400> SEQUENCE: 400

Gln Gln Gln Leu Leu Asp Val Val Lys Arg Gln Gln Glu Leu Leu Arg
 1               5                  10                  15

Leu Thr Val Trp Gly Thr Lys Asn Leu Gln Thr Arg Val Thr Ala Ile
            20                  25                  30

Glu Lys Tyr Leu Lys Asp
        35

<210> SEQ ID NO 401
<211> LENGTH: 38
<212> TYPE: PRT
<213> ORGANISM: Artificial Sequence
<220> FEATURE:
<223> OTHER INFORMATION: Core polypeptide

<400> SEQUENCE: 401

Gln Gln Leu Leu Asp Val Val Lys Arg Gln Gln Glu Leu Leu Arg Leu
 1               5                  10                  15

Thr Val Trp Gly Thr Lys Asn Leu Gln Thr Arg Val Thr Ala Ile Glu
            20                  25                  30

Lys Tyr Leu Lys Asp Gln
        35

<210> SEQ ID NO 402
<211> LENGTH: 38
<212> TYPE: PRT
<213> ORGANISM: Artificial Sequence
<220> FEATURE:
<223> OTHER INFORMATION: Core polypeptide

<400> SEQUENCE: 402

Gln Gln Leu Leu Asp Val Val Lys Arg Gln Gln Glu Leu Leu Arg Leu
 1               5                  10                  15

Thr Val Trp Gly Pro Lys Asn Leu Gln Thr Arg Val Thr Ala Ile Glu
            20                  25                  30

Lys Tyr Leu Lys Asp Gln
        35

<210> SEQ ID NO 403
<211> LENGTH: 38
```

```
<212> TYPE: PRT
<213> ORGANISM: Artificial Sequence
<220> FEATURE:
<223> OTHER INFORMATION: Core polypeptide

<400> SEQUENCE: 403

Asp Glu Arg Lys Gln Asp Lys Val Leu Val Val Gln Gln Thr Gly Thr
 1               5                  10                  15

Leu Gln Leu Thr Leu Ile Gln Leu Glu Lys Thr Ala Lys Leu Gln Trp
            20                  25                  30

Val Arg Leu Asn Arg Tyr
            35

<210> SEQ ID NO 404
<211> LENGTH: 35
<212> TYPE: PRT
<213> ORGANISM: Artificial Sequence
<220> FEATURE:
<223> OTHER INFORMATION: Core polypeptide

<400> SEQUENCE: 404

Gln Gln Gln Leu Leu Asp Val Val Lys Arg Gln Gln Glu Leu Leu Arg
 1               5                  10                  15

Leu Thr Val Trp Gly Thr Lys Asn Leu Gln Thr Arg Val Thr Ala Ile
            20                  25                  30

Glu Lys Tyr
        35

<210> SEQ ID NO 405
<211> LENGTH: 35
<212> TYPE: PRT
<213> ORGANISM: Artificial Sequence
<220> FEATURE:
<223> OTHER INFORMATION: Core polypeptide

<400> SEQUENCE: 405

Gln Gln Leu Leu Asp Val Val Lys Arg Gln Gln Glu Leu Leu Arg Leu
 1               5                  10                  15

Thr Val Trp Gly Thr Lys Asn Leu Gln Thr Arg Val Thr Ala Ile Glu
            20                  25                  30

Lys Tyr Leu
        35

<210> SEQ ID NO 406
<211> LENGTH: 35
<212> TYPE: PRT
<213> ORGANISM: Artificial Sequence
<220> FEATURE:
<223> OTHER INFORMATION: Core polypeptide

<400> SEQUENCE: 406

Gln Leu Leu Asp Val Val Lys Arg Gln Gln Glu Leu Leu Arg Leu Thr
 1               5                  10                  15

Val Trp Gly Thr Lys Asn Leu Gln Thr Arg Val Thr Ala Ile Glu Lys
            20                  25                  30

Tyr Leu Lys
        35

<210> SEQ ID NO 407
<211> LENGTH: 35
<212> TYPE: PRT
<213> ORGANISM: Artificial Sequence
<220> FEATURE:
```

<223> OTHER INFORMATION: Core polypeptide

<400> SEQUENCE: 407

```
Leu Leu Asp Val Val Lys Arg Gln Gln Glu Leu Leu Arg Leu Thr Val
  1               5                  10                  15

Trp Gly Thr Lys Asn Leu Gln Thr Arg Val Thr Ala Ile Glu Lys Tyr
             20                  25                  30

Leu Lys Asp
         35
```

<210> SEQ ID NO 408
<211> LENGTH: 35
<212> TYPE: PRT
<213> ORGANISM: Artificial Sequence
<220> FEATURE:
<223> OTHER INFORMATION: Core polypeptide

<400> SEQUENCE: 408

```
Leu Asp Val Val Lys Arg Gln Gln Glu Leu Leu Arg Leu Thr Val Trp
  1               5                  10                  15

Gly Thr Lys Asn Leu Gln Thr Arg Val Thr Ala Ile Glu Lys Tyr Leu
             20                  25                  30

Lys Asp Gln
         35
```

<210> SEQ ID NO 409
<211> LENGTH: 35
<212> TYPE: PRT
<213> ORGANISM: Artificial Sequence
<220> FEATURE:
<223> OTHER INFORMATION: Core polypeptide

<400> SEQUENCE: 409

```
Asp Val Val Lys Arg Gln Gln Glu Leu Leu Arg Leu Thr Val Trp Gly
  1               5                  10                  15

Thr Lys Asn Leu Gln Thr Arg Val Thr Ala Ile Glu Lys Tyr Leu Lys
             20                  25                  30

Asp Gln Ala
         35
```

<210> SEQ ID NO 410
<211> LENGTH: 35
<212> TYPE: PRT
<213> ORGANISM: Artificial Sequence
<220> FEATURE:
<223> OTHER INFORMATION: Core polypeptide

<400> SEQUENCE: 410

```
Val Val Lys Arg Gln Gln Glu Leu Leu Arg Leu Thr Val Trp Gly Thr
  1               5                  10                  15

Lys Asn Leu Gln Thr Arg Val Thr Ala Ile Glu Lys Tyr Leu Lys Asp
             20                  25                  30

Gln Ala Gln
         35
```

<210> SEQ ID NO 411
<211> LENGTH: 35
<212> TYPE: PRT
<213> ORGANISM: Artificial Sequence
<220> FEATURE:
<223> OTHER INFORMATION: Core polypeptide

<400> SEQUENCE: 411

```
Val Lys Arg Gln Gln Glu Leu Leu Arg Leu Thr Val Trp Gly Thr Lys
1               5                   10                  15

Asn Leu Gln Thr Arg Val Thr Ala Ile Glu Lys Tyr Leu Lys Asp Gln
                20                  25                  30

Ala Gln Leu
        35

<210> SEQ ID NO 412
<211> LENGTH: 35
<212> TYPE: PRT
<213> ORGANISM: Artificial Sequence
<220> FEATURE:
<223> OTHER INFORMATION: Core polypeptide

<400> SEQUENCE: 412

Lys Arg Gln Gln Glu Leu Leu Arg Leu Thr Val Trp Gly Thr Lys Asn
1               5                   10                  15

Leu Gln Thr Arg Val Thr Ala Ile Glu Lys Tyr Leu Lys Asp Gln Ala
                20                  25                  30

Gln Leu Asn
        35

<210> SEQ ID NO 413
<211> LENGTH: 35
<212> TYPE: PRT
<213> ORGANISM: Artificial Sequence
<220> FEATURE:
<223> OTHER INFORMATION: Core polypeptide

<400> SEQUENCE: 413

Arg Gln Gln Glu Leu Leu Arg Leu Thr Val Trp Gly Thr Lys Asn Leu
1               5                   10                  15

Gln Thr Arg Val Thr Ala Ile Glu Lys Tyr Leu Lys Asp Gln Ala Gln
                20                  25                  30

Leu Asn Ala
        35

<210> SEQ ID NO 414
<211> LENGTH: 35
<212> TYPE: PRT
<213> ORGANISM: Artificial Sequence
<220> FEATURE:
<223> OTHER INFORMATION: Core polypeptide

<400> SEQUENCE: 414

Gln Gln Glu Leu Leu Arg Leu Thr Val Trp Gly Thr Lys Asn Leu Gln
1               5                   10                  15

Thr Arg Val Thr Ala Ile Glu Lys Tyr Leu Lys Asp Gln Ala Gln Leu
                20                  25                  30

Asn Ala Trp
        35

<210> SEQ ID NO 415
<211> LENGTH: 35
<212> TYPE: PRT
<213> ORGANISM: Artificial Sequence
<220> FEATURE:
<223> OTHER INFORMATION: Core polypeptide

<400> SEQUENCE: 415

Gln Glu Leu Leu Arg Leu Thr Val Trp Gly Thr Lys Asn Leu Gln Thr
1               5                   10                  15
```

Arg Val Thr Ala Ile Glu Lys Tyr Leu Lys Asp Gln Ala Gln Leu Asn
            20                  25                  30

Ala Trp Gly
        35

<210> SEQ ID NO 416
<211> LENGTH: 35
<212> TYPE: PRT
<213> ORGANISM: Artificial Sequence
<220> FEATURE:
<223> OTHER INFORMATION: Core polypeptide

<400> SEQUENCE: 416

Glu Leu Leu Arg Leu Thr Val Trp Gly Thr Lys Asn Leu Gln Thr Arg
 1               5                  10                  15

Val Thr Ala Ile Glu Lys Tyr Leu Lys Asp Gln Ala Gln Leu Asn Ala
            20                  25                  30

Trp Gly Cys
        35

<210> SEQ ID NO 417
<211> LENGTH: 38
<212> TYPE: PRT
<213> ORGANISM: Artificial Sequence
<220> FEATURE:
<223> OTHER INFORMATION: Core polypeptide

<400> SEQUENCE: 417

Asn Asn Leu Leu Arg Ala Ile Glu Ala Gln Gln His Leu Leu Gln Leu
 1               5                  10                  15

Thr Val Trp Gly Pro Lys Gln Leu Gln Ala Arg Ile Leu Ala Val Glu
            20                  25                  30

Arg Tyr Leu Lys Asp Gln
        35

<210> SEQ ID NO 418
<211> LENGTH: 35
<212> TYPE: PRT
<213> ORGANISM: Artificial Sequence
<220> FEATURE:
<223> OTHER INFORMATION: Core polypeptide

<400> SEQUENCE: 418

Ser Glu Leu Glu Ile Lys Arg Tyr Lys Asn Arg Val Ala Ser Arg Lys
 1               5                  10                  15

Cys Arg Ala Lys Phe Lys Gln Leu Leu Gln His Tyr Arg Glu Val Ala
            20                  25                  30

Ala Ala Lys
        35

<210> SEQ ID NO 419
<211> LENGTH: 35
<212> TYPE: PRT
<213> ORGANISM: Artificial Sequence
<220> FEATURE:
<223> OTHER INFORMATION: Core polypeptide

<400> SEQUENCE: 419

Glu Leu Glu Ile Lys Arg Tyr Lys Asn Arg Val Ala Ser Arg Lys Cys
 1               5                  10                  15

Arg Ala Lys Phe Lys Gln Leu Leu Gln His Tyr Arg Glu Val Ala Ala
            20                  25                  30

Ala Lys Ser
         35

<210> SEQ ID NO 420
<211> LENGTH: 35
<212> TYPE: PRT
<213> ORGANISM: Artificial Sequence
<220> FEATURE:
<223> OTHER INFORMATION: Core polypeptide

<400> SEQUENCE: 420

Leu Glu Ile Lys Arg Tyr Lys Asn Arg Val Ala Ser Arg Lys Cys Arg
 1               5                  10                  15

Ala Lys Phe Lys Gln Leu Leu Gln His Tyr Arg Glu Val Ala Ala Ala
            20                  25                  30

Lys Ser Ser
         35

<210> SEQ ID NO 421
<211> LENGTH: 35
<212> TYPE: PRT
<213> ORGANISM: Artificial Sequence
<220> FEATURE:
<223> OTHER INFORMATION: Core polypeptide

<400> SEQUENCE: 421

Glu Ile Lys Arg Tyr Lys Asn Arg Val Ala Ser Arg Lys Cys Arg Ala
 1               5                  10                  15

Lys Phe Lys Gln Leu Leu Gln His Tyr Arg Glu Val Ala Ala Ala Lys
            20                  25                  30

Ser Ser Glu
         35

<210> SEQ ID NO 422
<211> LENGTH: 35
<212> TYPE: PRT
<213> ORGANISM: Artificial Sequence
<220> FEATURE:
<223> OTHER INFORMATION: Core polypeptide

<400> SEQUENCE: 422

Ile Lys Arg Tyr Lys Asn Arg Val Ala Ser Arg Lys Cys Arg Ala Lys
 1               5                  10                  15

Phe Lys Gln Leu Leu Gln His Tyr Arg Glu Val Ala Ala Ala Lys Ser
            20                  25                  30

Ser Glu Asn
         35

<210> SEQ ID NO 423
<211> LENGTH: 35
<212> TYPE: PRT
<213> ORGANISM: Artificial Sequence
<220> FEATURE:
<223> OTHER INFORMATION: Core polypeptide

<400> SEQUENCE: 423

Lys Arg Tyr Lys Asn Arg Val Ala Ser Arg Lys Cys Arg Ala Lys Phe
 1               5                  10                  15

Lys Gln Leu Leu Gln His Tyr Arg Glu Val Ala Ala Ala Lys Ser Ser
            20                  25                  30

Glu Asn Asp
         35

<210> SEQ ID NO 424
<211> LENGTH: 35
<212> TYPE: PRT
<213> ORGANISM: Artificial Sequence
<220> FEATURE:
<223> OTHER INFORMATION: Core polypeptide

<400> SEQUENCE: 424

Arg Tyr Lys Asn Arg Val Ala Ser Arg Lys Cys Arg Ala Lys Phe Lys
1               5                   10                  15

Gln Leu Leu Gln His Tyr Arg Glu Val Ala Ala Ala Lys Ser Ser Glu
            20                  25                  30

Asn Asp Arg
        35

<210> SEQ ID NO 425
<211> LENGTH: 35
<212> TYPE: PRT
<213> ORGANISM: Artificial Sequence
<220> FEATURE:
<223> OTHER INFORMATION: Core polypeptide

<400> SEQUENCE: 425

Tyr Lys Asn Arg Val Ala Ser Arg Lys Cys Arg Ala Lys Phe Lys Gln
1               5                   10                  15

Leu Leu Gln His Tyr Arg Glu Val Ala Ala Ala Lys Ser Ser Glu Asn
            20                  25                  30

Asp Arg Leu
        35

<210> SEQ ID NO 426
<211> LENGTH: 35
<212> TYPE: PRT
<213> ORGANISM: Artificial Sequence
<220> FEATURE:
<223> OTHER INFORMATION: Core polypeptide

<400> SEQUENCE: 426

Lys Asn Arg Val Ala Ser Arg Lys Cys Arg Ala Lys Phe Lys Gln Leu
1               5                   10                  15

Leu Gln His Tyr Arg Glu Val Ala Ala Ala Lys Ser Ser Glu Asn Asp
            20                  25                  30

Arg Leu Arg
        35

<210> SEQ ID NO 427
<211> LENGTH: 35
<212> TYPE: PRT
<213> ORGANISM: Artificial Sequence
<220> FEATURE:
<223> OTHER INFORMATION: Core polypeptide

<400> SEQUENCE: 427

Asn Arg Val Ala Ser Arg Lys Cys Arg Ala Lys Phe Lys Gln Leu Leu
1               5                   10                  15

Gln His Tyr Arg Glu Val Ala Ala Ala Lys Ser Ser Glu Asn Asp Arg
            20                  25                  30

Leu Arg Leu
        35

<210> SEQ ID NO 428

```
<211> LENGTH: 35
<212> TYPE: PRT
<213> ORGANISM: Artificial Sequence
<220> FEATURE:
<223> OTHER INFORMATION: Core polypeptide

<400> SEQUENCE: 428

Arg Val Ala Ser Arg Lys Cys Arg Ala Lys Phe Lys Gln Leu Leu Gln
 1               5                  10                  15

His Tyr Arg Glu Val Ala Ala Ala Lys Ser Ser Glu Asn Asp Arg Leu
            20                  25                  30

Arg Leu Leu
        35

<210> SEQ ID NO 429
<211> LENGTH: 35
<212> TYPE: PRT
<213> ORGANISM: Artificial Sequence
<220> FEATURE:
<223> OTHER INFORMATION: Core polypeptide

<400> SEQUENCE: 429

Val Ala Ser Arg Lys Cys Arg Ala Lys Phe Lys Gln Leu Leu Gln His
 1               5                  10                  15

Tyr Arg Glu Val Ala Ala Ala Lys Ser Ser Glu Asn Asp Arg Leu Arg
            20                  25                  30

Leu Leu Leu
        35

<210> SEQ ID NO 430
<211> LENGTH: 35
<212> TYPE: PRT
<213> ORGANISM: Artificial Sequence
<220> FEATURE:
<223> OTHER INFORMATION: Core polypeptide

<400> SEQUENCE: 430

Ala Ser Arg Lys Cys Arg Ala Lys Phe Lys Gln Leu Leu Gln His Tyr
 1               5                  10                  15

Arg Glu Val Ala Ala Ala Lys Ser Ser Glu Asn Asp Arg Leu Arg Leu
            20                  25                  30

Leu Leu Lys
        35

<210> SEQ ID NO 431
<211> LENGTH: 35
<212> TYPE: PRT
<213> ORGANISM: Artificial Sequence
<220> FEATURE:
<223> OTHER INFORMATION: Core polypeptide

<400> SEQUENCE: 431

Ser Arg Lys Cys Arg Ala Lys Phe Lys Gln Leu Leu Gln His Tyr Arg
 1               5                  10                  15

Glu Val Ala Ala Ala Lys Ser Ser Glu Asn Asp Arg Leu Arg Leu Leu
            20                  25                  30

Leu Lys Gln
        35

<210> SEQ ID NO 432
<211> LENGTH: 35
<212> TYPE: PRT
<213> ORGANISM: Artificial Sequence
```

```
<220> FEATURE:
<223> OTHER INFORMATION: Core polypeptide

<400> SEQUENCE: 432

Arg Lys Cys Arg Ala Lys Phe Lys Gln Leu Leu Gln His Tyr Arg Glu
 1               5                  10                  15

Val Ala Ala Lys Ser Ser Glu Asn Asp Arg Leu Arg Leu Leu Leu
            20                  25                  30

Lys Gln Met
        35

<210> SEQ ID NO 433
<211> LENGTH: 35
<212> TYPE: PRT
<213> ORGANISM: Artificial Sequence
<220> FEATURE:
<223> OTHER INFORMATION: Core polypeptide

<400> SEQUENCE: 433

Lys Cys Arg Ala Lys Phe Lys Gln Leu Leu Gln His Tyr Arg Glu Val
 1               5                  10                  15

Ala Ala Ala Lys Ser Ser Glu Asn Asp Arg Leu Arg Leu Leu Leu Lys
            20                  25                  30

Gln Met Cys
        35

<210> SEQ ID NO 434
<211> LENGTH: 35
<212> TYPE: PRT
<213> ORGANISM: Artificial Sequence
<220> FEATURE:
<223> OTHER INFORMATION: Core polypeptide

<400> SEQUENCE: 434

Cys Arg Ala Lys Phe Lys Gln Leu Leu Gln His Tyr Arg Glu Val Ala
 1               5                  10                  15

Ala Ala Lys Ser Ser Glu Asn Asp Arg Leu Arg Leu Leu Leu Lys Gln
            20                  25                  30

Met Cys Pro
        35

<210> SEQ ID NO 435
<211> LENGTH: 35
<212> TYPE: PRT
<213> ORGANISM: Artificial Sequence
<220> FEATURE:
<223> OTHER INFORMATION: Core polypeptide

<400> SEQUENCE: 435

Arg Ala Lys Phe Lys Gln Leu Leu Gln His Tyr Arg Glu Val Ala Ala
 1               5                  10                  15

Ala Lys Ser Ser Glu Asn Asp Arg Leu Arg Leu Leu Leu Lys Gln Met
            20                  25                  30

Cys Pro Ser
        35

<210> SEQ ID NO 436
<211> LENGTH: 35
<212> TYPE: PRT
<213> ORGANISM: Artificial Sequence
<220> FEATURE:
<223> OTHER INFORMATION: Core polypeptide
```

-continued

```
<400> SEQUENCE: 436

Ala Lys Phe Lys Gln Leu Leu Gln His Tyr Arg Glu Val Ala Ala Ala
 1               5                  10                  15
Lys Ser Ser Glu Asn Asp Arg Leu Arg Leu Leu Lys Gln Met Cys
            20                  25                  30
Pro Ser Leu
        35

<210> SEQ ID NO 437
<211> LENGTH: 35
<212> TYPE: PRT
<213> ORGANISM: Artificial Sequence
<220> FEATURE:
<223> OTHER INFORMATION: Core polypeptide

<400> SEQUENCE: 437

Lys Phe Lys Gln Leu Leu Gln His Tyr Arg Glu Val Ala Ala Ala Lys
 1               5                  10                  15
Ser Ser Glu Asn Asp Arg Leu Arg Leu Leu Lys Gln Met Cys Pro
            20                  25                  30
Ser Leu Asp
        35

<210> SEQ ID NO 438
<211> LENGTH: 35
<212> TYPE: PRT
<213> ORGANISM: Artificial Sequence
<220> FEATURE:
<223> OTHER INFORMATION: Core polypeptide

<400> SEQUENCE: 438

Phe Lys Gln Leu Leu Gln His Tyr Arg Glu Val Ala Ala Ala Lys Ser
 1               5                  10                  15
Ser Glu Asn Asp Arg Leu Arg Leu Leu Lys Gln Met Cys Pro Ser
            20                  25                  30
Leu Asp Val
        35

<210> SEQ ID NO 439
<211> LENGTH: 35
<212> TYPE: PRT
<213> ORGANISM: Artificial Sequence
<220> FEATURE:
<223> OTHER INFORMATION: Core polypeptide

<400> SEQUENCE: 439

Lys Gln Leu Leu Gln His Tyr Arg Glu Val Ala Ala Ala Lys Ser Ser
 1               5                  10                  15
Glu Asn Asp Arg Leu Arg Leu Leu Lys Gln Met Cys Pro Ser Leu
            20                  25                  30
Asp Val Asp
        35

<210> SEQ ID NO 440
<211> LENGTH: 35
<212> TYPE: PRT
<213> ORGANISM: Artificial Sequence
<220> FEATURE:
<223> OTHER INFORMATION: Core polypeptide

<400> SEQUENCE: 440

Gln Leu Leu Gln His Tyr Arg Glu Val Ala Ala Ala Lys Ser Ser Glu
```

```
            1               5              10              15
Asn Asp Arg Leu Arg Leu Leu Lys Gln Met Cys Pro Ser Leu Asp
                    20              25              30

Val Asp Ser
        35
```

<210> SEQ ID NO 441
<211> LENGTH: 35
<212> TYPE: PRT
<213> ORGANISM: Artificial Sequence
<220> FEATURE:
<223> OTHER INFORMATION: Core polypeptide

<400> SEQUENCE: 441

```
Leu Leu Gln His Tyr Arg Glu Val Ala Ala Ala Lys Ser Ser Glu Asn
 1               5                  10                  15
Asp Arg Leu Arg Leu Leu Lys Gln Met Cys Pro Ser Leu Asp Val
                    20              25              30

Asp Ser Ile
        35
```

<210> SEQ ID NO 442
<211> LENGTH: 35
<212> TYPE: PRT
<213> ORGANISM: Artificial Sequence
<220> FEATURE:
<223> OTHER INFORMATION: Core polypeptide

<400> SEQUENCE: 442

```
Leu Gln His Tyr Arg Glu Val Ala Ala Ala Lys Ser Ser Glu Asn Asp
 1               5                  10                  15
Arg Leu Arg Leu Leu Lys Gln Met Cys Pro Ser Leu Asp Val Asp
                    20              25              30

Ser Ile Ile
        35
```

<210> SEQ ID NO 443
<211> LENGTH: 35
<212> TYPE: PRT
<213> ORGANISM: Artificial Sequence
<220> FEATURE:
<223> OTHER INFORMATION: Core polypeptide

<400> SEQUENCE: 443

```
Gln His Tyr Arg Glu Val Ala Ala Ala Lys Ser Ser Glu Asn Asp Arg
 1               5                  10                  15
Leu Arg Leu Leu Lys Gln Met Cys Pro Ser Leu Asp Val Asp Ser
                    20              25              30

Ile Ile Pro
        35
```

<210> SEQ ID NO 444
<211> LENGTH: 35
<212> TYPE: PRT
<213> ORGANISM: Artificial Sequence
<220> FEATURE:
<223> OTHER INFORMATION: Core polypeptide

<400> SEQUENCE: 444

```
His Tyr Arg Glu Val Ala Ala Ala Lys Ser Ser Glu Asn Asp Arg Leu
 1               5                  10                  15
Arg Leu Leu Leu Lys Gln Met Cys Pro Ser Leu Asp Val Asp Ser Ile
```

```
                 20                  25                  30

Ile Pro Arg
         35

<210> SEQ ID NO 445
<211> LENGTH: 35
<212> TYPE: PRT
<213> ORGANISM: Artificial Sequence
<220> FEATURE:
<223> OTHER INFORMATION: Core polypeptide

<400> SEQUENCE: 445

Tyr Arg Glu Val Ala Ala Ala Lys Ser Ser Glu Asn Asp Arg Leu Arg
  1               5                  10                  15

Leu Leu Leu Lys Gln Met Cys Pro Ser Leu Asp Val Asp Ser Ile Ile
                 20                  25                  30

Pro Arg Thr
         35

<210> SEQ ID NO 446
<211> LENGTH: 35
<212> TYPE: PRT
<213> ORGANISM: Artificial Sequence
<220> FEATURE:
<223> OTHER INFORMATION: Core polypeptide

<400> SEQUENCE: 446

Arg Glu Val Ala Ala Ala Lys Ser Ser Glu Asn Asp Arg Leu Arg Leu
  1               5                  10                  15

Leu Leu Lys Gln Met Cys Pro Ser Leu Asp Val Asp Ser Ile Ile Pro
                 20                  25                  30

Arg Thr Pro
         35

<210> SEQ ID NO 447
<211> LENGTH: 35
<212> TYPE: PRT
<213> ORGANISM: Artificial Sequence
<220> FEATURE:
<223> OTHER INFORMATION: Core polypeptide

<400> SEQUENCE: 447

Glu Val Ala Ala Ala Lys Ser Ser Glu Asn Asp Arg Leu Arg Leu Leu
  1               5                  10                  15

Leu Lys Gln Met Cys Pro Ser Leu Asp Val Asp Ser Ile Ile Pro Arg
                 20                  25                  30

Thr Pro Asp
         35

<210> SEQ ID NO 448
<211> LENGTH: 35
<212> TYPE: PRT
<213> ORGANISM: Artificial Sequence
<220> FEATURE:
<223> OTHER INFORMATION: Core polypeptide

<400> SEQUENCE: 448

Val Ala Ala Ala Lys Ser Ser Glu Asn Asp Arg Leu Arg Leu Leu Leu
  1               5                  10                  15

Lys Gln Met Cys Pro Ser Leu Asp Val Asp Ser Ile Ile Pro Arg Thr
                 20                  25                  30

Pro Asp Val
```

<210> SEQ ID NO 449
<211> LENGTH: 35
<212> TYPE: PRT
<213> ORGANISM: Artificial Sequence
<220> FEATURE:
<223> OTHER INFORMATION: Core polypeptide

<400> SEQUENCE: 449

```
Ala Ala Ala Lys Ser Ser Glu Asn Asp Arg Leu Arg Leu Leu Lys
 1               5                  10                  15

Gln Met Cys Pro Ser Leu Asp Val Asp Ser Ile Ile Pro Arg Thr Pro
                20                  25                  30

Asp Val Leu
         35
```

<210> SEQ ID NO 450
<211> LENGTH: 35
<212> TYPE: PRT
<213> ORGANISM: Artificial Sequence
<220> FEATURE:
<223> OTHER INFORMATION: Core polypeptide

<400> SEQUENCE: 450

```
Ala Ala Lys Ser Ser Glu Asn Asp Arg Leu Arg Leu Leu Lys Gln
 1               5                  10                  15

Met Cys Pro Ser Leu Asp Val Asp Ser Ile Ile Pro Arg Thr Pro Asp
                20                  25                  30

Val Leu His
         35
```

<210> SEQ ID NO 451
<211> LENGTH: 35
<212> TYPE: PRT
<213> ORGANISM: Artificial Sequence
<220> FEATURE:
<223> OTHER INFORMATION: Core polypeptide

<400> SEQUENCE: 451

```
Ala Lys Ser Ser Glu Asn Asp Arg Leu Arg Leu Leu Lys Gln Met
 1               5                  10                  15

Cys Pro Ser Leu Asp Val Asp Ser Ile Ile Pro Arg Thr Pro Asp Val
                20                  25                  30

Leu His Glu
         35
```

<210> SEQ ID NO 452
<211> LENGTH: 35
<212> TYPE: PRT
<213> ORGANISM: Artificial Sequence
<220> FEATURE:
<223> OTHER INFORMATION: Core polypeptide

<400> SEQUENCE: 452

```
Lys Ser Ser Glu Asn Asp Arg Leu Arg Leu Leu Lys Gln Met Cys
 1               5                  10                  15

Pro Ser Leu Asp Val Asp Ser Ile Ile Pro Arg Thr Pro Asp Val Leu
                20                  25                  30

His Glu Asp
         35
```

<210> SEQ ID NO 453
<211> LENGTH: 35
<212> TYPE: PRT
<213> ORGANISM: Artificial Sequence
<220> FEATURE:
<223> OTHER INFORMATION: Core polypeptide

<400> SEQUENCE: 453

Ser Ser Glu Asn Asp Arg Leu Arg Leu Leu Leu Lys Gln Met Cys Pro
1               5                   10                  15

Ser Leu Asp Val Asp Ser Ile Ile Pro Arg Thr Pro Asp Val Leu His
            20                  25                  30

Glu Asp Leu
        35

<210> SEQ ID NO 454
<211> LENGTH: 35
<212> TYPE: PRT
<213> ORGANISM: Artificial Sequence
<220> FEATURE:
<223> OTHER INFORMATION: Core polypeptide

<400> SEQUENCE: 454

Ser Glu Asn Asp Arg Leu Arg Leu Leu Leu Lys Gln Met Cys Pro Ser
1               5                   10                  15

Leu Asp Val Asp Ser Ile Ile Pro Arg Thr Pro Asp Val Leu His Glu
            20                  25                  30

Asp Leu Leu
        35

<210> SEQ ID NO 455
<211> LENGTH: 35
<212> TYPE: PRT
<213> ORGANISM: Artificial Sequence
<220> FEATURE:
<223> OTHER INFORMATION: Core polypeptide

<400> SEQUENCE: 455

Glu Asn Asp Arg Leu Arg Leu Leu Leu Lys Gln Met Cys Pro Ser Leu
1               5                   10                  15

Asp Val Asp Ser Ile Ile Pro Arg Thr Pro Asp Val Leu His Glu Asp
            20                  25                  30

Leu Leu Asn
        35

<210> SEQ ID NO 456
<211> LENGTH: 35
<212> TYPE: PRT
<213> ORGANISM: Artificial Sequence
<220> FEATURE:
<223> OTHER INFORMATION: Core polypeptide

<400> SEQUENCE: 456

Asn Asp Arg Leu Arg Leu Leu Leu Lys Gln Met Cys Pro Ser Leu Asp
1               5                   10                  15

Val Asp Ser Ile Ile Pro Arg Thr Pro Asp Val Leu His Glu Asp Leu
            20                  25                  30

Leu Asn Phe
        35

<210> SEQ ID NO 457
<211> LENGTH: 35
<212> TYPE: PRT

```
<213> ORGANISM: Artificial Sequence
<220> FEATURE:
<223> OTHER INFORMATION: Core polypeptide

<400> SEQUENCE: 457

Ala Ala Gly Ser Thr Met Gly Ala Arg Ser Met Thr Leu Thr Val Gln
  1               5                  10                  15

Ala Arg Gln Leu Leu Ser Gly Ile Val Gln Gln Gln Asn Asn Leu Leu
             20                  25                  30

Arg Ala Ile
         35

<210> SEQ ID NO 458
<211> LENGTH: 35
<212> TYPE: PRT
<213> ORGANISM: Artificial Sequence
<220> FEATURE:
<223> OTHER INFORMATION: Core polypeptide

<400> SEQUENCE: 458

Pro Gly Tyr Arg Trp Met Cys Leu Arg Arg Phe Ile Ile Phe Leu Phe
  1               5                  10                  15

Ile Leu Leu Leu Cys Leu Ile Phe Leu Leu Val Leu Leu Asp Tyr Gln
             20                  25                  30

Gly Met Leu
         35

<210> SEQ ID NO 459
<211> LENGTH: 35
<212> TYPE: PRT
<213> ORGANISM: Artificial Sequence
<220> FEATURE:
<223> OTHER INFORMATION: Core polypeptide

<400> SEQUENCE: 459

Gly Tyr Arg Trp Met Cys Leu Arg Arg Phe Ile Ile Phe Leu Phe Ile
  1               5                  10                  15

Leu Leu Leu Cys Leu Ile Phe Leu Leu Val Leu Leu Asp Tyr Gln Gly
             20                  25                  30

Met Leu Pro
         35

<210> SEQ ID NO 460
<211> LENGTH: 35
<212> TYPE: PRT
<213> ORGANISM: Artificial Sequence
<220> FEATURE:
<223> OTHER INFORMATION: Core polypeptide

<400> SEQUENCE: 460

Tyr Arg Trp Met Cys Leu Arg Arg Phe Ile Ile Phe Leu Phe Ile Leu
  1               5                  10                  15

Leu Leu Cys Leu Ile Phe Leu Leu Val Leu Leu Asp Tyr Gln Gly Met
             20                  25                  30

Leu Pro Val
         35

<210> SEQ ID NO 461
<211> LENGTH: 35
<212> TYPE: PRT
<213> ORGANISM: Artificial Sequence
<220> FEATURE:
<223> OTHER INFORMATION: Core polypeptide
```

```
<400> SEQUENCE: 461

Arg Trp Met Cys Leu Arg Arg Phe Ile Ile Phe Leu Phe Ile Leu Leu
 1               5                  10                  15

Leu Cys Leu Ile Phe Leu Leu Val Leu Leu Asp Tyr Gln Gly Met Leu
                20                  25                  30

Pro Val Cys
        35

<210> SEQ ID NO 462
<211> LENGTH: 35
<212> TYPE: PRT
<213> ORGANISM: Artificial Sequence
<220> FEATURE:
<223> OTHER INFORMATION: Core polypeptide

<400> SEQUENCE: 462

Trp Met Cys Leu Arg Arg Phe Ile Ile Phe Leu Phe Ile Leu Leu Leu
 1               5                  10                  15

Cys Leu Ile Phe Leu Leu Val Leu Leu Asp Tyr Gln Gly Met Leu Pro
                20                  25                  30

Val Cys Pro
        35

<210> SEQ ID NO 463
<211> LENGTH: 35
<212> TYPE: PRT
<213> ORGANISM: Artificial Sequence
<220> FEATURE:
<223> OTHER INFORMATION: Core polypeptide

<400> SEQUENCE: 463

Met Cys Leu Arg Arg Phe Ile Ile Phe Leu Phe Ile Leu Leu Leu Cys
 1               5                  10                  15

Leu Ile Phe Leu Leu Val Leu Leu Asp Tyr Gln Gly Met Leu Pro Val
                20                  25                  30

Cys Pro Leu
        35

<210> SEQ ID NO 464
<211> LENGTH: 35
<212> TYPE: PRT
<213> ORGANISM: Artificial Sequence
<220> FEATURE:
<223> OTHER INFORMATION: Core polypeptide

<400> SEQUENCE: 464

Cys Leu Arg Arg Phe Ile Ile Phe Leu Phe Ile Leu Leu Leu Cys Leu
 1               5                  10                  15

Ile Phe Leu Leu Val Leu Leu Asp Tyr Gln Gly Met Leu Pro Val Cys
                20                  25                  30

Pro Leu Ile
        35

<210> SEQ ID NO 465
<211> LENGTH: 35
<212> TYPE: PRT
<213> ORGANISM: Artificial Sequence
<220> FEATURE:
<223> OTHER INFORMATION: Core polypeptide

<400> SEQUENCE: 465
```

-continued

Leu Arg Arg Phe Ile Ile Phe Leu Phe Ile Leu Leu Cys Leu Ile
1               5                   10                  15

Phe Leu Leu Val Leu Leu Asp Tyr Gln Gly Met Leu Pro Val Cys Pro
                20                  25                  30

Leu Ile Pro
        35

<210> SEQ ID NO 466
<211> LENGTH: 35
<212> TYPE: PRT
<213> ORGANISM: Artificial Sequence
<220> FEATURE:
<223> OTHER INFORMATION: Core polypeptide

<400> SEQUENCE: 466

Arg Arg Phe Ile Ile Phe Leu Phe Ile Leu Leu Cys Leu Ile Phe
1               5                   10                  15

Leu Leu Val Leu Leu Asp Tyr Gln Gly Met Leu Pro Val Cys Pro Leu
                20                  25                  30

Ile Pro Gly
        35

<210> SEQ ID NO 467
<211> LENGTH: 35
<212> TYPE: PRT
<213> ORGANISM: Artificial Sequence
<220> FEATURE:
<223> OTHER INFORMATION: Core polypeptide

<400> SEQUENCE: 467

Arg Phe Ile Ile Phe Leu Phe Ile Leu Leu Cys Leu Ile Phe Leu
1               5                   10                  15

Leu Val Leu Leu Asp Tyr Gln Gly Met Leu Pro Val Cys Pro Leu Ile
                20                  25                  30

Pro Gly Ser
        35

<210> SEQ ID NO 468
<211> LENGTH: 35
<212> TYPE: PRT
<213> ORGANISM: Artificial Sequence
<220> FEATURE:
<223> OTHER INFORMATION: Core polypeptide

<400> SEQUENCE: 468

Phe Ile Ile Phe Leu Phe Ile Leu Leu Cys Leu Ile Phe Leu Leu
1               5                   10                  15

Val Leu Leu Asp Tyr Gln Gly Met Leu Pro Val Cys Pro Leu Ile Pro
                20                  25                  30

Gly Ser Ser
        35

<210> SEQ ID NO 469
<211> LENGTH: 35
<212> TYPE: PRT
<213> ORGANISM: Artificial Sequence
<220> FEATURE:
<223> OTHER INFORMATION: Core polypeptide

<400> SEQUENCE: 469

Ile Ile Phe Leu Phe Ile Leu Leu Cys Leu Ile Phe Leu Leu Val
1               5                   10                  15

Leu Leu Asp Tyr Gln Gly Met Leu Pro Val Cys Pro Leu Ile Pro Gly
            20                  25                  30

Ser Ser Thr
        35

<210> SEQ ID NO 470
<211> LENGTH: 35
<212> TYPE: PRT
<213> ORGANISM: Artificial Sequence
<220> FEATURE:
<223> OTHER INFORMATION: Core polypeptide

<400> SEQUENCE: 470

Ile Phe Leu Phe Ile Leu Leu Cys Leu Ile Phe Leu Leu Val Leu
1               5                   10                  15

Leu Asp Tyr Gln Gly Met Leu Pro Val Cys Pro Leu Ile Pro Gly Ser
            20                  25                  30

Ser Thr Thr
        35

<210> SEQ ID NO 471
<211> LENGTH: 35
<212> TYPE: PRT
<213> ORGANISM: Artificial Sequence
<220> FEATURE:
<223> OTHER INFORMATION: Core polypeptide

<400> SEQUENCE: 471

Phe Leu Phe Ile Leu Leu Cys Leu Ile Phe Leu Leu Val Leu Leu
1               5                   10                  15

Asp Tyr Gln Gly Met Leu Pro Val Cys Pro Leu Ile Pro Gly Ser Ser
            20                  25                  30

Thr Thr Ser
        35

<210> SEQ ID NO 472
<211> LENGTH: 35
<212> TYPE: PRT
<213> ORGANISM: Artificial Sequence
<220> FEATURE:
<223> OTHER INFORMATION: Core polypeptide

<400> SEQUENCE: 472

Leu Phe Ile Leu Leu Cys Leu Ile Phe Leu Leu Val Leu Leu Asp
1               5                   10                  15

Tyr Gln Gly Met Leu Pro Val Cys Pro Leu Ile Pro Gly Ser Ser Thr
            20                  25                  30

Thr Ser Thr
        35

<210> SEQ ID NO 473
<211> LENGTH: 35
<212> TYPE: PRT
<213> ORGANISM: Artificial Sequence
<220> FEATURE:
<223> OTHER INFORMATION: Core polypeptide

<400> SEQUENCE: 473

Phe Ile Leu Leu Cys Leu Ile Phe Leu Leu Val Leu Leu Asp Tyr
1               5                   10                  15

Gln Gly Met Leu Pro Val Cys Pro Leu Ile Pro Gly Ser Ser Thr Thr
            20                  25                  30

```
-continued

Ser Thr Gly
        35

<210> SEQ ID NO 474
<211> LENGTH: 35
<212> TYPE: PRT
<213> ORGANISM: Artificial Sequence
<220> FEATURE:
<223> OTHER INFORMATION: Core polypeptide

<400> SEQUENCE: 474

Ile Leu Leu Leu Cys Leu Ile Phe Leu Leu Val Leu Leu Asp Tyr Gln
1               5                   10                  15

Gly Met Leu Pro Val Cys Pro Leu Ile Pro Gly Ser Ser Thr Thr Ser
            20                  25                  30

Thr Gly Pro
        35

<210> SEQ ID NO 475
<211> LENGTH: 35
<212> TYPE: PRT
<213> ORGANISM: Artificial Sequence
<220> FEATURE:
<223> OTHER INFORMATION: Core polypeptide

<400> SEQUENCE: 475

Leu Leu Leu Cys Leu Ile Phe Leu Leu Val Leu Leu Asp Tyr Gln Gly
1               5                   10                  15

Met Leu Pro Val Cys Pro Leu Ile Pro Gly Ser Ser Thr Thr Ser Thr
            20                  25                  30

Gly Pro Cys
        35

<210> SEQ ID NO 476
<211> LENGTH: 35
<212> TYPE: PRT
<213> ORGANISM: Artificial Sequence
<220> FEATURE:
<223> OTHER INFORMATION: Core polypeptide

<400> SEQUENCE: 476

Leu Leu Cys Leu Ile Phe Leu Leu Val Leu Leu Asp Tyr Gln Gly Met
1               5                   10                  15

Leu Pro Val Cys Pro Leu Ile Pro Gly Ser Ser Thr Thr Ser Thr Gly
            20                  25                  30

Pro Cys Arg
        35

<210> SEQ ID NO 477
<211> LENGTH: 35
<212> TYPE: PRT
<213> ORGANISM: Artificial Sequence
<220> FEATURE:
<223> OTHER INFORMATION: Core polypeptide

<400> SEQUENCE: 477

Leu Cys Leu Ile Phe Leu Leu Val Leu Leu Asp Tyr Gln Gly Met Leu
1               5                   10                  15

Pro Val Cys Pro Leu Ile Pro Gly Ser Ser Thr Thr Ser Thr Gly Pro
            20                  25                  30

Cys Arg Thr
        35
```

```
<210> SEQ ID NO 478
<211> LENGTH: 35
<212> TYPE: PRT
<213> ORGANISM: Artificial Sequence
<220> FEATURE:
<223> OTHER INFORMATION: Core polypeptide

<400> SEQUENCE: 478

Cys Leu Ile Phe Leu Leu Val Leu Leu Asp Tyr Gln Gly Met Leu Pro
 1               5                  10                  15

Val Cys Pro Leu Ile Pro Gly Ser Ser Thr Thr Ser Thr Gly Pro Cys
            20                  25                  30

Arg Thr Cys
        35

<210> SEQ ID NO 479
<211> LENGTH: 35
<212> TYPE: PRT
<213> ORGANISM: Artificial Sequence
<220> FEATURE:
<223> OTHER INFORMATION: Core polypeptide

<400> SEQUENCE: 479

Leu Ile Phe Leu Leu Val Leu Leu Asp Tyr Gln Gly Met Leu Pro Val
 1               5                  10                  15

Cys Pro Leu Ile Pro Gly Ser Ser Thr Thr Ser Thr Gly Pro Cys Arg
            20                  25                  30

Thr Cys Met
        35

<210> SEQ ID NO 480
<211> LENGTH: 35
<212> TYPE: PRT
<213> ORGANISM: Artificial Sequence
<220> FEATURE:
<223> OTHER INFORMATION: Core polypeptide

<400> SEQUENCE: 480

Ile Phe Leu Leu Val Leu Leu Asp Tyr Gln Gly Met Leu Pro Val Cys
 1               5                  10                  15

Pro Leu Ile Pro Gly Ser Ser Thr Thr Ser Thr Gly Pro Cys Arg Thr
            20                  25                  30

Cys Met Thr
        35

<210> SEQ ID NO 481
<211> LENGTH: 35
<212> TYPE: PRT
<213> ORGANISM: Artificial Sequence
<220> FEATURE:
<223> OTHER INFORMATION: Core polypeptide

<400> SEQUENCE: 481

Phe Leu Leu Val Leu Leu Asp Tyr Gln Gly Met Leu Pro Val Cys Pro
 1               5                  10                  15

Leu Ile Pro Gly Ser Ser Thr Thr Ser Thr Gly Pro Cys Arg Thr Cys
            20                  25                  30

Met Thr Thr
        35

<210> SEQ ID NO 482
<211> LENGTH: 35
```

<212> TYPE: PRT
<213> ORGANISM: Artificial Sequence
<220> FEATURE:
<223> OTHER INFORMATION: Core polypeptide

<400> SEQUENCE: 482

Pro Leu Leu Val Leu Gln Ala Gly Phe Phe Leu Leu Thr Arg Ile Leu
 1               5                   10                  15

Thr Ile Pro Gln Ser Leu Asp Ser Trp Trp Thr Ser Leu Asn Phe Leu
            20                  25                  30

Gly Gly Thr
        35

<210> SEQ ID NO 483
<211> LENGTH: 35
<212> TYPE: PRT
<213> ORGANISM: Artificial Sequence
<220> FEATURE:
<223> OTHER INFORMATION: Core polypeptide

<400> SEQUENCE: 483

Leu Leu Val Leu Gln Ala Gly Phe Phe Leu Leu Thr Arg Ile Leu Thr
 1               5                   10                  15

Ile Pro Gln Ser Leu Asp Ser Trp Trp Thr Ser Leu Asn Phe Leu Gly
            20                  25                  30

Gly Thr Thr
        35

<210> SEQ ID NO 484
<211> LENGTH: 35
<212> TYPE: PRT
<213> ORGANISM: Artificial Sequence
<220> FEATURE:
<223> OTHER INFORMATION: Core polypeptide

<400> SEQUENCE: 484

Leu Val Leu Gln Ala Gly Phe Phe Leu Leu Thr Arg Ile Leu Thr Ile
 1               5                   10                  15

Pro Gln Ser Leu Asp Ser Trp Trp Thr Ser Leu Asn Phe Leu Gly Gly
            20                  25                  30

Thr Thr Val
        35

<210> SEQ ID NO 485
<211> LENGTH: 35
<212> TYPE: PRT
<213> ORGANISM: Artificial Sequence
<220> FEATURE:
<223> OTHER INFORMATION: Core polypeptide

<400> SEQUENCE: 485

Val Leu Gln Ala Gly Phe Phe Leu Leu Thr Arg Ile Leu Thr Ile Pro
 1               5                   10                  15

Gln Ser Leu Asp Ser Trp Trp Thr Ser Leu Asn Phe Leu Gly Gly Thr
            20                  25                  30

Thr Val Cys
        35

<210> SEQ ID NO 486
<211> LENGTH: 35
<212> TYPE: PRT
<213> ORGANISM: Artificial Sequence
<220> FEATURE:

<223> OTHER INFORMATION: Core polypeptide

<400> SEQUENCE: 486

Leu Gln Ala Gly Phe Phe Leu Leu Thr Arg Ile Leu Thr Ile Pro Gln
1               5                   10                  15

Ser Leu Asp Ser Trp Trp Thr Ser Leu Asn Phe Leu Gly Gly Thr Thr
            20                  25                  30

Val Cys Leu
        35

<210> SEQ ID NO 487
<211> LENGTH: 35
<212> TYPE: PRT
<213> ORGANISM: Artificial Sequence
<220> FEATURE:
<223> OTHER INFORMATION: Core polypeptide

<400> SEQUENCE: 487

Gln Ala Gly Phe Phe Leu Leu Thr Arg Ile Leu Thr Ile Pro Gln Ser
1               5                   10                  15

Leu Asp Ser Trp Trp Thr Ser Leu Asn Phe Leu Gly Gly Thr Thr Val
            20                  25                  30

Cys Leu Gly
        35

<210> SEQ ID NO 488
<211> LENGTH: 35
<212> TYPE: PRT
<213> ORGANISM: Artificial Sequence
<220> FEATURE:
<223> OTHER INFORMATION: Core polypeptide

<400> SEQUENCE: 488

Ala Gly Phe Phe Leu Leu Thr Arg Ile Leu Thr Ile Pro Gln Ser Leu
1               5                   10                  15

Asp Ser Trp Trp Thr Ser Leu Asn Phe Leu Gly Gly Thr Thr Val Cys
            20                  25                  30

Leu Gly Gln
        35

<210> SEQ ID NO 489
<211> LENGTH: 35
<212> TYPE: PRT
<213> ORGANISM: Artificial Sequence
<220> FEATURE:
<223> OTHER INFORMATION: Core polypeptide

<400> SEQUENCE: 489

Gly Phe Phe Leu Leu Thr Arg Ile Leu Thr Ile Pro Gln Ser Leu Asp
1               5                   10                  15

Ser Trp Trp Thr Ser Leu Asn Phe Leu Gly Gly Thr Thr Val Cys Leu
            20                  25                  30

Gly Gln Asn
        35

<210> SEQ ID NO 490
<211> LENGTH: 35
<212> TYPE: PRT
<213> ORGANISM: Artificial Sequence
<220> FEATURE:
<223> OTHER INFORMATION: Core polypeptide

<400> SEQUENCE: 490

```
Phe Phe Leu Leu Thr Arg Ile Leu Thr Ile Pro Gln Ser Leu Asp Ser
 1               5                  10                  15

Trp Trp Thr Ser Leu Asn Phe Leu Gly Gly Thr Thr Val Cys Leu Gly
             20                  25                  30

Gln Asn Ser
        35
```

<210> SEQ ID NO 491
<211> LENGTH: 35
<212> TYPE: PRT
<213> ORGANISM: Artificial Sequence
<220> FEATURE:
<223> OTHER INFORMATION: Core polypeptide

<400> SEQUENCE: 491

```
Phe Leu Leu Thr Arg Ile Leu Thr Ile Pro Gln Ser Leu Asp Ser Trp
 1               5                  10                  15

Trp Thr Ser Leu Asn Phe Leu Gly Gly Thr Thr Val Cys Leu Gly Gln
             20                  25                  30

Asn Ser Gln
        35
```

<210> SEQ ID NO 492
<211> LENGTH: 35
<212> TYPE: PRT
<213> ORGANISM: Artificial Sequence
<220> FEATURE:
<223> OTHER INFORMATION: Core polypeptide

<400> SEQUENCE: 492

```
Leu Leu Thr Arg Ile Leu Thr Ile Pro Gln Ser Leu Asp Ser Trp Trp
 1               5                  10                  15

Thr Ser Leu Asn Phe Leu Gly Gly Thr Thr Val Cys Leu Gly Gln Asn
             20                  25                  30

Ser Gln Ser
        35
```

<210> SEQ ID NO 493
<211> LENGTH: 35
<212> TYPE: PRT
<213> ORGANISM: Artificial Sequence
<220> FEATURE:
<223> OTHER INFORMATION: Core polypeptide

<400> SEQUENCE: 493

```
Leu Thr Arg Ile Leu Thr Ile Pro Gln Ser Leu Asp Ser Trp Trp Thr
 1               5                  10                  15

Ser Leu Asn Phe Leu Gly Gly Thr Thr Val Cys Leu Gly Gln Asn Ser
             20                  25                  30

Gln Ser Pro
        35
```

<210> SEQ ID NO 494
<211> LENGTH: 28
<212> TYPE: PRT
<213> ORGANISM: Artificial Sequence
<220> FEATURE:
<223> OTHER INFORMATION: Core polypeptide

<400> SEQUENCE: 494

```
Phe Trp Asn Trp Leu Ser Ala Trp Lys Asp Leu Glu Leu Lys Ser Leu
 1               5                  10                  15
```

Leu Glu Glu Val Lys Asp Glu Leu Gln Lys Met Arg
            20                  25

<210> SEQ ID NO 495
<211> LENGTH: 19
<212> TYPE: PRT
<213> ORGANISM: Artificial Sequence
<220> FEATURE:
<223> OTHER INFORMATION: Core polypeptide

<400> SEQUENCE: 495

Asn Asn Leu Leu Arg Ala Ile Glu Ala Gln Gln His Leu Leu Gln Leu
 1               5                  10                  15

Thr Val Trp

<210> SEQ ID NO 496
<211> LENGTH: 41
<212> TYPE: PRT
<213> ORGANISM: Artificial Sequence
<220> FEATURE:
<223> OTHER INFORMATION: Core polypeptide

<400> SEQUENCE: 496

Cys Gly Gly Asn Asn Leu Leu Arg Ala Ile Glu Ala Gln Gln His Leu
 1               5                  10                  15

Leu Gln Leu Thr Val Trp Gly Ile Lys Gln Leu Gln Ala Arg Ile Leu
            20                  25                  30

Ala Val Glu Arg Tyr Leu Lys Asp Gln
            35                  40

<210> SEQ ID NO 497
<211> LENGTH: 36
<212> TYPE: PRT
<213> ORGANISM: Artificial Sequence
<220> FEATURE:
<223> OTHER INFORMATION: Core polypeptide

<400> SEQUENCE: 497

Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser Leu
            20                  25                  30

Trp Asn Trp Phe
            35

<210> SEQ ID NO 498
<211> LENGTH: 36
<212> TYPE: PRT
<213> ORGANISM: Artificial Sequence
<220> FEATURE:
<223> OTHER INFORMATION: Core polypeptide

<400> SEQUENCE: 498

Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser Leu
            20                  25                  30

Trp Asn Trp Phe
            35

<210> SEQ ID NO 499
<211> LENGTH: 35

```
<212> TYPE: PRT
<213> ORGANISM: Artificial Sequence
<220> FEATURE:
<223> OTHER INFORMATION: Core polypeptide

<400> SEQUENCE: 499

Ala Val Ser Lys Gly Tyr Leu Ser Ala Leu Arg Thr Gly Trp Tyr Thr
 1               5                  10                  15

Ser Val Ile Thr Ile Glu Leu Ser Asn Ile Lys Glu Asn Lys Asn Gly
            20                  25                  30

Thr Asp Ala
        35

<210> SEQ ID NO 500
<211> LENGTH: 36
<212> TYPE: PRT
<213> ORGANISM: Artificial Sequence
<220> FEATURE:
<223> OTHER INFORMATION: Core polypeptide

<400> SEQUENCE: 500

Ser Ile Ser Asn Ile Glu Thr Val Ile Glu Phe Gln Gln Lys Asn Asn
 1               5                  10                  15

Arg Leu Leu Glu Ile Thr Arg Glu Phe Ser Val Asn Ala Gly Val Thr
            20                  25                  30

Thr Pro Val Ser
        35

<210> SEQ ID NO 501
<211> LENGTH: 35
<212> TYPE: PRT
<213> ORGANISM: Artificial Sequence
<220> FEATURE:
<223> OTHER INFORMATION: Core polypeptide

<400> SEQUENCE: 501

Asp Gln Gln Ile Lys Gln Tyr Lys Arg Leu Leu Asp Arg Leu Ile Ile
 1               5                  10                  15

Pro Leu Tyr Asp Gly Leu Arg Gln Lys Asp Val Ile Val Ser Asn Gln
            20                  25                  30

Glu Ser Asn
        35

<210> SEQ ID NO 502
<211> LENGTH: 36
<212> TYPE: PRT
<213> ORGANISM: Artificial Sequence
<220> FEATURE:
<223> OTHER INFORMATION: Core polypeptide

<400> SEQUENCE: 502

Tyr Ser Glu Leu Thr Asn Ile Phe Gly Asp Asn Ile Gly Ser Leu Gln
 1               5                  10                  15

Glu Lys Gly Ile Lys Leu Gln Gly Ile Ala Ser Leu Tyr Arg Thr Asn
            20                  25                  30

Ile Thr Glu Ile
        35

<210> SEQ ID NO 503
<211> LENGTH: 36
<212> TYPE: PRT
<213> ORGANISM: Artificial Sequence
<220> FEATURE:
```

<223> OTHER INFORMATION: Core polypeptide

<400> SEQUENCE: 503

Thr Ser Ile Thr Leu Gln Val Arg Leu Pro Leu Leu Thr Arg Leu Leu
1               5                   10                  15
Asn Thr Gln Ile Tyr Arg Val Asp Ser Ile Ser Tyr Asn Ile Gln Asn
                20                  25                  30
Arg Glu Trp Tyr
            35

<210> SEQ ID NO 504
<211> LENGTH: 35
<212> TYPE: PRT
<213> ORGANISM: Artificial Sequence
<220> FEATURE:
<223> OTHER INFORMATION: Core polypeptide

<400> SEQUENCE: 504

Val Glu Ile Ala Glu Tyr Arg Arg Leu Leu Arg Thr Val Leu Glu Pro
1               5                   10                  15
Ile Arg Asp Ala Leu Asn Ala Met Thr Gln Asn Ile Arg Pro Val Gln
                20                  25                  30
Ser Val Ala
        35

<210> SEQ ID NO 505
<211> LENGTH: 36
<212> TYPE: PRT
<213> ORGANISM: Artificial Sequence
<220> FEATURE:
<223> OTHER INFORMATION: Core polypeptide

<400> SEQUENCE: 505

Ser Tyr Phe Ile Val Leu Ser Ile Ala Tyr Pro Thr Leu Ser Glu Ile
1               5                   10                  15
Lys Gly Val Ile Val His Arg Leu Glu Gly Val Ser Tyr Asn Ile Gly
                20                  25                  30
Ser Gln Glu Trp
            35

<210> SEQ ID NO 506
<211> LENGTH: 28
<212> TYPE: PRT
<213> ORGANISM: Artificial Sequence
<220> FEATURE:
<223> OTHER INFORMATION: Core polypeptide

<400> SEQUENCE: 506

Leu Lys Glu Ala Ile Arg Asp Thr Asn Lys Ala Val Gln Ser Val Gln
1               5                   10                  15
Ser Ser Ile Gly Asn Leu Ile Val Ala Ile Lys Ser
                20                  25

<210> SEQ ID NO 507
<211> LENGTH: 38
<212> TYPE: PRT
<213> ORGANISM: Artificial Sequence
<220> FEATURE:
<223> OTHER INFORMATION: Core polypeptide

<400> SEQUENCE: 507

Asn Asn Leu Leu Arg Ala Ile Glu Ala Gln Gln His Leu Leu Gln Leu
1               5                   10                  15

```
Thr Val Trp Gly Ile Lys Gln Leu Gln Ala Arg Ile Leu Ala Val Glu
            20                  25                  30

Arg Tyr Leu Lys Asp Gln
            35

<210> SEQ ID NO 508
<211> LENGTH: 16
<212> TYPE: PRT
<213> ORGANISM: Artificial Sequence
<220> FEATURE:
<223> OTHER INFORMATION: Core polypeptide

<400> SEQUENCE: 508

Gln Lys Gln Glu Pro Ile Asp Lys Glu Leu Tyr Pro Leu Thr Ser Leu
  1               5                  10                  15

<210> SEQ ID NO 509
<211> LENGTH: 14
<212> TYPE: PRT
<213> ORGANISM: Artificial Sequence
<220> FEATURE:
<223> OTHER INFORMATION: Core polypeptide

<400> SEQUENCE: 509

Tyr Pro Lys Phe Val Lys Gln Asn Thr Leu Lys Leu Ala Thr
  1               5                  10

<210> SEQ ID NO 510
<211> LENGTH: 14
<212> TYPE: PRT
<213> ORGANISM: Artificial Sequence
<220> FEATURE:
<223> OTHER INFORMATION: Core polypeptide

<400> SEQUENCE: 510

Gln Tyr Ile Lys Ala Asn Gln Lys Phe Ile Gly Ile Thr Glu
  1               5                  10

<210> SEQ ID NO 511
<211> LENGTH: 14
<212> TYPE: PRT
<213> ORGANISM: Artificial Sequence
<220> FEATURE:
<223> OTHER INFORMATION: Core polypeptide

<400> SEQUENCE: 511

Asn Gly Gln Ile Gly Asn Asp Pro Asn Arg Asp Ile Leu Tyr
  1               5                  10

<210> SEQ ID NO 512
<211> LENGTH: 6
<212> TYPE: PRT
<213> ORGANISM: Artificial Sequence
<220> FEATURE:
<223> OTHER INFORMATION: Core polypeptide

<400> SEQUENCE: 512

Arg Pro Asp Val Tyr His
  1               5

<210> SEQ ID NO 513
<211> LENGTH: 15
<212> TYPE: PRT
<213> ORGANISM: Artificial Sequence
<220> FEATURE:
<223> OTHER INFORMATION: Core polypeptide
```

```
<400> SEQUENCE: 513

Cys Leu Glu Leu Asp Lys Trp Ala Ser Leu Trp Asn Trp Phe Cys
1               5                   10                  15

<210> SEQ ID NO 514
<211> LENGTH: 15
<212> TYPE: PRT
<213> ORGANISM: Artificial Sequence
<220> FEATURE:
<223> OTHER INFORMATION: Core polypeptide

<400> SEQUENCE: 514

Cys Leu Glu Leu Asp Lys Trp Ala Ser Leu Ala Asn Trp Phe Cys
1               5                   10                  15

<210> SEQ ID NO 515
<211> LENGTH: 15
<212> TYPE: PRT
<213> ORGANISM: Artificial Sequence
<220> FEATURE:
<223> OTHER INFORMATION: Core polypeptide

<400> SEQUENCE: 515

Cys Leu Glu Leu Asp Lys Trp Ala Ser Leu Ala Asn Phe Phe Cys
1               5                   10                  15

<210> SEQ ID NO 516
<211> LENGTH: 39
<212> TYPE: PRT
<213> ORGANISM: Artificial Sequence
<220> FEATURE:
<223> OTHER INFORMATION: Core polypeptide

<400> SEQUENCE: 516

Asn Asn Leu Leu Arg Ala Ile Glu Ala Gln Gln Gln His Leu Leu Gln
1               5                   10                  15

Leu Thr Val Trp Gly Ile Lys Gln Leu Gln Ala Arg Ile Leu Ala Val
            20                  25                  30

Glu Arg Tyr Leu Lys Asp Gln
        35

<210> SEQ ID NO 517
<211> LENGTH: 39
<212> TYPE: PRT
<213> ORGANISM: Artificial Sequence
<220> FEATURE:
<223> OTHER INFORMATION: Core polypeptide

<400> SEQUENCE: 517

Cys Gly Gly Tyr Thr Ser Leu Ile His Ser Leu Ile Glu Glu Ser Gln
1               5                   10                  15

Asn Gln Gln Glu Lys Asn Glu Gln Glu Leu Leu Glu Leu Asp Lys Trp
            20                  25                  30

Ala Ser Leu Trp Asn Trp Phe
        35

<210> SEQ ID NO 518
<211> LENGTH: 35
<212> TYPE: PRT
<213> ORGANISM: Artificial Sequence
<220> FEATURE:
<223> OTHER INFORMATION: Core polypeptide

<400> SEQUENCE: 518
```

Pro Leu Val Leu Gln Ala Gly Phe Phe Leu Leu Thr Arg Ile Leu
1               5                   10                  15

Thr Ile Pro Gln Ser Leu Asp Ser Trp Trp Thr Ser Leu Asn Phe Leu
            20                  25                  30

Gly Gly Thr
        35

<210> SEQ ID NO 519
<211> LENGTH: 35
<212> TYPE: PRT
<213> ORGANISM: Artificial Sequence
<220> FEATURE:
<223> OTHER INFORMATION: Core polypeptide

<400> SEQUENCE: 519

Leu Leu Val Leu Gln Ala Gly Phe Phe Leu Leu Thr Arg Ile Leu Thr
1               5                   10                  15

Ile Pro Gln Ser Leu Asp Ser Trp Trp Thr Ser Leu Asn Phe Leu Gly
            20                  25                  30

Gly Thr Thr
        35

<210> SEQ ID NO 520
<211> LENGTH: 35
<212> TYPE: PRT
<213> ORGANISM: Artificial Sequence
<220> FEATURE:
<223> OTHER INFORMATION: Core polypeptide

<400> SEQUENCE: 520

Leu Val Leu Gln Ala Gly Phe Phe Leu Leu Thr Arg Ile Leu Thr Ile
1               5                   10                  15

Pro Gln Ser Leu Asp Ser Trp Trp Thr Ser Leu Asn Phe Leu Gly Gly
            20                  25                  30

Thr Thr Val
        35

<210> SEQ ID NO 521
<211> LENGTH: 35
<212> TYPE: PRT
<213> ORGANISM: Artificial Sequence
<220> FEATURE:
<223> OTHER INFORMATION: Core polypeptide

<400> SEQUENCE: 521

Val Leu Gln Ala Gly Phe Phe Leu Leu Thr Arg Ile Leu Thr Ile Pro
1               5                   10                  15

Gln Ser Leu Asp Ser Trp Trp Thr Ser Leu Asn Phe Leu Gly Gly Thr
            20                  25                  30

Thr Val Cys
        35

<210> SEQ ID NO 522
<211> LENGTH: 35
<212> TYPE: PRT
<213> ORGANISM: Artificial Sequence
<220> FEATURE:
<223> OTHER INFORMATION: Core polypeptide

<400> SEQUENCE: 522

Leu Gln Ala Gly Phe Phe Leu Leu Thr Arg Ile Leu Thr Ile Pro Gln
1               5                   10                  15

Ser Leu Asp Ser Trp Trp Thr Ser Leu Asn Phe Leu Gly Gly Thr Thr
            20                  25                  30

Val Cys Leu
        35

<210> SEQ ID NO 523
<211> LENGTH: 35
<212> TYPE: PRT
<213> ORGANISM: Artificial Sequence
<220> FEATURE:
<223> OTHER INFORMATION: Core polypeptide

<400> SEQUENCE: 523

Gln Ala Gly Phe Phe Leu Leu Thr Arg Ile Leu Thr Ile Pro Gln Ser
1               5                   10                  15

Leu Asp Ser Trp Trp Thr Ser Leu Asn Phe Leu Gly Gly Thr Thr Val
            20                  25                  30

Cys Leu Gly
        35

<210> SEQ ID NO 524
<211> LENGTH: 35
<212> TYPE: PRT
<213> ORGANISM: Artificial Sequence
<220> FEATURE:
<223> OTHER INFORMATION: Core polypeptide

<400> SEQUENCE: 524

Ala Gly Phe Phe Leu Leu Thr Arg Ile Leu Thr Ile Pro Gln Ser Leu
1               5                   10                  15

Asp Ser Trp Trp Thr Ser Leu Asn Phe Leu Gly Gly Thr Thr Val Cys
            20                  25                  30

Leu Gly Gln
        35

<210> SEQ ID NO 525
<211> LENGTH: 35
<212> TYPE: PRT
<213> ORGANISM: Artificial Sequence
<220> FEATURE:
<223> OTHER INFORMATION: Core polypeptide

<400> SEQUENCE: 525

Gly Phe Phe Leu Leu Thr Arg Ile Leu Thr Ile Pro Gln Ser Leu Asp
1               5                   10                  15

Ser Trp Trp Thr Ser Leu Asn Phe Leu Gly Gly Thr Thr Val Cys Leu
            20                  25                  30

Gly Gln Asn
        35

<210> SEQ ID NO 526
<211> LENGTH: 35
<212> TYPE: PRT
<213> ORGANISM: Artificial Sequence
<220> FEATURE:
<223> OTHER INFORMATION: Core polypeptide

<400> SEQUENCE: 526

Phe Phe Leu Leu Thr Arg Ile Leu Thr Ile Pro Gln Ser Leu Asp Ser
1               5                   10                  15

Trp Trp Thr Ser Leu Asn Phe Leu Gly Gly Thr Thr Val Cys Leu Gly
            20                  25                  30

Gln Asn Ser
        35

<210> SEQ ID NO 527
<211> LENGTH: 35
<212> TYPE: PRT
<213> ORGANISM: Artificial Sequence
<220> FEATURE:
<223> OTHER INFORMATION: Core polypeptide

<400> SEQUENCE: 527

Phe Leu Leu Thr Arg Ile Leu Thr Ile Pro Gln Ser Leu Asp Ser Trp
 1               5                  10                  15

Trp Thr Ser Leu Asn Phe Leu Gly Gly Thr Thr Val Cys Leu Gly Gln
            20                  25                  30

Asn Ser Gln
        35

<210> SEQ ID NO 528
<211> LENGTH: 35
<212> TYPE: PRT
<213> ORGANISM: Artificial Sequence
<220> FEATURE:
<223> OTHER INFORMATION: Core polypeptide

<400> SEQUENCE: 528

Leu Leu Thr Arg Ile Leu Thr Ile Pro Gln Ser Leu Asp Ser Trp Trp
 1               5                  10                  15

Thr Ser Leu Asn Phe Leu Gly Gly Thr Thr Val Cys Leu Gly Gln Asn
            20                  25                  30

Ser Gln Ser
        35

<210> SEQ ID NO 529
<211> LENGTH: 35
<212> TYPE: PRT
<213> ORGANISM: Artificial Sequence
<220> FEATURE:
<223> OTHER INFORMATION: Core polypeptide

<400> SEQUENCE: 529

Leu Thr Arg Ile Leu Thr Ile Pro Gln Ser Leu Asp Ser Trp Trp Thr
 1               5                  10                  15

Ser Leu Asn Phe Leu Gly Gly Thr Thr Val Cys Leu Gly Gln Asn Ser
            20                  25                  30

Gln Ser Pro
        35

<210> SEQ ID NO 530
<211> LENGTH: 13
<212> TYPE: PRT
<213> ORGANISM: Artificial Sequence
<220> FEATURE:
<223> OTHER INFORMATION: Core polypeptide

<400> SEQUENCE: 530

Leu Glu Leu Asp Lys Trp Ala Ser Leu Trp Asn Trp Ala
 1               5                  10

<210> SEQ ID NO 531
<211> LENGTH: 13
<212> TYPE: PRT
<213> ORGANISM: Artificial Sequence

```
<220> FEATURE:
<223> OTHER INFORMATION: Core polypeptide

<400> SEQUENCE: 531

Leu Glu Leu Asp Lys Trp Ala Ser Ala Trp Asn Trp Phe
 1               5                  10

<210> SEQ ID NO 532
<211> LENGTH: 13
<212> TYPE: PRT
<213> ORGANISM: Artificial Sequence
<220> FEATURE:
<223> OTHER INFORMATION: Core polypeptide

<400> SEQUENCE: 532

Leu Glu Leu Asp Lys Ala Ala Ser Leu Trp Asn Trp Phe
 1               5                  10

<210> SEQ ID NO 533
<211> LENGTH: 13
<212> TYPE: PRT
<213> ORGANISM: Artificial Sequence
<220> FEATURE:
<223> OTHER INFORMATION: Core polypeptide

<400> SEQUENCE: 533

Leu Lys Leu Asp Lys Trp Ala Ser Leu Trp Asn Trp Phe
 1               5                  10

<210> SEQ ID NO 534
<211> LENGTH: 13
<212> TYPE: PRT
<213> ORGANISM: Artificial Sequence
<220> FEATURE:
<223> OTHER INFORMATION: Core polypeptide

<400> SEQUENCE: 534

Leu Glu Leu Lys Lys Trp Ala Ser Leu Trp Asn Trp Phe
 1               5                  10

<210> SEQ ID NO 535
<211> LENGTH: 13
<212> TYPE: PRT
<213> ORGANISM: Artificial Sequence
<220> FEATURE:
<223> OTHER INFORMATION: Core polypeptide

<400> SEQUENCE: 535

Asp Glu Leu Leu His Asn Val Asn Ala Gly Lys Ser Thr
 1               5                  10

<210> SEQ ID NO 536
<211> LENGTH: 15
<212> TYPE: PRT
<213> ORGANISM: Artificial Sequence
<220> FEATURE:
<223> OTHER INFORMATION: Core polypeptide

<400> SEQUENCE: 536

Lys Ser Asp Glu Leu Leu His Asn Val Asn Ala Gly Lys Ser Thr
 1               5                  10                  15

<210> SEQ ID NO 537
<211> LENGTH: 17
<212> TYPE: PRT
<213> ORGANISM: Artificial Sequence
<220> FEATURE:
```

```
<223> OTHER INFORMATION: Core polypeptide

<400> SEQUENCE: 537

Ile Arg Lys Ser Asp Glu Leu Leu His Asn Val Asn Ala Gly Lys Ser
 1               5                  10                  15
Thr

<210> SEQ ID NO 538
<211> LENGTH: 19
<212> TYPE: PRT
<213> ORGANISM: Artificial Sequence
<220> FEATURE:
<223> OTHER INFORMATION: Core polypeptide

<400> SEQUENCE: 538

Ala Phe Ile Arg Lys Ser Asp Glu Leu Leu His Asn Val Asn Ala Gly
 1               5                  10                  15
Lys Ser Thr

<210> SEQ ID NO 539
<211> LENGTH: 19
<212> TYPE: PRT
<213> ORGANISM: Artificial Sequence
<220> FEATURE:
<223> OTHER INFORMATION: Core polypeptide

<400> SEQUENCE: 539

Phe Asp Ala Ser Ile Ser Gln Val Asn Glu Lys Ile Asn Gln Ser Leu
 1               5                  10                  15
Ala Phe Ile

<210> SEQ ID NO 540
<211> LENGTH: 36
<212> TYPE: PRT
<213> ORGANISM: Artificial Sequence
<220> FEATURE:
<223> OTHER INFORMATION: Core polypeptide

<400> SEQUENCE: 540

Tyr Ala Ala Asp Lys Glu Ser Thr Gln Lys Ala Phe Asp Gly Ile Thr
 1               5                  10                  15
Asn Lys Val Asn Ser Val Ile Glu Lys Met Asn Thr Gln Phe Glu Ala
                20                  25                  30
Val Gly Lys Glu
            35

<210> SEQ ID NO 541
<211> LENGTH: 36
<212> TYPE: PRT
<213> ORGANISM: Artificial Sequence
<220> FEATURE:
<223> OTHER INFORMATION: Core polypeptide

<400> SEQUENCE: 541

Ser Val Ile Glu Lys Met Asn Thr Gln Phe Glu Ala Val Gly Lys Glu
 1               5                  10                  15
Phe Gly Asn Leu Glu Arg Arg Leu Glu Asn Leu Asn Lys Arg Met Glu
                20                  25                  30
Asp Gly Phe Leu
            35

<210> SEQ ID NO 542
```

<211> LENGTH: 36
<212> TYPE: PRT
<213> ORGANISM: Artificial Sequence
<220> FEATURE:
<223> OTHER INFORMATION: Core polypeptide

<400> SEQUENCE: 542

Val Trp Thr Tyr Asn Ala Glu Leu Leu Val Leu Met Glu Asn Glu Arg
 1               5                  10                  15

Thr Leu Asp Phe His Asp Ser Asn Val Lys Asn Leu Tyr Asp Lys Val
            20                  25                  30

Arg Met Gln Leu
        35

<210> SEQ ID NO 543
<211> LENGTH: 33
<212> TYPE: PRT
<213> ORGANISM: Artificial Sequence
<220> FEATURE:
<223> OTHER INFORMATION: Core polypeptide

<400> SEQUENCE: 543

Glu Trp Asp Arg Glu Ile Asn Asn Tyr Thr Ser Leu Ile His Ser Leu
 1               5                  10                  15

Ile Glu Glu Ser Gln Asn Gln Gln Glu Lys Asn Glu Gln Glu Gly Gly
            20                  25                  30

Cys

<210> SEQ ID NO 544
<211> LENGTH: 35
<212> TYPE: PRT
<213> ORGANISM: Artificial Sequence
<220> FEATURE:
<223> OTHER INFORMATION: Core polypeptide

<400> SEQUENCE: 544

Ile Asn Asn Tyr Thr Ser Leu Ile His Ser Leu Ile Glu Glu Ser Gln
 1               5                  10                  15

Asn Gln Gln Glu Lys Asn Glu Gln Glu Leu Leu Glu Leu Asp Lys Trp
            20                  25                  30

Ala Ser Leu
        35

<210> SEQ ID NO 545
<211> LENGTH: 28
<212> TYPE: PRT
<213> ORGANISM: Artificial Sequence
<220> FEATURE:
<223> OTHER INFORMATION: Core polypeptide

<400> SEQUENCE: 545

Ile Asn Asn Tyr Thr Ser Leu Ile His Ser Leu Ile Glu Glu Ser Gln
 1               5                  10                  15

Asn Gln Gln Glu Lys Asn Glu Gln Glu Leu Leu Glu
            20                  25

<210> SEQ ID NO 546
<211> LENGTH: 35
<212> TYPE: PRT
<213> ORGANISM: Artificial Sequence
<220> FEATURE:
<223> OTHER INFORMATION: Core polypeptide

<400> SEQUENCE: 546

```
Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu Glu
        35
```

<210> SEQ ID NO 547
<211> LENGTH: 48
<212> TYPE: PRT
<213> ORGANISM: Artificial Sequence
<220> FEATURE:
<223> OTHER INFORMATION: Core polypeptide

<400> SEQUENCE: 547

```
Met Thr Trp Met Glu Trp Asp Arg Glu Ile Asn Asn Tyr Thr Ser Leu
1               5                   10                  15

Ile His Ser Leu Ile Glu Glu Ser Gln Asn Gln Gln Glu Lys Asn Glu
            20                  25                  30

Gln Glu Leu Leu Glu Leu Asp Lys Trp Ala Ser Leu Trp Asn Trp Phe
        35                  40                  45
```

<210> SEQ ID NO 548
<211> LENGTH: 35
<212> TYPE: PRT
<213> ORGANISM: Artificial Sequence
<220> FEATURE:
<223> OTHER INFORMATION: Core polypeptide

<400> SEQUENCE: 548

```
Ile Asp Ile Ser Ile Glu Leu Asn Lys Ala Lys Ser Asp Leu Glu Glu
1               5                   10                  15

Ser Lys Glu Trp Ile Lys Lys Ser Asn Gln Lys Leu Asp Ser Ile Gly
            20                  25                  30

Asn Trp His
        35
```

<210> SEQ ID NO 549
<211> LENGTH: 36
<212> TYPE: PRT
<213> ORGANISM: Artificial Sequence
<220> FEATURE:
<223> OTHER INFORMATION: Core polypeptide

<400> SEQUENCE: 549

```
Asn Gln Gln Glu Lys Asn Glu Gln Glu Leu Leu Glu Leu Asp Lys Trp
1               5                   10                  15

Ala Ser Leu Trp Asn Trp Phe Asn Ile Thr Asn Trp Leu Trp Tyr Ile
            20                  25                  30

Lys Ile Phe Ile
        35
```

<210> SEQ ID NO 550
<211> LENGTH: 36
<212> TYPE: PRT
<213> ORGANISM: Artificial Sequence
<220> FEATURE:
<223> OTHER INFORMATION: Core polypeptide

<400> SEQUENCE: 550

```
Gln Asn Gln Gln Glu Lys Asn Glu Gln Glu Leu Leu Glu Leu Asp Lys
1               5                   10                  15
```

Trp Ala Ser Leu Trp Asn Trp Phe Asn Ile Thr Asn Trp Leu Trp Tyr
            20                  25                  30

Ile Lys Ile Phe
        35

<210> SEQ ID NO 551
<211> LENGTH: 36
<212> TYPE: PRT
<213> ORGANISM: Artificial Sequence
<220> FEATURE:
<223> OTHER INFORMATION: Core polypeptide

<400> SEQUENCE: 551

Ser Gln Asn Gln Gln Glu Lys Asn Glu Gln Glu Leu Leu Glu Leu Asp
 1               5                  10                  15

Lys Trp Ala Ser Leu Trp Asn Trp Phe Asn Ile Thr Asn Trp Leu Trp
            20                  25                  30

Tyr Ile Lys Ile
        35

<210> SEQ ID NO 552
<211> LENGTH: 36
<212> TYPE: PRT
<213> ORGANISM: Artificial Sequence
<220> FEATURE:
<223> OTHER INFORMATION: Core polypeptide

<400> SEQUENCE: 552

Glu Ser Gln Asn Gln Gln Glu Lys Asn Glu Gln Glu Leu Leu Glu Leu
 1               5                  10                  15

Asp Lys Trp Ala Ser Leu Trp Asn Trp Phe Asn Ile Thr Asn Trp Leu
            20                  25                  30

Trp Tyr Ile Lys
        35

<210> SEQ ID NO 553
<211> LENGTH: 36
<212> TYPE: PRT
<213> ORGANISM: Artificial Sequence
<220> FEATURE:
<223> OTHER INFORMATION: Core polypeptide

<400> SEQUENCE: 553

Glu Glu Ser Gln Asn Gln Gln Glu Lys Asn Glu Gln Glu Leu Leu Glu
 1               5                  10                  15

Leu Asp Lys Trp Ala Ser Leu Trp Asn Trp Phe Asn Ile Thr Asn Trp
            20                  25                  30

Leu Trp Tyr Ile
        35

<210> SEQ ID NO 554
<211> LENGTH: 36
<212> TYPE: PRT
<213> ORGANISM: Artificial Sequence
<220> FEATURE:
<223> OTHER INFORMATION: Core polypeptide

<400> SEQUENCE: 554

Ile Glu Glu Ser Gln Asn Gln Gln Glu Lys Asn Glu Gln Glu Leu Leu
 1               5                  10                  15

Glu Leu Asp Lys Trp Ala Ser Leu Trp Asn Trp Phe Asn Ile Thr Asn
            20                  25                  30

-continued

Trp Leu Trp Tyr
         35

<210> SEQ ID NO 555
<211> LENGTH: 36
<212> TYPE: PRT
<213> ORGANISM: Artificial Sequence
<220> FEATURE:
<223> OTHER INFORMATION: Core polypeptide

<400> SEQUENCE: 555

Leu Ile Glu Glu Ser Gln Asn Gln Gln Glu Lys Asn Glu Gln Glu Leu
 1               5                  10                  15

Leu Glu Leu Asp Lys Trp Ala Ser Leu Trp Asn Trp Phe Asn Ile Thr
             20                  25                  30

Asn Trp Leu Trp
         35

<210> SEQ ID NO 556
<211> LENGTH: 36
<212> TYPE: PRT
<213> ORGANISM: Artificial Sequence
<220> FEATURE:
<223> OTHER INFORMATION: Core polypeptide

<400> SEQUENCE: 556

Ser Leu Ile Glu Glu Ser Gln Asn Gln Gln Glu Lys Asn Glu Gln Glu
 1               5                  10                  15

Leu Leu Glu Leu Asp Lys Trp Ala Ser Leu Trp Asn Trp Phe Asn Ile
             20                  25                  30

Thr Asn Trp Leu
         35

<210> SEQ ID NO 557
<211> LENGTH: 36
<212> TYPE: PRT
<213> ORGANISM: Artificial Sequence
<220> FEATURE:
<223> OTHER INFORMATION: Core polypeptide

<400> SEQUENCE: 557

His Ser Leu Ile Glu Glu Ser Gln Asn Gln Gln Glu Lys Asn Glu Gln
 1               5                  10                  15

Glu Leu Leu Glu Leu Asp Lys Trp Ala Ser Leu Trp Asn Trp Phe Asn
             20                  25                  30

Ile Thr Asn Trp
         35

<210> SEQ ID NO 558
<211> LENGTH: 36
<212> TYPE: PRT
<213> ORGANISM: Artificial Sequence
<220> FEATURE:
<223> OTHER INFORMATION: Core polypeptide

<400> SEQUENCE: 558

Ile His Ser Leu Ile Glu Glu Ser Gln Asn Gln Gln Glu Lys Asn Glu
 1               5                  10                  15

Gln Glu Leu Leu Glu Leu Asp Lys Trp Ala Ser Leu Trp Asn Trp Phe
             20                  25                  30

Asn Ile Thr Asn
         35

```
<210> SEQ ID NO 559
<211> LENGTH: 36
<212> TYPE: PRT
<213> ORGANISM: Artificial Sequence
<220> FEATURE:
<223> OTHER INFORMATION: Core polypeptide

<400> SEQUENCE: 559

Leu Ile His Ser Leu Ile Glu Glu Ser Gln Asn Gln Gln Glu Lys Asn
 1               5                  10                  15

Glu Gln Glu Leu Leu Glu Leu Asp Lys Trp Ala Ser Leu Trp Asn Trp
             20                  25                  30

Phe Asn Ile Thr
            35

<210> SEQ ID NO 560
<211> LENGTH: 36
<212> TYPE: PRT
<213> ORGANISM: Artificial Sequence
<220> FEATURE:
<223> OTHER INFORMATION: Core polypeptide

<400> SEQUENCE: 560

Ser Leu Ile His Ser Leu Ile Glu Glu Ser Gln Asn Gln Gln Glu Lys
 1               5                  10                  15

Asn Glu Gln Glu Leu Leu Glu Leu Asp Lys Trp Ala Ser Leu Trp Asn
             20                  25                  30

Trp Phe Asn Ile
            35

<210> SEQ ID NO 561
<211> LENGTH: 36
<212> TYPE: PRT
<213> ORGANISM: Artificial Sequence
<220> FEATURE:
<223> OTHER INFORMATION: Core polypeptide

<400> SEQUENCE: 561

Thr Ser Leu Ile His Ser Leu Ile Glu Glu Ser Gln Asn Gln Gln Glu
 1               5                  10                  15

Lys Asn Glu Gln Glu Leu Leu Glu Leu Asp Lys Trp Ala Ser Leu Trp
             20                  25                  30

Asn Trp Phe Asn
            35

<210> SEQ ID NO 562
<211> LENGTH: 36
<212> TYPE: PRT
<213> ORGANISM: Artificial Sequence
<220> FEATURE:
<223> OTHER INFORMATION: Core polypeptide

<400> SEQUENCE: 562

Asn Tyr Thr Ser Leu Ile His Ser Leu Ile Glu Glu Ser Gln Asn Gln
 1               5                  10                  15

Gln Glu Lys Asn Glu Gln Glu Leu Leu Glu Leu Asp Lys Trp Ala Ser
             20                  25                  30

Leu Trp Asn Trp
            35

<210> SEQ ID NO 563
```

<211> LENGTH: 36
<212> TYPE: PRT
<213> ORGANISM: Artificial Sequence
<220> FEATURE:
<223> OTHER INFORMATION: Core polypeptide

<400> SEQUENCE: 563

Asn Asn Tyr Thr Ser Leu Ile His Ser Leu Ile Glu Glu Ser Gln Asn
 1               5                  10                  15

Gln Gln Glu Lys Asn Glu Gln Glu Leu Leu Glu Leu Asp Lys Trp Ala
            20                  25                  30

Ser Leu Trp Asn
        35

<210> SEQ ID NO 564
<211> LENGTH: 36
<212> TYPE: PRT
<213> ORGANISM: Artificial Sequence
<220> FEATURE:
<223> OTHER INFORMATION: Core polypeptide

<400> SEQUENCE: 564

Ile Asn Asn Tyr Thr Ser Leu Ile His Ser Leu Ile Glu Glu Ser Gln
 1               5                  10                  15

Asn Gln Gln Glu Lys Asn Glu Gln Glu Leu Leu Glu Leu Asp Lys Trp
            20                  25                  30

Ala Ser Leu Trp
        35

<210> SEQ ID NO 565
<211> LENGTH: 36
<212> TYPE: PRT
<213> ORGANISM: Artificial Sequence
<220> FEATURE:
<223> OTHER INFORMATION: Core polypeptide

<400> SEQUENCE: 565

Glu Ile Asn Asn Tyr Thr Ser Leu Ile His Ser Leu Ile Glu Glu Ser
 1               5                  10                  15

Gln Asn Gln Gln Glu Lys Asn Glu Gln Glu Leu Leu Glu Leu Asp Lys
            20                  25                  30

Trp Ala Ser Leu
        35

<210> SEQ ID NO 566
<211> LENGTH: 36
<212> TYPE: PRT
<213> ORGANISM: Artificial Sequence
<220> FEATURE:
<223> OTHER INFORMATION: Core polypeptide

<400> SEQUENCE: 566

Arg Glu Ile Asn Asn Tyr Thr Ser Leu Ile His Ser Leu Ile Glu Glu
 1               5                  10                  15

Ser Gln Asn Gln Gln Glu Lys Asn Glu Gln Glu Leu Leu Glu Leu Asp
            20                  25                  30

Lys Trp Ala Ser
        35

<210> SEQ ID NO 567
<211> LENGTH: 36
<212> TYPE: PRT
<213> ORGANISM: Artificial Sequence

```
<220> FEATURE:
<223> OTHER INFORMATION: Core polypeptide

<400> SEQUENCE: 567

Asp Arg Glu Ile Asn Asn Tyr Thr Ser Leu Ile His Ser Leu Ile Glu
 1               5                  10                  15

Glu Ser Gln Asn Gln Gln Glu Lys Asn Glu Gln Glu Leu Leu Glu Leu
             20                  25                  30

Asp Lys Trp Ala
         35

<210> SEQ ID NO 568
<211> LENGTH: 36
<212> TYPE: PRT
<213> ORGANISM: Artificial Sequence
<220> FEATURE:
<223> OTHER INFORMATION: Core polypeptide

<400> SEQUENCE: 568

Trp Asp Arg Glu Ile Asn Asn Tyr Thr Ser Leu Ile His Ser Leu Ile
 1               5                  10                  15

Glu Glu Ser Gln Asn Gln Gln Glu Lys Asn Gln Glu Gln Leu Leu Glu
             20                  25                  30

Leu Asp Lys Trp
         35

<210> SEQ ID NO 569
<211> LENGTH: 36
<212> TYPE: PRT
<213> ORGANISM: Artificial Sequence
<220> FEATURE:
<223> OTHER INFORMATION: Core polypeptide

<400> SEQUENCE: 569

Glu Trp Asp Arg Glu Ile Asn Asn Tyr Thr Ser Leu Ile His Ser Leu
 1               5                  10                  15

Ile Glu Glu Ser Gln Asn Gln Gln Glu Lys Asn Glu Gln Glu Leu Leu
             20                  25                  30

Glu Leu Asp Lys
         35

<210> SEQ ID NO 570
<211> LENGTH: 38
<212> TYPE: PRT
<213> ORGANISM: Artificial Sequence
<220> FEATURE:
<223> OTHER INFORMATION: Core polypeptide

<400> SEQUENCE: 570

Met Glu Trp Asp Arg Glu Ile Asn Asn Tyr Thr Ser Leu Ile His Ser
 1               5                  10                  15

Leu Ile Glu Glu Ser Gln Asn Gln Gln Glu Lys Asn Glu Gln Glu Leu
             20                  25                  30

Leu Glu Leu Asp Asn His
         35

<210> SEQ ID NO 571
<211> LENGTH: 36
<212> TYPE: PRT
<213> ORGANISM: Artificial Sequence
<220> FEATURE:
<223> OTHER INFORMATION: Core polypeptide
```

<400> SEQUENCE: 571

Met Glu Trp Asp Arg Glu Ile Asn Asn Tyr Thr Ser Leu Ile His Ser
 1               5                  10                  15

Leu Ile Glu Glu Ser Gln Asn Gln Gln Glu Lys Asn Glu Gln Glu Leu
             20                  25                  30

Leu Glu Leu Asp
         35

<210> SEQ ID NO 572
<211> LENGTH: 36
<212> TYPE: PRT
<213> ORGANISM: Artificial Sequence
<220> FEATURE:
<223> OTHER INFORMATION: Core polypeptide

<400> SEQUENCE: 572

Trp Met Glu Trp Asp Arg Glu Ile Asn Asn Tyr Thr Ser Leu Ile His
 1               5                  10                  15

Ser Leu Ile Glu Glu Ser Gln Asn Gln Gln Glu Lys Asn Glu Gln Glu
             20                  25                  30

Leu Leu Glu Leu
         35

<210> SEQ ID NO 573
<211> LENGTH: 36
<212> TYPE: PRT
<213> ORGANISM: Artificial Sequence
<220> FEATURE:
<223> OTHER INFORMATION: Core polypeptide

<400> SEQUENCE: 573

Thr Trp Met Glu Trp Asp Arg Glu Ile Asn Asn Tyr Thr Ser Leu Ile
 1               5                  10                  15

His Ser Leu Ile Glu Glu Ser Gln Asn Gln Gln Glu Lys Asn Glu Gln
             20                  25                  30

Glu Leu Leu Glu
         35

<210> SEQ ID NO 574
<211> LENGTH: 36
<212> TYPE: PRT
<213> ORGANISM: Artificial Sequence
<220> FEATURE:
<223> OTHER INFORMATION: Core polypeptide

<400> SEQUENCE: 574

Met Thr Trp Met Glu Trp Asp Arg Glu Ile Asn Asn Tyr Thr Ser Leu
 1               5                  10                  15

Ile His Ser Leu Ile Glu Glu Ser Gln Asn Gln Gln Glu Lys Asn Glu
             20                  25                  30

Gln Glu Leu Leu
         35

<210> SEQ ID NO 575
<211> LENGTH: 36
<212> TYPE: PRT
<213> ORGANISM: Artificial Sequence
<220> FEATURE:
<223> OTHER INFORMATION: Core polypeptide

<400> SEQUENCE: 575

Asn Met Thr Trp Met Glu Trp Asp Arg Glu Ile Asn Asn Tyr Thr Ser

-continued

```
              1               5              10              15
Leu Ile His Ser Leu Ile Glu Glu Ser Gln Asn Gln Gln Glu Lys Asn
                     20              25              30

Glu Gln Glu Leu
         35

<210> SEQ ID NO 576
<211> LENGTH: 36
<212> TYPE: PRT
<213> ORGANISM: Artificial Sequence
<220> FEATURE:
<223> OTHER INFORMATION: Core polypeptide

<400> SEQUENCE: 576

Asn Asn Met Thr Trp Met Glu Trp Asp Arg Glu Ile Asn Asn Tyr Thr
  1               5              10              15

Ser Leu Ile His Ser Leu Ile Glu Glu Ser Gln Asn Gln Gln Glu Lys
                 20              25              30

Asn Glu Gln Glu
         35

<210> SEQ ID NO 577
<211> LENGTH: 36
<212> TYPE: PRT
<213> ORGANISM: Artificial Sequence
<220> FEATURE:
<223> OTHER INFORMATION: Core polypeptide

<400> SEQUENCE: 577

Trp Asn Asn Met Thr Trp Met Glu Trp Asp Arg Glu Ile Asn Asn Tyr
  1               5              10              15

Thr Ser Leu Ile His Ser Leu Ile Glu Glu Ser Gln Asn Gln Gln Glu
                 20              25              30

Lys Asn Glu Gln
         35

<210> SEQ ID NO 578
<211> LENGTH: 36
<212> TYPE: PRT
<213> ORGANISM: Artificial Sequence
<220> FEATURE:
<223> OTHER INFORMATION: Core polypeptide

<400> SEQUENCE: 578

Ile Trp Asn Asn Met Thr Trp Met Glu Trp Asp Arg Glu Ile Asn Asn
  1               5              10              15

Tyr Thr Ser Leu Ile His Ser Leu Ile Glu Glu Ser Gln Asn Gln Gln
                 20              25              30

Glu Lys Asn Glu
         35

<210> SEQ ID NO 579
<211> LENGTH: 36
<212> TYPE: PRT
<213> ORGANISM: Artificial Sequence
<220> FEATURE:
<223> OTHER INFORMATION: Core polypeptide

<400> SEQUENCE: 579

Gln Ile Trp Asn Asn Met Thr Trp Met Glu Trp Asp Arg Glu Ile Asn
  1               5              10              15

Asn Tyr Thr Ser Leu Ile His Ser Leu Ile Glu Glu Ser Gln Asn Gln
```

```
            20                  25                  30

Gln Glu Lys Asn
        35

<210> SEQ ID NO 580
<211> LENGTH: 36
<212> TYPE: PRT
<213> ORGANISM: Artificial Sequence
<220> FEATURE:
<223> OTHER INFORMATION: Core polypeptide

<400> SEQUENCE: 580

Glu Gln Ile Trp Asn Asn Met Thr Trp Met Glu Trp Asp Arg Glu Ile
1               5                  10                  15

Asn Asn Tyr Thr Ser Leu Ile His Ser Leu Ile Glu Glu Ser Gln Asn
            20                  25                  30

Gln Gln Glu Lys
        35

<210> SEQ ID NO 581
<211> LENGTH: 36
<212> TYPE: PRT
<213> ORGANISM: Artificial Sequence
<220> FEATURE:
<223> OTHER INFORMATION: Core polypeptide

<400> SEQUENCE: 581

Leu Glu Gln Ile Trp Asn Asn Met Thr Trp Met Glu Trp Asp Arg Glu
1               5                  10                  15

Ile Asn Asn Tyr Thr Ser Leu Ile His Ser Leu Ile Glu Glu Ser Gln
            20                  25                  30

Asn Gln Gln Glu
        35

<210> SEQ ID NO 582
<211> LENGTH: 36
<212> TYPE: PRT
<213> ORGANISM: Artificial Sequence
<220> FEATURE:
<223> OTHER INFORMATION: Core polypeptide

<400> SEQUENCE: 582

Ser Leu Glu Gln Ile Trp Asn Asn Met Thr Trp Met Glu Trp Asp Arg
1               5                  10                  15

Glu Ile Asn Asn Tyr Thr Ser Leu Ile His Ser Leu Ile Glu Glu Ser
            20                  25                  30

Gln Asn Gln Gln
        35

<210> SEQ ID NO 583
<211> LENGTH: 36
<212> TYPE: PRT
<213> ORGANISM: Artificial Sequence
<220> FEATURE:
<223> OTHER INFORMATION: Core polypeptide

<400> SEQUENCE: 583

Lys Ser Leu Glu Gln Ile Trp Asn Asn Met Thr Trp Met Glu Trp Asp
1               5                  10                  15

Arg Glu Ile Asn Asn Tyr Thr Ser Leu Ile His Ser Leu Ile Glu Glu
            20                  25                  30

Ser Gln Asn Gln
```

-continued

<210> SEQ ID NO 584
<211> LENGTH: 36
<212> TYPE: PRT
<213> ORGANISM: Artificial Sequence
<220> FEATURE:
<223> OTHER INFORMATION: Core polypeptide

<400> SEQUENCE: 584

Asn Lys Ser Leu Glu Gln Ile Trp Asn Asn Met Thr Trp Met Glu Trp
 1               5                  10                  15

Asp Arg Glu Ile Asn Asn Tyr Thr Ser Leu Ile His Ser Leu Ile Glu
            20                  25                  30

Glu Ser Gln Asn
        35

<210> SEQ ID NO 585
<211> LENGTH: 21
<212> TYPE: PRT
<213> ORGANISM: Artificial Sequence
<220> FEATURE:
<223> OTHER INFORMATION: Core polypeptide

<400> SEQUENCE: 585

Ser Leu Ala Phe Ile Arg Lys Ser Asp Glu Leu Leu His Asn Val Asn
 1               5                  10                  15

Ala Gly Lys Ser Thr
            20

<210> SEQ ID NO 586
<211> LENGTH: 21
<212> TYPE: PRT
<213> ORGANISM: Artificial Sequence
<220> FEATURE:
<223> OTHER INFORMATION: Core polypeptide

<400> SEQUENCE: 586

Phe Asp Ala Ser Ile Ser Gln Val Asn Glu Lys Ile Asn Gln Ser Leu
 1               5                  10                  15

Ala Phe Ile Arg Lys
            20

<210> SEQ ID NO 587
<211> LENGTH: 36
<212> TYPE: PRT
<213> ORGANISM: Artificial Sequence
<220> FEATURE:
<223> OTHER INFORMATION: Core polypeptide

<400> SEQUENCE: 587

Tyr Thr Ser Leu Ile His Ser Leu Ile Glu Glu Ser Gln Gln Gln
 1               5                  10                  15

Glu Lys Gln Glu Gln Glu Leu Leu Glu Leu Asp Lys Trp Ala Ser Leu
            20                  25                  30

Trp Asn Trp Phe
        35

<210> SEQ ID NO 588
<211> LENGTH: 33
<212> TYPE: PRT
<213> ORGANISM: Artificial Sequence
<220> FEATURE:
<223> OTHER INFORMATION: Core polypeptide

<400> SEQUENCE: 588

Phe Asp Ala Ser Ile Ser Gln Val Asn Glu Lys Ile Asn Gln Ser Leu
1               5                   10                  15

Ala Phe Ile Arg Lys Ser Asp Glu Leu Leu His Asn Val Asn Ala Gly
            20                  25                  30

Lys

<210> SEQ ID NO 589
<211> LENGTH: 31
<212> TYPE: PRT
<213> ORGANISM: Artificial Sequence
<220> FEATURE:
<223> OTHER INFORMATION: Core polypeptide

<400> SEQUENCE: 589

Phe Asp Ala Ser Ile Ser Gln Val Asn Glu Lys Ile Asn Gln Ser Leu
1               5                   10                  15

Ala Phe Ile Arg Lys Ser Asp Glu Leu Leu His Asn Val Asn Ala
            20                  25                  30

<210> SEQ ID NO 590
<211> LENGTH: 29
<212> TYPE: PRT
<213> ORGANISM: Artificial Sequence
<220> FEATURE:
<223> OTHER INFORMATION: Core polypeptide

<400> SEQUENCE: 590

Phe Asp Ala Ser Ile Ser Gln Val Asn Glu Lys Ile Asn Gln Ser Leu
1               5                   10                  15

Ala Phe Ile Arg Lys Ser Asp Glu Leu Leu His Asn Val
            20                  25

<210> SEQ ID NO 591
<211> LENGTH: 27
<212> TYPE: PRT
<213> ORGANISM: Artificial Sequence
<220> FEATURE:
<223> OTHER INFORMATION: Core polypeptide

<400> SEQUENCE: 591

Phe Asp Ala Ser Ile Ser Gln Val Asn Glu Lys Ile Asn Gln Ser Leu
1               5                   10                  15

Ala Phe Ile Arg Lys Ser Asp Glu Leu Leu His
            20                  25

<210> SEQ ID NO 592
<211> LENGTH: 25
<212> TYPE: PRT
<213> ORGANISM: Artificial Sequence
<220> FEATURE:
<223> OTHER INFORMATION: Core polypeptide

<400> SEQUENCE: 592

Phe Asp Ala Ser Ile Ser Gln Val Asn Glu Lys Ile Asn Gln Ser Leu
1               5                   10                  15

Ala Phe Ile Arg Lys Ser Asp Glu Leu
            20                  25

<210> SEQ ID NO 593
<211> LENGTH: 23
<212> TYPE: PRT

-continued

<213> ORGANISM: Artificial Sequence
<220> FEATURE:
<223> OTHER INFORMATION: Core polypeptide

<400> SEQUENCE: 593

Phe Asp Ala Ser Ile Ser Gln Val Asn Glu Lys Ile Asn Gln Ser Leu
1               5                   10                  15

Ala Phe Ile Arg Lys Ser Asp
            20

<210> SEQ ID NO 594
<211> LENGTH: 33
<212> TYPE: PRT
<213> ORGANISM: Artificial Sequence
<220> FEATURE:
<223> OTHER INFORMATION: Core polypeptide

<400> SEQUENCE: 594

Ala Ser Ile Ser Gln Val Asn Glu Lys Ile Asn Gln Ser Leu Ala Phe
1               5                   10                  15

Ile Arg Lys Ser Asp Glu Leu Leu His Asn Val Asn Ala Gly Lys Ser
            20                  25                  30

Thr

<210> SEQ ID NO 595
<211> LENGTH: 31
<212> TYPE: PRT
<213> ORGANISM: Artificial Sequence
<220> FEATURE:
<223> OTHER INFORMATION: Core polypeptide

<400> SEQUENCE: 595

Ile Ser Gln Val Asn Glu Lys Ile Asn Gln Ser Leu Ala Phe Ile Arg
1               5                   10                  15

Lys Ser Asp Glu Leu Leu His Asn Val Asn Ala Gly Lys Ser Thr
            20                  25                  30

<210> SEQ ID NO 596
<211> LENGTH: 29
<212> TYPE: PRT
<213> ORGANISM: Artificial Sequence
<220> FEATURE:
<223> OTHER INFORMATION: Core polypeptide

<400> SEQUENCE: 596

Gln Val Asn Glu Lys Ile Asn Gln Ser Leu Ala Phe Ile Arg Lys Ser
1               5                   10                  15

Asp Glu Leu Leu His Asn Val Asn Ala Gly Lys Ser Thr
            20                  25

<210> SEQ ID NO 597
<211> LENGTH: 27
<212> TYPE: PRT
<213> ORGANISM: Artificial Sequence
<220> FEATURE:
<223> OTHER INFORMATION: Core polypeptide

<400> SEQUENCE: 597

Asn Glu Lys Ile Asn Gln Ser Leu Ala Phe Ile Arg Lys Ser Asp Glu
1               5                   10                  15

Leu Leu His Asn Val Asn Ala Gly Lys Ser Thr
            20                  25

```
<210> SEQ ID NO 598
<211> LENGTH: 25
<212> TYPE: PRT
<213> ORGANISM: Artificial Sequence
<220> FEATURE:
<223> OTHER INFORMATION: Core polypeptide

<400> SEQUENCE: 598

Lys Ile Asn Gln Ser Leu Ala Phe Ile Arg Lys Ser Asp Glu Leu Leu
 1               5                  10                  15

His Asn Val Asn Ala Gly Lys Ser Thr
            20                  25

<210> SEQ ID NO 599
<211> LENGTH: 23
<212> TYPE: PRT
<213> ORGANISM: Artificial Sequence
<220> FEATURE:
<223> OTHER INFORMATION: Core polypeptide

<400> SEQUENCE: 599

Asn Gln Ser Leu Ala Phe Ile Arg Lys Ser Asp Glu Leu Leu His Asn
 1               5                  10                  15

Val Asn Ala Gly Lys Ser Thr
            20

<210> SEQ ID NO 600
<211> LENGTH: 30
<212> TYPE: PRT
<213> ORGANISM: Artificial Sequence
<220> FEATURE:
<223> OTHER INFORMATION: Core polypeptide

<400> SEQUENCE: 600

Phe Trp Asn Trp Leu Ser Ala Trp Lys Asp Leu Glu Leu Tyr Pro Gly
 1               5                  10                  15

Ser Leu Glu Leu Asp Lys Trp Ala Ser Leu Trp Asn Trp Phe
            20                  25                  30

<210> SEQ ID NO 601
<211> LENGTH: 41
<212> TYPE: PRT
<213> ORGANISM: Artificial Sequence
<220> FEATURE:
<223> OTHER INFORMATION: Core polypeptide

<400> SEQUENCE: 601

Cys Gly Gly Asn Asn Leu Leu Arg Ala Ile Glu Ala Gln Gln His Leu
 1               5                  10                  15

Leu Gln Leu Thr Val Trp Gly Ile Lys Gln Leu Gln Ala Arg Ile Leu
            20                  25                  30

Ala Val Glu Arg Tyr Leu Lys Asp Gln
        35                  40

<210> SEQ ID NO 602
<211> LENGTH: 39
<212> TYPE: PRT
<213> ORGANISM: Artificial Sequence
<220> FEATURE:
<223> OTHER INFORMATION: Core polypeptide

<400> SEQUENCE: 602

Cys Gly Gly Tyr Thr Ser Leu Ile His Ser Leu Ile Glu Glu Ser Gln
 1               5                  10                  15
```

-continued

Asn Gln Gln Glu Lys Asn Glu Gln Glu Leu Leu Glu Leu Asp Lys Trp
            20                  25                  30

Ala Ser Leu Trp Asn Trp Phe
            35

<210> SEQ ID NO 603
<211> LENGTH: 36
<212> TYPE: PRT
<213> ORGANISM: Artificial Sequence
<220> FEATURE:
<223> OTHER INFORMATION: Core polypeptide

<400> SEQUENCE: 603

Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser Leu
            20                  25                  30

Trp Asn Trp Phe
            35

<210> SEQ ID NO 604
<211> LENGTH: 38
<212> TYPE: PRT
<213> ORGANISM: Artificial Sequence
<220> FEATURE:
<223> OTHER INFORMATION: Core polypeptide

<400> SEQUENCE: 604

Asn Asn Leu Leu Arg Ala Ile Glu Ala Gln Gln His Leu Leu Gln Leu
 1               5                  10                  15

Thr Val Trp Gly Ile Lys Gln Leu Gln Ala Arg Ile Leu Ala Val Glu
            20                  25                  30

Arg Tyr Leu Lys Asp Gln
            35

<210> SEQ ID NO 605
<211> LENGTH: 36
<212> TYPE: PRT
<213> ORGANISM: Artificial Sequence
<220> FEATURE:
<223> OTHER INFORMATION: Core polypeptide

<400> SEQUENCE: 605

Glu Lys Asn Met Tyr Glu Leu Gln Lys Leu Asn Ser Trp Asp Val Phe
 1               5                  10                  15

Thr Asn Trp Leu Asp Phe Thr Ser Trp Val Arg Tyr Ile Gln Tyr Ile
            20                  25                  30

Gln Tyr Gly Val
            35

<210> SEQ ID NO 606
<211> LENGTH: 36
<212> TYPE: PRT
<213> ORGANISM: Artificial Sequence
<220> FEATURE:
<223> OTHER INFORMATION: Core polypeptide

<400> SEQUENCE: 606

Gln Glu Lys Asn Met Tyr Glu Leu Gln Lys Leu Asn Ser Trp Asp Val
 1               5                  10                  15

Phe Thr Asn Trp Leu Asp Phe Thr Ser Trp Val Arg Tyr Ile Gln Tyr
            20                  25                  30

```
Ile Gln Tyr Gly
        35

<210> SEQ ID NO 607
<211> LENGTH: 36
<212> TYPE: PRT
<213> ORGANISM: Artificial Sequence
<220> FEATURE:
<223> OTHER INFORMATION: Core polypeptide

<400> SEQUENCE: 607

Gln Gln Glu Lys Asn Met Tyr Glu Leu Gln Lys Leu Asn Ser Trp Asp
 1               5                  10                  15

Val Phe Thr Asn Trp Leu Asp Phe Thr Ser Trp Val Arg Tyr Ile Gln
            20                  25                  30

Tyr Ile Gln Tyr
        35

<210> SEQ ID NO 608
<211> LENGTH: 36
<212> TYPE: PRT
<213> ORGANISM: Artificial Sequence
<220> FEATURE:
<223> OTHER INFORMATION: Core polypeptide

<400> SEQUENCE: 608

Ile Gln Gln Glu Lys Asn Met Tyr Glu Leu Gln Lys Leu Asn Ser Trp
 1               5                  10                  15

Asp Val Phe Thr Asn Trp Leu Asp Phe Thr Ser Trp Val Arg Tyr Ile
            20                  25                  30

Gln Tyr Ile Gln
        35

<210> SEQ ID NO 609
<211> LENGTH: 36
<212> TYPE: PRT
<213> ORGANISM: Artificial Sequence
<220> FEATURE:
<223> OTHER INFORMATION: Core polypeptide

<400> SEQUENCE: 609

Gln Ile Gln Gln Glu Lys Asn Met Tyr Glu Leu Gln Lys Leu Asn Ser
 1               5                  10                  15

Trp Asp Val Phe Thr Asn Trp Leu Asp Phe Thr Ser Trp Val Arg Tyr
            20                  25                  30

Ile Gln Tyr Ile
        35

<210> SEQ ID NO 610
<211> LENGTH: 36
<212> TYPE: PRT
<213> ORGANISM: Artificial Sequence
<220> FEATURE:
<223> OTHER INFORMATION: Core polypeptide

<400> SEQUENCE: 610

Ala Gln Ile Gln Gln Glu Lys Asn Met Tyr Glu Leu Gln Lys Leu Asn
 1               5                  10                  15

Ser Trp Asp Val Phe Thr Asn Trp Leu Asp Phe Thr Ser Trp Val Arg
            20                  25                  30

Tyr Ile Gln Tyr
        35
```

```
<210> SEQ ID NO 611
<211> LENGTH: 36
<212> TYPE: PRT
<213> ORGANISM: Artificial Sequence
<220> FEATURE:
<223> OTHER INFORMATION: Core polypeptide

<400> SEQUENCE: 611
```

Gln Ala Gln Ile Gln Gln Glu Lys Asn Met Tyr Glu Leu Gln Lys Leu
1               5                   10                  15

Asn Ser Trp Asp Val Phe Thr Asn Trp Leu Asp Phe Thr Ser Trp Val
            20                  25                  30

Arg Tyr Ile Gln
        35

```
<210> SEQ ID NO 612
<211> LENGTH: 36
<212> TYPE: PRT
<213> ORGANISM: Artificial Sequence
<220> FEATURE:
<223> OTHER INFORMATION: Core polypeptide

<400> SEQUENCE: 612
```

Glu Gln Ala Gln Ile Gln Gln Glu Lys Asn Met Tyr Glu Leu Gln Lys
1               5                   10                  15

Leu Asn Ser Trp Asp Val Phe Thr Asn Trp Leu Asp Phe Thr Ser Trp
            20                  25                  30

Val Arg Tyr Ile
        35

```
<210> SEQ ID NO 613
<211> LENGTH: 36
<212> TYPE: PRT
<213> ORGANISM: Artificial Sequence
<220> FEATURE:
<223> OTHER INFORMATION: Core polypeptide

<400> SEQUENCE: 613
```

Leu Glu Gln Ala Gln Ile Gln Gln Glu Lys Asn Met Tyr Glu Leu Gln
1               5                   10                  15

Lys Leu Asn Ser Trp Asp Val Phe Thr Asn Trp Leu Asp Phe Thr Ser
            20                  25                  30

Trp Val Arg Tyr
        35

```
<210> SEQ ID NO 614
<211> LENGTH: 36
<212> TYPE: PRT
<213> ORGANISM: Artificial Sequence
<220> FEATURE:
<223> OTHER INFORMATION: Core polypeptide

<400> SEQUENCE: 614
```

Ser Leu Glu Gln Ala Gln Ile Gln Gln Glu Lys Asn Met Tyr Glu Leu
1               5                   10                  15

Gln Lys Leu Asn Ser Trp Asp Val Phe Thr Asn Trp Leu Asp Phe Thr
            20                  25                  30

Ser Trp Val Arg
        35

```
<210> SEQ ID NO 615
<211> LENGTH: 36
```

<212> TYPE: PRT
<213> ORGANISM: Artificial Sequence
<220> FEATURE:
<223> OTHER INFORMATION: Core polypeptide

<400> SEQUENCE: 615

Gln Ser Leu Glu Gln Ala Gln Ile Gln Gln Glu Lys Asn Met Tyr Glu
1               5                   10                  15

Leu Gln Lys Leu Asn Ser Trp Asp Val Phe Thr Asn Trp Leu Asp Phe
            20                  25                  30

Thr Ser Trp Val
        35

<210> SEQ ID NO 616
<211> LENGTH: 36
<212> TYPE: PRT
<213> ORGANISM: Artificial Sequence
<220> FEATURE:
<223> OTHER INFORMATION: Core polypeptide

<400> SEQUENCE: 616

Ser Gln Ser Leu Glu Gln Ala Gln Ile Gln Gln Glu Lys Asn Met Tyr
1               5                   10                  15

Glu Leu Gln Lys Leu Asn Ser Trp Asp Val Phe Thr Asn Trp Leu Asp
            20                  25                  30

Phe Thr Ser Trp
        35

<210> SEQ ID NO 617
<211> LENGTH: 36
<212> TYPE: PRT
<213> ORGANISM: Artificial Sequence
<220> FEATURE:
<223> OTHER INFORMATION: Core polypeptide

<400> SEQUENCE: 617

Ile Ser Gln Ser Leu Glu Gln Ala Gln Ile Gln Gln Glu Lys Asn Met
1               5                   10                  15

Tyr Glu Leu Gln Lys Leu Asn Ser Trp Asp Val Phe Thr Asn Trp Leu
            20                  25                  30

Asp Phe Thr Ser
        35

<210> SEQ ID NO 618
<211> LENGTH: 36
<212> TYPE: PRT
<213> ORGANISM: Artificial Sequence
<220> FEATURE:
<223> OTHER INFORMATION: Core polypeptide

<400> SEQUENCE: 618

Asn Ile Ser Gln Ser Leu Glu Gln Ala Gln Ile Gln Gln Glu Lys Asn
1               5                   10                  15

Met Tyr Glu Leu Gln Lys Leu Asn Ser Trp Asp Val Phe Thr Asn Trp
            20                  25                  30

Leu Asp Phe Thr
        35

<210> SEQ ID NO 619
<211> LENGTH: 36
<212> TYPE: PRT
<213> ORGANISM: Artificial Sequence
<220> FEATURE:

<223> OTHER INFORMATION: Core polypeptide

<400> SEQUENCE: 619

Ala Asn Ile Ser Gln Ser Leu Glu Gln Ala Gln Ile Gln Gln Glu Lys
1               5                   10                  15

Asn Met Tyr Glu Leu Gln Lys Leu Asn Ser Trp Asp Val Phe Thr Asn
            20                  25                  30

Trp Leu Asp Phe
        35

<210> SEQ ID NO 620
<211> LENGTH: 36
<212> TYPE: PRT
<213> ORGANISM: Artificial Sequence
<220> FEATURE:
<223> OTHER INFORMATION: Core polypeptide

<400> SEQUENCE: 620

Glu Ala Asn Ile Ser Gln Ser Leu Glu Gln Ala Gln Ile Gln Gln Glu
1               5                   10                  15

Lys Asn Met Tyr Glu Leu Gln Lys Leu Asn Ser Trp Asp Val Phe Thr
            20                  25                  30

Asn Trp Leu Asp
        35

<210> SEQ ID NO 621
<211> LENGTH: 36
<212> TYPE: PRT
<213> ORGANISM: Artificial Sequence
<220> FEATURE:
<223> OTHER INFORMATION: Core polypeptide

<400> SEQUENCE: 621

Leu Glu Ala Asn Ile Ser Gln Ser Leu Glu Gln Ala Gln Ile Gln Gln
1               5                   10                  15

Glu Lys Asn Met Tyr Glu Leu Gln Lys Leu Asn Ser Trp Asp Val Phe
            20                  25                  30

Thr Asn Trp Leu
        35

<210> SEQ ID NO 622
<211> LENGTH: 36
<212> TYPE: PRT
<213> ORGANISM: Artificial Sequence
<220> FEATURE:
<223> OTHER INFORMATION: Core polypeptide

<400> SEQUENCE: 622

Tyr Leu Glu Ala Asn Ile Ser Gln Ser Leu Glu Gln Ala Gln Ile Gln
1               5                   10                  15

Gln Glu Lys Asn Met Tyr Glu Leu Gln Lys Leu Asn Ser Trp Asp Val
            20                  25                  30

Phe Thr Asn Trp
        35

<210> SEQ ID NO 623
<211> LENGTH: 23
<212> TYPE: PRT
<213> ORGANISM: Artificial Sequence
<220> FEATURE:
<223> OTHER INFORMATION: Core polypeptide

<400> SEQUENCE: 623

Tyr Thr Ser Leu Ile His Ser Leu Ile Glu Glu Ser Gln Asn Gln Gln
1               5                   10                  15

Glu Lys Asn Glu Gln Glu Leu
            20

<210> SEQ ID NO 624
<211> LENGTH: 36
<212> TYPE: PRT
<213> ORGANISM: Artificial Sequence
<220> FEATURE:
<223> OTHER INFORMATION: Core polypeptide

<400> SEQUENCE: 624

Tyr Thr Ser Leu Ile His Ser Leu Ile Glu Glu Ser Gln Asn Leu Gln
1               5                   10                  15

Glu Lys Asn Glu Gln Glu Leu Leu Glu Leu Asp Lys Trp Ala Ser Leu
            20                  25                  30

Trp Asn Trp Phe
            35

<210> SEQ ID NO 625
<211> LENGTH: 36
<212> TYPE: PRT
<213> ORGANISM: Artificial Sequence
<220> FEATURE:
<223> OTHER INFORMATION: Core polypeptide

<400> SEQUENCE: 625

Tyr Thr Ser Leu Ile His Ser Leu Ile Glu Glu Ser Gln Asn Gln Gln
1               5                   10                  15

Glu Lys Leu Glu Gln Glu Leu Leu Glu Leu Asp Lys Trp Ala Ser Leu
            20                  25                  30

Trp Asn Trp Phe
            35

<210> SEQ ID NO 626
<211> LENGTH: 36
<212> TYPE: PRT
<213> ORGANISM: Artificial Sequence
<220> FEATURE:
<223> OTHER INFORMATION: Core polypeptide

<400> SEQUENCE: 626

Tyr Thr Ser Leu Ile His Ser Leu Ile Glu Glu Ser Gln Asn Gln Gln
1               5                   10                  15

Glu Lys Asn Glu Gln Glu Leu Leu Glu Phe Asp Lys Trp Ala Ser Leu
            20                  25                  30

Trp Asn Trp Phe
            35

<210> SEQ ID NO 627
<211> LENGTH: 36
<212> TYPE: PRT
<213> ORGANISM: Artificial Sequence
<220> FEATURE:
<223> OTHER INFORMATION: Core polypeptide

<400> SEQUENCE: 627

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Pro Ala Ser Leu
            20                  25                  30

Trp Asn Trp Phe
        35

<210> SEQ ID NO 628
<211> LENGTH: 36
<212> TYPE: PRT
<213> ORGANISM: Artificial Sequence
<220> FEATURE:
<223> OTHER INFORMATION: Core polypeptide

<400> SEQUENCE: 628

Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser Pro
            20                  25                  30

Trp Asn Trp Phe
        35

<210> SEQ ID NO 629
<211> LENGTH: 36
<212> TYPE: PRT
<213> ORGANISM: Artificial Sequence
<220> FEATURE:
<223> OTHER INFORMATION: Core polypeptide

<400> SEQUENCE: 629

Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser Leu
            20                  25                  30

Trp Asn Ser Phe
        35

<210> SEQ ID NO 630
<211> LENGTH: 36
<212> TYPE: PRT
<213> ORGANISM: Artificial Sequence
<220> FEATURE:
<223> OTHER INFORMATION: Core polypeptide

<400> SEQUENCE: 630

Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 631
<211> LENGTH: 36
<212> TYPE: PRT
<213> ORGANISM: Artificial Sequence
<220> FEATURE:
<223> OTHER INFORMATION: Core polypeptide

<400> SEQUENCE: 631

Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 632
<211> LENGTH: 39
<212> TYPE: PRT
<213> ORGANISM: Artificial Sequence
<220> FEATURE:
<223> OTHER INFORMATION: Core polypeptide

<400> SEQUENCE: 632

Phe Met Cys Tyr Thr Ser Leu Ile His Ser Leu Ile Glu Glu Ser Gln
1               5                   10                  15

Asn Gln Gln Glu Lys Asn Glu Gln Glu Leu Leu Glu Leu Asp Lys Trp
            20                  25                  30

Ala Ser Leu Trp Asn Trp Phe
        35

<210> SEQ ID NO 633
<211> LENGTH: 41
<212> TYPE: PRT
<213> ORGANISM: Artificial Sequence
<220> FEATURE:
<223> OTHER INFORMATION: Core polypeptide

<400> SEQUENCE: 633

Phe Met Cys Asn Asn Leu Leu Arg Ala Ile Glu Ala Gln Gln His Leu
1               5                   10                  15

Leu Gln Leu Thr Val Trp Gly Ile Lys Gln Leu Gln Ala Arg Ile Leu
            20                  25                  30

Ala Val Glu Arg Tyr Leu Lys Asp Gln
        35                  40

<210> SEQ ID NO 634
<211> LENGTH: 30
<212> TYPE: PRT
<213> ORGANISM: Artificial Sequence
<220> FEATURE:
<223> OTHER INFORMATION: Core polypeptide

<400> SEQUENCE: 634

Glu Trp Asp Arg Glu Ile Asn Asn Tyr Thr Ser Leu Ile His Ser Leu
1               5                   10                  15

Ile Glu Glu Ser Gln Asn Gln Gln Glu Lys Asn Glu Gln Glu
            20                  25                  30

<210> SEQ ID NO 635
<211> LENGTH: 29
<212> TYPE: PRT
<213> ORGANISM: Artificial Sequence
<220> FEATURE:
<223> OTHER INFORMATION: Core polypeptide

<400> SEQUENCE: 635

Leu Ile Glu Glu Ser Gln Asn Gln Gln Glu Lys Asn Glu Gln Glu Leu
1               5                   10                  15

Leu Glu Leu Asp Lys Trp Ala Ser Leu Trp Asn Trp Phe
            20                  25

<210> SEQ ID NO 636
<211> LENGTH: 35
<212> TYPE: PRT
<213> ORGANISM: Artificial Sequence
<220> FEATURE:
<223> OTHER INFORMATION: Core polypeptide

```
<400> SEQUENCE: 636

Phe Trp Asn Trp Leu Ser Ala Trp Lys Asp Leu Glu Leu Gly Gly Pro
 1               5                  10                  15

Gly Ser Gly Pro Gly Gly Leu Glu Leu Asp Lys Trp Ala Ser Leu Trp
            20                  25                  30

Asn Trp Phe
        35

<210> SEQ ID NO 637
<211> LENGTH: 29
<212> TYPE: PRT
<213> ORGANISM: Artificial Sequence
<220> FEATURE:
<223> OTHER INFORMATION: Core polypeptide

<400> SEQUENCE: 637

Leu Ile His Ser Leu Ile Glu Glu Ser Gln Asn Gln Gln Glu Lys Asn
 1               5                  10                  15

Glu Gln Glu Leu Leu Glu Leu Asp Lys Trp Ala Ser Leu
            20                  25

<210> SEQ ID NO 638
<211> LENGTH: 35
<212> TYPE: PRT
<213> ORGANISM: Artificial Sequence
<220> FEATURE:
<223> OTHER INFORMATION: Core polypeptide

<400> SEQUENCE: 638

Thr Ser Leu Ile His Ser Leu Ile Glu Glu Ser Gln Asn Gln Gln Glu
 1               5                  10                  15

Lys Asn Glu Gln Glu Leu Leu Glu Leu Asp Lys Trp Ala Ser Leu Trp
            20                  25                  30

Asn Trp Phe
        35

<210> SEQ ID NO 639
<211> LENGTH: 33
<212> TYPE: PRT
<213> ORGANISM: Artificial Sequence
<220> FEATURE:
<223> OTHER INFORMATION: Core polypeptide

<400> SEQUENCE: 639

Leu Ile His Ser Leu Ile Glu Glu Ser Gln Asn Gln Gln Glu Lys Asn
 1               5                  10                  15

Glu Gln Glu Leu Leu Glu Leu Asp Lys Trp Ala Ser Leu Trp Asn Trp
            20                  25                  30

Phe

<210> SEQ ID NO 640
<211> LENGTH: 41
<212> TYPE: PRT
<213> ORGANISM: Artificial Sequence
<220> FEATURE:
<223> OTHER INFORMATION: Core polypeptide

<400> SEQUENCE: 640

Gly Gly Gly Gly Gly Tyr Thr Ser Leu Ile His Ser Leu Ile Glu Glu
 1               5                  10                  15

Ser Gln Asn Gln Gln Glu Lys Asn Glu Gln Glu Leu Leu Glu Leu Asp
            20                  25                  30
```

```
Lys Trp Ala Ser Leu Trp Asn Trp Phe
        35                  40
```

<210> SEQ ID NO 641
<211> LENGTH: 31
<212> TYPE: PRT
<213> ORGANISM: Artificial Sequence
<220> FEATURE:
<223> OTHER INFORMATION: Core polypeptide

<400> SEQUENCE: 641

```
His Ser Leu Ile Glu Glu Ser Gln Asn Gln Gln Glu Lys Asn Glu Gln
 1               5                  10                  15
Glu Leu Leu Glu Leu Asp Lys Trp Ala Ser Leu Trp Asn Trp Phe
            20                  25                  30
```

<210> SEQ ID NO 642
<211> LENGTH: 36
<212> TYPE: PRT
<213> ORGANISM: Artificial Sequence
<220> FEATURE:
<223> OTHER INFORMATION: Core polypeptide

<400> SEQUENCE: 642

```
Tyr Thr Ser Leu Ile Tyr Ser Leu Ile Glu Ser Gln Asn Gln Gln
 1               5                  10                  15
Glu Lys Asn Glu Gln Glu Leu Leu Glu Leu Asp Lys Trp Ala Ser Leu
            20                  25                  30
Trp Asn Trp Phe
        35
```

<210> SEQ ID NO 643
<211> LENGTH: 36
<212> TYPE: PRT
<213> ORGANISM: Artificial Sequence
<220> FEATURE:
<223> OTHER INFORMATION: Core polypeptide

<400> SEQUENCE: 643

```
Tyr Thr Ser Leu Ile His Ser Leu Ile Glu Lys Ser Gln Asn Gln Gln
 1               5                  10                  15
Glu Lys Asn Glu Gln Glu Leu Leu Glu Leu Asp Lys Trp Ala Ser Leu
            20                  25                  30
Trp Asn Trp Phe
        35
```

<210> SEQ ID NO 644
<211> LENGTH: 36
<212> TYPE: PRT
<213> ORGANISM: Artificial Sequence
<220> FEATURE:
<223> OTHER INFORMATION: Core polypeptide

<400> SEQUENCE: 644

```
Tyr Thr Ser Leu Ile His Ser Ser Ile Glu Gly Ser Gln Asn Gln Gln
 1               5                  10                  15
Glu Lys Asn Glu Gln Glu Leu Leu Glu Leu Asp Lys Trp Ala Ser Leu
            20                  25                  30
Trp Asn Trp Phe
        35
```

<210> SEQ ID NO 645

```
<211> LENGTH: 36
<212> TYPE: PRT
<213> ORGANISM: Artificial Sequence
<220> FEATURE:
<223> OTHER INFORMATION: Core polypeptide

<400> SEQUENCE: 645

Leu Glu Ala Asn Ile Ser Gln Leu Leu Glu Gln Ala Gln Ile Gln Gln
 1               5                  10                  15
Glu Lys Asn Met Tyr Glu Leu Gln Lys Leu Asn Ser Trp Asp Val Phe
            20                  25                  30
Thr Asn Trp Leu
            35

<210> SEQ ID NO 646
<211> LENGTH: 35
<212> TYPE: PRT
<213> ORGANISM: Artificial Sequence
<220> FEATURE:
<223> OTHER INFORMATION: Core polypeptide

<400> SEQUENCE: 646

Ser Leu Glu Glu Cys Asp Ser Glu Leu Glu Ile Lys Arg Tyr Lys Asn
 1               5                  10                  15
Arg Val Ala Ser Arg Lys Cys Arg Ala Lys Phe Lys Gln Leu Leu Gln
            20                  25                  30
His Tyr Arg
        35

<210> SEQ ID NO 647
<211> LENGTH: 35
<212> TYPE: PRT
<213> ORGANISM: Artificial Sequence
<220> FEATURE:
<223> OTHER INFORMATION: Core polypeptide

<400> SEQUENCE: 647

Leu Glu Glu Cys Asp Ser Glu Leu Glu Ile Lys Arg Tyr Lys Asn Arg
 1               5                  10                  15
Val Ala Ser Arg Lys Cys Arg Ala Lys Phe Lys Gln Leu Leu Gln His
            20                  25                  30
Tyr Arg Glu
        35

<210> SEQ ID NO 648
<211> LENGTH: 35
<212> TYPE: PRT
<213> ORGANISM: Artificial Sequence
<220> FEATURE:
<223> OTHER INFORMATION: Core polypeptide

<400> SEQUENCE: 648

Glu Glu Cys Asp Ser Glu Leu Glu Ile Lys Arg Tyr Lys Asn Arg Val
 1               5                  10                  15
Ala Ser Arg Lys Cys Arg Ala Lys Phe Lys Gln Leu Leu Gln His Tyr
            20                  25                  30
Arg Glu Val
        35

<210> SEQ ID NO 649
<211> LENGTH: 35
<212> TYPE: PRT
<213> ORGANISM: Artificial Sequence
```

```
<220> FEATURE:
<223> OTHER INFORMATION: Core polypeptide

<400> SEQUENCE: 649

Glu Cys Asp Ser Glu Leu Glu Ile Lys Arg Tyr Lys Asn Arg Val Ala
 1               5                  10                  15

Ser Arg Lys Cys Arg Ala Lys Phe Lys Gln Leu Leu Gln His Tyr Arg
             20                  25                  30

Glu Val Ala
         35

<210> SEQ ID NO 651
<211> LENGTH: 35
<212> TYPE: PRT
<213> ORGANISM: Artificial Sequence
<220> FEATURE:
<223> OTHER INFORMATION: Core polypeptide

<400> SEQUENCE: 650

Cys Asp Ser Glu Leu Glu Ile Lys Arg Tyr Lys Asn Arg Val Ala Ser
 1               5                  10                  15

Arg Lys Cys Arg Ala Lys Phe Lys Gln Leu Leu Gln His Tyr Arg Glu
             20                  25                  30

Val Ala Ala
         35

<210> SEQ ID NO 651
<211> LENGTH: 35
<212> TYPE: PRT
<213> ORGANISM: Artificial Sequence
<220> FEATURE:
<223> OTHER INFORMATION: Core polypeptide

<400> SEQUENCE: 651

Asp Ser Glu Leu Glu Ile Lys Arg Tyr Lys Asn Arg Val Ala Ser Arg
 1               5                  10                  15

Lys Cys Arg Ala Lys Phe Lys Gln Leu Leu Gln His Tyr Arg Glu Val
             20                  25                  30

Ala Ala Ala
         35

<210> SEQ ID NO 652
<211> LENGTH: 49
<212> TYPE: PRT
<213> ORGANISM: Artificial Sequence
<220> FEATURE:
<223> OTHER INFORMATION: Core polypeptide

<400> SEQUENCE: 652

Asp Glu Ser Ala Met Ile Asn Thr Tyr Arg Ser Ile Asn Glu Phe Asp
 1               5                  10                  15

Ala Ser Ile Ser Gln Val Asn Glu Lys Ile Asn Gln Ser Leu Ala Phe
             20                  25                  30

Ile Arg Lys Ser Asp Glu Leu Leu His Asn Val Asn Ala Gly Lys Ser
             35                  40                  45

Thr

<210> SEQ ID NO 653
<211> LENGTH: 7
<212> TYPE: PRT
<213> ORGANISM: Artificial Sequence
<220> FEATURE:
```

<223> OTHER INFORMATION: Core polypeptide

<400> SEQUENCE: 653

Trp Ala Ser Leu Trp Asn Trp
1               5

<210> SEQ ID NO 654
<211> LENGTH: 38
<212> TYPE: PRT
<213> ORGANISM: Artificial Sequence
<220> FEATURE:
<223> OTHER INFORMATION: Core polypeptide

<400> SEQUENCE: 654

Glu Ala Gln Gln His Leu Leu Gln Leu Thr Val Trp Gly Ile Lys Gln
1               5                   10                  15

Leu Gln Ala Arg Ile Leu Ala Val Glu Arg Tyr Leu Lys Asp Gln Gln
            20                  25                  30

Leu Leu Gly Ile Trp Gly
        35

<210> SEQ ID NO 655
<211> LENGTH: 38
<212> TYPE: PRT
<213> ORGANISM: Artificial Sequence
<220> FEATURE:
<223> OTHER INFORMATION: Core polypeptide

<400> SEQUENCE: 655

Ile Glu Ala Gln Gln His Leu Leu Gln Leu Thr Val Trp Gly Ile Lys
1               5                   10                  15

Gln Leu Gln Ala Arg Ile Leu Ala Val Glu Arg Tyr Leu Lys Asp Gln
            20                  25                  30

Gln Leu Leu Gly Ile Trp
        35

<210> SEQ ID NO 656
<211> LENGTH: 38
<212> TYPE: PRT
<213> ORGANISM: Artificial Sequence
<220> FEATURE:
<223> OTHER INFORMATION: Core polypeptide

<400> SEQUENCE: 656

Ala Ile Glu Ala Gln Gln His Leu Leu Gln Leu Thr Val Trp Gly Ile
1               5                   10                  15

Lys Gln Leu Gln Ala Arg Ile Leu Ala Val Glu Arg Tyr Leu Lys Asp
            20                  25                  30

Gln Gln Leu Leu Gly Ile
        35

<210> SEQ ID NO 657
<211> LENGTH: 38
<212> TYPE: PRT
<213> ORGANISM: Artificial Sequence
<220> FEATURE:
<223> OTHER INFORMATION: Core polypeptide

<400> SEQUENCE: 657

Arg Ala Ile Glu Ala Gln Gln His Leu Leu Gln Leu Thr Val Trp Gly
1               5                   10                  15

Ile Lys Gln Leu Gln Ala Arg Ile Leu Ala Val Glu Arg Tyr Leu Lys
            20                  25                  30

Asp Gln Gln Leu Leu Gly
        35

<210> SEQ ID NO 658
<211> LENGTH: 38
<212> TYPE: PRT
<213> ORGANISM: Artificial Sequence
<220> FEATURE:
<223> OTHER INFORMATION: Core polypeptide

<400> SEQUENCE: 658

Leu Arg Ala Ile Glu Ala Gln Gln His Leu Gln Leu Thr Val Trp
 1               5                  10                  15

Gly Ile Lys Gln Leu Gln Ala Arg Ile Leu Ala Val Glu Arg Tyr Leu
                20                  25                  30

Lys Asp Gln Gln Leu Leu
        35

<210> SEQ ID NO 659
<211> LENGTH: 38
<212> TYPE: PRT
<213> ORGANISM: Artificial Sequence
<220> FEATURE:
<223> OTHER INFORMATION: Core polypeptide

<400> SEQUENCE: 659

Leu Leu Arg Ala Ile Glu Ala Gln Gln His Leu Gln Leu Thr Val
 1               5                  10                  15

Trp Gly Ile Lys Gln Leu Gln Ala Arg Ile Leu Ala Val Glu Arg Tyr
                20                  25                  30

Leu Lys Asp Gln Gln Leu
        35

<210> SEQ ID NO 660
<211> LENGTH: 38
<212> TYPE: PRT
<213> ORGANISM: Artificial Sequence
<220> FEATURE:
<223> OTHER INFORMATION: Core polypeptide

<400> SEQUENCE: 660

Asn Leu Leu Arg Ala Ile Glu Ala Gln Gln His Leu Gln Leu Thr
 1               5                  10                  15

Val Trp Gly Ile Lys Gln Leu Gln Ala Arg Ile Leu Ala Val Glu Arg
                20                  25                  30

Tyr Leu Lys Asp Gln Gln
        35

<210> SEQ ID NO 661
<211> LENGTH: 38
<212> TYPE: PRT
<213> ORGANISM: Artificial Sequence
<220> FEATURE:
<223> OTHER INFORMATION: Core polypeptide

<400> SEQUENCE: 661

Gln Asn Asn Leu Leu Arg Ala Ile Glu Ala Gln Gln His Leu Gln
 1               5                  10                  15

Leu Thr Val Trp Gly Ile Lys Gln Leu Gln Ala Arg Ile Leu Ala Val
                20                  25                  30

Glu Arg Tyr Leu Lys Asp
        35

<210> SEQ ID NO 662
<211> LENGTH: 38
<212> TYPE: PRT
<213> ORGANISM: Artificial Sequence
<220> FEATURE:
<223> OTHER INFORMATION: Core polypeptide

<400> SEQUENCE: 662

Gln Gln Asn Asn Leu Leu Arg Ala Ile Glu Ala Gln Gln His Leu Leu
 1               5                  10                  15

Gln Leu Thr Val Trp Gly Ile Lys Gln Leu Gln Ala Arg Ile Leu Ala
            20                  25                  30

Val Glu Arg Tyr Leu Lys
        35

<210> SEQ ID NO 663
<211> LENGTH: 38
<212> TYPE: PRT
<213> ORGANISM: Artificial Sequence
<220> FEATURE:
<223> OTHER INFORMATION: Core polypeptide

<400> SEQUENCE: 663

Gln Gln Gln Asn Asn Leu Leu Arg Ala Ile Glu Ala Gln Gln His Leu
 1               5                  10                  15

Leu Gln Leu Thr Val Trp Gly Ile Lys Gln Leu Gln Ala Arg Ile Leu
            20                  25                  30

Ala Val Glu Arg Tyr Leu
        35

<210> SEQ ID NO 664
<211> LENGTH: 38
<212> TYPE: PRT
<213> ORGANISM: Artificial Sequence
<220> FEATURE:
<223> OTHER INFORMATION: Core polypeptide

<400> SEQUENCE: 664

Val Gln Gln Gln Asn Asn Leu Leu Arg Ala Ile Glu Ala Gln Gln His
 1               5                  10                  15

Leu Leu Gln Leu Thr Val Trp Gly Ile Lys Gln Leu Gln Ala Arg Ile
            20                  25                  30

Leu Ala Val Glu Arg Tyr
        35

<210> SEQ ID NO 665
<211> LENGTH: 38
<212> TYPE: PRT
<213> ORGANISM: Artificial Sequence
<220> FEATURE:
<223> OTHER INFORMATION: Core polypeptide

<400> SEQUENCE: 665

Ile Val Gln Gln Gln Asn Asn Leu Leu Arg Ala Ile Glu Ala Gln Gln
 1               5                  10                  15

His Leu Leu Gln Leu Thr Val Trp Gly Ile Lys Gln Leu Gln Ala Arg
            20                  25                  30

Ile Leu Ala Val Glu Arg
        35

<210> SEQ ID NO 666

```
<211> LENGTH: 38
<212> TYPE: PRT
<213> ORGANISM: Artificial Sequence
<220> FEATURE:
<223> OTHER INFORMATION: Core polypeptide

<400> SEQUENCE: 666

Gly Ile Val Gln Gln Gln Asn Asn Leu Leu Arg Ala Ile Glu Ala Gln
 1               5                  10                  15

Gln His Leu Leu Gln Leu Thr Val Trp Gly Ile Lys Gln Leu Gln Ala
            20                  25                  30

Arg Ile Leu Ala Val Glu
        35

<210> SEQ ID NO 667
<211> LENGTH: 38
<212> TYPE: PRT
<213> ORGANISM: Artificial Sequence
<220> FEATURE:
<223> OTHER INFORMATION: Core polypeptide

<400> SEQUENCE: 667

Ser Gly Ile Val Gln Gln Gln Asn Asn Leu Leu Arg Ala Ile Glu Ala
 1               5                  10                  15

Gln Gln His Leu Leu Gln Leu Thr Val Trp Gly Ile Lys Gln Leu Gln
            20                  25                  30

Ala Arg Ile Leu Ala Val
        35

<210> SEQ ID NO 668
<211> LENGTH: 38
<212> TYPE: PRT
<213> ORGANISM: Artificial Sequence
<220> FEATURE:
<223> OTHER INFORMATION: Core polypeptide

<400> SEQUENCE: 668

Arg Ser Met Thr Leu Thr Val Gln Ala Arg Gln Leu Leu Ser Gly Ile
 1               5                  10                  15

Val Gln Gln Gln Asn Asn Leu Leu Arg Ala Ile Glu Ala Gln Gln His
            20                  25                  30

Leu Leu Gln Leu Thr Val
        35

<210> SEQ ID NO 669
<211> LENGTH: 38
<212> TYPE: PRT
<213> ORGANISM: Artificial Sequence
<220> FEATURE:
<223> OTHER INFORMATION: Core polypeptide

<400> SEQUENCE: 669

Gly Ala Arg Ser Met Thr Leu Thr Val Gln Ala Arg Gln Leu Leu Ser
 1               5                  10                  15

Gly Ile Val Gln Gln Gln Asn Asn Leu Leu Arg Ala Ile Glu Ala Gln
            20                  25                  30

Gln His Leu Leu Gln Leu
        35

<210> SEQ ID NO 670
<211> LENGTH: 38
<212> TYPE: PRT
<213> ORGANISM: Artificial Sequence
```

```
<220> FEATURE:
<223> OTHER INFORMATION: Core polypeptide

<400> SEQUENCE: 670

Gly Ser Thr Met Gly Ala Arg Ser Met Thr Leu Thr Val Gln Ala Arg
 1               5                  10                  15

Gln Leu Leu Ser Gly Ile Val Gln Gln Asn Asn Leu Leu Arg Ala
            20                  25                  30

Ile Glu Ala Gln Gln His
        35

<210> SEQ ID NO 671
<211> LENGTH: 38
<212> TYPE: PRT
<213> ORGANISM: Artificial Sequence
<220> FEATURE:
<223> OTHER INFORMATION: Core polypeptide

<400> SEQUENCE: 671

Gly Ser Thr Met Gly Ala Arg Ser Met Thr Leu Thr Val Gln Ala Arg
 1               5                  10                  15

Gln Leu Leu Ser Gly Ile Val Gln Gln Asn Asn Leu Leu Arg Ala
            20                  25                  30

Ile Glu Ala Gln Gln His
        35

<210> SEQ ID NO 672
<211> LENGTH: 38
<212> TYPE: PRT
<213> ORGANISM: Artificial Sequence
<220> FEATURE:
<223> OTHER INFORMATION: Core polypeptide

<400> SEQUENCE: 672

Glu Gly Ser Thr Met Gly Ala Arg Ser Met Thr Leu Thr Val Gln Ala
 1               5                  10                  15

Arg Gln Leu Leu Ser Gly Ile Val Gln Gln Asn Asn Leu Leu Arg
            20                  25                  30

Ala Ile Glu Ala Gln Gln
        35

<210> SEQ ID NO 673
<211> LENGTH: 28
<212> TYPE: PRT
<213> ORGANISM: Artificial Sequence
<220> FEATURE:
<223> OTHER INFORMATION: Core polypeptide

<400> SEQUENCE: 673

Arg Ala Lys Phe Lys Gln Leu Leu Gln His Tyr Arg Glu Val Ala Ala
 1               5                  10                  15

Ala Lys Ser Ser Glu Asn Asp Arg Leu Arg Leu Leu
            20                  25

<210> SEQ ID NO 674
<211> LENGTH: 28
<212> TYPE: PRT
<213> ORGANISM: Artificial Sequence
<220> FEATURE:
<223> OTHER INFORMATION: Core polypeptide

<400> SEQUENCE: 674

Ala Lys Phe Lys Gln Leu Leu Gln His Tyr Arg Glu Val Ala Ala Ala
```

```
                1               5                  10                 15
Lys Ser Ser Glu Asn Asp Arg Leu Arg Leu Leu Leu
                     20                 25

<210> SEQ ID NO 675
<211> LENGTH: 28
<212> TYPE: PRT
<213> ORGANISM: Artificial Sequence
<220> FEATURE:
<223> OTHER INFORMATION: Core polypeptide

<400> SEQUENCE: 675

Lys Phe Lys Gln Leu Leu Gln His Tyr Arg Glu Val Ala Ala Ala Lys
 1               5                  10                 15

Ser Ser Glu Asn Asp Arg Leu Arg Leu Leu Leu Lys
                     20                 25

<210> SEQ ID NO 676
<211> LENGTH: 28
<212> TYPE: PRT
<213> ORGANISM: Artificial Sequence
<220> FEATURE:
<223> OTHER INFORMATION: Core polypeptide

<400> SEQUENCE: 676

Phe Lys Gln Leu Leu Gln His Tyr Arg Glu Val Ala Ala Ala Lys Ser
 1               5                  10                 15

Ser Glu Asn Asp Arg Leu Arg Leu Leu Leu Lys Gln
                     20                 25

<210> SEQ ID NO 677
<211> LENGTH: 35
<212> TYPE: PRT
<213> ORGANISM: Artificial Sequence
<220> FEATURE:
<223> OTHER INFORMATION: Core polypeptide

<400> SEQUENCE: 677

Arg Ala Lys Phe Lys Gln Glu Leu Gln His Tyr Arg Glu Val Ala Ala
 1               5                  10                 15

Ala Lys Ser Ser Glu Asn Asp Arg Leu Arg Leu Leu Leu Lys Gln Met
                     20                 25                  30

Cys Pro Ser
         35

<210> SEQ ID NO 678
<211> LENGTH: 10
<212> TYPE: PRT
<213> ORGANISM: Artificial Sequence
<220> FEATURE:
<223> OTHER INFORMATION: Core polypeptide

<400> SEQUENCE: 678

Asp Lys Trp Ala Ser Leu Trp Asn Trp Phe
 1               5                  10

<210> SEQ ID NO 679
<211> LENGTH: 35
<212> TYPE: PRT
<213> ORGANISM: Artificial Sequence
<220> FEATURE:
<223> OTHER INFORMATION: Core polypeptide

<400> SEQUENCE: 679
```

-continued

```
Phe Asp Ala Ser Ile Ser Gln Val Asn Glu Lys Ile Asn Gln Ser Leu
 1               5                  10                  15

Ala Phe Ile Arg Lys Ser Asp Glu Leu Leu His Asn Val Asn Ala Gly
            20                  25                  30

Lys Ser Thr
        35

<210> SEQ ID NO 680
<211> LENGTH: 35
<212> TYPE: PRT
<213> ORGANISM: Artificial Sequence
<220> FEATURE:
<223> OTHER INFORMATION: Core polypeptide

<400> SEQUENCE: 680

Tyr Asp Ala Ser Ile Ser Gln Val Asn Glu Lys Ile Asn Gln Ser Leu
 1               5                  10                  15

Ala Phe Ile Arg Lys Ser Asp Glu Leu Leu His Asn Val Asn Ala Gly
            20                  25                  30

Lys Ser Thr
        35

<210> SEQ ID NO 681
<211> LENGTH: 35
<212> TYPE: PRT
<213> ORGANISM: Artificial Sequence
<220> FEATURE:
<223> OTHER INFORMATION: Core polypeptide

<400> SEQUENCE: 681

Tyr Asp Ala Ser Ile Ser Gln Val Asn Glu Lys Ile Asn Gln Ser Leu
 1               5                  10                  15

Ala Tyr Ile Arg Lys Ser Asp Glu Leu Leu His Asn Val Asn Ala Gly
            20                  25                  30

Lys Ser Thr
        35

<210> SEQ ID NO 682
<211> LENGTH: 35
<212> TYPE: PRT
<213> ORGANISM: Artificial Sequence
<220> FEATURE:
<223> OTHER INFORMATION: Core polypeptide

<400> SEQUENCE: 682

Phe Asp Ala Ser Ile Ser Gln Val Asn Glu Lys Ile Asn Gln Ser Leu
 1               5                  10                  15

Ala Tyr Ile Arg Lys Ser Asp Glu Leu Leu His Asn Val Asn Ala Gly
            20                  25                  30

Lys Ser Thr
        35

<210> SEQ ID NO 683
<211> LENGTH: 35
<212> TYPE: PRT
<213> ORGANISM: Artificial Sequence
<220> FEATURE:
<223> OTHER INFORMATION: Core polypeptide

<400> SEQUENCE: 683

Phe Asp Ala Ser Ile Ser Gln Val Gln Glu Lys Ile Gln Gln Ser Leu
 1               5                  10                  15
```

Ala Phe Ile Arg Lys Ser Asp Glu Leu Leu His Gln Val Gln Ala Gly
            20                  25                  30

Lys Ser Thr
        35

<210> SEQ ID NO 684
<211> LENGTH: 35
<212> TYPE: PRT
<213> ORGANISM: Artificial Sequence
<220> FEATURE:
<223> OTHER INFORMATION: Core polypeptide

<400> SEQUENCE: 684

Phe Asp Ala Ser Ile Ser Gln Val Asn Glu Lys Ile Asn Gln Ala Leu
1               5                   10                  15

Ala Phe Ile Arg Lys Ala Asp Glu Leu Leu His Asn Val Asn Ala Gly
            20                  25                  30

Lys Ser Thr
        35

<210> SEQ ID NO 685
<211> LENGTH: 35
<212> TYPE: PRT
<213> ORGANISM: Artificial Sequence
<220> FEATURE:
<223> OTHER INFORMATION: Core polypeptide

<400> SEQUENCE: 685

Phe Asp Ala Ser Ile Ser Gln Val Asn Glu Lys Ile Asn Gln Ala Leu
1               5                   10                  15

Ala Phe Ile Arg Lys Ser Asp Glu Leu Leu His Asn Val Asn Ala Gly
            20                  25                  30

Lys Ser Thr
        35

<210> SEQ ID NO 686
<211> LENGTH: 35
<212> TYPE: PRT
<213> ORGANISM: Artificial Sequence
<220> FEATURE:
<223> OTHER INFORMATION: Core polypeptide

<400> SEQUENCE: 686

Phe Asp Ala Ser Ile Ser Gln Val Asn Glu Lys Ile Asn Gln Ser Leu
1               5                   10                  15

Ala Phe Ile Arg Lys Ala Asp Glu Leu Leu His Asn Val Asn Ala Gly
            20                  25                  30

Lys Ser Thr
        35

<210> SEQ ID NO 687
<211> LENGTH: 35
<212> TYPE: PRT
<213> ORGANISM: Artificial Sequence
<220> FEATURE:
<223> OTHER INFORMATION: Core polypeptide

<400> SEQUENCE: 687

Tyr Asp Ala Ser Ile Ser Gln Val Gln Glu Ile Gln Gln Ala Leu
1               5                   10                  15

Ala Phe Ile Arg Lys Ala Asp Glu Leu Leu Glu Gln Val Gln Ala Gly
            20                  25                  30

Lys Ser Thr
        35

<210> SEQ ID NO 688
<211> LENGTH: 35
<212> TYPE: PRT
<213> ORGANISM: Artificial Sequence
<220> FEATURE:
<223> OTHER INFORMATION: Core polypeptide

<400> SEQUENCE: 688

Phe Asp Ala Ser Ile Ser Gln Val Asn Glu Lys Ile Asn Gln Ser Leu
1               5                   10                  15

Ala Phe Ile Arg Lys Ser Asp Glu Leu Leu Glu Asn Val Asn Ala Gly
            20                  25                  30

Lys Ser Thr
        35

<210> SEQ ID NO 689
<211> LENGTH: 35
<212> TYPE: PRT
<213> ORGANISM: Artificial Sequence
<220> FEATURE:
<223> OTHER INFORMATION: Core polypeptide

<400> SEQUENCE: 689

Phe Asp Ala Ser Ile Ser Gln Val Asn Glu Glu Ile Asn Gln Ser Leu
1               5                   10                  15

Ala Phe Ile Arg Lys Ser Asp Glu Leu Leu His Asn Val Asn Ala Gly
            20                  25                  30

Lys Ser Thr
        35

<210> SEQ ID NO 690
<211> LENGTH: 35
<212> TYPE: PRT
<213> ORGANISM: Artificial Sequence
<220> FEATURE:
<223> OTHER INFORMATION: Core polypeptide

<400> SEQUENCE: 690

Val Phe Pro Ser Asp Glu Phe Asp Ala Ser Ile Ser Gln Val Asn Glu
1               5                   10                  15

Lys Ile Asn Gln Ser Leu Ala Phe Ile Arg Lys Ser Asp Glu Leu Leu
            20                  25                  30

Glu Asn Val
        35

<210> SEQ ID NO 691
<211> LENGTH: 35
<212> TYPE: PRT
<213> ORGANISM: Artificial Sequence
<220> FEATURE:
<223> OTHER INFORMATION: Core polypeptide

<400> SEQUENCE: 691

Val Phe Pro Ser Asp Glu Phe Asp Ala Ser Ile Ser Gln Val Asn Glu
1               5                   10                  15

Glu Ile Asn Gln Ser Leu Ala Phe Ile Arg Lys Ser Asp Glu Leu Leu
            20                  25                  30

Glu Asn Val
        35

<210> SEQ ID NO 692
<211> LENGTH: 35
<212> TYPE: PRT
<213> ORGANISM: Artificial Sequence
<220> FEATURE:
<223> OTHER INFORMATION: Core polypeptide

<400> SEQUENCE: 692

```
Val Tyr Pro Ser Asp Glu Tyr Asp Ala Ser Ile Ser Gln Val Asn Glu
 1               5                  10                  15
Glu Ile Asn Gln Ala Leu Ala Tyr Ile Arg Lys Ala Asp Glu Leu Leu
            20                  25                  30
Glu Asn Val
         35
```

<210> SEQ ID NO 693
<211> LENGTH: 35
<212> TYPE: PRT
<213> ORGANISM: Artificial Sequence
<220> FEATURE:
<223> OTHER INFORMATION: Core polypeptide

<400> SEQUENCE: 693

```
Val Phe Pro Ser Asp Glu Phe Asp Ala Ser Ile Ser Gln Val Asn Glu
 1               5                  10                  15
Glu Ile Asn Gln Ser Leu Ala Phe Ile Arg Lys Ser Asp Glu Leu Leu
            20                  25                  30
His Asn Val
         35
```

<210> SEQ ID NO 694
<211> LENGTH: 36
<212> TYPE: PRT
<213> ORGANISM: Artificial Sequence
<220> FEATURE:
<223> OTHER INFORMATION: Core polypeptide

<400> SEQUENCE: 694

```
Ser Asn Lys Ser Leu Glu Gln Ile Trp Asn Asn Met Thr Trp Met Glu
 1               5                  10                  15
Trp Asp Arg Glu Ile Asn Asn Tyr Thr Ser Leu Ile His Ser Leu Ile
            20                  25                  30
Glu Glu Ser Gln
         35
```

<210> SEQ ID NO 695
<211> LENGTH: 36
<212> TYPE: PRT
<213> ORGANISM: Artificial Sequence
<220> FEATURE:
<223> OTHER INFORMATION: Core polypeptide

<400> SEQUENCE: 695

```
Trp Ser Asn Lys Ser Leu Glu Gln Ile Trp Asn Asn Met Thr Trp Met
 1               5                  10                  15
Glu Trp Asp Arg Glu Ile Asn Asn Tyr Thr Ser Leu Ile His Ser Leu
            20                  25                  30
Ile Glu Glu Ser
         35
```

<210> SEQ ID NO 696
<211> LENGTH: 36

```
<212> TYPE: PRT
<213> ORGANISM: Artificial Sequence
<220> FEATURE:
<223> OTHER INFORMATION: Core polypeptide

<400> SEQUENCE: 696

Ser Trp Ser Asn Lys Ser Leu Glu Gln Ile Trp Asn Asn Met Thr Trp
 1               5                  10                  15

Met Glu Trp Asp Arg Glu Ile Asn Asn Tyr Thr Ser Leu Ile His Ser
            20                  25                  30

Leu Ile Glu Glu
        35

<210> SEQ ID NO 697
<211> LENGTH: 36
<212> TYPE: PRT
<213> ORGANISM: Artificial Sequence
<220> FEATURE:
<223> OTHER INFORMATION: Core polypeptide

<400> SEQUENCE: 697

Ala Ser Trp Ser Asn Lys Ser Leu Glu Gln Ile Trp Asn Asn Met Thr
 1               5                  10                  15

Trp Met Glu Trp Asp Arg Glu Ile Asn Asn Tyr Thr Ser Leu Ile His
            20                  25                  30

Ser Leu Ile Glu
        35

<210> SEQ ID NO 698
<211> LENGTH: 36
<212> TYPE: PRT
<213> ORGANISM: Artificial Sequence
<220> FEATURE:
<223> OTHER INFORMATION: Core polypeptide

<400> SEQUENCE: 698

Asn Ala Ser Trp Ser Asn Lys Ser Leu Glu Gln Ile Trp Asn Asn Met
 1               5                  10                  15

Thr Trp Met Glu Trp Asp Arg Glu Ile Asn Asn Tyr Thr Ser Leu Ile
            20                  25                  30

His Ser Leu Ile
        35

<210> SEQ ID NO 699
<211> LENGTH: 36
<212> TYPE: PRT
<213> ORGANISM: Artificial Sequence
<220> FEATURE:
<223> OTHER INFORMATION: Core polypeptide

<400> SEQUENCE: 699

Trp Asn Ala Ser Trp Ser Asn Lys Ser Leu Glu Gln Ile Trp Asn Asn
 1               5                  10                  15

Met Thr Trp Met Glu Trp Asp Arg Glu Ile Asn Asn Tyr Thr Ser Leu
            20                  25                  30

Ile His Ser Leu
        35

<210> SEQ ID NO 700
<211> LENGTH: 36
<212> TYPE: PRT
<213> ORGANISM: Artificial Sequence
<220> FEATURE:
```

-continued

<223> OTHER INFORMATION: Core polypeptide

<400> SEQUENCE: 700

Pro Trp Asn Ala Ser Trp Ser Asn Lys Ser Leu Glu Gln Ile Trp Asn
1               5                   10                  15

Asn Met Thr Trp Met Glu Trp Asp Arg Glu Ile Asn Asn Tyr Thr Ser
            20                  25                  30

Leu Ile His Ser
        35

<210> SEQ ID NO 701
<211> LENGTH: 36
<212> TYPE: PRT
<213> ORGANISM: Artificial Sequence
<220> FEATURE:
<223> OTHER INFORMATION: Core polypeptide

<400> SEQUENCE: 701

Val Pro Trp Asn Ala Ser Trp Ser Asn Lys Ser Leu Glu Gln Ile Trp
1               5                   10                  15

Asn Asn Met Thr Trp Met Glu Trp Asp Arg Glu Ile Asn Asn Tyr Thr
            20                  25                  30

Ser Leu Ile His
        35

<210> SEQ ID NO 702
<211> LENGTH: 36
<212> TYPE: PRT
<213> ORGANISM: Artificial Sequence
<220> FEATURE:
<223> OTHER INFORMATION: Core polypeptide

<400> SEQUENCE: 702

Ala Val Pro Trp Asn Ala Ser Trp Ser Asn Lys Ser Leu Glu Gln Ile
1               5                   10                  15

Trp Asn Asn Met Thr Trp Met Glu Trp Asp Arg Glu Ile Asn Asn Tyr
            20                  25                  30

Thr Ser Leu Ile
        35

<210> SEQ ID NO 703
<211> LENGTH: 36
<212> TYPE: PRT
<213> ORGANISM: Artificial Sequence
<220> FEATURE:
<223> OTHER INFORMATION: Core polypeptide

<400> SEQUENCE: 703

Thr Ala Val Pro Trp Asn Ala Ser Trp Ser Asn Lys Ser Leu Glu Gln
1               5                   10                  15

Ile Trp Asn Asn Met Thr Trp Met Glu Trp Asp Arg Glu Ile Asn Asn
            20                  25                  30

Tyr Thr Ser Leu
        35

<210> SEQ ID NO 704
<211> LENGTH: 36
<212> TYPE: PRT
<213> ORGANISM: Artificial Sequence
<220> FEATURE:
<223> OTHER INFORMATION: Core polypeptide

<400> SEQUENCE: 704

```
Thr Thr Ala Val Pro Trp Asn Ala Ser Trp Ser Asn Lys Ser Leu Glu
 1               5                  10                  15

Gln Ile Trp Asn Asn Met Thr Trp Met Glu Trp Asp Arg Glu Ile Asn
                20                  25                  30

Asn Tyr Thr Ser
            35
```

<210> SEQ ID NO 705
<211> LENGTH: 36
<212> TYPE: PRT
<213> ORGANISM: Artificial Sequence
<220> FEATURE:
<223> OTHER INFORMATION: Core polypeptide

<400> SEQUENCE: 705

```
Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser Leu
                20                  25                  30

Trp Asn Trp Phe
            35
```

<210> SEQ ID NO 706
<211> LENGTH: 35
<212> TYPE: PRT
<213> ORGANISM: Artificial Sequence
<220> FEATURE:
<223> OTHER INFORMATION: Core polypeptide

<400> SEQUENCE: 706

```
Ala Ala Ala Ser Asp Glu Phe Asp Ala Ser Ile Ser Gln Val Asn Glu
 1               5                  10                  15

Lys Ile Asn Gln Ser Leu Ala Phe Ile Arg Lys Ser Asp Glu Leu Leu
                20                  25                  30

His Asn Val
        35
```

<210> SEQ ID NO 707
<211> LENGTH: 35
<212> TYPE: PRT
<213> ORGANISM: Artificial Sequence
<220> FEATURE:
<223> OTHER INFORMATION: Core polypeptide

<400> SEQUENCE: 707

```
Val Phe Pro Ala Ala Ala Phe Asp Ala Ser Ile Ser Gln Val Asn Glu
 1               5                  10                  15

Lys Ile Asn Gln Ser Leu Ala Phe Ile Arg Lys Ser Asp Glu Leu Leu
                20                  25                  30

His Asn Val
        35
```

<210> SEQ ID NO 708
<211> LENGTH: 35
<212> TYPE: PRT
<213> ORGANISM: Artificial Sequence
<220> FEATURE:
<223> OTHER INFORMATION: Core polypeptide

<400> SEQUENCE: 708

```
Val Phe Pro Ser Asp Glu Ala Ala Ala Ser Ile Ser Gln Val Asn Glu
 1               5                  10                  15
```

Lys Ile Asn Gln Ser Leu Ala Phe Ile Arg Lys Ser Asp Glu Leu Leu
            20                  25                  30

His Asn Val
        35

<210> SEQ ID NO 709
<211> LENGTH: 35
<212> TYPE: PRT
<213> ORGANISM: Artificial Sequence
<220> FEATURE:
<223> OTHER INFORMATION: Core polypeptide

<400> SEQUENCE: 709

Val Phe Pro Ser Asp Glu Phe Asp Ala Ala Ala Ala Gln Val Asn Glu
1               5                   10                  15

Lys Ile Asn Gln Ser Leu Ala Phe Ile Arg Lys Ser Asp Glu Leu Leu
            20                  25                  30

His Asn Val
        35

<210> SEQ ID NO 710
<211> LENGTH: 35
<212> TYPE: PRT
<213> ORGANISM: Artificial Sequence
<220> FEATURE:
<223> OTHER INFORMATION: Core polypeptide

<400> SEQUENCE: 710

Val Phe Pro Ser Asp Glu Phe Asp Ala Ser Ile Ser Ala Ala Ala Glu
1               5                   10                  15

Lys Ile Asn Gln Ser Leu Ala Phe Ile Arg Lys Ser Asp Glu Leu Leu
            20                  25                  30

His Asn Val
        35

<210> SEQ ID NO 711
<211> LENGTH: 35
<212> TYPE: PRT
<213> ORGANISM: Artificial Sequence
<220> FEATURE:
<223> OTHER INFORMATION: Core polypeptide

<400> SEQUENCE: 711

Val Phe Pro Ser Asp Glu Phe Asp Ala Ser Ile Ser Gln Val Asn Ala
1               5                   10                  15

Ala Ala Asn Gln Ser Leu Ala Phe Ile Arg Lys Ser Asp Glu Leu Leu
            20                  25                  30

His Asn Val
        35

<210> SEQ ID NO 712
<211> LENGTH: 35
<212> TYPE: PRT
<213> ORGANISM: Artificial Sequence
<220> FEATURE:
<223> OTHER INFORMATION: Core polypeptide

<400> SEQUENCE: 712

Val Phe Pro Ser Asp Glu Phe Asp Ala Ser Ile Ser Gln Val Asn Glu
1               5                   10                  15

Lys Ile Ala Ala Ala Leu Ala Phe Ile Arg Lys Ser Asp Glu Leu Leu
            20                  25                  30

His Asn Val
        35

<210> SEQ ID NO 713
<211> LENGTH: 35
<212> TYPE: PRT
<213> ORGANISM: Artificial Sequence
<220> FEATURE:
<223> OTHER INFORMATION: Core polypeptide

<400> SEQUENCE: 713

Val Phe Pro Ser Asp Glu Phe Asp Ala Ser Ile Ser Gln Val Asn Glu
1               5                   10                  15

Lys Ile Asn Gln Ser Ala Ala Ala Ile Arg Lys Ser Asp Glu Leu Leu
            20                  25                  30

His Asn Val
        35

<210> SEQ ID NO 714
<211> LENGTH: 35
<212> TYPE: PRT
<213> ORGANISM: Artificial Sequence
<220> FEATURE:
<223> OTHER INFORMATION: Core polypeptide

<400> SEQUENCE: 714

Val Phe Pro Ser Asp Glu Phe Asp Ala Ser Ile Ser Gln Val Asn Glu
1               5                   10                  15

Lys Ile Asn Gln Ser Leu Ala Phe Ala Ala Ser Asp Glu Leu Leu
            20                  25                  30

His Asn Val
        35

<210> SEQ ID NO 715
<211> LENGTH: 35
<212> TYPE: PRT
<213> ORGANISM: Artificial Sequence
<220> FEATURE:
<223> OTHER INFORMATION: Core polypeptide

<400> SEQUENCE: 715

Val Phe Pro Ser Asp Glu Phe Asp Ala Ser Ile Ser Gln Val Asn Glu
1               5                   10                  15

Lys Ile Asn Gln Ser Leu Ala Phe Ile Arg Lys Ala Ala Ala Leu Leu
            20                  25                  30

His Asn Val
        35

<210> SEQ ID NO 716
<211> LENGTH: 35
<212> TYPE: PRT
<213> ORGANISM: Artificial Sequence
<220> FEATURE:
<223> OTHER INFORMATION: Core polypeptide

<400> SEQUENCE: 716

Val Phe Pro Ser Asp Glu Phe Asp Ala Ser Ile Ser Gln Val Asn Glu
1               5                   10                  15

Lys Ile Asn Gln Ser Leu Ala Phe Ile Arg Lys Ser Asp Glu Ala Ala
            20                  25                  30

Ala Asn Val
        35

<210> SEQ ID NO 717
<211> LENGTH: 35
<212> TYPE: PRT
<213> ORGANISM: Artificial Sequence
<220> FEATURE:
<223> OTHER INFORMATION: Core polypeptide

<400> SEQUENCE: 717

```
Val Phe Pro Ser Asp Glu Phe Asp Ala Ser Ile Ser Gln Val Asn Glu
 1               5                  10                  15

Lys Ile Asn Gln Ser Leu Ala Phe Ile Arg Lys Ser Asp Glu Leu Leu
             20                  25                  30

Ala Ala Ala
         35
```

<210> SEQ ID NO 718
<211> LENGTH: 35
<212> TYPE: PRT
<213> ORGANISM: Artificial Sequence
<220> FEATURE:
<223> OTHER INFORMATION: Core polypeptide

<400> SEQUENCE: 718

```
Val Tyr Pro Ser Asp Glu Phe Asp Ala Ser Ile Ser Gln Val Asn Glu
 1               5                  10                  15

Lys Ile Asn Gln Ser Leu Ala Phe Ile Arg Lys Ser Asp Glu Leu Leu
             20                  25                  30

His Asn Val
         35
```

<210> SEQ ID NO 719
<211> LENGTH: 36
<212> TYPE: PRT
<213> ORGANISM: Artificial Sequence
<220> FEATURE:
<223> OTHER INFORMATION: Core polypeptide

<400> SEQUENCE: 719

```
Ala Ala Ala Ala Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser Leu
             20                  25                  30

Trp Asn Trp Phe
             35
```

<210> SEQ ID NO 720
<211> LENGTH: 36
<212> TYPE: PRT
<213> ORGANISM: Artificial Sequence
<220> FEATURE:
<223> OTHER INFORMATION: Core polypeptide

<400> SEQUENCE: 720

```
Tyr Thr Ser Leu Ile His Ser Leu Ile Glu Glu Ser Gln Gln Gln Gln
 1               5                  10                  15

Glu Lys Asn Glu Gln Glu Leu Leu Glu Leu Asp Lys Trp Ala Ser Leu
             20                  25                  30

Trp Asn Trp Phe
             35
```

<210> SEQ ID NO 721

```
<211> LENGTH: 36
<212> TYPE: PRT
<213> ORGANISM: Artificial Sequence
<220> FEATURE:
<223> OTHER INFORMATION: Core polypeptide

<400> SEQUENCE: 721

Tyr Thr Ser Leu Ile His Ser Leu Ile Glu Glu Ser Gln Asn Gln Gln
 1               5                   10                  15

Glu Lys Gln Glu Gln Glu Leu Leu Glu Leu Asp Lys Trp Ala Ser Leu
            20                  25                  30

Trp Asn Trp Phe
            35

<210> SEQ ID NO 722
<211> LENGTH: 36
<212> TYPE: PRT
<213> ORGANISM: Artificial Sequence
<220> FEATURE:
<223> OTHER INFORMATION: Core polypeptide

<400> SEQUENCE: 722

Gln Ile Trp Asn Asn Met Thr Trp Met Glu Trp Asp Arg Glu Ile Asn
 1               5                   10                  15

Asn Tyr Thr Ser Leu Ile His Ser Leu Ile Glu Glu Ser Gln Asn Gln
            20                  25                  30

Gln Glu Lys Gln
            35

<210> SEQ ID NO 723
<211> LENGTH: 36
<212> TYPE: PRT
<213> ORGANISM: Artificial Sequence
<220> FEATURE:
<223> OTHER INFORMATION: Core polypeptide

<400> SEQUENCE: 723

Gln Ile Trp Asn Asn Met Thr Trp Met Glu Trp Asp Arg Glu Ile Asn
 1               5                   10                  15

Asn Tyr Thr Ser Leu Ile His Ser Leu Ile Glu Glu Ser Gln Gln Gln
            20                  25                  30

Gln Glu Lys Asn
            35

<210> SEQ ID NO 724
<211> LENGTH: 36
<212> TYPE: PRT
<213> ORGANISM: Artificial Sequence
<220> FEATURE:
<223> OTHER INFORMATION: Core polypeptide

<400> SEQUENCE: 724

Gln Ile Trp Asn Asn Met Thr Trp Met Glu Trp Asp Arg Glu Ile Asn
 1               5                   10                  15

Asn Tyr Thr Ser Leu Ile His Ser Leu Ile Glu Glu Ser Gln Gln Gln
            20                  25                  30

Gln Glu Lys Gln
            35

<210> SEQ ID NO 725
<211> LENGTH: 36
<212> TYPE: PRT
<213> ORGANISM: Artificial Sequence
```

```
<220> FEATURE:
<223> OTHER INFORMATION: Core polypeptide

<400> SEQUENCE: 725

Asn Lys Ser Leu Glu Gln Ile Trp Asn Asn Met Thr Trp Met Glu Trp
 1               5                  10                  15

Asp Arg Glu Ile Asn Asn Tyr Thr Ser Leu Ile His Ser Leu Ile Glu
            20                  25                  30

Glu Ser Gln Gln
        35

<210> SEQ ID NO 726
<211> LENGTH: 35
<212> TYPE: PRT
<213> ORGANISM: Artificial Sequence
<220> FEATURE:
<223> OTHER INFORMATION: Core polypeptide

<400> SEQUENCE: 726

Phe Asp Ala Ser Ile Ser Gln Val Asn Glu Lys Ile Asn Gln Ser Leu
 1               5                  10                  15

Ala Phe Ile Glu Glu Ser Asp Glu Leu Leu His Asn Val Asn Ala Gly
            20                  25                  30

Lys Ser Thr
        35

<210> SEQ ID NO 727
<211> LENGTH: 9
<212> TYPE: PRT
<213> ORGANISM: Artificial Sequence
<220> FEATURE:
<223> OTHER INFORMATION: Core polypeptide

<400> SEQUENCE: 727

Ile Arg Lys Ser Asp Glu Leu Cys Leu
 1               5

<210> SEQ ID NO 728
<211> LENGTH: 36
<212> TYPE: PRT
<213> ORGANISM: Artificial Sequence
<220> FEATURE:
<223> OTHER INFORMATION: Core polypeptide

<400> SEQUENCE: 728

Tyr Thr Ser Leu Ile His Ser Leu Ile Glu Glu Ser Gln Asn Gln Gln
 1               5                  10                  15

Glu Lys Asp Glu Gln Glu Leu Leu Glu Leu Asp Lys Trp Ala Ser Leu
            20                  25                  30

Trp Asn Trp Phe
        35

<210> SEQ ID NO 729
<211> LENGTH: 36
<212> TYPE: PRT
<213> ORGANISM: Artificial Sequence
<220> FEATURE:
<223> OTHER INFORMATION: Core polypeptide

<400> SEQUENCE: 729

Tyr Thr Ser Leu Ile His Ser Leu Ile Glu Glu Ser Gln Asp Gln Gln
 1               5                  10                  15

Glu Lys Asn Glu Gln Glu Leu Leu Glu Leu Asp Lys Trp Ala Ser Leu
```

```
                    20                  25                  30

Trp Asn Trp Phe
        35

<210> SEQ ID NO 730
<211> LENGTH: 36
<212> TYPE: PRT
<213> ORGANISM: Artificial Sequence
<220> FEATURE:
<223> OTHER INFORMATION: Core polypeptide

<400> SEQUENCE: 730

Tyr Thr Ser Leu Ile His Ser Leu Ile Glu Glu Ser Gln Asp Gln Gln
 1               5                  10                  15

Glu Lys Asp Glu Gln Glu Leu Leu Glu Leu Asp Lys Trp Ala Ser Leu
                20                  25                  30

Trp Asn Trp Phe
        35

<210> SEQ ID NO 731
<211> LENGTH: 36
<212> TYPE: PRT
<213> ORGANISM: Artificial Sequence
<220> FEATURE:
<223> OTHER INFORMATION: Core polypeptide

<400> SEQUENCE: 731

Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser Leu
                20                  25                  30

Trp Asp Trp Phe
        35

<210> SEQ ID NO 732
<211> LENGTH: 36
<212> TYPE: PRT
<213> ORGANISM: Artificial Sequence
<220> FEATURE:
<223> OTHER INFORMATION: Core polypeptide

<400> SEQUENCE: 732

Leu Glu Ala Asn Ile Thr Gln Ser Leu Glu Gln Ala Gln Ile Gln Gln
 1               5                  10                  15

Glu Lys Asn Met Tyr Glu Leu Gln Lys Leu Asn Ser Trp Asp Val Phe
                20                  25                  30

Thr Asn Trp Leu
        35

<210> SEQ ID NO 733
<211> LENGTH: 36
<212> TYPE: PRT
<213> ORGANISM: Artificial Sequence
<220> FEATURE:
<223> OTHER INFORMATION: Core polypeptide

<400> SEQUENCE: 733

Leu Glu Ala Asn Ile Ser Ala Ser Leu Glu Gln Ala Gln Ile Gln Gln
 1               5                  10                  15

Glu Lys Asn Met Tyr Glu Leu Gln Lys Leu Asn Ser Trp Asp Val Phe
                20                  25                  30

Thr Asn Trp Leu
```

<210> SEQ ID NO 734
<211> LENGTH: 36
<212> TYPE: PRT
<213> ORGANISM: Artificial Sequence
<220> FEATURE:
<223> OTHER INFORMATION: Core polypeptide

<400> SEQUENCE: 734

Leu Glu Ala Asn Ile Ser Ala Leu Leu Glu Gln Ala Gln Ile Gln Gln
1               5                   10                  15

Glu Lys Asn Met Tyr Glu Leu Gln Lys Leu Asn Ser Trp Asp Val Phe
            20                  25                  30

Thr Asn Trp Leu
        35

<210> SEQ ID NO 735
<211> LENGTH: 36
<212> TYPE: PRT
<213> ORGANISM: Artificial Sequence
<220> FEATURE:
<223> OTHER INFORMATION: Core polypeptide

<400> SEQUENCE: 735

Leu Glu Ala Asn Ile Thr Ala Leu Leu Glu Gln Ala Gln Ile Gln Gln
1               5                   10                  15

Glu Lys Asn Met Tyr Glu Leu Gln Lys Leu Asn Ser Trp Asp Val Phe
            20                  25                  30

Thr Asn Trp Leu
        35

<210> SEQ ID NO 736
<211> LENGTH: 36
<212> TYPE: PRT
<213> ORGANISM: Artificial Sequence
<220> FEATURE:
<223> OTHER INFORMATION: Core polypeptide

<400> SEQUENCE: 736

Leu Glu Ala Asn Ile Thr Ala Ser Leu Glu Gln Ala Gln Ile Gln Gln
1               5                   10                  15

Glu Lys Asn Met Tyr Glu Leu Gln Lys Leu Asn Ser Trp Asp Val Phe
            20                  25                  30

Thr Asn Trp Leu
        35

<210> SEQ ID NO 737
<211> LENGTH: 34
<212> TYPE: PRT
<213> ORGANISM: Artificial Sequence
<220> FEATURE:
<223> OTHER INFORMATION: Core polypeptide

<400> SEQUENCE: 737

Arg Ala Lys Phe Lys Gln Leu Leu Gln His Tyr Arg Glu Val Ala Ala
1               5                   10                  15

Ala Lys Ser Ser Glu Asn Asp Arg Leu Arg Leu Leu Lys Gln Met
            20                  25                  30

Pro Ser

<210> SEQ ID NO 738

```
<211> LENGTH: 30
<212> TYPE: PRT
<213> ORGANISM: Artificial Sequence
<220> FEATURE:
<223> OTHER INFORMATION: Core polypeptide

<400> SEQUENCE: 738

Met Asn Ser Val Lys Asn Gly Thr Tyr Asp Tyr Pro Lys Tyr Glu Glu
 1               5                  10                  15

Glu Ser Lys Leu Asn Arg Asn Glu Ile Lys Gly Val Lys Leu
            20                  25                  30

<210> SEQ ID NO 739
<211> LENGTH: 36
<212> TYPE: PRT
<213> ORGANISM: Artificial Sequence
<220> FEATURE:
<223> OTHER INFORMATION: Core polypeptide

<400> SEQUENCE: 739

Trp Gln Glu Trp Glu Gln Lys Val Arg Tyr Leu Glu Ala Asn Ile Ser
 1               5                  10                  15

Gln Ser Leu Glu Gln Ala Gln Ile Gln Gln Glu Lys Asn Met Tyr Glu
            20                  25                  30

Leu Gln Lys Leu
        35

<210> SEQ ID NO 740
<211> LENGTH: 35
<212> TYPE: PRT
<213> ORGANISM: Artificial Sequence
<220> FEATURE:
<223> OTHER INFORMATION: Core polypeptide

<400> SEQUENCE: 740

Asp Glu Tyr Asp Ala Ser Ile Ser Gln Val Asn Glu Lys Ile Asn Gln
 1               5                  10                  15

Ser Leu Ala Phe Ile Arg Lys Ser Asp Glu Leu Leu His Asn Val Asn
            20                  25                  30

Ala Gly Lys
        35

<210> SEQ ID NO 741
<211> LENGTH: 34
<212> TYPE: PRT
<213> ORGANISM: Artificial Sequence
<220> FEATURE:
<223> OTHER INFORMATION: Core polypeptide

<400> SEQUENCE: 741

Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser Leu
            20                  25                  30

Trp Asn

<210> SEQ ID NO 742
<211> LENGTH: 33
<212> TYPE: PRT
<213> ORGANISM: Artificial Sequence
<220> FEATURE:
<223> OTHER INFORMATION: Core polypeptide

<400> SEQUENCE: 742
```

```
Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser Leu
            20                  25                  30

Trp
```

<210> SEQ ID NO 743
<211> LENGTH: 32
<212> TYPE: PRT
<213> ORGANISM: Artificial Sequence
<220> FEATURE:
<223> OTHER INFORMATION: Core polypeptide

<400> SEQUENCE: 743

```
Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser Leu
            20                  25                  30
```

<210> SEQ ID NO 744
<211> LENGTH: 31
<212> TYPE: PRT
<213> ORGANISM: Artificial Sequence
<220> FEATURE:
<223> OTHER INFORMATION: Core polypeptide

<400> SEQUENCE: 744

```
Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser
            20                  25                  30
```

<210> SEQ ID NO 745
<211> LENGTH: 51
<212> TYPE: PRT
<213> ORGANISM: Artificial Sequence
<220> FEATURE:
<223> OTHER INFORMATION: Core polypeptide

<400> SEQUENCE: 745

```
Gln Ala Arg Gln Leu Leu Ser Gly Ile Val Gln Gln Asn Asn Leu
 1               5                  10                  15

Leu Arg Ala Ile Glu Ala Gln Gln His Leu Leu Gln Leu Thr Val Trp
            20                  25                  30

Gly Ile Lys Gln Leu Gln Ala Arg Ile Leu Ala Val Glu Arg Tyr Leu
                35                  40                  45

Lys Asp Gln
    50
```

<210> SEQ ID NO 746
<211> LENGTH: 42
<212> TYPE: PRT
<213> ORGANISM: Artificial Sequence
<220> FEATURE:
<223> OTHER INFORMATION: Core polypeptide

<400> SEQUENCE: 746

```
Asp Arg Glu Ile Asn Asn Tyr Thr Ser Leu Ile His Ser Leu Ile Glu
 1               5                  10                  15

Glu Ser Gln Asn Gln Gln Glu Lys Asn Glu Gln Glu Leu Leu Glu Leu
            20                  25                  30
```

```
Asp Lys Trp Ala Ser Leu Trp Asn Trp Phe
        35                  40
```

<210> SEQ ID NO 747
<211> LENGTH: 42
<212> TYPE: PRT
<213> ORGANISM: Artificial Sequence
<220> FEATURE:
<223> OTHER INFORMATION: Core polypeptide

<400> SEQUENCE: 747

```
Asn Asn Met Thr Trp Met Glu Trp Asp Arg Glu Ile Asn Asn Tyr Thr
 1               5                  10                  15

Ser Leu Ile His Ser Leu Ile Glu Gly Ser Gln Asn Gln Gln Glu Lys
            20                  25                  30

Asn Glu Gln Glu Leu Leu Glu Leu Asp Lys
        35                  40
```

<210> SEQ ID NO 748
<211> LENGTH: 36
<212> TYPE: PRT
<213> ORGANISM: Artificial Sequence
<220> FEATURE:
<223> OTHER INFORMATION: Core polypeptide

<400> SEQUENCE: 748

```
Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser Leu
            20                  25                  30

Trp Ala Ala Ala
        35
```

<210> SEQ ID NO 749
<211> LENGTH: 36
<212> TYPE: PRT
<213> ORGANISM: Artificial Sequence
<220> FEATURE:
<223> OTHER INFORMATION: Core polypeptide

<400> SEQUENCE: 749

```
Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ala Ala
            20                  25                  30

Ala Asn Trp Phe
        35
```

<210> SEQ ID NO 750
<211> LENGTH: 36
<212> TYPE: PRT
<213> ORGANISM: Artificial Sequence
<220> FEATURE:
<223> OTHER INFORMATION: Core polypeptide

<400> SEQUENCE: 750

```
Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Ala Ala Ala Ser Leu
            20                  25                  30

Trp Asn Trp Phe
        35
```

```
<210> SEQ ID NO 751
<211> LENGTH: 36
<212> TYPE: PRT
<213> ORGANISM: Artificial Sequence
<220> FEATURE:
<223> OTHER INFORMATION: Core polypeptide

<400> SEQUENCE: 751

Tyr Thr Ser Leu Ile His Ser Leu Ile Glu Glu Ser Gln Asn Gln Gln
 1               5                  10                  15

Glu Lys Asn Glu Gln Glu Leu Leu Ala Ala Lys Trp Ala Ser Leu
            20                  25                  30

Trp Asn Trp Phe
        35

<210> SEQ ID NO 752
<211> LENGTH: 36
<212> TYPE: PRT
<213> ORGANISM: Artificial Sequence
<220> FEATURE:
<223> OTHER INFORMATION: Core polypeptide

<400> SEQUENCE: 752

Tyr Thr Ser Leu Ile His Ser Leu Ile Glu Glu Ser Gln Asn Gln Gln
 1               5                  10                  15

Glu Lys Asn Glu Gln Ala Ala Ala Glu Leu Asp Lys Trp Ala Ser Leu
            20                  25                  30

Trp Asn Trp Phe
        35

<210> SEQ ID NO 753
<211> LENGTH: 36
<212> TYPE: PRT
<213> ORGANISM: Artificial Sequence
<220> FEATURE:
<223> OTHER INFORMATION: Core polypeptide

<400> SEQUENCE: 753

Tyr Thr Ser Leu Ile His Ser Leu Ile Glu Glu Ser Gln Asn Gln Gln
 1               5                  10                  15

Glu Lys Ala Ala Ala Glu Leu Leu Glu Leu Asp Lys Trp Ala Ser Leu
            20                  25                  30

Trp Asn Trp Phe
        35

<210> SEQ ID NO 754
<211> LENGTH: 36
<212> TYPE: PRT
<213> ORGANISM: Artificial Sequence
<220> FEATURE:
<223> OTHER INFORMATION: Core polypeptide

<400> SEQUENCE: 754

Tyr Thr Ser Leu Ile His Ser Leu Ile Glu Glu Ser Gln Asn Gln Ala
 1               5                  10                  15

Ala Ala Asn Glu Gln Glu Leu Leu Glu Leu Asp Lys Trp Ala Ser Leu
            20                  25                  30

Trp Asn Trp Phe
        35

<210> SEQ ID NO 755
<211> LENGTH: 36
```

```
<212> TYPE: PRT
<213> ORGANISM: Artificial Sequence
<220> FEATURE:
<223> OTHER INFORMATION: Core polypeptide

<400> SEQUENCE: 755

Tyr Thr Ser Leu Ile His Ser Leu Ile Glu Glu Ser Ala Ala Ala Gln
 1               5                  10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 756
<211> LENGTH: 36
<212> TYPE: PRT
<213> ORGANISM: Artificial Sequence
<220> FEATURE:
<223> OTHER INFORMATION: Core polypeptide

<400> SEQUENCE: 756

Tyr Thr Ser Leu Ile His Ser Leu Ile Ala Ala Ala Gln Asn Gln Gln
 1               5                  10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 757
<211> LENGTH: 36
<212> TYPE: PRT
<213> ORGANISM: Artificial Sequence
<220> FEATURE:
<223> OTHER INFORMATION: Core polypeptide

<400> SEQUENCE: 757

Tyr Thr Ser Leu Ile His Ala Ala Ala Glu Glu Ser Gln Asn Gln Gln
 1               5                  10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 758
<211> LENGTH: 36
<212> TYPE: PRT
<213> ORGANISM: Artificial Sequence
<220> FEATURE:
<223> OTHER INFORMATION: Core polypeptide

<400> SEQUENCE: 758

Tyr Thr Ser Ala Ala Ala Ser Leu Ile Glu Glu Ser Gln Asn Gln Gln
 1               5                  10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 759
<211> LENGTH: 35
<212> TYPE: PRT
<213> ORGANISM: Artificial Sequence
<220> FEATURE:
```

<223> OTHER INFORMATION: Core polypeptide

<400> SEQUENCE: 759

Glu Ile Trp Asn Asn Met Thr Trp Met Glu Trp Asp Arg Glu Asn Glu
1               5                   10                  15

Lys Ile Asn Gln Ser Leu Ala Phe Ile Arg Lys Ser Asp Glu Leu Leu
            20                  25                  30

His Asn Val
        35

<210> SEQ ID NO 760
<211> LENGTH: 36
<212> TYPE: PRT
<213> ORGANISM: Artificial Sequence
<220> FEATURE:
<223> OTHER INFORMATION: Core polypeptide

<400> SEQUENCE: 760

Tyr Ile Ser Glu Val Asn Glu Ile Asn Gln Ser Leu Ala Phe Ile
1               5                   10                  15

Arg Lys Ala Asp Glu Leu Leu Gly Asn Val Asp Lys Trp Ala Ser Leu
            20                  25                  30

Trp Asn Trp Phe
        35

<210> SEQ ID NO 761
<211> LENGTH: 35
<212> TYPE: PRT
<213> ORGANISM: Artificial Sequence
<220> FEATURE:
<223> OTHER INFORMATION: Core polypeptide

<400> SEQUENCE: 761

Thr Ser Val Ile Thr Ile Glu Leu Ser Asn Ile Lys Glu Asn Lys Ala
1               5                   10                  15

Asn Gly Thr Asp Ala Lys Val Lys Leu Ile Lys Gln Glu Leu Asp Lys
            20                  25                  30

Tyr Lys Asn
        35

<210> SEQ ID NO 762
<211> LENGTH: 38
<212> TYPE: PRT
<213> ORGANISM: Artificial Sequence
<220> FEATURE:
<223> OTHER INFORMATION: Core polypeptide

<400> SEQUENCE: 762

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe Met Gly
        35

<210> SEQ ID NO 763
<211> LENGTH: 21
<212> TYPE: PRT
<213> ORGANISM: Artificial Sequence
<220> FEATURE:
<223> OTHER INFORMATION: Core polypeptide

<400> SEQUENCE: 763

Asn Glu Lys Ile Asn Gln Ser Leu Ala Phe Ile Arg Lys Ser Asp Glu
1               5                   10                  15

Leu Leu His Asn Val
            20

<210> SEQ ID NO 764
<211> LENGTH: 35
<212> TYPE: PRT
<213> ORGANISM: Artificial Sequence
<220> FEATURE:
<223> OTHER INFORMATION: Core polypeptide

<400> SEQUENCE: 764

Tyr Asp Pro Leu Val Phe Pro Ser Asp Glu Phe Asp Ala Ser Ile Ser
1               5                   10                  15

Gln Val Asn Glu Lys Ile Asn Gln Ser Leu Ala Phe Ile Arg Lys Ser
            20                  25                  30

Asp Glu Leu
        35

<210> SEQ ID NO 765
<211> LENGTH: 35
<212> TYPE: PRT
<213> ORGANISM: Artificial Sequence
<220> FEATURE:
<223> OTHER INFORMATION: Core polypeptide

<400> SEQUENCE: 765

Pro Leu Val Phe Pro Ser Asp Glu Phe Asp Ala Ser Ile Ser Gln Val
1               5                   10                  15

Asn Glu Lys Ile Asn Gln Ser Leu Ala Phe Ile Arg Lys Ser Asp Glu
            20                  25                  30

Leu Leu His
        35

<210> SEQ ID NO 766
<211> LENGTH: 35
<212> TYPE: PRT
<213> ORGANISM: Artificial Sequence
<220> FEATURE:
<223> OTHER INFORMATION: Core polypeptide

<400> SEQUENCE: 766

Val Phe Pro Ser Asp Glu Phe Asp Ala Ser Ile Ser Gln Val Asn Glu
1               5                   10                  15

Lys Ile Asn Gln Ser Leu Ala Phe Ile Arg Lys Ser Asp Glu Leu Leu
            20                  25                  30

His Asn Val
        35

<210> SEQ ID NO 767
<211> LENGTH: 35
<212> TYPE: PRT
<213> ORGANISM: Artificial Sequence
<220> FEATURE:
<223> OTHER INFORMATION: Core polypeptide

<400> SEQUENCE: 767

Asp Glu Phe Asp Ala Ser Ile Ser Gln Val Asn Glu Lys Ile Asn Gln
1               5                   10                  15

Ser Leu Ala Phe Ile Arg Lys Ser Asp Glu Leu Leu His Asn Val Asn
            20                  25                  30

Ala Gly Lys
        35

<210> SEQ ID NO 768
<211> LENGTH: 35
<212> TYPE: PRT
<213> ORGANISM: Artificial Sequence
<220> FEATURE:
<223> OTHER INFORMATION: Core polypeptide

<400> SEQUENCE: 768

Val Tyr Pro Ser Asp Glu Phe Asp Ala Ser Ile Ser Gln Val Asn Glu
1               5                   10                  15

Lys Ile Asn Gln Ser Leu Ala Phe Ile Arg Lys Ser Asp Glu Leu Leu
            20                  25                  30

His Asn Val
        35

<210> SEQ ID NO 769
<211> LENGTH: 35
<212> TYPE: PRT
<213> ORGANISM: Artificial Sequence
<220> FEATURE:
<223> OTHER INFORMATION: Core polypeptide

<400> SEQUENCE: 769

Val Tyr Pro Ser Asp Glu Tyr Asp Ala Ser Ile Ser Gln Val Asn Glu
1               5                   10                  15

Glu Ile Asn Gln Ala Leu Ala Tyr Ile Arg Lys Ala Asp Glu Leu Leu
            20                  25                  30

Glu Asn Val
        35

<210> SEQ ID NO 770
<211> LENGTH: 35
<212> TYPE: PRT
<213> ORGANISM: Artificial Sequence
<220> FEATURE:
<223> OTHER INFORMATION: Core polypeptide

<400> SEQUENCE: 770

Val Tyr Pro Ser Asp Glu Phe Asp Ala Ser Ile Ser Gln Val Gln Glu
1               5                   10                  15

Glu Ile Gln Gln Ala Leu Ala Phe Ile Arg Lys Ala Asp Glu Leu Leu
            20                  25                  30

Glu Gln Val
        35

<210> SEQ ID NO 771
<211> LENGTH: 37
<212> TYPE: PRT
<213> ORGANISM: Artificial Sequence
<220> FEATURE:
<223> OTHER INFORMATION: Core polypeptide

<400> SEQUENCE: 771

Asn Tyr Thr Ser Leu Ile His Ser Leu Ile Glu Glu Ser Gln Asn Gln
1               5                   10                  15

Gln Glu Lys Asn Glu Gln Glu Leu Leu Glu Leu Asp Lys Trp Ala Ser
            20                  25                  30

Leu Trp Asn Trp Phe
        35

<210> SEQ ID NO 772
<211> LENGTH: 38
<212> TYPE: PRT
<213> ORGANISM: Artificial Sequence
<220> FEATURE:
<223> OTHER INFORMATION: Core polypeptide

<400> SEQUENCE: 772

Asn Asn Tyr Thr Ser Leu Ile His Ser Leu Ile Glu Glu Ser Gln Asn
1               5                   10                  15

Gln Gln Glu Lys Asn Glu Gln Glu Leu Leu Glu Leu Asp Lys Trp Ala
            20                  25                  30

Ser Leu Trp Asn Trp Phe
        35

<210> SEQ ID NO 773
<211> LENGTH: 39
<212> TYPE: PRT
<213> ORGANISM: Artificial Sequence
<220> FEATURE:
<223> OTHER INFORMATION: Core polypeptide

<400> SEQUENCE: 773

Ile Asn Asn Tyr Thr Ser Leu Ile His Ser Leu Ile Glu Glu Ser Gln
1               5                   10                  15

Asn Gln Gln Glu Lys Asn Glu Gln Glu Leu Leu Glu Leu Asp Lys Trp
            20                  25                  30

Ala Ser Leu Trp Asn Trp Phe
        35

<210> SEQ ID NO 774
<211> LENGTH: 40
<212> TYPE: PRT
<213> ORGANISM: Artificial Sequence
<220> FEATURE:
<223> OTHER INFORMATION: Core polypeptide

<400> SEQUENCE: 774

Glu Ile Asn Asn Tyr Thr Ser Leu Ile His Ser Leu Ile Glu Glu Ser
1               5                   10                  15

Gln Asn Gln Gln Glu Lys Asn Glu Gln Glu Leu Leu Glu Leu Asp Lys
            20                  25                  30

Trp Ala Ser Leu Trp Asn Trp Phe
        35                  40

<210> SEQ ID NO 775
<211> LENGTH: 37
<212> TYPE: PRT
<213> ORGANISM: Artificial Sequence
<220> FEATURE:
<223> OTHER INFORMATION: Core polypeptide

<400> SEQUENCE: 775

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe Asn
        35

<210> SEQ ID NO 776

```
<211> LENGTH: 38
<212> TYPE: PRT
<213> ORGANISM: Artificial Sequence
<220> FEATURE:
<223> OTHER INFORMATION: Core polypeptide

<400> SEQUENCE: 776

Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser Leu
            20                  25                  30

Trp Asn Trp Phe Asn Ile
            35

<210> SEQ ID NO 777
<211> LENGTH: 39
<212> TYPE: PRT
<213> ORGANISM: Artificial Sequence
<220> FEATURE:
<223> OTHER INFORMATION: Core polypeptide

<400> SEQUENCE: 777

Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser Leu
            20                  25                  30

Trp Asn Trp Phe Asn Ile Thr
            35

<210> SEQ ID NO 778
<211> LENGTH: 40
<212> TYPE: PRT
<213> ORGANISM: Artificial Sequence
<220> FEATURE:
<223> OTHER INFORMATION: Core polypeptide

<400> SEQUENCE: 778

Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser Leu
            20                  25                  30

Trp Asn Trp Phe Asn Ile Thr Asn
            35                  40

<210> SEQ ID NO 779
<211> LENGTH: 43
<212> TYPE: PRT
<213> ORGANISM: Artificial Sequence
<220> FEATURE:
<223> OTHER INFORMATION: Core polypeptide

<400> SEQUENCE: 779

Tyr Asp Pro Leu Val Phe Pro Ser Asp Glu Phe Asp Ala Ser Ile Ser
 1               5                  10                  15

Gln Val Asn Glu Lys Ile Asn Gln Ser Leu Ala Phe Ile Arg Lys Ser
            20                  25                  30

Asp Glu Leu Leu His Asn Val Asn Ala Gly Lys
            35                  40

<210> SEQ ID NO 780
<211> LENGTH: 38
<212> TYPE: PRT
<213> ORGANISM: Artificial Sequence
```

-continued

```
<220> FEATURE:
<223> OTHER INFORMATION: Core polypeptide

<400> SEQUENCE: 780

Asn Tyr Thr Ser Leu Ile His Ser Leu Ile Glu Glu Ser Gln Asn Gln
1               5                   10                  15

Gln Glu Lys Asn Glu Gln Glu Leu Leu Glu Leu Asp Lys Trp Ala Ser
            20                  25                  30

Leu Trp Asn Trp Phe Asn
            35

<210> SEQ ID NO 781
<211> LENGTH: 40
<212> TYPE: PRT
<213> ORGANISM: Artificial Sequence
<220> FEATURE:
<223> OTHER INFORMATION: Core polypeptide

<400> SEQUENCE: 781

Asn Asn Tyr Thr Ser Leu Ile His Ser Leu Ile Glu Glu Ser Gln Asn
1               5                   10                  15

Gln Gln Glu Lys Asn Glu Gln Glu Leu Leu Glu Leu Asp Lys Trp Ala
            20                  25                  30

Ser Leu Trp Asn Trp Phe Asn Ile
            35                  40

<210> SEQ ID NO 782
<211> LENGTH: 49
<212> TYPE: PRT
<213> ORGANISM: Artificial Sequence
<220> FEATURE:
<223> OTHER INFORMATION: Core polypeptide

<400> SEQUENCE: 782

Lys Cys Arg Ala Lys Phe Lys Gln Leu Leu Gln His Tyr Arg Glu Val
1               5                   10                  15

Ala Ala Ala Lys Ser Ser Glu Asn Asp Arg Leu Arg Leu Leu Leu Lys
            20                  25                  30

Gln Met Cys Pro Ser Leu Asp Val Asp Ser Ile Ile Pro Arg Thr Pro
            35                  40                  45

Asp

<210> SEQ ID NO 783
<211> LENGTH: 47
<212> TYPE: PRT
<213> ORGANISM: Artificial Sequence
<220> FEATURE:
<223> OTHER INFORMATION: Core polypeptide

<400> SEQUENCE: 783

Arg Ala Lys Phe Lys Gln Leu Leu Gln His Tyr Arg Glu Val Ala Ala
1               5                   10                  15

Ala Lys Ser Ser Glu Asn Asp Arg Leu Arg Leu Leu Leu Lys Gln Met
            20                  25                  30

Cys Pro Ser Leu Asp Val Asp Ser Ile Ile Pro Arg Thr Pro Asp
            35                  40                  45

<210> SEQ ID NO 784
<211> LENGTH: 35
<212> TYPE: PRT
<213> ORGANISM: Artificial Sequence
<220> FEATURE:
```

<223> OTHER INFORMATION: Core polypeptide

<400> SEQUENCE: 784

Val Tyr Pro Ser Asp Glu Tyr Asp Ala Ser Ile Ser Gln Val Asn Glu
1               5                   10                  15

Glu Ile Asn Gln Ala Leu Ala Tyr Ile Ala Ala Ala Asp Glu Leu Leu
            20                  25                  30

Glu Asn Val
        35

<210> SEQ ID NO 785
<211> LENGTH: 26
<212> TYPE: PRT
<213> ORGANISM: Artificial Sequence
<220> FEATURE:
<223> OTHER INFORMATION: Core polypeptide

<400> SEQUENCE: 785

Tyr Asp Ala Ser Ile Ser Gln Val Asn Glu Glu Ile Asn Gln Ala Leu
1               5                   10                  15

Ala Tyr Ile Arg Lys Ala Asp Glu Leu Leu
            20                  25

<210> SEQ ID NO 786
<211> LENGTH: 40
<212> TYPE: PRT
<213> ORGANISM: Artificial Sequence
<220> FEATURE:
<223> OTHER INFORMATION: Core polypeptide

<400> SEQUENCE: 786

Met Asn Leu Glu Trp Met Glu Trp Asp Arg Glu Ile Asn Asn Tyr Thr
1               5                   10                  15

Ser Leu Ile His Ser Leu Ile Glu Glu Ser Gln Asn Gln Gln Glu Lys
            20                  25                  30

Asn Glu Gln Glu Leu Leu Glu Leu
        35                  40

<210> SEQ ID NO 787
<211> LENGTH: 34
<212> TYPE: PRT
<213> ORGANISM: Artificial Sequence
<220> FEATURE:
<223> OTHER INFORMATION: Core polypeptide

<400> SEQUENCE: 787

Lys Asn Gly Thr Tyr Asp Tyr Pro Lys Tyr Glu Glu Glu Ser Lys Leu
1               5                   10                  15

Asn Arg Asn Glu Ile Lys Gly Val Lys Leu Ser Ser Met Gly Val Tyr
            20                  25                  30

Gln Ile

<210> SEQ ID NO 788
<211> LENGTH: 35
<212> TYPE: PRT
<213> ORGANISM: Artificial Sequence
<220> FEATURE:
<223> OTHER INFORMATION: Core polypeptide

<400> SEQUENCE: 788

Val Thr Glu Lys Ile Gln Met Ala Ser Asp Asn Ile Asn Asp Leu Ile
1               5                   10                  15

-continued

Gln Ser Gly Val Asn Thr Arg Leu Leu Thr Ile Gln Ser His Val Gln
                20                  25                  30

Asn Tyr Ile
        35

<210> SEQ ID NO 789
<211> LENGTH: 24
<212> TYPE: PRT
<213> ORGANISM: Artificial Sequence
<220> FEATURE:
<223> OTHER INFORMATION: Core polypeptide

<400> SEQUENCE: 789

Gln Asn Gln Gln Glu Lys Asn Glu Gln Glu Leu Leu Glu Leu Asp Lys
1               5                   10                  15

Trp Ala Ser Leu Trp Asn Trp Phe
            20

<210> SEQ ID NO 790
<211> LENGTH: 24
<212> TYPE: PRT
<213> ORGANISM: Artificial Sequence
<220> FEATURE:
<223> OTHER INFORMATION: Core polypeptide

<400> SEQUENCE: 790

Gln Asn Gln Gln Glu Lys Asn Glu Gln Glu Leu Leu Glu Leu Asp Lys
1               5                   10                  15

Trp Ala Ser Leu Trp Asn Trp Phe
            20

<210> SEQ ID NO 791
<211> LENGTH: 5
<212> TYPE: PRT
<213> ORGANISM: Artificial Sequence
<220> FEATURE:
<223> OTHER INFORMATION: Core polypeptide

<400> SEQUENCE: 791

Leu Trp Asn Trp Phe
1               5

<210> SEQ ID NO 792
<211> LENGTH: 15
<212> TYPE: PRT
<213> ORGANISM: Artificial Sequence
<220> FEATURE:
<223> OTHER INFORMATION: Core polypeptide

<400> SEQUENCE: 792

Glu Leu Leu Glu Leu Asp Lys Trp Ala Ser Leu Trp Asn Trp Phe
1               5                   10                  15

<210> SEQ ID NO 793
<211> LENGTH: 20
<212> TYPE: PRT
<213> ORGANISM: Artificial Sequence
<220> FEATURE:
<223> OTHER INFORMATION: Core polypeptide

<400> SEQUENCE: 793

Glu Lys Asn Glu Gln Glu Leu Leu Glu Leu Asp Lys Trp Ala Ser Leu
1               5                   10                  15

Trp Asn Trp Phe
            20

-continued

<210> SEQ ID NO 794
<211> LENGTH: 30
<212> TYPE: PRT
<213> ORGANISM: Artificial Sequence
<220> FEATURE:
<223> OTHER INFORMATION: Core polypeptide

<400> SEQUENCE: 794

Ser Leu Ile Glu Glu Ser Gln Asn Gln Gln Glu Lys Asn Glu Gln Glu
1               5                   10                  15

Leu Leu Glu Leu Asp Lys Trp Ala Ser Leu Trp Asn Trp Phe
            20                  25                  30

<210> SEQ ID NO 795
<211> LENGTH: 35
<212> TYPE: PRT
<213> ORGANISM: Artificial Sequence
<220> FEATURE:
<223> OTHER INFORMATION: Core polypeptide

<400> SEQUENCE: 795

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp
        35

<210> SEQ ID NO 796
<211> LENGTH: 34
<212> TYPE: PRT
<213> ORGANISM: Artificial Sequence
<220> FEATURE:
<223> OTHER INFORMATION: Core polypeptide

<400> SEQUENCE: 796

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn

<210> SEQ ID NO 797
<211> LENGTH: 33
<212> TYPE: PRT
<213> ORGANISM: Artificial Sequence
<220> FEATURE:
<223> OTHER INFORMATION: Core polypeptide

<400> SEQUENCE: 797

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp

<210> SEQ ID NO 798
<211> LENGTH: 32
<212> TYPE: PRT
<213> ORGANISM: Artificial Sequence
<220> FEATURE:
<223> OTHER INFORMATION: Core polypeptide

```
<400> SEQUENCE: 798

Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser Leu
             20                  25                  30

<210> SEQ ID NO 799
<211> LENGTH: 35
<212> TYPE: PRT
<213> ORGANISM: Artificial Sequence
<220> FEATURE:
<223> OTHER INFORMATION: Core polypeptide

<400> SEQUENCE: 799

Thr Ser Leu Ile His Ser Leu Ile Glu Glu Ser Gln Asn Gln Gln Glu
 1               5                  10                  15

Lys Asn Glu Gln Glu Leu Leu Glu Leu Asp Lys Trp Ala Ser Leu Trp
             20                  25                  30

Asn Trp Phe
         35

<210> SEQ ID NO 800
<211> LENGTH: 34
<212> TYPE: PRT
<213> ORGANISM: Artificial Sequence
<220> FEATURE:
<223> OTHER INFORMATION: Core polypeptide

<400> SEQUENCE: 800

Ser Leu Ile His Ser Leu Ile Glu Glu Ser Gln Asn Gln Gln Glu Lys
 1               5                  10                  15

Asn Glu Gln Glu Leu Leu Glu Leu Asp Lys Trp Ala Ser Leu Trp Asn
             20                  25                  30

Trp Phe

<210> SEQ ID NO 801
<211> LENGTH: 33
<212> TYPE: PRT
<213> ORGANISM: Artificial Sequence
<220> FEATURE:
<223> OTHER INFORMATION: Core polypeptide

<400> SEQUENCE: 801

Leu Ile His Ser Leu Ile Glu Glu Ser Gln Asn Gln Gln Glu Lys Asn
 1               5                  10                  15

Glu Gln Glu Leu Leu Glu Leu Asp Lys Trp Ala Ser Leu Trp Asn Trp
             20                  25                  30

Phe

<210> SEQ ID NO 802
<211> LENGTH: 32
<212> TYPE: PRT
<213> ORGANISM: Artificial Sequence
<220> FEATURE:
<223> OTHER INFORMATION: Core polypeptide

<400> SEQUENCE: 802

Ile His Ser Leu Ile Glu Glu Ser Gln Asn Gln Gln Glu Lys Asn Glu
 1               5                  10                  15

Gln Glu Leu Leu Glu Leu Asp Lys Trp Ala Ser Leu Trp Asn Trp Phe
             20                  25                  30
```

<210> SEQ ID NO 803
<211> LENGTH: 51
<212> TYPE: PRT
<213> ORGANISM: Artificial Sequence
<220> FEATURE:
<223> OTHER INFORMATION: Core polypeptide

<400> SEQUENCE: 803

Ala Ala Val Ala Leu Leu Pro Ala Val Leu Leu Ala Leu Leu Ala Pro
1               5                   10                  15

Ser Glu Leu Glu Ile Lys Arg Tyr Lys Asn Arg Val Ala Ser Arg Lys
            20                  25                  30

Cys Arg Ala Lys Phe Lys Gln Leu Leu Gln His Tyr Arg Glu Val Ala
        35                  40                  45

Ala Ala Lys
    50

<210> SEQ ID NO 804
<211> LENGTH: 51
<212> TYPE: PRT
<213> ORGANISM: Artificial Sequence
<220> FEATURE:
<223> OTHER INFORMATION: Core polypeptide

<400> SEQUENCE: 804

Ala Ala Val Ala Leu Leu Pro Ala Val Leu Leu Ala Leu Leu Ala Pro
1               5                   10                  15

Cys Arg Ala Lys Phe Lys Gln Leu Leu Gln His Tyr Arg Glu Val Ala
            20                  25                  30

Ala Ala Lys Ser Ser Glu Asn Asp Arg Leu Arg Leu Leu Leu Lys Gln
        35                  40                  45

Met Cys Pro
    50

<210> SEQ ID NO 805
<211> LENGTH: 36
<212> TYPE: PRT
<213> ORGANISM: Artificial Sequence
<220> FEATURE:
<223> OTHER INFORMATION: Core polypeptide

<400> SEQUENCE: 805

Tyr Thr Ser Leu Ile His Ser Leu Ile Glu Glu Ser Gln Asn Gln Gln
1               5                   10                  15

Glu Lys Asn Asn Asn Ile Glu Arg Asp Trp Glu Met Trp Thr Met Asn
            20                  25                  30

Asn Trp Ile Gln
        35

<210> SEQ ID NO 806
<211> LENGTH: 35
<212> TYPE: PRT
<213> ORGANISM: Artificial Sequence
<220> FEATURE:
<223> OTHER INFORMATION: Core polypeptide

<400> SEQUENCE: 806

Val Tyr Pro Ser Asp Glu Tyr Asp Ala Ser Ile Ser Gln Val Asn Glu
1               5                   10                  15

Glu Ile Asn Gln Ala Leu Ala Tyr Ile Arg Lys Ala Asp Glu Leu Leu
            20                  25                  30

<210> SEQ ID NO 807
<211> LENGTH: 35
<212> TYPE: PRT
<213> ORGANISM: Artificial Sequence
<220> FEATURE:
<223> OTHER INFORMATION: Core polypeptide

<400> SEQUENCE: 807

```
Leu Met Gln Leu Ala Arg Gln Leu Met Gln Leu Ala Arg Gln Met Lys
 1               5                  10                  15

Gln Leu Ala Asp Ser Leu Met Gln Leu Ala Arg Gln Val Ser Arg Leu
            20                  25                  30

Glu Ser Ala
        35
```

<210> SEQ ID NO 808
<211> LENGTH: 34
<212> TYPE: PRT
<213> ORGANISM: Artificial Sequence
<220> FEATURE:
<223> OTHER INFORMATION: Core polypeptide

<400> SEQUENCE: 808

```
Trp Met Glu Trp Asp Arg Glu Ile Asn Asn Tyr Thr Ser Leu Ile His
 1               5                  10                  15

Ser Leu Ile Glu Glu Ser Gln Asn Gln Gln Glu Lys Asn Glu Gln Glu
            20                  25                  30

Leu Leu
```

<210> SEQ ID NO 809
<211> LENGTH: 35
<212> TYPE: PRT
<213> ORGANISM: Artificial Sequence
<220> FEATURE:
<223> OTHER INFORMATION: Core polypeptide

<400> SEQUENCE: 809

```
Met Glu Trp Asp Arg Glu Ile Asn Asn Tyr Thr Ser Leu Ile His Ser
 1               5                  10                  15

Leu Ile Glu Glu Ser Gln Asn Gln Gln Glu Lys Asn Glu Gln Glu Leu
            20                  25                  30

Leu Glu Leu
        35
```

<210> SEQ ID NO 810
<211> LENGTH: 34
<212> TYPE: PRT
<213> ORGANISM: Artificial Sequence
<220> FEATURE:
<223> OTHER INFORMATION: Core polypeptide

<400> SEQUENCE: 810

```
Glu Trp Asp Arg Glu Ile Asn Asn Tyr Thr Ser Leu Ile His Ser Leu
 1               5                  10                  15

Ile Glu Glu Ser Gln Asn Gln Gln Glu Lys Asn Glu Gln Glu Leu Leu
            20                  25                  30

Glu Leu
```

```
<210> SEQ ID NO 811
<211> LENGTH: 34
<212> TYPE: PRT
<213> ORGANISM: Artificial Sequence
<220> FEATURE:
<223> OTHER INFORMATION: Core polypeptide

<400> SEQUENCE: 811

Met Glu Trp Asp Arg Glu Ile Asn Asn Tyr Thr Ser Leu Ile His Ser
1               5                   10                  15

Leu Ile Glu Glu Ser Gln Asn Gln Gln Glu Lys Asn Glu Gln Glu Leu
            20                  25                  30

Leu Glu

<210> SEQ ID NO 812
<211> LENGTH: 36
<212> TYPE: PRT
<213> ORGANISM: Artificial Sequence
<220> FEATURE:
<223> OTHER INFORMATION: Core polypeptide

<400> SEQUENCE: 812

Trp Asn Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu Glu Leu
        35

<210> SEQ ID NO 813
<211> LENGTH: 36
<212> TYPE: PRT
<213> ORGANISM: Artificial Sequence
<220> FEATURE:
<223> OTHER INFORMATION: Core polypeptide

<400> SEQUENCE: 813

Tyr Leu Glu Tyr Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu Leu Glu Leu
        35

<210> SEQ ID NO 814
<211> LENGTH: 17
<212> TYPE: PRT
<213> ORGANISM: Artificial Sequence
<220> FEATURE:
<223> OTHER INFORMATION: Core polypeptide

<400> SEQUENCE: 814

Ile Lys Gln Phe Ile Asn Met Trp Gln Glu Val Gly Lys Ala Met Tyr
1               5                   10                  15

Ala

<210> SEQ ID NO 815
<211> LENGTH: 8
<212> TYPE: PRT
<213> ORGANISM: Artificial Sequence
<220> FEATURE:
<223> OTHER INFORMATION: Core polypeptide

<400> SEQUENCE: 815
```

```
Ile Arg Lys Ser Asp Glu Leu Leu
 1               5
```

<210> SEQ ID NO 816
<211> LENGTH: 8
<212> TYPE: PRT
<213> ORGANISM: Artificial Sequence
<220> FEATURE:
<223> OTHER INFORMATION: Core polypeptide

<400> SEQUENCE: 816

```
Tyr Asp Ala Ser Ile Ser Gln Val
 1               5
```

<210> SEQ ID NO 817
<211> LENGTH: 8
<212> TYPE: PRT
<213> ORGANISM: Artificial Sequence
<220> FEATURE:
<223> OTHER INFORMATION: Core polypeptide

<400> SEQUENCE: 817

```
Asn Glu Lys Ile Asn Gln Ser Leu
 1               5
```

<210> SEQ ID NO 818
<211> LENGTH: 23
<212> TYPE: PRT
<213> ORGANISM: Artificial Sequence
<220> FEATURE:
<223> OTHER INFORMATION: Core polypeptide

<400> SEQUENCE: 818

```
Ser Ile Ser Gln Val Asn Glu Glu Ile Asn Gln Ala Leu Ala Tyr Ile
 1               5                  10                  15

Arg Lys Ala Asp Glu Leu Leu
            20
```

<210> SEQ ID NO 819
<211> LENGTH: 20
<212> TYPE: PRT
<213> ORGANISM: Artificial Sequence
<220> FEATURE:
<223> OTHER INFORMATION: Core polypeptide

<400> SEQUENCE: 819

```
Gln Val Asn Glu Glu Ile Asn Gln Ala Leu Ala Tyr Ile Arg Lys Ala
 1               5                  10                  15

Asp Glu Leu Leu
            20
```

<210> SEQ ID NO 820
<211> LENGTH: 17
<212> TYPE: PRT
<213> ORGANISM: Artificial Sequence
<220> FEATURE:
<223> OTHER INFORMATION: Core polypeptide

<400> SEQUENCE: 820

```
Glu Glu Ile Asn Gln Ala Leu Ala Tyr Ile Arg Lys Ala Asp Glu Leu
 1               5                  10                  15

Leu
```

<210> SEQ ID NO 821

```
<211> LENGTH: 14
<212> TYPE: PRT
<213> ORGANISM: Artificial Sequence
<220> FEATURE:
<223> OTHER INFORMATION: Core polypeptide

<400> SEQUENCE: 821

Asn Gln Ala Leu Ala Tyr Ile Arg Lys Ala Asp Glu Leu Leu
 1               5                  10

<210> SEQ ID NO 822
<211> LENGTH: 11
<212> TYPE: PRT
<213> ORGANISM: Artificial Sequence
<220> FEATURE:
<223> OTHER INFORMATION: Core polypeptide

<400> SEQUENCE: 822

Leu Ala Tyr Ile Arg Lys Ala Asp Glu Leu Leu
 1               5                  10

<210> SEQ ID NO 823
<211> LENGTH: 26
<212> TYPE: PRT
<213> ORGANISM: Artificial Sequence
<220> FEATURE:
<223> OTHER INFORMATION: Core polypeptide

<400> SEQUENCE: 823

Phe Asp Ala Ser Ile Ser Gln Val Asn Glu Lys Ile Asn Gln Ala Leu
 1               5                  10                  15

Ala Phe Ile Arg Lys Ser Asp Glu Leu Leu
            20                  25

<210> SEQ ID NO 824
<211> LENGTH: 36
<212> TYPE: PRT
<213> ORGANISM: Artificial Sequence
<220> FEATURE:
<223> OTHER INFORMATION: Core polypeptide

<400> SEQUENCE: 824

Trp Asn Glu Trp Asp Arg Glu Ile Asn Asn Tyr Thr Ser Leu Ile His
 1               5                  10                  15

Ser Leu Ile Glu Glu Ser Gln Asn Gln Gln Glu Lys Asn Glu Gln Glu
            20                  25                  30

Leu Leu Glu Leu
        35

<210> SEQ ID NO 825
<211> LENGTH: 45
<212> TYPE: PRT
<213> ORGANISM: Artificial Sequence
<220> FEATURE:
<223> OTHER INFORMATION: Core polypeptide

<400> SEQUENCE: 825

Ala Ser Arg Lys Cys Arg Ala Lys Phe Lys Gln Leu Leu Gln His Tyr
 1               5                  10                  15

Arg Glu Val Ala Ala Ala Lys Ser Ser Glu Asn Asp Arg Leu Arg Leu
            20                  25                  30

Leu Leu Lys Gln Met Cys Pro Ser Leu Asp Val Asp Ser
        35                  40                  45
```

```
<210> SEQ ID NO 826
<211> LENGTH: 4
<212> TYPE: PRT
<213> ORGANISM: Artificial Sequence
<220> FEATURE:
<223> OTHER INFORMATION: Core polypeptide

<400> SEQUENCE: 826

Glx Phe Phe Gly
 1

<210> SEQ ID NO 827
<211> LENGTH: 36
<212> TYPE: PRT
<213> ORGANISM: Artificial Sequence
<220> FEATURE:
<223> OTHER INFORMATION: Core polypeptide

<400> SEQUENCE: 827

Trp Leu Glu Trp Asp Arg Glu Ile Asn Asn Tyr Thr Ser Leu Ile His
 1               5                  10                  15

Ser Leu Ile Glu Glu Ser Gln Asn Gln Gln Glu Lys Asn Glu Gln Glu
            20                  25                  30

Leu Leu Glu Leu
        35

<210> SEQ ID NO 828
<211> LENGTH: 36
<212> TYPE: PRT
<213> ORGANISM: Artificial Sequence
<220> FEATURE:
<223> OTHER INFORMATION: Core polypeptide

<400> SEQUENCE: 828

Tyr Val Lys Gly Glu Pro Ile Ile Asn Phe Tyr Asp Pro Leu Val Phe
 1               5                  10                  15

Pro Ser Asp Glu Phe Asp Ala Ser Ile Ser Gln Val Asn Glu Lys Ile
            20                  25                  30

Asn Gln Ser Leu
        35

<210> SEQ ID NO 829
<211> LENGTH: 35
<212> TYPE: PRT
<213> ORGANISM: Artificial Sequence
<220> FEATURE:
<223> OTHER INFORMATION: Core polypeptide

<400> SEQUENCE: 829

Val Tyr Pro Ser Asp Glu Tyr Asp Ala Ser Ile Ser Gln Val Asn Glu
 1               5                  10                  15

Glu Ile Asn Gln Ser Leu Ala Tyr Ile Arg Lys Ala Asp Glu Leu Leu
            20                  25                  30

His Asn Val
        35

<210> SEQ ID NO 830
<211> LENGTH: 29
<212> TYPE: PRT
<213> ORGANISM: Artificial Sequence
<220> FEATURE:
<223> OTHER INFORMATION: Core polypeptide

<400> SEQUENCE: 830
```

-continued

```
Tyr Asp Ala Ser Ile Ser Gln Val Asn Glu Ile Asn Gln Ala Leu
 1               5                  10                  15

Ala Tyr Ile Arg Lys Ala Asp Glu Leu Leu Glu Asn Val
            20                  25
```

<210> SEQ ID NO 831
<211> LENGTH: 27
<212> TYPE: PRT
<213> ORGANISM: Artificial Sequence
<220> FEATURE:
<223> OTHER INFORMATION: Core polypeptide

<400> SEQUENCE: 831

```
Tyr Asp Ala Ser Ile Ser Gln Val Asn Glu Ile Asn Gln Ala Leu
 1               5                  10                  15

Ala Tyr Ile Arg Lys Ala Asp Glu Leu Leu Glu
            20                  25
```

<210> SEQ ID NO 832
<211> LENGTH: 35
<212> TYPE: PRT
<213> ORGANISM: Artificial Sequence
<220> FEATURE:
<223> OTHER INFORMATION: Core polypeptide

<400> SEQUENCE: 832

```
Val Tyr Pro Ser Asp Glu Tyr Asp Ala Ser Ile Ser Gln Val Asn Glu
 1               5                  10                  15

Glu Ile Asn Gln Ala Leu Ala Tyr Ile Arg Lys Ala Ala Glu Leu Leu
            20                  25                  30

His Asn Val
        35
```

<210> SEQ ID NO 833
<211> LENGTH: 35
<212> TYPE: PRT
<213> ORGANISM: Artificial Sequence
<220> FEATURE:
<223> OTHER INFORMATION: Core polypeptide

<400> SEQUENCE: 833

```
Val Tyr Pro Ser Asp Glu Tyr Asp Ala Ser Ile Ser Gln Val Asn Glu
 1               5                  10                  15

Glu Ile Asn Gln Ala Leu Ala Tyr Ile Arg Lys Ala Leu Glu Leu Leu
            20                  25                  30

His Asn Val
        35
```

<210> SEQ ID NO 834
<211> LENGTH: 36
<212> TYPE: PRT
<213> ORGANISM: Artificial Sequence
<220> FEATURE:
<223> OTHER INFORMATION: Core polypeptide

<400> SEQUENCE: 834

```
Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser Leu
            20                  25                  30

Trp Asn Trp Phe
        35
```

```
<210> SEQ ID NO 835
<211> LENGTH: 35
<212> TYPE: PRT
<213> ORGANISM: Artificial Sequence
<220> FEATURE:
<223> OTHER INFORMATION: Core polypeptide

<400> SEQUENCE: 835

Val Tyr Pro Ser Asp Glu Tyr Asp Ala Ser Ile Ser Gln Val Asn Glu
1               5                   10                  15

Glu Ile Asn Gln Leu Leu Ala Tyr Ile Arg Lys Leu Asp Glu Leu Leu
            20                  25                  30

Glu Asn Val
        35

<210> SEQ ID NO 836
<211> LENGTH: 28
<212> TYPE: PRT
<213> ORGANISM: Artificial Sequence
<220> FEATURE:
<223> OTHER INFORMATION: Core polypeptide

<400> SEQUENCE: 836

Asp Glu Tyr Asp Ala Ser Ile Ser Gln Val Asn Glu Lys Ile Asn Gln
1               5                   10                  15

Ser Leu Ala Phe Ile Arg Lys Ser Asp Glu Leu Leu
            20                  25

<210> SEQ ID NO 837
<211> LENGTH: 35
<212> TYPE: PRT
<213> ORGANISM: Artificial Sequence
<220> FEATURE:
<223> OTHER INFORMATION: Core polypeptide

<400> SEQUENCE: 837

Ser Asn Asp Gln Gly Ser Gly Tyr Ala Ala Asp Lys Glu Ser Thr Gln
1               5                   10                  15

Lys Ala Phe Asp Gly Ile Thr Asn Lys Val Asn Ser Val Ile Glu Lys
            20                  25                  30

Thr Asn Thr
        35

<210> SEQ ID NO 838
<211> LENGTH: 38
<212> TYPE: PRT
<213> ORGANISM: Artificial Sequence
<220> FEATURE:
<223> OTHER INFORMATION: Core polypeptide

<400> SEQUENCE: 838

Glu Ser Thr Gln Lys Ala Phe Asp Gly Ile Thr Asn Lys Val Asn Ser
1               5                   10                  15

Val Ile Glu Lys Thr Asn Thr Gln Phe Glu Ala Val Gly Lys Glu Phe
            20                  25                  30

Gly Asn Leu Glu Lys Arg
        35

<210> SEQ ID NO 839
<211> LENGTH: 37
<212> TYPE: PRT
<213> ORGANISM: Artificial Sequence
<220> FEATURE:
```

```
<223> OTHER INFORMATION: Core polypeptide

<400> SEQUENCE: 839

Asp Gly Ile Thr Asn Lys Val Asn Ser Val Ile Glu Lys Thr Asn Thr
 1               5                  10                  15

Gln Phe Glu Ala Val Gly Lys Glu Phe Gly Asn Leu Glu Lys Arg Leu
                20                  25                  30

Glu Asn Leu Asn Lys
            35

<210> SEQ ID NO 840
<211> LENGTH: 32
<212> TYPE: PRT
<213> ORGANISM: Artificial Sequence
<220> FEATURE:
<223> OTHER INFORMATION: Core polypeptide

<400> SEQUENCE: 840

Asp Ser Asn Val Lys Asn Leu Tyr Asp Lys Val Arg Ser Gln Leu Arg
 1               5                  10                  15

Asp Asn Val Lys Glu Leu Gly Asn Gly Ala Phe Glu Phe Tyr His Lys
                20                  25                  30

<210> SEQ ID NO 841
<211> LENGTH: 36
<212> TYPE: PRT
<213> ORGANISM: Artificial Sequence
<220> FEATURE:
<223> OTHER INFORMATION: Core polypeptide

<400> SEQUENCE: 841

Arg Asp Asn Val Lys Glu Leu Gly Asn Gly Ala Phe Glu Phe Tyr His
 1               5                  10                  15

Lys Ala Asp Asp Glu Ala Leu Asn Ser Val Lys Asn Gly Thr Tyr Asp
                20                  25                  30

Tyr Pro Lys Tyr
            35

<210> SEQ ID NO 842
<211> LENGTH: 24
<212> TYPE: PRT
<213> ORGANISM: Artificial Sequence
<220> FEATURE:
<223> OTHER INFORMATION: Core polypeptide

<400> SEQUENCE: 842

Glu Phe Tyr His Lys Ala Asp Asp Glu Ala Leu Asn Ser Val Lys Asn
 1               5                  10                  15

Gly Thr Tyr Asp Tyr Pro Lys Tyr
                20

<210> SEQ ID NO 843
<211> LENGTH: 36
<212> TYPE: PRT
<213> ORGANISM: Artificial Sequence
<220> FEATURE:
<223> OTHER INFORMATION: Core polypeptide

<400> SEQUENCE: 843

Ala Ala Val Ala Leu Leu Pro Ala Val Leu Leu Ala Leu Leu Ala Pro
 1               5                  10                  15

Ala Ala Asp Lys Glu Ser Thr Gln Lys Ala Phe Asp Gly Ile Thr Asn
                20                  25                  30
```

```
Lys Val Asn Ser
         35

<210> SEQ ID NO 844
<211> LENGTH: 36
<212> TYPE: PRT
<213> ORGANISM: Artificial Sequence
<220> FEATURE:
<223> OTHER INFORMATION: Core polypeptide

<400> SEQUENCE: 844

Ala Ala Val Ala Leu Leu Pro Ala Val Leu Leu Ala Leu Leu Ala Pro
 1               5                  10                  15

Ala Ala Asp Ser Asn Val Lys Asn Leu Tyr Asp Lys Val Arg Ser Gln
             20                  25                  30

Leu Arg Asp Asn
         35

<210> SEQ ID NO 845
<211> LENGTH: 18
<212> TYPE: PRT
<213> ORGANISM: Artificial Sequence
<220> FEATURE:
<223> OTHER INFORMATION: Core polypeptide

<400> SEQUENCE: 845

Lys Glu Ser Thr Gln Lys Ala Phe Asp Gly Ile Thr Asn Lys Val Asn
 1               5                  10                  15

Ser Val

<210> SEQ ID NO 846
<211> LENGTH: 20
<212> TYPE: PRT
<213> ORGANISM: Artificial Sequence
<220> FEATURE:
<223> OTHER INFORMATION: Core polypeptide

<400> SEQUENCE: 846

Ile Glu Lys Thr Asn Thr Gln Phe Glu Ala Val Gly Lys Glu Phe Gly
 1               5                  10                  15

Asn Leu Glu Arg
         20

<210> SEQ ID NO 847
<211> LENGTH: 30
<212> TYPE: PRT
<213> ORGANISM: Artificial Sequence
<220> FEATURE:
<223> OTHER INFORMATION: Core polypeptide

<400> SEQUENCE: 847

Arg Leu Glu Asn Leu Asn Lys Arg Val Glu Asp Gly Phe Leu Asp Val
 1               5                  10                  15

Trp Thr Tyr Asn Ala Glu Leu Leu Val Ala Leu Glu Asn Glu
             20                  25                  30

<210> SEQ ID NO 848
<211> LENGTH: 17
<212> TYPE: PRT
<213> ORGANISM: Artificial Sequence
<220> FEATURE:
<223> OTHER INFORMATION: Core polypeptide

<400> SEQUENCE: 848
```

Ser Asn Val Lys Asn Leu Tyr Asp Lys Val Arg Ser Gln Leu Arg Asp
1               5                   10                  15

Asn

<210> SEQ ID NO 849
<211> LENGTH: 33
<212> TYPE: PRT
<213> ORGANISM: Artificial Sequence
<220> FEATURE:
<223> OTHER INFORMATION: Core polypeptide

<400> SEQUENCE: 849

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Leu

<210> SEQ ID NO 850
<211> LENGTH: 32
<212> TYPE: PRT
<213> ORGANISM: Artificial Sequence
<220> FEATURE:
<223> OTHER INFORMATION: Core polypeptide

<400> SEQUENCE: 850

Trp Met Glu Trp Asp Arg Glu Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

<210> SEQ ID NO 851
<211> LENGTH: 32
<212> TYPE: PRT
<213> ORGANISM: Artificial Sequence
<220> FEATURE:
<223> OTHER INFORMATION: Core polypeptide

<400> SEQUENCE: 851

Met Glu Trp Asp Arg Glu Ile Asn Asn Tyr Thr Ser Leu Ile His Ser
1               5                   10                  15

Leu Ile Glu Glu Ser Gln Asn Gln Gln Glu Lys Asn Glu Gln Glu Leu
            20                  25                  30

<210> SEQ ID NO 852
<211> LENGTH: 31
<212> TYPE: PRT
<213> ORGANISM: Artificial Sequence
<220> FEATURE:
<223> OTHER INFORMATION: Core polypeptide

<400> SEQUENCE: 852

Met Glu Trp Asp Arg Glu Ile Asn Asn Tyr Thr Ser Leu Ile His Ser
1               5                   10                  15

Leu Ile Glu Glu Ser Gln Asn Gln Gln Glu Lys Asn Glu Gln Glu
            20                  25                  30

<210> SEQ ID NO 853
<211> LENGTH: 33
<212> TYPE: PRT
<213> ORGANISM: Artificial Sequence
<220> FEATURE:
<223> OTHER INFORMATION: Core polypeptide -continued

```
<400> SEQUENCE: 853

Glu Trp Asp Arg Glu Ile Asn Asn Tyr Thr Ser Leu Ile His Ser Leu
 1               5                  10                  15

Ile Glu Glu Ser Gln Asn Gln Gln Glu Lys Asn Glu Gln Glu Leu Leu
            20                  25                  30

Glu

<210> SEQ ID NO 854
<211> LENGTH: 32
<212> TYPE: PRT
<213> ORGANISM: Artificial Sequence
<220> FEATURE:
<223> OTHER INFORMATION: Core polypeptide

<400> SEQUENCE: 854

Glu Trp Asp Arg Glu Ile Asn Asn Tyr Thr Ser Leu Ile His Ser Leu
 1               5                  10                  15

Ile Glu Glu Ser Gln Asn Gln Gln Glu Lys Asn Glu Gln Glu Leu Leu
            20                  25                  30

<210> SEQ ID NO 855
<211> LENGTH: 31
<212> TYPE: PRT
<213> ORGANISM: Artificial Sequence
<220> FEATURE:
<223> OTHER INFORMATION: Core polypeptide

<400> SEQUENCE: 855

Glu Trp Asp Arg Glu Ile Asn Asn Tyr Thr Ser Leu Ile His Ser Leu
 1               5                  10                  15

Ile Glu Glu Ser Gln Asn Gln Gln Glu Lys Asn Glu Gln Glu Leu
            20                  25                  30

<210> SEQ ID NO 856
<211> LENGTH: 36
<212> TYPE: PRT
<213> ORGANISM: Artificial Sequence
<220> FEATURE:
<223> OTHER INFORMATION: Core polypeptide

<400> SEQUENCE: 856

Tyr Thr Lys Phe Ile Tyr Thr Leu Leu Glu Glu Ser Gln Asn Gln Gln
 1               5                  10                  15

Glu Lys Asn Glu Gln Glu Leu Leu Glu Leu Asp Lys Trp Ala Ser Leu
            20                  25                  30

Trp Asn Trp Phe
            35

<210> SEQ ID NO 857
<211> LENGTH: 22
<212> TYPE: PRT
<213> ORGANISM: Artificial Sequence
<220> FEATURE:
<223> OTHER INFORMATION: Core polypeptide

<400> SEQUENCE: 857

Tyr Met Lys Gln Leu Ala Asp Ser Leu Met Gln Leu Ala Arg Gln Val
 1               5                  10                  15

Ser Arg Leu Glu Ser Ala
            20
```

<210> SEQ ID NO 858
<211> LENGTH: 29
<212> TYPE: PRT
<213> ORGANISM: Artificial Sequence
<220> FEATURE:
<223> OTHER INFORMATION: Core polypeptide

<400> SEQUENCE: 858

Tyr Leu Met Gln Leu Ala Arg Gln Met Lys Gln Leu Ala Asp Ser Leu
1               5                   10                  15

Met Gln Leu Ala Arg Gln Val Ser Arg Leu Glu Ser Ala
            20                  25

<210> SEQ ID NO 859
<211> LENGTH: 36
<212> TYPE: PRT
<213> ORGANISM: Artificial Sequence
<220> FEATURE:
<223> OTHER INFORMATION: Core polypeptide

<400> SEQUENCE: 859

Tyr Gln Glu Trp Glu Arg Lys Val Asp Phe Leu Glu Glu Asn Ile Thr
1               5                   10                  15

Ala Leu Leu Glu Glu Ala Gln Ile Gln Gln Glu Lys Asn Met Tyr Glu
            20                  25                  30

Leu Gln Lys Leu
            35

<210> SEQ ID NO 860
<211> LENGTH: 36
<212> TYPE: PRT
<213> ORGANISM: Artificial Sequence
<220> FEATURE:
<223> OTHER INFORMATION: Core polypeptide

<400> SEQUENCE: 860

Trp Met Ala Trp Ala Ala Ala Ile Asn Asn Tyr Thr Ser Leu Ile His
1               5                   10                  15

Ser Leu Ile Glu Glu Ser Gln Asn Gln Gln Glu Lys Asn Glu Gln Glu
            20                  25                  30

Glu Glu Glu Glu
            35

<210> SEQ ID NO 861
<211> LENGTH: 36
<212> TYPE: PRT
<213> ORGANISM: Artificial Sequence
<220> FEATURE:
<223> OTHER INFORMATION: Core polypeptide

<400> SEQUENCE: 861

Tyr Ala Ser Leu Ile Ala Ala Leu Ile Glu Ser Gln Asn Gln Gln
1               5                   10                  15

Glu Lys Asn Glu Gln Glu Leu Leu Glu Leu Ala Lys Trp Ala Ala Leu
            20                  25                  30

Trp Ala Trp Phe
            35

<210> SEQ ID NO 862
<211> LENGTH: 38
<212> TYPE: PRT
<213> ORGANISM: Artificial Sequence
<220> FEATURE:
<223> OTHER INFORMATION: Core polypeptide

```
<400> SEQUENCE: 862

Glu Trp Asp Arg Glu Ile Asn Asn Tyr Thr Ser Leu Ile His Ser Leu
 1               5                  10                  15

Ile Glu Glu Ser Gln Asn Gln Gln Glu Lys Asn Glu Gln Glu Gly Gly
             20                  25                  30

Cys Asp Ile Met Glu Arg
         35

<210> SEQ ID NO 863
<211> LENGTH: 35
<212> TYPE: PRT
<213> ORGANISM: Artificial Sequence
<220> FEATURE:
<223> OTHER INFORMATION: Core polypeptide

<400> SEQUENCE: 863

Tyr Asp Ile Ser Ile Glu Leu Asn Lys Ala Lys Ser Asp Leu Glu Glu
 1               5                  10                  15

Ser Lys Glu Trp Ile Lys Lys Ser Asn Gln Lys Leu Asp Ser Ile Gly
             20                  25                  30

Asn Trp His
         35

<210> SEQ ID NO 864
<211> LENGTH: 35
<212> TYPE: PRT
<213> ORGANISM: Artificial Sequence
<220> FEATURE:
<223> OTHER INFORMATION: Core polypeptide

<400> SEQUENCE: 864

Ile Asp Ile Ser Ile Glu Leu Asn Lys Ala Lys Ser Asp Leu Glu Glu
 1               5                  10                  15

Ser Lys Glu Trp Ile Lys Lys Ser Asn Gln Lys Leu Asp Ser Ile Gly
             20                  25                  30

Asn Trp His
         35

<210> SEQ ID NO 865
<211> LENGTH: 6
<212> TYPE: PRT
<213> ORGANISM: Artificial Sequence
<220> FEATURE:
<223> OTHER INFORMATION: Core polypeptide

<400> SEQUENCE: 865

Tyr Thr Ser Leu Ile His
 1               5

<210> SEQ ID NO 866
<211> LENGTH: 7
<212> TYPE: PRT
<213> ORGANISM: Artificial Sequence
<220> FEATURE:
<223> OTHER INFORMATION: Core polypeptide

<400> SEQUENCE: 866

His Ser Leu Ile Glu Glu His
 1               5

<210> SEQ ID NO 867
<211> LENGTH: 8
```

```
<212> TYPE: PRT
<213> ORGANISM: Artificial Sequence
<220> FEATURE:
<223> OTHER INFORMATION: Core polypeptide

<400> SEQUENCE: 867

Ser Gln Asn Gln Gln Glu Lys His
 1               5

<210> SEQ ID NO 868
<211> LENGTH: 9
<212> TYPE: PRT
<213> ORGANISM: Artificial Sequence
<220> FEATURE:
<223> OTHER INFORMATION: Core polypeptide

<400> SEQUENCE: 868

Asn Glu Gln Glu Leu Leu Glu Leu His
 1               5

<210> SEQ ID NO 869
<211> LENGTH: 7
<212> TYPE: PRT
<213> ORGANISM: Artificial Sequence
<220> FEATURE:
<223> OTHER INFORMATION: Core polypeptide

<400> SEQUENCE: 869

Asp Lys Trp Ala Ser Leu His
 1               5

<210> SEQ ID NO 870
<211> LENGTH: 5
<212> TYPE: PRT
<213> ORGANISM: Artificial Sequence
<220> FEATURE:
<223> OTHER INFORMATION: Core polypeptide

<400> SEQUENCE: 870

Trp Asn Trp Phe His
 1               5

<210> SEQ ID NO 871
<211> LENGTH: 36
<212> TYPE: PRT
<213> ORGANISM: Artificial Sequence
<220> FEATURE:
<223> OTHER INFORMATION: Core polypeptide

<400> SEQUENCE: 871

Ala Lys Thr Leu Glu Arg Thr Trp Asp Thr Leu Asn His Leu Leu Phe
 1               5                  10                  15

Ile Ser Ser Ala Leu Tyr Lys Leu Asn Leu Lys Ser Val Ala Gln Ile
                20                  25                  30

Thr Leu Ser Ile
            35

<210> SEQ ID NO 872
<211> LENGTH: 24
<212> TYPE: PRT
<213> ORGANISM: Artificial Sequence
<220> FEATURE:
<223> OTHER INFORMATION: Core polypeptide

<400> SEQUENCE: 872

Asn Ile Thr Leu Gln Ala Lys Ile Lys Gln Phe Ile Asn Met Trp Gln
```

```
                1               5              10              15

Glu Val Gly Lys Ala Met Tyr Ala
                20
```

<210> SEQ ID NO 873
<211> LENGTH: 28
<212> TYPE: PRT
<213> ORGANISM: Artificial Sequence
<220> FEATURE:
<223> OTHER INFORMATION: Core polypeptide

<400> SEQUENCE: 873

```
Leu Glu Asn Glu Arg Thr Leu Asp Phe His Asp Ser Asn Val Lys Asn
 1               5                  10                  15

Leu Tyr Asp Lys Val Arg Leu Gln Leu Arg Asp Asn
                20                  25
```

<210> SEQ ID NO 874
<211> LENGTH: 35
<212> TYPE: PRT
<213> ORGANISM: Artificial Sequence
<220> FEATURE:
<223> OTHER INFORMATION: Core polypeptide

<400> SEQUENCE: 874

```
Leu Glu Asn Glu Arg Thr Leu Asp Phe His Asp Ser Asn Val Lys Asn
 1               5                  10                  15

Leu Tyr Asp Lys Val Arg Leu Gln Leu Arg Asp Asn Val Lys Glu Leu
                20                  25                  30

Gly Asn Gly
         35
```

<210> SEQ ID NO 875
<211> LENGTH: 34
<212> TYPE: PRT
<213> ORGANISM: Artificial Sequence
<220> FEATURE:
<223> OTHER INFORMATION: Core polypeptide

<400> SEQUENCE: 875

```
Thr Leu Asp Phe His Asp Ser Asn Val Lys Asn Leu Tyr Asp Lys Val
 1               5                  10                  15

Arg Leu Gln Leu Arg Asp Asn Val Lys Glu Leu Gly Asn Gly Ala Phe
                20                  25                  30

Glu Phe
```

<210> SEQ ID NO 876
<211> LENGTH: 26
<212> TYPE: PRT
<213> ORGANISM: Artificial Sequence
<220> FEATURE:
<223> OTHER INFORMATION: Core polypeptide

<400> SEQUENCE: 876

```
Phe Asp Ala Ser Ile Ser Gln Val Asn Glu Lys Ile Asn Gln Ala Leu
 1               5                  10                  15

Ala Phe Ile Arg Lys Ser Asp Glu Leu Leu
                20                  25
```

<210> SEQ ID NO 877
<211> LENGTH: 23
<212> TYPE: PRT
<213> ORGANISM: Artificial Sequence

```
<220> FEATURE:
<223> OTHER INFORMATION: Core polypeptide

<400> SEQUENCE: 877

Ser Ile Ser Gln Val Asn Glu Glu Ile Asn Gln Ala Leu Ala Tyr Ile
 1               5                  10                  15

Arg Lys Ala Asp Glu Leu Leu
            20

<210> SEQ ID NO 878
<211> LENGTH: 23
<212> TYPE: PRT
<213> ORGANISM: Artificial Sequence
<220> FEATURE:
<223> OTHER INFORMATION: Core polypeptide

<400> SEQUENCE: 878

Ser Ile Ser Gln Val Asn Glu Glu Ile Asn Gln Ser Leu Ala Tyr Ile
 1               5                  10                  15

Arg Lys Ser Asp Glu Leu Leu
            20

<210> SEQ ID NO 879
<211> LENGTH: 23
<212> TYPE: PRT
<213> ORGANISM: Artificial Sequence
<220> FEATURE:
<223> OTHER INFORMATION: Core polypeptide

<400> SEQUENCE: 879

Ser Ile Ser Gln Val Asn Glu Glu Ile Asn Gln Ser Leu Ala Tyr Ile
 1               5                  10                  15

Arg Lys Ser Asp Glu Leu Leu
            20

<210> SEQ ID NO 880
<211> LENGTH: 35
<212> TYPE: PRT
<213> ORGANISM: Artificial Sequence
<220> FEATURE:
<223> OTHER INFORMATION: Core polypeptide

<400> SEQUENCE: 880

Asn Ser Val Ala Leu Asp Pro Ile Asp Ile Ser Ile Glu Leu Asn Lys
 1               5                  10                  15

Ala Lys Ser Asp Leu Glu Glu Ser Lys Glu Trp Ile Lys Lys Ser Asn
            20                  25                  30

Gln Lys Leu
        35

<210> SEQ ID NO 881
<211> LENGTH: 35
<212> TYPE: PRT
<213> ORGANISM: Artificial Sequence
<220> FEATURE:
<223> OTHER INFORMATION: Core polypeptide

<400> SEQUENCE: 881

Ala Leu Asp Pro Ile Asp Ile Ser Ile Glu Leu Asn Lys Ala Lys Ser
 1               5                  10                  15

Asp Leu Glu Glu Ser Lys Glu Trp Ile Lys Lys Ser Asn Gln Lys Leu
            20                  25                  30

Asp Ser Ile
```

<210> SEQ ID NO 882
<211> LENGTH: 35
<212> TYPE: PRT
<213> ORGANISM: Artificial Sequence
<220> FEATURE:
<223> OTHER INFORMATION: Core polypeptide

<400> SEQUENCE: 882

Asn Ser Val Ala Leu Asp Pro Ile Asp Ile Ser Ile Glu Leu Asn Lys
1               5                   10                  15

Ala Lys Ser Asp Leu Glu Glu Ser Lys Glu Trp Ile Lys Lys Ser Asn
            20                  25                  30

Gln Lys Leu
        35

<210> SEQ ID NO 883
<211> LENGTH: 35
<212> TYPE: PRT
<213> ORGANISM: Artificial Sequence
<220> FEATURE:
<223> OTHER INFORMATION: Core polypeptide

<400> SEQUENCE: 883

Ala Leu Asp Pro Ile Asp Ile Ser Ile Glu Leu Asn Lys Ala Lys Ser
1               5                   10                  15

Asp Leu Glu Glu Ser Lys Glu Trp Ile Lys Lys Ser Asn Gln Lys Leu
            20                  25                  30

Asp Ser Ile
        35

<210> SEQ ID NO 884
<211> LENGTH: 26
<212> TYPE: PRT
<213> ORGANISM: Artificial Sequence
<220> FEATURE:
<223> OTHER INFORMATION: Core polypeptide

<400> SEQUENCE: 884

Tyr Asp Ala Ser Ile Ser Gln Val Asn Glu Glu Ile Asn Gln Ala Leu
1               5                   10                  15

Ala Tyr Ile Arg Lys Ala Asp Glu Leu Leu
            20                  25

<210> SEQ ID NO 885
<211> LENGTH: 26
<212> TYPE: PRT
<213> ORGANISM: Artificial Sequence
<220> FEATURE:
<223> OTHER INFORMATION: Core polypeptide

<400> SEQUENCE: 885

Tyr Asp Ala Ser Ile Ser Gln Val Asn Glu Glu Ile Asn Gln Ser Leu
1               5                   10                  15

Ala Phe Ile Arg Lys Ser Asp Glu Leu Leu
            20                  25

<210> SEQ ID NO 886
<211> LENGTH: 26
<212> TYPE: PRT
<213> ORGANISM: Artificial Sequence
<220> FEATURE:
<223> OTHER INFORMATION: Core polypeptide

```
<400> SEQUENCE: 886

Tyr Asp Ala Ser Ile Ser Gln Val Asn Glu Glu Ile Asn Gln Ser Leu
 1               5                  10                  15

Ala Phe Ile Arg Lys Ser Asp Glu Leu Leu
            20                  25

<210> SEQ ID NO 887
<211> LENGTH: 33
<212> TYPE: PRT
<213> ORGANISM: Artificial Sequence
<220> FEATURE:
<223> OTHER INFORMATION: Core polypeptide

<400> SEQUENCE: 887

Trp Leu Glu Trp Asp Arg Glu Ile Asn Asn Tyr Thr Ser Leu Ile His
 1               5                  10                  15

Ser Leu Ile Glu Glu Ser Gln Asn Gln Gln Lys Asn Glu Gln Glu
            20                  25                  30

Leu

<210> SEQ ID NO 888
<211> LENGTH: 35
<212> TYPE: PRT
<213> ORGANISM: Artificial Sequence
<220> FEATURE:
<223> OTHER INFORMATION: Core polypeptide

<400> SEQUENCE: 888

Ile Asp Ile Ser Ile Glu Leu Asn Lys Ala Lys Ser Asp Leu Glu Glu
 1               5                  10                  15

Ser Lys Glu Trp Ile Arg Arg Ser Asn Gln Lys Leu Asp Ser Ile Gly
            20                  25                  30

Asn Trp His
        35

<210> SEQ ID NO 889
<211> LENGTH: 35
<212> TYPE: PRT
<213> ORGANISM: Artificial Sequence
<220> FEATURE:
<223> OTHER INFORMATION: Core polypeptide

<400> SEQUENCE: 889

Asn Ser Val Ala Leu Asp Pro Ile Asp Ile Ser Ile Glu Leu Asn Lys
 1               5                  10                  15

Ala Lys Ser Asp Leu Glu Glu Ser Lys Glu Trp Ile Lys Lys Ser Asn
            20                  25                  30

Gln Lys Leu
        35

<210> SEQ ID NO 890
<211> LENGTH: 26
<212> TYPE: PRT
<213> ORGANISM: Artificial Sequence
<220> FEATURE:
<223> OTHER INFORMATION: Core polypeptide

<400> SEQUENCE: 890

Tyr Asp Ala Ser Ile Ser Gln Val Asn Glu Glu Ile Asn Gln Ala Leu
 1               5                  10                  15

Ala Tyr Ile Arg Lys Ala Asp Glu Leu Leu
            20                  25
```

```
<210> SEQ ID NO 891
<211> LENGTH: 28
<212> TYPE: PRT
<213> ORGANISM: Artificial Sequence
<220> FEATURE:
<223> OTHER INFORMATION: Core polypeptide

<400> SEQUENCE: 891

Asp Glu Tyr Asp Ala Ser Ile Ser Gln Val Asn Glu Lys Ile Asn Gln
 1               5                  10                  15
Ser Leu Ala Phe Ile Arg Lys Ser Asp Glu Leu Leu
            20                  25

<210> SEQ ID NO 892
<211> LENGTH: 33
<212> TYPE: PRT
<213> ORGANISM: Artificial Sequence
<220> FEATURE:
<223> OTHER INFORMATION: Core polypeptide

<400> SEQUENCE: 892

Trp Gln Glu Trp Glu Gln Lys Val Arg Tyr Leu Glu Ala Asn Ile Ser
 1               5                  10                  15
Gln Ser Leu Glu Gln Ala Gln Ile Gln Gln Lys Asn Met Tyr Glu
            20                  25                  30
Leu

<210> SEQ ID NO 893
<211> LENGTH: 33
<212> TYPE: PRT
<213> ORGANISM: Artificial Sequence
<220> FEATURE:
<223> OTHER INFORMATION: Core polypeptide

<400> SEQUENCE: 893

Trp Gln Glu Trp Glu Gln Lys Val Arg Tyr Leu Glu Ala Asn Ile Ser
 1               5                  10                  15
Gln Ser Leu Glu Gln Ala Gln Ile Gln Gln Glu Lys Asn Glu Tyr Glu
            20                  25                  30
Leu

<210> SEQ ID NO 894
<211> LENGTH: 33
<212> TYPE: PRT
<213> ORGANISM: Artificial Sequence
<220> FEATURE:
<223> OTHER INFORMATION: Core polypeptide

<400> SEQUENCE: 894

Trp Gln Glu Trp Glu Gln Lys Val Arg Tyr Leu Glu Ala Asn Ile Thr
 1               5                  10                  15
Ala Leu Leu Glu Gln Ala Gln Ile Gln Gln Lys Asn Glu Tyr Glu
            20                  25                  30
Leu

<210> SEQ ID NO 895
<211> LENGTH: 33
<212> TYPE: PRT
<213> ORGANISM: Artificial Sequence
<220> FEATURE:
<223> OTHER INFORMATION: Core polypeptide
```

```
<400> SEQUENCE: 895

Trp Gln Glu Trp Glu Gln Lys Val Arg Tyr Leu Glu Ala Asn Ile Thr
 1               5                  10                  15

Ala Leu Leu Glu Gln Ala Gln Ile Gln Gln Glu Lys Asn Met Tyr Glu
                20                  25                  30

Leu

<210> SEQ ID NO 896
<211> LENGTH: 36
<212> TYPE: PRT
<213> ORGANISM: Artificial Sequence
<220> FEATURE:
<223> OTHER INFORMATION: Core polypeptide

<400> SEQUENCE: 896

Trp Gln Glu Trp Glu Gln Lys Val Arg Tyr Leu Glu Ala Asn Ile Ser
 1               5                  10                  15

Gln Ser Leu Glu Gln Ala Gln Ile Gln Gln Glu Lys Asn Glu Tyr Glu
                20                  25                  30

Leu Gln Lys Leu
        35

<210> SEQ ID NO 897
<211> LENGTH: 36
<212> TYPE: PRT
<213> ORGANISM: Artificial Sequence
<220> FEATURE:
<223> OTHER INFORMATION: Core polypeptide

<400> SEQUENCE: 897

Trp Gln Glu Trp Glu Gln Lys Val Arg Tyr Leu Glu Ala Asn Ile Thr
 1               5                  10                  15

Ala Leu Leu Glu Gln Ala Gln Ile Gln Gln Glu Lys Asn Glu Tyr Glu
                20                  25                  30

Leu Gln Lys Leu
        35

<210> SEQ ID NO 898
<211> LENGTH: 36
<212> TYPE: PRT
<213> ORGANISM: Artificial Sequence
<220> FEATURE:
<223> OTHER INFORMATION: Core polypeptide

<400> SEQUENCE: 898

Trp Gln Glu Trp Glu Gln Lys Val Arg Tyr Leu Glu Ala Asn Ile Thr
 1               5                  10                  15

Ala Leu Leu Glu Gln Ala Gln Ile Gln Gln Glu Lys Asn Met Tyr Glu
                20                  25                  30

Leu Gln Lys Leu
        35

<210> SEQ ID NO 899
<211> LENGTH: 37
<212> TYPE: PRT
<213> ORGANISM: Artificial Sequence
<220> FEATURE:
<223> OTHER INFORMATION: Core polypeptide

<400> SEQUENCE: 899

Glu Phe Gly Asn Leu Glu Lys Arg Leu Glu Asn Leu Asn Lys Arg Val
```

```
                1               5              10              15
Glu Asp Gly Phe Leu Asp Val Trp Thr Tyr Asn Ala Glu Leu Leu Val
                                20                  25              30

Ala Leu Glu Asn Glu
             35

<210> SEQ ID NO 900
<211> LENGTH: 42
<212> TYPE: PRT
<213> ORGANISM: Artificial Sequence
<220> FEATURE:
<223> OTHER INFORMATION: Core polypeptide

<400> SEQUENCE: 900

Glu Asp Gly Phe Leu Asp Val Trp Thr Tyr Asn Ala Glu Leu Leu Val
 1               5                  10                  15

Leu Met Glu Asn Glu Arg Thr Leu Asp Phe His Asp Ser Asn Val Lys
             20                  25                  30

Asn Leu Tyr Asp Lys Val Arg Met Gln Leu
             35                  40

<210> SEQ ID NO 901
<211> LENGTH: 23
<212> TYPE: PRT
<213> ORGANISM: Artificial Sequence
<220> FEATURE:
<223> OTHER INFORMATION: Core polypeptide

<400> SEQUENCE: 901

Ser Ile Ser Gln Val Asn Glu Lys Ile Asn Gln Ser Leu Ala Phe Ile
 1               5                  10                  15

Arg Lys Ser Asp Glu Leu Leu
             20

<210> SEQ ID NO 902
<211> LENGTH: 23
<212> TYPE: PRT
<213> ORGANISM: Artificial Sequence
<220> FEATURE:
<223> OTHER INFORMATION: Core polypeptide

<400> SEQUENCE: 902

Ser Ile Ser Gln Val Asn Glu Lys Ile Asn Gln Ser Leu Ala Phe Ile
 1               5                  10                  15

Arg Lys Ser Asp Glu Leu Leu
             20

<210> SEQ ID NO 903
<211> LENGTH: 23
<212> TYPE: PRT
<213> ORGANISM: Artificial Sequence
<220> FEATURE:
<223> OTHER INFORMATION: Core polypeptide

<400> SEQUENCE: 903

Ser Ile Ser Gln Val Asn Glu Lys Ile Asn Gln Ser Leu Ala Tyr Ile
 1               5                  10                  15

Arg Lys Ser Asp Glu Leu Leu
             20

<210> SEQ ID NO 904
<211> LENGTH: 38
<212> TYPE: PRT
```

-continued

<213> ORGANISM: Artificial Sequence
<220> FEATURE:
<223> OTHER INFORMATION: Core polypeptide

<400> SEQUENCE: 904

Gln Gln Leu Leu Asp Val Val Lys Arg Gln Gln Glu Met Leu Arg Leu
1               5                   10                  15

Thr Val Trp Gly Thr Lys Asn Leu Gln Ala Arg Val Thr Ala Ile Glu
            20                  25                  30

Lys Tyr Leu Lys Asp Gln
        35

<210> SEQ ID NO 905
<211> LENGTH: 37
<212> TYPE: PRT
<213> ORGANISM: Artificial Sequence
<220> FEATURE:
<223> OTHER INFORMATION: Core polypeptide

<400> SEQUENCE: 905

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe Cys
        35

<210> SEQ ID NO 906
<211> LENGTH: 26
<212> TYPE: PRT
<213> ORGANISM: Artificial Sequence
<220> FEATURE:
<223> OTHER INFORMATION: Core polypeptide

<400> SEQUENCE: 906

Phe Asp Ala Ser Ile Ser Gln Val Asn Glu Lys Ile Asn Gln Ser Leu
1               5                   10                  15

Ala Tyr Ile Arg Lys Ser Asp Glu Leu Leu
            20                  25

<210> SEQ ID NO 907
<211> LENGTH: 30
<212> TYPE: PRT
<213> ORGANISM: Artificial Sequence
<220> FEATURE:
<223> OTHER INFORMATION: Core polypeptide

<400> SEQUENCE: 907

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala
            20                  25                  30

<210> SEQ ID NO 908
<211> LENGTH: 28
<212> TYPE: PRT
<213> ORGANISM: Artificial Sequence
<220> FEATURE:
<223> OTHER INFORMATION: Core polypeptide

<400> SEQUENCE: 908

Asp Glu Phe Asp Ala Ser Ile Ser Gln Val Asn Glu Lys Ile Asn Gln
1               5                   10                  15

-continued

Ser Leu Ala Phe Ile Arg Lys Ser Asp Glu Leu Leu
            20                  25

<210> SEQ ID NO 909
<211> LENGTH: 28
<212> TYPE: PRT
<213> ORGANISM: Artificial Sequence
<220> FEATURE:
<223> OTHER INFORMATION: Core polypeptide

<400> SEQUENCE: 909

Asp Glu Phe Asp Glu Ser Ile Ser Gln Val Asn Glu Lys Ile Asn Gln
1               5                   10                  15

Ser Leu Ala Phe Ile Arg Lys Ser Asp Glu Leu Leu
            20                  25

<210> SEQ ID NO 910
<211> LENGTH: 28
<212> TYPE: PRT
<213> ORGANISM: Artificial Sequence
<220> FEATURE:
<223> OTHER INFORMATION: Core polypeptide

<400> SEQUENCE: 910

Asp Glu Phe Asp Glu Ser Ile Ser Gln Val Asn Glu Lys Ile Glu Gln
1               5                   10                  15

Ser Leu Ala Phe Ile Arg Lys Ser Asp Glu Leu Leu
            20                  25

<210> SEQ ID NO 911
<211> LENGTH: 28
<212> TYPE: PRT
<213> ORGANISM: Artificial Sequence
<220> FEATURE:
<223> OTHER INFORMATION: Core polypeptide

<400> SEQUENCE: 911

Asp Glu Phe Asp Glu Ser Ile Ser Gln Val Asn Glu Lys Ile Glu Glu
1               5                   10                  15

Ser Leu Ala Phe Ile Arg Lys Ser Asp Glu Leu Leu
            20                  25

<210> SEQ ID NO 912
<211> LENGTH: 28
<212> TYPE: PRT
<213> ORGANISM: Artificial Sequence
<220> FEATURE:
<223> OTHER INFORMATION: Core polypeptide

<400> SEQUENCE: 912

Asp Glu Phe Asp Glu Ser Ile Ser Gln Val Asn Glu Lys Ile Glu Glu
1               5                   10                  15

Ser Leu Gln Phe Ile Arg Lys Ser Asp Glu Leu Leu
            20                  25

<210> SEQ ID NO 913
<211> LENGTH: 33
<212> TYPE: PRT
<213> ORGANISM: Artificial Sequence
<220> FEATURE:
<223> OTHER INFORMATION: Core polypeptide

<400> SEQUENCE: 913

Gly Gly Gly Gly Gly Asp Glu Phe Asp Ala Ser Ile Ser Gln Val Asn
1               5                   10                  15

Glu Lys Ile Asn Gln Ser Leu Ala Phe Ile Arg Lys Ser Asp Glu Leu
            20                  25                  30

Leu

<210> SEQ ID NO 914
<211> LENGTH: 28
<212> TYPE: PRT
<213> ORGANISM: Artificial Sequence
<220> FEATURE:
<223> OTHER INFORMATION: Core polypeptide

<400> SEQUENCE: 914

Asp Glu Phe Asp Ala Ser Ile Ser Gln Val Asn Glu Lys Ile Asn Gln
 1               5                  10                  15

Ser Leu Ala Phe Ile Arg Lys Ser Asp Glu Leu Leu
            20                  25

<210> SEQ ID NO 915
<211> LENGTH: 28
<212> TYPE: PRT
<213> ORGANISM: Artificial Sequence
<220> FEATURE:
<223> OTHER INFORMATION: Core polypeptide

<400> SEQUENCE: 915

Asp Glu Phe Asp Ala Ser Ile Ser Gln Val Asn Glu Lys Ile Asn Gln
 1               5                  10                  15

Ser Leu Ala Phe Ile Arg Lys Ser Asp Glu Leu Leu
            20                  25

<210> SEQ ID NO 916
<211> LENGTH: 35
<212> TYPE: PRT
<213> ORGANISM: Artificial Sequence
<220> FEATURE:
<223> OTHER INFORMATION: Core polypeptide

<400> SEQUENCE: 916

Ala Leu Asp Pro Ile Asp Ile Ser Ile Glu Leu Asn Lys Ala Lys Ser
 1               5                  10                  15

Asp Leu Glu Glu Ser Lys Glu Trp Ile Arg Arg Ser Asn Gln Lys Leu
            20                  25                  30

Asp Ser Ile
        35

<210> SEQ ID NO 917
<211> LENGTH: 35
<212> TYPE: PRT
<213> ORGANISM: Artificial Sequence
<220> FEATURE:
<223> OTHER INFORMATION: Core polypeptide

<400> SEQUENCE: 917

Tyr Asp Ala Ser Ile Ser Gln Val Asn Glu Lys Ile Asn Gln Ala Leu
 1               5                  10                  15

Ala Tyr Ile Arg Lys Ala Asp Glu Leu Leu His Asn Val Asn Ala Gly
            20                  25                  30

Lys Ser Thr
        35

<210> SEQ ID NO 918
<211> LENGTH: 35

```
<212> TYPE: PRT
<213> ORGANISM: Artificial Sequence
<220> FEATURE:
<223> OTHER INFORMATION: Core polypeptide

<400> SEQUENCE: 918

Val Tyr Pro Ser Asp Glu Tyr Asp Ala Ser Ile Ser Gln Val Asn Glu
 1               5                  10                  15

Lys Ile Asn Gln Ala Leu Ala Tyr Ile Arg Lys Ala Asp Glu Leu Leu
             20                  25                  30

His Asn Val
        35

<210> SEQ ID NO 919
<211> LENGTH: 8
<212> TYPE: PRT
<213> ORGANISM: Artificial Sequence
<220> FEATURE:
<223> OTHER INFORMATION: Core polypeptide

<400> SEQUENCE: 919

Trp Gly Trp Gly Tyr Gly Tyr Gly
 1               5

<210> SEQ ID NO 920
<211> LENGTH: 9
<212> TYPE: PRT
<213> ORGANISM: Artificial Sequence
<220> FEATURE:
<223> OTHER INFORMATION: Core polypeptide

<400> SEQUENCE: 920

Tyr Gly Trp Gly Trp Gly Trp Gly Phe
 1               5

<210> SEQ ID NO 921
<211> LENGTH: 36
<212> TYPE: PRT
<213> ORGANISM: Artificial Sequence
<220> FEATURE:
<223> OTHER INFORMATION: Core polypeptide

<400> SEQUENCE: 921

Trp Gln Glu Trp Glu Gln Lys Val Arg Tyr Leu Glu Ala Asn Ile Thr
 1               5                  10                  15

Ala Leu Gln Glu Gln Ala Gln Ile Gln Ala Glu Lys Ala Glu Tyr Glu
             20                  25                  30

Leu Gln Lys Leu
        35

<210> SEQ ID NO 922
<211> LENGTH: 36
<212> TYPE: PRT
<213> ORGANISM: Artificial Sequence
<220> FEATURE:
<223> OTHER INFORMATION: Core polypeptide

<400> SEQUENCE: 922

Trp Gln Glu Trp Glu Gln Lys Val Arg Tyr Leu Glu Ala Glu Ile Thr
 1               5                  10                  15

Ala Leu Gln Glu Glu Ala Gln Ile Gln Ala Glu Lys Ala Glu Tyr Glu
             20                  25                  30

Leu Gln Lys Leu
        35
```

```
<210> SEQ ID NO 923
<211> LENGTH: 31
<212> TYPE: PRT
<213> ORGANISM: Artificial Sequence
<220> FEATURE:
<223> OTHER INFORMATION: Core polypeptide

<400> SEQUENCE: 923

Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser
            20                  25                  30

<210> SEQ ID NO 924
<211> LENGTH: 35
<212> TYPE: PRT
<213> ORGANISM: Artificial Sequence
<220> FEATURE:
<223> OTHER INFORMATION: Core polypeptide

<400> SEQUENCE: 924

Val Trp Pro Ser Asp Glu Phe Asp Ala Ser Ile Ser Gln Val Asn Glu
 1               5                  10                  15

Lys Ile Asn Gln Ser Leu Ala Phe Ile Arg Lys Ser Asp Glu Leu Leu
            20                  25                  30

His Asn Val
        35

<210> SEQ ID NO 925
<211> LENGTH: 35
<212> TYPE: PRT
<213> ORGANISM: Artificial Sequence
<220> FEATURE:
<223> OTHER INFORMATION: Core polypeptide

<400> SEQUENCE: 925

Ser Lys Asn Ile Ser Glu Gln Ile Asp Gln Ile Lys Lys Asp Glu Gln
 1               5                  10                  15

Lys Glu Gly Thr Gly Trp Gly Leu Gly Gly Lys Trp Trp Thr Ser Asp
            20                  25                  30

Trp Gly Val
        35

<210> SEQ ID NO 926
<211> LENGTH: 35
<212> TYPE: PRT
<213> ORGANISM: Artificial Sequence
<220> FEATURE:
<223> OTHER INFORMATION: Core polypeptide

<400> SEQUENCE: 926

Leu Ser Lys Asn Ile Ser Glu Gln Ile Asp Gln Ile Lys Lys Asp Glu
 1               5                  10                  15

Gln Lys Glu Gly Thr Gly Trp Gly Leu Gly Gly Lys Trp Trp Thr Ser
            20                  25                  30

Asp Trp Gly
        35

<210> SEQ ID NO 927
<211> LENGTH: 35
<212> TYPE: PRT
<213> ORGANISM: Artificial Sequence
```

```
<220> FEATURE:
<223> OTHER INFORMATION: Core polypeptide

<400> SEQUENCE: 927

Asp Leu Ser Lys Asn Ile Ser Glu Gln Ile Asp Gln Ile Lys Lys Asp
 1               5                   10                  15

Glu Gln Lys Glu Gly Thr Gly Trp Gly Leu Gly Gly Lys Trp Trp Thr
            20                  25                  30

Ser Asp Trp
        35

<210> SEQ ID NO 928
<211> LENGTH: 35
<212> TYPE: PRT
<213> ORGANISM: Artificial Sequence
<220> FEATURE:
<223> OTHER INFORMATION: Core polypeptide

<400> SEQUENCE: 928

Glu Asp Leu Ser Lys Asn Ile Ser Glu Gln Ile Asp Gln Ile Lys Lys
 1               5                   10                  15

Asp Glu Gln Lys Glu Gly Thr Gly Trp Gly Leu Gly Gly Lys Trp Trp
            20                  25                  30

Thr Ser Asp
        35

<210> SEQ ID NO 929
<211> LENGTH: 35
<212> TYPE: PRT
<213> ORGANISM: Artificial Sequence
<220> FEATURE:
<223> OTHER INFORMATION: Core polypeptide

<400> SEQUENCE: 929

Ile Glu Asp Leu Ser Lys Asn Ile Ser Glu Gln Ile Asp Gln Ile Lys
 1               5                   10                  15

Lys Asp Glu Gln Lys Glu Gly Thr Gly Trp Gly Leu Gly Gly Lys Trp
            20                  25                  30

Trp Thr Ser
        35

<210> SEQ ID NO 930
<211> LENGTH: 35
<212> TYPE: PRT
<213> ORGANISM: Artificial Sequence
<220> FEATURE:
<223> OTHER INFORMATION: Core polypeptide

<400> SEQUENCE: 930

Gly Ile Glu Asp Leu Ser Lys Asn Ile Ser Glu Gln Ile Asp Gln Ile
 1               5                   10                  15

Lys Lys Asp Glu Gln Lys Glu Gly Thr Gly Trp Gly Leu Gly Gly Lys
            20                  25                  30

Trp Trp Thr
        35

<210> SEQ ID NO 931
<211> LENGTH: 35
<212> TYPE: PRT
<213> ORGANISM: Artificial Sequence
<220> FEATURE:
<223> OTHER INFORMATION: Core polypeptide
```

<400> SEQUENCE: 931

Ile Gly Ile Glu Asp Leu Ser Lys Asn Ile Ser Glu Gln Ile Asp Gln
1               5                   10                  15

Ile Lys Lys Asp Glu Gln Lys Glu Gly Thr Gly Trp Gly Leu Gly Gly
                20                  25                  30

Lys Trp Trp
        35

<210> SEQ ID NO 932
<211> LENGTH: 34
<212> TYPE: PRT
<213> ORGANISM: Artificial Sequence
<220> FEATURE:
<223> OTHER INFORMATION: Core polypeptide

<400> SEQUENCE: 932

Pro Ser Asp Glu Phe Asp Ala Ser Ile Ser Gln Val Asn Glu Lys Ile
1               5                   10                  15

Asn Gln Ser Leu Ala Phe Ile Arg Lys Ser Asp Glu Leu Leu His Asn
                20                  25                  30

Val Asn

<210> SEQ ID NO 933
<211> LENGTH: 35
<212> TYPE: PRT
<213> ORGANISM: Artificial Sequence
<220> FEATURE:
<223> OTHER INFORMATION: Core polypeptide

<400> SEQUENCE: 933

Val Tyr Pro Ser Asp Glu Tyr Asp Ala Ser Ile Ser Gln Val Asn Glu
1               5                   10                  15

Lys Ile Asn Gln Ala Leu Ala Tyr Ile Arg Lys Ala Asp Glu Leu Leu
                20                  25                  30

Glu Asn Val
        35

<210> SEQ ID NO 934
<211> LENGTH: 35
<212> TYPE: PRT
<213> ORGANISM: Artificial Sequence
<220> FEATURE:
<223> OTHER INFORMATION: Core polypeptide

<400> SEQUENCE: 934

Val Tyr Pro Ser Asp Glu Phe Asp Ala Ser Ile Ser Gln Val Asn Glu
1               5                   10                  15

Lys Ile Asn Gln Ala Leu Ala Phe Ile Arg Lys Ala Asp Glu Leu Leu
                20                  25                  30

Glu Asn Val
        35

<210> SEQ ID NO 935
<211> LENGTH: 35
<212> TYPE: PRT
<213> ORGANISM: Artificial Sequence
<220> FEATURE:
<223> OTHER INFORMATION: Core polypeptide

<400> SEQUENCE: 935

Val Tyr Pro Ser Asp Glu Tyr Asp Ala Ser Ile Ser Gln Val Asn Glu
1               5                   10                  15

```
Lys Ile Asn Gln Ala Leu Ala Tyr Ile Arg Glu Ala Asp Glu Leu Leu
                20                  25                  30

Glu Asn Val
        35

<210> SEQ ID NO 936
<211> LENGTH: 26
<212> TYPE: PRT
<213> ORGANISM: Artificial Sequence
<220> FEATURE:
<223> OTHER INFORMATION: Core polypeptide

<400> SEQUENCE: 936

Tyr Asp Ala Ser Ile Ser Gln Val Asn Glu Lys Ile Asn Gln Ser Leu
  1               5                  10                  15

Ala Phe Ile Arg Glu Ser Asp Glu Leu Leu
                20                  25

<210> SEQ ID NO 937
<211> LENGTH: 35
<212> TYPE: PRT
<213> ORGANISM: Artificial Sequence
<220> FEATURE:
<223> OTHER INFORMATION: Core polypeptide

<400> SEQUENCE: 937

Ala Ile Gly Ile Glu Asp Leu Ser Lys Asn Ile Ser Glu Gln Ile Asp
  1               5                  10                  15

Gln Ile Lys Lys Asp Glu Gln Lys Glu Gly Thr Gly Trp Gly Leu Gly
                20                  25                  30

Gly Lys Trp
        35

<210> SEQ ID NO 938
<211> LENGTH: 35
<212> TYPE: PRT
<213> ORGANISM: Artificial Sequence
<220> FEATURE:
<223> OTHER INFORMATION: Core polypeptide

<400> SEQUENCE: 938

Ala Ala Ile Gly Ile Glu Asp Leu Ser Lys Asn Ile Ser Glu Gln Ile
  1               5                  10                  15

Asp Gln Ile Lys Lys Asp Glu Gln Lys Glu Gly Thr Gly Trp Gly Leu
                20                  25                  30

Gly Gly Lys
        35

<210> SEQ ID NO 939
<211> LENGTH: 35
<212> TYPE: PRT
<213> ORGANISM: Artificial Sequence
<220> FEATURE:
<223> OTHER INFORMATION: Core polypeptide

<400> SEQUENCE: 939

Asp Ala Ala Ile Gly Ile Glu Asp Leu Ser Lys Asn Ile Ser Glu Gln
  1               5                  10                  15

Ile Asp Gln Ile Lys Lys Asp Glu Gln Lys Glu Gly Thr Gly Trp Gly
                20                  25                  30

Leu Gly Gly
        35
```

<210> SEQ ID NO 940
<211> LENGTH: 35
<212> TYPE: PRT
<213> ORGANISM: Artificial Sequence
<220> FEATURE:
<223> OTHER INFORMATION: Core polypeptide

<400> SEQUENCE: 940

Pro Asp Ala Ala Ile Gly Ile Glu Asp Leu Ser Lys Asn Ile Ser Glu
1               5                   10                  15

Gln Ile Asp Gln Ile Lys Lys Asp Glu Gln Lys Glu Gly Thr Gly Trp
            20                  25                  30

Gly Leu Gly
        35

<210> SEQ ID NO 941
<211> LENGTH: 35
<212> TYPE: PRT
<213> ORGANISM: Artificial Sequence
<220> FEATURE:
<223> OTHER INFORMATION: Core polypeptide

<400> SEQUENCE: 941

Asn Ile Thr Asp Lys Ile Asp Gln Ile Ile His Asp Phe Val Asp Lys
1               5                   10                  15

Thr Leu Pro Asp Gln Gly Asp Asn Asp Asn Trp Trp Thr Gly Trp Arg
            20                  25                  30

Gln Trp Ile
        35

<210> SEQ ID NO 942
<211> LENGTH: 35
<212> TYPE: PRT
<213> ORGANISM: Artificial Sequence
<220> FEATURE:
<223> OTHER INFORMATION: Core polypeptide

<400> SEQUENCE: 942

Lys Asn Ile Thr Asp Lys Ile Asp Gln Ile Ile His Asp Phe Val Asp
1               5                   10                  15

Lys Thr Leu Pro Asp Gln Gly Asp Asn Asp Asn Trp Trp Thr Gly Trp
            20                  25                  30

Arg Gln Trp
        35

<210> SEQ ID NO 943
<211> LENGTH: 35
<212> TYPE: PRT
<213> ORGANISM: Artificial Sequence
<220> FEATURE:
<223> OTHER INFORMATION: Core polypeptide

<400> SEQUENCE: 943

Thr Lys Asn Ile Thr Asp Lys Ile Asp Gln Ile Ile His Asp Phe Val
1               5                   10                  15

Asp Lys Thr Leu Pro Asp Gln Gly Asp Asn Asp Asn Trp Trp Thr Gly
            20                  25                  30

Trp Arg Gln
        35

<210> SEQ ID NO 944

```
<211> LENGTH: 35
<212> TYPE: PRT
<213> ORGANISM: Artificial Sequence
<220> FEATURE:
<223> OTHER INFORMATION: Core polypeptide

<400> SEQUENCE: 944

Trp Thr Lys Asn Ile Thr Asp Lys Ile Asp Gln Ile Ile His Asp Phe
1               5                   10                  15

Val Asp Lys Thr Leu Pro Asp Gln Gly Asp Asn Asp Asn Trp Trp Thr
            20                  25                  30

Gly Trp Arg
        35

<210> SEQ ID NO 945
<211> LENGTH: 35
<212> TYPE: PRT
<213> ORGANISM: Artificial Sequence
<220> FEATURE:
<223> OTHER INFORMATION: Core polypeptide

<400> SEQUENCE: 945

Asp Trp Thr Lys Asn Ile Thr Asp Lys Ile Asp Gln Ile Ile His Asp
1               5                   10                  15

Phe Val Asp Lys Thr Leu Pro Asp Gln Gly Asp Asn Asp Asn Trp Trp
            20                  25                  30

Thr Gly Trp
        35

<210> SEQ ID NO 946
<211> LENGTH: 35
<212> TYPE: PRT
<213> ORGANISM: Artificial Sequence
<220> FEATURE:
<223> OTHER INFORMATION: Core polypeptide

<400> SEQUENCE: 946

His Asp Trp Thr Lys Asn Ile Thr Asp Lys Ile Asp Gln Ile Ile His
1               5                   10                  15

Asp Phe Val Asp Lys Thr Leu Pro Asp Gln Gly Asp Asn Asp Asn Trp
            20                  25                  30

Trp Thr Gly
        35

<210> SEQ ID NO 947
<211> LENGTH: 35
<212> TYPE: PRT
<213> ORGANISM: Artificial Sequence
<220> FEATURE:
<223> OTHER INFORMATION: Core polypeptide

<400> SEQUENCE: 947

Pro His Asp Trp Thr Lys Asn Ile Thr Asp Lys Ile Asp Gln Ile Ile
1               5                   10                  15

His Asp Phe Val Asp Lys Thr Leu Pro Asp Gln Gly Asp Asn Asp Asn
            20                  25                  30

Trp Trp Thr
        35

<210> SEQ ID NO 948
<211> LENGTH: 35
<212> TYPE: PRT
<213> ORGANISM: Artificial Sequence
```

```
<220> FEATURE:
<223> OTHER INFORMATION: Core polypeptide

<400> SEQUENCE: 948

Glu Pro His Asp Trp Thr Lys Asn Ile Thr Asp Lys Ile Asp Gln Ile
1               5                   10                  15

Ile His Asp Phe Val Asp Lys Thr Leu Pro Asp Gln Gly Asp Asn Asp
            20                  25                  30

Asn Trp Trp
        35

<210> SEQ ID NO 949
<211> LENGTH: 35
<212> TYPE: PRT
<213> ORGANISM: Artificial Sequence
<220> FEATURE:
<223> OTHER INFORMATION: Core polypeptide

<400> SEQUENCE: 949

Ile Glu Pro His Asp Trp Thr Lys Asn Ile Thr Asp Lys Ile Asp Gln
1               5                   10                  15

Ile Ile His Asp Phe Val Asp Lys Thr Leu Pro Asp Gln Gly Asp Asn
            20                  25                  30

Asp Asn Trp
        35

<210> SEQ ID NO 950
<211> LENGTH: 35
<212> TYPE: PRT
<213> ORGANISM: Artificial Sequence
<220> FEATURE:
<223> OTHER INFORMATION: Core polypeptide

<400> SEQUENCE: 950

Ala Ile Glu Pro His Asp Trp Thr Lys Asn Ile Thr Asp Lys Ile Asp
1               5                   10                  15

Gln Ile Ile His Asp Phe Val Asp Lys Thr Leu Pro Asp Gln Gly Asp
            20                  25                  30

Asn Asp Asn
        35

<210> SEQ ID NO 951
<211> LENGTH: 35
<212> TYPE: PRT
<213> ORGANISM: Artificial Sequence
<220> FEATURE:
<223> OTHER INFORMATION: Core polypeptide

<400> SEQUENCE: 951

Ala Ala Ile Glu Pro His Asp Trp Thr Lys Asn Ile Thr Asp Lys Ile
1               5                   10                  15

Asp Gln Ile Ile His Asp Phe Val Asp Lys Thr Leu Pro Asp Gln Gly
            20                  25                  30

Asp Asn Asp
        35

<210> SEQ ID NO 952
<211> LENGTH: 35
<212> TYPE: PRT
<213> ORGANISM: Artificial Sequence
<220> FEATURE:
<223> OTHER INFORMATION: Core polypeptide
```

```
<400> SEQUENCE: 952

Asp Ala Ala Ile Glu Pro His Asp Trp Thr Lys Asn Ile Thr Asp Lys
 1               5                  10                  15

Ile Asp Gln Ile Ile His Asp Phe Val Asp Lys Thr Leu Pro Asp Gln
            20                  25                  30

Gly Asp Asn
        35

<210> SEQ ID NO 953
<211> LENGTH: 35
<212> TYPE: PRT
<213> ORGANISM: Artificial Sequence
<220> FEATURE:
<223> OTHER INFORMATION: Core polypeptide

<400> SEQUENCE: 953

Leu Ser Pro Thr Val Trp Leu Ser Val Ile Trp Met Met Trp Tyr Trp
 1               5                  10                  15

Gly Pro Ser Leu Tyr Ser Ile Leu Ser Pro Phe Leu Pro Leu Leu Pro
            20                  25                  30

Ile Phe Phe
        35

<210> SEQ ID NO 954
<211> LENGTH: 45
<212> TYPE: PRT
<213> ORGANISM: Artificial Sequence
<220> FEATURE:
<223> OTHER INFORMATION: Core polypeptide

<400> SEQUENCE: 954

His Asn His Thr Thr Trp Met Glu Trp Asp Arg Glu Ile Asn Asn Tyr
 1               5                  10                  15

Thr Ser Leu Ile His Ser Leu Ile Glu Glu Ser Gln Asn Gln Gln Glu
            20                  25                  30

Lys Asn Glu Gln Glu Leu Leu Glu Leu Asp Lys Trp His
        35                  40                  45

<210> SEQ ID NO 955
<211> LENGTH: 53
<212> TYPE: PRT
<213> ORGANISM: Artificial Sequence
<220> FEATURE:
<223> OTHER INFORMATION: Core polypeptide

<400> SEQUENCE: 955

His Gln Ala Arg Gln Leu Leu Ser Gly Ile Val Gln Gln Gln Asn Asn
 1               5                  10                  15

Leu Leu Arg Ala Ile Glu Ala Gln His Leu Leu Gln Leu Thr Val
            20                  25                  30

Trp Gly Ile Lys Gln Leu Gln Ala Arg Ile Leu Ala Val Glu Arg Tyr
        35                  40                  45

Leu Lys Asp Gln His
    50

<210> SEQ ID NO 956
<211> LENGTH: 35
<212> TYPE: PRT
<213> ORGANISM: Artificial Sequence
<220> FEATURE:
<223> OTHER INFORMATION: Core polypeptide
```

-continued

```
<400> SEQUENCE: 956

Val Tyr Pro Ser Asp Glu Phe Asp Ala Ser Ile Ser Gln Val Asn Glu
 1               5                  10                  15

Lys Ile Asn Gln Ser Leu Ala Phe Ile Arg Glu Ala Asp Glu Leu Leu
            20                  25                  30

Glu Asn Val
        35

<210> SEQ ID NO 957
<211> LENGTH: 35
<212> TYPE: PRT
<213> ORGANISM: Artificial Sequence
<220> FEATURE:
<223> OTHER INFORMATION: Core polypeptide

<400> SEQUENCE: 957

Val Phe Pro Ser Asp Glu Phe Asp Ala Ser Ile Ser Gln Val Asn Glu
 1               5                  10                  15

Lys Ile Asn Gln Ser Leu Ala Tyr Ile Arg Glu Ala Asp Glu Leu Leu
            20                  25                  30

Glu Asn Val
        35

<210> SEQ ID NO 958
<211> LENGTH: 28
<212> TYPE: PRT
<213> ORGANISM: Artificial Sequence
<220> FEATURE:
<223> OTHER INFORMATION: Core polypeptide

<400> SEQUENCE: 958

Asp Glu Phe Asp Ala Ser Ile Ser Gln Val Asn Glu Lys Ile Asn Gln
 1               5                  10                  15

Ser Leu Ala Tyr Ile Arg Glu Ala Asp Glu Leu Leu
            20                  25

<210> SEQ ID NO 959
<211> LENGTH: 50
<212> TYPE: PRT
<213> ORGANISM: Artificial Sequence
<220> FEATURE:
<223> OTHER INFORMATION: Core polypeptide

<400> SEQUENCE: 959

Asn Glu Gln Glu Leu Leu Glu Leu Asp Lys Trp Ala Ser Leu Trp Asn
 1               5                  10                  15

Trp Phe Gly Gly Gly Gly Asp Glu Phe Asp Ala Ser Ile Ser Gln Val
            20                  25                  30

Asn Glu Lys Ile Asn Gln Ser Leu Ala Phe Ile Arg Lys Ser Asp Glu
        35                  40                  45

Leu Leu
    50

<210> SEQ ID NO 960
<211> LENGTH: 45
<212> TYPE: PRT
<213> ORGANISM: Artificial Sequence
<220> FEATURE:
<223> OTHER INFORMATION: Core polypeptide

<400> SEQUENCE: 960

Leu Glu Leu Asp Lys Trp Ala Ser Leu Trp Asn Trp Phe Gly Gly Gly
```

```
             1               5                  10                 15
Gly Asp Glu Phe Asp Ala Ser Ile Ser Gln Val Asn Glu Lys Ile Asn
                    20                  25                  30

Gln Ser Leu Ala Phe Ile Arg Lys Ser Asp Glu Leu Leu
            35                  40                  45

<210> SEQ ID NO 961
<211> LENGTH: 36
<212> TYPE: PRT
<213> ORGANISM: Artificial Sequence
<220> FEATURE:
<223> OTHER INFORMATION: Core polypeptide

<400> SEQUENCE: 961

Glu Gly Glu Gly Glu Gly Glu Gly Asp Glu Phe Asp Ala Ser Ile Ser
 1               5                  10                  15

Gln Val Asn Glu Lys Ile Asn Gln Ser Leu Ala Phe Ile Arg Lys Ser
                20                  25                  30

Asp Glu Leu Leu
            35

<210> SEQ ID NO 962
<211> LENGTH: 43
<212> TYPE: PRT
<213> ORGANISM: Artificial Sequence
<220> FEATURE:
<223> OTHER INFORMATION: Core polypeptide

<400> SEQUENCE: 962

Ala Ser Arg Lys Cys Arg Ala Lys Phe Lys Gln Leu Leu Gln His Tyr
 1               5                  10                  15

Arg Glu Val Ala Ala Ala Lys Ser Ser Glu Asn Asp Arg Leu Arg Leu
                20                  25                  30

Leu Leu Lys Gln Met Cys Pro Ser Leu Asp Val
            35                  40

<210> SEQ ID NO 963
<211> LENGTH: 29
<212> TYPE: PRT
<213> ORGANISM: Artificial Sequence
<220> FEATURE:
<223> OTHER INFORMATION: Core polypeptide

<400> SEQUENCE: 963

Gly Asp Glu Glu Asp Ala Ser Ile Ser Gln Val Asn Glu Lys Ile Asn
 1               5                  10                  15

Gln Ser Leu Ala Phe Ile Arg Lys Ser Asp Glu Leu Leu
                20                  25

<210> SEQ ID NO 964
<211> LENGTH: 29
<212> TYPE: PRT
<213> ORGANISM: Artificial Sequence
<220> FEATURE:
<223> OTHER INFORMATION: Core polypeptide

<400> SEQUENCE: 964

Gly Asp Glu Glu Asp Ala Ser Glu Ser Gln Val Asn Glu Lys Ile Asn
 1               5                  10                  15

Gln Ser Leu Ala Phe Ile Arg Lys Ser Asp Glu Leu Leu
                20                  25
```

```
<210> SEQ ID NO 965
<211> LENGTH: 29
<212> TYPE: PRT
<213> ORGANISM: Artificial Sequence
<220> FEATURE:
<223> OTHER INFORMATION: Core polypeptide

<400> SEQUENCE: 965

Gly Asp Glu Glu Asp Ala Ser Glu Ser Gln Gln Asn Glu Lys Ile Asn
 1               5                  10                  15

Gln Ser Leu Ala Phe Ile Arg Lys Ser Asp Glu Leu Leu
            20                  25

<210> SEQ ID NO 966
<211> LENGTH: 29
<212> TYPE: PRT
<213> ORGANISM: Artificial Sequence
<220> FEATURE:
<223> OTHER INFORMATION: Core polypeptide

<400> SEQUENCE: 966

Gly Asp Glu Glu Asp Ala Ser Glu Ser Gln Gln Asn Glu Lys Gln Asn
 1               5                  10                  15

Gln Ser Leu Ala Phe Ile Arg Lys Ser Asp Glu Leu Leu
            20                  25

<210> SEQ ID NO 967
<211> LENGTH: 29
<212> TYPE: PRT
<213> ORGANISM: Artificial Sequence
<220> FEATURE:
<223> OTHER INFORMATION: Core polypeptide

<400> SEQUENCE: 967

Gly Asp Glu Glu Asp Ala Ser Glu Ser Gln Gln Asn Glu Lys Gln Asn
 1               5                  10                  15

Gln Ser Glu Ala Phe Ile Arg Lys Ser Asp Glu Leu Leu
            20                  25

<210> SEQ ID NO 968
<211> LENGTH: 30
<212> TYPE: PRT
<213> ORGANISM: Artificial Sequence
<220> FEATURE:
<223> OTHER INFORMATION: Core polypeptide

<400> SEQUENCE: 968

Trp Gly Asp Glu Phe Asp Glu Ser Ile Ser Gln Val Asn Glu Lys Ile
 1               5                  10                  15

Glu Glu Ser Leu Ala Phe Ile Arg Lys Ser Asp Glu Leu Leu
            20                  25                  30

<210> SEQ ID NO 969
<211> LENGTH: 40
<212> TYPE: PRT
<213> ORGANISM: Artificial Sequence
<220> FEATURE:
<223> OTHER INFORMATION: Core polypeptide

<400> SEQUENCE: 969

Tyr Thr Ser Leu Gly Gly Asp Glu Phe Asp Glu Ser Ile Ser Gln Val
 1               5                  10                  15

Asn Glu Lys Ile Glu Glu Ser Leu Ala Phe Ile Arg Lys Ser Asp Glu
            20                  25                  30
```

```
Leu Leu Gly Gly Trp Asn Trp Phe
        35                  40

<210> SEQ ID NO 970
<211> LENGTH: 48
<212> TYPE: PRT
<213> ORGANISM: Artificial Sequence
<220> FEATURE:
<223> OTHER INFORMATION: Core polypeptide

<400> SEQUENCE: 970

Tyr Thr Ser Leu Ile His Ser Leu Gly Gly Asp Glu Phe Asp Glu Ser
 1               5                  10                  15

Ile Ser Gln Val Asn Glu Lys Ile Glu Glu Ser Leu Ala Phe Ile Arg
            20                  25                  30

Lys Ser Asp Glu Leu Leu Gly Gly Trp Ala Ser Leu Trp Asn Trp Phe
        35                  40                  45

<210> SEQ ID NO 971
<211> LENGTH: 29
<212> TYPE: PRT
<213> ORGANISM: Artificial Sequence
<220> FEATURE:
<223> OTHER INFORMATION: Core polypeptide

<400> SEQUENCE: 971

Gly Asp Glu Phe Asp Glu Ser Ile Ser Gln Val Asn Glu Lys Ile Glu
 1               5                  10                  15

Glu Ser Leu Ala Phe Ile Arg Lys Ser Asp Glu Leu Leu
            20                  25

<210> SEQ ID NO 972
<211> LENGTH: 29
<212> TYPE: PRT
<213> ORGANISM: Artificial Sequence
<220> FEATURE:
<223> OTHER INFORMATION: Core polypeptide

<400> SEQUENCE: 972

Gly Asp Glu Glu Asp Glu Ser Ile Ser Gln Val Asn Glu Lys Ile Glu
 1               5                  10                  15

Glu Ser Leu Ala Phe Ile Arg Lys Ser Asp Glu Leu Leu
            20                  25

<210> SEQ ID NO 973
<211> LENGTH: 29
<212> TYPE: PRT
<213> ORGANISM: Artificial Sequence
<220> FEATURE:
<223> OTHER INFORMATION: Core polypeptide

<400> SEQUENCE: 973

Gly Asp Glu Glu Asp Glu Ser Ile Ser Gln Val Gln Glu Lys Ile Glu
 1               5                  10                  15

Glu Ser Leu Ala Phe Ile Arg Lys Ser Asp Glu Leu Leu
            20                  25

<210> SEQ ID NO 974
<211> LENGTH: 29
<212> TYPE: PRT
<213> ORGANISM: Artificial Sequence
<220> FEATURE:
<223> OTHER INFORMATION: Core polypeptide

<400> SEQUENCE: 974
```

```
Gly Asp Glu Glu Asp Glu Ser Ile Ser Gln Val Gln Glu Lys Ile Glu
1               5                   10                  15

Glu Ser Leu Leu Phe Ile Arg Lys Ser Asp Glu Leu Leu
            20                  25
```

<210> SEQ ID NO 975
<211> LENGTH: 29
<212> TYPE: PRT
<213> ORGANISM: Artificial Sequence
<220> FEATURE:
<223> OTHER INFORMATION: Core polypeptide

<400> SEQUENCE: 975

```
Gly Asp Glu Tyr Asp Glu Ser Ile Ser Gln Val Asn Glu Lys Ile Glu
1               5                   10                  15

Glu Ser Leu Ala Phe Ile Arg Lys Ser Asp Glu Leu Leu
            20                  25
```

<210> SEQ ID NO 976
<211> LENGTH: 29
<212> TYPE: PRT
<213> ORGANISM: Artificial Sequence
<220> FEATURE:
<223> OTHER INFORMATION: Core polypeptide

<400> SEQUENCE: 976

```
Gly Asp Glu Tyr Asp Glu Ser Ile Ser Gln Val Asn Glu Lys Ile Glu
1               5                   10                  15

Glu Ser Leu Ala Phe Ile Arg Lys Ser Asp Glu Leu Leu
            20                  25
```

<210> SEQ ID NO 977
<211> LENGTH: 36
<212> TYPE: PRT
<213> ORGANISM: Artificial Sequence
<220> FEATURE:
<223> OTHER INFORMATION: Core polypeptide

<400> SEQUENCE: 977

```
Tyr Thr Ser Leu Ile His Ser Leu Ile Asp Glu Gln Glu Lys Ile Glu
1               5                   10                  15

Glu Leu Ala Phe Ile Arg Lys Ser Asp Glu Leu Leu Glu Leu Asp Lys
            20                  25                  30

Trp Asn Trp Phe
        35
```

<210> SEQ ID NO 978
<211> LENGTH: 35
<212> TYPE: PRT
<213> ORGANISM: Artificial Sequence
<220> FEATURE:
<223> OTHER INFORMATION: Core polypeptide

<400> SEQUENCE: 978

```
Val Tyr Pro Ser Asp Glu Tyr Asp Ala Ser Ile Ser Gln Val Asn Glu
1               5                   10                  15

Glu Ile Asn Gln Ala Leu Ala Tyr Ile Arg Lys Ala Asp Glu Leu Leu
            20                  25                  30

Glu Asn Val
        35
```

<210> SEQ ID NO 979

```
<211> LENGTH: 38
<212> TYPE: PRT
<213> ORGANISM: Artificial Sequence
<220> FEATURE:
<223> OTHER INFORMATION: Core polypeptide

<400> SEQUENCE: 979

Asn Asn Leu Leu Arg Ala Ile Glu Ala Gln Gln His Leu Leu Gln Leu
 1               5                  10                  15

Thr Val Trp Gly Ser Lys Gln Leu Gln Ala Arg Ile Leu Ala Val Glu
            20                  25                  30

Arg Tyr Leu Lys Asp Gln
            35

<210> SEQ ID NO 980
<211> LENGTH: 38
<212> TYPE: PRT
<213> ORGANISM: Artificial Sequence
<220> FEATURE:
<223> OTHER INFORMATION: Core polypeptide

<400> SEQUENCE: 980

Gly Gly Gly Val Tyr Pro Ser Asp Glu Tyr Asp Ala Ser Ile Ser Gln
 1               5                  10                  15

Val Asn Glu Glu Ile Asn Gln Ala Leu Ala Tyr Ile Arg Lys Ala Asp
            20                  25                  30

Glu Leu Leu Glu Asn Val
            35

<210> SEQ ID NO 981
<211> LENGTH: 38
<212> TYPE: PRT
<213> ORGANISM: Artificial Sequence
<220> FEATURE:
<223> OTHER INFORMATION: Core polypeptide

<400> SEQUENCE: 981

Asn Asn Leu Leu Arg Ala Ile Glu Ala Gln Gln His Leu Leu Gln Leu
 1               5                  10                  15

Thr Val Trp Gly Glu Lys Gln Leu Gln Ala Arg Ile Leu Ala Val Glu
            20                  25                  30

Arg Tyr Leu Lys Asp Gln
            35

<210> SEQ ID NO 982
<211> LENGTH: 28
<212> TYPE: PRT
<213> ORGANISM: Artificial Sequence
<220> FEATURE:
<223> OTHER INFORMATION: Core polypeptide

<400> SEQUENCE: 982

Pro Thr Arg Val Asn Tyr Ile Leu Ile Ile Gly Val Leu Val Leu Ala
 1               5                  10                  15

Glu Val Thr Gly Val Arg Ala Asp Val His Leu Leu
            20                  25

<210> SEQ ID NO 983
<211> LENGTH: 35
<212> TYPE: PRT
<213> ORGANISM: Artificial Sequence
<220> FEATURE:
<223> OTHER INFORMATION: Core polypeptide
```

-continued

```
<400> SEQUENCE: 983

Pro Thr Arg Val Asn Tyr Ile Leu Ile Ile Gly Val Leu Val Leu Ala
1               5                   10                  15

Glu Val Thr Gly Val Arg Ala Asp Val His Leu Leu Glu Gln Pro Gly
            20                  25                  30

Asn Leu Trp
        35

<210> SEQ ID NO 984
<211> LENGTH: 36
<212> TYPE: PRT
<213> ORGANISM: Artificial Sequence
<220> FEATURE:
<223> OTHER INFORMATION: Core polypeptide

<400> SEQUENCE: 984

Pro Glu Lys Thr Pro Leu Leu Pro Thr Arg Val Asn Tyr Ile Leu Ile
1               5                   10                  15

Ile Gly Val Leu Val Leu Ala Asx Glu Val Thr Gly Val Arg Ala Asp
            20                  25                  30

Val His Leu Leu
        35

<210> SEQ ID NO 985
<211> LENGTH: 38
<212> TYPE: PRT
<213> ORGANISM: Artificial Sequence
<220> FEATURE:
<223> OTHER INFORMATION: Core polypeptide

<400> SEQUENCE: 985

Gly Gly Gly Val Tyr Pro Ser Asp Glu Tyr Asp Ala Ser Ile Ser Gln
1               5                   10                  15

Val Asn Glu Glu Ile Asn Gln Ala Leu Ala Tyr Ile Arg Lys Ala Asp
            20                  25                  30

Glu Leu Leu Glu Asn Val
        35

<210> SEQ ID NO 986
<211> LENGTH: 38
<212> TYPE: PRT
<213> ORGANISM: Artificial Sequence
<220> FEATURE:
<223> OTHER INFORMATION: Core polypeptide

<400> SEQUENCE: 986

Tyr Thr Ser Leu Ile His Ser Leu Gly Gly Asp Glu Phe Asp Glu Ser
1               5                   10                  15

Ile Ser Gln Val Asn Glu Lys Ile Glu Glu Ser Leu Ala Phe Ile Arg
            20                  25                  30

Lys Ser Asp Glu Leu Leu
        35

<210> SEQ ID NO 987
<211> LENGTH: 34
<212> TYPE: PRT
<213> ORGANISM: Artificial Sequence
<220> FEATURE:
<223> OTHER INFORMATION: Core polypeptide

<400> SEQUENCE: 987

Tyr Thr Ser Leu Gly Gly Asp Glu Phe Asp Glu Ser Ile Ser Gln Val
```

```
             1               5                  10                 15
Asn Glu Lys Ile Glu Glu Ser Leu Ala Phe Ile Arg Lys Ser Asp Glu
                    20                 25                 30
Leu Leu

<210> SEQ ID NO 988
<211> LENGTH: 38
<212> TYPE: PRT
<213> ORGANISM: Artificial Sequence
<220> FEATURE:
<223> OTHER INFORMATION: Core polypeptide

<400> SEQUENCE: 988

Asp Glu Phe Asp Glu Ser Ile Ser Gln Val Asn Glu Lys Ile Glu Glu
 1               5                  10                 15

Ser Leu Ala Phe Ile Arg Lys Ser Asp Glu Leu Leu Gly Gly Trp Ala
                20                  25                 30

Ser Leu Trp Asn Trp Phe
             35

<210> SEQ ID NO 989
<211> LENGTH: 34
<212> TYPE: PRT
<213> ORGANISM: Artificial Sequence
<220> FEATURE:
<223> OTHER INFORMATION: Core polypeptide

<400> SEQUENCE: 989

Asp Glu Phe Asp Glu Ser Ile Ser Gln Val Asn Glu Lys Ile Glu Glu
 1               5                  10                 15

Ser Leu Ala Phe Ile Arg Lys Ser Asp Glu Leu Leu Gly Gly Trp Asn
                20                  25                 30

Trp Phe

<210> SEQ ID NO 990
<211> LENGTH: 35
<212> TYPE: PRT
<213> ORGANISM: Artificial Sequence
<220> FEATURE:
<223> OTHER INFORMATION: Core polypeptide

<400> SEQUENCE: 990

Tyr Thr Ser Leu Ile His Ser Leu Ile Glu Glu Ser Gln Asn Gln Gln
 1               5                  10                 15

Glu Lys Asn Glu Gln Glu Leu Leu Glu Leu Asp Lys Ala Ser Leu Trp
                20                  25                 30

Asn Trp Phe
       35

<210> SEQ ID NO 991
<211> LENGTH: 34
<212> TYPE: PRT
<213> ORGANISM: Artificial Sequence
<220> FEATURE:
<223> OTHER INFORMATION: Core polypeptide

<400> SEQUENCE: 991

Tyr Thr Ser Leu Ile His Ser Leu Ile Glu Glu Ser Gln Asn Gln Gln
 1               5                  10                 15

Glu Lys Asn Glu Gln Glu Leu Leu Glu Leu Asp Lys Ser Leu Trp Asn
                20                  25                 30
```

Trp Phe

<210> SEQ ID NO 992
<211> LENGTH: 33
<212> TYPE: PRT
<213> ORGANISM: Artificial Sequence
<220> FEATURE:
<223> OTHER INFORMATION: Core polypeptide

<400> SEQUENCE: 992

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Leu Trp Asn Trp
            20                  25                  30

Phe

<210> SEQ ID NO 993
<211> LENGTH: 32
<212> TYPE: PRT
<213> ORGANISM: Artificial Sequence
<220> FEATURE:
<223> OTHER INFORMATION: Core polypeptide

<400> SEQUENCE: 993

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Asn Trp Phe
            20                  25                  30

<210> SEQ ID NO 994
<211> LENGTH: 47
<212> TYPE: PRT
<213> ORGANISM: Artificial Sequence
<220> FEATURE:
<223> OTHER INFORMATION: Core polypeptide

<400> SEQUENCE: 994

Met Thr Trp Met Glu Trp Asp Arg Glu Ile Asn Asn Tyr Thr Ser Leu
1               5                   10                  15

Ile His Ser Leu Ile Glu Glu Ser Gln Asn Gln Gln Glu Lys Asn Glu
            20                  25                  30

Gln Glu Leu Leu Glu Leu Asp Lys Ala Ser Leu Trp Asn Trp Phe
        35                  40                  45

<210> SEQ ID NO 995
<211> LENGTH: 46
<212> TYPE: PRT
<213> ORGANISM: Artificial Sequence
<220> FEATURE:
<223> OTHER INFORMATION: Core polypeptide

<400> SEQUENCE: 995

Met Thr Trp Met Glu Trp Asp Arg Glu Ile Asn Asn Tyr Thr Ser Leu
1               5                   10                  15

Ile His Ser Leu Ile Glu Glu Ser Gln Asn Gln Gln Glu Lys Asn Glu
            20                  25                  30

Gln Glu Leu Leu Glu Leu Asp Lys Ser Leu Trp Asn Trp Phe
        35                  40                  45

<210> SEQ ID NO 996
<211> LENGTH: 45
<212> TYPE: PRT
<213> ORGANISM: Artificial Sequence
<220> FEATURE:
<223> OTHER INFORMATION: Core polypeptide

<400> SEQUENCE: 996

Met Thr Trp Met Glu Trp Asp Arg Glu Ile Asn Asn Tyr Thr Ser Leu
1               5                   10                  15

Ile His Ser Leu Ile Glu Glu Ser Gln Asn Gln Gln Glu Lys Asn Glu
            20                  25                  30

Gln Glu Leu Leu Glu Leu Asp Lys Leu Trp Asn Trp Phe
        35                  40                  45

<210> SEQ ID NO 997
<211> LENGTH: 44
<212> TYPE: PRT
<213> ORGANISM: Artificial Sequence
<220> FEATURE:
<223> OTHER INFORMATION: Core polypeptide

<400> SEQUENCE: 997

Met Thr Trp Met Glu Trp Asp Arg Glu Ile Asn Asn Tyr Thr Ser Leu
1               5                   10                  15

Ile His Ser Leu Ile Glu Glu Ser Gln Asn Gln Gln Glu Lys Asn Glu
            20                  25                  30

Gln Glu Leu Leu Glu Leu Asp Lys Trp Asn Trp Phe
        35                  40

<210> SEQ ID NO 998
<211> LENGTH: 46
<212> TYPE: PRT
<213> ORGANISM: Artificial Sequence
<220> FEATURE:
<223> OTHER INFORMATION: Core polypeptide

<400> SEQUENCE: 998

Met Thr Trp Met Glu Trp Asp Arg Glu Ile Asn Asn Tyr Thr Ser Leu
1               5                   10                  15

Ile His Ser Leu Ile Glu Glu Ser Gln Asn Gln Gln Glu Lys Asn Glu
            20                  25                  30

Gln Glu Leu Leu Glu Leu Asp Lys Trp Ala Ser Leu Trp Asn
        35                  40                  45

<210> SEQ ID NO 999
<211> LENGTH: 44
<212> TYPE: PRT
<213> ORGANISM: Artificial Sequence
<220> FEATURE:
<223> OTHER INFORMATION: Core polypeptide

<400> SEQUENCE: 999

Met Thr Trp Met Glu Trp Asp Arg Glu Ile Asn Asn Tyr Thr Ser Leu
1               5                   10                  15

Ile His Ser Leu Ile Glu Glu Ser Gln Asn Gln Gln Glu Lys Asn Glu
            20                  25                  30

Gln Glu Leu Leu Glu Leu Asp Lys Trp Ala Ser Leu
        35                  40

<210> SEQ ID NO 1000
<211> LENGTH: 8
<212> TYPE: PRT
<213> ORGANISM: Artificial Sequence
<220> FEATURE:
<223> OTHER INFORMATION: Core polypeptide -continued

```
<400> SEQUENCE: 1000

His Trp Ser Tyr Leu Arg Pro Gly
1               5

<210> SEQ ID NO 1001
<211> LENGTH: 36
<212> TYPE: PRT
<213> ORGANISM: Artificial Sequence
<220> FEATURE:
<223> OTHER INFORMATION: Core polypeptide

<400> SEQUENCE: 1001

Trp Asn Trp Phe Asp Glu Phe Asp Glu Ser Ile Ser Gln Val Asn Glu
1               5                   10                  15

Lys Ile Glu Glu Ser Leu Ala Phe Ile Arg Lys Ser Asp Glu Leu Leu
            20                  25                  30

Trp Asn Trp Phe
        35

<210> SEQ ID NO 1002
<211> LENGTH: 36
<212> TYPE: PRT
<213> ORGANISM: Artificial Sequence
<220> FEATURE:
<223> OTHER INFORMATION: Core polypeptide

<400> SEQUENCE: 1002

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Tyr Ala Ser Leu
            20                  25                  30

Tyr Asn Tyr Phe
        35

<210> SEQ ID NO 1003
<211> LENGTH: 36
<212> TYPE: PRT
<213> ORGANISM: Artificial Sequence
<220> FEATURE:
<223> OTHER INFORMATION: Core polypeptide

<400> SEQUENCE: 1003

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Tyr Ala Tyr Leu
            20                  25                  30

Tyr Asn Tyr Phe
        35

<210> SEQ ID NO 1004
<211> LENGTH: 29
<212> TYPE: PRT
<213> ORGANISM: Artificial Sequence
<220> FEATURE:
<223> OTHER INFORMATION: Core polypeptide

<400> SEQUENCE: 1004

Asp Glu Phe Asp Glu Ser Ile Ser Gln Val Asn Glu Lys Ile Glu Glu
1               5                   10                  15

Ser Leu Ala Phe Ile Arg Lys Ser Asp Glu Leu Leu Trp
            20                  25
```

<210> SEQ ID NO 1005
<211> LENGTH: 31
<212> TYPE: PRT
<213> ORGANISM: Artificial Sequence
<220> FEATURE:
<223> OTHER INFORMATION: Core polypeptide

<400> SEQUENCE: 1005

Gly Asp Glu Phe Asp Glu Ser Ile Ser Gln Val Asn Glu Lys Ile Glu
1               5                   10                  15

Glu Ser Leu Ala Phe Ile Arg Lys Ser Asp Glu Leu Leu Gly Trp
            20                  25                  30

<210> SEQ ID NO 1006
<211> LENGTH: 29
<212> TYPE: PRT
<213> ORGANISM: Artificial Sequence
<220> FEATURE:
<223> OTHER INFORMATION: Core polypeptide

<400> SEQUENCE: 1006

Gly Asp Glu Phe Asp Glu Ser Ile Ser Gln Val Asn Glu Lys Ile Glu
1               5                   10                  15

Glu Ser Leu Ala Phe Ile Arg Glu Ser Asp Glu Leu Leu
            20                  25

<210> SEQ ID NO 1007
<211> LENGTH: 29
<212> TYPE: PRT
<213> ORGANISM: Artificial Sequence
<220> FEATURE:
<223> OTHER INFORMATION: Core polypeptide

<400> SEQUENCE: 1007

Gly Asp Glu Phe Asp Glu Ser Ile Ser Gln Val Asn Glu Lys Ile Glu
1               5                   10                  15

Glu Ser Leu Ala Phe Ile Glu Glu Ser Asp Glu Leu Leu
            20                  25

<210> SEQ ID NO 1008
<211> LENGTH: 36
<212> TYPE: PRT
<213> ORGANISM: Artificial Sequence
<220> FEATURE:
<223> OTHER INFORMATION: Core polypeptide

<400> SEQUENCE: 1008

Trp Gln Glu Trp Glu Gln Lys Val Asn Tyr Leu Glu Ala Asn Ile Thr
1               5                   10                  15

Ala Leu Leu Glu Gln Ala Gln Ile Gln Gln Glu Lys Asn Glu Tyr Glu
            20                  25                  30

Leu Gln Lys Leu
        35

<210> SEQ ID NO 1009
<211> LENGTH: 36
<212> TYPE: PRT
<213> ORGANISM: Artificial Sequence
<220> FEATURE:
<223> OTHER INFORMATION: Core polypeptide

<400> SEQUENCE: 1009

Trp Gln Glu Trp Glu Gln Lys Val Asp Tyr Leu Glu Ala Asn Ile Thr
1               5                   10                  15

-continued

Ala Leu Leu Glu Gln Ala Gln Ile Gln Gln Glu Lys Asn Glu Tyr Glu
            20                  25                  30

Leu Gln Lys Leu
        35

<210> SEQ ID NO 1010
<211> LENGTH: 36
<212> TYPE: PRT
<213> ORGANISM: Artificial Sequence
<220> FEATURE:
<223> OTHER INFORMATION: Core polypeptide

<400> SEQUENCE: 1010

Trp Gln Glu Trp Glu Gln Lys Val Arg Trp Leu Glu Ala Asn Ile Thr
 1               5                  10                  15

Ala Leu Leu Glu Gln Ala Gln Ile Gln Gln Glu Lys Asn Glu Tyr Glu
            20                  25                  30

Leu Gln Lys Leu
        35

<210> SEQ ID NO 1011
<211> LENGTH: 36
<212> TYPE: PRT
<213> ORGANISM: Artificial Sequence
<220> FEATURE:
<223> OTHER INFORMATION: Core polypeptide

<400> SEQUENCE: 1011

Trp Gln Glu Trp Glu Lys Gln Val Arg Tyr Leu Glu Ala Asn Ile Thr
 1               5                  10                  15

Ala Leu Leu Glu Gln Ala Gln Ile Gln Gln Glu Lys Asn Glu Tyr Glu
            20                  25                  30

Leu Gln Lys Leu
        35

<210> SEQ ID NO 1012
<211> LENGTH: 36
<212> TYPE: PRT
<213> ORGANISM: Artificial Sequence
<220> FEATURE:
<223> OTHER INFORMATION: Core polypeptide

<400> SEQUENCE: 1012

Trp Gln Glu Trp Glu His Gln Val Arg Tyr Leu Glu Ala Asn Ile Thr
 1               5                  10                  15

Ala Leu Leu Glu Gln Ala Gln Ile Gln Gln Glu Lys Asn Glu Tyr Glu
            20                  25                  30

Leu Gln Lys Leu
        35

<210> SEQ ID NO 1013
<211> LENGTH: 36
<212> TYPE: PRT
<213> ORGANISM: Artificial Sequence
<220> FEATURE:
<223> OTHER INFORMATION: Core polypeptide

<400> SEQUENCE: 1013

Trp Gln Glu Trp Glu His Lys Val Arg Tyr Leu Glu Ala Asn Ile Thr
 1               5                  10                  15

Ala Leu Leu Glu Gln Ala Gln Ile Gln Gln Glu Lys Asn Glu Tyr Glu
            20                  25                  30

-continued

Leu Gln Lys Leu
        35

<210> SEQ ID NO 1014
<211> LENGTH: 36
<212> TYPE: PRT
<213> ORGANISM: Artificial Sequence
<220> FEATURE:
<223> OTHER INFORMATION: Core polypeptide

<400> SEQUENCE: 1014

Trp Gln Glu Trp Asp Arg Glu Val Arg Tyr Leu Glu Ala Asn Ile Thr
1               5                  10                  15

Ala Leu Leu Glu Gln Ala Gln Ile Gln Gln Glu Lys Asn Glu Tyr Glu
            20                  25                  30

Leu Gln Lys Leu
        35

<210> SEQ ID NO 1015
<211> LENGTH: 36
<212> TYPE: PRT
<213> ORGANISM: Artificial Sequence
<220> FEATURE:
<223> OTHER INFORMATION: Core polypeptide

<400> SEQUENCE: 1015

Trp Gln Glu Trp Glu Arg Glu Val Arg Tyr Leu Glu Ala Asn Ile Thr
1               5                  10                  15

Ala Leu Leu Glu Gln Ala Gln Ile Gln Gln Glu Lys Asn Glu Tyr Glu
            20                  25                  30

Leu Gln Lys Leu
        35

<210> SEQ ID NO 1016
<211> LENGTH: 36
<212> TYPE: PRT
<213> ORGANISM: Artificial Sequence
<220> FEATURE:
<223> OTHER INFORMATION: Core polypeptide

<400> SEQUENCE: 1016

Trp Gln Glu Trp Glu Arg Gln Val Arg Tyr Leu Glu Ala Asn Ile Thr
1               5                  10                  15

Ala Leu Leu Glu Gln Ala Gln Ile Gln Gln Glu Lys Asn Glu Tyr Glu
            20                  25                  30

Leu Gln Lys Leu
        35

<210> SEQ ID NO 1017
<211> LENGTH: 36
<212> TYPE: PRT
<213> ORGANISM: Artificial Sequence
<220> FEATURE:
<223> OTHER INFORMATION: Core polypeptide

<400> SEQUENCE: 1017

Trp Gln Glu Trp Glu Gln Lys Val Lys Tyr Leu Glu Ala Asn Ile Thr
1               5                  10                  15

Ala Leu Leu Glu Gln Ala Gln Ile Gln Gln Glu Lys Asn Glu Tyr Glu
            20                  25                  30

Leu Gln Lys Leu
        35

<210> SEQ ID NO 1018
<211> LENGTH: 36
<212> TYPE: PRT
<213> ORGANISM: Artificial Sequence
<220> FEATURE:
<223> OTHER INFORMATION: Core polypeptide

<400> SEQUENCE: 1018

Trp Gln Glu Trp Glu Gln Lys Val Arg Phe Leu Glu Ala Asn Ile Thr
1               5                   10                  15
Ala Leu Leu Glu Gln Ala Gln Ile Gln Gln Lys Asn Glu Tyr Glu
            20                  25                  30
Leu Gln Lys Leu
        35

<210> SEQ ID NO 1019
<211> LENGTH: 35
<212> TYPE: PRT
<213> ORGANISM: Artificial Sequence
<220> FEATURE:
<223> OTHER INFORMATION: Core polypeptide

<400> SEQUENCE: 1019

Val Asn Pro Ser Asp Glu Tyr Asp Ala Ser Ile Ser Gln Val Asn Glu
1               5                   10                  15
Glu Ile Asn Gln Ala Leu Ala Tyr Ile Arg Lys Ala Asp Glu Leu Leu
            20                  25                  30
Glu Asn Val
        35

<210> SEQ ID NO 1020
<211> LENGTH: 35
<212> TYPE: PRT
<213> ORGANISM: Artificial Sequence
<220> FEATURE:
<223> OTHER INFORMATION: Core polypeptide

<400> SEQUENCE: 1020

Val Asn Pro Ser Asp Glu Asn Asp Ala Ser Ile Ser Gln Val Asn Glu
1               5                   10                  15
Glu Ile Asn Gln Ala Leu Ala Tyr Ile Arg Lys Ala Asp Glu Leu Leu
            20                  25                  30
Glu Asn Val
        35

<210> SEQ ID NO 1021
<211> LENGTH: 35
<212> TYPE: PRT
<213> ORGANISM: Artificial Sequence
<220> FEATURE:
<223> OTHER INFORMATION: Core polypeptide

<400> SEQUENCE: 1021

Val Asn Pro Ser Asp Glu Tyr Asp Ala Ser Ile Ser Gln Val Asn Glu
1               5                   10                  15
Glu Ile Asn Gln Ala Leu Ala Asn Ile Arg Lys Ala Asp Glu Leu Leu
            20                  25                  30
Glu Asn Val
        35

<210> SEQ ID NO 1022
<211> LENGTH: 36

```
<212> TYPE: PRT
<213> ORGANISM: Artificial Sequence
<220> FEATURE:
<223> OTHER INFORMATION: Core polypeptide

<400> SEQUENCE: 1022
```

Val Tyr Pro Ser Asp Glu Phe Asp Ala Ser Ile Ser Gln Val Asn Glu
 1               5                  10                  15

Lys Ile Asn Gln Ser Leu Ala Phe Ile Arg Glu Ala Asp Glu Leu Leu
            20                  25                  30

Phe Asn Phe Phe
            35

```
<210> SEQ ID NO 1023
<211> LENGTH: 36
<212> TYPE: PRT
<213> ORGANISM: Artificial Sequence
<220> FEATURE:
<223> OTHER INFORMATION: Core polypeptide

<400> SEQUENCE: 1023
```

Val Tyr Pro Ser Asp Glu Tyr Asp Ala Ser Ile Ser Gln Val Asn Glu
 1               5                  10                  15

Glu Ile Asn Gln Ala Leu Ala Tyr Ile Arg Lys Ala Asp Glu Leu Leu
            20                  25                  30

Phe Asn Phe Phe
            35

```
<210> SEQ ID NO 1024
<211> LENGTH: 36
<212> TYPE: PRT
<213> ORGANISM: Artificial Sequence
<220> FEATURE:
<223> OTHER INFORMATION: Core polypeptide

<400> SEQUENCE: 1024
```

Tyr Thr Ser Leu Ile Thr Ala Leu Leu Glu Gln Ala Gln Ile Gln Gln
 1               5                  10                  15

Glu Lys Asn Glu Tyr Glu Leu Gln Lys Leu Asp Lys Trp Ala Ser Leu
            20                  25                  30

Trp Asn Trp Phe
            35

```
<210> SEQ ID NO 1025
<211> LENGTH: 36
<212> TYPE: PRT
<213> ORGANISM: Artificial Sequence
<220> FEATURE:
<223> OTHER INFORMATION: Core polypeptide

<400> SEQUENCE: 1025
```

Tyr Thr Ser Leu Ile Thr Ala Leu Leu Glu Gln Ala Gln Ile Gln Gln
 1               5                  10                  15

Glu Lys Asn Glu Tyr Glu Leu Gln Lys Leu Asp Lys Trp Ala Ser Leu
            20                  25                  30

Trp Glu Trp Phe
            35

```
<210> SEQ ID NO 1026
<211> LENGTH: 36
<212> TYPE: PRT
<213> ORGANISM: Artificial Sequence
<220> FEATURE:
```

<223> OTHER INFORMATION: Core polypeptide

<400> SEQUENCE: 1026

Tyr Thr Ser Leu Ile Thr Ala Leu Leu Glu Gln Ala Gln Ile Gln Gln
1               5                   10                  15
Glu Lys Asn Glu Tyr Glu Leu Gln Lys Leu Asp Glu Trp Ala Ser Leu
            20                  25                  30
Trp Glu Trp Phe
        35

<210> SEQ ID NO 1027
<211> LENGTH: 36
<212> TYPE: PRT
<213> ORGANISM: Artificial Sequence
<220> FEATURE:
<223> OTHER INFORMATION: Core polypeptide

<400> SEQUENCE: 1027

Tyr Thr Ser Leu Ile Thr Ala Leu Leu Glu Gln Ala Gln Ile Gln Gln
1               5                   10                  15
Glu Lys Asn Glu Tyr Glu Leu Gln Glu Leu Asp Glu Trp Ala Ser Leu
            20                  25                  30
Trp Glu Trp Phe
        35

<210> SEQ ID NO 1028
<211> LENGTH: 36
<212> TYPE: PRT
<213> ORGANISM: Artificial Sequence
<220> FEATURE:
<223> OTHER INFORMATION: Core polypeptide

<400> SEQUENCE: 1028

Tyr Thr Ser Leu Ile Thr Ala Leu Leu Glu Glu Ala Gln Ile Gln Gln
1               5                   10                  15
Glu Lys Asn Glu Tyr Glu Leu Gln Glu Leu Asp Glu Trp Ala Ser Leu
            20                  25                  30
Trp Glu Trp Phe
        35

<210> SEQ ID NO 1029
<211> LENGTH: 28
<212> TYPE: PRT
<213> ORGANISM: Artificial Sequence
<220> FEATURE:
<223> OTHER INFORMATION: Core polypeptide

<400> SEQUENCE: 1029

Ala Ala Ala Thr Ala Leu Leu Glu Gln Ala Gln Ile Gln Gln Glu Lys
1               5                   10                  15
Asn Glu Tyr Glu Leu Gln Lys Leu Ala Ala Ala Trp
            20                  25

<210> SEQ ID NO 1030
<211> LENGTH: 36
<212> TYPE: PRT
<213> ORGANISM: Artificial Sequence
<220> FEATURE:
<223> OTHER INFORMATION: Core polypeptide

<400> SEQUENCE: 1030

Trp Ala Ala Trp Glu Gln Lys Val Arg Tyr Leu Glu Ala Asn Ile Thr
1               5                   10                  15

```
Ala Leu Leu Glu Gln Ala Gln Ile Gln Gln Lys Asn Glu Tyr Glu
            20                  25                  30

Leu Gln Lys Leu
        35

<210> SEQ ID NO 1031
<211> LENGTH: 36
<212> TYPE: PRT
<213> ORGANISM: Artificial Sequence
<220> FEATURE:
<223> OTHER INFORMATION: Core polypeptide

<400> SEQUENCE: 1031

Trp Gln Glu Ala Ala Gln Lys Val Arg Tyr Leu Glu Ala Asn Ile Thr
  1               5                  10                  15

Ala Leu Leu Glu Gln Ala Gln Ile Gln Gln Lys Asn Glu Tyr Glu
            20                  25                  30

Leu Gln Lys Leu
        35

<210> SEQ ID NO 1032
<211> LENGTH: 36
<212> TYPE: PRT
<213> ORGANISM: Artificial Sequence
<220> FEATURE:
<223> OTHER INFORMATION: Core polypeptide

<400> SEQUENCE: 1032

Trp Gln Glu Trp Ala Ala Lys Val Arg Tyr Leu Glu Ala Asn Ile Thr
  1               5                  10                  15

Ala Leu Leu Glu Gln Ala Gln Ile Gln Gln Glu Lys Asn Glu Tyr Glu
            20                  25                  30

Leu Gln Lys Leu
        35

<210> SEQ ID NO 1033
<211> LENGTH: 36
<212> TYPE: PRT
<213> ORGANISM: Artificial Sequence
<220> FEATURE:
<223> OTHER INFORMATION: Core polypeptide

<400> SEQUENCE: 1033

Trp Gln Glu Trp Glu Gln Lys Ala Ala Tyr Leu Glu Ala Asn Ile Thr
  1               5                  10                  15

Ala Leu Leu Glu Gln Ala Gln Ile Gln Gln Lys Asn Glu Tyr Glu
            20                  25                  30

Leu Gln Lys Leu
        35

<210> SEQ ID NO 1034
<211> LENGTH: 36
<212> TYPE: PRT
<213> ORGANISM: Artificial Sequence
<220> FEATURE:
<223> OTHER INFORMATION: Core polypeptide

<400> SEQUENCE: 1034

Trp Gln Glu Trp Glu Gln Lys Val Ala Ala Leu Glu Ala Asn Ile Thr
  1               5                  10                  15

Ala Leu Leu Glu Gln Ala Gln Ile Gln Gln Lys Asn Glu Tyr Glu
            20                  25                  30
```

Leu Gln Lys Leu
         35

<210> SEQ ID NO 1035
<211> LENGTH: 29
<212> TYPE: PRT
<213> ORGANISM: Artificial Sequence
<220> FEATURE:
<223> OTHER INFORMATION: Core polypeptide

<400> SEQUENCE: 1035

Gly Asp Glu Phe Asp Ala Ser Ile Ser Gln Val Asn Glu Lys Ile Asn
 1               5                  10                  15

Gln Ser Leu Ala Phe Ile Arg Lys Ser Asp Glu Leu Thr
             20                  25

<210> SEQ ID NO 1036
<211> LENGTH: 29
<212> TYPE: PRT
<213> ORGANISM: Artificial Sequence
<220> FEATURE:
<223> OTHER INFORMATION: Core polypeptide

<400> SEQUENCE: 1036

Gly Asp Glu Phe Asp Ala Ser Ile Ser Gln Val Asn Glu Lys Ile Asn
 1               5                  10                  15

Gln Ser Leu Ala Phe Thr Arg Lys Ser Asp Glu Leu Thr
             20                  25

<210> SEQ ID NO 1037
<211> LENGTH: 29
<212> TYPE: PRT
<213> ORGANISM: Artificial Sequence
<220> FEATURE:
<223> OTHER INFORMATION: Core polypeptide

<400> SEQUENCE: 1037

Gly Asp Glu Phe Asp Ala Ser Ile Ser Gln Val Asn Glu Lys Thr Asn
 1               5                  10                  15

Gln Ser Leu Ala Phe Thr Arg Lys Ser Asp Glu Leu Thr
             20                  25

<210> SEQ ID NO 1038
<211> LENGTH: 29
<212> TYPE: PRT
<213> ORGANISM: Artificial Sequence
<220> FEATURE:
<223> OTHER INFORMATION: Core polypeptide

<400> SEQUENCE: 1038

Gly Asp Glu Phe Asp Ala Ser Ile Ser Gln Thr Asn Glu Lys Thr Asn
 1               5                  10                  15

Gln Ser Leu Ala Phe Thr Arg Lys Ser Asp Glu Leu Thr
             20                  25

<210> SEQ ID NO 1039
<211> LENGTH: 29
<212> TYPE: PRT
<213> ORGANISM: Artificial Sequence
<220> FEATURE:
<223> OTHER INFORMATION: Core polypeptide

<400> SEQUENCE: 1039

Gly Asp Glu Phe Asp Ala Ser Thr Ser Gln Thr Asn Glu Lys Thr Asn

```
                    1               5               10              15
Gln Ser Leu Ala Phe Thr Arg Lys Ser Asp Glu Leu Thr
                    20              25
```

<210> SEQ ID NO 1040
<211> LENGTH: 29
<212> TYPE: PRT
<213> ORGANISM: Artificial Sequence
<220> FEATURE:
<223> OTHER INFORMATION: Core polypeptide

<400> SEQUENCE: 1040

```
Gly Asp Glu Tyr Asp Ala Ser Thr Ser Gln Thr Asn Glu Lys Thr Asn
1               5                   10                  15
Gln Ser Leu Ala Phe Thr Arg Lys Ser Asp Glu Leu Thr
                    20              25
```

<210> SEQ ID NO 1041
<211> LENGTH: 29
<212> TYPE: PRT
<213> ORGANISM: Artificial Sequence
<220> FEATURE:
<223> OTHER INFORMATION: Core polypeptide

<400> SEQUENCE: 1041

```
Gly Asp Glu Phe Asp Glu Glu Ile Ser Gln Val Asn Glu Lys Ile Glu
1               5                   10                  15
Glu Ser Leu Ala Phe Ile Arg Lys Ser Asp Glu Leu Leu
                    20              25
```

<210> SEQ ID NO 1042
<211> LENGTH: 29
<212> TYPE: PRT
<213> ORGANISM: Artificial Sequence
<220> FEATURE:
<223> OTHER INFORMATION: Core polypeptide

<400> SEQUENCE: 1042

```
Gly Asp Glu Phe Asp Ala Ser Ile Ser Gln Val Asn Glu Lys Ile Asn
1               5                   10                  15
Gln Ser Leu Ala Phe Ile Arg Lys Ser Asp Glu Leu Ala
                    20              25
```

<210> SEQ ID NO 1043
<211> LENGTH: 29
<212> TYPE: PRT
<213> ORGANISM: Artificial Sequence
<220> FEATURE:
<223> OTHER INFORMATION: Core polypeptide

<400> SEQUENCE: 1043

```
Gly Asp Glu Phe Asp Ala Ser Ala Ser Gln Ala Asn Glu Lys Ala Asn
1               5                   10                  15
Gln Ser Leu Ala Phe Ala Arg Lys Ser Asp Glu Leu Ala
                    20              25
```

<210> SEQ ID NO 1044
<211> LENGTH: 29
<212> TYPE: PRT
<213> ORGANISM: Artificial Sequence
<220> FEATURE:
<223> OTHER INFORMATION: Core polypeptide

<400> SEQUENCE: 1044

```
Gly Asp Glu Phe Asp Glu Ser Ile Ser Gln Val Asn Glu Lys Ile Glu
 1               5                  10                  15

Glu Ser Leu Ala Phe Thr Arg Lys Ser Asp Glu Leu Leu
            20                  25
```

<210> SEQ ID NO 1045
<211> LENGTH: 29
<212> TYPE: PRT
<213> ORGANISM: Artificial Sequence
<220> FEATURE:
<223> OTHER INFORMATION: Core polypeptide

<400> SEQUENCE: 1045

```
Gly Asp Glu Phe Asp Glu Ser Ile Ser Gln Val Asn Glu Lys Thr Glu
 1               5                  10                  15

Glu Ser Leu Ala Phe Ile Arg Lys Ser Asp Glu Leu Leu
            20                  25
```

<210> SEQ ID NO 1046
<211> LENGTH: 29
<212> TYPE: PRT
<213> ORGANISM: Artificial Sequence
<220> FEATURE:
<223> OTHER INFORMATION: Core polypeptide

<400> SEQUENCE: 1046

```
Gly Asp Glu Phe Asp Glu Ser Ile Ser Gln Thr Asn Glu Lys Ile Glu
 1               5                  10                  15

Glu Ser Leu Ala Phe Ile Arg Lys Ser Asp Glu Leu Leu
            20                  25
```

<210> SEQ ID NO 1047
<211> LENGTH: 29
<212> TYPE: PRT
<213> ORGANISM: Artificial Sequence
<220> FEATURE:
<223> OTHER INFORMATION: Core polypeptide

<400> SEQUENCE: 1047

```
Gly Asp Glu Phe Asp Glu Ser Thr Ser Gln Val Asn Glu Lys Ile Glu
 1               5                  10                  15

Glu Ser Leu Ala Phe Ile Arg Lys Ser Asp Glu Leu Leu
            20                  25
```

<210> SEQ ID NO 1048
<211> LENGTH: 36
<212> TYPE: PRT
<213> ORGANISM: Artificial Sequence
<220> FEATURE:
<223> OTHER INFORMATION: Core polypeptide

<400> SEQUENCE: 1048

```
Trp Asn Trp Phe Asp Glu Phe Asp Glu Ser Thr Ser Gln Val Asn Glu
 1               5                  10                  15

Lys Ile Glu Glu Ser Leu Ala Phe Ile Arg Lys Ser Asp Glu Leu Leu
            20                  25                  30

Trp Asn Trp Phe
            35
```

<210> SEQ ID NO 1049
<211> LENGTH: 36
<212> TYPE: PRT
<213> ORGANISM: Artificial Sequence
<220> FEATURE:

<223> OTHER INFORMATION: Core polypeptide

<400> SEQUENCE: 1049

Trp Asn Trp Phe Asp Glu Phe Asp Glu Ser Thr Ser Gln Thr Asn Glu
1               5                   10                  15

Lys Ile Glu Glu Ser Leu Ala Phe Ile Arg Lys Ser Asp Glu Leu Leu
            20                  25                  30

Trp Asn Trp Phe
        35

<210> SEQ ID NO 1050
<211> LENGTH: 36
<212> TYPE: PRT
<213> ORGANISM: Artificial Sequence
<220> FEATURE:
<223> OTHER INFORMATION: Core polypeptide

<400> SEQUENCE: 1050

Trp Asn Trp Phe Asp Glu Phe Asp Glu Ser Thr Ser Gln Thr Asn Glu
1               5                   10                  15

Lys Thr Glu Glu Ser Leu Ala Phe Ile Arg Lys Ser Asp Glu Leu Leu
            20                  25                  30

Trp Asn Trp Phe
        35

<210> SEQ ID NO 1051
<211> LENGTH: 36
<212> TYPE: PRT
<213> ORGANISM: Artificial Sequence
<220> FEATURE:
<223> OTHER INFORMATION: Core polypeptide

<400> SEQUENCE: 1051

Tyr Thr Asn Leu Ile Tyr Thr Leu Leu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Ser Trp Phe
        35

<210> SEQ ID NO 1052
<211> LENGTH: 46
<212> TYPE: PRT
<213> ORGANISM: Artificial Sequence
<220> FEATURE:
<223> OTHER INFORMATION: Core polypeptide

<400> SEQUENCE: 1052

Trp Gln Glu Trp Glu Gln Lys Val Arg Tyr Leu Glu Ala Asn Ile Thr
1               5                   10                  15

Ala Leu Leu Glu Gln Ala Gln Ile Gln Gln Glu Lys Asn Glu Tyr Glu
            20                  25                  30

Leu Gln Lys Leu Asp Lys Trp Ala Ser Leu Trp Asn Trp Phe
        35                  40                  45

<210> SEQ ID NO 1053
<211> LENGTH: 50
<212> TYPE: PRT
<213> ORGANISM: Artificial Sequence
<220> FEATURE:
<223> OTHER INFORMATION: Core polypeptide

<400> SEQUENCE: 1053

Asn Asn Met Thr Trp Gln Glu Trp Glu Gln Lys Val Arg Tyr Leu Glu
1               5                   10                  15

Ala Asn Ile Thr Ala Leu Leu Glu Gln Ala Gln Ile Gln Gln Glu Lys
            20                  25                  30

Asn Glu Tyr Glu Leu Gln Lys Leu Asp Lys Trp Ala Ser Leu Trp Asn
        35                  40                  45

Trp Phe
    50

<210> SEQ ID NO 1054
<211> LENGTH: 16
<212> TYPE: PRT
<213> ORGANISM: Artificial Sequence
<220> FEATURE:
<223> OTHER INFORMATION: Core polypeptide

<400> SEQUENCE: 1054

Trp Asn Trp Phe Ile Glu Glu Ser Asp Glu Leu Leu Trp Asn Trp Phe
1               5                   10                  15

<210> SEQ ID NO 1055
<211> LENGTH: 11
<212> TYPE: PRT
<213> ORGANISM: Artificial Sequence
<220> FEATURE:
<223> OTHER INFORMATION: Core polypeptide

<400> SEQUENCE: 1055

Gly Phe Ile Glu Glu Ser Asp Glu Leu Leu Trp
1               5                   10

<210> SEQ ID NO 1056
<211> LENGTH: 11
<212> TYPE: PRT
<213> ORGANISM: Artificial Sequence
<220> FEATURE:
<223> OTHER INFORMATION: Core polypeptide

<400> SEQUENCE: 1056

Trp Phe Ile Glu Glu Ser Asp Glu Leu Leu Trp
1               5                   10

<210> SEQ ID NO 1057
<211> LENGTH: 17
<212> TYPE: PRT
<213> ORGANISM: Artificial Sequence
<220> FEATURE:
<223> OTHER INFORMATION: Core polypeptide

<400> SEQUENCE: 1057

Gly Phe Asn Phe Phe Ile Glu Glu Ser Asp Glu Leu Leu Phe Asn Phe
1               5                   10                  15

Phe

<210> SEQ ID NO 1058
<211> LENGTH: 7
<212> TYPE: PRT
<213> ORGANISM: Artificial Sequence
<220> FEATURE:
<223> OTHER INFORMATION: Core polypeptide

<400> SEQUENCE: 1058

Gly Glu Ser Asp Glu Leu Trp
1               5

<210> SEQ ID NO 1059
<211> LENGTH: 39
<212> TYPE: PRT
<213> ORGANISM: Artificial Sequence
<220> FEATURE:
<223> OTHER INFORMATION: Core polypeptide

<400> SEQUENCE: 1059

Trp Asn Trp Phe Gly Asp Glu Phe Asp Glu Ser Ile Ser Gln Val Gln
 1               5                  10                  15

Glu Glu Ile Glu Glu Ser Leu Ala Phe Ile Glu Glu Ser Asp Glu Leu
            20                  25                  30

Leu Gly Gly Trp Asn Trp Phe
        35

<210> SEQ ID NO 1060
<211> LENGTH: 48
<212> TYPE: PRT
<213> ORGANISM: Artificial Sequence
<220> FEATURE:
<223> OTHER INFORMATION: Core polypeptide

<400> SEQUENCE: 1060

Tyr Thr Ser Leu Ile His Ser Leu Gly Gly Asp Glu Phe Asp Glu Ser
 1               5                  10                  15

Ile Ser Gln Val Asn Glu Glu Ile Glu Glu Ser Leu Ala Phe Ile Glu
            20                  25                  30

Glu Ser Asp Glu Leu Leu Gly Gly Trp Ala Ser Leu Trp Asn Trp Phe
        35                  40                  45

<210> SEQ ID NO 1061
<211> LENGTH: 29
<212> TYPE: PRT
<213> ORGANISM: Artificial Sequence
<220> FEATURE:
<223> OTHER INFORMATION: Core polypeptide

<400> SEQUENCE: 1061

Gly Asp Glu Phe Asp Glu Ser Ile Ser Gln Val Gln Glu Glu Ile Glu
 1               5                  10                  15

Glu Ser Leu Ala Phe Ile Glu Glu Ser Asp Glu Leu Leu
            20                  25

<210> SEQ ID NO 1062
<211> LENGTH: 53
<212> TYPE: PRT
<213> ORGANISM: Artificial Sequence
<220> FEATURE:
<223> OTHER INFORMATION: Core polypeptide

<400> SEQUENCE: 1062

His Gln Ala Arg Gln Leu Leu Ser Ser Ile Met Gln Gln Gln Asn Asn
 1               5                  10                  15

Leu Leu Arg Ala Ile Glu Ala Gln Gln His Leu Leu Gln Leu Thr Val
            20                  25                  30

Trp Gly Ile Lys Gln Leu Gln Ala Arg Ile Leu Ala Val Glu Arg Tyr
        35                  40                  45

Leu Lys Asp Gln His
        50

<210> SEQ ID NO 1063

```
<211> LENGTH: 25
<212> TYPE: PRT
<213> ORGANISM: Artificial Sequence
<220> FEATURE:
<223> OTHER INFORMATION: Core polypeptide

<400> SEQUENCE: 1063

Cys Pro Lys Tyr Val Lys Gln Asn Thr Leu Lys Leu Ala Thr Gly Met
 1               5                  10                  15

Arg Asn Val Pro Glu Lys Gln Thr Arg
            20                  25

<210> SEQ ID NO 1064
<211> LENGTH: 30
<212> TYPE: PRT
<213> ORGANISM: Artificial Sequence
<220> FEATURE:
<223> OTHER INFORMATION: Core polypeptide

<400> SEQUENCE: 1064

Gly Leu Phe Gly Ala Ile Ala Gly Phe Ile Glu Asn Gly Trp Glu Gly
 1               5                  10                  15

Met Ile Asp Gly Trp Tyr Gly Phe Arg His Gln Asn Ser Cys
            20                  25                  30

<210> SEQ ID NO 1065
<211> LENGTH: 7
<212> TYPE: PRT
<213> ORGANISM: Artificial Sequence
<220> FEATURE:
<223> OTHER INFORMATION: Core polypeptide

<400> SEQUENCE: 1065

Leu Asn Phe Leu Gly Gly Thr
 1               5

<210> SEQ ID NO 1066
<211> LENGTH: 14
<212> TYPE: PRT
<213> ORGANISM: Artificial Sequence
<220> FEATURE:
<223> OTHER INFORMATION: Core polypeptide

<400> SEQUENCE: 1066

Leu Asp Ser Trp Trp Thr Ser Leu Asn Phe Leu Gly Gly Thr
 1               5                  10

<210> SEQ ID NO 1067
<211> LENGTH: 21
<212> TYPE: PRT
<213> ORGANISM: Artificial Sequence
<220> FEATURE:
<223> OTHER INFORMATION: Core polypeptide

<400> SEQUENCE: 1067

Ile Leu Thr Ile Pro Gln Ser Leu Asp Ser Trp Trp Thr Ser Leu Asn
 1               5                  10                  15

Phe Leu Gly Gly Thr
            20

<210> SEQ ID NO 1068
<211> LENGTH: 28
<212> TYPE: PRT
<213> ORGANISM: Artificial Sequence
<220> FEATURE:
<223> OTHER INFORMATION: Core polypeptide
```

```
<400> SEQUENCE: 1068

Gly Phe Phe Leu Leu Thr Arg Ile Leu Thr Ile Pro Gln Ser Leu Asp
1               5                   10                  15

Ser Trp Trp Thr Ser Leu Asn Phe Leu Gly Gly Thr
            20                  25

<210> SEQ ID NO 1069
<211> LENGTH: 39
<212> TYPE: PRT
<213> ORGANISM: Artificial Sequence
<220> FEATURE:
<223> OTHER INFORMATION: Core polypeptide

<400> SEQUENCE: 1069

Trp Gln Glu Trp Glu Gln Lys Ile Thr Ala Leu Leu Glu Gln Ala Gln
1               5                   10                  15

Ile Gln Gln Glu Lys Asn Glu Tyr Glu Leu Gln Lys Leu Asp Lys Trp
            20                  25                  30

Ala Ser Leu Trp Asn Trp Phe
        35

<210> SEQ ID NO 1070
<211> LENGTH: 36
<212> TYPE: PRT
<213> ORGANISM: Artificial Sequence
<220> FEATURE:
<223> OTHER INFORMATION: Core polypeptide

<400> SEQUENCE: 1070

Trp Asn Trp Phe Ile Thr Ala Leu Leu Glu Gln Ala Gln Ile Gln Gln
1               5                   10                  15

Glu Lys Asn Glu Tyr Glu Leu Gln Lys Leu Asp Lys Trp Ala Ser Leu
            20                  25                  30

Trp Asn Trp Phe
        35

<210> SEQ ID NO 1071
<211> LENGTH: 39
<212> TYPE: PRT
<213> ORGANISM: Artificial Sequence
<220> FEATURE:
<223> OTHER INFORMATION: Core polypeptide

<400> SEQUENCE: 1071

Trp Gln Glu Trp Glu Gln Lys Ile Thr Ala Leu Leu Glu Gln Ala Gln
1               5                   10                  15

Ile Gln Gln Glu Lys Asn Glu Tyr Glu Leu Gln Lys Leu Asp Lys Trp
            20                  25                  30

Ala Ser Leu Trp Glu Trp Phe
        35

<210> SEQ ID NO 1072
<211> LENGTH: 36
<212> TYPE: PRT
<213> ORGANISM: Artificial Sequence
<220> FEATURE:
<223> OTHER INFORMATION: Core polypeptide

<400> SEQUENCE: 1072

Trp Gln Glu Trp Glu Gln Lys Val Arg Tyr Leu Glu Ala Asn Ile Thr
1               5                   10                  15
```

```
Ala Leu Leu Glu Gln Ala Gln Ile Gln Gln Glu Lys Ile Glu Tyr Glu
            20                  25                  30

Leu Gln Lys Leu
            35
```

<210> SEQ ID NO 1073
<211> LENGTH: 36
<212> TYPE: PRT
<213> ORGANISM: Artificial Sequence
<220> FEATURE:
<223> OTHER INFORMATION: Core polypeptide

<400> SEQUENCE: 1073

```
Trp Gln Glu Trp Glu Gln Lys Val Arg Tyr Leu Glu Ala Gln Ile Thr
 1               5                  10                  15

Ala Leu Leu Glu Gln Ala Gln Ile Gln Gln Glu Lys Ile Glu Tyr Glu
            20                  25                  30

Leu Gln Lys Leu
            35
```

<210> SEQ ID NO 1074
<211> LENGTH: 35
<212> TYPE: PRT
<213> ORGANISM: Artificial Sequence
<220> FEATURE:
<223> OTHER INFORMATION: Core polypeptide

<400> SEQUENCE: 1074

```
Lys Glu Asn Lys Ala Asn Gly Thr Asp Ala Lys Val Lys Leu Ile Lys
 1               5                  10                  15

Gln Glu Leu Asp Lys Tyr Lys Asn Ala Val Thr Glu Leu Gln Leu Leu
            20                  25                  30

Met Gln Ser
            35
```

<210> SEQ ID NO 1075
<211> LENGTH: 35
<212> TYPE: PRT
<213> ORGANISM: Artificial Sequence
<220> FEATURE:
<223> OTHER INFORMATION: Core polypeptide

<400> SEQUENCE: 1075

```
Asn Ile Lys Glu Asn Lys Ala Asn Gly Thr Asp Ala Lys Val Lys Leu
 1               5                  10                  15

Ile Lys Gln Glu Leu Asp Lys Tyr Lys Asn Ala Val Thr Glu Leu Gln
            20                  25                  30

Leu Leu Met
            35
```

<210> SEQ ID NO 1076
<211> LENGTH: 36
<212> TYPE: PRT
<213> ORGANISM: Artificial Sequence
<220> FEATURE:
<223> OTHER INFORMATION: Core polypeptide

<400> SEQUENCE: 1076

```
Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser Leu
            20                  25                  30
```

Trp Asn Trp Phe
        35

<210> SEQ ID NO 1077
<211> LENGTH: 37
<212> TYPE: PRT
<213> ORGANISM: Artificial Sequence
<220> FEATURE:
<223> OTHER INFORMATION: Core polypeptide

<400> SEQUENCE: 1077

Gly Trp Asn Trp Phe Asp Glu Phe Asp Glu Ser Ile Ser Gln Val Gln
 1               5                  10                  15

Glu Glu Ile Glu Glu Ser Leu Ala Phe Ile Glu Glu Ser Asp Glu Leu
            20                  25                  30

Leu Trp Asn Trp Phe
        35

<210> SEQ ID NO 1078
<211> LENGTH: 38
<212> TYPE: PRT
<213> ORGANISM: Artificial Sequence
<220> FEATURE:
<223> OTHER INFORMATION: Core polypeptide

<400> SEQUENCE: 1078

Trp Asn Trp Phe Gly Asp Glu Phe Asp Glu Ser Ile Ser Gln Val Asn
 1               5                  10                  15

Glu Lys Ile Glu Glu Ser Leu Ala Phe Ile Glu Glu Ser Asp Glu Leu
            20                  25                  30

Leu Gly Trp Asn Trp Phe
        35

<210> SEQ ID NO 1079
<211> LENGTH: 38
<212> TYPE: PRT
<213> ORGANISM: Artificial Sequence
<220> FEATURE:
<223> OTHER INFORMATION: Core polypeptide

<400> SEQUENCE: 1079

Trp Asn Trp Phe Gly Asp Glu Phe Asp Glu Ser Ile Ser Gln Val Asn
 1               5                  10                  15

Glu Lys Ile Glu Glu Ser Leu Ala Phe Ile Arg Lys Ser Asp Glu Leu
            20                  25                  30

Leu Gly Trp Asn Trp Phe
        35

<210> SEQ ID NO 1080
<211> LENGTH: 36
<212> TYPE: PRT
<213> ORGANISM: Artificial Sequence
<220> FEATURE:
<223> OTHER INFORMATION: Core polypeptide

<400> SEQUENCE: 1080

Trp Asn Trp Phe Asp Glu Phe Asp Glu Ser Ile Ser Gln Val Asn Glu
 1               5                  10                  15

Lys Ile Glu Glu Ser Leu Ala Phe Ile Arg Lys Ser Asp Glu Leu Leu
            20                  25                  30

Trp Asn Trp Phe
        35

```
<210> SEQ ID NO 1081
<211> LENGTH: 36
<212> TYPE: PRT
<213> ORGANISM: Artificial Sequence
<220> FEATURE:
<223> OTHER INFORMATION: Core polypeptide

<400> SEQUENCE: 1081
```

Trp Asn Trp Phe Asp Glu Phe Asp Glu Ser Ile Ser Gln Val Asn Glu
 1               5                  10                  15

Lys Ile Glu Glu Ser Leu Ala Phe Ile Glu Gly Ser Asp Glu Leu Leu
             20                  25                  30

Trp Asn Trp Phe
         35

```
<210> SEQ ID NO 1082
<211> LENGTH: 21
<212> TYPE: PRT
<213> ORGANISM: Artificial Sequence
<220> FEATURE:
<223> OTHER INFORMATION: Core polypeptide

<400> SEQUENCE: 1082
```

Glu Glu Ser Gln Asn Gln Gln Glu Lys Asn Glu Gln Glu Leu Leu Glu
 1               5                  10                  15

Leu Asp Lys Trp Ala
             20

```
<210> SEQ ID NO 1083
<211> LENGTH: 21
<212> TYPE: PRT
<213> ORGANISM: Artificial Sequence
<220> FEATURE:
<223> OTHER INFORMATION: Core polypeptide

<400> SEQUENCE: 1083
```

Glu Glu Ser Gln Asn Gln Gln Glu Lys Asn Glu Gln Glu Leu Leu Glu
 1               5                  10                  15

Leu Asp Lys Trp Ala
             20

```
<210> SEQ ID NO 1084
<211> LENGTH: 36
<212> TYPE: PRT
<213> ORGANISM: Artificial Sequence
<220> FEATURE:
<223> OTHER INFORMATION: Core polypeptide

<400> SEQUENCE: 1084
```

Cys Gly Thr Thr Asp Arg Ser Gly Ala Pro Thr Tyr Ser Trp Gly Ala
 1               5                  10                  15

Asn Asp Thr Asp Val Phe Val Leu Asn Asn Thr Arg Pro Pro Leu Gly
             20                  25                  30

Asn Trp Phe Gly
         35

```
<210> SEQ ID NO 1085
<211> LENGTH: 28
<212> TYPE: PRT
<213> ORGANISM: Artificial Sequence
<220> FEATURE:
<223> OTHER INFORMATION: Core polypeptide

<400> SEQUENCE: 1085
```

```
Gly Val Glu His Arg Leu Glu Ala Asn Trp Thr Arg Gly Glu Arg Ala
1               5                   10                  15

Asp Leu Glu Asp Arg Asp Arg Ser Glu Leu Ser Pro
            20                  25
```

<210> SEQ ID NO 1086
<211> LENGTH: 27
<212> TYPE: PRT
<213> ORGANISM: Artificial Sequence
<220> FEATURE:
<223> OTHER INFORMATION: Core polypeptide

<400> SEQUENCE: 1086

```
Cys Val Arg Glu Gly Asn Ala Ser Arg Ala Trp Val Ala Val Thr Pro
1               5                   10                  15

Thr Val Ala Thr Arg Asp Gly Lys Leu Pro Thr
            20                  25
```

<210> SEQ ID NO 1087
<211> LENGTH: 20
<212> TYPE: PRT
<213> ORGANISM: Artificial Sequence
<220> FEATURE:
<223> OTHER INFORMATION: Core polypeptide

<400> SEQUENCE: 1087

```
Cys Phe Ser Pro Arg His His Trp Thr Thr Gln Asp Ala Asn Ala Ser
1               5                   10                  15

Ile Tyr Pro Gly
            20
```

<210> SEQ ID NO 1088
<211> LENGTH: 33
<212> TYPE: PRT
<213> ORGANISM: Artificial Sequence
<220> FEATURE:
<223> OTHER INFORMATION: Core polypeptide

<400> SEQUENCE: 1088

```
Leu Gln His Tyr Arg Glu Val Ala Ala Ala Lys Ser Ser Glu Asn Asp
1               5                   10                  15

Arg Leu Arg Leu Leu Lys Gln Met Cys Pro Ser Leu Asp Val Asp
            20                  25                  30

Ser
```

<210> SEQ ID NO 1089
<211> LENGTH: 46
<212> TYPE: PRT
<213> ORGANISM: Artificial Sequence
<220> FEATURE:
<223> OTHER INFORMATION: Core polypeptide

<400> SEQUENCE: 1089

```
Trp Gln Glu Trp Asp Arg Glu Ile Ser Asn Tyr Thr Ser Leu Ile Thr
1               5                   10                  15

Ala Leu Leu Glu Gln Ala Gln Ile Gln Gln Glu Lys Asn Glu Tyr Glu
            20                  25                  30

Leu Gln Lys Leu Asp Glu Trp Ala Ser Leu Trp Glu Trp Phe
        35                  40                  45
```

<210> SEQ ID NO 1090
<211> LENGTH: 48

```
<212> TYPE: PRT
<213> ORGANISM: Artificial Sequence
<220> FEATURE:
<223> OTHER INFORMATION: Core polypeptide

<400> SEQUENCE: 1090

Cys Trp Gln Glu Trp Asp Arg Glu Ile Ser Asn Tyr Thr Ser Leu Ile
 1               5                  10                  15

Thr Ala Leu Leu Glu Gln Ala Gln Ile Gln Gln Glu Lys Asn Glu Tyr
            20                  25                  30

Glu Leu Gln Lys Leu Asp Glu Trp Ala Ser Leu Trp Glu Trp Phe Cys
        35                  40                  45

<210> SEQ ID NO 1091
<211> LENGTH: 42
<212> TYPE: PRT
<213> ORGANISM: Artificial Sequence
<220> FEATURE:
<223> OTHER INFORMATION: Core polypeptide

<400> SEQUENCE: 1091

Trp Gln Glu Trp Asp Arg Glu Ile Ser Asn Tyr Thr Ser Leu Ile Thr
 1               5                  10                  15

Ala Leu Leu Glu Gln Ala Gln Ile Gln Gln Glu Lys Asn Glu Tyr Glu
            20                  25                  30

Leu Gln Lys Leu Asp Glu Trp Glu Trp Phe
        35                  40

<210> SEQ ID NO 1092
<211> LENGTH: 44
<212> TYPE: PRT
<213> ORGANISM: Artificial Sequence
<220> FEATURE:
<223> OTHER INFORMATION: Core polypeptide

<400> SEQUENCE: 1092

Cys Trp Gln Glu Trp Asp Arg Glu Ile Ser Asn Tyr Thr Ser Leu Ile
 1               5                  10                  15

Thr Ala Leu Leu Glu Gln Ala Gln Ile Gln Gln Glu Lys Asn Glu Tyr
            20                  25                  30

Glu Leu Gln Lys Leu Asp Glu Trp Glu Trp Phe Cys
        35                  40

<210> SEQ ID NO 1093
<211> LENGTH: 26
<212> TYPE: PRT
<213> ORGANISM: Artificial Sequence
<220> FEATURE:
<223> OTHER INFORMATION: Core polypeptide

<400> SEQUENCE: 1093

Gly Gln Asn Ser Gln Ser Pro Thr Ser Asn His Ser Pro Thr Ser Ala
 1               5                  10                  15

Pro Pro Thr Ala Pro Gly Tyr Arg Trp Ala
            20                  25

<210> SEQ ID NO 1094
<211> LENGTH: 27
<212> TYPE: PRT
<213> ORGANISM: Artificial Sequence
<220> FEATURE:
<223> OTHER INFORMATION: Core polypeptide

<400> SEQUENCE: 1094
```

```
Pro Gly Ser Ser Thr Thr Ser Thr Gly Pro Ala Arg Thr Ala Leu Thr
 1               5                  10                  15

Thr Ala Gln Gly Thr Ser Leu Tyr Pro Ser Ala
             20                  25
```

<210> SEQ ID NO 1095
<211> LENGTH: 39
<212> TYPE: PRT
<213> ORGANISM: Artificial Sequence
<220> FEATURE:
<223> OTHER INFORMATION: Core polypeptide

<400> SEQUENCE: 1095

```
Pro Gly Ser Ser Thr Thr Ser Thr Gly Pro Ala Arg Thr Ala Leu Thr
 1               5                  10                  15

Thr Ala Gln Gly Thr Ser Leu Tyr Pro Ser Ala Ala Thr Lys Pro
             20                  25                  30

Ser Asp Gly Asn Ala Thr Ala
             35
```

<210> SEQ ID NO 1096
<211> LENGTH: 16
<212> TYPE: PRT
<213> ORGANISM: Artificial Sequence
<220> FEATURE:
<223> OTHER INFORMATION: Core polypeptide

<400> SEQUENCE: 1096

```
Gln Lys Gln Glu Pro Ile Asp Lys Glu Leu Tyr Pro Leu Thr Ser Leu
 1               5                  10                  15
```

<210> SEQ ID NO 1097
<211> LENGTH: 39
<212> TYPE: PRT
<213> ORGANISM: Artificial Sequence
<220> FEATURE:
<223> OTHER INFORMATION: Core polypeptide

<400> SEQUENCE: 1097

```
Trp Gln Glu Trp Asp Arg Glu Ile Thr Ala Leu Leu Glu Gln Ala Gln
 1               5                  10                  15

Ile Gln Gln Glu Lys Asn Glu Tyr Glu Leu Gln Lys Leu Asp Lys Trp
             20                  25                  30

Ala Ser Leu Trp Asn Trp Phe
             35
```

<210> SEQ ID NO 1098
<211> LENGTH: 39
<212> TYPE: PRT
<213> ORGANISM: Artificial Sequence
<220> FEATURE:
<223> OTHER INFORMATION: Core polypeptide

<400> SEQUENCE: 1098

```
Trp Gln Glu Trp Asp Arg Glu Ile Thr Ala Leu Leu Gln Ala Gln
 1               5                  10                  15

Ile Gln Gln Glu Lys Asn Glu Tyr Glu Leu Gln Lys Leu Asp Glu Trp
             20                  25                  30

Ala Ser Leu Trp Glu Trp Phe
             35
```

<210> SEQ ID NO 1099

```
<211> LENGTH: 35
<212> TYPE: PRT
<213> ORGANISM: Artificial Sequence
<220> FEATURE:
<223> OTHER INFORMATION: Core polypeptide

<400> SEQUENCE: 1099
```

Trp Gln Glu Trp Asp Arg Glu Ile Thr Ala Leu Leu Glu Gln Ala Gln
 1               5                  10                  15

Ile Gln Gln Glu Lys Asn Glu Tyr Glu Leu Gln Lys Leu Asp Glu Trp
            20                  25                  30

Glu Trp Phe
        35

```
<210> SEQ ID NO 1100
<211> LENGTH: 35
<212> TYPE: PRT
<213> ORGANISM: Artificial Sequence
<220> FEATURE:
<223> OTHER INFORMATION: Core polypeptide

<400> SEQUENCE: 1100
```

Trp Gln Glu Trp Glu Arg Glu Ile Thr Ala Leu Leu Glu Gln Ala Gln
 1               5                  10                  15

Ile Gln Gln Glu Lys Ile Glu Tyr Glu Leu Gln Lys Leu Ile Glu Trp
            20                  25                  30

Glu Trp Phe
        35

```
<210> SEQ ID NO 1101
<211> LENGTH: 35
<212> TYPE: PRT
<213> ORGANISM: Artificial Sequence
<220> FEATURE:
<223> OTHER INFORMATION: Core polypeptide

<400> SEQUENCE: 1101
```

Trp Gln Glu Trp Glu Arg Glu Ile Thr Ala Leu Leu Glu Gln Ala Gln
 1               5                  10                  15

Ile Gln Gln Glu Lys Asn Glu Tyr Glu Leu Gln Lys Leu Ile Glu Trp
            20                  25                  30

Glu Trp Phe
        35

```
<210> SEQ ID NO 1102
<211> LENGTH: 35
<212> TYPE: PRT
<213> ORGANISM: Artificial Sequence
<220> FEATURE:
<223> OTHER INFORMATION: Core polypeptide

<400> SEQUENCE: 1102
```

Trp Gln Glu Trp Glu Arg Glu Ile Thr Ala Leu Leu Glu Gln Ala Gln
 1               5                  10                  15

Ile Gln Gln Glu Lys Ile Glu Tyr Glu Leu Gln Lys Leu Asp Glu Trp
            20                  25                  30

Glu Trp Phe
        35

```
<210> SEQ ID NO 1103
<211> LENGTH: 33
<212> TYPE: PRT
<213> ORGANISM: Artificial Sequence
```

```
<220> FEATURE:
<223> OTHER INFORMATION: Core polypeptide

<400> SEQUENCE: 1103

Trp Gln Glu Trp Glu Ile Thr Ala Leu Leu Glu Gln Ala Gln Ile Gln
 1               5                  10                  15
Gln Glu Lys Asn Glu Tyr Glu Leu Gln Lys Leu Asp Glu Trp Glu Trp
                20                  25                  30
Phe

<210> SEQ ID NO 1104
<211> LENGTH: 33
<212> TYPE: PRT
<213> ORGANISM: Artificial Sequence
<220> FEATURE:
<223> OTHER INFORMATION: Core polypeptide

<400> SEQUENCE: 1104

Trp Gln Glu Trp Glu Ile Thr Ala Leu Leu Glu Gln Ala Gln Ile Gln
 1               5                  10                  15
Gln Glu Lys Asn Glu Tyr Glu Leu Gln Lys Leu Ile Glu Trp Glu Trp
                20                  25                  30
Phe

<210> SEQ ID NO 1105
<211> LENGTH: 33
<212> TYPE: PRT
<213> ORGANISM: Artificial Sequence
<220> FEATURE:
<223> OTHER INFORMATION: Core polypeptide

<400> SEQUENCE: 1105

Trp Gln Glu Trp Glu Ile Thr Ala Leu Leu Glu Gln Ala Gln Ile Gln
 1               5                  10                  15
Gln Glu Lys Ile Glu Tyr Glu Leu Gln Lys Leu Asp Glu Trp Glu Trp
                20                  25                  30
Phe

<210> SEQ ID NO 1106
<211> LENGTH: 33
<212> TYPE: PRT
<213> ORGANISM: Artificial Sequence
<220> FEATURE:
<223> OTHER INFORMATION: Core polypeptide

<400> SEQUENCE: 1106

Trp Gln Glu Trp Glu Ile Thr Ala Leu Leu Glu Gln Ala Gln Ile Gln
 1               5                  10                  15
Gln Glu Lys Ile Glu Tyr Glu Leu Gln Lys Leu Ile Glu Trp Glu Trp
                20                  25                  30
Phe

<210> SEQ ID NO 1107
<211> LENGTH: 39
<212> TYPE: PRT
<213> ORGANISM: Artificial Sequence
<220> FEATURE:
<223> OTHER INFORMATION: Core polypeptide

<400> SEQUENCE: 1107

Trp Gln Glu Trp Asp Arg Glu Ile Asp Glu Tyr Asp Ala Ser Ile Ser
 1               5                  10                  15
```

Gln Val Asn Glu Lys Ile Asn Gln Ala Leu Ala Tyr Ile Arg Glu Ala
            20                  25                  30

Asp Glu Leu Trp Glu Trp Phe
            35

<210> SEQ ID NO 1108
<211> LENGTH: 39
<212> TYPE: PRT
<213> ORGANISM: Artificial Sequence
<220> FEATURE:
<223> OTHER INFORMATION: Core polypeptide

<400> SEQUENCE: 1108

Trp Gln Glu Trp Glu Arg Glu Ile Asp Glu Tyr Asp Ala Ser Ile Ser
 1               5                  10                  15

Gln Val Asn Glu Lys Ile Asn Gln Ala Leu Ala Tyr Ile Arg Glu Ala
            20                  25                  30

Asp Glu Leu Trp Glu Trp Phe
            35

<210> SEQ ID NO 1109
<211> LENGTH: 37
<212> TYPE: PRT
<213> ORGANISM: Artificial Sequence
<220> FEATURE:
<223> OTHER INFORMATION: Core polypeptide

<400> SEQUENCE: 1109

Trp Gln Glu Trp Glu Ile Asp Glu Tyr Asp Ala Ser Ile Ser Gln Val
 1               5                  10                  15

Asn Glu Lys Ile Asn Gln Ala Leu Ala Tyr Ile Arg Glu Ala Asp Glu
            20                  25                  30

Leu Trp Glu Trp Phe
            35

<210> SEQ ID NO 1110
<211> LENGTH: 39
<212> TYPE: PRT
<213> ORGANISM: Artificial Sequence
<220> FEATURE:
<223> OTHER INFORMATION: Core polypeptide

<400> SEQUENCE: 1110

Trp Gln Glu Trp Asp Arg Glu Ile Asp Glu Tyr Asp Ala Ser Ile Ser
 1               5                  10                  15

Gln Val Asn Glu Glu Ile Asn Gln Ala Leu Ala Tyr Ile Arg Glu Ala
            20                  25                  30

Asp Glu Leu Trp Glu Trp Phe
            35

<210> SEQ ID NO 1111
<211> LENGTH: 39
<212> TYPE: PRT
<213> ORGANISM: Artificial Sequence
<220> FEATURE:
<223> OTHER INFORMATION: Core polypeptide

<400> SEQUENCE: 1111

Trp Gln Glu Trp Glu Arg Glu Ile Asp Glu Tyr Asp Ala Ser Ile Ser
 1               5                  10                  15

Gln Val Asn Glu Glu Ile Asn Gln Ala Leu Ala Tyr Ile Arg Glu Ala
            20                  25                  30

Asp Glu Leu Trp Glu Trp Phe
        35

<210> SEQ ID NO 1112
<211> LENGTH: 37
<212> TYPE: PRT
<213> ORGANISM: Artificial Sequence
<220> FEATURE:
<223> OTHER INFORMATION: Core polypeptide

<400> SEQUENCE: 1112

Trp Gln Glu Trp Glu Ile Asp Glu Tyr Asp Ala Ser Ile Ser Gln Val
1               5                   10                  15

Asn Glu Glu Ile Asn Gln Ala Leu Ala Tyr Ile Arg Glu Ala Asp Glu
            20                  25                  30

Leu Trp Glu Trp Phe
        35

<210> SEQ ID NO 1113
<211> LENGTH: 35
<212> TYPE: PRT
<213> ORGANISM: Artificial Sequence
<220> FEATURE:
<223> OTHER INFORMATION: Core polypeptide

<400> SEQUENCE: 1113

Trp Gln Glu Trp Asp Glu Tyr Asp Ala Ser Ile Ser Gln Val Asn Glu
1               5                   10                  15

Lys Ile Asn Gln Ala Leu Ala Tyr Ile Arg Glu Ala Asp Glu Leu Trp
            20                  25                  30

Glu Trp Phe
        35

<210> SEQ ID NO 1114
<211> LENGTH: 35
<212> TYPE: PRT
<213> ORGANISM: Artificial Sequence
<220> FEATURE:
<223> OTHER INFORMATION: Core polypeptide

<400> SEQUENCE: 1114

Trp Gln Glu Trp Asp Glu Tyr Asp Ala Ser Ile Ser Gln Val Asn Glu
1               5                   10                  15

Glu Ile Asn Gln Ala Leu Ala Tyr Ile Arg Glu Ala Asp Glu Leu Trp
            20                  25                  30

Glu Trp Phe
        35

<210> SEQ ID NO 1115
<211> LENGTH: 35
<212> TYPE: PRT
<213> ORGANISM: Artificial Sequence
<220> FEATURE:
<223> OTHER INFORMATION: Core polypeptide

<400> SEQUENCE: 1115

Trp Gln Glu Trp Glu Gln Lys Ile Thr Ala Leu Leu Glu Gln Ala Gln
1               5                   10                  15

Ile Gln Gln Glu Lys Ile Glu Tyr Glu Leu Gln Lys Leu Ile Glu Trp
            20                  25                  30

Glu Trp Phe
        35

<210> SEQ ID NO 1116
<211> LENGTH: 39
<212> TYPE: PRT
<213> ORGANISM: Artificial Sequence
<220> FEATURE:
<223> OTHER INFORMATION: Core polypeptide

<400> SEQUENCE: 1116

Trp Gln Glu Trp Glu Gln Lys Ile Thr Ala Leu Leu Glu Gln Ala Gln
 1               5                  10                  15

Ile Gln Gln Glu Lys Ile Glu Tyr Glu Leu Gln Lys Leu Ile Glu Trp
            20                  25                  30

Ala Ser Leu Trp Glu Trp Phe
        35

<210> SEQ ID NO 1117
<211> LENGTH: 37
<212> TYPE: PRT
<213> ORGANISM: Artificial Sequence
<220> FEATURE:
<223> OTHER INFORMATION: Core polypeptide

<400> SEQUENCE: 1117

Trp Gln Glu Trp Glu Ile Thr Ala Leu Leu Glu Gln Ala Gln Ile Gln
 1               5                  10                  15

Gln Glu Lys Ile Glu Tyr Glu Leu Gln Lys Leu Ile Glu Trp Ala Ser
            20                  25                  30

Leu Trp Glu Trp Phe
        35

<210> SEQ ID NO 1118
<211> LENGTH: 44
<212> TYPE: PRT
<213> ORGANISM: Artificial Sequence
<220> FEATURE:
<223> OTHER INFORMATION: Core polypeptide

<400> SEQUENCE: 1118

Asn His Thr Thr Trp Met Glu Trp Asp Arg Glu Ile Asn Asn Tyr Thr
 1               5                  10                  15

Ser Leu Ile His Ser Leu Ile Glu Glu Ser Gln Asn Gln Gln Glu Lys
            20                  25                  30

Asn Glu Gln Glu Leu Leu Glu Leu Asp Lys Trp His
        35                  40

<210> SEQ ID NO 1119
<211> LENGTH: 52
<212> TYPE: PRT
<213> ORGANISM: Artificial Sequence
<220> FEATURE:
<223> OTHER INFORMATION: Core polypeptide

<400> SEQUENCE: 1119

Gln Ala Arg Gln Leu Leu Ser Gly Ile Val Gln Gln Asn Asn Leu
 1               5                  10                  15

Leu Arg Ala Ile Glu Ala Gln Gln His Leu Leu Gln Leu Thr Val Trp
            20                  25                  30

Gly Ile Lys Gln Leu Gln Ala Arg Ile Leu Ala Val Glu Arg Tyr Leu
        35                  40                  45

Lys Asp Gln His
    50

<210> SEQ ID NO 1120
<211> LENGTH: 40
<212> TYPE: PRT
<213> ORGANISM: Artificial Sequence
<220> FEATURE:
<223> OTHER INFORMATION: Core polypeptide

<400> SEQUENCE: 1120

Trp Val Tyr Pro Ser Asp Glu Tyr Asp Ala Ser Ile Ser Gln Val Asn
1               5                   10                  15

Glu Glu Ile Asn Gln Ala Leu Ala Tyr Ile Arg Lys Ala Asp Glu Leu
            20                  25                  30

Leu Glu Asn Val Trp Asn Trp Phe
        35                  40

<210> SEQ ID NO 1121
<211> LENGTH: 36
<212> TYPE: PRT
<213> ORGANISM: Artificial Sequence
<220> FEATURE:
<223> OTHER INFORMATION: Core polypeptide

<400> SEQUENCE: 1121

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 1122
<211> LENGTH: 35
<212> TYPE: PRT
<213> ORGANISM: Artificial Sequence
<220> FEATURE:
<223> OTHER INFORMATION: Core polypeptide

<400> SEQUENCE: 1122

Trp Gln Glu Trp Asp Glu Tyr Asp Ala Ser Ile Ser Gln Val Asn Glu
1               5                   10                  15

Lys Ile Asn Gln Ala Leu Ala Tyr Ile Arg Glu Ala Asp Glu Leu Trp
            20                  25                  30

Ala Trp Phe
        35

<210> SEQ ID NO 1123
<211> LENGTH: 35
<212> TYPE: PRT
<213> ORGANISM: Artificial Sequence
<220> FEATURE:
<223> OTHER INFORMATION: Core polypeptide

<400> SEQUENCE: 1123

Trp Gln Ala Trp Asp Glu Tyr Asp Ala Ser Ile Ser Gln Val Asn Glu
1               5                   10                  15

Lys Ile Asn Gln Ala Leu Ala Tyr Ile Arg Glu Ala Asp Glu Leu Trp
            20                  25                  30

Ala Trp Phe
        35

<210> SEQ ID NO 1124

```
<211> LENGTH: 35
<212> TYPE: PRT
<213> ORGANISM: Artificial Sequence
<220> FEATURE:
<223> OTHER INFORMATION: Core polypeptide

<400> SEQUENCE: 1124

Trp Gln Ala Trp Asp Glu Tyr Asp Ala Ser Ile Ser Gln Val Asn Glu
 1               5                  10                  15

Lys Ile Asn Gln Ala Leu Ala Tyr Ile Arg Glu Ala Asp Glu Leu Trp
            20                  25                  30

Glu Trp Phe
        35

<210> SEQ ID NO 1125
<211> LENGTH: 35
<212> TYPE: PRT
<213> ORGANISM: Artificial Sequence
<220> FEATURE:
<223> OTHER INFORMATION: Core polypeptide

<400> SEQUENCE: 1125

Tyr Asp Pro Leu Val Phe Pro Ser Asp Glu Phe Asp Ala Ser Ile Ser
 1               5                  10                  15

Gln Val Asn Glu Lys Ile Asn Gln Ser Leu Ala Phe Ile Arg Lys Ser
            20                  25                  30

Asp Glu Leu
        35

<210> SEQ ID NO 1126
<211> LENGTH: 28
<212> TYPE: PRT
<213> ORGANISM: Artificial Sequence
<220> FEATURE:
<223> OTHER INFORMATION: Core polypeptide

<400> SEQUENCE: 1126

Tyr Asp Pro Leu Val Phe Pro Ser Asp Glu Phe Asp Ala Ser Ile Ser
 1               5                  10                  15

Gln Val Asn Glu Lys Ile Asn Gln Ser Leu Ala Phe
            20                  25

<210> SEQ ID NO 1127
<211> LENGTH: 29
<212> TYPE: PRT
<213> ORGANISM: Artificial Sequence
<220> FEATURE:
<223> OTHER INFORMATION: Core polypeptide

<400> SEQUENCE: 1127

Gln Val Asn Glu Lys Ile Asn Gln Ser Leu Ala Phe Ile Arg Lys Ser
 1               5                  10                  15

Asp Glu Leu Leu His Asn Val Asn Ala Gly Lys Ser Thr
            20                  25

<210> SEQ ID NO 1128
<211> LENGTH: 8
<212> TYPE: PRT
<213> ORGANISM: Artificial Sequence
<220> FEATURE:
<223> OTHER INFORMATION: Core polypeptide

<400> SEQUENCE: 1128

Trp Met Glu Trp Asp Arg Glu Ile
```

```
                           1               5

<210> SEQ ID NO 1129
<211> LENGTH: 8
<212> TYPE: PRT
<213> ORGANISM: Artificial Sequence
<220> FEATURE:
<223> OTHER INFORMATION: Core polypeptide

<400> SEQUENCE: 1129

Trp Gln Glu Trp Glu Gln Lys Ile
  1               5

<210> SEQ ID NO 1130
<211> LENGTH: 39
<212> TYPE: PRT
<213> ORGANISM: Artificial Sequence
<220> FEATURE:
<223> OTHER INFORMATION: Core polypeptide

<400> SEQUENCE: 1130

Trp Gln Glu Trp Glu Gln Lys Ile Thr Ala Leu Leu Glu Gln Ala Gln
  1               5                  10                  15

Ile Gln Gln Glu Lys Ile Glu Tyr Glu Leu Gln Lys Leu Ile Lys Trp
             20                  25                  30

Ala Ser Leu Trp Glu Trp Phe
         35

<210> SEQ ID NO 1131
<211> LENGTH: 39
<212> TYPE: PRT
<213> ORGANISM: Artificial Sequence
<220> FEATURE:
<223> OTHER INFORMATION: Core polypeptide

<400> SEQUENCE: 1131

Trp Gln Glu Trp Glu Gln Lys Ile Thr Ala Leu Leu Glu Gln Ala Gln
  1               5                  10                  15

Ile Gln Gln Glu Lys Ile Glu Tyr Glu Leu Gln Lys Leu Ile Glu Trp
             20                  25                  30

Ala Ser Leu Trp Glu Trp Phe
         35

<210> SEQ ID NO 1132
<211> LENGTH: 42
<212> TYPE: PRT
<213> ORGANISM: Artificial Sequence
<220> FEATURE:
<223> OTHER INFORMATION: Core polypeptide

<400> SEQUENCE: 1132

Trp Gln Glu Trp Glu Arg Glu Ile Ser Ala Tyr Thr Ser Leu Ile Thr
  1               5                  10                  15

Ala Leu Leu Glu Gln Ala Gln Ile Gln Gln Glu Lys Ile Glu Tyr Glu
             20                  25                  30

Leu Gln Lys Leu Ile Glu Trp Glu Trp Phe
         35                  40

<210> SEQ ID NO 1133
<211> LENGTH: 40
<212> TYPE: PRT
<213> ORGANISM: Artificial Sequence
<220> FEATURE:
<223> OTHER INFORMATION: Core polypeptide
```

```
<400> SEQUENCE: 1133

Trp Gln Glu Trp Glu Arg Glu Ile Ser Ala Tyr Thr Ser Leu Ile Thr
 1               5                  10                  15

Ala Leu Leu Glu Gln Ala Gln Ile Gln Gln Glu Lys Ile Glu Tyr Glu
            20                  25                  30

Leu Gln Lys Glu Trp Glu Trp Phe
        35                  40

<210> SEQ ID NO 1134
<211> LENGTH: 39
<212> TYPE: PRT
<213> ORGANISM: Artificial Sequence
<220> FEATURE:
<223> OTHER INFORMATION: Core polypeptide

<400> SEQUENCE: 1134

Trp Gln Glu Trp Glu Arg Glu Ile Ser Ala Tyr Thr Ser Leu Ile Thr
 1               5                  10                  15

Ala Leu Leu Glu Gln Ala Gln Ile Gln Gln Glu Lys Ile Glu Tyr Glu
            20                  25                  30

Leu Gln Lys Glu Trp Glu Trp
        35

<210> SEQ ID NO 1135
<211> LENGTH: 41
<212> TYPE: PRT
<213> ORGANISM: Artificial Sequence
<220> FEATURE:
<223> OTHER INFORMATION: Core polypeptide

<400> SEQUENCE: 1135

Trp Gln Glu Trp Glu Arg Glu Ile Ser Ala Tyr Thr Ser Leu Ile Thr
 1               5                  10                  15

Ala Leu Leu Glu Gln Ala Gln Ile Gln Gln Glu Lys Ile Glu Tyr Glu
            20                  25                  30

Leu Gln Lys Leu Ile Glu Trp Glu Trp
        35                  40

<210> SEQ ID NO 1136
<211> LENGTH: 36
<212> TYPE: PRT
<213> ORGANISM: Artificial Sequence
<220> FEATURE:
<223> OTHER INFORMATION: Core polypeptide

<400> SEQUENCE: 1136

Phe Asn Leu Ser Asp His Ser Glu Ser Ile Gln Lys Lys Phe Gln Leu
 1               5                  10                  15

Met Lys Lys His Val Asn Lys Ile Gly Val Asp Ser Asp Pro Ile Gly
            20                  25                  30

Ser Trp Leu Arg
        35

<210> SEQ ID NO 1137
<211> LENGTH: 35
<212> TYPE: PRT
<213> ORGANISM: Artificial Sequence
<220> FEATURE:
<223> OTHER INFORMATION: Core polypeptide

<400> SEQUENCE: 1137
```

-continued

Asp His Ser Glu Ser Ile Gln Lys Lys Phe Gln Leu Met Lys Lys His
1               5                   10                  15

Val Asn Lys Ile Gly Val Asp Ser Asp Pro Ile Gly Ser Trp Leu Arg
            20                  25                  30

Gly Ile Phe
        35

<210> SEQ ID NO 1138
<211> LENGTH: 40
<212> TYPE: PRT
<213> ORGANISM: Artificial Sequence
<220> FEATURE:
<223> OTHER INFORMATION: Core polypeptide

<400> SEQUENCE: 1138

Trp Ser Val Lys Gln Ala Asn Leu Thr Thr Ser Leu Leu Gly Asp Leu
1               5                   10                  15

Leu Asp Asp Val Thr Ser Ile Arg His Ala Val Leu Gln Asn Arg Ala
            20                  25                  30

Trp Met Glu Trp Asp Arg Glu Ile
        35                  40

<210> SEQ ID NO 1139
<211> LENGTH: 18
<212> TYPE: PRT
<213> ORGANISM: Artificial Sequence
<220> FEATURE:
<223> OTHER INFORMATION: Core polypeptide

<400> SEQUENCE: 1139

Asn Asn Met Thr Trp Met Glu Trp Asp Arg Glu Ile Asn Asn Tyr Thr
1               5                   10                  15

Ser Leu

<210> SEQ ID NO 1140
<211> LENGTH: 36
<212> TYPE: PRT
<213> ORGANISM: Artificial Sequence
<220> FEATURE:
<223> OTHER INFORMATION: Core polypeptide

<400> SEQUENCE: 1140

Gly Ala Ala Ser Leu Thr Leu Thr Val Gln Ala Arg Gln Leu Leu Ser
1               5                   10                  15

Gly Ile Val Gln Gln Gln Asn Asn Leu Leu Arg Ala Ile Glu Ala Gln
            20                  25                  30

Gln His Leu Leu
        35

<210> SEQ ID NO 1141
<211> LENGTH: 36
<212> TYPE: PRT
<213> ORGANISM: Artificial Sequence
<220> FEATURE:
<223> OTHER INFORMATION: Core polypeptide

<400> SEQUENCE: 1141

Ala Ser Leu Thr Leu Thr Val Gln Ala Arg Gln Leu Leu Ser Gly Ile
1               5                   10                  15

Val Gln Gln Gln Asn Asn Leu Leu Arg Ala Ile Glu Ala Gln Gln His
            20                  25                  30

Leu Leu Gln Leu

<210> SEQ ID NO 1142
<211> LENGTH: 34
<212> TYPE: PRT
<213> ORGANISM: Artificial Sequence
<220> FEATURE:
<223> OTHER INFORMATION: Core polypeptide

<400> SEQUENCE: 1142

Val Ser Val Gly Asn Thr Leu Tyr Tyr Val Asn Lys Gln Gly Lys
1               5                   10                  15

Ser Leu Tyr Val Lys Gly Glu Pro Ile Ile Asn Phe Tyr Asp Pro Leu
            20                  25                  30

Val Phe

<210> SEQ ID NO 1143
<211> LENGTH: 10
<212> TYPE: PRT
<213> ORGANISM: Artificial Sequence
<220> FEATURE:
<223> OTHER INFORMATION: Core polypeptide

<400> SEQUENCE: 1143

Gln His Trp Ser Tyr Gly Leu Arg Pro Gly
1               5                   10

<210> SEQ ID NO 1144
<211> LENGTH: 26
<212> TYPE: PRT
<213> ORGANISM: Artificial Sequence
<220> FEATURE:
<223> OTHER INFORMATION: Core polypeptide

<400> SEQUENCE: 1144

Trp Gln Glu Trp Glu Gln Lys Ile Gln His Trp Ser Tyr Gly Leu Arg
1               5                   10                  15

Pro Gly Trp Ala Ser Leu Trp Glu Trp Phe
            20                  25

<210> SEQ ID NO 1145
<211> LENGTH: 22
<212> TYPE: PRT
<213> ORGANISM: Artificial Sequence
<220> FEATURE:
<223> OTHER INFORMATION: Core polypeptide

<400> SEQUENCE: 1145

Trp Gln Glu Trp Glu Gln Lys Ile Gln His Trp Ser Tyr Gly Leu Arg
1               5                   10                  15

Pro Gly Trp Glu Trp Phe
            20

<210> SEQ ID NO 1146
<211> LENGTH: 18
<212> TYPE: PRT
<213> ORGANISM: Artificial Sequence
<220> FEATURE:
<223> OTHER INFORMATION: Core polypeptide

<400> SEQUENCE: 1146

Trp Asn Trp Phe Gln His Trp Ser Tyr Gly Leu Arg Pro Gly Trp Asn
1               5                   10                  15

Trp Phe

<210> SEQ ID NO 1147
<211> LENGTH: 18
<212> TYPE: PRT
<213> ORGANISM: Artificial Sequence
<220> FEATURE:
<223> OTHER INFORMATION: Core polypeptide

<400> SEQUENCE: 1147

Phe Asn Phe Phe Gln His Trp Ser Tyr Gly Leu Arg Pro Gly Phe Asn
 1               5                  10                  15

Phe Phe

<210> SEQ ID NO 1148
<211> LENGTH: 18
<212> TYPE: PRT
<213> ORGANISM: Artificial Sequence
<220> FEATURE:
<223> OTHER INFORMATION: Core polypeptide

<400> SEQUENCE: 1148

Gly Ala Gly Ala Gln His Trp Ser Tyr Gly Leu Arg Pro Gly Ala Gly
 1               5                  10                  15

Ala Gly

<210> SEQ ID NO 1149
<211> LENGTH: 39
<212> TYPE: PRT
<213> ORGANISM: Artificial Sequence
<220> FEATURE:
<223> OTHER INFORMATION: Core polypeptide

<400> SEQUENCE: 1149

Trp Gln Glu Trp Glu Gln Lys Ile Thr Ala Leu Leu Glu Gln Ala Gln
 1               5                  10                  15

Ile Gln Gln Glu Lys Ile Glu Tyr Glu Leu Gln Lys Leu Ala Lys Trp
            20                  25                  30

Ala Ser Leu Trp Glu Trp Phe
        35

<210> SEQ ID NO 1150
<211> LENGTH: 39
<212> TYPE: PRT
<213> ORGANISM: Artificial Sequence
<220> FEATURE:
<223> OTHER INFORMATION: Core polypeptide

<400> SEQUENCE: 1150

Trp Gln Glu Trp Glu Gln Lys Ile Thr Ala Leu Leu Glu Gln Ala Gln
 1               5                  10                  15

Ile Gln Gln Glu Lys Ile Glu Tyr Glu Leu Gln Lys Leu Ala Glu Trp
            20                  25                  30

Ala Ser Leu Trp Glu Trp Phe
        35

<210> SEQ ID NO 1151
<211> LENGTH: 39
<212> TYPE: PRT
<213> ORGANISM: Artificial Sequence
<220> FEATURE:
<223> OTHER INFORMATION: Core polypeptide

<400> SEQUENCE: 1151

Trp Gln Glu Trp Glu Gln Lys Ile Thr Ala Leu Leu Glu Gln Ala Gln
1               5                   10                  15

Ile Gln Gln Glu Lys Ala Glu Tyr Glu Leu Gln Lys Leu Ala Glu Trp
            20                  25                  30

Ala Ser Leu Trp Glu Trp Phe
            35

<210> SEQ ID NO 1152
<211> LENGTH: 39
<212> TYPE: PRT
<213> ORGANISM: Artificial Sequence
<220> FEATURE:
<223> OTHER INFORMATION: Core polypeptide

<400> SEQUENCE: 1152

Trp Gln Glu Trp Glu Gln Lys Ile Thr Ala Leu Leu Glu Gln Ala Gln
1               5                   10                  15

Ile Gln Gln Glu Lys Ala Glu Tyr Glu Leu Gln Lys Leu Ala Glu Trp
            20                  25                  30

Ala Ser Leu Trp Ala Trp Phe
            35

<210> SEQ ID NO 1153
<211> LENGTH: 39
<212> TYPE: PRT
<213> ORGANISM: Artificial Sequence
<220> FEATURE:
<223> OTHER INFORMATION: Core polypeptide

<400> SEQUENCE: 1153

Trp Gln Glu Trp Glu Gln Lys Ile Thr Ala Leu Leu Glu Gln Ala Gln
1               5                   10                  15

Ile Gln Gln Glu Lys Ala Glu Tyr Glu Leu Gln Lys Leu Ala Lys Trp
            20                  25                  30

Ala Ser Leu Trp Ala Trp Phe
            35

<210> SEQ ID NO 1154
<211> LENGTH: 36
<212> TYPE: PRT
<213> ORGANISM: Artificial Sequence
<220> FEATURE:
<223> OTHER INFORMATION: Core polypeptide

<400> SEQUENCE: 1154

Thr Asn Lys Ala Val Val Ser Leu Ser Asn Gly Val Ser Val Leu Thr
1               5                   10                  15

Ser Lys Val Leu Asp Leu Lys Asn Tyr Ile Asp Lys Gln Leu Leu Pro
            20                  25                  30

Ile Val Asn Lys
            35

<210> SEQ ID NO 1155
<211> LENGTH: 36
<212> TYPE: PRT
<213> ORGANISM: Artificial Sequence
<220> FEATURE:
<223> OTHER INFORMATION: Core polypeptide

<400> SEQUENCE: 1155

Lys Ala Val Val Ser Leu Ser Asn Gly Val Ser Val Leu Thr Ser Lys
1               5                   10                  15

```
Val Leu Asp Leu Lys Asn Tyr Ile Asp Lys Gln Leu Pro Ile Val
            20                  25                  30

Asn Lys Gln Ser
            35
```

<210> SEQ ID NO 1156
<211> LENGTH: 35
<212> TYPE: PRT
<213> ORGANISM: Artificial Sequence
<220> FEATURE:
<223> OTHER INFORMATION: Core polypeptide

<400> SEQUENCE: 1156

```
Trp Gln Glu Trp Glu Gln Lys Ile Thr Ala Leu Leu Glu Gln Ala Gln
  1               5                  10                  15

Ile Gln Gln Glu Lys Asn Glu Tyr Glu Leu Gln Lys Leu Ile Glu Trp
            20                  25                  30

Glu Trp Phe
            35
```

<210> SEQ ID NO 1157
<211> LENGTH: 35
<212> TYPE: PRT
<213> ORGANISM: Artificial Sequence
<220> FEATURE:
<223> OTHER INFORMATION: Core polypeptide

<400> SEQUENCE: 1157

```
Trp Gln Glu Trp Glu Gln Lys Ile Thr Ala Leu Leu Glu Gln Ala Gln
  1               5                  10                  15

Ile Gln Gln Glu Lys Gly Glu Tyr Glu Leu Gln Lys Leu Ile Glu Trp
            20                  25                  30

Glu Trp Phe
            35
```

<210> SEQ ID NO 1158
<211> LENGTH: 35
<212> TYPE: PRT
<213> ORGANISM: Artificial Sequence
<220> FEATURE:
<223> OTHER INFORMATION: Core polypeptide

<400> SEQUENCE: 1158

```
Trp Gln Glu Trp Glu Gln Lys Ile Thr Ala Leu Leu Glu Gln Ala Gln
  1               5                  10                  15

Ile Gln Gln Glu Lys Ile Glu Tyr Glu Leu Gln Lys Leu Asp Lys Trp
            20                  25                  30

Glu Trp Phe
            35
```

<210> SEQ ID NO 1159
<211> LENGTH: 28
<212> TYPE: PRT
<213> ORGANISM: Artificial Sequence
<220> FEATURE:
<223> OTHER INFORMATION: Core polypeptide

<400> SEQUENCE: 1159

```
Tyr Asp Pro Leu Val Phe Pro Ser Asp Glu Phe Asp Ala Ser Ile Ser
  1               5                  10                  15

Gln Val Asn Glu Lys Ile Asn Gln Ser Leu Ala Phe
            20                  25
```

-continued

```
<210> SEQ ID NO 1160
<211> LENGTH: 35
<212> TYPE: PRT
<213> ORGANISM: Artificial Sequence
<220> FEATURE:
<223> OTHER INFORMATION: Core polypeptide

<400> SEQUENCE: 1160

Val Tyr Pro Ser Asp Glu Tyr Asp Ala Ser Ile Ser Gln Val Asn Glu
 1               5                  10                  15

Glu Ile Asn Gln Ala Leu Ala Tyr Ile Arg Lys Ala Asp Glu Leu Leu
            20                  25                  30

Glu Asn Val
        35

<210> SEQ ID NO 1161
<211> LENGTH: 36
<212> TYPE: PRT
<213> ORGANISM: Artificial Sequence
<220> FEATURE:
<223> OTHER INFORMATION: Core polypeptide

<400> SEQUENCE: 1161

Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser Leu
            20                  25                  30

Trp Asn Trp Phe
        35

<210> SEQ ID NO 1162
<211> LENGTH: 36
<212> TYPE: PRT
<213> ORGANISM: Artificial Sequence
<220> FEATURE:
<223> OTHER INFORMATION: Core polypeptide

<400> SEQUENCE: 1162

Ser Gly Ile Val Gln Gln Gln Asn Asn Leu Leu Arg Ala Ile Glu Ala
 1               5                  10                  15

Gln Gln His Leu Leu Gln Leu Thr Val Trp Gly Ile Lys Gln Leu Gln
            20                  25                  30

Ala Arg Ile Leu
        35

<210> SEQ ID NO 1163
<211> LENGTH: 41
<212> TYPE: PRT
<213> ORGANISM: Artificial Sequence
<220> FEATURE:
<223> OTHER INFORMATION: Core polypeptide

<400> SEQUENCE: 1163

Gln Gln Gln Asn Asn Leu Leu Arg Ala Ile Glu Ala Gln Gln His Leu
 1               5                  10                  15

Leu Gln Leu Thr Val Trp Gly Ile Lys Gln Leu Gln Ala Arg Ile Leu
            20                  25                  30

Ala Val Glu Arg Tyr Leu Lys Asp Gln
        35                  40

<210> SEQ ID NO 1164
<211> LENGTH: 45
```

<212> TYPE: PRT
<213> ORGANISM: Artificial Sequence
<220> FEATURE:
<223> OTHER INFORMATION: Core polypeptide

<400> SEQUENCE: 1164

Ser Gly Ile Val Gln Gln Gln Asn Asn Leu Leu Arg Ala Ile Glu Ala
1               5                   10                  15

Gln Gln His Leu Leu Gln Leu Thr Val Trp Gly Ile Lys Gln Leu Gln
            20                  25                  30

Ala Arg Ile Leu Ala Val Glu Arg Tyr Leu Lys Asp Gln
        35                  40                  45

<210> SEQ ID NO 1165
<211> LENGTH: 39
<212> TYPE: PRT
<213> ORGANISM: Artificial Sequence
<220> FEATURE:
<223> OTHER INFORMATION: Core polypeptide

<400> SEQUENCE: 1165

Trp Gln Glu Trp Glu Gln Lys Ile Thr Ala Leu Leu Glu Gln Ala Gln
1               5                   10                  15

Ile Gln Gln Glu Lys Asn Glu Tyr Glu Leu Gln Lys Leu Ala Glu Trp
            20                  25                  30

Ala Ser Leu Trp Ala Trp Phe
        35

<210> SEQ ID NO 1166
<211> LENGTH: 38
<212> TYPE: PRT
<213> ORGANISM: Artificial Sequence
<220> FEATURE:
<223> OTHER INFORMATION: Core polypeptide

<400> SEQUENCE: 1166

Trp Gln Glu Trp Glu Gln Lys Ile Thr Ala Leu Leu Glu Gln Ala Gln
1               5                   10                  15

Ile Gln Gln Glu Lys Asn Glu Tyr Glu Leu Gln Lys Leu Ala Glu Trp
            20                  25                  30

Ala Ser Leu Trp Ala Trp
        35

<210> SEQ ID NO 1167
<211> LENGTH: 38
<212> TYPE: PRT
<213> ORGANISM: Artificial Sequence
<220> FEATURE:
<223> OTHER INFORMATION: Core polypeptide

<400> SEQUENCE: 1167

Trp Gln Glu Trp Glu Gln Lys Ile Thr Ala Leu Leu Glu Gln Ala Gln
1               5                   10                  15

Ile Gln Gln Glu Lys Ala Glu Tyr Glu Leu Gln Lys Leu Ala Glu Trp
            20                  25                  30

Ala Ser Leu Trp Ala Trp
        35

<210> SEQ ID NO 1168
<211> LENGTH: 39
<212> TYPE: PRT
<213> ORGANISM: Artificial Sequence
<220> FEATURE:

-continued

<223> OTHER INFORMATION: Core polypeptide

<400> SEQUENCE: 1168

Trp Gln Glu Trp Glu Gln Lys Ile Thr Ala Leu Leu Glu Gln Ala Gln
1               5                   10                  15

Ile Gln Gln Glu Lys Asn Glu Tyr Glu Leu Gln Lys Leu Ala Glu Trp
            20                  25                  30

Ala Gly Leu Trp Ala Trp Phe
        35

<210> SEQ ID NO 1169
<211> LENGTH: 38
<212> TYPE: PRT
<213> ORGANISM: Artificial Sequence
<220> FEATURE:
<223> OTHER INFORMATION: Core polypeptide

<400> SEQUENCE: 1169

Trp Gln Glu Trp Glu Gln Lys Ile Thr Ala Leu Leu Glu Gln Ala Gln
1               5                   10                  15

Ile Gln Gln Glu Lys Asn Glu Tyr Glu Leu Gln Lys Leu Ala Glu Trp
            20                  25                  30

Ala Gly Leu Trp Ala Trp
        35

<210> SEQ ID NO 1170
<211> LENGTH: 38
<212> TYPE: PRT
<213> ORGANISM: Artificial Sequence
<220> FEATURE:
<223> OTHER INFORMATION: Core polypeptide

<400> SEQUENCE: 1170

Trp Gln Glu Trp Glu Gln Lys Ile Thr Ala Leu Leu Glu Gln Ala Gln
1               5                   10                  15

Ile Gln Gln Glu Lys Ala Glu Tyr Glu Leu Gln Lys Leu Ala Glu Trp
            20                  25                  30

Ala Gly Leu Trp Ala Trp
        35

<210> SEQ ID NO 1171
<211> LENGTH: 39
<212> TYPE: PRT
<213> ORGANISM: Artificial Sequence
<220> FEATURE:
<223> OTHER INFORMATION: Core polypeptide

<400> SEQUENCE: 1171

Trp Gln Glu Trp Glu Gln Lys Ile Thr Ala Leu Leu Glu Gln Ala Gln
1               5                   10                  15

Ile Gln Gln Glu Lys Asn Glu Tyr Glu Leu Gln Lys Leu Asp Lys Trp
            20                  25                  30

Ala Gly Leu Trp Glu Trp Phe
        35

<210> SEQ ID NO 1172
<211> LENGTH: 18
<212> TYPE: PRT
<213> ORGANISM: Artificial Sequence
<220> FEATURE:
<223> OTHER INFORMATION: Core polypeptide

<400> SEQUENCE: 1172

-continued

Trp Gln Glu Trp Gln His Trp Ser Tyr Gly Leu Arg Pro Gly Trp Glu
1               5                   10                  15

Trp Phe

<210> SEQ ID NO 1173
<211> LENGTH: 18
<212> TYPE: PRT
<213> ORGANISM: Artificial Sequence
<220> FEATURE:
<223> OTHER INFORMATION: Core polypeptide

<400> SEQUENCE: 1173

Trp Gln Ala Trp Gln His Trp Ser Tyr Gly Leu Arg Pro Gly Trp Ala
1               5                   10                  15

Trp Phe

<210> SEQ ID NO 1174
<211> LENGTH: 39
<212> TYPE: PRT
<213> ORGANISM: Artificial Sequence
<220> FEATURE:
<223> OTHER INFORMATION: Core polypeptide

<400> SEQUENCE: 1174

Trp Gln Glu Trp Glu Gln Lys Ile Thr Ala Leu Leu Glu Gln Ala Gln
1               5                   10                  15

Ile Gln Gln Glu Lys Asn Glu Tyr Glu Leu Gln Lys Leu Asp Lys Trp
            20                  25                  30

Ala Ser Leu Trp Glu Trp Phe
        35

<210> SEQ ID NO 1175
<211> LENGTH: 39
<212> TYPE: PRT
<213> ORGANISM: Artificial Sequence
<220> FEATURE:
<223> OTHER INFORMATION: Core polypeptide

<400> SEQUENCE: 1175

Trp Gln Glu Trp Glu Gln Lys Ile Thr Ala Leu Leu Glu Gln Ala Gln
1               5                   10                  15

Ile Gln Gln Glu Lys Asn Glu Tyr Glu Leu Gln Lys Leu Asp Lys Trp
            20                  25                  30

Ala Ser Leu Trp Glu Trp Phe
        35

<210> SEQ ID NO 1176
<211> LENGTH: 35
<212> TYPE: PRT
<213> ORGANISM: Artificial Sequence
<220> FEATURE:
<223> OTHER INFORMATION: Core polypeptide

<400> SEQUENCE: 1176

Trp Gln Glu Trp Glu Gln Lys Ile Thr Ala Leu Leu Glu Gln Ala Gln
1               5                   10                  15

Ile Gln Gln Glu Lys Ile Glu Tyr Glu Leu Gln Lys Leu Ile Glu Trp
            20                  25                  30

Glu Trp Phe
        35

```
<210> SEQ ID NO 1177
<211> LENGTH: 34
<212> TYPE: PRT
<213> ORGANISM: Artificial Sequence
<220> FEATURE:
<223> OTHER INFORMATION: Core polypeptide

<400> SEQUENCE: 1177

Trp Gln Glu Trp Glu Gln Lys Ile Ala Leu Leu Glu Gln Ala Gln Ile
 1               5                  10                  15

Gln Gln Glu Lys Ile Glu Tyr Glu Leu Gln Lys Leu Ile Glu Trp Glu
            20                  25                  30

Trp Phe

<210> SEQ ID NO 1178
<211> LENGTH: 38
<212> TYPE: PRT
<213> ORGANISM: Artificial Sequence
<220> FEATURE:
<223> OTHER INFORMATION: Core polypeptide

<400> SEQUENCE: 1178

Trp Gln Glu Trp Glu Gln Lys Ile Ala Leu Leu Glu Gln Ala Gln Ile
 1               5                  10                  15

Gln Gln Glu Lys Asn Glu Tyr Glu Leu Gln Lys Leu Asp Lys Trp Ala
            20                  25                  30

Ser Leu Trp Glu Trp Phe
        35

<210> SEQ ID NO 1179
<211> LENGTH: 38
<212> TYPE: PRT
<213> ORGANISM: Artificial Sequence
<220> FEATURE:
<223> OTHER INFORMATION: Core polypeptide

<400> SEQUENCE: 1179

Ala Gly Ser Thr Met Gly Ala Arg Ser Met Thr Leu Thr Val Gln Ala
 1               5                  10                  15

Arg Gln Leu Leu Ser Gly Ile Val Gln Gln Asn Asn Leu Leu Arg
            20                  25                  30

Ala Ile Glu Ala Gln Gln
        35

<210> SEQ ID NO 1180
<211> LENGTH: 38
<212> TYPE: PRT
<213> ORGANISM: Artificial Sequence
<220> FEATURE:
<223> OTHER INFORMATION: Core polypeptide

<400> SEQUENCE: 1180

Ala Gly Ser Ala Met Gly Ala Ala Ser Leu Thr Leu Ser Ala Gln Ser
 1               5                  10                  15

Arg Thr Leu Leu Ala Gly Ile Val Gln Gln Gln Gln Leu Leu Asp
            20                  25                  30

Val Val Lys Arg Gln Gln
        35

<210> SEQ ID NO 1181
<211> LENGTH: 38
<212> TYPE: PRT
<213> ORGANISM: Artificial Sequence
```

```
<220> FEATURE:
<223> OTHER INFORMATION: Core polypeptide

<400> SEQUENCE: 1181

Ala Gly Ser Ala Met Gly Ala Ala Ser Thr Ala Leu Thr Ala Gln Ser
 1               5                  10                  15
Arg Thr Leu Leu Ala Gly Ile Val Gln Gln Gln Gln Leu Leu Asp
            20                  25                  30
Val Val Lys Arg Gln Gln
        35

<210> SEQ ID NO 1182
<211> LENGTH: 38
<212> TYPE: PRT
<213> ORGANISM: Artificial Sequence
<220> FEATURE:
<223> OTHER INFORMATION: Core polypeptide

<400> SEQUENCE: 1182

Ala Leu Thr Ala Gln Ser Arg Thr Leu Leu Ala Gly Ile Val Gln Gln
 1               5                  10                  15
Gln Gln Gln Leu Leu Asp Val Val Lys Arg Gln Gln Glu Leu Leu Arg
            20                  25                  30
Leu Thr Val Trp Gly Thr
        35

<210> SEQ ID NO 1183
<211> LENGTH: 38
<212> TYPE: PRT
<213> ORGANISM: Artificial Sequence
<220> FEATURE:
<223> OTHER INFORMATION: Core polypeptide

<400> SEQUENCE: 1183

Thr Leu Ser Ala Gln Ser Arg Thr Leu Leu Ala Gly Ile Val Gln Gln
 1               5                  10                  15
Gln Gln Gln Leu Leu Asp Val Val Lys Arg Gln Gln Glu Met Leu Arg
            20                  25                  30
Leu Thr Val Trp Gly Thr
        35

<210> SEQ ID NO 1184
<211> LENGTH: 38
<212> TYPE: PRT
<213> ORGANISM: Artificial Sequence
<220> FEATURE:
<223> OTHER INFORMATION: Core polypeptide

<400> SEQUENCE: 1184

Thr Leu Thr Val Gln Ala Arg Gln Leu Leu Ser Gly Ile Val Gln Gln
 1               5                  10                  15
Gln Asn Asn Leu Leu Arg Ala Ile Glu Ala Gln Gln His Leu Leu Gln
            20                  25                  30
Leu Thr Val Trp Gly Ile
        35

<210> SEQ ID NO 1185
<211> LENGTH: 35
<212> TYPE: PRT
<213> ORGANISM: Artificial Sequence
<220> FEATURE:
<223> OTHER INFORMATION: Core polypeptide
```

```
<400> SEQUENCE: 1185

Trp Gln Ala Trp Ile Glu Tyr Glu Ala Glu Leu Ser Gln Val Lys Glu
 1               5                  10                  15

Lys Ile Glu Gln Ser Leu Ala Tyr Ile Arg Glu Ala Asp Glu Leu Trp
            20                  25                  30

Ala Trp Phe
        35

<210> SEQ ID NO 1186
<211> LENGTH: 35
<212> TYPE: PRT
<213> ORGANISM: Artificial Sequence
<220> FEATURE:
<223> OTHER INFORMATION: Core polypeptide

<400> SEQUENCE: 1186

Trp Gln Ala Trp Ile Glu Tyr Glu Ala Ser Leu Ser Gln Ala Lys Glu
 1               5                  10                  15

Lys Ile Glu Glu Ser Lys Ala Tyr Ile Arg Glu Ala Asp Glu Leu Trp
            20                  25                  30

Ala Trp Phe
        35

<210> SEQ ID NO 1187
<211> LENGTH: 35
<212> TYPE: PRT
<213> ORGANISM: Artificial Sequence
<220> FEATURE:
<223> OTHER INFORMATION: Core polypeptide

<400> SEQUENCE: 1187

Trp Gln Ala Trp Ile Glu Tyr Glu Arg Leu Leu Val Gln Ala Lys Leu
 1               5                  10                  15

Lys Ile Ala Ile Ala Lys Leu Tyr Ile Ala Lys Glu Leu Leu Glu Trp
            20                  25                  30

Ala Trp Phe
        35

<210> SEQ ID NO 1188
<211> LENGTH: 35
<212> TYPE: PRT
<213> ORGANISM: Artificial Sequence
<220> FEATURE:
<223> OTHER INFORMATION: Core polypeptide

<400> SEQUENCE: 1188

Trp Gln Ala Trp Ile Glu Tyr Glu Arg Leu Leu Val Gln Val Lys Leu
 1               5                  10                  15

Lys Ile Ala Ile Ala Leu Leu Tyr Ile Ala Lys Glu Leu Leu Glu Trp
            20                  25                  30

Ala Trp Phe
        35

<210> SEQ ID NO 1189
<211> LENGTH: 35
<212> TYPE: PRT
<213> ORGANISM: Artificial Sequence
<220> FEATURE:
<223> OTHER INFORMATION: Core polypeptide

<400> SEQUENCE: 1189

Trp Gln Ala Trp Ile Glu Leu Glu Arg Leu Leu Val Gln Val Lys Leu
```

```
                1               5              10              15
Lys Leu Ala Ile Ala Lys Leu Glu Ile Ala Lys Glu Leu Leu Glu Trp
                20              25              30
Ala Trp Phe
        35

<210> SEQ ID NO 1190
<211> LENGTH: 19
<212> TYPE: PRT
<213> ORGANISM: Artificial Sequence
<220> FEATURE:
<223> OTHER INFORMATION: Core polypeptide

<400> SEQUENCE: 1190

Gly Glu Trp Thr Tyr Asp Asp Ala Thr Lys Thr Phe Thr Val Thr Glu
  1               5              10              15
Gly Gly His

<210> SEQ ID NO 1191
<211> LENGTH: 35
<212> TYPE: PRT
<213> ORGANISM: Artificial Sequence
<220> FEATURE:
<223> OTHER INFORMATION: Core polypeptide

<400> SEQUENCE: 1191

Trp Gln Glu Trp Glu Gln Lys Ile Gly Glu Trp Thr Tyr Asp Asp Ala
  1               5              10              15
Thr Lys Thr Phe Thr Val Thr Glu Gly Gly His Trp Ala Ser Leu Trp
                20              25              30
Glu Trp Phe
        35

<210> SEQ ID NO 1192
<211> LENGTH: 16
<212> TYPE: PRT
<213> ORGANISM: Artificial Sequence
<220> FEATURE:
<223> OTHER INFORMATION: Core polypeptide

<400> SEQUENCE: 1192

Gly Glu Trp Thr Tyr Asp Asp Ala Thr Lys Thr Phe Thr Val Thr Glu
  1               5              10              15

<210> SEQ ID NO 1193
<211> LENGTH: 32
<212> TYPE: PRT
<213> ORGANISM: Artificial Sequence
<220> FEATURE:
<223> OTHER INFORMATION: Core polypeptide

<400> SEQUENCE: 1193

Trp Gln Glu Trp Glu Gln Lys Ile Gly Glu Trp Thr Tyr Asp Asp Ala
  1               5              10              15
Thr Lys Thr Phe Thr Val Thr Glu Trp Ala Ser Leu Trp Glu Trp Phe
                20              25              30

<210> SEQ ID NO 1194
<211> LENGTH: 8
<212> TYPE: PRT
<213> ORGANISM: Artificial Sequence
<220> FEATURE:
<223> OTHER INFORMATION: Core polypeptide
```

```
<400> SEQUENCE: 1194

Met His Arg Phe Asp Tyr Arg Thr
1               5

<210> SEQ ID NO 1195
<211> LENGTH: 24
<212> TYPE: PRT
<213> ORGANISM: Artificial Sequence
<220> FEATURE:
<223> OTHER INFORMATION: Core polypeptide

<400> SEQUENCE: 1195

Trp Gln Glu Trp Glu Gln Lys Ile Met His Arg Phe Asp Tyr Arg Thr
1               5                   10                  15

Trp Ala Ser Leu Trp Glu Trp Phe
            20

<210> SEQ ID NO 1196
<211> LENGTH: 11
<212> TYPE: PRT
<213> ORGANISM: Artificial Sequence
<220> FEATURE:
<223> OTHER INFORMATION: Core polypeptide

<400> SEQUENCE: 1196

Met His Arg Phe Asn Trp Ser Thr Gly Gly Gly
1               5                   10

<210> SEQ ID NO 1197
<211> LENGTH: 27
<212> TYPE: PRT
<213> ORGANISM: Artificial Sequence
<220> FEATURE:
<223> OTHER INFORMATION: Core polypeptide

<400> SEQUENCE: 1197

Trp Gln Glu Trp Glu Gln Lys Ile Met His Arg Phe Asn Trp Ser Thr
1               5                   10                  15

Gly Gly Gly Trp Ala Ser Leu Trp Glu Trp Phe
            20                  25

<210> SEQ ID NO 1198
<211> LENGTH: 8
<212> TYPE: PRT
<213> ORGANISM: Artificial Sequence
<220> FEATURE:
<223> OTHER INFORMATION: Core polypeptide

<400> SEQUENCE: 1198

Met His Arg Phe Asn Trp Ser Thr
1               5

<210> SEQ ID NO 1199
<211> LENGTH: 24
<212> TYPE: PRT
<213> ORGANISM: Artificial Sequence
<220> FEATURE:
<223> OTHER INFORMATION: Core polypeptide

<400> SEQUENCE: 1199

Trp Gln Glu Trp Glu Gln Lys Ile Met His Arg Phe Asn Trp Ser Thr
1               5                   10                  15

Trp Ala Ser Leu Trp Glu Trp Phe
            20
```

```
<210> SEQ ID NO 1200
<211> LENGTH: 18
<212> TYPE: PRT
<213> ORGANISM: Artificial Sequence
<220> FEATURE:
<223> OTHER INFORMATION: Core polypeptide

<400> SEQUENCE: 1200

Leu Leu Val Pro Leu Ala Arg Ile Met Thr Met Ser Ser Val His Gly
 1               5                  10                  15

Gly Gly

<210> SEQ ID NO 1201
<211> LENGTH: 34
<212> TYPE: PRT
<213> ORGANISM: Artificial Sequence
<220> FEATURE:
<223> OTHER INFORMATION: Core polypeptide

<400> SEQUENCE: 1201

Trp Gln Glu Trp Glu Gln Lys Ile Leu Leu Val Pro Leu Ala Arg Ile
 1               5                  10                  15

Met Thr Met Ser Ser Val His Gly Gly Gly Trp Ala Ser Leu Trp Glu
                20                  25                  30

Trp Phe

<210> SEQ ID NO 1202
<211> LENGTH: 15
<212> TYPE: PRT
<213> ORGANISM: Artificial Sequence
<220> FEATURE:
<223> OTHER INFORMATION: Core polypeptide

<400> SEQUENCE: 1202

Leu Leu Val Pro Leu Ala Arg Ile Met Thr Met Ser Ser Val His
 1               5                  10                  15

<210> SEQ ID NO 1203
<211> LENGTH: 31
<212> TYPE: PRT
<213> ORGANISM: Artificial Sequence
<220> FEATURE:
<223> OTHER INFORMATION: Core polypeptide

<400> SEQUENCE: 1203

Trp Gln Glu Trp Glu Gln Lys Ile Leu Leu Val Pro Leu Ala Arg Ile
 1               5                  10                  15

Met Thr Met Ser Ser Val His Trp Ala Ser Leu Trp Glu Trp Phe
                20                  25                  30

<210> SEQ ID NO 1204
<211> LENGTH: 23
<212> TYPE: PRT
<213> ORGANISM: Artificial Sequence
<220> FEATURE:
<223> OTHER INFORMATION: Core polypeptide

<400> SEQUENCE: 1204

Thr Ala Leu Leu Glu Gln Ala Gln Ile Gln Gln Glu Lys Asn Glu Tyr
 1               5                  10                  15

Glu Leu Gln Lys Leu Asp Lys
                20
```

<210> SEQ ID NO 1205
<211> LENGTH: 23
<212> TYPE: PRT
<213> ORGANISM: Artificial Sequence
<220> FEATURE:
<223> OTHER INFORMATION: Core polypeptide

<400> SEQUENCE: 1205

Thr Ala Leu Leu Glu Gln Ala Gln Ile Gln Gln Glu Lys Asn Glu Tyr
1               5                   10                  15

Glu Leu Gln Lys Leu Asp Lys
            20

<210> SEQ ID NO 1206
<211> LENGTH: 23
<212> TYPE: PRT
<213> ORGANISM: Artificial Sequence
<220> FEATURE:
<223> OTHER INFORMATION: Core polypeptide

<400> SEQUENCE: 1206

Thr Ala Leu Leu Glu Gln Ala Gln Ile Gln Gln Glu Lys Ile Glu Tyr
1               5                   10                  15

Glu Leu Gln Lys Leu Ile Glu
            20

<210> SEQ ID NO 1207
<211> LENGTH: 23
<212> TYPE: PRT
<213> ORGANISM: Artificial Sequence
<220> FEATURE:
<223> OTHER INFORMATION: Core polypeptide

<400> SEQUENCE: 1207

Thr Ala Leu Leu Glu Gln Ala Gln Ile Gln Gln Glu Lys Ile Glu Tyr
1               5                   10                  15

Glu Leu Gln Lys Leu Ile Glu
            20

<210> SEQ ID NO 1208
<211> LENGTH: 47
<212> TYPE: PRT
<213> ORGANISM: Artificial Sequence
<220> FEATURE:
<223> OTHER INFORMATION: Core polypeptide

<400> SEQUENCE: 1208

Gln Ala Arg Gln Leu Leu Ser Gly Ile Val Gln Gln Gln Asn Asn Leu
1               5                   10                  15

Leu Arg Ala Ile Glu Ala Gln Gln His Leu Leu Gln Leu Thr Val Trp
            20                  25                  30

Gly Ile Lys Gln Leu Gln Ala Arg Ile Leu Ala Val Glu Arg Tyr
        35                  40                  45

<210> SEQ ID NO 1209
<211> LENGTH: 47
<212> TYPE: PRT
<213> ORGANISM: Artificial Sequence
<220> FEATURE:
<223> OTHER INFORMATION: Core polypeptide

<400> SEQUENCE: 1209

Gln Ala Arg Gln Leu Leu Ser Gly Ile Val Gln Gln Gln Asn Asn Leu
1               5                   10                  15

Leu Arg Ala Ile Glu Ala Gln Gln His Leu Leu Gln Leu Thr Val Trp
        20                  25                  30

Gly Ile Lys Gln Leu Gln Ala Arg Ile Leu Ala Val Glu Arg Tyr
        35                  40                  45

<210> SEQ ID NO 1210
<211> LENGTH: 36
<212> TYPE: PRT
<213> ORGANISM: Artificial Sequence
<220> FEATURE:
<223> OTHER INFORMATION: Core polypeptide

<400> SEQUENCE: 1210

Gly Ala Ala Ser Leu Thr Leu Ser Ala Gln Ser Arg Thr Leu Leu Ala
1               5                   10                  15

Gly Ile Val Gln Gln Gln Gln Leu Leu Asp Val Val Lys Arg Gln
        20                  25                  30

Gln Glu Met Leu
        35

<210> SEQ ID NO 1211
<211> LENGTH: 40
<212> TYPE: PRT
<213> ORGANISM: Artificial Sequence
<220> FEATURE:
<223> OTHER INFORMATION: Core polypeptide

<400> SEQUENCE: 1211

Gly Ser Ala Met Gly Ala Ala Ser Leu Thr Leu Ser Ala Gln Ser Arg
1               5                   10                  15

Thr Leu Leu Ala Gly Ile Val Gln Gln Gln Gln Leu Leu Asp Val
        20                  25                  30

Val Lys Arg Gln Gln Glu Met Leu
        35                  40

<210> SEQ ID NO 1212
<211> LENGTH: 36
<212> TYPE: PRT
<213> ORGANISM: Artificial Sequence
<220> FEATURE:
<223> OTHER INFORMATION: Core polypeptide

<400> SEQUENCE: 1212

Pro Ala Leu Ser Thr Gly Leu Ile His Leu His Gln Asn Ile Val Asp
1               5                   10                  15

Val Gln Phe Leu Phe Gly Val Gly Ser Ser Ile Ala Ser Trp Ala Ile
        20                  25                  30

Lys Trp Glu Tyr
        35

<210> SEQ ID NO 1213
<211> LENGTH: 33
<212> TYPE: PRT
<213> ORGANISM: Artificial Sequence
<220> FEATURE:
<223> OTHER INFORMATION: Core polypeptide

<400> SEQUENCE: 1213

Pro Ala Leu Ser Thr Gly Leu Ile His Leu His Gln Asn Ile Val Asp
1               5                   10                  15

Val Gln Phe Leu Tyr Gly Val Gly Ser Ser Ile Ala Ser Trp Ala Ile
        20                  25                  30

-continued

Lys

<210> SEQ ID NO 1214
<211> LENGTH: 34
<212> TYPE: PRT
<213> ORGANISM: Artificial Sequence
<220> FEATURE:
<223> OTHER INFORMATION: Core polypeptide

<400> SEQUENCE: 1214

Leu Ser Thr Thr Gln Trp Gln Val Leu Pro Ser Phe Thr Thr Leu Pro
 1               5                  10                  15

Ala Leu Ser Thr Gly Leu Ile His Leu His Gln Asn Ile Val Asp Val
            20                  25                  30

Gln Tyr

<210> SEQ ID NO 1215
<211> LENGTH: 31
<212> TYPE: PRT
<213> ORGANISM: Artificial Sequence
<220> FEATURE:
<223> OTHER INFORMATION: Core polypeptide

<400> SEQUENCE: 1215

Phe Arg Lys Phe Pro Glu Ala Thr Phe Ser Arg Gly Ser Gly Pro Arg
 1               5                  10                  15

Ile Thr Pro Arg Met Val Asp Phe Pro Phe Arg Leu Trp His Tyr
            20                  25                  30

<210> SEQ ID NO 1216
<211> LENGTH: 37
<212> TYPE: PRT
<213> ORGANISM: Artificial Sequence
<220> FEATURE:
<223> OTHER INFORMATION: Core polypeptide

<400> SEQUENCE: 1216

Asp Phe Pro Phe Arg Leu Trp His Phe Pro Thr Ile Asn Tyr Thr Ile
 1               5                  10                  15

Phe Lys Val Arg Leu Phe Val Gly Gly Val Glu His Arg Leu Glu Ala
            20                  25                  30

Ala Asn Trp Thr Arg
        35

<210> SEQ ID NO 1217
<211> LENGTH: 32
<212> TYPE: PRT
<213> ORGANISM: Artificial Sequence
<220> FEATURE:
<223> OTHER INFORMATION: Core polypeptide

<400> SEQUENCE: 1217

Tyr Val Gly Gly Val Glu His Arg Leu Glu Ala Ala Asn Trp Thr Arg
 1               5                  10                  15

Gly Glu Arg Asp Leu Glu Asp Arg Asp Arg Ser Glu Leu Ser Pro Leu
            20                  25                  30

<210> SEQ ID NO 1218
<211> LENGTH: 36
<212> TYPE: PRT
<213> ORGANISM: Artificial Sequence
<220> FEATURE:
<223> OTHER INFORMATION: Core polypeptide

<400> SEQUENCE: 1218

Met Val Tyr Pro Ser Asp Glu Tyr Asp Ala Ser Ile Ser Gln Val Asn
1               5                   10                  15

Glu Glu Ile Asn Gln Ala Leu Ala Tyr Ile Arg Lys Ala Asp Glu Leu
            20                  25                  30

Leu Glu Asn Val
        35

<210> SEQ ID NO 1219
<211> LENGTH: 36
<212> TYPE: PRT
<213> ORGANISM: Artificial Sequence
<220> FEATURE:
<223> OTHER INFORMATION: Core polypeptide

<400> SEQUENCE: 1219

Met Val Tyr Pro Ser Asp Glu Tyr Asp Ala Ser Ile Ser Gln Val Asn
1               5                   10                  15

Glu Glu Ile Asn Gln Ala Leu Ala Tyr Ile Arg Lys Ala Asp Glu Leu
            20                  25                  30

Leu Glu Asn Val
        35

<210> SEQ ID NO 1220
<211> LENGTH: 35
<212> TYPE: PRT
<213> ORGANISM: Artificial Sequence
<220> FEATURE:
<223> OTHER INFORMATION: Core polypeptide

<400> SEQUENCE: 1220

Gly Pro Leu Leu Val Leu Gln Ala Gly Phe Phe Leu Leu Thr Arg Ile
1               5                   10                  15

Leu Thr Ile Pro Gln Ser Leu Asp Ser Trp Trp Thr Ser Leu Asn Phe
            20                  25                  30

Leu Gly Gly
        35

<210> SEQ ID NO 1221
<211> LENGTH: 35
<212> TYPE: PRT
<213> ORGANISM: Artificial Sequence
<220> FEATURE:
<223> OTHER INFORMATION: Core polypeptide

<400> SEQUENCE: 1221

Leu Gly Pro Leu Leu Val Leu Gln Ala Gly Phe Phe Leu Leu Thr Arg
1               5                   10                  15

Ile Leu Thr Ile Pro Gln Ser Leu Asp Ser Trp Trp Thr Ser Leu Asn
            20                  25                  30

Phe Leu Gly
        35

<210> SEQ ID NO 1222
<211> LENGTH: 35
<212> TYPE: PRT
<213> ORGANISM: Artificial Sequence
<220> FEATURE:
<223> OTHER INFORMATION: Core polypeptide

<400> SEQUENCE: 1222

Phe Leu Gly Pro Leu Leu Val Leu Gln Ala Gly Phe Phe Leu Leu Thr

-continued

```
                1               5                  10                 15
Arg Ile Leu Thr Ile Pro Gln Ser Leu Asp Ser Trp Trp Thr Ser Leu
                    20                 25                 30
Asn Phe Leu
        35

<210> SEQ ID NO 1223
<211> LENGTH: 36
<212> TYPE: PRT
<213> ORGANISM: Artificial Sequence
<220> FEATURE:
<223> OTHER INFORMATION: Core polypeptide

<400> SEQUENCE: 1223

Tyr Thr Ser Leu Ile Gly Ser Leu Ile Glu Glu Ser Gln Ile Gln Gln
 1               5                  10                 15
Glu Arg Asn Glu Gln Glu Leu Leu Glu Leu Asp Arg Trp Ala Ser Leu
                    20                 25                 30
Trp Glu Trp Phe
        35

<210> SEQ ID NO 1224
<211> LENGTH: 34
<212> TYPE: PRT
<213> ORGANISM: Artificial Sequence
<220> FEATURE:
<223> OTHER INFORMATION: Core polypeptide

<400> SEQUENCE: 1224

Val Tyr Pro Ser Asp Glu Tyr Asp Ala Ser Ile Ser Gln Val Asn Glu
 1               5                  10                 15
Glu Ile Asn Gln Ala Leu Ala Tyr Ile Arg Lys Ala Asp Glu Leu Leu
                    20                 25                 30
Glu His

<210> SEQ ID NO 1225
<211> LENGTH: 33
<212> TYPE: PRT
<213> ORGANISM: Artificial Sequence
<220> FEATURE:
<223> OTHER INFORMATION: Core polypeptide

<400> SEQUENCE: 1225

Val Tyr Pro Ser Asp Glu Tyr Asp Ala Ser Ile Ser Gln Val Asn Glu
 1               5                  10                 15
Glu Ile Asn Gln Ala Leu Ala Tyr Ile Arg Lys Ala Asp Glu Leu Leu
                    20                 25                 30
His

<210> SEQ ID NO 1226
<211> LENGTH: 32
<212> TYPE: PRT
<213> ORGANISM: Artificial Sequence
<220> FEATURE:
<223> OTHER INFORMATION: Core polypeptide

<400> SEQUENCE: 1226

Val Tyr Pro Ser Asp Glu Tyr Asp Ala Ser Ile Ser Gln Val Asn Glu
 1               5                  10                 15
Glu Ile Asn Gln Ala Leu Ala Tyr Ile Arg Lys Ala Asp Glu Leu His
                    20                 25                 30
```

<210> SEQ ID NO 1227
<211> LENGTH: 34
<212> TYPE: PRT
<213> ORGANISM: Artificial Sequence
<220> FEATURE:
<223> OTHER INFORMATION: Core polypeptide

<400> SEQUENCE: 1227

Tyr Pro Ser Asp Glu Tyr Asp Ala Ser Ile Ser Gln Val Asn Glu Glu
 1               5                  10                  15

Ile Asn Gln Ala Leu Ala Tyr Ile Arg Lys Ala Asp Glu Leu Leu Glu
                20                  25                  30

Asn Val

<210> SEQ ID NO 1228
<211> LENGTH: 33
<212> TYPE: PRT
<213> ORGANISM: Artificial Sequence
<220> FEATURE:
<223> OTHER INFORMATION: Core polypeptide

<400> SEQUENCE: 1228

Pro Ser Asp Glu Tyr Asp Ala Ser Ile Ser Gln Val Asn Glu Glu Ile
 1               5                  10                  15

Asn Gln Ala Leu Ala Tyr Ile Arg Lys Ala Asp Glu Leu Leu Glu Asn
                20                  25                  30

Val

<210> SEQ ID NO 1229
<211> LENGTH: 32
<212> TYPE: PRT
<213> ORGANISM: Artificial Sequence
<220> FEATURE:
<223> OTHER INFORMATION: Core polypeptide

<400> SEQUENCE: 1229

Ser Asp Glu Tyr Asp Ala Ser Ile Ser Gln Val Asn Glu Glu Ile Asn
 1               5                  10                  15

Gln Ala Leu Ala Tyr Ile Arg Lys Ala Asp Glu Leu Leu Glu Asn Val
                20                  25                  30

<210> SEQ ID NO 1230
<211> LENGTH: 31
<212> TYPE: PRT
<213> ORGANISM: Artificial Sequence
<220> FEATURE:
<223> OTHER INFORMATION: Core polypeptide

<400> SEQUENCE: 1230

Asp Glu Tyr Asp Ala Ser Ile Ser Gln Val Asn Glu Glu Ile Asn Gln
 1               5                  10                  15

Ala Leu Ala Tyr Ile Arg Lys Ala Asp Glu Leu Leu Glu Asn Val
                20                  25                  30

<210> SEQ ID NO 1231
<211> LENGTH: 35
<212> TYPE: PRT
<213> ORGANISM: Artificial Sequence
<220> FEATURE:
<223> OTHER INFORMATION: Core polypeptide

<400> SEQUENCE: 1231

Val Tyr Pro Ser Asp Glu Tyr Asp Ala Ser Ile Ser Gln Val Asp Glu

```
                 1               5                  10                 15
Glu Ile Asn Gln Ala Leu Ala Tyr Ile Arg Lys Ala Asp Glu Leu Leu
                20                 25                 30

Glu Asn Val
         35

<210> SEQ ID NO 1232
<211> LENGTH: 35
<212> TYPE: PRT
<213> ORGANISM: Artificial Sequence
<220> FEATURE:
<223> OTHER INFORMATION: Core polypeptide

<400> SEQUENCE: 1232

Val Tyr Pro Ser Asp Glu Tyr Asp Ala Ser Ile Ser Gln Val Asn Glu
 1               5                  10                 15

Glu Ile Asp Gln Ala Leu Ala Tyr Ile Arg Lys Ala Asp Glu Leu Leu
                20                 25                 30

Glu Asn Val
         35

<210> SEQ ID NO 1233
<211> LENGTH: 35
<212> TYPE: PRT
<213> ORGANISM: Artificial Sequence
<220> FEATURE:
<223> OTHER INFORMATION: Core polypeptide

<400> SEQUENCE: 1233

Val Tyr Pro Ser Asp Glu Tyr Asp Ala Ser Ile Ser Gln Val Asn Glu
 1               5                  10                 15

Glu Ile Asn Gln Ala Leu Ala Tyr Ile Arg Lys Ala Asp Glu Leu Leu
                20                 25                 30

Glu Asp Val
         35

<210> SEQ ID NO 1234
<211> LENGTH: 35
<212> TYPE: PRT
<213> ORGANISM: Artificial Sequence
<220> FEATURE:
<223> OTHER INFORMATION: Core polypeptide

<400> SEQUENCE: 1234

Val Tyr Pro Ser Asp Glu Tyr Asp Ala Ser Ile Ser Gln Val Asp Glu
 1               5                  10                 15

Glu Ile Asp Gln Ala Leu Ala Tyr Ile Arg Lys Ala Asp Glu Leu Leu
                20                 25                 30

Glu Asn Val
         35

<210> SEQ ID NO 1235
<211> LENGTH: 35
<212> TYPE: PRT
<213> ORGANISM: Artificial Sequence
<220> FEATURE:
<223> OTHER INFORMATION: Core polypeptide

<400> SEQUENCE: 1235

Leu Leu Ser Thr Asn Lys Ala Val Val Ser Leu Ser Asn Gly Val Ser
 1               5                  10                 15

Val Leu Thr Ser Lys Val Leu Asp Leu Lys Asn Tyr Ile Asp Lys Gln
```

-continued

```
                20                  25                  30

Leu Leu Pro
        35

<210> SEQ ID NO 1236
<211> LENGTH: 35
<212> TYPE: PRT
<213> ORGANISM: Artificial Sequence
<220> FEATURE:
<223> OTHER INFORMATION: Core polypeptide

<400> SEQUENCE: 1236

Leu Ser Thr Asn Lys Ala Val Val Ser Leu Ser Asn Gly Val Ser Val
 1               5                  10                  15

Leu Thr Ser Lys Val Leu Asp Leu Lys Asn Tyr Ile Asp Lys Gln Leu
                20                  25                  30

Leu Pro Ile
        35

<210> SEQ ID NO 1237
<211> LENGTH: 35
<212> TYPE: PRT
<213> ORGANISM: Artificial Sequence
<220> FEATURE:
<223> OTHER INFORMATION: Core polypeptide

<400> SEQUENCE: 1237

Val Tyr Pro Ser Asp Glu Tyr Asp Ala Ser Ile Ser Gln Val Asn Glu
 1               5                  10                  15

Glu Ile Asn Gln Ala Leu Ala Tyr Ile Arg Lys Ala Asp Glu Leu Leu
                20                  25                  30

Glu Asn Val
        35

<210> SEQ ID NO 1238
<211> LENGTH: 27
<212> TYPE: PRT
<213> ORGANISM: Artificial Sequence
<220> FEATURE:
<223> OTHER INFORMATION: Core polypeptide

<400> SEQUENCE: 1238

Asp Glu Tyr Asp Ala Ser Ile Ser Gln Val Asn Glu Glu Ile Asn Gln
 1               5                  10                  15

Ala Leu Ala Tyr Ile Arg Glu Ala Asp Glu Leu
                20                  25

<210> SEQ ID NO 1239
<211> LENGTH: 27
<212> TYPE: PRT
<213> ORGANISM: Artificial Sequence
<220> FEATURE:
<223> OTHER INFORMATION: Core polypeptide

<400> SEQUENCE: 1239

Asp Glu Tyr Asp Ala Ser Ile Ser Gln Val Asn Glu Lys Ile Asn Gln
 1               5                  10                  15

Ala Leu Ala Tyr Ile Arg Glu Ala Asp Glu Leu
                20                  25

<210> SEQ ID NO 1240
<211> LENGTH: 35
<212> TYPE: PRT
```

<213> ORGANISM: Artificial Sequence
<220> FEATURE:
<223> OTHER INFORMATION: Core polypeptide

<400> SEQUENCE: 1240

Asp Asp Glu Cys Leu Asn Ser Val Lys Asn Gly Thr Tyr Asp Phe Pro
1               5                   10                  15

Lys Phe Glu Glu Glu Ser Lys Leu Asn Arg Asn Glu Ile Lys Gly Val
            20                  25                  30

Lys Leu Ser
        35

<210> SEQ ID NO 1241
<211> LENGTH: 36
<212> TYPE: PRT
<213> ORGANISM: Artificial Sequence
<220> FEATURE:
<223> OTHER INFORMATION: Core polypeptide

<400> SEQUENCE: 1241

Asp Asp Glu Ala Asx Leu Asn Ser Val Lys Asn Gly Thr Tyr Asp Phe
1               5                   10                  15

Pro Lys Phe Glu Glu Glu Ser Lys Leu Asn Arg Asn Glu Ile Lys Gly
            20                  25                  30

Val Lys Leu Ser
        35

<210> SEQ ID NO 1242
<211> LENGTH: 40
<212> TYPE: PRT
<213> ORGANISM: Artificial Sequence
<220> FEATURE:
<223> OTHER INFORMATION: Core polypeptide

<400> SEQUENCE: 1242

Tyr His Lys Cys Asp Asp Glu Cys Leu Asn Ser Val Lys Asn Gly Thr
1               5                   10                  15

Phe Asp Phe Pro Lys Phe Glu Glu Glu Ser Lys Leu Asn Arg Asn Glu
            20                  25                  30

Ile Lys Gly Val Lys Leu Ser Ser
        35                  40

<210> SEQ ID NO 1243
<211> LENGTH: 42
<212> TYPE: PRT
<213> ORGANISM: Artificial Sequence
<220> FEATURE:
<223> OTHER INFORMATION: Core polypeptide

<400> SEQUENCE: 1243

Tyr His Lys Ala Asx Asp Asp Glu Ala Asx Leu Asn Ser Val Lys Asn
1               5                   10                  15

Gly Thr Phe Asp Phe Pro Lys Phe Glu Glu Glu Ser Lys Leu Asn Arg
            20                  25                  30

Asn Glu Ile Lys Gly Val Lys Leu Ser Ser
        35                  40

<210> SEQ ID NO 1244
<211> LENGTH: 36
<212> TYPE: PRT
<213> ORGANISM: Artificial Sequence
<220> FEATURE:
<223> OTHER INFORMATION: Core polypeptide

```
<400> SEQUENCE: 1244

Tyr Thr Ser Leu Ile His Ser Leu Ile Glu Glu Ser Gln Ile Gln Gln
 1               5                  10                  15
Glu Lys Asn Glu Tyr Glu Leu Gln Lys Leu Asp Lys Trp Ala Ser Leu
            20                  25                  30
Trp Asn Trp Phe
        35

<210> SEQ ID NO 1245
<211> LENGTH: 36
<212> TYPE: PRT
<213> ORGANISM: Artificial Sequence
<220> FEATURE:
<223> OTHER INFORMATION: Core polypeptide

<400> SEQUENCE: 1245

Tyr Thr Ser Leu Ile His Ser Leu Ile Glu Glu Ser Gln Asn Gln Gln
 1               5                  10                  15
Glu Lys Asn Glu Gln Glu Leu Gln Lys Leu Asp Lys Trp Ala Ser Leu
            20                  25                  30
Trp Asn Trp Phe
        35

<210> SEQ ID NO 1246
<211> LENGTH: 36
<212> TYPE: PRT
<213> ORGANISM: Artificial Sequence
<220> FEATURE:
<223> OTHER INFORMATION: Core polypeptide

<400> SEQUENCE: 1246

Tyr Thr Ser Leu Ile His Ser Leu Ile Glu Glu Ser Gln Asn Gln Gln
 1               5                  10                  15
Glu Lys Asn Glu Tyr Glu Leu Gln Lys Leu Asp Lys Trp Ala Ser Leu
            20                  25                  30
Trp Asn Trp Phe
        35

<210> SEQ ID NO 1247
<211> LENGTH: 36
<212> TYPE: PRT
<213> ORGANISM: Artificial Sequence
<220> FEATURE:
<223> OTHER INFORMATION: Core polypeptide

<400> SEQUENCE: 1247

Tyr Thr Ser Leu Ile His Ser Leu Ile Glu Glu Ser Gln Ile Gln Gln
 1               5                  10                  15
Glu Lys Asn Glu Gln Glu Leu Gln Lys Leu Asp Lys Trp Ala Ser Leu
            20                  25                  30
Trp Asn Trp Phe
        35

<210> SEQ ID NO 1248
<211> LENGTH: 36
<212> TYPE: PRT
<213> ORGANISM: Artificial Sequence
<220> FEATURE:
<223> OTHER INFORMATION: Core polypeptide

<400> SEQUENCE: 1248
```

Tyr Thr Ser Leu Ile His Ser Leu Ile Glu Glu Ser Gln Asn Gln Gln
1               5                   10                  15

Glu Lys Asn Glu Gln Glu Leu Leu Glu Leu Asp Lys Trp Ala Ser Leu
            20                  25                  30

Trp Glu Trp Phe
        35

<210> SEQ ID NO 1249
<211> LENGTH: 36
<212> TYPE: PRT
<213> ORGANISM: Artificial Sequence
<220> FEATURE:
<223> OTHER INFORMATION: Core polypeptide

<400> SEQUENCE: 1249

Tyr Thr Ser Leu Ile His Ser Leu Ile Glu Glu Ser Gln Ile Gln Gln
1               5                   10                  15

Glu Lys Asn Glu Gln Glu Leu Leu Glu Leu Asp Lys Trp Ala Ser Leu
            20                  25                  30

Trp Glu Trp Phe
        35

<210> SEQ ID NO 1250
<211> LENGTH: 36
<212> TYPE: PRT
<213> ORGANISM: Artificial Sequence
<220> FEATURE:
<223> OTHER INFORMATION: Core polypeptide

<400> SEQUENCE: 1250

Tyr Thr Ser Leu Ile His Ser Leu Ile Glu Glu Ser Gln Asn Gln Gln
1               5                   10                  15

Glu Lys Asn Glu Tyr Glu Leu Leu Glu Leu Asp Lys Trp Ala Ser Leu
            20                  25                  30

Trp Glu Trp Phe
        35

<210> SEQ ID NO 1251
<211> LENGTH: 36
<212> TYPE: PRT
<213> ORGANISM: Artificial Sequence
<220> FEATURE:
<223> OTHER INFORMATION: Core polypeptide

<400> SEQUENCE: 1251

Tyr Thr Ser Leu Ile His Ser Leu Ile Glu Glu Ser Gln Ile Gln Gln
1               5                   10                  15

Glu Lys Asn Glu Tyr Glu Leu Leu Glu Leu Asp Lys Trp Ala Ser Leu
            20                  25                  30

Trp Glu Trp Phe
        35

<210> SEQ ID NO 1252
<211> LENGTH: 36
<212> TYPE: PRT
<213> ORGANISM: Artificial Sequence
<220> FEATURE:
<223> OTHER INFORMATION: Core polypeptide

<400> SEQUENCE: 1252

Tyr Thr Ser Leu Ile His Ser Leu Ile Glu Glu Ser Gln Ile Gln Gln
1               5                   10                  15

Glu Lys Asn Glu Tyr Glu Leu Gln Lys Leu Asp Lys Trp Ala Ser Leu
            20                  25                  30

Trp Glu Trp Phe
        35

<210> SEQ ID NO 1253
<211> LENGTH: 36
<212> TYPE: PRT
<213> ORGANISM: Artificial Sequence
<220> FEATURE:
<223> OTHER INFORMATION: Core polypeptide

<400> SEQUENCE: 1253

Tyr Thr Ser Leu Ile His Ser Leu Ile Glu Glu Ser Gln Asn Gln Gln
1               5                   10                  15

Glu Lys Asn Glu Gln Glu Leu Gln Lys Leu Asp Lys Trp Ala Ser Leu
            20                  25                  30

Trp Glu Trp Phe
        35

<210> SEQ ID NO 1254
<211> LENGTH: 36
<212> TYPE: PRT
<213> ORGANISM: Artificial Sequence
<220> FEATURE:
<223> OTHER INFORMATION: Core polypeptide

<400> SEQUENCE: 1254

Tyr Thr Ser Leu Ile His Ser Leu Ile Glu Glu Ser Gln Asn Gln Gln
1               5                   10                  15

Glu Lys Asn Glu Tyr Glu Leu Gln Lys Leu Asp Lys Trp Ala Ser Leu
            20                  25                  30

Trp Glu Trp Phe
        35

<210> SEQ ID NO 1255
<211> LENGTH: 36
<212> TYPE: PRT
<213> ORGANISM: Artificial Sequence
<220> FEATURE:
<223> OTHER INFORMATION: Core polypeptide

<400> SEQUENCE: 1255

Tyr Thr Ser Leu Ile His Ser Leu Ile Glu Glu Ser Gln Ile Gln Gln
1               5                   10                  15

Glu Lys Asn Glu Gln Glu Leu Gln Lys Leu Asp Lys Trp Ala Ser Leu
            20                  25                  30

Trp Glu Trp Phe
        35

<210> SEQ ID NO 1256
<211> LENGTH: 39
<212> TYPE: PRT
<213> ORGANISM: Artificial Sequence
<220> FEATURE:
<223> OTHER INFORMATION: Core polypeptide

<400> SEQUENCE: 1256

Trp Gln Glu Trp Glu Gln Lys Ile Thr Ala Leu Leu Glu Gln Ala Gln
1               5                   10                  15

Ile Gln Gln Glu Lys Asn Glu Tyr Glu Leu Gln Lys Leu Ala Lys Trp
            20                  25                  30

-continued

Ala Ser Leu Trp Glu Trp Phe
         35

<210> SEQ ID NO 1257
<211> LENGTH: 39
<212> TYPE: PRT
<213> ORGANISM: Artificial Sequence
<220> FEATURE:
<223> OTHER INFORMATION: Core polypeptide

<400> SEQUENCE: 1257

Trp Gln Glu Trp Glu Gln Lys Ile Thr Ala Leu Leu Glu Gln Ala Gln
 1               5                  10                  15

Ile Gln Gln Glu Lys Asn Glu Tyr Glu Leu Gln Lys Leu Ile Lys Trp
            20                  25                  30

Ala Ser Leu Trp Glu Trp Phe
         35

<210> SEQ ID NO 1258
<211> LENGTH: 39
<212> TYPE: PRT
<213> ORGANISM: Artificial Sequence
<220> FEATURE:
<223> OTHER INFORMATION: Core polypeptide

<400> SEQUENCE: 1258

Trp Gln Glu Trp Glu Gln Lys Ile Thr Ala Leu Leu Glu Gln Ala Gln
 1               5                  10                  15

Ile Gln Gln Glu Lys Asn Glu Tyr Glu Leu Gln Lys Leu Ile Glu Trp
            20                  25                  30

Ala Gly Leu Trp Glu Trp Phe
         35

<210> SEQ ID NO 1259
<211> LENGTH: 39
<212> TYPE: PRT
<213> ORGANISM: Artificial Sequence
<220> FEATURE:
<223> OTHER INFORMATION: Core polypeptide

<400> SEQUENCE: 1259

Trp Gln Glu Trp Glu Gln Lys Ile Thr Ala Leu Leu Glu Gln Ala Gln
 1               5                  10                  15

Ile Gln Gln Glu Lys Asn Glu Tyr Glu Leu Gln Lys Leu Ile Lys Trp
            20                  25                  30

Ala Gly Leu Trp Glu Trp Phe
         35

<210> SEQ ID NO 1260
<211> LENGTH: 39
<212> TYPE: PRT
<213> ORGANISM: Artificial Sequence
<220> FEATURE:
<223> OTHER INFORMATION: Core polypeptide

<400> SEQUENCE: 1260

Trp Gln Glu Trp Glu Gln Lys Ile Thr Ala Leu Leu Glu Gln Ala Gln
 1               5                  10                  15

Ile Gln Gln Glu Lys Asn Glu Tyr Glu Leu Gln Lys Leu Ala Lys Trp
            20                  25                  30

Ala Gly Leu Trp Glu Trp Phe
         35

```
<210> SEQ ID NO 1261
<211> LENGTH: 39
<212> TYPE: PRT
<213> ORGANISM: Artificial Sequence
<220> FEATURE:
<223> OTHER INFORMATION: Core polypeptide

<400> SEQUENCE: 1261

Trp Gln Glu Trp Glu Gln Lys Ile Thr Ala Leu Leu Glu Gln Ala Gln
 1               5                  10                  15

Ile Gln Gln Glu Lys Asn Glu Tyr Glu Leu Gln Lys Leu Ile Glu Trp
            20                  25                  30

Ala Gly Leu Trp Ala Trp Phe
        35

<210> SEQ ID NO 1262
<211> LENGTH: 39
<212> TYPE: PRT
<213> ORGANISM: Artificial Sequence
<220> FEATURE:
<223> OTHER INFORMATION: Core polypeptide

<400> SEQUENCE: 1262

Trp Gln Glu Trp Glu Gln Lys Ile Thr Ala Leu Leu Glu Gln Ala Gln
 1               5                  10                  15

Ile Gln Gln Glu Lys Asn Glu Tyr Glu Leu Gln Lys Leu Ala Lys Trp
            20                  25                  30

Ala Gly Leu Trp Ala Trp Phe
        35

<210> SEQ ID NO 1263
<211> LENGTH: 39
<212> TYPE: PRT
<213> ORGANISM: Artificial Sequence
<220> FEATURE:
<223> OTHER INFORMATION: Core polypeptide

<400> SEQUENCE: 1263

Trp Gln Glu Trp Glu Gln Lys Ile Thr Ala Leu Leu Glu Gln Ala Gln
 1               5                  10                  15

Ile Gln Gln Glu Lys Asn Glu Tyr Glu Leu Gln Lys Leu Ile Lys Trp
            20                  25                  30

Ala Gly Leu Trp Ala Trp Phe
        35

<210> SEQ ID NO 1264
<211> LENGTH: 35
<212> TYPE: PRT
<213> ORGANISM: Artificial Sequence
<220> FEATURE:
<223> OTHER INFORMATION: Core polypeptide

<400> SEQUENCE: 1264

Trp Gln Glu Trp Glu Gln Lys Ile Thr Ala Leu Leu Glu Gln Ala Gln
 1               5                  10                  15

Ile Gln Gln Glu Lys Gly Glu Tyr Glu Leu Gln Lys Leu Asp Lys Trp
            20                  25                  30

Glu Trp Phe
        35

<210> SEQ ID NO 1265
<211> LENGTH: 35
```

-continued

```
<212> TYPE: PRT
<213> ORGANISM: Artificial Sequence
<220> FEATURE:
<223> OTHER INFORMATION: Core polypeptide

<400> SEQUENCE: 1265
```

Trp Gln Glu Trp Glu Gln Lys Ile Thr Ala Leu Leu Glu Gln Ala Gln
1               5                   10                  15

Ile Gln Gln Glu Lys Gly Glu Tyr Glu Leu Leu Glu Leu Asp Lys Trp
            20                  25                  30

Glu Trp Phe
        35

```
<210> SEQ ID NO 1266
<211> LENGTH: 35
<212> TYPE: PRT
<213> ORGANISM: Artificial Sequence
<220> FEATURE:
<223> OTHER INFORMATION: Core polypeptide

<400> SEQUENCE: 1266
```

Trp Gln Glu Trp Glu Gln Lys Ile Thr Ala Leu Leu Glu Gln Ala Gln
1               5                   10                  15

Ile Gln Gln Glu Lys Gly Glu Tyr Glu Leu Gln Lys Leu Ala Lys Trp
            20                  25                  30

Glu Trp Phe
        35

```
<210> SEQ ID NO 1267
<211> LENGTH: 35
<212> TYPE: PRT
<213> ORGANISM: Artificial Sequence
<220> FEATURE:
<223> OTHER INFORMATION: Core polypeptide

<400> SEQUENCE: 1267
```

Trp Gln Glu Trp Glu Gln Lys Ile Thr Ala Leu Leu Glu Gln Ala Gln
1               5                   10                  15

Ile Gln Gln Glu Lys Gly Glu Tyr Glu Leu Gln Lys Leu Asp Glu Trp
            20                  25                  30

Glu Trp Phe
        35

```
<210> SEQ ID NO 1268
<211> LENGTH: 35
<212> TYPE: PRT
<213> ORGANISM: Artificial Sequence
<220> FEATURE:
<223> OTHER INFORMATION: Core polypeptide

<400> SEQUENCE: 1268
```

Trp Gln Glu Trp Glu Gln Lys Ile Thr Ala Leu Leu Glu Gln Ala Gln
1               5                   10                  15

Ile Gln Gln Glu Lys Gly Glu Tyr Glu Leu Leu Glu Leu Ala Lys Trp
            20                  25                  30

Glu Trp Phe
        35

```
<210> SEQ ID NO 1269
<211> LENGTH: 35
<212> TYPE: PRT
<213> ORGANISM: Artificial Sequence
<220> FEATURE:
```

<223> OTHER INFORMATION: Core polypeptide

<400> SEQUENCE: 1269

Trp Gln Glu Trp Glu Gln Lys Ile Thr Ala Leu Leu Glu Gln Ala Gln
1               5                   10                  15

Ile Gln Gln Glu Lys Asn Glu Tyr Glu Leu Leu Glu Leu Asp Lys Trp
            20                  25                  30

Glu Trp Phe
        35

<210> SEQ ID NO 1270
<211> LENGTH: 39
<212> TYPE: PRT
<213> ORGANISM: Artificial Sequence
<220> FEATURE:
<223> OTHER INFORMATION: Core polypeptide

<400> SEQUENCE: 1270

Trp Gln Glu Trp Glu Gln Lys Ile Thr Ala Leu Leu Glu Gln Ala Gln
1               5                   10                  15

Ile Gln Gln Glu Lys Asn Glu Tyr Glu Leu Leu Glu Leu Ile Glu Trp
            20                  25                  30

Ala Ser Leu Trp Glu Trp Phe
        35

<210> SEQ ID NO 1271
<211> LENGTH: 39
<212> TYPE: PRT
<213> ORGANISM: Artificial Sequence
<220> FEATURE:
<223> OTHER INFORMATION: Core polypeptide

<400> SEQUENCE: 1271

Trp Gln Glu Trp Glu Gln Lys Ile Thr Ala Leu Leu Glu Gln Ala Gln
1               5                   10                  15

Ile Gln Gln Glu Lys Asn Glu Tyr Glu Leu Leu Glu Leu Ile Glu Trp
            20                  25                  30

Ala Gly Leu Trp Glu Trp Phe
        35

<210> SEQ ID NO 1272
<211> LENGTH: 39
<212> TYPE: PRT
<213> ORGANISM: Artificial Sequence
<220> FEATURE:
<223> OTHER INFORMATION: Core polypeptide

<400> SEQUENCE: 1272

Trp Gln Glu Trp Glu Gln Lys Ile Thr Ala Leu Leu Glu Gln Ala Gln
1               5                   10                  15

Ile Gln Gln Glu Lys Asn Glu Tyr Glu Leu Leu Glu Leu Ile Glu Trp
            20                  25                  30

Ala Gly Leu Trp Ala Trp Phe
        35

<210> SEQ ID NO 1273
<211> LENGTH: 39
<212> TYPE: PRT
<213> ORGANISM: Artificial Sequence
<220> FEATURE:
<223> OTHER INFORMATION: Core polypeptide

<400> SEQUENCE: 1273

```
Trp Gln Glu Trp Glu Arg Glu Ile Thr Ala Leu Leu Glu Gln Ala Gln
1               5                   10                  15

Ile Gln Gln Glu Lys Asn Glu Tyr Glu Leu Gln Lys Leu Ile Glu Trp
            20                  25                  30

Ala Ser Leu Trp Glu Trp Phe
        35

<210> SEQ ID NO 1274
<211> LENGTH: 30
<212> TYPE: PRT
<213> ORGANISM: Artificial Sequence
<220> FEATURE:
<223> OTHER INFORMATION: Core polypeptide

<400> SEQUENCE: 1274

Trp Gln Glu Trp Glu Arg Glu Ile Gln Gln Glu Lys Asn Glu Tyr Glu
1               5                   10                  15

Leu Gln Lys Leu Asp Lys Trp Ala Ser Leu Trp Glu Trp Phe
            20                  25                  30

<210> SEQ ID NO 1275
<211> LENGTH: 25
<212> TYPE: PRT
<213> ORGANISM: Artificial Sequence
<220> FEATURE:
<223> OTHER INFORMATION: Core polypeptide

<400> SEQUENCE: 1275

Trp Gln Glu Trp Glu Arg Glu Ile Gln Gln Glu Lys Gly Glu Tyr Glu
1               5                   10                  15

Leu Gln Lys Leu Glu Trp Glu Trp Phe
            20                  25

<210> SEQ ID NO 1276
<211> LENGTH: 29
<212> TYPE: PRT
<213> ORGANISM: Artificial Sequence
<220> FEATURE:
<223> OTHER INFORMATION: Core polypeptide

<400> SEQUENCE: 1276

Trp Gln Glu Trp Gln Ala Gln Ile Gln Gln Glu Lys Asn Glu Tyr Glu
1               5                   10                  15

Leu Gln Lys Leu Asp Trp Ala Ser Leu Trp Glu Trp Phe
            20                  25

<210> SEQ ID NO 1277
<211> LENGTH: 26
<212> TYPE: PRT
<213> ORGANISM: Artificial Sequence
<220> FEATURE:
<223> OTHER INFORMATION: Core polypeptide

<400> SEQUENCE: 1277

Trp Gln Glu Trp Gln Ala Gln Ile Gln Gln Glu Lys Gly Glu Tyr Glu
1               5                   10                  15

Leu Gln Lys Leu Ile Glu Trp Glu Trp Phe
            20                  25

<210> SEQ ID NO 1278
<211> LENGTH: 28
<212> TYPE: PRT
<213> ORGANISM: Artificial Sequence
```

```
<220> FEATURE:
<223> OTHER INFORMATION: Core polypeptide

<400> SEQUENCE: 1278

Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys
            20                  25

<210> SEQ ID NO 1279
<211> LENGTH: 28
<212> TYPE: PRT
<213> ORGANISM: Artificial Sequence
<220> FEATURE:
<223> OTHER INFORMATION: Core polypeptide

<400> SEQUENCE: 1279

Leu Glu Glu Asn Ile Thr Ala Leu Leu Glu Glu Ala Gln Ile Gln Gln
 1               5                  10                  15

Glu Lys Asn Met Tyr Glu Leu Gln Lys Leu Asn Ser
            20                  25

<210> SEQ ID NO 1280
<211> LENGTH: 28
<212> TYPE: PRT
<213> ORGANISM: Artificial Sequence
<220> FEATURE:
<223> OTHER INFORMATION: Core polypeptide

<400> SEQUENCE: 1280

Leu Glu Ala Asn Ile Ser Gln Ser Leu Glu Gln Ala Gln Ile Gln Gln
 1               5                  10                  15

Glu Lys Asn Met Tyr Glu Leu Gln Lys Leu Asn Ser
            20                  25

<210> SEQ ID NO 1281
<211> LENGTH: 28
<212> TYPE: PRT
<213> ORGANISM: Artificial Sequence
<220> FEATURE:
<223> OTHER INFORMATION: Core polypeptide

<400> SEQUENCE: 1281

Asn Asn Tyr Thr Ser Leu Ile His Ser Leu Ile Glu Glu Ser Gln Asn
 1               5                  10                  15

Gln Gln Glu Lys Asn Glu Gln Glu Leu Leu Glu Leu
            20                  25

<210> SEQ ID NO 1282
<211> LENGTH: 28
<212> TYPE: PRT
<213> ORGANISM: Artificial Sequence
<220> FEATURE:
<223> OTHER INFORMATION: Core polypeptide

<400> SEQUENCE: 1282

Asp Phe Leu Glu Glu Asn Ile Thr Ala Leu Leu Glu Glu Ala Gln Ile
 1               5                  10                  15

Gln Gln Glu Lys Asn Met Tyr Glu Leu Gln Lys Leu
            20                  25

<210> SEQ ID NO 1283
<211> LENGTH: 28
<212> TYPE: PRT
```

```
<213> ORGANISM: Artificial Sequence
<220> FEATURE:
<223> OTHER INFORMATION: Core polypeptide

<400> SEQUENCE: 1283

Arg Tyr Leu Glu Ala Asn Ile Ser Gln Ser Leu Glu Gln Ala Gln Ile
 1               5                  10                  15

Gln Gln Glu Lys Asn Met Tyr Glu Leu Gln Lys Leu
            20                  25

<210> SEQ ID NO 1284
<211> LENGTH: 28
<212> TYPE: PRT
<213> ORGANISM: Artificial Sequence
<220> FEATURE:
<223> OTHER INFORMATION: Core polypeptide

<400> SEQUENCE: 1284

Arg Tyr Leu Glu Ala Asn Ile Thr Ala Leu Leu Glu Gln Ala Gln Ile
 1               5                  10                  15

Gln Gln Glu Lys Asn Glu Tyr Glu Leu Gln Lys Leu
            20                  25

<210> SEQ ID NO 1285
<211> LENGTH: 30
<212> TYPE: PRT
<213> ORGANISM: Artificial Sequence
<220> FEATURE:
<223> OTHER INFORMATION: Core polypeptide

<400> SEQUENCE: 1285

Asn Asn Tyr Thr Ser Leu Ile His Ser Leu Ile Glu Glu Ser Gln Asn
 1               5                  10                  15

Gln Gln Glu Lys Asn Glu Gln Glu Leu Leu Glu Leu Asp Lys
            20                  25                  30

<210> SEQ ID NO 1286
<211> LENGTH: 23
<212> TYPE: PRT
<213> ORGANISM: Artificial Sequence
<220> FEATURE:
<223> OTHER INFORMATION: Core polypeptide

<400> SEQUENCE: 1286

Thr Ala Leu Leu Glu Gln Ala Gln Ile Gln Gln Glu Lys Asn Glu Tyr
 1               5                  10                  15

Glu Leu Gln Lys Leu Asp Lys
            20

<210> SEQ ID NO 1287
<211> LENGTH: 23
<212> TYPE: PRT
<213> ORGANISM: Artificial Sequence
<220> FEATURE:
<223> OTHER INFORMATION: Core polypeptide

<400> SEQUENCE: 1287

Thr Ala Leu Leu Glu Gln Ala Gln Ile Gln Gln Glu Lys Asn Glu Tyr
 1               5                  10                  15

Glu Leu Gln Lys Leu Asp Glu
            20

<210> SEQ ID NO 1288
<211> LENGTH: 23
```

```
<212> TYPE: PRT
<213> ORGANISM: Artificial Sequence
<220> FEATURE:
<223> OTHER INFORMATION: Core polypeptide

<400> SEQUENCE: 1288

Thr Ala Leu Leu Glu Gln Ala Gln Ile Gln Gln Glu Lys Asn Glu Tyr
1               5                   10                  15

Glu Leu Gln Lys Leu Ile Glu
            20

<210> SEQ ID NO 1289
<211> LENGTH: 23
<212> TYPE: PRT
<213> ORGANISM: Artificial Sequence
<220> FEATURE:
<223> OTHER INFORMATION: Core polypeptide

<400> SEQUENCE: 1289

Thr Ala Leu Leu Glu Gln Ala Gln Ile Gln Gln Glu Lys Ile Glu Tyr
1               5                   10                  15

Glu Leu Gln Lys Leu Asp Lys
            20

<210> SEQ ID NO 1290
<211> LENGTH: 23
<212> TYPE: PRT
<213> ORGANISM: Artificial Sequence
<220> FEATURE:
<223> OTHER INFORMATION: Core polypeptide

<400> SEQUENCE: 1290

Thr Ala Leu Leu Glu Gln Ala Gln Ile Gln Gln Glu Lys Ile Glu Tyr
1               5                   10                  15

Glu Leu Gln Lys Leu Asp Glu
            20

<210> SEQ ID NO 1291
<211> LENGTH: 23
<212> TYPE: PRT
<213> ORGANISM: Artificial Sequence
<220> FEATURE:
<223> OTHER INFORMATION: Core polypeptide

<400> SEQUENCE: 1291

Thr Ala Leu Leu Glu Gln Ala Gln Ile Gln Gln Glu Lys Ile Glu Tyr
1               5                   10                  15

Glu Leu Gln Lys Leu Ile Glu
            20

<210> SEQ ID NO 1292
<211> LENGTH: 22
<212> TYPE: PRT
<213> ORGANISM: Artificial Sequence
<220> FEATURE:
<223> OTHER INFORMATION: Core polypeptide

<400> SEQUENCE: 1292

Thr Ala Leu Leu Glu Gln Ala Gln Ile Gln Gln Glu Lys Ile Glu Tyr
1               5                   10                  15

Glu Leu Gln Lys Leu Glu
            20

<210> SEQ ID NO 1293
```

```
<211> LENGTH: 23
<212> TYPE: PRT
<213> ORGANISM: Artificial Sequence
<220> FEATURE:
<223> OTHER INFORMATION: Core polypeptide

<400> SEQUENCE: 1293

Thr Ala Leu Leu Glu Gln Ala Gln Ile Gln Gln Glu Lys Ile Glu Tyr
1               5                   10                  15
Glu Leu Gln Lys Leu Ala Lys
            20

<210> SEQ ID NO 1294
<211> LENGTH: 23
<212> TYPE: PRT
<213> ORGANISM: Artificial Sequence
<220> FEATURE:
<223> OTHER INFORMATION: Core polypeptide

<400> SEQUENCE: 1294

Thr Ala Leu Leu Glu Gln Ala Gln Ile Gln Gln Glu Lys Ile Glu Tyr
1               5                   10                  15
Glu Leu Gln Lys Leu Ala Glu
            20

<210> SEQ ID NO 1295
<211> LENGTH: 22
<212> TYPE: PRT
<213> ORGANISM: Artificial Sequence
<220> FEATURE:
<223> OTHER INFORMATION: Core polypeptide

<400> SEQUENCE: 1295

Thr Ala Leu Leu Glu Gln Ala Gln Ile Gln Gln Glu Lys Ala Glu Tyr
1               5                   10                  15
Glu Leu Gln Lys Leu Glu
            20

<210> SEQ ID NO 1296
<211> LENGTH: 22
<212> TYPE: PRT
<213> ORGANISM: Artificial Sequence
<220> FEATURE:
<223> OTHER INFORMATION: Core polypeptide

<400> SEQUENCE: 1296

Thr Ala Leu Leu Glu Gln Ala Gln Ile Gln Gln Glu Lys Asn Glu Tyr
1               5                   10                  15
Glu Leu Gln Lys Leu Glu
            20

<210> SEQ ID NO 1297
<211> LENGTH: 22
<212> TYPE: PRT
<213> ORGANISM: Artificial Sequence
<220> FEATURE:
<223> OTHER INFORMATION: Core polypeptide

<400> SEQUENCE: 1297

Thr Ala Leu Leu Glu Gln Ala Gln Ile Gln Gln Glu Lys Gly Glu Tyr
1               5                   10                  15
Glu Leu Gln Lys Leu Glu
            20
```

```
<210> SEQ ID NO 1298
<211> LENGTH: 23
<212> TYPE: PRT
<213> ORGANISM: Artificial Sequence
<220> FEATURE:
<223> OTHER INFORMATION: Core polypeptide

<400> SEQUENCE: 1298

Thr Ala Leu Leu Glu Gln Ala Gln Ile Gln Gln Glu Lys Ala Glu Tyr
 1               5                  10                  15

Glu Leu Gln Lys Leu Ala Lys
            20

<210> SEQ ID NO 1299
<211> LENGTH: 23
<212> TYPE: PRT
<213> ORGANISM: Artificial Sequence
<220> FEATURE:
<223> OTHER INFORMATION: Core polypeptide

<400> SEQUENCE: 1299

Thr Ala Leu Leu Glu Gln Ala Gln Ile Gln Gln Glu Lys Asn Glu Tyr
 1               5                  10                  15

Glu Leu Gln Lys Leu Ala Lys
            20

<210> SEQ ID NO 1300
<211> LENGTH: 23
<212> TYPE: PRT
<213> ORGANISM: Artificial Sequence
<220> FEATURE:
<223> OTHER INFORMATION: Core polypeptide

<400> SEQUENCE: 1300

Thr Ala Leu Leu Glu Gln Ala Gln Ile Gln Gln Glu Lys Gly Glu Tyr
 1               5                  10                  15

Glu Leu Gln Lys Leu Ala Lys
            20

<210> SEQ ID NO 1301
<211> LENGTH: 23
<212> TYPE: PRT
<213> ORGANISM: Artificial Sequence
<220> FEATURE:
<223> OTHER INFORMATION: Core polypeptide

<400> SEQUENCE: 1301

Thr Ala Leu Leu Glu Gln Ala Gln Ile Gln Gln Glu Lys Ala Glu Tyr
 1               5                  10                  15

Glu Leu Gln Lys Leu Ala Glu
            20

<210> SEQ ID NO 1302
<211> LENGTH: 23
<212> TYPE: PRT
<213> ORGANISM: Artificial Sequence
<220> FEATURE:
<223> OTHER INFORMATION: Core polypeptide

<400> SEQUENCE: 1302

Thr Ala Leu Leu Glu Gln Ala Gln Ile Gln Gln Glu Lys Asn Glu Tyr
 1               5                  10                  15

Glu Leu Gln Lys Leu Ala Glu
            20
```

<210> SEQ ID NO 1303
<211> LENGTH: 23
<212> TYPE: PRT
<213> ORGANISM: Artificial Sequence
<220> FEATURE:
<223> OTHER INFORMATION: Core polypeptide

<400> SEQUENCE: 1303

Thr Ala Leu Leu Glu Gln Ala Gln Ile Gln Gln Glu Lys Gly Glu Tyr
1               5                   10                  15

Glu Leu Gln Lys Leu Ala Glu
            20

<210> SEQ ID NO 1304
<211> LENGTH: 28
<212> TYPE: PRT
<213> ORGANISM: Artificial Sequence
<220> FEATURE:
<223> OTHER INFORMATION: Core polypeptide

<400> SEQUENCE: 1304

Asp Glu Phe Asp Ala Ser Ile Ser Gln Val Asn Glu Lys Ile Asn Gln
1               5                   10                  15

Ser Leu Ala Phe Ile Arg Lys Ser Asp Glu Leu Leu
            20                  25

<210> SEQ ID NO 1305
<211> LENGTH: 27
<212> TYPE: PRT
<213> ORGANISM: Artificial Sequence
<220> FEATURE:
<223> OTHER INFORMATION: Core polypeptide

<400> SEQUENCE: 1305

Asp Glu Tyr Asp Ala Ser Ile Ser Gln Val Asn Glu Lys Ile Asn Gln
1               5                   10                  15

Ala Leu Ala Tyr Ile Arg Glu Ala Asp Glu Leu
            20                  25

<210> SEQ ID NO 1306
<211> LENGTH: 27
<212> TYPE: PRT
<213> ORGANISM: Artificial Sequence
<220> FEATURE:
<223> OTHER INFORMATION: Core polypeptide

<400> SEQUENCE: 1306

Asp Glu Tyr Asp Ala Ser Ile Ser Gln Val Asn Glu Glu Ile Asn Gln
1               5                   10                  15

Ala Leu Ala Tyr Ile Arg Lys Ala Asp Glu Leu
            20                  25

<210> SEQ ID NO 1307
<211> LENGTH: 28
<212> TYPE: PRT
<213> ORGANISM: Artificial Sequence
<220> FEATURE:
<223> OTHER INFORMATION: Core polypeptide

<400> SEQUENCE: 1307

Asp Glu Phe Asp Glu Ser Ile Ser Gln Val Asn Glu Lys Ile Glu Glu
1               5                   10                  15

Ser Leu Ala Phe Ile Arg Lys Ser Asp Glu Leu Leu
            20                  25

<210> SEQ ID NO 1308
<211> LENGTH: 27
<212> TYPE: PRT
<213> ORGANISM: Artificial Sequence
<220> FEATURE:
<223> OTHER INFORMATION: Core polypeptide

<400> SEQUENCE: 1308

```
Asp Glu Phe Asp Glu Ser Ile Ser Gln Val Asn Glu Lys Ile Glu Glu
 1               5                  10                  15
Ser Leu Ala Phe Ile Arg Lys Ser Asp Glu Leu
            20                  25
```

<210> SEQ ID NO 1309
<211> LENGTH: 10
<212> TYPE: PRT
<213> ORGANISM: Artificial Sequence
<220> FEATURE:
<223> OTHER INFORMATION: Core polypeptide

<400> SEQUENCE: 1309

```
Gln His Trp Ser Tyr Gly Leu Arg Pro Gly
 1               5                  10
```

<210> SEQ ID NO 1310
<211> LENGTH: 39
<212> TYPE: PRT
<213> ORGANISM: Artificial Sequence
<220> FEATURE:
<223> OTHER INFORMATION: Core polypeptide

<400> SEQUENCE: 1310

```
Trp Gln Glu Trp Glu Gln Lys Ile Thr Ala Leu Leu Glu Gln Ala Gln
 1               5                  10                  15
Ile Gln Gln Glu Lys Asn Glu Tyr Glu Leu Gln Lys Leu Asp Lys Trp
            20                  25                  30
Ala Ser Leu Trp Glu Trp Phe
        35
```

<210> SEQ ID NO 1311
<211> LENGTH: 35
<212> TYPE: PRT
<213> ORGANISM: Artificial Sequence
<220> FEATURE:
<223> OTHER INFORMATION: Core polypeptide

<400> SEQUENCE: 1311

```
Trp Gln Glu Trp Glu Gln Lys Ile Thr Ala Leu Leu Glu Gln Ala Gln
 1               5                  10                  15
Ile Gln Gln Glu Lys Ile Glu Tyr Glu Leu Gln Lys Leu Ile Glu Trp
            20                  25                  30
Glu Trp Phe
        35
```

<210> SEQ ID NO 1312
<211> LENGTH: 35
<212> TYPE: PRT
<213> ORGANISM: Artificial Sequence
<220> FEATURE:
<223> OTHER INFORMATION: Core polypeptide

<400> SEQUENCE: 1312

```
Val Tyr Pro Ser Asp Glu Tyr Asp Ala Ser Ile Ser Gln Val Asn Glu
```

```
            1               5              10              15
Glu Ile Asn Gln Ala Leu Ala Tyr Ile Arg Lys Ala Asp Glu Leu Leu
                    20              25              30
Glu Asn Val
         35

<210> SEQ ID NO 1313
<211> LENGTH: 28
<212> TYPE: PRT
<213> ORGANISM: Artificial Sequence
<220> FEATURE:
<223> OTHER INFORMATION: Core polypeptide

<400> SEQUENCE: 1313

Tyr Thr Ser Leu Ile His Ser Leu Ile Glu Glu Ser Gln Asn Gln Gln
 1               5              10              15
Glu Lys Asn Glu Gln Glu Leu Leu Glu Leu Asp Lys
             20              25

<210> SEQ ID NO 1314
<211> LENGTH: 28
<212> TYPE: PRT
<213> ORGANISM: Artificial Sequence
<220> FEATURE:
<223> OTHER INFORMATION: Core polypeptide

<400> SEQUENCE: 1314

Leu Glu Glu Asn Ile Thr Ala Leu Leu Glu Glu Ala Gln Ile Gln Gln
 1               5              10              15
Glu Lys Asn Met Tyr Glu Leu Gln Lys Leu Asn Ser
             20              25

<210> SEQ ID NO 1315
<211> LENGTH: 28
<212> TYPE: PRT
<213> ORGANISM: Artificial Sequence
<220> FEATURE:
<223> OTHER INFORMATION: Core polypeptide

<400> SEQUENCE: 1315

Leu Glu Ala Asn Ile Ser Gln Ser Leu Glu Gln Ala Gln Ile Gln Gln
 1               5              10              15
Glu Lys Asn Met Tyr Glu Leu Gln Lys Leu Asn Ser
             20              25

<210> SEQ ID NO 1316
<211> LENGTH: 28
<212> TYPE: PRT
<213> ORGANISM: Artificial Sequence
<220> FEATURE:
<223> OTHER INFORMATION: Core polypeptide

<400> SEQUENCE: 1316

Asn Asn Tyr Thr Ser Leu Ile His Ser Leu Ile Glu Glu Ser Gln Asn
 1               5              10              15
Gln Gln Glu Lys Asn Glu Gln Glu Leu Leu Glu Leu
             20              25

<210> SEQ ID NO 1317
<211> LENGTH: 28
<212> TYPE: PRT
<213> ORGANISM: Artificial Sequence
<220> FEATURE:
<223> OTHER INFORMATION: Core polypeptide
```

```
<400> SEQUENCE: 1317

Asp Phe Leu Glu Glu Asn Ile Thr Ala Leu Leu Glu Glu Ala Gln Ile
  1               5                  10                  15

Gln Gln Glu Lys Asn Met Tyr Glu Leu Gln Lys Leu
             20                  25

<210> SEQ ID NO 1318
<211> LENGTH: 28
<212> TYPE: PRT
<213> ORGANISM: Artificial Sequence
<220> FEATURE:
<223> OTHER INFORMATION: Core polypeptide

<400> SEQUENCE: 1318

Arg Tyr Leu Glu Ala Asn Ile Ser Gln Ser Leu Glu Gln Ala Gln Ile
  1               5                  10                  15

Gln Gln Glu Lys Asn Met Tyr Glu Leu Gln Lys Leu
             20                  25

<210> SEQ ID NO 1319
<211> LENGTH: 28
<212> TYPE: PRT
<213> ORGANISM: Artificial Sequence
<220> FEATURE:
<223> OTHER INFORMATION: Core polypeptide

<400> SEQUENCE: 1319

Arg Tyr Leu Glu Ala Asn Ile Thr Ala Leu Leu Glu Gln Ala Gln Ile
  1               5                  10                  15

Gln Gln Glu Lys Asn Glu Tyr Glu Leu Gln Lys Leu
             20                  25

<210> SEQ ID NO 1320
<211> LENGTH: 30
<212> TYPE: PRT
<213> ORGANISM: Artificial Sequence
<220> FEATURE:
<223> OTHER INFORMATION: Core polypeptide

<400> SEQUENCE: 1320

Asn Asn Tyr Thr Ser Leu Ile His Ser Leu Ile Glu Glu Ser Gln Asn
  1               5                  10                  15

Gln Gln Glu Lys Asn Glu Gln Glu Leu Leu Glu Leu Asp Lys
             20                  25                  30

<210> SEQ ID NO 1321
<211> LENGTH: 23
<212> TYPE: PRT
<213> ORGANISM: Artificial Sequence
<220> FEATURE:
<223> OTHER INFORMATION: Core polypeptide

<400> SEQUENCE: 1321

Thr Ala Leu Leu Glu Gln Ala Gln Ile Gln Gln Glu Lys Asn Glu Tyr
  1               5                  10                  15

Glu Leu Gln Lys Leu Asp Lys
             20

<210> SEQ ID NO 1322
<211> LENGTH: 23
<212> TYPE: PRT
<213> ORGANISM: Artificial Sequence
<220> FEATURE:
```

-continued

<223> OTHER INFORMATION: Core polypeptide

<400> SEQUENCE: 1322

Thr Ala Leu Leu Glu Gln Ala Gln Ile Gln Gln Glu Lys Asn Glu Tyr
1               5                   10                  15

Glu Leu Gln Lys Leu Asp Glu
            20

<210> SEQ ID NO 1323
<211> LENGTH: 23
<212> TYPE: PRT
<213> ORGANISM: Artificial Sequence
<220> FEATURE:
<223> OTHER INFORMATION: Core polypeptide

<400> SEQUENCE: 1323

Thr Ala Leu Leu Glu Gln Ala Gln Ile Gln Gln Glu Lys Asn Glu Tyr
1               5                   10                  15

Glu Leu Gln Lys Leu Ile Glu
            20

<210> SEQ ID NO 1324
<211> LENGTH: 23
<212> TYPE: PRT
<213> ORGANISM: Artificial Sequence
<220> FEATURE:
<223> OTHER INFORMATION: Core polypeptide

<400> SEQUENCE: 1324

Thr Ala Leu Leu Glu Gln Ala Gln Ile Gln Gln Glu Lys Ile Glu Tyr
1               5                   10                  15

Glu Leu Gln Lys Leu Asp Lys
            20

<210> SEQ ID NO 1325
<211> LENGTH: 23
<212> TYPE: PRT
<213> ORGANISM: Artificial Sequence
<220> FEATURE:
<223> OTHER INFORMATION: Core polypeptide

<400> SEQUENCE: 1325

Thr Ala Leu Leu Glu Gln Ala Gln Ile Gln Gln Glu Lys Ile Glu Tyr
1               5                   10                  15

Glu Leu Gln Lys Leu Asp Glu
            20

<210> SEQ ID NO 1326
<211> LENGTH: 23
<212> TYPE: PRT
<213> ORGANISM: Artificial Sequence
<220> FEATURE:
<223> OTHER INFORMATION: Core polypeptide

<400> SEQUENCE: 1326

Thr Ala Leu Leu Glu Gln Ala Gln Ile Gln Gln Glu Lys Ile Glu Tyr
1               5                   10                  15

Glu Leu Gln Lys Leu Ile Glu
            20

<210> SEQ ID NO 1327
<211> LENGTH: 22
<212> TYPE: PRT
<213> ORGANISM: Artificial Sequence

```
<220> FEATURE:
<223> OTHER INFORMATION: Core polypeptide

<400> SEQUENCE: 1327

Thr Ala Leu Leu Glu Gln Ala Gln Ile Gln Gln Glu Lys Ile Glu Tyr
 1               5                  10                  15

Glu Leu Gln Lys Leu Glu
            20

<210> SEQ ID NO 1328
<211> LENGTH: 23
<212> TYPE: PRT
<213> ORGANISM: Artificial Sequence
<220> FEATURE:
<223> OTHER INFORMATION: Core polypeptide

<400> SEQUENCE: 1328

Thr Ala Leu Leu Glu Gln Ala Gln Ile Gln Gln Glu Lys Ile Glu Tyr
 1               5                  10                  15

Glu Leu Gln Lys Leu Ala Lys
            20

<210> SEQ ID NO 1329
<211> LENGTH: 23
<212> TYPE: PRT
<213> ORGANISM: Artificial Sequence
<220> FEATURE:
<223> OTHER INFORMATION: Core polypeptide

<400> SEQUENCE: 1329

Thr Ala Leu Leu Glu Gln Ala Gln Ile Gln Gln Glu Lys Ile Glu Tyr
 1               5                  10                  15

Glu Leu Gln Lys Leu Ala Glu
            20

<210> SEQ ID NO 1330
<211> LENGTH: 22
<212> TYPE: PRT
<213> ORGANISM: Artificial Sequence
<220> FEATURE:
<223> OTHER INFORMATION: Core polypeptide

<400> SEQUENCE: 1330

Thr Ala Leu Leu Glu Gln Ala Gln Ile Gln Gln Glu Lys Ala Glu Tyr
 1               5                  10                  15

Glu Leu Gln Lys Leu Glu
            20

<210> SEQ ID NO 1331
<211> LENGTH: 22
<212> TYPE: PRT
<213> ORGANISM: Artificial Sequence
<220> FEATURE:
<223> OTHER INFORMATION: Core polypeptide

<400> SEQUENCE: 1331

Thr Ala Leu Leu Glu Gln Ala Gln Ile Gln Gln Glu Lys Asn Glu Tyr
 1               5                  10                  15

Glu Leu Gln Lys Leu Glu
            20

<210> SEQ ID NO 1332
<211> LENGTH: 22
<212> TYPE: PRT
```

```
<213> ORGANISM: Artificial Sequence
<220> FEATURE:
<223> OTHER INFORMATION: Core polypeptide

<400> SEQUENCE: 1332

Thr Ala Leu Leu Glu Gln Ala Gln Ile Gln Gln Glu Lys Gly Glu Tyr
 1               5                  10                  15

Glu Leu Gln Lys Leu Glu
            20

<210> SEQ ID NO 1333
<211> LENGTH: 23
<212> TYPE: PRT
<213> ORGANISM: Artificial Sequence
<220> FEATURE:
<223> OTHER INFORMATION: Core polypeptide

<400> SEQUENCE: 1333

Thr Ala Leu Leu Glu Gln Ala Gln Ile Gln Gln Glu Lys Ala Glu Tyr
 1               5                  10                  15

Glu Leu Gln Lys Leu Ala Lys
            20

<210> SEQ ID NO 1334
<211> LENGTH: 23
<212> TYPE: PRT
<213> ORGANISM: Artificial Sequence
<220> FEATURE:
<223> OTHER INFORMATION: Core polypeptide

<400> SEQUENCE: 1334

Thr Ala Leu Leu Glu Gln Ala Gln Ile Gln Gln Glu Lys Asn Glu Tyr
 1               5                  10                  15

Glu Leu Gln Lys Leu Ala Lys
            20

<210> SEQ ID NO 1335
<211> LENGTH: 23
<212> TYPE: PRT
<213> ORGANISM: Artificial Sequence
<220> FEATURE:
<223> OTHER INFORMATION: Core polypeptide

<400> SEQUENCE: 1335

Thr Ala Leu Leu Glu Gln Ala Gln Ile Gln Gln Glu Lys Gly Glu Tyr
 1               5                  10                  15

Glu Leu Gln Lys Leu Ala Lys
            20

<210> SEQ ID NO 1336
<211> LENGTH: 23
<212> TYPE: PRT
<213> ORGANISM: Artificial Sequence
<220> FEATURE:
<223> OTHER INFORMATION: Core polypeptide

<400> SEQUENCE: 1336

Thr Ala Leu Leu Glu Gln Ala Gln Ile Gln Gln Glu Lys Ala Glu Tyr
 1               5                  10                  15

Glu Leu Gln Lys Leu Ala Glu
            20

<210> SEQ ID NO 1337
<211> LENGTH: 23
```

-continued

```
<212> TYPE: PRT
<213> ORGANISM: Artificial Sequence
<220> FEATURE:
<223> OTHER INFORMATION: Core polypeptide

<400> SEQUENCE: 1337

Thr Ala Leu Leu Glu Gln Ala Gln Ile Gln Gln Glu Lys Asn Glu Tyr
 1               5                  10                  15

Glu Leu Gln Lys Leu Ala Glu
            20

<210> SEQ ID NO 1338
<211> LENGTH: 23
<212> TYPE: PRT
<213> ORGANISM: Artificial Sequence
<220> FEATURE:
<223> OTHER INFORMATION: Core polypeptide

<400> SEQUENCE: 1338

Thr Ala Leu Leu Glu Gln Ala Gln Ile Gln Gln Glu Lys Gly Glu Tyr
 1               5                  10                  15

Glu Leu Gln Lys Leu Ala Glu
            20

<210> SEQ ID NO 1339
<211> LENGTH: 28
<212> TYPE: PRT
<213> ORGANISM: Artificial Sequence
<220> FEATURE:
<223> OTHER INFORMATION: Core polypeptide

<400> SEQUENCE: 1339

Asp Glu Phe Asp Ala Ser Ile Ser Gln Val Asn Glu Lys Ile Asn Gln
 1               5                  10                  15

Ser Leu Ala Phe Ile Arg Lys Ser Asp Glu Leu Leu
            20                  25

<210> SEQ ID NO 1340
<211> LENGTH: 27
<212> TYPE: PRT
<213> ORGANISM: Artificial Sequence
<220> FEATURE:
<223> OTHER INFORMATION: Core polypeptide

<400> SEQUENCE: 1340

Asp Glu Tyr Asp Ala Ser Ile Ser Gln Val Asn Glu Lys Ile Asn Gln
 1               5                  10                  15

Ala Leu Ala Tyr Ile Arg Glu Ala Asp Glu Leu
            20                  25

<210> SEQ ID NO 1341
<211> LENGTH: 27
<212> TYPE: PRT
<213> ORGANISM: Artificial Sequence
<220> FEATURE:
<223> OTHER INFORMATION: Core polypeptide

<400> SEQUENCE: 1341

Asp Glu Tyr Asp Ala Ser Ile Ser Gln Val Asn Glu Glu Ile Asn Gln
 1               5                  10                  15

Ala Leu Ala Tyr Ile Arg Lys Ala Asp Glu Leu
            20                  25

<210> SEQ ID NO 1342
```

```
<211> LENGTH: 28
<212> TYPE: PRT
<213> ORGANISM: Artificial Sequence
<220> FEATURE:
<223> OTHER INFORMATION: Core polypeptide

<400> SEQUENCE: 1342

Asp Glu Phe Asp Glu Ser Ile Ser Gln Val Asn Glu Lys Ile Glu Glu
  1               5                  10                  15

Ser Leu Ala Phe Ile Arg Lys Ser Asp Glu Leu Leu
             20                  25

<210> SEQ ID NO 1343
<211> LENGTH: 27
<212> TYPE: PRT
<213> ORGANISM: Artificial Sequence
<220> FEATURE:
<223> OTHER INFORMATION: Core polypeptide

<400> SEQUENCE: 1343

Asp Glu Phe Asp Glu Ser Ile Ser Gln Val Asn Glu Lys Ile Glu Glu
  1               5                  10                  15

Ser Leu Ala Phe Ile Arg Lys Ser Asp Glu Leu
             20                  25

<210> SEQ ID NO 1344
<211> LENGTH: 10
<212> TYPE: PRT
<213> ORGANISM: Artificial Sequence
<220> FEATURE:
<223> OTHER INFORMATION: Core polypeptide

<400> SEQUENCE: 1344

Gln His Trp Ser Tyr Gly Leu Arg Pro Gly
  1               5                  10

<210> SEQ ID NO 1345
<211> LENGTH: 35
<212> TYPE: PRT
<213> ORGANISM: Artificial Sequence
<220> FEATURE:
<223> OTHER INFORMATION: Core polypeptide

<400> SEQUENCE: 1345

Gly Leu Ser Pro Thr Val Trp Leu Ser Val Ile Trp Met Met Trp Tyr
  1               5                  10                  15

Trp Gly Pro Ser Leu Tyr Ser Ile Leu Ser Pro Phe Leu Pro Leu Leu
             20                  25                  30

Pro Ile Phe
         35

<210> SEQ ID NO 1346
<211> LENGTH: 36
<212> TYPE: PRT
<213> ORGANISM: Artificial Sequence
<220> FEATURE:
<223> OTHER INFORMATION: Core polypeptide

<400> SEQUENCE: 1346

Val Gly Leu Ser Pro Thr Val Trp Leu Ser Val Ile Trp Met Met Trp
  1               5                  10                  15

Tyr Trp Trp Gly Pro Ser Leu Tyr Ser Ile Leu Ser Pro Phe Leu Pro
             20                  25                  30

Leu Leu Pro Ile
```

```
<210> SEQ ID NO 1347
<211> LENGTH: 35
<212> TYPE: PRT
<213> ORGANISM: Artificial Sequence
<220> FEATURE:
<223> OTHER INFORMATION: Core polypeptide

<400> SEQUENCE: 1347

Phe Val Gly Leu Ser Pro Thr Val Trp Leu Ser Val Ile Trp Met Met
 1               5                  10                  15

Trp Tyr Trp Gly Pro Ser Leu Tyr Ser Ile Leu Ser Pro Phe Leu Pro
            20                  25                  30

Leu Leu Pro
        35

<210> SEQ ID NO 1348
<211> LENGTH: 35
<212> TYPE: PRT
<213> ORGANISM: Artificial Sequence
<220> FEATURE:
<223> OTHER INFORMATION: Core polypeptide

<400> SEQUENCE: 1348

Trp Phe Val Gly Leu Ser Pro Thr Val Trp Leu Ser Val Ile Trp Met
 1               5                  10                  15

Met Trp Tyr Trp Gly Pro Ser Leu Tyr Ser Ile Leu Ser Pro Phe Leu
            20                  25                  30

Pro Leu Leu
        35

<210> SEQ ID NO 1349
<211> LENGTH: 35
<212> TYPE: PRT
<213> ORGANISM: Artificial Sequence
<220> FEATURE:
<223> OTHER INFORMATION: Core polypeptide

<400> SEQUENCE: 1349

Gln Trp Phe Val Gly Leu Ser Pro Thr Val Trp Leu Ser Val Ile Trp
 1               5                  10                  15

Met Met Trp Tyr Trp Gly Pro Ser Leu Tyr Ser Ile Leu Ser Pro Phe
            20                  25                  30

Leu Pro Leu
        35

<210> SEQ ID NO 1350
<211> LENGTH: 35
<212> TYPE: PRT
<213> ORGANISM: Artificial Sequence
<220> FEATURE:
<223> OTHER INFORMATION: Core polypeptide

<400> SEQUENCE: 1350

Val Gln Trp Phe Val Gly Leu Ser Pro Thr Val Trp Leu Ser Val Ile
 1               5                  10                  15

Trp Met Met Trp Tyr Trp Gly Pro Ser Leu Tyr Ser Ile Leu Ser Pro
            20                  25                  30

Phe Leu Pro
        35
```

<210> SEQ ID NO 1351
<211> LENGTH: 35
<212> TYPE: PRT
<213> ORGANISM: Artificial Sequence
<220> FEATURE:
<223> OTHER INFORMATION: Core polypeptide

<400> SEQUENCE: 1351

Phe Val Gln Trp Phe Val Gly Leu Ser Pro Thr Val Trp Leu Ser Val
1               5                   10                  15

Ile Trp Met Met Trp Tyr Trp Gly Pro Ser Leu Tyr Ser Ile Leu Ser
            20                  25                  30

Pro Phe Leu
        35

<210> SEQ ID NO 1352
<211> LENGTH: 35
<212> TYPE: PRT
<213> ORGANISM: Artificial Sequence
<220> FEATURE:
<223> OTHER INFORMATION: Core polypeptide

<400> SEQUENCE: 1352

Pro Phe Val Gln Trp Phe Val Gly Leu Ser Pro Thr Val Trp Leu Ser
1               5                   10                  15

Val Ile Trp Met Met Trp Tyr Trp Gly Pro Ser Leu Tyr Ser Ile Leu
            20                  25                  30

Ser Pro Phe
        35

<210> SEQ ID NO 1353
<211> LENGTH: 35
<212> TYPE: PRT
<213> ORGANISM: Artificial Sequence
<220> FEATURE:
<223> OTHER INFORMATION: Core polypeptide

<400> SEQUENCE: 1353

Val Pro Phe Val Gln Trp Phe Val Gly Leu Ser Pro Thr Val Trp Leu
1               5                   10                  15

Ser Val Ile Trp Met Met Trp Tyr Trp Gly Pro Ser Leu Tyr Ser Ile
            20                  25                  30

Leu Ser Pro
        35

<210> SEQ ID NO 1354
<211> LENGTH: 35
<212> TYPE: PRT
<213> ORGANISM: Artificial Sequence
<220> FEATURE:
<223> OTHER INFORMATION: Core polypeptide

<400> SEQUENCE: 1354

Leu Val Pro Phe Val Gln Trp Phe Val Gly Leu Ser Pro Thr Val Trp
1               5                   10                  15

Leu Ser Val Ile Trp Met Met Trp Tyr Trp Gly Pro Ser Leu Tyr Ser
            20                  25                  30

Ile Leu Ser
        35

<210> SEQ ID NO 1355
<211> LENGTH: 35
<212> TYPE: PRT

```
<213> ORGANISM: Artificial Sequence
<220> FEATURE:
<223> OTHER INFORMATION: Core polypeptide

<400> SEQUENCE: 1355

Leu Gln Ala Gly Phe Phe Leu Leu Thr Arg Ile Leu Thr Ile Pro Gln
 1               5                  10                  15

Ser Leu Asp Ser Trp Trp Thr Ser Leu Asn Phe Leu Gly Gly Thr Thr
            20                  25                  30

Val Ala Leu
         35

<210> SEQ ID NO 1356
<211> LENGTH: 36
<212> TYPE: PRT
<213> ORGANISM: Artificial Sequence
<220> FEATURE:
<223> OTHER INFORMATION: Core polypeptide

<400> SEQUENCE: 1356

Trp Asn Trp Phe Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser Leu
            20                  25                  30

Trp Asn Trp Phe
         35

<210> SEQ ID NO 1357
<211> LENGTH: 36
<212> TYPE: PRT
<213> ORGANISM: Artificial Sequence
<220> FEATURE:
<223> OTHER INFORMATION: Core polypeptide

<400> SEQUENCE: 1357

Tyr Thr Asn Thr Ile Tyr Thr Leu Leu Glu Glu Ser Gln Asn Gln Gln
 1               5                  10                  15

Glu Lys Asn Glu Gln Glu Leu Leu Glu Leu Asp Lys Trp Ala Ser Leu
            20                  25                  30

Trp Asn Trp Phe
         35

<210> SEQ ID NO 1358
<211> LENGTH: 36
<212> TYPE: PRT
<213> ORGANISM: Artificial Sequence
<220> FEATURE:
<223> OTHER INFORMATION: Core polypeptide

<400> SEQUENCE: 1358

Tyr Thr Gly Ile Ile Tyr Asn Leu Leu Glu Glu Ser Gln Asn Gln Gln
 1               5                  10                  15

Glu Lys Asn Glu Gln Glu Leu Leu Glu Leu Asp Lys Trp Ala Asn Leu
            20                  25                  30

Trp Asn Trp Phe
         35

<210> SEQ ID NO 1359
<211> LENGTH: 36
<212> TYPE: PRT
<213> ORGANISM: Artificial Sequence
<220> FEATURE:
<223> OTHER INFORMATION: Core polypeptide
```

```
<400> SEQUENCE: 1359

Tyr Thr Gly Ile Ile Tyr Asn Leu Leu Glu Glu Ser Gln Asn Gln Gln
1               5                   10                  15

Glu Lys Asn Glu Gln Glu Leu Leu Glu Leu Asp Lys Trp Ala Asn Leu
            20                  25                  30

Trp Asn Trp Phe
            35

<210> SEQ ID NO 1360
<211> LENGTH: 36
<212> TYPE: PRT
<213> ORGANISM: Artificial Sequence
<220> FEATURE:
<223> OTHER INFORMATION: Core polypeptide

<400> SEQUENCE: 1360

Tyr Thr Ser Leu Ile Tyr Ser Leu Leu Glu Lys Ser Gln Ile Gln Gln
1               5                   10                  15

Glu Lys Asn Glu Gln Glu Leu Leu Glu Leu Asp Lys Trp Ala Ser Leu
            20                  25                  30

Trp Asn Trp Phe
            35

<210> SEQ ID NO 1361
<211> LENGTH: 36
<212> TYPE: PRT
<213> ORGANISM: Artificial Sequence
<220> FEATURE:
<223> OTHER INFORMATION: Core polypeptide

<400> SEQUENCE: 1361

Tyr Thr Ser Leu Ile Tyr Ser Leu Leu Glu Lys Ser Gln Ile Gln Gln
1               5                   10                  15

Glu Lys Asn Glu Gln Glu Leu Leu Gln Leu Asp Lys Trp Ala Ser Leu
            20                  25                  30

Trp Asn Trp Phe
            35

<210> SEQ ID NO 1362
<211> LENGTH: 21
<212> TYPE: PRT
<213> ORGANISM: Artificial Sequence
<220> FEATURE:
<223> OTHER INFORMATION: Core polypeptide

<400> SEQUENCE: 1362

Glu Lys Ser Gln Ile Gln Gln Glu Lys Asn Glu Gln Glu Leu Leu Glu
1               5                   10                  15

Leu Asp Lys Trp Ala
            20

<210> SEQ ID NO 1364
<211> LENGTH: 21
<212> TYPE: PRT
<213> ORGANISM: Artificial Sequence
<220> FEATURE:
<223> OTHER INFORMATION: Core polypeptide

<400> SEQUENCE: 1364

Glu Gln Ala Gln Ile Gln Gln Glu Lys Asn Glu Tyr Glu Leu Gln Lys
1               5                   10                  15
```

Leu Asp Lys Trp Ala
            20

<210> SEQ ID NO 1365
<211> LENGTH: 21
<212> TYPE: PRT
<213> ORGANISM: Artificial Sequence
<220> FEATURE:
<223> OTHER INFORMATION: Core polypeptide

<400> SEQUENCE: 1365

Glu Gln Ala Gln Ile Gln Gln Glu Lys Asn Glu Tyr Glu Leu Gln Lys
 1               5                  10                  15

Leu Asp Lys Trp Ala
            20

<210> SEQ ID NO 1366
<211> LENGTH: 36
<212> TYPE: PRT
<213> ORGANISM: Artificial Sequence
<220> FEATURE:
<223> OTHER INFORMATION: Core polypeptide
<221> NAME/KEY: SITE
<222> LOCATION: (3)...(3)
<223> OTHER INFORMATION: Xaa=any amino acid
<221> NAME/KEY: SITE
<222> LOCATION: (10)...(10)
<223> OTHER INFORMATION: Xaa=any amino acid
<221> NAME/KEY: SITE
<222> LOCATION: (17)...(17)
<223> OTHER INFORMATION: Xaa=any amino acid
<221> NAME/KEY: SITE
<222> LOCATION: (24)...(24)
<223> OTHER INFORMATION: Xaa=any amino acid

<400> SEQUENCE: 1366

Tyr Thr Xaa Leu Ile His Ser Leu Ile Xaa Glu Ser Gln Asn Gln Gln
 1               5                  10                  15

Xaa Lys Asn Glu Gln Glu Leu Xaa Glu Leu Asp Lys Trp Ala Ser Leu
            20                  25                  30

Trp Asn Trp Phe
        35

<210> SEQ ID NO 1367
<211> LENGTH: 27
<212> TYPE: PRT
<213> ORGANISM: Artificial Sequence
<220> FEATURE:
<223> OTHER INFORMATION: Core polypeptide
<221> NAME/KEY: SITE
<222> LOCATION: (3)...(3)
<223> OTHER INFORMATION: Xaa=any amino acid
<221> NAME/KEY: SITE
<222> LOCATION: (10)...(10)
<223> OTHER INFORMATION: Xaa=any amino acid
<221> NAME/KEY: SITE
<222> LOCATION: (17)...(17)
<223> OTHER INFORMATION: Xaa=any amino acid
<221> NAME/KEY: SITE
<222> LOCATION: (24)...(24)
<223> OTHER INFORMATION: Xaa=any amino acid

<400> SEQUENCE: 1367

Tyr Thr Xaa Leu Ile His Ser Leu Ile Xaa Glu Ser Gln Asn Gln Gln
 1               5                  10                  15

Xaa Lys Asn Glu Gln Glu Leu Xaa Glu Leu Asp
            20                  25

```
<210> SEQ ID NO 1368
<211> LENGTH: 27
<212> TYPE: PRT
<213> ORGANISM: Artificial Sequence
<220> FEATURE:
<223> OTHER INFORMATION: Core polypeptide

<400> SEQUENCE: 1368

Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp
            20                  25

<210> SEQ ID NO 1369
<211> LENGTH: 39
<212> TYPE: PRT
<213> ORGANISM: Artificial Sequence
<220> FEATURE:
<223> OTHER INFORMATION: Core polypeptide
<221> NAME/KEY: SITE
<222> LOCATION: (6)...(6)
<223> OTHER INFORMATION: Xaa=any amino acid
<221> NAME/KEY: SITE
<222> LOCATION: (13)...(13)
<223> OTHER INFORMATION: Xaa=any amino acid
<221> NAME/KEY: SITE
<222> LOCATION: (20)...(20)
<223> OTHER INFORMATION: Xaa=any amino acid
<221> NAME/KEY: SITE
<222> LOCATION: (27)...(27)
<223> OTHER INFORMATION: Xaa=any amino acid

<400> SEQUENCE: 1369

Trp Gln Glu Trp Glu Xaa Lys Ile Thr Ala Leu Leu Xaa Gln Ala Gln
 1               5                  10                  15

Ile Gln Gln Xaa Lys Asn Glu Tyr Glu Leu Xaa Lys Leu Asp Lys Trp
            20                  25                  30

Ala Ser Leu Trp Glu Trp Phe
        35

<210> SEQ ID NO 1370
<211> LENGTH: 34
<212> TYPE: PRT
<213> ORGANISM: Artificial Sequence
<220> FEATURE:
<223> OTHER INFORMATION: Core polypeptide
<221> NAME/KEY: SITE
<222> LOCATION: (1)...(1)
<223> OTHER INFORMATION: Xaa=any amino acid
<221> NAME/KEY: SITE
<222> LOCATION: (8)...(8)
<223> OTHER INFORMATION: Xaa=any amino acid
<221> NAME/KEY: SITE
<222> LOCATION: (15)...(15)
<223> OTHER INFORMATION: Xaa=any amino acid
<221> NAME/KEY: SITE
<222> LOCATION: (22)...(22)
<223> OTHER INFORMATION: Xaa=any amino acid

<400> SEQUENCE: 1370

Xaa Lys Ile Thr Ala Leu Leu Xaa Gln Ala Gln Ile Gln Gln Xaa Lys
 1               5                  10                  15

Asn Glu Tyr Glu Leu Xaa Lys Leu Asp Lys Trp Ala Ser Leu Trp Glu
            20                  25                  30

Trp Phe

<210> SEQ ID NO 1371
<211> LENGTH: 30
```

```
<212> TYPE: PRT
<213> ORGANISM: Artificial Sequence
<220> FEATURE:
<223> OTHER INFORMATION: Core polypeptide
<221> NAME/KEY: SITE
<222> LOCATION: (6)...(6)
<223> OTHER INFORMATION: Xaa=any amino acid
<221> NAME/KEY: SITE
<222> LOCATION: (13)...(13)
<223> OTHER INFORMATION: Xaa=any amino acid
<221> NAME/KEY: SITE
<222> LOCATION: (20)...(20)
<223> OTHER INFORMATION: Xaa=any amino acid
<221> NAME/KEY: SITE
<222> LOCATION: (27)...(27)
<223> OTHER INFORMATION: Xaa=any amino acid

<400> SEQUENCE: 1371

Trp Gln Glu Trp Glu Xaa Lys Ile Thr Ala Leu Leu Xaa Gln Ala Gln
 1               5                  10                  15

Ile Gln Gln Xaa Lys Asn Glu Tyr Glu Leu Xaa Lys Leu Asp
            20                  25                  30

<210> SEQ ID NO 1372
<211> LENGTH: 27
<212> TYPE: PRT
<213> ORGANISM: Artificial Sequence
<220> FEATURE:
<223> OTHER INFORMATION: Core polypeptide

<400> SEQUENCE: 1372

Trp Glu Gln Lys Ile Thr Ala Leu Leu Glu Gln Ala Gln Ile Gln Gln
 1               5                  10                  15

Glu Lys Asn Glu Tyr Glu Leu Gln Lys Leu Asp
            20                  25

<210> SEQ ID NO 1373
<211> LENGTH: 25
<212> TYPE: PRT
<213> ORGANISM: Artificial Sequence
<220> FEATURE:
<223> OTHER INFORMATION: Core polypeptide
<221> NAME/KEY: SITE
<222> LOCATION: (3)...(3)
<223> OTHER INFORMATION: Xaa=any amino acid
<221> NAME/KEY: SITE
<222> LOCATION: (10)...(10)
<223> OTHER INFORMATION: Xaa=any amino acid
<221> NAME/KEY: SITE
<222> LOCATION: (15)...(15)
<223> OTHER INFORMATION: Xaa=any amino acid
<221> NAME/KEY: SITE
<222> LOCATION: (22)...(22)
<223> OTHER INFORMATION: Xaa=any amino acid

<400> SEQUENCE: 1373

Trp Glu Xaa Lys Ile Thr Ala Leu Leu Xaa Gln Ala Gln Gln Xaa Lys
 1               5                  10                  15

Asn Glu Tyr Glu Leu Xaa Lys Leu Asp
            20                  25

<210> SEQ ID NO 1374
<211> LENGTH: 25
<212> TYPE: PRT
<213> ORGANISM: Artificial Sequence
<220> FEATURE:
<223> OTHER INFORMATION: Core polypeptide
<221> NAME/KEY: SITE
<222> LOCATION: (1)...(1)
<223> OTHER INFORMATION: Xaa=any amino acid
```

```
<221> NAME/KEY: SITE
<222> LOCATION: (8)...(8)
<223> OTHER INFORMATION: Xaa=any amino acid
<221> NAME/KEY: SITE
<222> LOCATION: (15)...(15)
<223> OTHER INFORMATION: Xaa=any amino acid
<221> NAME/KEY: SITE
<222> LOCATION: (22)...(22)
<223> OTHER INFORMATION: Xaa=any amino acid

<400> SEQUENCE: 1374

Xaa Lys Ile Thr Ala Leu Leu Xaa Gln Ala Gln Ile Gln Gln Xaa Lys
 1               5                  10                  15

Asn Glu Tyr Glu Leu Xaa Lys Leu Asp
            20                  25

<210> SEQ ID NO 1375
<211> LENGTH: 25
<212> TYPE: PRT
<213> ORGANISM: Artificial Sequence
<220> FEATURE:
<223> OTHER INFORMATION: Core polypeptide

<400> SEQUENCE: 1375

Gln Lys Ile Thr Ala Leu Leu Glu Gln Ala Gln Ile Gln Gln Glu Lys
 1               5                  10                  15

Asn Glu Tyr Glu Leu Gln Lys Leu Asp
            20                  25

<210> SEQ ID NO 1376
<211> LENGTH: 32
<212> TYPE: PRT
<213> ORGANISM: Artificial Sequence
<220> FEATURE:
<223> OTHER INFORMATION: Core polypeptide

<400> SEQUENCE: 1376

Val Tyr Pro Ser Asp Glu Tyr Asp Ala Ser Ile Ser Gln Val Asn Glu
 1               5                  10                  15

Glu Ile Asn Gln Ala Leu Ala Tyr Ile Arg Lys Ala Asp Glu Leu Leu
            20                  25                  30

<210> SEQ ID NO 1377
<211> LENGTH: 25
<212> TYPE: PRT
<213> ORGANISM: Artificial Sequence
<220> FEATURE:
<223> OTHER INFORMATION: Core polypeptide

<400> SEQUENCE: 1377

Gln Lys Ile Thr Ala Leu Leu Glu Gln Ala Gln Ile Gln Gln Glu Lys
 1               5                  10                  15

Asn Glu Tyr Glu Leu Gln Lys Leu Asp
            20                  25

<210> SEQ ID NO 1378
<211> LENGTH: 31
<212> TYPE: PRT
<213> ORGANISM: Artificial Sequence
<220> FEATURE:
<223> OTHER INFORMATION: Core polypeptide

<400> SEQUENCE: 1378

Val Tyr Pro Ser Asp Glu Tyr Asp Ala Ser Ile Ser Gln Val Asn Glu
 1               5                  10                  15
```

```
Glu Ile Asn Gln Ala Leu Ala Tyr Ile Arg Lys Ala Asp Glu Leu
            20                  25                  30

<210> SEQ ID NO 1379
<211> LENGTH: 30
<212> TYPE: PRT
<213> ORGANISM: Artificial Sequence
<220> FEATURE:
<223> OTHER INFORMATION: Core polypeptide

<400> SEQUENCE: 1379

Trp Gln Glu Trp Glu Gln Lys Ile Thr Ala Leu Leu Glu Gln Ala Gln
  1               5                  10                  15

Ile Gln Gln Glu Lys Asn Glu Tyr Glu Leu Gln Lys Leu Asp
            20                  25                  30

<210> SEQ ID NO 1380
<211> LENGTH: 34
<212> TYPE: PRT
<213> ORGANISM: Artificial Sequence
<220> FEATURE:
<223> OTHER INFORMATION: Core polypeptide

<400> SEQUENCE: 1380

Val Tyr Pro Ser Asp Glu Tyr Asp Ala Ser Ile Ser Gln Val Asn Glu
  1               5                  10                  15

Glu Ile Asn Gln Ala Leu Ala Tyr Ile Arg Lys Ala Asp Glu Leu Leu
            20                  25                  30

Glu Asn

<210> SEQ ID NO 1381
<211> LENGTH: 34
<212> TYPE: PRT
<213> ORGANISM: Artificial Sequence
<220> FEATURE:
<223> OTHER INFORMATION: Core polypeptide

<400> SEQUENCE: 1381

Gln Lys Ile Thr Ala Leu Leu Glu Gln Ala Gln Ile Gln Gln Glu Lys
  1               5                  10                  15

Asn Glu Tyr Glu Leu Gln Lys Leu Asp Lys Trp Ala Ser Leu Trp Glu
            20                  25                  30

Trp Phe

<210> SEQ ID NO 1382
<211> LENGTH: 35
<212> TYPE: PRT
<213> ORGANISM: Artificial Sequence
<220> FEATURE:
<223> OTHER INFORMATION: Core polypeptide

<400> SEQUENCE: 1382

Ser Thr Asn Lys Ala Val Val Ser Leu Ser Asn Gly Val Ser Val Leu
  1               5                  10                  15

Thr Ser Lys Val Leu Asp Leu Lys Asn Tyr Ile Asp Lys Gln Leu Leu
            20                  25                  30

Pro Ile Val
        35

<210> SEQ ID NO 1383
<211> LENGTH: 35
<212> TYPE: PRT
<213> ORGANISM: Artificial Sequence
```

```
<220> FEATURE:
<223> OTHER INFORMATION: Core polypeptide

<400> SEQUENCE: 1383

Thr Asn Lys Ala Val Val Ser Leu Ser Asn Gly Val Ser Val Leu Thr
 1               5                   10                  15

Ser Lys Val Leu Asp Leu Lys Asn Tyr Ile Asp Lys Gln Leu Leu Pro
                20                  25                  30

Ile Val Asn
        35

<210> SEQ ID NO 1384
<211> LENGTH: 35
<212> TYPE: PRT
<213> ORGANISM: Artificial Sequence
<220> FEATURE:
<223> OTHER INFORMATION: Core polypeptide

<400> SEQUENCE: 1384

Asn Lys Ala Val Val Ser Leu Ser Asn Gly Val Ser Val Leu Thr Ser
 1               5                   10                  15

Lys Val Leu Asp Leu Lys Asn Tyr Ile Asp Lys Gln Leu Leu Pro Ile
                20                  25                  30

Val Asn Lys
        35

<210> SEQ ID NO 1385
<211> LENGTH: 35
<212> TYPE: PRT
<213> ORGANISM: Artificial Sequence
<220> FEATURE:
<223> OTHER INFORMATION: Core polypeptide

<400> SEQUENCE: 1385

Lys Ala Val Val Ser Leu Ser Asn Gly Val Ser Val Leu Thr Ser Lys
 1               5                   10                  15

Val Leu Asp Leu Lys Asn Tyr Ile Asp Lys Gln Leu Leu Pro Ile Val
                20                  25                  30

Asn Lys Gln
        35

<210> SEQ ID NO 1386
<211> LENGTH: 36
<212> TYPE: PRT
<213> ORGANISM: Artificial Sequence
<220> FEATURE:
<223> OTHER INFORMATION: Core polypeptide

<400> SEQUENCE: 1386

Ala Val Val Ser Leu Ser Asn Gly Val Ser Val Leu Thr Ser Lys Val
 1               5                   10                  15

Leu Asp Leu Lys Asn Tyr Ile Asp Lys Gln Leu Leu Pro Ile Val
                20                  25                  30

Asn Lys Gln Ser
        35

<210> SEQ ID NO 1387
<211> LENGTH: 34
<212> TYPE: PRT
<213> ORGANISM: Artificial Sequence
<220> FEATURE:
<223> OTHER INFORMATION: Core polypeptide
```

```
<400> SEQUENCE: 1387

Val Val Ser Leu Ser Asn Gly Val Ser Val Leu Thr Ser Lys Val Leu
 1               5                  10                  15

Asp Leu Lys Asn Tyr Ile Asp Lys Gln Leu Leu Pro Ile Val Asn Lys
            20                  25                  30

Gln Ser

<210> SEQ ID NO 1388
<211> LENGTH: 34
<212> TYPE: PRT
<213> ORGANISM: Artificial Sequence
<220> FEATURE:
<223> OTHER INFORMATION: Core polypeptide

<400> SEQUENCE: 1388

Val Ser Leu Ser Asn Gly Val Ser Val Leu Thr Ser Lys Val Leu Asp
 1               5                  10                  15

Leu Lys Asn Tyr Ile Asp Lys Gln Leu Leu Pro Ile Val Asn Lys Gln
            20                  25                  30

Ser Ser

<210> SEQ ID NO 1389
<211> LENGTH: 34
<212> TYPE: PRT
<213> ORGANISM: Artificial Sequence
<220> FEATURE:
<223> OTHER INFORMATION: Core polypeptide

<400> SEQUENCE: 1389

Ser Leu Ser Asn Gly Val Ser Val Leu Thr Ser Lys Val Leu Asp Leu
 1               5                  10                  15

Lys Asn Tyr Ile Asp Lys Gln Leu Leu Pro Ile Val Asn Lys Gln Ser
            20                  25                  30

Ser Ile

<210> SEQ ID NO 1390
<211> LENGTH: 34
<212> TYPE: PRT
<213> ORGANISM: Artificial Sequence
<220> FEATURE:
<223> OTHER INFORMATION: Core polypeptide

<400> SEQUENCE: 1390

Leu Ser Asn Gly Val Ser Val Leu Thr Ser Lys Val Leu Asp Leu Lys
 1               5                  10                  15

Asn Tyr Ile Asp Lys Gln Leu Leu Pro Ile Val Asn Lys Gln Ser Ser
            20                  25                  30

Ile Ser

<210> SEQ ID NO 1391
<211> LENGTH: 34
<212> TYPE: PRT
<213> ORGANISM: Artificial Sequence
<220> FEATURE:
<223> OTHER INFORMATION: Core polypeptide

<400> SEQUENCE: 1391

Ser Asn Gly Val Ser Val Leu Thr Ser Lys Val Leu Asp Leu Lys Asn
 1               5                  10                  15

Tyr Ile Asp Lys Gln Leu Leu Pro Ile Val Asn Lys Gln Ser Ser Ile
            20                  25                  30
```

Ser Asn

<210> SEQ ID NO 1392
<211> LENGTH: 34
<212> TYPE: PRT
<213> ORGANISM: Artificial Sequence
<220> FEATURE:
<223> OTHER INFORMATION: Core polypeptide

<400> SEQUENCE: 1392

Asn Gly Val Ser Val Leu Thr Ser Lys Val Leu Asp Leu Lys Asn Tyr
 1               5                  10                  15

Ile Asp Lys Gln Leu Leu Pro Ile Val Asn Lys Gln Ser Ser Ile Ser
                20                  25                  30

Asn Ile

<210> SEQ ID NO 1393
<211> LENGTH: 34
<212> TYPE: PRT
<213> ORGANISM: Artificial Sequence
<220> FEATURE:
<223> OTHER INFORMATION: Core polypeptide

<400> SEQUENCE: 1393

Gly Val Ser Val Leu Thr Ser Lys Val Leu Asp Leu Lys Asn Tyr Ile
 1               5                  10                  15

Asp Lys Gln Leu Leu Pro Ile Val Asn Lys Gln Ser Ser Ile Ser Asn
                20                  25                  30

Ile Glu

<210> SEQ ID NO 1394
<211> LENGTH: 34
<212> TYPE: PRT
<213> ORGANISM: Artificial Sequence
<220> FEATURE:
<223> OTHER INFORMATION: Core polypeptide

<400> SEQUENCE: 1394

Val Ser Val Leu Thr Ser Lys Val Leu Asp Leu Lys Asn Tyr Ile Asp
 1               5                  10                  15

Lys Gln Leu Leu Pro Ile Val Asn Lys Gln Ser Ser Ile Ser Asn Ile
                20                  25                  30

Glu Thr

<210> SEQ ID NO 1395
<211> LENGTH: 34
<212> TYPE: PRT
<213> ORGANISM: Artificial Sequence
<220> FEATURE:
<223> OTHER INFORMATION: Core polypeptide

<400> SEQUENCE: 1395

Ser Val Leu Thr Ser Lys Val Leu Asp Leu Lys Asn Tyr Ile Asp Lys
 1               5                  10                  15

Gln Leu Leu Pro Ile Val Asn Lys Gln Ser Ser Ile Ser Asn Ile Glu
                20                  25                  30

Thr Val

<210> SEQ ID NO 1396
<211> LENGTH: 34
<212> TYPE: PRT

```
<213> ORGANISM: Artificial Sequence
<220> FEATURE:
<223> OTHER INFORMATION: Core polypeptide

<400> SEQUENCE: 1396

Val Leu Thr Ser Lys Val Leu Asp Leu Lys Asn Tyr Ile Asp Lys Gln
 1               5                  10                  15

Leu Leu Pro Ile Val Asn Lys Gln Ser Ser Ile Ser Asn Ile Glu Thr
            20                  25                  30

Val Ile

<210> SEQ ID NO 1397
<211> LENGTH: 33
<212> TYPE: PRT
<213> ORGANISM: Artificial Sequence
<220> FEATURE:
<223> OTHER INFORMATION: Core polypeptide

<400> SEQUENCE: 1397

Leu Thr Ser Lys Val Leu Asp Lys Asn Tyr Ile Asp Lys Gln Leu Leu
 1               5                  10                  15

Pro Ile Val Asn Lys Gln Ser Ser Ile Ser Asn Ile Glu Thr Val Ile
            20                  25                  30

Glu

<210> SEQ ID NO 1398
<211> LENGTH: 34
<212> TYPE: PRT
<213> ORGANISM: Artificial Sequence
<220> FEATURE:
<223> OTHER INFORMATION: Core polypeptide

<400> SEQUENCE: 1398

Thr Ser Lys Val Leu Asp Leu Lys Asn Tyr Ile Asp Lys Gln Leu Leu
 1               5                  10                  15

Pro Ile Val Asn Lys Gln Ser Ser Ile Ser Asn Ile Glu Thr Val Ile
            20                  25                  30

Glu Phe

<210> SEQ ID NO 1399
<211> LENGTH: 34
<212> TYPE: PRT
<213> ORGANISM: Artificial Sequence
<220> FEATURE:
<223> OTHER INFORMATION: Core polypeptide

<400> SEQUENCE: 1399

Ser Lys Val Leu Asp Leu Lys Asn Tyr Ile Asp Lys Gln Leu Leu Pro
 1               5                  10                  15

Ile Val Asn Lys Gln Ser Ser Ile Ser Asn Ile Glu Thr Val Ile Glu
            20                  25                  30

Phe Gln

<210> SEQ ID NO 1400
<211> LENGTH: 34
<212> TYPE: PRT
<213> ORGANISM: Artificial Sequence
<220> FEATURE:
<223> OTHER INFORMATION: Core polypeptide

<400> SEQUENCE: 1400

Lys Val Leu Asp Leu Lys Asn Tyr Ile Asp Lys Gln Leu Leu Pro Ile
```

-continued

```
                1               5                  10                 15
Val Asn Lys Gln Ser Ser Ile Ser Asn Ile Glu Thr Val Ile Glu Phe
            20                  25                 30
Gln Gln

<210> SEQ ID NO 1401
<211> LENGTH: 34
<212> TYPE: PRT
<213> ORGANISM: Artificial Sequence
<220> FEATURE:
<223> OTHER INFORMATION: Core polypeptide

<400> SEQUENCE: 1401

Val Leu Asp Leu Lys Asn Tyr Ile Asp Lys Gln Leu Leu Pro Ile Val
 1               5                  10                 15
Asn Lys Gln Ser Ser Ile Ser Asn Ile Glu Thr Val Ile Glu Phe Gln
            20                  25                 30
Gln Lys

<210> SEQ ID NO 1402
<211> LENGTH: 34
<212> TYPE: PRT
<213> ORGANISM: Artificial Sequence
<220> FEATURE:
<223> OTHER INFORMATION: Core polypeptide

<400> SEQUENCE: 1402

Leu Asp Leu Lys Asn Tyr Ile Asp Lys Gln Leu Leu Pro Ile Val Asn
 1               5                  10                 15
Lys Gln Ser Ser Ile Ser Asn Ile Glu Thr Val Ile Glu Phe Gln Gln
            20                  25                 30
Lys Asn

<210> SEQ ID NO 1403
<211> LENGTH: 34
<212> TYPE: PRT
<213> ORGANISM: Artificial Sequence
<220> FEATURE:
<223> OTHER INFORMATION: Core polypeptide

<400> SEQUENCE: 1403

Asp Leu Lys Asn Tyr Ile Asp Lys Gln Leu Leu Pro Ile Val Asn Lys
 1               5                  10                 15
Gln Ser Ser Ile Ser Asn Ile Glu Thr Val Ile Glu Phe Gln Gln Lys
            20                  25                 30
Asn Asn

<210> SEQ ID NO 1404
<211> LENGTH: 34
<212> TYPE: PRT
<213> ORGANISM: Artificial Sequence
<220> FEATURE:
<223> OTHER INFORMATION: Core polypeptide

<400> SEQUENCE: 1404

Leu Lys Asn Tyr Ile Asp Lys Gln Leu Leu Pro Ile Val Asn Lys Gln
 1               5                  10                 15
Ser Ser Ile Ser Asn Ile Glu Thr Val Ile Glu Phe Gln Gln Lys Asn
            20                  25                 30
Asn Arg
```

```
<210> SEQ ID NO 1405
<211> LENGTH: 34
<212> TYPE: PRT
<213> ORGANISM: Artificial Sequence
<220> FEATURE:
<223> OTHER INFORMATION: Core polypeptide

<400> SEQUENCE: 1405

Lys Asn Tyr Ile Asp Lys Gln Leu Leu Pro Ile Val Asn Lys Gln Ser
 1               5                  10                  15

Ser Ile Ser Asn Ile Glu Thr Val Ile Glu Phe Gln Gln Lys Asn Asn
            20                  25                  30

Arg Leu

<210> SEQ ID NO 1406
<211> LENGTH: 35
<212> TYPE: PRT
<213> ORGANISM: Artificial Sequence
<220> FEATURE:
<223> OTHER INFORMATION: Core polypeptide

<400> SEQUENCE: 1406

Asn Tyr Ile Asp Lys Gln Leu Leu Pro Ile Val Asn Lys Gln Ser Ile
 1               5                  10                  15

Ser Ile Ser Asn Ile Glu Thr Val Ile Glu Phe Gln Gln Lys Asn Asn
            20                  25                  30

Arg Leu Leu
        35

<210> SEQ ID NO 1407
<211> LENGTH: 34
<212> TYPE: PRT
<213> ORGANISM: Artificial Sequence
<220> FEATURE:
<223> OTHER INFORMATION: Core polypeptide

<400> SEQUENCE: 1407

Tyr Ile Asp Lys Gln Leu Leu Pro Ile Val Asn Lys Gln Ser Ser Ile
 1               5                  10                  15

Ser Asn Ile Glu Thr Val Ile Glu Phe Gln Gln Lys Asn Asn Arg Leu
            20                  25                  30

Leu Glu

<210> SEQ ID NO 1408
<211> LENGTH: 34
<212> TYPE: PRT
<213> ORGANISM: Artificial Sequence
<220> FEATURE:
<223> OTHER INFORMATION: Core polypeptide

<400> SEQUENCE: 1408

Ile Asp Lys Gln Leu Leu Pro Ile Val Asn Lys Gln Ser Ser Ile Ser
 1               5                  10                  15

Asn Ile Glu Thr Val Ile Glu Phe Gln Gln Lys Asn Asn Arg Leu Leu
            20                  25                  30

Glu Ile

<210> SEQ ID NO 1409
<211> LENGTH: 34
<212> TYPE: PRT
<213> ORGANISM: Artificial Sequence
<220> FEATURE:
```

<223> OTHER INFORMATION: Core polypeptide

<400> SEQUENCE: 1409

Asp Lys Gln Leu Leu Pro Ile Val Asn Lys Gln Ser Ser Ile Ser Asn
1               5                   10                  15

Ile Glu Thr Val Ile Glu Phe Gln Gln Lys Asn Asn Arg Leu Leu Glu
            20                  25                  30

Ile Thr

<210> SEQ ID NO 1410
<211> LENGTH: 34
<212> TYPE: PRT
<213> ORGANISM: Artificial Sequence
<220> FEATURE:
<223> OTHER INFORMATION: Core polypeptide

<400> SEQUENCE: 1410

Lys Gln Leu Leu Pro Ile Val Asn Lys Gln Ser Ser Ile Ser Asn Ile
1               5                   10                  15

Glu Thr Val Ile Glu Phe Gln Gln Lys Asn Asn Arg Leu Leu Glu Ile
            20                  25                  30

Thr Arg

<210> SEQ ID NO 1411
<211> LENGTH: 34
<212> TYPE: PRT
<213> ORGANISM: Artificial Sequence
<220> FEATURE:
<223> OTHER INFORMATION: Core polypeptide

<400> SEQUENCE: 1411

Gln Leu Leu Pro Ile Val Asn Lys Gln Ser Ser Ile Ser Asn Ile Glu
1               5                   10                  15

Thr Val Ile Glu Phe Gln Gln Lys Asn Asn Arg Leu Leu Glu Ile Thr
            20                  25                  30

Arg Glu

<210> SEQ ID NO 1412
<211> LENGTH: 23
<212> TYPE: PRT
<213> ORGANISM: Artificial Sequence
<220> FEATURE:
<223> OTHER INFORMATION: Core polypeptide

<400> SEQUENCE: 1412

Val Tyr Pro Ser Asp Glu Tyr Asp Ala Ser Ile Ser Gln Val Asn Glu
1               5                   10                  15

Glu Ile Asn Gln Ala Leu Ala
            20

<210> SEQ ID NO 1413
<211> LENGTH: 23
<212> TYPE: PRT
<213> ORGANISM: Artificial Sequence
<220> FEATURE:
<223> OTHER INFORMATION: Core polypeptide

<400> SEQUENCE: 1413

Gln Val Asn Glu Glu Ile Asn Gln Ala Leu Ala Tyr Ile Arg Lys Ala
1               5                   10                  15

Asp Glu Leu Leu Glu Asn Val
            20

<210> SEQ ID NO 1414
<211> LENGTH: 35
<212> TYPE: PRT
<213> ORGANISM: Artificial Sequence
<220> FEATURE:
<223> OTHER INFORMATION: Core polypeptide

<400> SEQUENCE: 1414

Val Tyr Pro Ser Asp Glu Tyr Asp Ala Ser Ile Ser Gln Val Asn Glu
 1               5                  10                  15

Glu Ile Asn Gln Ala Leu Ala Tyr Ile Arg Lys Ala Asp Glu Leu Leu
            20                  25                  30

Glu Asn Val
        35

<210> SEQ ID NO 1415
<211> LENGTH: 27
<212> TYPE: PRT
<213> ORGANISM: Artificial Sequence
<220> FEATURE:
<223> OTHER INFORMATION: Core polypeptide

<400> SEQUENCE: 1415

Asp Glu Tyr Asp Ala Ser Ile Ser Gln Val Asn Glu Glu Ile Asn Gln
 1               5                  10                  15

Ala Leu Ala Tyr Ile Arg Glu Ala Asp Glu Leu
            20                  25

<210> SEQ ID NO 1416
<211> LENGTH: 27
<212> TYPE: PRT
<213> ORGANISM: Artificial Sequence
<220> FEATURE:
<223> OTHER INFORMATION: Core polypeptide

<400> SEQUENCE: 1416

Asp Glu Tyr Asp Ala Ser Ile Ser Gln Val Asn Glu Lys Ile Asn Gln
 1               5                  10                  15

Ala Leu Ala Tyr Ile Arg Glu Ala Asp Glu Leu
            20                  25

<210> SEQ ID NO 1417
<211> LENGTH: 35
<212> TYPE: PRT
<213> ORGANISM: Artificial Sequence
<220> FEATURE:
<223> OTHER INFORMATION: Core polypeptide

<400> SEQUENCE: 1417

Asp Asp Glu Cys Leu Asn Ser Val Lys Asn Gly Thr Tyr Asp Phe Pro
 1               5                  10                  15

Lys Phe Glu Glu Glu Ser Lys Leu Asn Arg Asn Glu Ile Lys Gly Val
            20                  25                  30

Lys Leu Ser
        35

<210> SEQ ID NO 1418
<211> LENGTH: 34
<212> TYPE: PRT
<213> ORGANISM: Artificial Sequence
<220> FEATURE:
<223> OTHER INFORMATION: Core polypeptide

```
<400> SEQUENCE: 1418

Asp Asp Glu Leu Asn Ser Val Lys Asn Gly Thr Tyr Asp Phe Pro Lys
 1               5                  10                  15

Phe Glu Glu Ser Lys Leu Asn Arg Asn Gly Ile Lys Gly Val Lys
            20                  25                  30

Leu Ser

<210> SEQ ID NO 1419
<211> LENGTH: 39
<212> TYPE: PRT
<213> ORGANISM: Artificial Sequence
<220> FEATURE:
<223> OTHER INFORMATION: Core polypeptide

<400> SEQUENCE: 1419

Tyr His Lys Cys Asp Asp Glu Cys Leu Asn Ser Val Lys Asn Gly Thr
 1               5                  10                  15

Phe Asp Phe Pro Lys Phe Glu Glu Ser Lys Leu Asn Arg Glu Ile
            20                  25                  30

Lys Gly Val Lys Leu Ser Ser
            35

<210> SEQ ID NO 1420
<211> LENGTH: 38
<212> TYPE: PRT
<213> ORGANISM: Artificial Sequence
<220> FEATURE:
<223> OTHER INFORMATION: Core polypeptide

<400> SEQUENCE: 1420

Tyr His Lys Asp Asp Glu Leu Asn Ser Val Lys Asn Gly Thr Phe Asp
 1               5                  10                  15

Phe Pro Lys Phe Glu Glu Glu Ser Lys Leu Asn Arg Asn Glu Ile Lys
            20                  25                  30

Gly Val Lys Leu Ser Ser
            35

<210> SEQ ID NO 1421
<211> LENGTH: 36
<212> TYPE: PRT
<213> ORGANISM: Artificial Sequence
<220> FEATURE:
<223> OTHER INFORMATION: Core polypeptide

<400> SEQUENCE: 1421

Tyr Thr Ser Leu Ile His Ser Leu Ile Glu Glu Ser Gln Asn Gln Gln
 1               5                  10                  15

Glu Lys Asn Glu Tyr Glu Leu Gln Lys Leu Asp Lys Trp Ala Ser Leu
            20                  25                  30

Trp Asn Trp Phe
            35

<210> SEQ ID NO 1422
<211> LENGTH: 36
<212> TYPE: PRT
<213> ORGANISM: Artificial Sequence
<220> FEATURE:
<223> OTHER INFORMATION: Core polypeptide

<400> SEQUENCE: 1422

Tyr Thr Ser Leu Ile His Ser Leu Ile Glu Glu Ser Gln Ile Gln Gln
 1               5                  10                  15
```

Glu Lys Asn Glu Gln Glu Leu Gln Lys Leu Asp Lys Trp Ala Ser Leu
            20                  25                  30

Trp Asn Trp Phe
        35

<210> SEQ ID NO 1423
<211> LENGTH: 36
<212> TYPE: PRT
<213> ORGANISM: Artificial Sequence
<220> FEATURE:
<223> OTHER INFORMATION: Core polypeptide

<400> SEQUENCE: 1423

Tyr Thr Ser Leu Ile His Ser Leu Ile Glu Glu Ser Gln Asn Gln Gln
 1               5                  10                  15

Glu Lys Asn Glu Gln Glu Leu Leu Glu Leu Asp Lys Trp Ala Ser Leu
            20                  25                  30

Trp Glu Trp Phe
        35

<210> SEQ ID NO 1424
<211> LENGTH: 36
<212> TYPE: PRT
<213> ORGANISM: Artificial Sequence
<220> FEATURE:
<223> OTHER INFORMATION: Core polypeptide

<400> SEQUENCE: 1424

Tyr Thr Ser Leu Ile His Ser Leu Ile Glu Glu Ser Gln Ile Gln Gln
 1               5                  10                  15

Glu Lys Asn Glu Gln Glu Leu Leu Glu Leu Asp Lys Trp Ala Ser Leu
            20                  25                  30

Trp Glu Trp Phe
        35

<210> SEQ ID NO 1425
<211> LENGTH: 36
<212> TYPE: PRT
<213> ORGANISM: Artificial Sequence
<220> FEATURE:
<223> OTHER INFORMATION: Core polypeptide

<400> SEQUENCE: 1425

Tyr Thr Ser Leu Ile His Ser Leu Ile Glu Glu Ser Gln Asn Gln Gln
 1               5                  10                  15

Glu Lys Asn Glu Tyr Glu Leu Leu Glu Leu Asp Lys Trp Ala Ser Leu
            20                  25                  30

Trp Glu Trp Phe
        35

<210> SEQ ID NO 1426
<211> LENGTH: 36
<212> TYPE: PRT
<213> ORGANISM: Artificial Sequence
<220> FEATURE:
<223> OTHER INFORMATION: Core polypeptide

<400> SEQUENCE: 1426

Tyr Thr Ser Leu Ile His Ser Leu Ile Glu Glu Ser Gln Ile Gln Gln
 1               5                  10                  15

Glu Lys Asn Glu Tyr Glu Leu Leu Glu Leu Asp Lys Trp Ala Ser Leu
            20                  25                  30

Trp Glu Trp Phe
        35

<210> SEQ ID NO 1427
<211> LENGTH: 35
<212> TYPE: PRT
<213> ORGANISM: Artificial Sequence
<220> FEATURE:
<223> OTHER INFORMATION: Core polypeptide

<400> SEQUENCE: 1427

Tyr Thr Ser Leu Ile His Ser Leu Ile Glu Glu Ser Gln Ile Gln Gln
1               5                   10                  15

Glu Lys Asn Glu Tyr Glu Leu Gln Lys Leu Asp Trp Ala Ser Leu Trp
            20                  25                  30

Glu Trp Phe
        35

<210> SEQ ID NO 1428
<211> LENGTH: 36
<212> TYPE: PRT
<213> ORGANISM: Artificial Sequence
<220> FEATURE:
<223> OTHER INFORMATION: Core polypeptide

<400> SEQUENCE: 1428

Tyr Thr Ser Leu Ile His Ser Leu Ile Glu Glu Ser Gln Asn Gln Gln
1               5                   10                  15

Glu Lys Asn Glu Gln Glu Leu Gln Lys Leu Asp Lys Trp Ala Ser Leu
            20                  25                  30

Trp Glu Trp Phe
        35

<210> SEQ ID NO 1429
<211> LENGTH: 36
<212> TYPE: PRT
<213> ORGANISM: Artificial Sequence
<220> FEATURE:
<223> OTHER INFORMATION: Core polypeptide

<400> SEQUENCE: 1429

Tyr Thr Ser Leu Ile His Ser Leu Ile Glu Glu Ser Gln Asn Gln Gln
1               5                   10                  15

Glu Lys Asn Glu Tyr Glu Leu Gln Lys Leu Asp Lys Trp Ala Ser Leu
            20                  25                  30

Trp Glu Trp Phe
        35

<210> SEQ ID NO 1430
<211> LENGTH: 36
<212> TYPE: PRT
<213> ORGANISM: Artificial Sequence
<220> FEATURE:
<223> OTHER INFORMATION: Core polypeptide

<400> SEQUENCE: 1430

Tyr Thr Ser Leu Ile His Ser Leu Ile Glu Glu Ser Gln Ile Gln Gln
1               5                   10                  15

Glu Lys Asn Glu Gln Glu Leu Gln Lys Leu Asp Lys Trp Ala Ser Leu
            20                  25                  30

Trp Glu Trp Phe
        35

<210> SEQ ID NO 1431
<211> LENGTH: 35
<212> TYPE: PRT
<213> ORGANISM: Artificial Sequence
<220> FEATURE:
<223> OTHER INFORMATION: Core polypeptide

<400> SEQUENCE: 1431

Trp Gln Glu Trp Glu Gln Lys Ile Thr Ala Leu Leu Glu Gln Ala Gln
 1               5                  10                  15

Ile Gln Gln Glu Lys Asn Glu Tyr Glu Leu Gln Lys Leu Asp Lys Trp
            20                  25                  30

Glu Trp Phe
        35

<210> SEQ ID NO 1432
<211> LENGTH: 39
<212> TYPE: PRT
<213> ORGANISM: Artificial Sequence
<220> FEATURE:
<223> OTHER INFORMATION: Core polypeptide

<400> SEQUENCE: 1432

Trp Gln Glu Trp Glu Gln Lys Ile Thr Ala Leu Leu Glu Gln Ala Gln
 1               5                  10                  15

Ile Gln Gln Glu Lys Asn Glu Tyr Glu Leu Gln Lys Leu Ile Glu Trp
            20                  25                  30

Ala Ser Leu Trp Glu Trp Phe
        35

<210> SEQ ID NO 1433
<211> LENGTH: 8
<212> TYPE: PRT
<213> ORGANISM: Artificial Sequence
<220> FEATURE:
<223> OTHER INFORMATION: Core polypeptide

<400> SEQUENCE: 1433

Trp Ala Ser Leu Trp Glu Trp Phe
 1               5

<210> SEQ ID NO 1434
<211> LENGTH: 35
<212> TYPE: PRT
<213> ORGANISM: Artificial Sequence
<220> FEATURE:
<223> OTHER INFORMATION: Core polypeptide

<400> SEQUENCE: 1434

Trp Gln Glu Trp Asp Glu Tyr Asp Ala Ser Ile Ser Gln Val Asn Glu
 1               5                  10                  15

Lys Ile Asn Gln Ala Leu Ala Tyr Ile Arg Glu Ala Asp Glu Leu Trp
            20                  25                  30

Ala Trp Phe
        35

<210> SEQ ID NO 1435
<211> LENGTH: 35
<212> TYPE: PRT
<213> ORGANISM: Artificial Sequence
<220> FEATURE:
<223> OTHER INFORMATION: Core polypeptide -continued

```
<400> SEQUENCE: 1435

Trp Gln Ala Trp Asp Glu Tyr Asp Ala Ser Ile Ser Gln Val Asn Glu
 1               5                  10                  15

Lys Ile Asn Gln Ala Leu Ala Tyr Ile Arg Glu Ala Asp Glu Leu Trp
             20                  25                  30

Ala Trp Phe
         35

<210> SEQ ID NO 1436
<211> LENGTH: 31
<212> TYPE: PRT
<213> ORGANISM: Artificial Sequence
<220> FEATURE:
<223> OTHER INFORMATION: Core polypeptide

<400> SEQUENCE: 1436

Trp Gln Ala Trp Asp Glu Tyr Asp Ala Ser Ile Ser Asp Val Asn Glu
 1               5                  10                  15

Lys Ile Asn Gln Ala Leu Ala Tyr Ile Arg Glu Ala Asp Glu Leu
             20                  25                  30

<210> SEQ ID NO 1437
<211> LENGTH: 8
<212> TYPE: PRT
<213> ORGANISM: SIV and HIV-2

<400> SEQUENCE: 1437

Trp Leu Glu Trp Glu Arg Gln Ile
 1               5

<210> SEQ ID NO 1438
<211> LENGTH: 8
<212> TYPE: PRT
<213> ORGANISM: SIV and HIV-2

<400> SEQUENCE: 1438

Trp Leu Glu Trp Glu Lys Gln Ile
 1               5

<210> SEQ ID NO 1439
<211> LENGTH: 8
<212> TYPE: PRT
<213> ORGANISM: SIV and HIV-2

<400> SEQUENCE: 1439

Trp Gln Gln Trp Glu Gln Gln Ile
 1               5

<210> SEQ ID NO 1440
<211> LENGTH: 8
<212> TYPE: PRT
<213> ORGANISM: SIV and HIV-2

<400> SEQUENCE: 1440

Trp Gln Gln Trp Glu Lys Gln Ile
 1               5

<210> SEQ ID NO 1441
<211> LENGTH: 8
<212> TYPE: PRT
<213> ORGANISM: SIV and HIV-2

<400> SEQUENCE: 1441
```

Trp Gln Glu Trp Glu His Lys Ile
1               5

<210> SEQ ID NO 1442
<211> LENGTH: 8
<212> TYPE: PRT
<213> ORGANISM: SIV and HIV-2

<400> SEQUENCE: 1442

Trp Gln Glu Trp Glu Gly Lys Ile
1               5

<210> SEQ ID NO 1443
<211> LENGTH: 8
<212> TYPE: PRT
<213> ORGANISM: SIV and HIV-2

<400> SEQUENCE: 1443

Trp Gln Glu Trp Glu Gln Gln Ile
1               5

<210> SEQ ID NO 1444
<211> LENGTH: 8
<212> TYPE: PRT
<213> ORGANISM: SIV and HIV-2

<400> SEQUENCE: 1444

Trp Gln Lys Trp Glu Gln Gln Ile
1               5

<210> SEQ ID NO 1445
<211> LENGTH: 8
<212> TYPE: PRT
<213> ORGANISM: SIV and HIV-2

<400> SEQUENCE: 1445

Trp Gln Glu Trp Glu Gln Arg Ile
1               5

<210> SEQ ID NO 1446
<211> LENGTH: 8
<212> TYPE: PRT
<213> ORGANISM: HIV-1

<400> SEQUENCE: 1446

Trp Leu Gln Trp Asp Lys Glu Ile
1               5

<210> SEQ ID NO 1447
<211> LENGTH: 8
<212> TYPE: PRT
<213> ORGANISM: HIV-1

<400> SEQUENCE: 1447

Trp Met Asp Trp Glu Arg Glu Ile
1               5

<210> SEQ ID NO 1448
<211> LENGTH: 8
<212> TYPE: PRT
<213> ORGANISM: HIV-1

<400> SEQUENCE: 1448

Trp Met Glu Trp Glu Lys Glu Ile
1               5

-continued

<210> SEQ ID NO 1449
<211> LENGTH: 8
<212> TYPE: PRT
<213> ORGANISM: HIV-1

<400> SEQUENCE: 1449

Trp Met Glu Trp Asp Arg Glu Ile
1               5

<210> SEQ ID NO 1450
<211> LENGTH: 8
<212> TYPE: PRT
<213> ORGANISM: HIV-1

<400> SEQUENCE: 1450

Trp Met Glu Trp Glu Arg Glu Ile
1               5

<210> SEQ ID NO 1451
<211> LENGTH: 8
<212> TYPE: PRT
<213> ORGANISM: HIV-1

<400> SEQUENCE: 1451

Trp Ile Glu Trp Glu Arg Glu Ile
1               5

<210> SEQ ID NO 1452
<211> LENGTH: 8
<212> TYPE: PRT
<213> ORGANISM: HIV-1

<400> SEQUENCE: 1452

Trp Ile Glu Trp Asp Arg Glu Ile
1               5

<210> SEQ ID NO 1453
<211> LENGTH: 8
<212> TYPE: PRT
<213> ORGANISM: HIV-1

<400> SEQUENCE: 1453

Trp Met Gln Trp Asp Arg Glu Ile
1               5

<210> SEQ ID NO 1454
<211> LENGTH: 8
<212> TYPE: PRT
<213> ORGANISM: HIV-1

<400> SEQUENCE: 1454

Trp Ile Gln Trp Glu Arg Glu Ile
1               5

<210> SEQ ID NO 1455
<211> LENGTH: 8
<212> TYPE: PRT
<213> ORGANISM: HIV-1

<400> SEQUENCE: 1455

Trp Gly Ile Trp Arg Trp Gly Ile
1               5

```
<210> SEQ ID NO 1456
<211> LENGTH: 8
<212> TYPE: PRT
<213> ORGANISM: HIV-1

<400> SEQUENCE: 1456

Trp Ile Gln Trp Asp Arg Glu Ile
 1               5

<210> SEQ ID NO 1457
<211> LENGTH: 8
<212> TYPE: PRT
<213> ORGANISM: HIV-1

<400> SEQUENCE: 1457

Trp Ile Gln Trp Glu Lys Glu Ile
 1               5

<210> SEQ ID NO 1458
<211> LENGTH: 8
<212> TYPE: PRT
<213> ORGANISM: HIV-1

<400> SEQUENCE: 1458

Trp Met Gln Trp Glu Lys Glu Ile
 1               5

<210> SEQ ID NO 1459
<211> LENGTH: 8
<212> TYPE: PRT
<213> ORGANISM: HIV-1

<400> SEQUENCE: 1459

Trp Gln Gln Trp Asp Gln His Ile
 1               5

<210> SEQ ID NO 1460
<211> LENGTH: 8
<212> TYPE: PRT
<213> ORGANISM: HIV-1

<400> SEQUENCE: 1460

Trp Met Gln Trp Glu Arg Glu Ile
 1               5

<210> SEQ ID NO 1461
<211> LENGTH: 8
<212> TYPE: PRT
<213> ORGANISM: HIV-1

<400> SEQUENCE: 1461

Trp Gln Glu Trp Asp Arg Gln Ile
 1               5

<210> SEQ ID NO 1462
<211> LENGTH: 8
<212> TYPE: PRT
<213> ORGANISM: HIV-1

<400> SEQUENCE: 1462

Trp Gln Gln Trp Asp Gln Gln Ile
 1               5

<210> SEQ ID NO 1463
<211> LENGTH: 8
```

```
<212> TYPE: PRT
<213> ORGANISM: HIV-1

<400> SEQUENCE: 1463

Trp Ile Glu Trp Lys Arg Glu Ile
 1               5

<210> SEQ ID NO 1464
<211> LENGTH: 8
<212> TYPE: PRT
<213> ORGANISM: HIV-1

<400> SEQUENCE: 1464

Trp Met Glu Trp Glu Met Glu Ile
 1               5

<210> SEQ ID NO 1465
<211> LENGTH: 8
<212> TYPE: PRT
<213> ORGANISM: HIV-1

<400> SEQUENCE: 1465

Trp Ile Glu Trp Glu Lys Glu Ile
 1               5

<210> SEQ ID NO 1466
<211> LENGTH: 8
<212> TYPE: PRT
<213> ORGANISM: HIV-1

<400> SEQUENCE: 1466

Trp Met Gln Trp Lys Arg Glu Ile
 1               5

<210> SEQ ID NO 1467
<211> LENGTH: 8
<212> TYPE: PRT
<213> ORGANISM: HIV-1

<400> SEQUENCE: 1467

Trp Met Glu Trp Asn Arg Glu Ile
 1               5

<210> SEQ ID NO 1468
<211> LENGTH: 8
<212> TYPE: PRT
<213> ORGANISM: HIV-1

<400> SEQUENCE: 1468

Trp Arg Glu Trp Asp Arg Glu Ile
 1               5

<210> SEQ ID NO 1469
<211> LENGTH: 8
<212> TYPE: PRT
<213> ORGANISM: HIV-1

<400> SEQUENCE: 1469

Trp Thr Glu Trp Glu Arg Glu Ile
 1               5

<210> SEQ ID NO 1470
<211> LENGTH: 8
<212> TYPE: PRT
<213> ORGANISM: HIV-1
```

-continued

<400> SEQUENCE: 1470

Trp Leu Glu Trp Glu Arg Glu Ile
 1               5

<210> SEQ ID NO 1471
<211> LENGTH: 8
<212> TYPE: PRT
<213> ORGANISM: HIV-1

<400> SEQUENCE: 1471

Trp Met Gly Trp Glu Arg Glu Ile
 1               5

<210> SEQ ID NO 1472
<211> LENGTH: 8
<212> TYPE: PRT
<213> ORGANISM: HIV-1

<400> SEQUENCE: 1472

Trp Gln Glu Trp Asp Gln Gln Ile
 1               5

<210> SEQ ID NO 1473
<211> LENGTH: 8
<212> TYPE: PRT
<213> ORGANISM: HIV-1

<400> SEQUENCE: 1473

Trp Met Lys Trp Glu Arg Glu Ile
 1               5

<210> SEQ ID NO 1474
<211> LENGTH: 8
<212> TYPE: PRT
<213> ORGANISM: SIV

<400> SEQUENCE: 1474

Trp Ala Gly Leu Trp Glu Trp Phe
 1               5

<210> SEQ ID NO 1475
<211> LENGTH: 8
<212> TYPE: PRT
<213> ORGANISM: SIV

<400> SEQUENCE: 1475

Trp Ser Asn Phe Trp Ser Trp Phe
 1               5

<210> SEQ ID NO 1476
<211> LENGTH: 8
<212> TYPE: PRT
<213> ORGANISM: SIV

<400> SEQUENCE: 1476

Trp Asp Ser Leu Trp Ser Trp Phe
 1               5

<210> SEQ ID NO 1477
<211> LENGTH: 8
<212> TYPE: PRT
<213> ORGANISM: SIV

<400> SEQUENCE: 1477

Trp Ser Gly Phe Trp Ser Trp Phe
1               5

<210> SEQ ID NO 1478
<211> LENGTH: 8
<212> TYPE: PRT
<213> ORGANISM: SIV

<400> SEQUENCE: 1478

Trp Ser Ser Leu Trp Asn Trp Phe
1               5

<210> SEQ ID NO 1479
<211> LENGTH: 8
<212> TYPE: PRT
<213> ORGANISM: SIV

<400> SEQUENCE: 1479

Trp Ser Asp Phe Trp Ser Trp Phe
1               5

<210> SEQ ID NO 1480
<211> LENGTH: 8
<212> TYPE: PRT
<213> ORGANISM: SIV

<400> SEQUENCE: 1480

Trp Ser Asp Ile Trp Ser Trp Val
1               5

<210> SEQ ID NO 1481
<211> LENGTH: 8
<212> TYPE: PRT
<213> ORGANISM: SIV

<400> SEQUENCE: 1481

Trp Ala Ser Leu Trp Asn Trp Phe
1               5

<210> SEQ ID NO 1482
<211> LENGTH: 8
<212> TYPE: PRT
<213> ORGANISM: SIV

<400> SEQUENCE: 1482

Trp Ser Ser Phe Trp Ser Trp Phe
1               5

<210> SEQ ID NO 1483
<211> LENGTH: 8
<212> TYPE: PRT
<213> ORGANISM: HIV-2

<400> SEQUENCE: 1483

Trp Asp Val Phe Gly Asn Trp Phe
1               5

<210> SEQ ID NO 1484
<211> LENGTH: 8
<212> TYPE: PRT
<213> ORGANISM: HIV-2

<400> SEQUENCE: 1484

Trp Asp Val Phe Thr Asn Trp Leu

-continued

<210> SEQ ID NO 1485
<211> LENGTH: 8
<212> TYPE: PRT
<213> ORGANISM: HIV-2

<400> SEQUENCE: 1485

Trp Asp Ile Phe Gly Asn Trp Phe
1               5

<210> SEQ ID NO 1486
<211> LENGTH: 8
<212> TYPE: PRT
<213> ORGANISM: HIV-2

<400> SEQUENCE: 1486

Trp Asp Val Phe Gly Asn Trp Leu
1               5

<210> SEQ ID NO 1487
<211> LENGTH: 8
<212> TYPE: PRT
<213> ORGANISM: HIV-2

<400> SEQUENCE: 1487

Trp Asp Ile Phe Gly Asn Trp Ser
1               5

<210> SEQ ID NO 1488
<211> LENGTH: 8
<212> TYPE: PRT
<213> ORGANISM: HIV-2

<400> SEQUENCE: 1488

Trp Asp Val Phe Ser Asn Trp Phe
1               5

<210> SEQ ID NO 1489
<211> LENGTH: 8
<212> TYPE: PRT
<213> ORGANISM: HIV-2

<400> SEQUENCE: 1489

Trp Asp Ile Leu Gly Asn Trp Phe
1               5

<210> SEQ ID NO 1490
<211> LENGTH: 8
<212> TYPE: PRT
<213> ORGANISM: HIV-1

<400> SEQUENCE: 1490

Trp Ala Asn Leu Trp Asn Trp Phe
1               5

<210> SEQ ID NO 1491
<211> LENGTH: 8
<212> TYPE: PRT
<213> ORGANISM: HIV-1

<400> SEQUENCE: 1491

Trp Ala Ser Leu Trp Asn Trp Phe
1               5

<210> SEQ ID NO 1492
<211> LENGTH: 8
<212> TYPE: PRT
<213> ORGANISM: HIV-1

<400> SEQUENCE: 1492

Trp Glu Asn Leu Trp Asn Trp Phe
 1               5

<210> SEQ ID NO 1493
<211> LENGTH: 8
<212> TYPE: PRT
<213> ORGANISM: HIV-1

<400> SEQUENCE: 1493

Trp Ala Ser Leu Trp Asn Trp Val
 1               5

<210> SEQ ID NO 1494
<211> LENGTH: 8
<212> TYPE: PRT
<213> ORGANISM: HIV-1

<400> SEQUENCE: 1494

Trp Glu Asn Leu Trp Ser Trp Phe
 1               5

<210> SEQ ID NO 1495
<211> LENGTH: 8
<212> TYPE: PRT
<213> ORGANISM: HIV-1

<400> SEQUENCE: 1495

Trp Asp Ser Leu Trp Gly Trp Phe
 1               5

<210> SEQ ID NO 1496
<211> LENGTH: 8
<212> TYPE: PRT
<213> ORGANISM: HIV-1

<400> SEQUENCE: 1496

Trp Asp Ser Leu Trp Asn Trp Phe
 1               5

<210> SEQ ID NO 1497
<211> LENGTH: 8
<212> TYPE: PRT
<213> ORGANISM: HIV-1

<400> SEQUENCE: 1497

Trp Ala Ser Leu Trp Thr Trp Phe
 1               5

<210> SEQ ID NO 1498
<211> LENGTH: 8
<212> TYPE: PRT
<213> ORGANISM: HIV-1

<400> SEQUENCE: 1498

Trp Lys Asn Leu Trp Asn Trp Phe
 1               5

<210> SEQ ID NO 1499

```
<211> LENGTH: 8
<212> TYPE: PRT
<213> ORGANISM: HIV-1

<400> SEQUENCE: 1499

Trp Thr Ser Leu Trp Ser Trp Phe
 1               5

<210> SEQ ID NO 1500
<211> LENGTH: 8
<212> TYPE: PRT
<213> ORGANISM: HIV-1

<400> SEQUENCE: 1500

Trp Ala Ser Ile Trp Asn Trp Leu
 1               5

<210> SEQ ID NO 1501
<211> LENGTH: 8
<212> TYPE: PRT
<213> ORGANISM: HIV-1

<400> SEQUENCE: 1501

Trp Gln Asn Leu Trp Asn Trp Phe
 1               5

<210> SEQ ID NO 1502
<211> LENGTH: 8
<212> TYPE: PRT
<213> ORGANISM: HIV-1

<400> SEQUENCE: 1502

Trp Gln Asn Leu Trp Ser Trp Phe
 1               5

<210> SEQ ID NO 1503
<211> LENGTH: 8
<212> TYPE: PRT
<213> ORGANISM: HIV-1

<400> SEQUENCE: 1503

Trp Pro Asn Leu Trp Asn Trp Phe
 1               5

<210> SEQ ID NO 1504
<211> LENGTH: 8
<212> TYPE: PRT
<213> ORGANISM: HIV-1

<400> SEQUENCE: 1504

Trp Ala Ser Leu Trp Ser Trp Phe
 1               5

<210> SEQ ID NO 1505
<211> LENGTH: 8
<212> TYPE: PRT
<213> ORGANISM: HIV-1

<400> SEQUENCE: 1505

Trp Ser Ser Leu Trp Asn Trp Phe
 1               5

<210> SEQ ID NO 1506
<211> LENGTH: 8
<212> TYPE: PRT
```

<213> ORGANISM: HIV-1

<400> SEQUENCE: 1506

Trp Gly Ser Leu Trp Ser Trp Phe
1               5

<210> SEQ ID NO 1507
<211> LENGTH: 8
<212> TYPE: PRT
<213> ORGANISM: HIV-1

<400> SEQUENCE: 1507

Trp Ala Asn Leu Trp Ser Trp Phe
 1               5

<210> SEQ ID NO 1508
<211> LENGTH: 8
<212> TYPE: PRT
<213> ORGANISM: HIV-1

<400> SEQUENCE: 1508

Trp Ala Gly Leu Trp Asn Trp Phe
 1               5

<210> SEQ ID NO 1509
<211> LENGTH: 8
<212> TYPE: PRT
<213> ORGANISM: HIV-1

<400> SEQUENCE: 1509

Trp Thr Asn Leu Trp Asn Trp Phe
 1               5

<210> SEQ ID NO 1510
<211> LENGTH: 8
<212> TYPE: PRT
<213> ORGANISM: HIV-1

<400> SEQUENCE: 1510

Trp Pro Ser Leu Trp Asn Trp Phe
 1               5

<210> SEQ ID NO 1511
<211> LENGTH: 8
<212> TYPE: PRT
<213> ORGANISM: HIV-1

<400> SEQUENCE: 1511

Trp Ala Gly Leu Trp Ser Trp Phe
 1               5

<210> SEQ ID NO 1512
<211> LENGTH: 8
<212> TYPE: PRT
<213> ORGANISM: HIV-1

<400> SEQUENCE: 1512

Trp Ala Ser Leu Trp Thr Trp Ser
 1               5

<210> SEQ ID NO 1513
<211> LENGTH: 50
<212> TYPE: PRT
<213> ORGANISM: HIV-1

-continued

```
<400> SEQUENCE: 1513

Asn Asn Met Thr Trp Met Glu Trp Asp Arg Glu Ile Asn Asn Tyr Thr
1               5                   10                  15

Ser Leu Ile His Ser Leu Ile Glu Glu Ser Gln Asn Gln Gln Glu Lys
                20                  25                  30

Asn Glu Gln Glu Leu Leu Glu Leu Asp Lys Trp Ala Ser Leu Trp Asn
            35                  40                  45

Trp Phe
    50

<210> SEQ ID NO 1514
<211> LENGTH: 36
<212> TYPE: PRT
<213> ORGANISM: HIV-1

<400> SEQUENCE: 1514

Leu Glu Ala Asn Ile Ser Gln Ser Leu Glu Gln Ala Gln Ile Gln Gln
1               5                   10                  15

Glu Lys Asn Met Tyr Glu Leu Gln Lys Leu Asn Ser Trp Asp Val Phe
                20                  25                  30

Thr Asn Trp Leu
            35

<210> SEQ ID NO 1515
<211> LENGTH: 30
<212> TYPE: PRT
<213> ORGANISM: HIV-1

<400> SEQUENCE: 1515

Asn Asn Tyr Thr Ser Leu Ile His Ser Leu Ile Glu Glu Ser Gln Asn
1               5                   10                  15

Gln Gln Glu Lys Asn Glu Gln Glu Leu Leu Glu Leu Asp Lys
                20                  25                  30
```

HYBRID POLYPEPTIDES WITH ENHANCED PHARMACOKINETIC PROPERTIES

1. INTRODUCTION

The present invention relates to enhancer peptide sequences originally derived from various retroviral envelope (gp41) protein sequences that enhance the pharmacokinetic properties of any core polypeptide to which they are linked. The invention is based on the discovery that hybrid polypeptides comprising the enhancer peptide sequences linked to a core polypeptide possess enhanced pharmacokinetic properties such as increased half life. The invention further relates to methods for enhancing the pharmacokinetic properties of any core polypeptide through linkage of the enhancer peptide sequences to the core polypeptide. The core polypeptides to be used in the practice of the invention can include any pharmacologically useful peptide that can be used, for example, as a therapeutic or prophylactic reagent. In a non-limiting embodiment, the invention is demonstrated by way of example wherein a hybrid polypeptide comprising, for example, an HIV core polypeptide linked to enhancer peptide sequences, is shown to be a potent, non-cytotoxic inhibitor of HIV-1, HIV-2 and SIV infection. Additionally, the enhancer peptide sequences of the invention have been linked to a respiratory syncytial virus (RSV) core polypeptide and a luteinizing hormone receptor (LH-RH) core polypeptide. In each instance, the hybrid polypeptide was found to possess enhanced pharmacokinetic properties, and the RSV hybrid polypeptide exhibited substantial anti-RSV activity.

2. BACKGROUND OF THE INVENTION

Polypeptide products have a wide range of uses as therapeutic and/or prophylactic reagents for prevention and treatment of disease. Many polypeptides are able to regulate biochemical or physiological processes to either prevent disease or provide relief from symptoms associated with disease. For example, polypeptides such as viral or bacterial polypeptides have been utilized successfully as vaccines for prevention of pathological diseases. Additionally, peptides have been successfully utilized as therapeutic agents for treatment of disease symptoms. Such peptides fall into diverse categories such, for example, as hormones, enzymes, immunomodulators, serum proteins and cytokines.

For polypeptides to manifest their proper biological and therapeutic effect on the target sites, the polypeptides must be present in appropriate concentrations at the sites of action. In addition, their structural integrity must generally be maintained. Therefore, the formulation of polypeptides as drugs for therapeutic use is directed by the chemical nature and the characteristics of the polypeptides, such as their size and complexity, their conformational requirements, and their often complicated stability, and solubility profiles. The pharmacokinetics of any particular therapeutic peptide is dependent on the bioavailability, distribution and clearance of said peptide.

Since many bioactive substances, such as peptides and proteins, are rapidly destroyed by the body, it is critical to develop effective systems for maintaining a steady concentration of peptide in blood circulation, to increase the efficacy of such peptides, and to minimize the incidence and severity of adverse side effects.

3. SUMMARY OF THE INVENTION

The present invention relates, first, to enhancer peptide sequences derived from various retroviral envelope (gp41) protein sequences i.e., HIV-1, HIV-2 and SIV, that enhance the pharmacokinetic properties of any core polypeptide to which they are linked. The invention is based on the surprising result that when the disclosed enhancer peptide sequences are linked to any core polypeptide, the resulting hybrid polypeptide possesses enhanced pharmacokinetic properties including, for example, increased half life and reduced clearance rate relative to the core polypeptide alone. The present invention further relates to such hybrid polypeptides and core polypeptides.

The core polypeptides to be used in the practice of the invention can comprise any peptides which may be introduced into a living system, for example, any peptides capable of functioning as therapeutic or prophylactic reagents useful for treatment or prevention of disease. Such peptides include, for example, growth factors, hormones, cytokines, angiogenic growth factors, extracellular matrix polypeptides or polypeptides that exhibit antifusogenic and/or antiviral activity, and peptides or polypeptides that function as immunogens including, for example, viral and bacterial polypeptides.

The invention further relates to methods for enhancing the pharmacokinetic properties of any core polypeptide through linkage of the core polypeptide to the enhancer peptide sequences to form hybrid polypeptides.

The invention is demonstrated by way of examples wherein hybrid polypeptides containing an HIV core polypeptide linked to enhancer peptide sequences are shown to exhibit greatly enhanced pharmacokinetic properties and act as a potent, non-cytotoxic inhibitors of HIV-1, HIV-2 and SIV infection. The invention is further demonstrated by examples wherein hybrid polypeptides containing an RSV core polypeptide or a luteinizing hormone polypeptide are shown to exhibit greatly enhanced pharmacokinetic properties. In addition, the RSV hybrid polypeptide exhibited substantial anti-RSV activity.

3.1. Definitions

Peptides are defined herein as organic compounds comprising two or more amino acids covalently joined by peptide bonds. Peptides may be referred to with respect to the number of constituent natural L-amino acids, i.e., a dipeptide contains two amino acid residues, a tripeptide contains three, etc. Peptides containing ten or fewer amino acids may be referred to as oligopeptides, while those with more than ten amino acid residues are polypeptides. Such peptides may also include non-natural amino acids and any of the modifications and additional amino and carboxyl groups as are described herein.

Peptide sequences defined herein are represented by one-letter symbols for amino acid residues as follows:
A (alanine)
R (arginine)
N (asparagine)
D (aspartic acid)
C (cysteine)
Q (glutamine)
E (glutamic acid)
G (glycine)
H (histidine)
I (isoleucine)
L (leucine)
K (lysine)
M (methionine)
F (phenylalanine)
P (proline)

S (serine)
T (threonine)
W (tryptophan)
Y (tyrosine)
V (valine)
X (any amino acid)

"Enhancer peptide sequences" are defined as peptides having the following consensus amino acid sequences: "WXXWXXXI", "WXXWXXX", "WXXWXX", "WXXWX", "WXXW", "WXXXWXWX", "XXXWXWX", "XXWXWX", "XWXWX", "WXWX", "WXXXWXW", "WXXXWX", "WXXXW", "IXXXWXXW", "XXXWXXW", "XXWXXW", "XWXXW", "XWXWXXXW", "XWXWXXX", "XWXWXX", "XWXWX", "XWXW", "WXWXXXW", or "XWXXXW", wherein X can be any amino acid, W represents tryptophan and I represents isoleucine. As discussed below, the enhancer peptide sequences of the invention also include peptide sequences that are otherwise the same as the consensus amino acid sequences but contain amino acid substitutions, insertions or deletions but which do not abolish the ability of the peptide to enhance the pharmacokinetic properties of a core peptide to which it is linked.

"Core polypeptide" as used herein, refers to any polypeptide which may be introduced into a living system and, thus, represents a bioactive molecule, for example any polypeptide that can function as a pharmacologically useful peptide for treatment or prevention of disease.

"Hybrid polypeptide" as used herein, refers to any polypeptide comprising a terminal enhancer peptide sequence and a core polypeptide.

4. BRIEF DESCRIPTION OF DRAWINGS

Figure 7A:
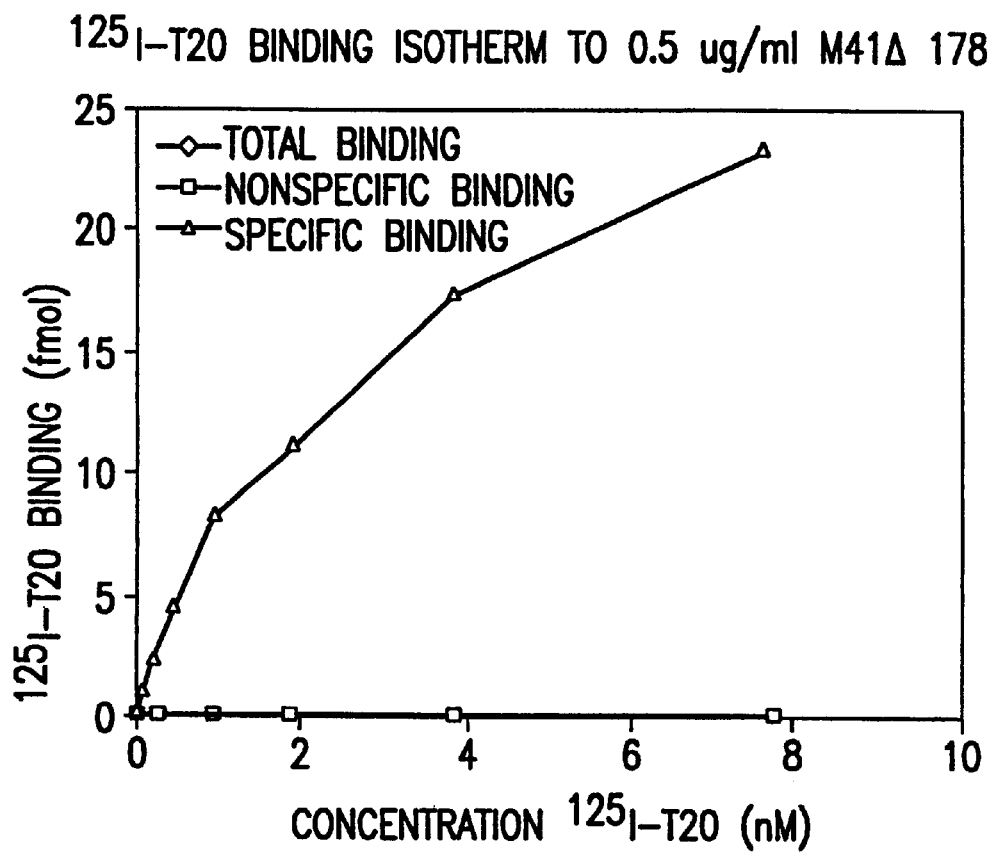
Figures 1, 7A:
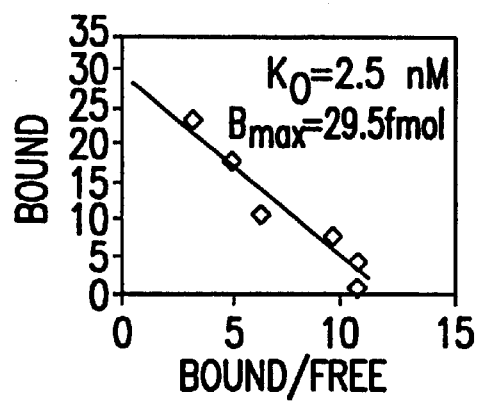
Figure 7B:
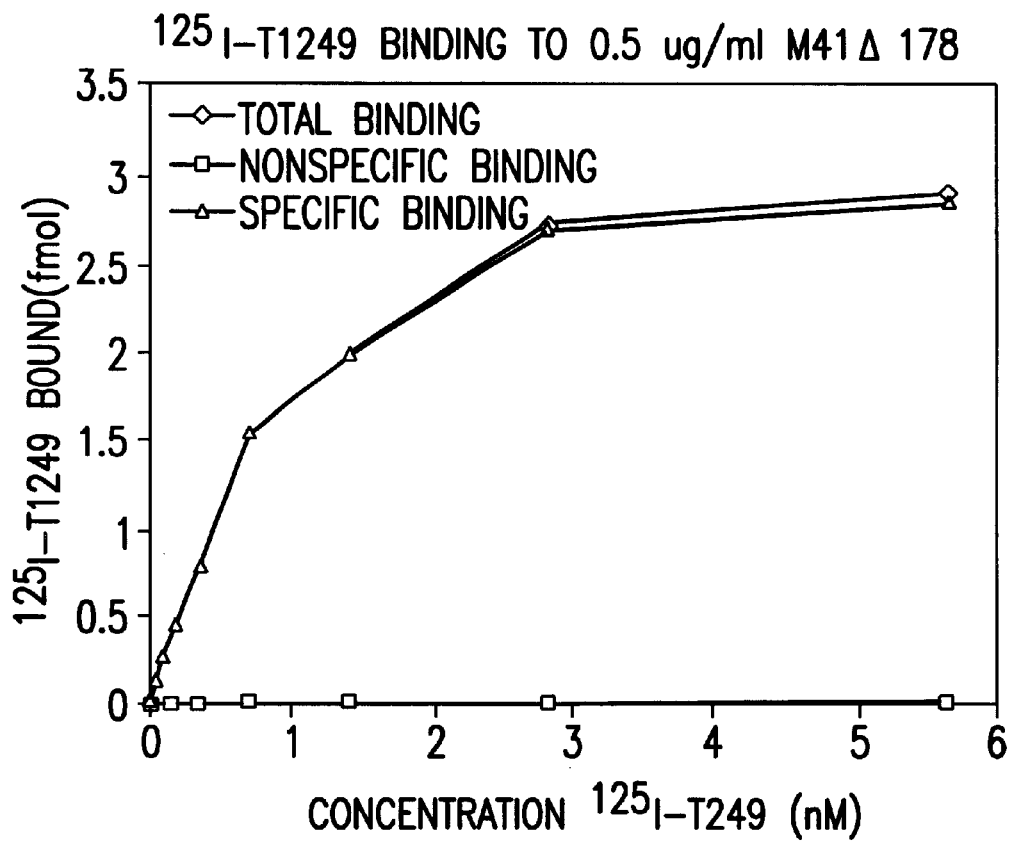
Figures 1, 7B:
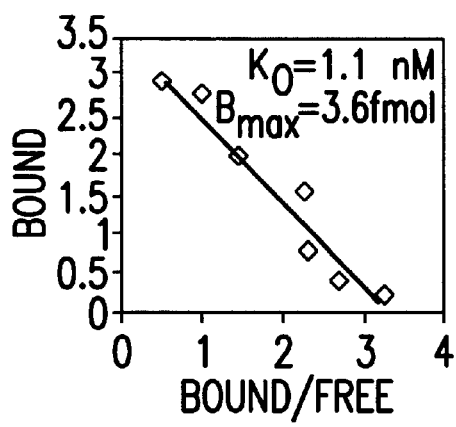

FIG. 1. Hybrid polypeptides. Enhancer peptide sequences derived from putative N-terminal and C-terminal interactive regions are depicted linked to a core polypeptide. The critical enhancer peptide sequences are shaded. It is to be noted that the enhancer peptide sequences indicated may be used either as N- or C-terminal additions. Further, the enhancer peptide sequences can be added to a core polypeptide in forward or reverse orientation, individually or in any of the possible combinations, to enhance pharmacokinetic properties of the peptide.

FIG. 2A. Enhancer peptide sequences derived from various envelope (gp41) protein sequences, representing the N-terminal interactive region observed in all currently published isolate sequences of HIV-1, HIV-2 and SIV (SEQ ID NOS:1129 and 1437–1473, respedtively. The final sequence "WXXWXXXI" represents a consensus sequence.

FIG. 2B. Enhancer peptide sequence variants derived from various envelope (gp41) protein sequences, representing the C-terminal interactive region observed in all currently published isolate sequences of HIV-1, HIV-2 and SIV (SEQ ID NOS:1474–1512, respectively. The final sequence "WXXXWXWX" represents a consensus sequence.

FIG. 3. Comparison of HIV-1 titres in tissues of HIV-1 9320 infected SCID-HuPBMC mice as measured by P24 Levels in HuPBMC co-culture assays. The figure shows a comparison of in vivo T20 and T1249 viral inhibition.

Figure 4A:
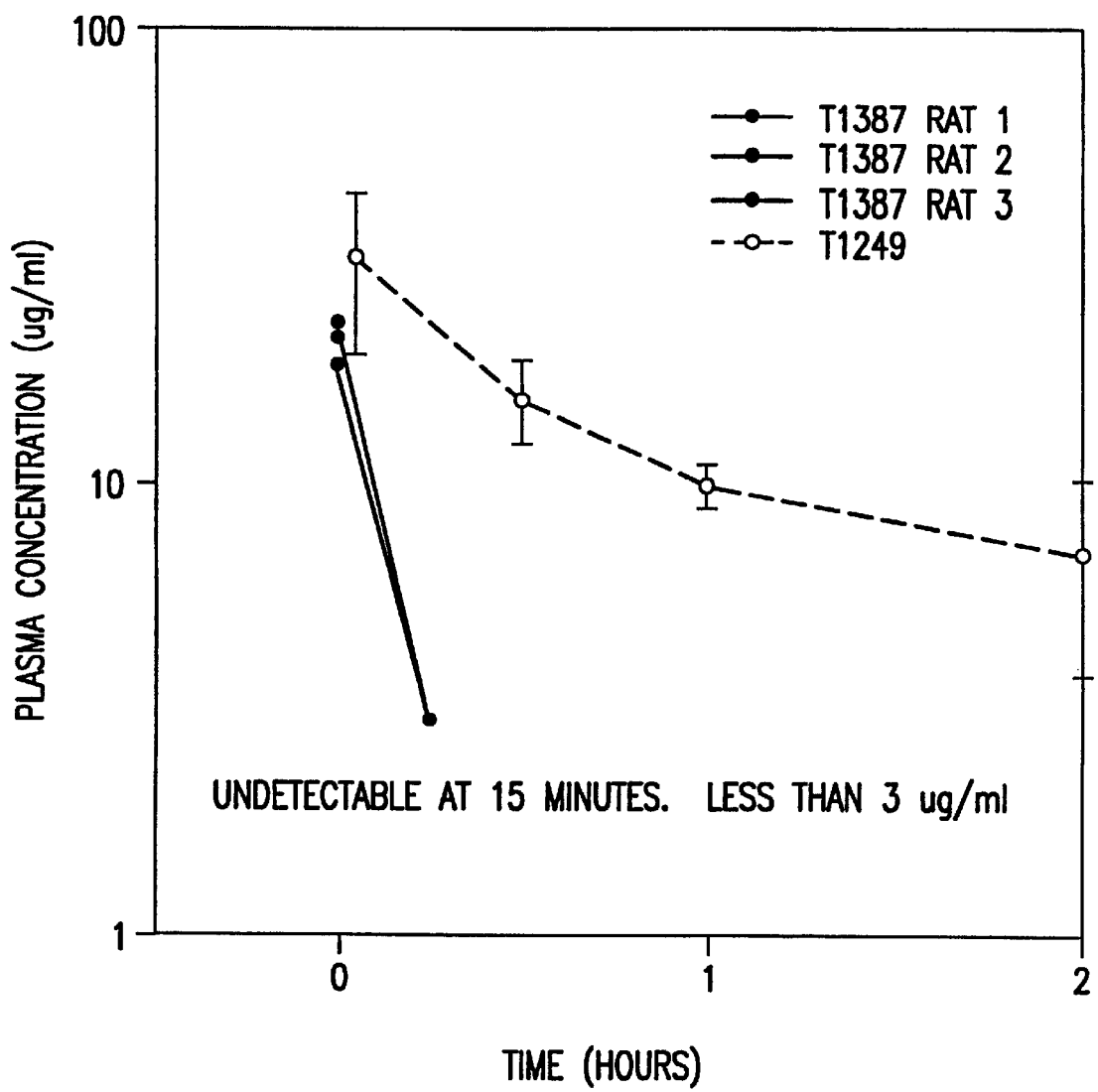
Figure 4B:
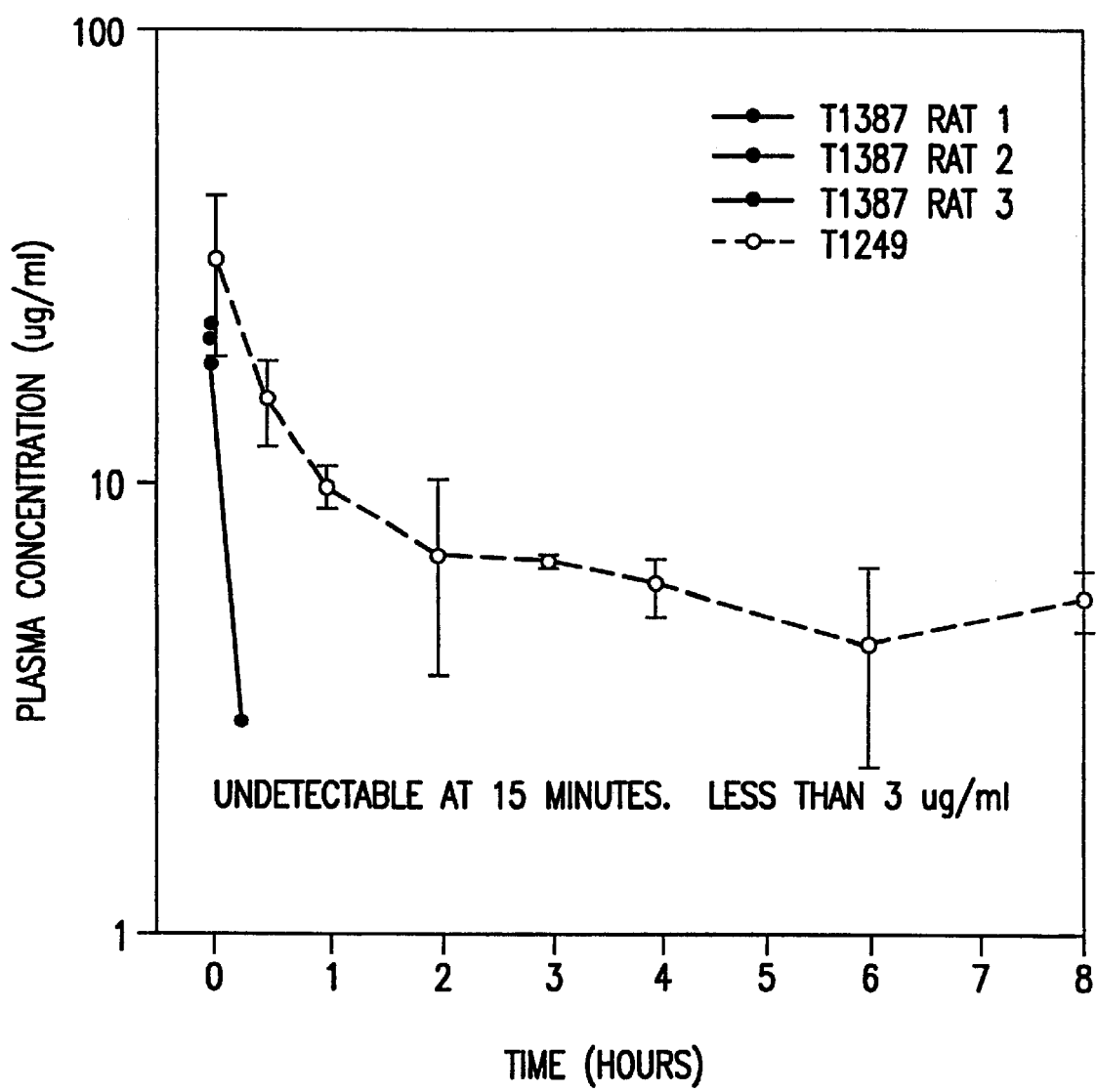

FIGS. 4A–4B. Plasma pharmacokinetic profile of T1249 vs T1387 core control in CD-rats following IV injection for up to 2 hrs (FIG. 4A) and 8 hrs (FIG. 4B). The T1387 polypeptide is a core polypeptide and the T1249 polypeptide is the core polypeptide linked to enhancer peptide sequences.

Figure 5:
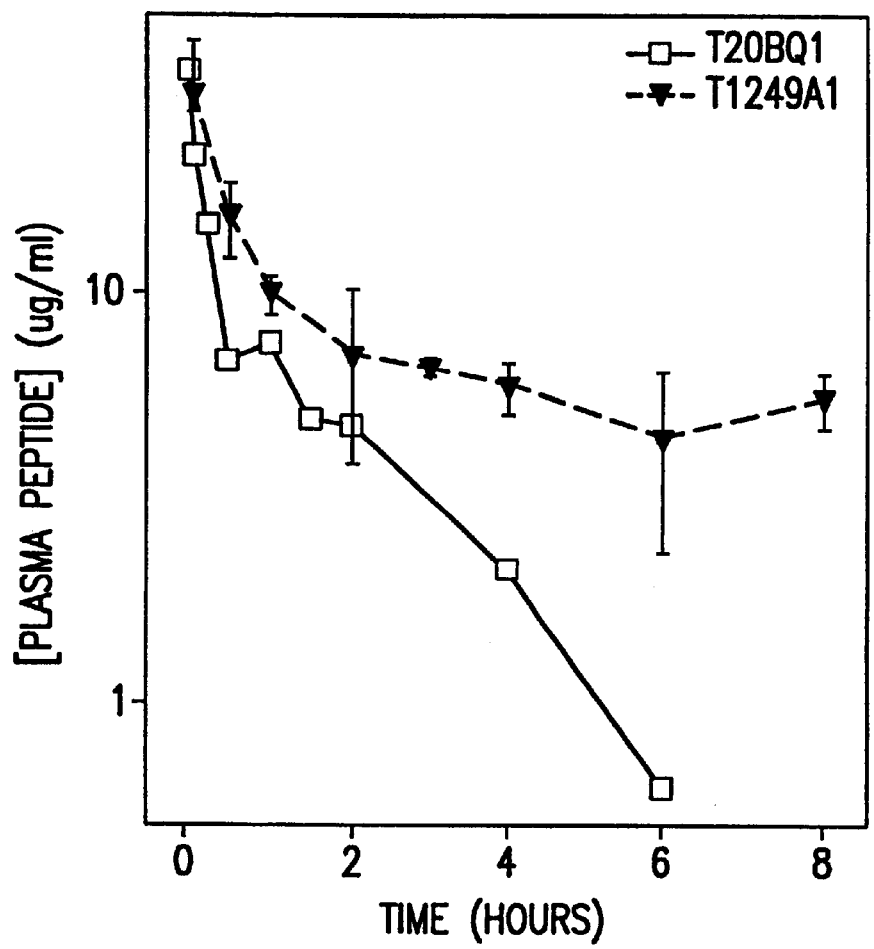

FIG. 5. Plasma pharmacokinetic profile of T1249 vs T20 control in CD-rats following IV administration. The T1249 polypeptide is a hybrid polypeptide of a core polypeptide (T1387) linked to enhancer peptide sequences. T20: n=4; T1249: n=3.

Figure 6:
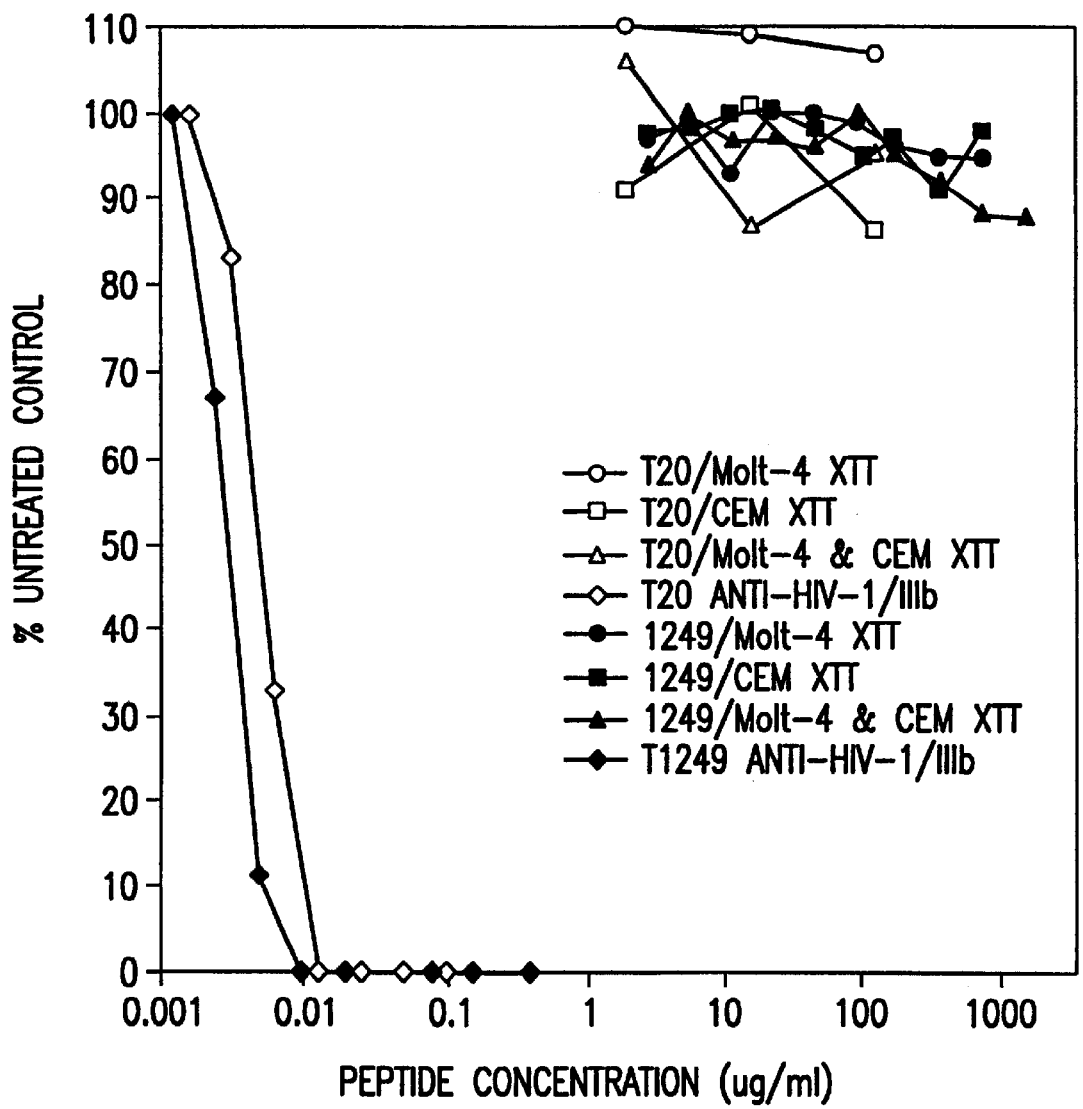

FIG. 6. Comparison of T20/T1249 Anti-HIV-1/IIIb activity and cytotoxicity.

FIG. 7. Direct Binding of T1249 to gp41construct M41Δ178. $^{125}$I-T1249 was HPLC purified to maximum specific activity. Saturation binding to M41Δ178 (a gp41ectodomain fusion protein lacking the T20 amino acid sequence) immobilized in microtitre plates at 0.5 mg/ml is shown.

Figure 8A:
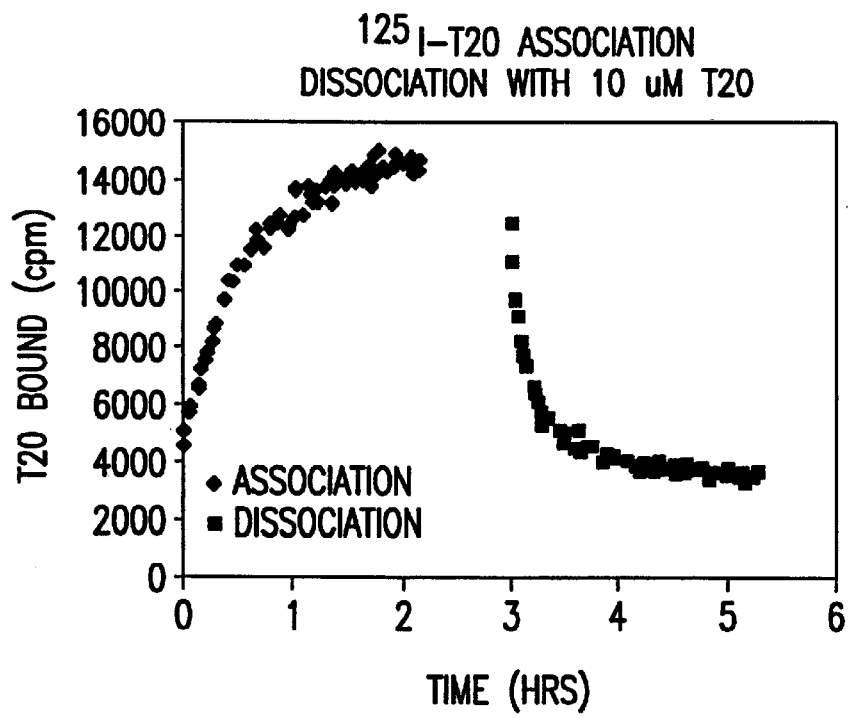
Figure 8B:
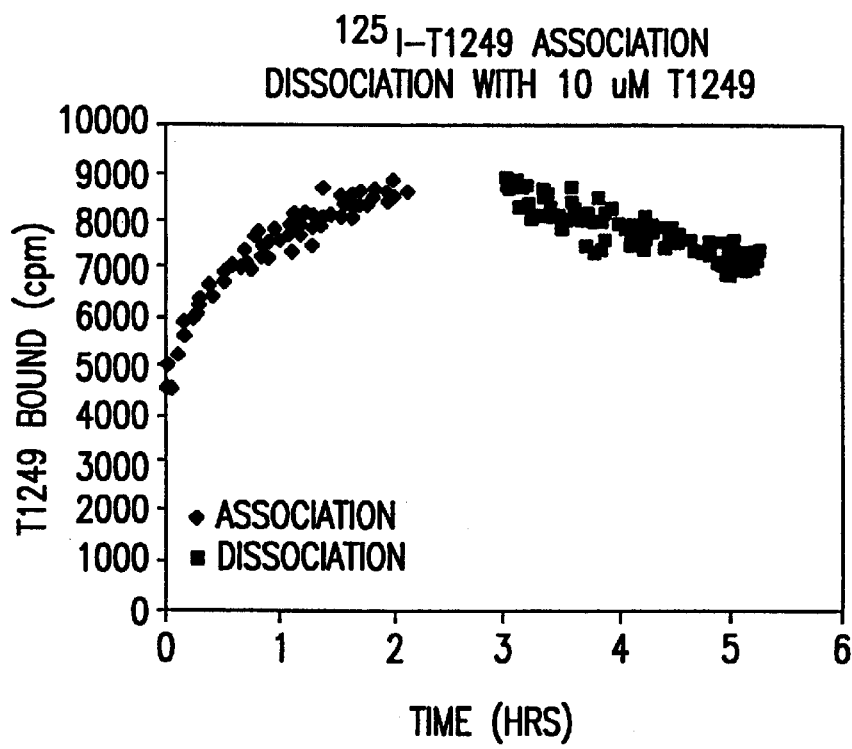

FIG. 8. Time Course of T1249 Association/Dissociation. Dissociation of bound radioligand was measured following the addition of unlabeled peptide to a final concentration of 10 μM in 1/10 total assay volume.

Figure 9A:
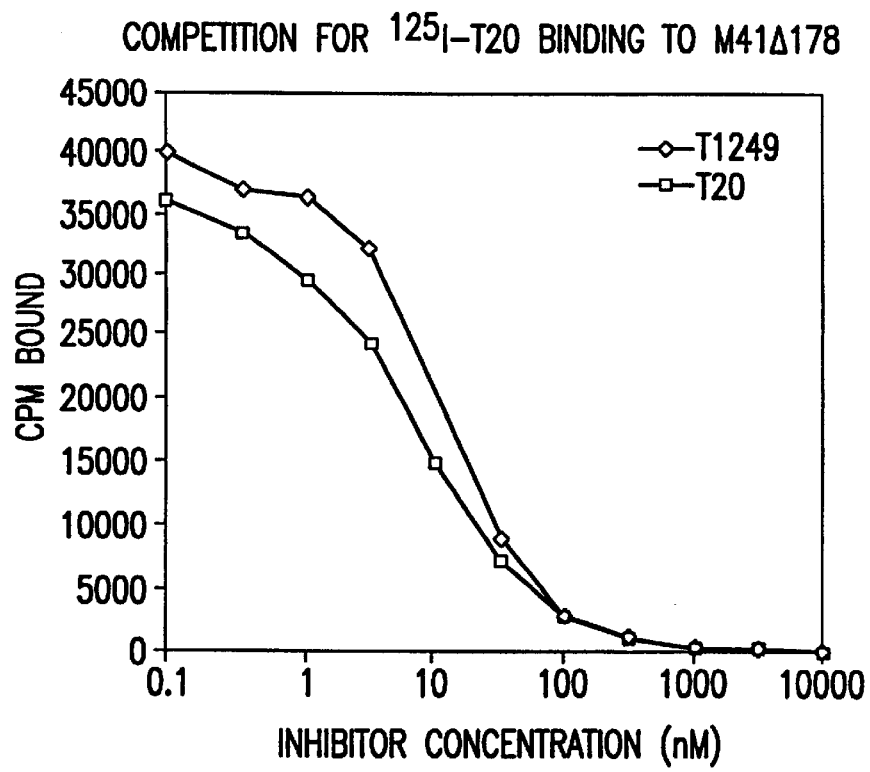
Figure 9B:
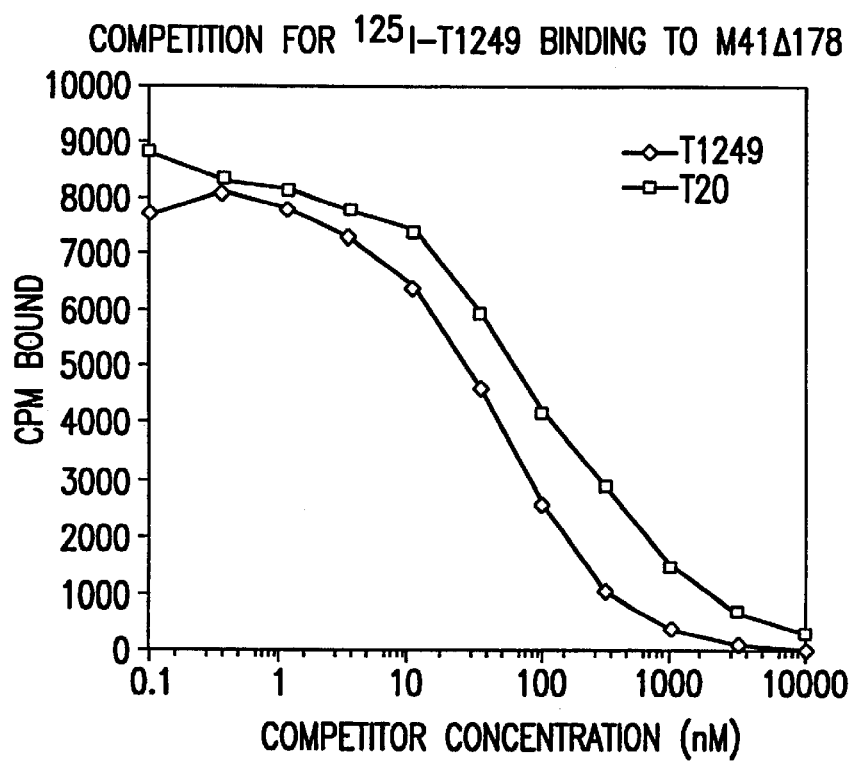

FIG. 9. Competition for T1249 Binding to M41Δ178. Unlabeled T1249 and T20 were titrated in the presence of a single concentration of either $^{125}$I-T1249 or $^{125}$I-T20. Ligand was added just after the unlabeled peptide to start the incubation.

Figure 10A:
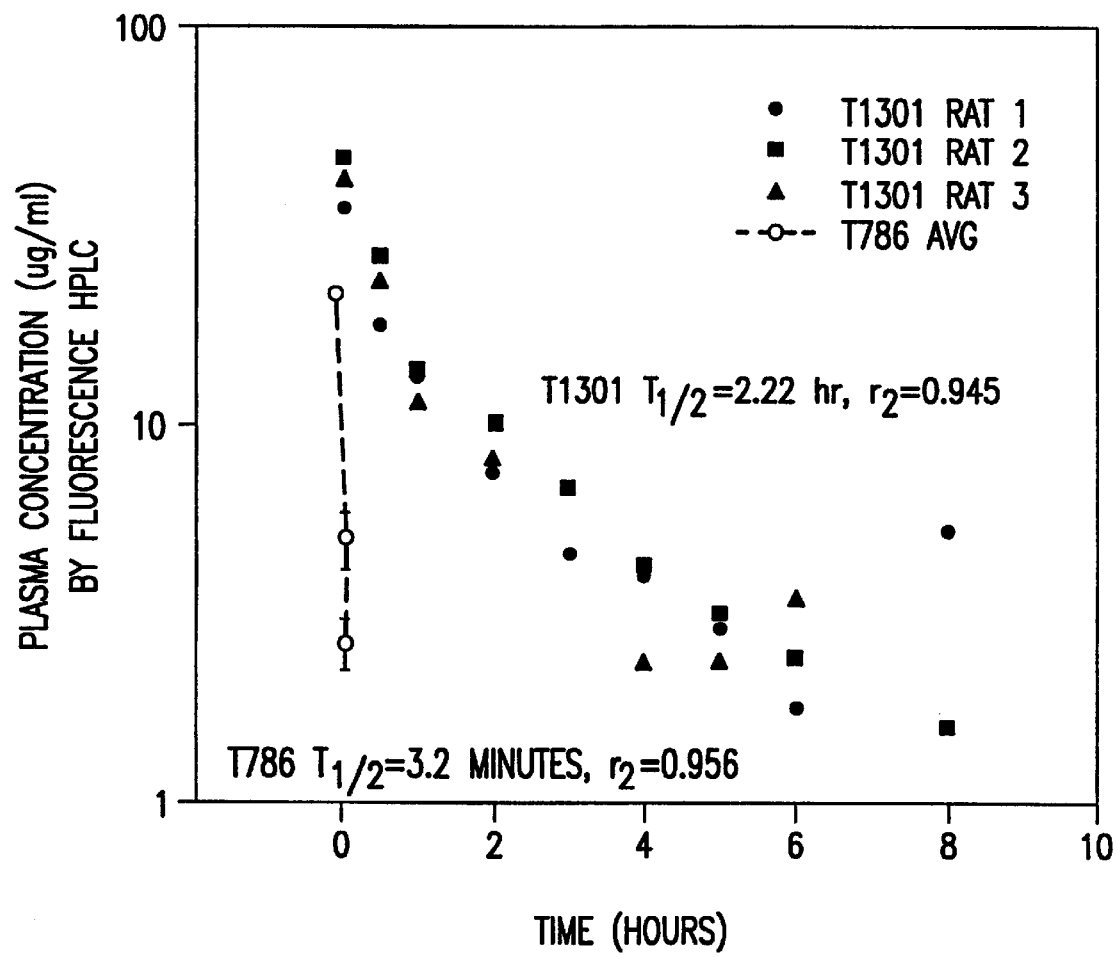
Figure 10B:
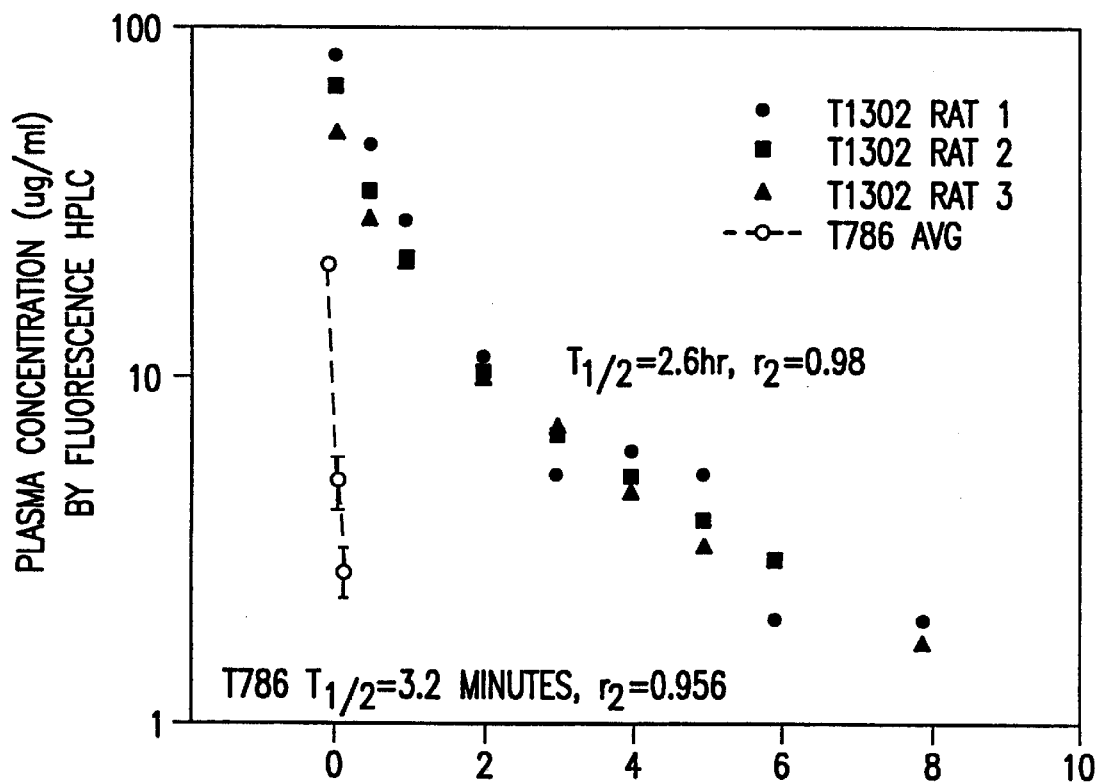

FIGS. 10A–10B. Plasma pharmacokinetic profile of RSV hybrid polypeptides T1301 (10A) and T1302 (10B) vs T786 in CD rats.

FIG. 11A. Plaque Reduction Assay. Hybrid polypeptide T1293 is capable of inhibiting RSV infection with an IC$_{50}$ 2.6 μg/ml.

Figure 11B:
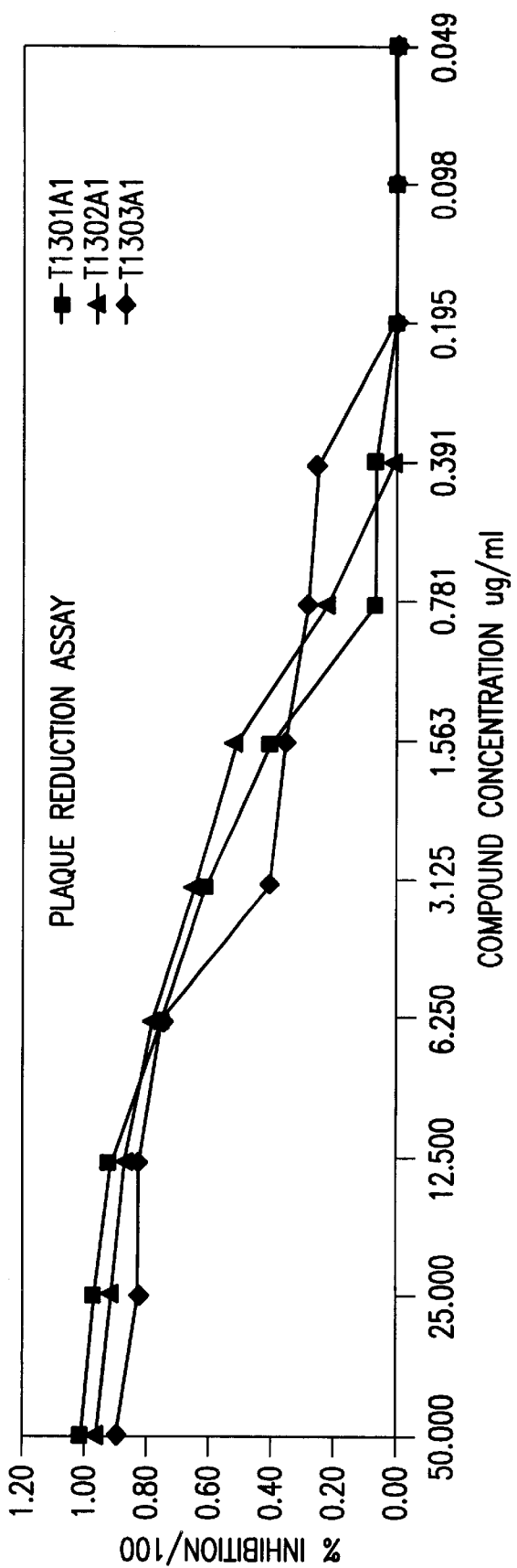

FIG. 11B. Plaque Reduction Assay demonstrates the ability of RSV Hybrid Polypeptides T1301, T1302 and T1303 to inhibit RSV infection.

Figure 12A:
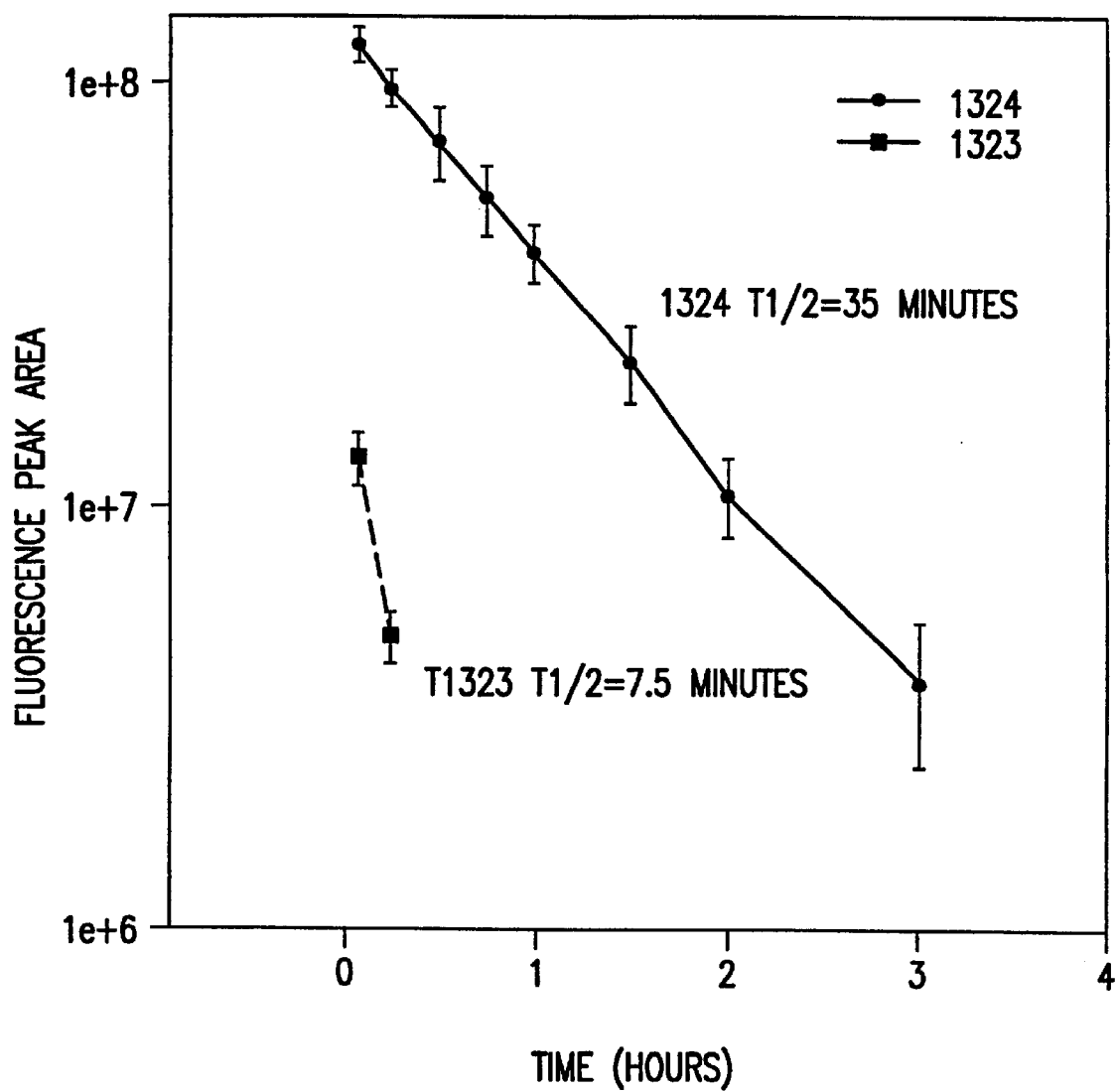
Figure 12B:
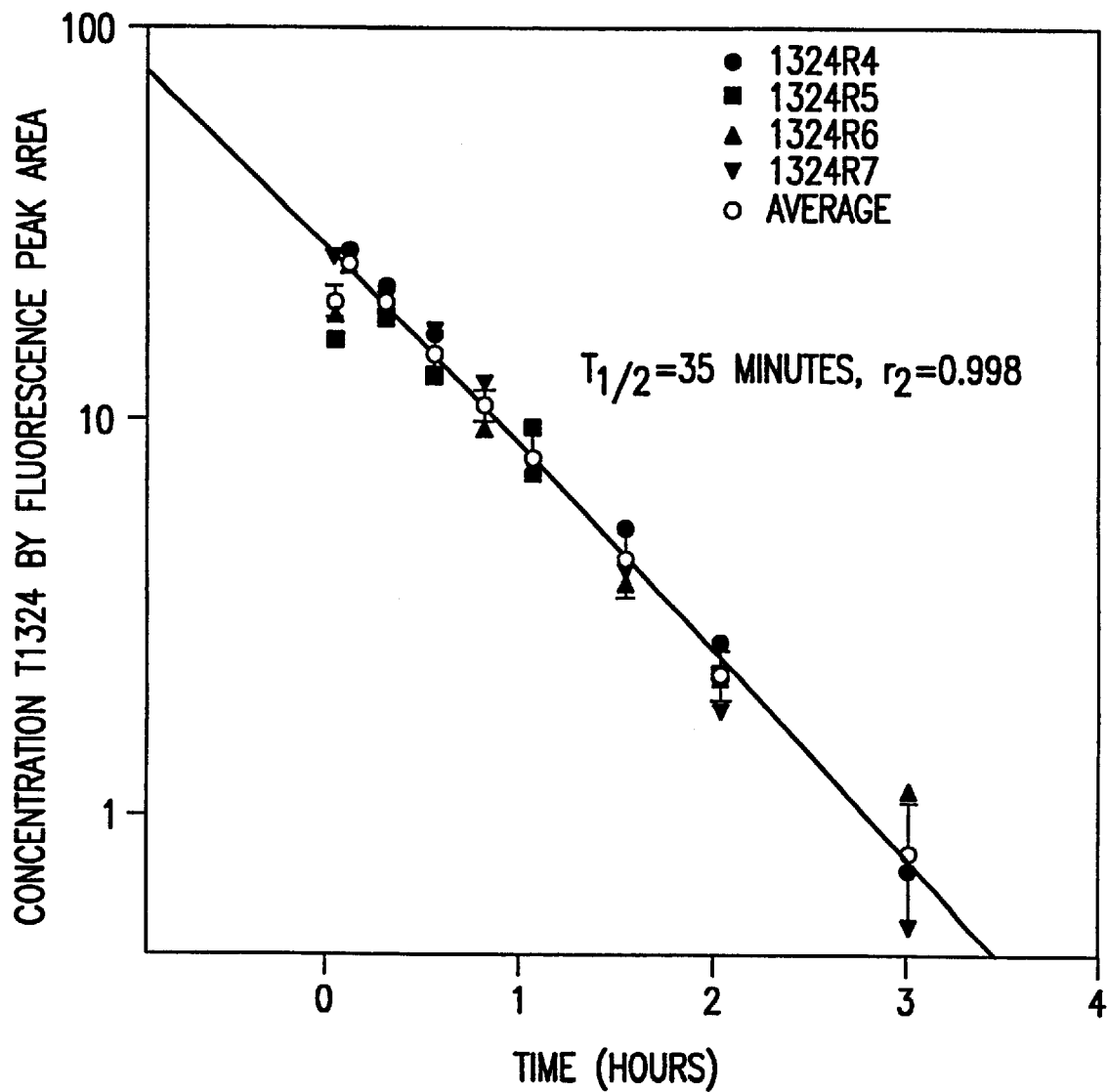

FIGS. 12A and 12B. Plasma pharmacokinetic profile of luteinizing hormone hybrid polypeptide T1324 vs T1323 in CD male rats. The T1323 polypeptide is a luteinizing hormone core polypeptide and the T1324 polypeptide is a hybrid polypeptide comprising a core polypeptide linked to enhancer peptide sequences.

FIG. 13. Hybrid polypeptide sequences derived from various core polypeptides. Core polypeptide sequences are shown shaded (SEQ ID NOS: 1513, 15, 375, 397, 1514, 572, 386, 739, 897, 1515, 547, 746, 747, 1205, 1206, 1052, 1053, 1070, 1089, 1091, 1132, 1135, 1133, 1134, 1097, 1098, 1099, 1100, 1101, 1102, 1069, 1071, 1171, 1149, 1150, 1151, 1152, 1153, 1165, 1168, 1166, 1169, 1167, 1170, 1158, 1115, 1156, 1157, 1116, 1130, 1103, 1104, 1105, 1106, 1117, 63, 692, 970, 986, 969, 987, 988, 989, 1001, 1416, 1415, 1107, 1110, 1108, 1111, 1109, 1112, 1113, 1114, 1122, 1123, 1124, 1143, 1146, 1147, 1148, 1144, 1145, 1172, and 1173, in the order that sequences appear in the table).

5. DETAILED DESCRIPTION OF THE INVENTION

Described herein are peptide sequences, referred to as enhancer peptide sequences, derived from various retroviral envelope (gp41) protein sequences that are capable of enhancing the pharmacokinetic properties of core polypeptides to which they are linked. Such enhancer peptide sequences can be utilized in methods for enhancing the pharmacokinetic properties of any core polypeptide through linkage of the enhancer peptide sequences to the core polypeptide to form a hybrid polypeptide with enhanced pharmalokinetic properties relative to the core polypeptide alone.

The core polypeptides of the hybrid polypeptides of the invention comprise any peptide which may be introduced into a living system, for example, any peptide that can function as a therapeutic or prophylactic reagent useful for treatment or prevention of disease.

5.1. Hybrid Polypeptides

The hybrid polypeptides of the invention comprise at least one enhancer peptide sequence and a core polypeptide. The enhancer peptide sequences of the invention comprise peptide sequences originally derived from various retroviral envelope (gp 41) protein sequences including HIV-1, HIV-2 and SIV. While not wishing to be bound by any particular theory, the structure of the envelope protein is such that the putative α-helix region located in the C-terminal region of the protein is believed to associate with the leucine zipper region located in the N-terminal region of the protein. Alignment of the N-terminal and C-terminal enhancer peptide sequence gp41 regions observed in all currently published isolate sequences of HIV-1, HIV-2 and SIV identified consensus amino acid sequences.

In particular, the following consensus amino acid sequences were identified (the consensus sequences are listed below in forward and reverse orientations because said enhancer sequences can be utilized either in forward or reverse orientation): "WXXWXXXI", "WXXWXXX", "WXXWXX", "WXXWX", "WXXW", "WXXXWXWX", "XXXWXWX", "XXWXWX", "XWXWX", "WXWX", "WXXXWXW", "WXXXWX", "WXXXW", "IXXXWXXW", "XXWXXW", "XXWXXW", "XWXXW", "XWXWXXXW", "XWXWXXX", "XWXWXX", "XWXWX", "XXWXXW", "WXWXXW", or "XWXXXW", wherein X can be any amino acid, W represents tryptophan and I represents isoleucine. Forward orientations of consensus amino acid sequences are shown in FIGS. 1 and 2.

In a preferred embodiment of the invention, enhancer peptide sequences which may be used to enhance the pharmacokinetic properties of the resultant hybrid polypeptides comprise the enhancer sequences depicted in FIG. 2. In another preferred embodiment, enhancer peptide sequences of the invention comprise the enhancer peptide sequences depicted in FIG. 2 exhibiting conserved amino acid substitutions at one or more residues wherein said substitutions do not abolish the ability of the enhancer peptide sequence to enhance the pharmacokinetic properties of a hybrid polypeptide relative to its corresponding core polypeptide. Among the most preferred enhancer peptide sequences are ones comprising the following amino acid sequence: "WQEWEQKI (SEQ ID NO:1129)" and "WASLWEWF (SEQ NO:1433)".

The present invention further provides enhancer peptide sequences comprising amino acid sequences of FIGS. 1 and 2 that are otherwise the same, but, that said enhancer peptide sequences comprise one or more amino acid substitutions, additions (generally no greater than about 15 amino acid residues in length) or deletions (for example, amino- or terminal-truncations) which nevertheless are able to increase the pharmacokinetic properties of core polypeptides to which they are linked relative to core polypeptides without such enhancer sequences.

In particular, it is understood that certain amino acid residues comprising the consensus amino acid sequence of the enhancer peptide sequences can be replaced with other amino acid residues without significantly deleteriously affecting, and in some instances even enhancing, the activity of the peptides. Thus, also contemplated by the present invention are altered forms of the enhancer peptide sequence wherein at least one defined amino acid residue in the structure is substituted with another amino acid residue. Such amino acid substitutions may be conservative i.e., the replacing amino acid residue has physical and chemical properties (e.g., similar charge, size and/or hydrophobicity characteristics) that are similar to the amino acid residue being replaced, or non-conservative amino acid substitutions.

A critical feature affecting the activity of the peptides of the invention is their ability to increase the pharmacokinetic properties of core polypeptides to which they are linked relative to the core polypeptides above, thus it will be recognized that in preferred embodiments of the invention, the amino acid substitutions do not affect the ability of the enhancer peptides to increase the pharmacokinetic properties of the peptide. In general, such changes involve the "X" amino acid residues of the enhancer peptide consensus sequences.

In addition, the amino acid substitutions need not be, and in certain embodiments preferably are not, restricted to the genetically encoded amino acids. Indeed, the peptides may contain genetically non-encoded amino acids. Thus, in addition to the naturally occurring genetically encoded amino acids, amino acid residues in the peptides may be substituted with naturally occurring non-encoded amino acids and synthetic amino acids.

Certain commonly encountered amino acids which provide useful substitutions include, but are not limited to, β-alanine (β-Ala) and other omega-amino acids such as 3-aminopropionic acid, 2,3-diaminopropionic acid (Dpr), 4-aminobutyric acid and so forth; α-aminoisobutyric acid (Aib); ε-aminohexanoic acid (Aha); δ-aminovaleric acid (Ava); N-methylglycine or sarcosine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); naphthylalanine (Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); β-2-thienylalanine (Thi); methionine sulfoxide (MSO); homoarginine (hArg); N-acetyl lysine (AcLys); 2,4-diaminobutyric acid (Dbu); 2,4-diaminobutyric acid (Dab); p-aminophenylalanine (Phe($pNH_2$)); N-methyl valine (MeVal); homocysteine (hCys), homophenylalanine (hphe) and homoserine (hSer); hydroxyproline (Hyp), homoproline (hPro), N-methylated amino acids and peptoids (N-substituted glycines).

While in most instances, the amino acids of the peptide will be substituted with L-enantiomeric amino acids, the substitutions are not limited to L-enantiomeric amino acids. Thus, also included in the definition of "mutated" or "altered" forms are those situations where an L-amino acid is replaced with an identical D-amino acid (e.g., L-Arg→D-Arg) or with a D-amino acid of the same category or subcategory (e.g., L-Arg→D-Lys), and vice versa.

It is to be understood that the present invention also contemplates peptide analogues wherein one or more amide linkage is optionally replaced with a linkage other than amide, preferably a substituted amide or an isostere of amide. Thus, while the amino acid residues within peptides are generally described in terms of amino acids, and preferred embodiments of the invention are exemplified by way of peptides, one having skill in the art will recognize that in embodiments having non-amide linkages, the term "amino acid" or "residue" as used herein refers to other bifunctional moieties bearing groups similar in structure to the side chains of the amino acids. In addition the amino acid residues may be blocked or unblocked.

Additionally, one or more amide linkages can be replaced with peptidomimetic or amide mimetic moieties which do not significantly interfere with the structure or activity of the peptides. Suitable amide mimetic moieties are described, for example, in Olson et al., 1993, J. Med. Chem. 36:3049.

Enhancer peptide sequences can be used to enhance the pharmacokinetic properties of the core polypeptide as either N-terminal or C-terminal additions. While it is preferable for the enhancer peptide sequences to be utilized in a pairwise fashion, that is, preferably hybrid polypeptides comprise an enhancer peptide sequence at both the amino- and carboxy-termini, hybrid polypeptides can also comprise a single enhancer peptide, said peptide present at either the amino- or carboxy-terminus of the hybrid polypeptide. Further, the enhancer peptides can be used in either forward or reverse orientation, or in any possible combination, linked to a core polypeptide. It is noted that any of the enhancer peptides can be introduced at either the N-terminus on the C-terminus of the core polypeptide.

It is understood that the core polypeptide may be linked to the enhancer peptides via a peptide amide linkage, although linkages other than amide linkages can be utilized to join the enhancer peptide sequences to the core polypeptides. Such linkages include for example any carbon-carbon, ester or chemical bond that functions to link the enhancer peptide sequences of the invention to a core peptide.

The amino- and/or carboxy-termini of the resulting hybrid polypeptide can comprise an amino group (—NH$_2$) or a carboxy (—COOH) group, respectively. Alternatively, the hybrid polypeptide amino-terminus may, for example, represent a hydrophobic group, including but not limited to carbobenzyl, dansyl, T-butoxycarbonyl, decanoyl, napthoyl or other carbohydrate group; an acetyl group; 9-fluorenylmethoxy-carbonyl (FMOC) group; or a modified, non-naturally occurring amino acid residue. Alternatively, the hybrid polypeptide carboxy-terminus can, for example, represent an amido group; a T-buxoxycarbonyl group; or a modified non-naturally occurring amino acid residue. As a non-limiting example, the amino- and/or carboxy-termini of the resulting hybrid polypeptide can comprise any of the amino- and/or carboxy-terminal modifications depicted in the peptides shown in FIG. 13 or Table 1, below.

The core polypeptides to be used in the practice of the invention comprise any polypeptide which may be introduced into a living system, for example, any polypeptide that can function as a pharmacologically useful polypeptide. Such core polypeptides may be useful for the treatment or prevention of disease. Examples of possible core polypeptides include growth factors, cytokines, therapeutic polypeptides, hormones and peptide fragments of hormones, inhibitors of cytokines, peptide growth and differentiation factors, interleukins, chemokines, interferons, colony stimulating factors, angiogenic factors and extracellular matrix proteins such as collagen, laminin and fibronectin to name a few. In addition, possible core polypeptides may include viral or bacterial polypeptides that may function either directly or as immunogens, and thus may be useful in the treatment or prevention of pathological disease.

Representative examples of hybrid polypeptides which comprise core polypeptides derived from viral protein sequences are shown in FIG. 13. Core polypeptide sequences are shaded. Core polypeptides also include, but are not limited to, the polypeptides disclosed in U.S. Pat. No. 5,464,933, U.S. Pat. No. 5,656,480 and WO 96/19495, each of which is incorporated herein by reference in its entirety.

Core polypeptide sequences can further include, but are not limited to the core polypeptide sequences depicted in FIG. 13 and Table 1, below.

It is to be understood that such core polypeptide sequences, per se, can exhibit antiviral and/or anti-fusogenic activity and are considered part of the present invention. Among the core polypeptide sequences are, for example, ones which have been derived from individual viral protein sequences. Also among the core polypeptide sequences are, for example, ones whose amino acid sequences are derived from greater than one viral protein sequence (e.g., an HIV-1, HIV-2 and SIV-derived core polypeptide).

The amino- and carboxy-termini of such core polypeptides (either Per se or as part of a hybrid polypeptide) can be as discussed above for hybrid polypeptides. It is noted that while a number of the core polypeptides listed in Table 1, above, are depicted with modified, e.g., blocked amino and/or carboxy termini, that any core polypeptide comprising an unmodified primary amino acid sequence as depicted in Table 1 are to also be considered part of the present invention.

In addition, such core polypeptides can exhibit amino acid substitutions, deletions and/or insertions as discussed, above, for enhancer polypeptide sequences as long as the particular core polypeptide's antiviral and/or antifusogenic activity (either per se or as part of a hybrid polypeptide) is not abolished. With respect to amino acid deletions, it is preferable that the resulting core polypeptide is at least about 4–6 amino acid residues in length. With respect to amino acid insertions, preferable insertions are no greater than about 50 amino acid residues, and, more preferably no more than about 15 amino acid residues. It is also preferable that core polypeptide insertions be amino- and/or carboxy-terminal insertions.

Among such amino and/or carboxy-terminal insertions are ones which comprise amino acid sequences amino and/or carboxy to the endogenous protein sequence from which the core polypeptide is derived. For example, if the core polypeptide is derived from gp41protein, such an insertion would comprise an amino and/or carboxy-terminal insertion comprising a gp41 amino acid sequence adjacent to the gp41 core polypeptide sequence.

The invention further relates to the association of the enhancer core polypeptide sequences to types of molecules other than peptides. For example, the enhancer peptide sequences may be linked to nucleic acid molecules (e.g., DNA or RNA) or any type of small organic molecule for the purpose of enhancing the pharmacokinetic properties of said molecules.

5.2. Synthesis of Peptides

The enhancer, core and hybrid polypeptides of the invention may be synthesized or prepared by techniques well known in the art. See, for example, Creighton, 1983, Proteins: Structures and Molecular Principles, W. H. Freeman and Co., N.Y., which is incorporated herein by reference in its entirety. Hybrid polypeptides may be prepared using conventional step-wise solution or solid phase synthesis, fragment condensation, F-MOC or T-BOC chemistry. (see, e.g., Chemical Approaches to the Synthesis of Peptides and Proteins, Williams et al., Eds., 1997, CRC Press, Boca Raton Fla., and references cited therein; Solid Phase Peptide Synthesis: A Practical Approach, Atherton & Sheppard, Eds., 1989, IRL Press, Oxford, England, and references cited therein). Likewise the amino- and/or carboxy-terminal modifications.

The enhancer, core and hybrid polypeptides of the invention can be purified by art-known techniques such as normal and reverse phase high performance liquid chromatography, ion exchange chromatography, gel electrophoresis, affinity chromatography, size exclusion, precipitation and the like. The actual conditions used to purify a particular polypeptide will depend, in part, on synthesis strategy and on factors such as net charge, hydrophobicity, hydrophilicity, solubility, stability etc., and will be apparent to those having skill in the art.

Hybrid, enhancer and core polypeptides may also be made using recombinant DNA techniques. Here, the nucleotide sequences encoding the polypeptides of the invention may be synthesized, and/or cloned, and expressed according to techniques well known to those of ordinary skill in the art. See, for example, Sambrook, et al., 1989, Molecular Cloning, A Laboratory Manual, Vols. 1–3, Cold Spring Harbor Press, N.Y.

One may obtain the DNA segment encoding the polypeptide of interest using a variety of molecular biological techniques, generally known to those skilled in the art. For example, polymerase chain reaction (PCR) may be used to generate the DNA fragment encoding the protein of interest. Alternatively, the DNA fragment may be obtained from a commercial source.

The DNA encoding the polypeptides of interest may be recombinantly engineered into a variety of host vector systems that also provide for replication of the DNA in large scale. These vectors can be designed to contain the necessary elements for directing the transcription and/or translation of the DNA sequence encoding the hybrid polypeptide.

Vectors that may be used include, but are not limited to, those derived from recombinant bacteriophage DNA, plasmid DNA or cosmid DNA. For example, plasmid vectors such as pcDNA3, pBR322, pUC 19/18, pUC 118, 119 and the M13 mp series of vectors may be used. Bacteriophage vectors may include λgt10, λgt11, λgt18–23, λZAP/R and the EMBL series of bacteriophage vectors. Cosmid vectors that may be utilized include, but are not limited to, pJB8, pCV 103, pCV 107, pCV 108, pTM, pMCS, pNNL, pHSG274, COS202, COS203, pWE15, pWE16 and the charomid 9 series of vectors.

Alternatively, recombinant virus vectors including, but not limited to, those derived from viruses such as herpes virus, retroviruses, vaccinia viruses, adenoviruses, adeno-associated viruses or bovine papilloma viruses plant viruses, such as tobacco mosaic virus and baculovirus may be engineered.

In order to express a biologically active polypeptide, the nucleotide sequence coding for the protein may be inserted into an appropriate expression vector, i.e., a vector which contains the necessary elements for the transcription and translation of the inserted coding sequences. Methods which are well known to those skilled in the art can be used to construct expression vectors having the hybrid polypeptide coding sequence operatively associated with appropriate transcriptional/translational control signals. These methods include in vitro recombinant DNA techniques and synthetic techniques. See, for example, the techniques described in Sambrook, et al., 1992, Molecular Cloning, A Laboratory Manual, Cold Spring Harbor Laboratory, N.Y. and Ausubel et al., 1989, Current Protocols in Molecular Biology, Greene Publishing Associates & Wiley Interscience, N.Y., each of which are incorporated herein by reference in its entirety.

The nucleic acid molecule encoding the hybrid, enhancer and core polypeptides of interest may be operatively associated with a variety of different promoter/enhancer elements. The promoter/enhancer elements may be selected to optimize for the expression of therapeutic amounts of protein. The expression elements of these vectors may vary in their strength and specificities. Depending on the host/vector system utilized, any one of a number of suitable transcription and translation elements may be used. The promoter may be in the form of the promoter which is naturally associated with the gene of interest. Alternatively, the DNA may be positioned under the control of a recombinant or heterologous promoter, i.e., a promoter that is not normally associated with that gene. For example, tissue specific promoter/enhancer elements may be used to regulate the expression of the transferred DNA in specific cell types.

Examples of transcriptional control regions that exhibit tissue specificity which have been described and could be used include, but are not limited to, elastase I gene control region which is active in pancreatic acinar cells (Swift et al., 1984, Cell 38:639–646; Ornitz et al., 1986, Cold Spring Harbor Symp. Ouant. Biol. 50:399–409; MacDonald, 1987, Hepatolocgy 7:42S–51S); insulin gene control region which is active in pancreatic beta cells (Hanahan, 1985, Nature 315:115–122); immunoglobulin gene control region which is active in lymphoid cells (Grosschedl et al., 1984, Cell 38:647–658; Adams et al., 1985, Nature 318:533–538; Alexander et al., 1987, Mol. Cell. Biol. 7:1436–1444): albumin gene control region which is active in liver (Pinkert et al., 1987, Genes and Devel. 1:268–276) alpha-fetoprotein gene control region which is active in liver (Krumlauf et al., 1985, Mol. Cell. Biol. 5:1639–1648; Hammer et al., 1987, Science 235:53–58); alpha-1-antitrypsin gene control region which is active in liver (Kelsey et al., 1987, Genes and Devel. 1:161–171); beta-globin gene control region which is active in myeloid cells (Magram et al., 1985, Nature 315:338–340; Kollias et al., 1986, Cell 46:89–94); myelin basic protein gene control region which is active in oligodendrocyte cells in the brain (Readhead et al., 1987, Cell 48:703–712); myosin light chain-2 gene control region which is active in skeletal muscle (Shani, 1985, Nature 314:283–286); and gonadotropic releasing hormone gene control region which is active in the hypothalamus (Mason et al., 1986, Science 234:1372–1378). Promoters isolated from the genome of viruses that grow in mammalian cells, (e.g., vaccinia virus 7.5K, SV40, HSV, adenoviruses MLP, MMTV, LTR and CMV promoters) may be used, as well as promoters produced by recombinant DNA or synthetic techniques.

In some instances, the promoter elements may be constitutive or inducible promoters and can be used under the appropriate conditions to direct high level or regulated expression of the nucleotide sequence of interest. Expression of genes under the control of constitutive promoters does not require the presence of a specific substrate to induce gene expression and will occur under all conditions of cell growth. In contrast, expression of genes controlled by inducible promoters is responsive to the presence or absence of an inducing agent.

Specific initiation signals are also required for sufficient translation of inserted protein coding sequences. These signals include the ATG initiation codon and adjacent sequences. In cases where the entire coding sequence, including the initiation codon and adjacent sequences are inserted into the appropriate expression vectors, no additional translational control signals may be needed. However, in cases where only a portion of the coding sequence is inserted, exogenous translational control signals, including the ATG initiation codon must be provided. Furthermore, the initiation codon must be in phase with the reading frame of the protein coding sequences to ensure translation of the entire insert. These exogenous translational control signals and initiation codons can be of a variety of origins, both natural and synthetic. The efficiency of expression may be enhanced by the inclusion of transcription attenuation sequences, enhancer elements, etc.

5.3. Pharmaceutical Formulations, Dosages and Modes of Administration

The peptides of the invention may be administered using techniques well known to those in the art. Preferably, agents are formulated and administered systemically. Techniques for formulation and administration may be found in "Remington's Pharmaceutical Sciences", 18th ed., 1990, Mack Publishing Co., Easton, Pa. Suitable routes may include oral, rectal, vaginal, lung, transdermal, transmucosal, or intestinal administration; parenteral delivery, including intramuscular, subcutaneous, intramedullary injections, as well as, intrathecal, direct intraventricular, intravenous, intraperitoneal, intranasal, or intraocular injections, just to name a few. For intravenous injection, the agents of the invention may be formulated in aqueous solutions, preferably in physiologically compatible buffers such as Hanks' solution, Ringer's solution, or physiological saline buffer to name a few. In addition, infusion pumps may be used to deliver the peptides of the invention. For such transmucosal administration, penetrants appropriate to the barrier to be permeated are used in the formulation. Such penetrants are generally known in the art.

In instances wherein intracellular administration of the peptides of the invention or other inhibitory agents is preferred, techniques well known to those of ordinary skill in the art may be utilized. For example, such agents may be encapsulated into liposomes, or microspheres then administered as described above. Liposomes are spherical lipid bilayers with aqueous interiors. All molecules present in an aqueous solution at the time of liposome formation are incorporated into the aqueous interior. The liposomal contents are both protected from the external microenvironment and, because liposomes fuse with cell membranes, are effectively delivered into the cell cytoplasm. Additionally, due to their hydrophobicity, when small molecules are to be administered, direct intracellular administration may be achieved.

Nucleotide sequences encoding the peptides of the invention which are to be intracellularly administered may be expressed in cells of interest, using techniques well known to those of skill in the art. For example, expression vectors derived from viruses such as retroviruses, vaccinia viruses, adeno-associated viruses, herpes viruses, or bovine papilloma viruses, may be used for delivery and expression of such nucleotide sequences into the targeted cell population. Methods for the construction of such vectors and expression constructs are well known. See, for example, Sambrook et al., 1989, Molecular Cloning, A Laboratory Manual, Cold Spring Harbor Press, Cold Spring Harbor N.Y., and Ausubel et al., 1989, Current Protocols in Molecular Biology, Greene Publishing Associates and Wiley Interscience, N.Y.

Effective dosages of the peptides of the invention to be administered may be determined through procedures well known to those in the art which address such parameters as biological half-life, bioavailability, and toxicity. In one embodiment, an effective hybrid polypeptide dosage range is from 0.1–100 $\mu$g/kg body weight. A therapeutically effective dose refers to that amount of the compound sufficient to result in amelioration of symptoms or a prolongation of survival in a patient. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ ( (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (e.g., the concentration of the test compound which achieves a half-maximal inhibition of the fusogenic event, such as a half-maximal inhibition of viral infection relative to the amount of the event in the absence of the test compound) as determined in cell culture. Such information can be used to more accurately determine useful doses in humans. Levels in plasma may be measured, for example, by high performance liquid chromatography (HPLC) or any biological or immunological assay capable of measuring peptide levels.

The hybrid polypeptides of the invention can also be administered in combination with at least one other therapeutic agent. Administration can be concomitantly or sequentially, including cycling therapy (that is, administration of a first compound for a period of time, followed by administration of a second antiviral compound for a period of time and repeating this sequential administration in order to reduce the development of resistance to one of the therapies).

In the case of viral infections, an effective amount of a hybrid polypeptide or a pharmaceutically acceptable derivative thereof can be administered in combination with at least one other antiviral agent. Such antiviral agents can include, but are not limited to DP-107, DP-178, cytokines, e.g., rIFN $\alpha$, rIFN $\beta$, rIFN $\gamma$; inhibitors of reverse transcriptase, e.g., AZT, 3TC, D4T, ddI, and other dideoxynucleosides or dideoxyfluoronucleosides; inhibitors of viral mRNA capping, such as ribavirin; inhibitors of HIV protease, such as ABT-538 and MK-639; amphotericin B as a lipid-binding molecule with anti-HIV activity; and castanospermine as an inhibitor of glycoprotein processing.

The hybrid and/or core polypeptides of the invention may, further, be utilized prophylactically for the prevention of disease. Hybrid and/or core polypeptides can act directly to prevent disease or, alternatively, can be used as vaccines, wherein the host raises antibodies against the hybrid polypeptides of the invention, which then serve to neutralize pathogenic organisms including, for example, inhibiting viral, bacterial and parasitic infection.

For all such treatments described above, the exact formulation, route of administration and dosage can be chosen by the individual physician in view of the patient's condition. (See e.g. Fingl et al., 1975, in "The Pharmacological Basis of Therapeutics", Ch. 1 p1).

It should be noted that the attending physician would know how to and when to terminate, interrupt, or adjust administration due to toxicity, or to organ dysfunctions.

Conversely, the attending physician would also know to adjust treatment to higher levels if the clinical response were not adequate (precluding toxicity). The magnitude of an administrated dose in the management of the oncogenic disorder of interest will vary with the severity of the condition to be treated and the route of administration. The dose and perhaps dose frequency, will also vary according to the age, body weight, and response of the individual patient. A program comparable to that discussed above may be used in veterinary medicine.

Use of pharmaceutically acceptable carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known, e.g., by means of conventional mixing, dissolving, granulating, dragee-making, levigating, spray drying, emulsifying, encapsulating, entrapping or lyophilizing processes.

Pharmaceutical formulations for parenteral administration include aqueous solutions of the active compounds in water-soluble form. Additionally, emulsions and suspensions of the active compounds may be prepared as appropriate oily injection mixtures. Suitable lipophilic solvents or vehicles include fatty oils such as sesame oil, or synthetic fatty acid esters, such as ethyl oleate or triglycerides, liposomes or other substances known in the art for making lipid or lipoptilic emulsions. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, trehalose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

In instances where an enhancement of the host immune response is desired, the hybrid polypeptides may be formulated with a suitable adjuvant in order to enhance the immunological response. Such adjuvants may include, but are not limited to mineral gels such as aluminum hydroxide; surface active substances such as lysolecithin, pluronic polyols, polyanions; other peptides; oil emulsions; and potentially useful human adjuvants such as BCG and Corynebacterium parvum. Many methods may be used to introduce the vaccine formulations described here. These methods include but are not limited to oral, intradermal, intramuscular, intraperitoneal, intravenous, subcutaneous, and intranasal routes.

6. EXAMPLE

IDENTIFICATION OF CONSENSUS AMINO ACID SEQUENCES THAT COMPRISE ENHANCER PEPTIDE SEQUENCES

The retroviral gp41protein contains structural domains referred to as the α-helix region located in the C-terminal region of the protein and the leucine zipper region located in the N-terminal region of the protein. Alignment of the enhancer sequence regions contained within gp41(FIGS. 2A and 2B) of gp41from all currently published isolate sequences of HIV-1, HIV-2 and SIV identified the consensus amino acid sequences shown in FIG. 1.

As described in detail in the Examples presented below, such sequences represent enhancer peptide sequences in that linkage of these peptide sequences to a variety of different core polypeptides enhances the pharmacokinetic properties of the resultant hybrid polypeptides.

7. EXAMPLE

HYBRID POLYPEPTIDES THAT FUNCTION AS POTENT INHIBITORS OF HIV-1 INFECTION

T1249, as depicted in FIG. 13, is a hybrid polypeptide comprising enhancer peptide sequences linked to an HIV core polypeptide. As demonstrated below, the T1249 hybrid polypeptide exhibits enhanced pharmacokinetic properties and potent in vitro activity against HIV-1, HIV-2, and SIV isolates, with enhanced activity against HIV-1 clinical isolates in HuPBMC infectivity assays in vitro as well as in the HuPBMC SCID mouse model of HIV-1 infection in vivo. In the biological assays described below, the activity of the T1249 is compared to the potent anti-viral T20 polypeptide. The T20 polypeptide, also known as DP-178, is derived from HIV-1 gp41 protein sequence, and is disclosed and claimed in U.S. Pat. No. 5,464,933.

7.1. Materials and Methods
7.1.1. Peptide Synthesis and Purification

Peptides were synthesized using Fast Moc chemistry. Generally, unless otherwise noted, the peptides contained amidated carboxyl termini and acetylated amino termini. Purification was carried out by reverse phase HPLC.

T1249 (Ac-WQEWEQKITALLEQAQIQQEKNEYELQKLDKWASLWEWF-NH$_2$) (SEQ ID: 1071) is a 39 amino acid peptide (MW=5036.7) composed entirely of naturally occurring amino acids and is blocked at the amino terminus by an acetyl group and the carboxyl terminus is blocked by an amido group to enhance stability. T1387 is a 23 amino acid peptide lacking enhancer peptide sequences (Ac-TALLEQAQIQQEKNEYELQKLDK-NH$_2$) (SEQ ID: 1286). Thus, T1387 represents the core polypeptide of the T1249 hybrid polypeptide. T1387 is blocked at its amino- and carboxy-termini in the same manner as T1249.

In particular, T1249 was synthesized using standard solid-phase synthesis techniques. The identity of the principal peak in the HPLC trace was confirmed by mass spectroscopy to be T1249.

T1249 was readily purified by reverse phase chromatography on a 6-inch column packed with a C18, 10 micron, 120A support.

7.1.2. Virus

The HIV-1$_{LAI}$ virus (Popovic, M. et al., 1984, Science 224:497–508) was propagated in CEM cells cultured in RPMI 1640 containing 10% fetal calf serum. Supernatant from the infected CEM cells was passed through a 0.2 μm filter and the infectious titer estimated in a microinfectivity assay using the AA5 cell line to support virus replication. For this purpose, 20 μl of serially diluted virus was added to 20 μl CEM cells at a concentration of 6×10$^5$/ml in a 96-well microtitre plate. Each virus dilution was tested in triplicate. Cells were cultured for seven days by addition of fresh medium every other day. On day 7 post infection, supernatant samples were tested for virus replication as evidenced by reverse transcriptase activity released to the supernatant. The TCID$_{50}$ was calculated according to the Reed and Muench formula (Reed, L. J. et al., 1938, Am. J. Hyg. 27:493–497).

7.1.3. Cell Fusion Assay

Approximately 7×10$^4$ Molt-4 cells were incubated with 1×10$^4$ CEM cells chronically infected with the HIV-1$_{LAI}$ virus in 96-well tissue culture plates in a final volume of 100 μl culture medium (RPM11640 containing 10% heat inactivated FBS, supplemented with 1% L-glutamine and 1% Pen-Strep) as previously described (Matthews, T. J. et al., 1987, Proc. Natl. Acad. Sci. USA 84: 5424–5428). Peptide inhibitors were added in a volume of 10 μl and the cell mixtures were incubated for 24 hr. at 37° C. in 5% CO$_2$. At that time, multinucleated giant cells (syncytia, five cell widths or larger) were counted by microscopic examination at 10× and 40×magnification which allowed visualization of the entire well in a single field. Treated cells were compared to infected, untreated controls and results expressed as percent inhibition of infected controls.

7.1.4. Magi-CCR-5 Infectivily Assays

Approximately 1×10$^6$ Magi-CCR-5 cells (obtained through the NIH AIDS Research and Reference Reagent Program, Division of AIDS, NIAID; Chackerian, B. et al., 1997, J. Virol. 71: 3932–3939) were seeded into a 48-well tissue culture plate (approximately 2×10$^4$ cells/well in a volume of 300 μl/well selective growth medium consisting of DMEM supplemented with 10% heat inactivated FBS, 1% L-glutamine, 1% Pen/Strep, Hygromycin B, Geneticin, and Puromycin) and allowed to attach overnight at 37° C., 5% CO$_2$. Cell confluency was approximately 30% by the following day. Seeding medium was removed and diluted peptide inhibitor added in volumes of 50 μl/well (media only in untreated controls), followed by 100 μl/well of diluted virus (desired input virus titre of 100–200 pfu/well). Finally, 250 μl of selective growth medium was added to each well and the plate incubated for 2 days at 37° C., 5% CO$_2$. Fixing and staining were done according to the 30 protocol provided by NIAID with the MAGI-CCR5 cells. Briefly, medium was removed from the plate and 500 μl of fixative added to each well. Plates were allowed to fix for 5 minutes at room temp. Fixative was removed, each well washed twice with DPBS, and 200 μl of staining solution added to each well. The plate was then incubated at 37° C., 5% CO$_2$, for 50 minutes, staining solution removed, and each well washed twice with DPBS. The plate was allowed to air dry before blue cells were counted by microscopic, enumerating the entire well. Treated wells were compared to infected, untreated controls and results expressed as percent inhibition of infected controls.

7.1.5. Reverse Transcriptase Assay

The micro-reverse transcriptase (RT) assay was adapted from Goff et al. (Goff, S. et al., 1981, J. Virol. 38: 239–248) and Willey et al. (Willey, R. et al., 1988, J. Virol. 62: 139–147). Supernatants from virus/cell cultures were adjusted to 1% Triton-X100. 10 ul of each supernatant/ Triton X-100 sample were added to 50 ul of RT cocktail (75 mM KCl, 2 mM Clevelands reagent, 5 mM MgCl$_2$, 5 μg/ml poly A, 0.25 units/ml oligo dT, 0.05% NP40, 50 mM Tris-HCl, pH 7.8, 0.5 μM non-radioactive dTTP, and 10 cCi/ml $^{32}$P-dTTP) in a 96-well U-bottom microtitre plate and incubated at 37° C. for 90 min. After incubation, 40 μl of reaction mixture from each well was transferred to a Schleicher and Schuell (S+S) dot blot apparatus, under partial vacuum, containing a gridded 96-well filter-mat (Wallac catalog #1450-423) and filter backing saturated with 2×SSC buffer (0.3M NaCl and 0.003M sodium citrate). Each well was washed 4 times with at least 200 μl 2×SSC using full vacuum. Minifold was disassembled and gridded filter paper removed and washed 3 times with 2×SSC. Finally, the filter membrane was drained on absorbent paper, allowed to air dry, and sealed in heat sealable bags. Samples were placed in a phosphorscreen cassette and an erased (at least 8 min) phosphorscreen applied and closed. Exposure was for 16 hr. Pixel Index Values (PIV), generated in volume reporting format retrieved from phosphorimaging (Molecular Dynamics Phosphorimager) blots, were used to determine the affected or inhibited fraction (Fa) for all doses of inhibitor(s) when compared to untreated, infected controls (analyzed by ImageQuant volume report, corrected for background).

7.1.6. Human PBMC Infectivity/Neutralization Assay

The prototypic assay used cell lines where the primary isolate assay utilizes PBMC, obtained through Interstate Blood Bank, activated for 2–3 days with a combination of OKT3 (0.5 μ/ml) and CD28 antibodies (0.1 μ/ml). The target cells were banded on lymphocyte separation medium (LSM), washed, and frozen. Cells were thawed as required and activated as indicated above a minimum of 2–3 days prior to assay. In this 96-well format assay, cells were at a concentration of 2×10$^6$/ml in 5% IL-2 medium and a final volume of 100 μl. Peptide stock solutions were made in DPBS (1 mg/ml). Peptide dilutions were performed in 20% FBS RPM1 1640/5% IL-2 complete medium.

7.1.7. In Vivo HU-PBMC SCID Model of HIV-1 Infection

Female SCID mice (5–7 weeks old) received 5–10×10$^7$ adult human PBMC injected intraperitoneally. Two weeks after reconstitution, mice were infected IP on day 0 with 10$^3$ TCID$_{50}$ HIV-1 9320 (AZT-sensitive isolate A018). Treatment with peptides was IP, bid, beginning day-1 and continuing through day 6. The extent of infection in blood cells, splenocytes, lymph nodes, and peritoneal cells was assayed by quantitative co-culture with human PBMC blasts weekly for three consecutive weeks following animal exanguinations and tissue harvest (day 7, approximately 12–18 hours following the last drug treatment). Co-culture supernatants were evaluated for HIV-1 p24 antigen production as a measure of virus infection (Immunotek Coulter kits and protocol).

7.1.8. Rat Pharmacokinetic Studies

250–300 g male CD rats, double jugular catheter, obtained from Charles River Laboratories were used. Peptides were injected in one jugular catheter in a volume of 200 μl of peptide solution (approximately 3.75 mg/ml), dosing solution concentration was determined using the Edelhoch method, (Edelhoch, 1967, Biochemistry 6:1948–1954) method and adjusted based on animal weight such that each animal received a dose of 2.5 mg/kg). Approximately 250–300 μl of blood was removed at predetermined time intervals (0, 15, 30 min and 1,2,4, 6, and 8 hours) and added to EDTA capiject tubes. Plasma was removed from pelleted cells upon centrifugation and either frozen or immediately processed for fluorescence HPLC analysis.

7.1.9. Fluorescence HPLC Analysis of Plasma Samples

100 μl of sample plasma was added to 900 μl of precipitation buffer (acetonitrile, 0.1% TFA, detergent) resulting in precipitation of the majority of plasma proteins. Following centrifugation at 10,000 rpm for 10 min, 400 μl of the supernatant was removed and added to 600 μl of HPLC grade water. Serial dilutions were performed as dictated by concentration of peptide present in each sample in dilution buffer comprised of 40% precipitation buffer and 60% HPLC water. In addition to sample dilutions, serial dilutions of dosing solution were performed in buffer as well as in plasma and used to generate a standard curve relating peak area to known concentration of peptide. This curve was then used to calculate concentration of peptide in plasma taking into account all dilutions performed and quantity injected onto column.

7.1.10. XTT Protocol

In order to measure cytotoxic/cytostatic effects of peptides, XTT assays (Weislow, O. S. et al., 1989, J. Natl. Cancer Inst. 81:577–586) were performed in the presence of varying concentrations of peptide in order to effectively establish a selective index (SI). A TC$_{50}$ was determined in this assay by incubating cells in the presence and absence of serially diluted peptide followed by the addition of XTT. In surviving/metabolizing cells XTT is reduced to a soluble brown dye, XTT-formazan. Absorbance is read and comparisons made between readings in the presence and absence of peptide to determine a TC$_{50}$ utilizing the Karber method (see. e.g., Lennette, E. H. et al., eds., 1969, "Diagnostic Procedures for Viral and Rickettsial Infections," American Public Health Association, Inc., fourth ed., pp. 47–52). Molt 4, CEM (80,000 cells/well) and a combination of the two cell types (70,000 and 10,000 respectively) were plated and incubated with serially diluted peptide for 24 hours in a total volume of 100 μl. Following incubation, 25 μl of XTT working stock (1 mg/ml XTT, 250 μM PMS in complete medium containing 5% DMSO) was added to each well and the plates incubated at 37° C. Color development was read and results used to express values generated from peptide containing wells as a percentage of the untreated control wells.

7.2. Results 7.2.1. Antiviral Activity—Fusion Assays

T1249 was directly compared to T20 in virus mediated cell-cell fusion assays conducted using chronically infected CEM cells mixed with uninfected Molt-4 cells, as shown in Table 2, below. T1249 fusion inhibition against lab isolates such as IIIb, MN, and RF is comparable to T20, and displays an approximately 2.5–5-fold improvement over T20. T1249 was also more active (3–28 fold improvement) than T20 against several syncytia-inducing clinical isolates, including an AZT resistant isolate (G691-2), a pre-AZT treatment isolate (G762-3), and 9320 (isolate used in HuPBMC-SCID studies). Most notably, T1249 was over 800-fold more potent than T20 against HIV-2 NIHZ.

TABLE 2

| Virus Isolate | T20 (ng/ml) | n | T1249 (ng/ml) | n | Fold Difference |
|---|---|---|---|---|---|
| HIV-1 IIIb | 2.5 | 9 | 1.0 | 9 | 2.5 |
| HIV-1 G691-2 (AZT-R) | 406.0 | 1 | 16.0 | 1 | 25 |
| HIV-1 G762-3 (Pre-AZT) | 340.1 | 1 | 12.2 | 1 | 28 |
| HIV-1 MN | 20.0 | 7 | 3.1 | 7 | 6 |
| HIV-1 RF | 6.1 | 7 | 2.1 | 7 | 3 |
| HIV-1 9320 | 118.4 | 1 | 34.5 | 1 | 3 |
| HIV-2 NIHZ | 3610.0 | >10 | 4.3 | 2 | 840 |

7.2.2. Antiviral Activity-Magi-CCR-5 Infectivity Assays

Magi-CCR-5 infectivity assays allow direct comparisons to be made of syncytia and non-syncytia inducing virus isolates, as well as comparisons between laboratory and clinical isolates. The assay is also a direct measure of virus infection (TAT expression following infection, transactivating an LTR driven beta-galactosidase production), as opposed to commonly used indirect measures of infectivity such as p24 antigen or reverse transcriptase production. Magi-CCR-5 infectivity assays (see Table 3 below) reveal that T1249 is consistently more effective than T20 against all isolates tested, in terms of both EC$_{50}$ and Vn/Vo=0.1 inhibition calculations. T1249 shows considerable improvement in potency against the clinical isolate HIV-1 301714 (>25-fold), which is one of the least sensitive isolates to T20. In addition, T1249 is at least 100-fold more potent than T20 against the SIV isolate B670. These data, along with fusion data suggest that T1249 is a potent peptide inhibitor of HIV-1, HIV-2, and SIV.

TABLE 3

| Virus Isolate | EC-50 | Vn/Vo = 0.1 | EC-50 | Vn/Vo = 0.1 | EC-50 Fold Difference | Vn/Vo = 0.1 Fold Difference |
|---|---|---|---|---|---|---|
| HIV-1 | | | | | | |
| IIIB | 42 | 80 | 8 | 10 | 5 | 8 |
| 9320 | 11 | 50 | 1 | 6 | 11 | 8 |
| 301714 (subtype B, NSI) | 1065 | 4000 | 43 | 105 | 25 | 38 |
| G691-2 (AZT-R) | 13 | 200 | 0.3 | 20 | 43 | 10 |
| pNL4-3 | 166 | 210 | 1 | 13 | 166 | 16 |
| SIV-B670 | 2313 | >10000 | 21 | 100 | 110 | >100 |

7.2.3. Antiviral Activity—HuPBMC Infectivity Assays

T1249 was directly compared to T20 in HuPBMC infectivity assays (Table 4, below), which represent a recognized surrogate in vitro system to predict plasma drug concentrations required for viral inhibition in vivo. These comparisons revealed that T1249 is more potent against all HIV-1 isolates tested to date, with all Vn/Vo=0.1 (dose required to reduce virus titer by one log) values being reduced to sub-microgram concentrations. Many of the least sensitive clinical isolates to T20 exhibited 10-fold or greater sensitivity to T1249. It is noteworthy that HIV-1 9320, the isolate used in the HuPBMC SCID mouse model of infection, is 46-fold less sensitive to T20 than to T1249, indicating a very good correlation with the in vivo results.

TABLE 4

| Virus Isolate (HIV-1 | T20 Vn/Vo = 0.1 (ng/ml) | T1249 Vn/Vo = 0.1 (ng/ml) | Fold Difference |
|---|---|---|---|
| IIIB | 250 | 80 | 3 |
| 9320 | 6000 | 130 | 46 |
| 301714 (subtype B, NSI) | 8000 | 700 | 11 |
| 302056 (subtype B, NSI) | 800 | 90 | 9 |
| 301593 (subtype B, SI) | 3500 | 200 | 18 |
| 302077 (subtype A) | 3300 | 230 | 14 |
| 302143 (SI) | 1600 | 220 | 7 |
| G691-2 (AZT-R) | 1300 | 400 | 3 |

7.2.4. Antiviral Activity—T20 Resistant Lab Isolates

T1249 was directly compared to T20 in virus mediated cell-cell fusion assays conducted using chronically infected CEM cells mixed with uninfected Molt-4 cells (Table 5, below). T1249 was nearly 200-fold more potent than T20 against a T20-resistant isolate.

TABLE 5

| Virus Isolate | T20 (ng/ml) | n | T1249 (ng/ml) | n | Fold Difference |
|---|---|---|---|---|---|
| HIV-1 pNL4-3 SM | 405.3 | 3 | 2.1 | 3 | 193 |

In Magi-CCR-5 assays (see Table 6, below), T1249 is as much as 50,000-fold more potent than T20 against T20-resistant isolates such as pNL4-3 SM and pNL4-3 STM (Rimsky, L. and Matthews, T., 1998, J. Virol. 72:986–993).

TABLE 6

| Virus Isolate | T20 EC-50 | T20 Vn/Vo = 0.1 | T1249 EC-50 | T1249 Vn/Vo = 0.1 | EC-50 Fold Difference | Vn/Vo = 0.1 Fold Difference |
|---|---|---|---|---|---|---|
| HIV-1 | | | | | | |
| pNL4-3 | 166 | 210 | 1 | 13 | 166 | 16 |
| pNL4-3 SM (T20-R) | 90 | 900 | 4 | 11 | 23 | 82 |
| pNL4-3 SM (T20-R) Duke | 410 | 2600 | 4 | 11 | 103 | 236 |
| pNL4-3 STM (T20/T649-R) Duke | >5000 | >5000 | 1 | 13 | >50000 | >3846 |

T1249 was directly compared to T20 in HUPBMC infectivity assays (see Table 7, below), evaluating differences in potency against a resistant isolate. T1249 is greater than 250-fold more potent than T20 against the resistant isolate pNL4-3SM.

TABLE 7

| Virus Isolate (HIV-1 | T20 Vn/Vo = 0.1 (ng/ml) | T1249 Vn/Vo = 0.1 (ng/ml) | Fold Difference |
|---|---|---|---|
| HIV-1 | | | |
| pNL4-3 | 3500 | 30 | 117 |
| pNL4-3 SM (T20-R) | >10000 | 40 | >250 |

7.2.5. Antiviral Activity—In Vivo SCID-HuPBMC Model

In vivo antiviral activity of T1249 was directly compared to T20 activity in the HuPBMC-SCID mouse model of HIV-1 9320 infection (FIG. 3). Two weeks after reconstitution with HuPBMCs, mice were infected IP on day 0 with $10^3$ $TCID_{50}$ HIV-1 9320 passed in PBMCs (AZT-sensitive isolate A018). Treatment with peptides was IP, bid, for total daily doses of 67 mg/kg (T20), 20 mg/kg (T1249), 6.7 mg/kg (T1249), 2.0 mg/kg (T1249), and 0.67 mg/kg (T1249), for 8 days beginning on day-1. The extent of infection in blood cells, splenocytes, lymph nodes, and peritoneal cells was assayed by quantitative co-culture with human PBMC blasts weekly for three consecutive weeks following animal exanguinations and tissue harvest (day 7, approx. 12 to 18 hours following last drug treatment). Co-culture supernatants were evaluated for HIV-1 p24 antigen production as a measure of virus infection. Infectious virus was not detectable in the blood or lymph tissues of the T20-treated animals, although, virus was detected in the peritoneal washes and spleen preparation. All compartments were negative for infectious virus at the 6.7 mg/kg dose of T1249, indicating at least a 10-fold improvement over T20 treatment. At the 2.0 mg/kg dose of T1249, both the lymph and the spleen were completely free of detectable infectious virus, with a 2 $\log_{10}$ reduction in virus titer in the peritoneal wash and a 1 $\log_{10}$ reduction in virus titer in the blood, compared to infected controls. At the lowest dose of T1249, 0.67 mg/kg, the peritoneal washes and blood were equivalent to infected control; however, at least a 1 $\log_{10}$ drop in infectious virus titer was observed in both the lymph and the spleen tissues. Overall, the results indicate that T1249 is between 30 and 100-fold more potent against HIV-1 9320, in vivo, under these conditions.

7.2.6. Pharmacokinetic Studies—Rat

Cannulated rats were used to further define the pharmacokinetic profile of T1249. Male CD rats, 250–300 g, were dosed IV through a jugular catheter with T1249 and T20 (FIGS. 4A–5). The resulting plasma samples were evaluated using fluorescence HPLC to estimate peptide quantities in extracted plasma. The beta-phase half-life and total AUC of T1249 was nearly three times greater than T20 (FIG. 5).

7.2.7. Cytotosicity

No overt evidence of T1249 cytotoxicity has been observed in vitro, as demonstrated in FIG. 6.

In addition, T1249 is not acutely toxic (death within 24 hours) at 167 mg/kg (highest dose tested) given IV through jugular cannula (0.3 ml over 2–3 min).

7.2.8. Direct Binding to gp41 Construct M41 Δ178

T1249 was radiolabelled with $^{125}$I and HPLC- purified to maximum specific activity. T20 was iodinated in the same manner. Saturation binding of to M41Δ178 (a truncated gp41 actodomain fusion protein lacking the T20 amino acid sequence) immobilized on microtitre plates at 0.5 gm/μl is shown in FIG. 7. Nonspecific binding was defined as binding of the radioligand in the presence of 1 μM unlabeled peptide. Specific binding was the difference between total and nonspecific binding. The results demonstrate that $^{125}$I-

T1249 and $^{125}$I-T20 have similar binding affinities of 1–2 nM. Linear inverse Scatchard plots suggests that each ligand binds to a homogeneous class of sites.

The kinetics of $^{125}$I-T1249 and $^{125}$I-T20 binding was determined on scintillating microtitre plates coated with 0.5 µg/ml M41Δ178. The time course for association and dissociation is shown in FIG. 8. Dissociation of bound radioligand was measured following the addition of unlabeled peptide to a final concentration of 10 µM in one-tenth of the total assay volume. Initial on- and off-rates for $^{125}$I-T1249 were significantly slower than those of $^{125}$I-T20. Dissociation patterns for both radioligands were unchanged when dissociation was initiated with the other unlabeled peptide (i.e., $^{125}$I-T1249 with T20).

To further demonstrate that both ligands compete for the same target site, unlabeled T1249 and T20 were titrated in the presence of a single concentration of either $^{125}$I-T1249 or $^{125}$I-T20. Ligand was added just after the unlabeled peptide to start the incubation. The competition curves shown in FIG. 9 suggest that although both ligands have similar affinities, a higher concentration of unlabeled peptide is required to fully compete for bound $^{125}$I-T1249.

8. EXAMPLE

RESPIRATORY SYNCYTIAL VIRUS HYBRID POLYPEPTIDES

The following example describes respiratory syncytial irus (RSV) hybrid polypeptides with enhanced pharmacokinetic roperties. In addition, results are presented, below, which demonstrate that the RSV hybrid polypeptides represent potent inhibitors of RSV infection.

8.1. Materials and Methods
8.1.1. Peptide-Synetheis and Purification

RSV polypeptides were synthesized using standard Fast Moc chemistry. Generally, unless otherwise noted, the peptides contained amidated carboxyl termini and acetylated amino termini. Purification was carried out by reverse phase HPLC.

8.1.2. Respiratory Syncytial Virus Plaque Reduction Assay

All necessary dilutions of peptides were performed in clean, sterile 96-well TC plate. A total of eleven dilutions for each peptide and one control well containing no peptide were assembled. The final concentration range of peptide started at 50 μg/ml or 100 μg/ml, with a total of eleven two-fold dilutions. The RSV was prepared at a concentration of 100PFU/well in 100 μl 3% EMEM, as determined by a known titer of RSV. The virus is then added to all of the wells.

The media was removed from one sub-confluent 96-well plate of Hep2 cells. The material from the dilution plate was transferred onto the cell plates starting with row 1 and then transferring row 12, row 11, etc. until all rows were transferred. Plates were placed back into the incubator for 48 hours.

The cells were checked to ensure that syncytia were present in the control wells. Media was removed and approximately 50 μls of 0.25% Crystal Violet in methanol was added to each well. The wells were rinsed immediately in water to remove excess stain and allowed to dry. Using a dissecting microscope, the number of syncytia in each well was counted.

8.2. RESULTS

Pharmacokinetic studies with the RSV hybrid peptides T1301 (Ac-WQEWDEYDASISQVNEKINQALAYIREADELWA WF-$NH_2$) (SEQ ID NO:1434) and T1302 (Ac-WQAWDEYDASISQVNEKINQALAYIREADELW AWF-$NH_2$) (SEQ ID NO:1435) containing enhancer peptide sequences demonstrated a greatly enhanced half-life relative to core peptide T786 (Ac-VYPSDEYDASISQVNEEINQALAYIRKADELLENV-$NH_2$) (SEQ ID NO:1312), as demonstrated in FIGS. 10A–10B. Hybrid polypeptides T1301, T1302 and T1303 WQAWDEYDASISQVNEKINQALAYIREADELWEWF (SEQ ID NO:1124) also showed a greatly enhanced half-size relative to core peptide T1476 (Ac-DEYDASISQVNEKINQALAYIREADEL-$NH_2$) (SEQ ID NO:1340).

RSV hybrid polypeptides T1301, T1302 and T1303, as well as polypeptide T786 and T1293, were tested for their ability to inhibit RSV plaque formation of HEp2 cells. As indicated in FIGS. 11A and 11B, both the tested hybrid RSV polypeptides, as well as the T786 core polypeptide were able to inhibit RSV infection. Surprisingly, the T1293 hybrid polypeptide was also revealed to be a potent anti-RSV compound (FIG. 13).

9. EXAMPLE

LUTEINIZING HORMONE HYBRID POLYPEPTIDES

The example presented herein describes luteinizing hormone (LH) hybrid proteins with enhanced pharmacokinetic properties. The following LH hybrid peptides were synthesized and purified using the methods described above: core peptide T1323 (Ac-QHWSYGLRPG-$NH_2$) (SEQ ID NO:1309) and hybrid polypeptide T1324 (Ac-WQEWEQKIQHWSYGLRPGWASLWEWF-$NH_2$) (SEQ ID NO:1144) which comprises the core polypeptide T1323 amino acid sequence coupled with enhancer peptides at its amino- and carboxy-termini. As demonstrated in FIGS. 12A and 12B, the T1324 hybrid peptide exhibited a significantly increased half-life when compared to the T1323 core peptide which lacks the enhancer peptide sequences.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

TABLE 1

| T No. | Sequence | Seq. ID No. |
|---|---|---|
| 1 | GIKQLQARILAVERYLKDQ | 1 |
| 2 | NNLLRAIEAQQHLLQLTVW | 2 |

TABLE 1-continued

| T No. | Sequence | Seq. ID No. |
|---|---|---|
| 3 | NEQELLELDKWASLWNWF | 3 |
| 4 | YTSLIHSLIEESQNQQEK | 4 |
| 5 | Ac-VWGIKQLQARILAVERYLKDQQLLGIWG-NH2 | 5 |
| 6 | QHLLQLTVWGIKQLQARILAVERYLKDQ | 6 |
| 7 | LRAIEAQQHLLQLTVWGIKQLQARILAV | 7 |
| 8 | VQQQNNLLARIEAQQHLLQLTVWGIKQL | 8 |
| 9 | RQLLSGIVQQQNNLLRAIEAQQHLLQLT | 9 |
| 10 | MTLTVQARQLLSGIVQQQNNLLRAIEAQ | 10 |
| 12 | VVSLSNGVSVLTSKVLDLKNYIDKQLL | 11 |
| 13 | LLSTNKAVVSLSNGVSVLTSKVLDLKNY | 12 |
| 15 | Ac-VLHLEGEVNKIKSALLSTKKAVVSLSNG-NH2 | 13 |
| 19 | Ac-LLSTNKAVVSLSNGVSVLTSKVLDLKNY-NH2 | 14 |
| 20 | Ac-YTSLIHSLIEESQNQQEKNEQELLELDKWASLWNWF-NH2 | 15 |
| 21 | Ac-NNLLRAIEAQQHLLQLTVWGIKQLQARILAVERYLKDQ-NH2 | 16 |
| 22 | Ac-IELSNIKENKCNGTDAKVKLIKQELDKYKNAVTELQLLMQST-NH2 | 17 |
| 23 | Ac-IELSNIKENKCNGTDAKVKLIKQELDKY-NH2 | 18 |
| 24 | Ac-ENKCNGTDAKVKLIKQELDKYKNAVTEL-NH2 | 19 |
| 25 | Ac-DAKVKLIKQELDKYKNAVTELQLLMQST-NH2 | 20 |
| 26 | Ac-CNGTDAKVKLIKQELDKYKNAVTELQLL-NH2 | 21 |
| 27 | Ac-SNIKENKCNGTDAKVKLIKQELDKYKNAVTELQLL-NH2 | 22 |
| 28 | Ac-ASGVAVSKVLHLEGEVNKIKSALLSTNKAVVSLSNGV-NH2 | 23 |
| 29 | Ac-SGVAVSKVLHLEGEVNKIKSALLSTNKAVVSLSNG-NH2 | 24 |
| 30 | Ac-VLHLEGEVNKIKSALLSTHKAVVSLSNGVSVLTSK-NH2 | 25 |
| 31 | Ac-ARKLQRMKQLEDKVEELLSKNYHYLENEVARLKKLV-NH2 | 26 |
| 32 | Ac-RMKQLEDKVEELLSKNYHYLENEVARLKKLVGER-NH2 | 27 |
| 33 | Ac-VQQQNNLLRAIEAQQHLLQLTVWGIKQL-NH2 | 28 |
| 34 | Ac-LRAIEAQQHLLQLTVWGIKQLQARILAV-NH2 | 29 |
| 35 | Ac-QHLLQLTVWGIKQLQARILAVERYLKDQ-NH2 | 30 |
| 36 | Ac-RQLLSGIVQQQNNLLRAIEAQQHLLQLT-NH2 | 31 |
| 37 | Ac-MTLTVQARQLLSGIVQQQNNLLRAIEAQ-NH2 | 32 |
| 38 | Ac-AKQARSDIEKLKEAIRDTNKAVQSVQSS-NH2 | 33 |
| 39 | Ac-AAVALVEAKQARSDIEKLKEAIRDTNKAVQSVQSS-NH2 | 34 |
| 40 | Ac-AKQARSDIEKLKEAIRDTNKAVQSVQSSIGNLIVA-NH2 | 35 |
| 41 | Ac-GTIALGVATSAQITAAVALVEAKQARSD-NH2 | 36 |
| 42 | Ac-ATSAQITAAVALVEAKQARSDIEKLKEA-NH2 | 37 |
| 43 | Ac-AAVALVEAKQARSDIEKLKEAIRDTNKANH2 | 38 |
| 44 | Ac-IEKLKEAIRDTNKAVQSVQSSIGNLIVA-NH2 | 40 |
| 45 | Ac-IRDTNKAVQSVQSSIGNLIVAIKSVQDY-NH2 | 41 |
| 46 | Ac-AVQSVQSSIGNLIVAIKSVQDYVNKEIV-NH2 | 42 |
| 47 | Ac-QARQLLSGIVQQQNNLLRAIEAQQHLLQLTVWGIKQLQARILAVERYLKDQ-NH2 | 43 |
| 48 | Ac-QARQLLSGIVQQQNNLLRAIEAQQHLLQ-NH2 | 44 |
| 49 | Ac-MTWMEMDREINNYTSLIGSLIEESQNQQEKNEQELLELDKWASLWNWF-NH2 | 45 |
| 50 | Ac-WMEWDREINNYTSLIGSLIEESQNQQEKNEQELLE-NH2 | 46 |
| 51 | Ac-INNYTSLIGSLIEESQNQQEKNEQELLE-NH2 | 47 |
| 52 | Ac-INNYTSLIGSLIEESQNQQEKNEQELLELDKWASL-NH2 | 48 |
| 53 | Ac-EWDREINNYTSLIGSLIEESQNQQEKNEQEGGC-NH2 | 49 |
| 54 | Ac-QSRTLLAGIVQQQQQLLDVVKRQQELLWNH2 | 50 |
| 55 | Ac-NNDTWQEWERKVDFLEENITALLEEAQIQQEKNMYELQKLNSWD-NH2 | 51 |
| 56 | Ac-WQEWERKVDFLEENITALLEEAQIQQEK-NH2 | 52 |
| 57 | Ac-VDFLEENITALLEEAQIQQEKNMYELQK-NH2 | 53 |
| 58 | Ac-ITALLEEAQIQQEKNMYELQKLNSWDVF-NH2 | 54 |
| 59 | Ac-SSESFTLLEQWNNWKLQLAEQWLEQINEKHYLEDIS-NH2 | 55 |
| 60 | Ac-DKWASLWNWF-NH2 | 56 |
| 61 | Ac-NEQELLELDKWASLWNWF-NH2 | 57 |
| 62 | Ac-EKNEQELLELDKWASLWNWF-NH2 | 58 |
| 63 | Ac-NQQEKNEQELLELDKWASLWNWF-NH2 | 59 |
| 64 | Ac-ESQNQQEKNEQELLELDKWASLWNWF-NH2 | 60 |
| 65 | Ac-LIHSLIEESQNQQEKNEQELLELDKWASLWNWF-NH2 | 61 |
| 66 | Ac-NDQKKLMSNNVQIVRQQSYSIMSIIKEE-NH2 | 62 |
| 67 | Ac-DEFDASISQVNEKINQSLAFIRKSDELL-NH2 | 63 |
| 68 | Ac-VSKGYSALRTGWYTSVITIELSNIKEN-NH2 | 64 |
| 69 | Ac-VVSLSNGVSVLTSKVLDLKNYIDKQLL-NH2 | 65 |
| 70 | Ac-VNKIKSALLSTNKAVVSLSNGVSVLTSK-NH2 | 66 |
| 71 | Ac-PIINFYDPLVFPSDEFDASISQVNEKINQSLAFIR-NH2 | 67 |
| 72 | Ac-NLVYAQLQFTYDTLRGYINRALAQIAEA-NH2 | 68 |
| 73 | Ac-LNQVDLTETLERYQQRLNTYALVSKDASYRS-NH2 | 69 |
| 74 | Ac-ELLVLKKAQLNRHSYLKDSDFLDAALD-NH2 | 70 |
| 75 | Ac-LAEAGEESVTEDTEREDTEEEREDEEE-NH2 | 71 |
| 76 | Ac-ALLAEAGEESVTEDTEREDTEEEREDEEEENEART-NH2 | 72 |
| 77 | Ac-ETERSVDLVAALLAEAGEESVTEDTEREDTEEERE-NH2 | 73 |
| 78 | Ac-EESVTEDTEREDTEEEREDEEEENEART-NH2 | 74 |
| 79 | Ac-VDLVAALLAEAGEESVTEDTEREDTEEE-NH2 | 75 |
| 80 | Ac-NSETERSVDLVAALLAEAGEESVTE-NH2 | 76 |
| 81 | Ac-DISYAQLQFTYDVLKDYINDALRNIMDA-NH2 | 77 |
| 82 | Ac-SNVFSKDEIMREYNSQKQHIRTLSAKVNDN-NH2 | 78 |
| 83 | Biotin-YTSLIHSLIEESQNQQEKNEQELLELDKWASLWNWF-NH2 | 1076 |

TABLE 1-continued

| T No. | Sequence | Seq. ID No. |
|---|---|---|
| 84 | Dig-YTSLIHSLIEESQNQQEKNEQELLELDKWASLWNWF-NH2 | 1076 |
| 85 | Biotin-NNLLRAIEAQQHLLQLTVWGIKQLQARILAVERYLKDG-NH2 | 16 |
| 86 | Dig-NNLLRAIEAQQHLLQLTVWGIKQLQARILAVERYLKDQ-NH2 | 16 |
| 87 | Ac-VLHQLNIQLKQYLETQERLLAGNRIAARQLLQIWKDVA-NH2 | 83 |
| 88 | Ac-LWHEQLLNTAQRAGLQLQLINQALAVREKVLIRYDIQK-NH2 | 84 |
| 89 | Ac-LLDNFESTWEQSKELWEQQEISIQNLHKSALQEYW-NH2 | 85 |
| 90 | Ac-LSNLLQISNNSDEWLEALEIEHEKWKLTQWQSYEQF-NH2 | 86 |
| 91 | Ac-KLEALEGKLEALEGKLEALEGKLEALEGKLEALEGK-NH2 | 87 |
| 92 | Ac-ELRALRGELRALRGELRALRGELRALRGK-NH2 | 88 |
| 93 | Ac-ELKAKELEGEGLAEGEEALKGLLEKAAKLEGLELLK-NH2 | 89 |
| 94 | Ac-WEAAAREAAAREAAAREAAARA-NH2 | 90 |
| 95 | Ac-YTSLIHSLIEESQNQQEKNEQELLELDKWASLWNAF-NH2 | 91 |
| 96 | Ac-YTSLIHSLIEESQNQQEKNEQELLELDKWASLANWF-NH2 | 92 |
| 97 | Ac-YTSLIHSLIEESQNQQEKNQQELLELDKWASLWNWF-NH2 | 93 |
| 98 | Ac-YTSLIHSLIEESQNQQEKNEQELLQLDKWASLWNWF-NH2 | 94 |
| 99 | Ac-YTSLIHSLIEESQNQQEKNQQELLQLDKWASLWNWF-NH2 | 95 |
| 100 | Ac-RMKQLEDKVEELLSKNYHLENEVARLKKLVGER-NH2 | 96 |
| 101 | Ac-QQLLQLTVWGIKQLQARILAVERYLKNQ-NH2 | 97 |
| 102 | Ac-NEQELLELDKWASLWNWF-NH2 | 98 |
| 103 | Ac-YTSLIQSLIEESQNQQEKNEQELLELDKWASLWNWF-NH2 | 99 |
| 104 | Ac-IINFYDPLVFPSDEFDASISQVNEKINQSLAFIRK-NH2 | 100 |
| 105 | Ac-INFYDPLVFPSDEFDASISQVNEKINQSLAFIRKS-NH2 | 101 |
| 106 | Ac-NFYDPLVFPSDEFDASISQVNEKINQSLAFIKKSD-NH2 | 102 |
| 107 | Ac-FYDPLVFPSDEFDASISQVNEKINQSLAFIRKSDE-NH2 | 103 |
| 108 | Ac-YDPLVFPSDEFDASISQVNEKINQSLAFIRKSDEL-NH2 | 104 |
| 109 | Ac-DPLVFPSDEFDASISQVNEKINQSLAFIRKSDELL-NH2 | 105 |
| 110 | Ac-PLVFPSDEFDASISQVNEKINQSLAFIRKSDELLH-NH2 | 106 |
| 111 | Ac-LVFPSDEFDASISQVNEKINQSLAFIRKSDELLHN-NH2 | 107 |
| 112 | Ac-VFPSDEFDASISQVNEKINQSLAFIRKSDELLHNV-NH2 | 108 |
| 113 | Ac-FPSDEFDASISQVNEKINQSLAFIRKSDELLHNVN-NH2 | 109 |
| 114 | Ac-PSDEFDASISQVNEKINQSLAFIRKSDELLHNVNA-NH2 | 110 |
| 115 | Ac-SDEFDASISQVNEKINQSLAFIRKSDELLHNVNAG-NH2 | 111 |
| 116 | Ac-DEFDASISQVNEKINQSLAFIRKSDELLHNVNAGK-NH2 | 112 |
| 117 | Ac-EFDASISQVNEKINQSLAFIPKSDELLHNVNAGKS-NH2 | 113 |
| 118 | Ac-FDASISQVNEKINQSLAFIRKSDELLHNVNAGKST-NH2 | 114 |
| 119 | Ac-DASISQVNEKINQSLAFIRKSDELLHNVNAGKSTT-NH2 | 115 |
| 120 | Ac-ASGVAVSKVLHLEGEVNKIKSALLSTNKAVVSLSN-NH2 | 116 |
| 121 | Ac-SGVAVSKVLHLEGEVNKIKSALLSTNKAVVSLSNG-NH2 | 117 |
| 122 | Ac-GVAVSKVLHLEGEVNKIKSALLSTNKAVVSLSNGV-NH2 | 118 |
| 123 | Ac-VAVSKVLHLEGEVNKIKSALLSTNKAVVSLSNGVS-NH2 | 119 |
| 124 | Ac-AVSKVLHLEGEVNKIKSALLSTNKAVVSLSNGVSV-NH2 | 120 |
| 125 | Ac-VSKVLHLEGEVNKIKSALLSTNKAVVSLSNGVSVL-NH2 | 121 |
| 126 | Ac-SKVLHLEGEVNKIKSALLSTNKAVVSLSNGVSVLT-NH2 | 122 |
| 127 | Ac-KVLHLEGEVNKIKSALLSTNKAVVSLSNGVSVLTS-NH2 | 123 |
| 128 | Ac-VLHLEGEVNKIKSALLSTNKAVVSLSNGVSVLTSK-NH2 | 124 |
| 129 | Ac-LHLEGEVNKIKSALLSTNKAVVSLSNGVSVLTSKV-NH2 | 125 |
| 130 | Ac-HLEGEVNKIKSALLSTNKAVVSLSNGVSVLTSKVL-NH2 | 126 |
| 131 | Ac-LEGEVNKIKSALLSTNKAVVSLSNGVSVLTSKVLD-NH2 | 127 |
| 132 | Ac-EGEVNKIKSALLSTNKAVVSLSNGVSVLTSKVLDL-NH2 | 128 |
| 133 | Ac-GEVNKIKSALLSTNKAVVSLSNGVSVLTSKVLDLK-NH2 | 129 |
| 134 | Ac-EVNKIKSALLSTNKAVVSLSNGVSVLTSKVLDLKN-NH2 | 130 |
| 135 | Ac-VNKIKSALLSTNKAVVSLSNGVSVLTSKVLDLKNY-NH2 | 131 |
| 136 | Ac-NKIKSALLSTNKAVVSLSNGVSVLTSKVLDLKNYI-NH2 | 132 |
| 137 | Ac-KIKSALLSTNKAVVSLSNGVSVLTSKVLDLKNYID-NH2 | 133 |
| 138 | Ac-IKSALLSTNKAVVSLSNGVSVLTSKVLDLKNYIDK-NH2 | 134 |
| 139 | Ac-KSALLSTNKAVVSLSNGVSVLTSKVLDLKNYIDKQ-NH2 | 135 |
| 140 | Ac-SALLSTNKAVVSLSNQVSVLTSKVLDLKNYIDKQL-NH2 | 136 |
| 141 | Ac-ALLSTNKAVVSLSNGVSVLTSKVLDLKNYIDKQLL-NH2 | 137 |
| 142 | Ac-YTSVITIELSNIKENKCNGTDAKVKLIKQELDKYK-NH2 | 138 |
| 143 | Ac-TSVITIELSNIKENKCNGTDAKVKLIKQELDKYKN-NH2 | 139 |
| 144 | Ac-SVITIELSNIKENKCNGTDAKVKLIKQELDKYKNA-NH2 | 140 |
| 145 | Ac-VITIELSNIKBNKCNGTDAKVKLIKQELDKYKNAV-NH2 | 141 |
| 146 | Ac-ITIELSNIKENKCNGTDAKVKLIKQELDKYKNAVT-NH2 | 142 |
| 147 | Ac-TIELSMKENKCNGTDAKVKLIKQELDKYKNAVTE-NH2 | 143 |
| 148 | Ac-IELSNIKENKCNGTDAKVKLIKQELDKYKNAVTEL-NH2 | 144 |
| 149 | Ac-ELSNIKENKCNGTDAKVKLIKQELDKYKNAVTELQ-NH2 | 145 |
| 150 | Ac-LSNIKENKCNGTDAKVKLIKQELDKYKNAVTELQL-NH2 | 146 |
| 151 | Ac-SNIKENKCNGTDAKVKLIKQELDKYKNAVTELQLL-NH2 | 147 |
| 152 | Ac-NIKENKCNGTDAKVKLIKQELDKYKNAVTELQLLM-NH2 | 148 |
| 153 | Ac-IKENKCNGTDAKVKLIKQELDKYKNAVTELQLLMQ-NH2 | 149 |
| 154 | Ac-KENKCNGTDAKVKLIKQELDKYKNAVTELQLLMQS-NH2 | 150 |
| 155 | Ac-ENKCNGTDAKVKLIKQELDKYKNAVTELQLLMQST-NH2 | 151 |
| 156 | Ac-LLDNFESTWEQSKELWELQEISIQNLHKSALQEYWN-NH2 | 152 |
| 157 | Ac-ALGVATSAQITAAVALVEAKQARSDIEKLKEAIRD-NH2 | 153 |
| 158 | Ac-LGVATSAQITAAVALVEAKQARSDIEKLKEAIRDT-NH2 | 154 |
| 159 | Ac-GVATSAQITAAVALVEAKQARSDIEKLKEAIRDTN-NH2 | 155 |

TABLE 1-continued

| T No. | Sequence | Seq. ID No. |
|---|---|---|
| 160 | Ac-VATSAQITAAVALVEAKQARSDIEKLKEAIRDTNK-NH2 | 156 |
| 161 | Ac-ATSAQITAAVALVEAKQARSDIEKLKEAIRDTNKA-NH2 | 157 |
| 162 | Ac-TSAQITAAVALVEAKQARSDIEKLKEAIRDTNKAV-NH2 | 158 |
| 163 | Ac-SAQITAAVALVEAKQARSDIEKLKEAIRDTNKAVQ-NH2 | 159 |
| 164 | Ac-AQITAAVALVEAKQARSDIEKLKEAIRDTNKAVQS-NH2 | 160 |
| 165 | Ac-QITXAVALVEAKQARSDIEKLKEAIRDTNKAVQSV-NH2 | 161 |
| 166 | Ac-ITAAVALVEAKQARSDIEKLKEAIRDTNKAVQSVQ-NH2 | 162 |
| 167 | Ac-TAAVALVEAKQARSDIEKLKEAIRDTNKAVQSVQS-NH2 | 163 |
| 168 | Ac-AAVALVEAKQARSDIEKLKEAIRDTNKAVQSVQSS-NH2 | 164 |
| 169 | Ac-AVALVEAKQARSDIEKLKEAIRDTNKAVQSVQSSI-NH2 | 165 |
| 170 | Ac-VALVEAKQARSDIEKLKEAIRDTNKAVQSVQSSIG-NH2 | 166 |
| 171 | Ac-ALVEAKQARSDIEKLKEAIRDTNKAVQSVQSSIGN-NH2 | 167 |
| 172 | Ac-LVEAKQARSDIEKLKEAIRDTNKAVQSVQSSIGNL-NH2 | 168 |
| 173 | Ac-VEAKQARSDIEKLKEAIRDTNKAVQSVQSSIGNLI-NH2 | 169 |
| 174 | Ac-EAKQARSDIEKLKEAIRDTNKAVQSVQSSIGNLIV-NH2 | 170 |
| 175 | Ac-KQARSDIEKLKEAIRDTNKAVQSVQSSIGNLIVAI-NH2 | 171 |
| 176 | Ac-QARSDIEKLKEAIRDTNKAVQSVQSSIGNLIVAIK-NH2 | 172 |
| 177 | Ac-ARSDIEKLKEAIRDTNKAVQSVQSSIGNLIVAIKS-NH2 | 174 |
| 178 | Ac-RSDIEKLKEAIRDTNKAVQSVQSSIGNLIVAIKSV-NH2 | 175 |
| 179 | Ac-SDIEKLKEAIRDTNKAVQSVQSSIGNLIVAIKSVQ-NH2 | 176 |
| 180 | Ac-DIEKLKEAIRDTNKAVQSVQSSIGNLIVAIKSVQD-NH2 | 177 |
| 181 | Ac-IEKLKEAIRDTNKAVQSVQSSIGNLIVAIKSVQDY-NH2 | 178 |
| 182 | Ac-EKLKEAIRDTNKAVQSVQSSIGNLIVAIKSVQDYV-NH2 | 179 |
| 183 | Ac-KLKEAIRDTNKAVQSVQSSIGNLIVAIKSVQDYVN-NH2 | 180 |
| 184 | Ac-LKEAIRDTNKAVQSVQSSIGNLIVAIKSVQDYVNK-NH2 | 181 |
| 185 | Ac-KEAIRDTNKAVQSVQSSIGNLIVAIKSVQDYVNKE-NH2 | 182 |
| 186 | Ac-EAIRDTNKAVQSVQSSIGNLIVAIKSVQDYVNKEI-NH2 | 183 |
| 187 | Ac-AIRDTNKAVQSVQSSIGNLIVAIKSVQDYVNKEIV-NH2 | 184 |
| 188 | Ac-IRDTNKAVQSVQSSIGNLIVAIKSVQDYVKKEIV-NH2 | 185 |
| 189 | Ac-YTFNDITLNNSVALDFIDISIELNKAKSDLEESKE-NH2 | 186 |
| 190 | Ac-TPNDITLNNSVALDPIDISIELNKAKSDLEESKEW-NH2 | 187 |
| 191 | Ac-PNDITLNNSVALDPIDISIELNKAKSDLEESKEWI-NH2 | 188 |
| 192 | Ac-NDITLNNSVALDPIDISIELNKAKSDLEESKEWIR-NH2 | 189 |
| 193 | Ac-DITLNNSVALDPIDISIELNKAKSDLEESKEWIRR-NH2 | 190 |
| 194 | Ac-ITLNNSVALDPIDISIELNKAKSDLEESKEWIRRS-NH2 | 191 |
| 195 | Ac-TLNNSVALDPIDISIELNKAKSDLEESKEWIRRSN-NH2 | 192 |
| 196 | Ac-LNNSVALDPIDISIELNKAKSDLEESKEWIRRSNQ-NH2 | 193 |
| 197 | Ac-NNSVALDPIDISIELNKAKSDLEESKEWIRRSNQK-NH2 | 194 |
| 198 | Ac-NSVALDPIDISIELNKAKSDLEESKEWIRRSNQKL-NH2 | 195 |
| 200 | Ac-SVALDPIDISIELNKAKSDLEESKEWIRRSNQKLD-NH2 | 197 |
| 201 | Ac-VALDPIDISIELNKAKSDLEESKEWIRRSNQKLDS-NH2 | 198 |
| 202 | Ac-ALDPIDISIELNKAKSDLEESKEWIRRSNQKLDSI-NH2 | 199 |
| 203 | Ac-LDPIDISIELNKAKSDLEESKEWIRRSNQKLDSIG-NH2 | 200 |
| 204 | Ac-DPIDISIELNKAKSDLEESKEWIRRSNQKLDSIGN-NH2 | 201 |
| 205 | Ac-PIDISIELNKAKSDLEESKEWIRRSNQKLDSIGNW-NH2 | 202 |
| 206 | Ac-IDISIELNKAKSDLEESKEWIRRSNQKLDSIGNWH-NH2 | 203 |
| 207 | Ac-DISIELNAAKSDLEESKEWIRRSNQKLDSIGNWHQ-NH2 | 204 |
| 208 | Ac-ISIELNKAKSDLEESKEWIRRSNQKLDSIGNWHQS-NH2 | 205 |
| 209 | Ac-SIELNKAKSDLEESKEWIRRSNQKLDSIGNWHQSS-NH2 | 206 |
| 210 | Ac-IELNKAKSDLEESKEWIRRSNQKLDSIGNWHQSST-NH2 | 207 |
| 211 | Ac-ELNKAKSDLEESKEWIRRSNQKLDSIGNWHQSSTT-NH2 | 208 |
| 212 | Ac-ELRALRGELRALRGELRALRGELRALRGELRALRGK-NH2 | 209 |
| 213 | Ac-YTSLIHSLIEESQNQQQKNEQELLELDKWASLWNWF-NH2 | 210 |
| 214 | Ac-YTSLIHSLIEESQNQQEKNEQELLELNKWASLWNWF-NH2 | 211 |
| 215 | Ac-YTSHHSLIEQSQNQQEKNEQELLELDKWASLWNWF-NH2 | 212 |
| 216 | Ac-YTSLIHSLIQESQNQQEKNEQELLELDKWASLWNWF-NH2 | 213 |
| 217 | Ac-YTSLIHSLIQQSQNQQQKNQQQLLQLNKWASLWNWF-NH2 | 214 |
| 218 | Ac-EQELLELDKWASLWNWF-NH2 | 215 |
| 219 | Ac-QELLELDKWASLWNWF-NH2 | 216 |
| 220 | Ac-ELLELDKWASLWNWF-NH2 | 217 |
| 221 | Ac-LELDKWASLWNWF-NH2 | 218 |
| 222 | Ac-ELDKWASLWNWF-NH2 | 219 |
| 226 | Ac-WASLWNWF-NH2 | 223 |
| 227 | Ac-ASLWNWF-NH2 | 224 |
| 229 | Ac-YTSLIHSLIEESQNQQEKNEQELLELDKWASLANAA-NH2 | 226 |
| 230 | Ac-YTSLIHSLIEESQNQQEKNEQQLLELDKWASLWNWF-NH2 | 227 |
| 231 | Ac-YTSLIQSLIEESQNQQEKNQQELLELDKWASLWNWF-NH2 | 228 |
| 234 | Ac-EAAAREAAAREAAARLELDKWASLWNWF-NH2 | 231 |
| 236 | Ac-PSLRDPISAEISIQALSYALGGDINKVLEKLGYSG-NH2 | 233 |
| 237 | Ac-SLRDPISAEISIQALSYALGGDINKVLEKLGYSGG-NH2 | 234 |
| 238 | Ac-LRDPISAEISIQALSYALGGDINKVLEKLGYSGGD-NH2 | 235 |
| 239 | Ac-RDPISAEISIQALSYALGGDINKVLEKLGYSGGDL-NH2 | 236 |
| 240 | Ac-DPISAEISIQALSYAIIGGDINKVLEKLGYSGGDLL-NH2 | 237 |
| 241 | Ac-PISAEISIQALSYALGGDINKVLEKLGYSGGDLLG-NH2 | 238 |
| 242 | Ac-ISAEISIQALSYALGGDINKVLEKLGYSGGDLLGI-NH2 | 239 |
| 243 | Ac-SAEISIQALSYALGGDINKVLEKLGYSGGDLLGIL-NH2 | 240 |

TABLE 1-continued

| T No. | Sequence | Seq. ID No. |
|---|---|---|
| 244 | Ac-AEISIQALSYALGGDINKVLEKLGYSGGDLLGILE-NH2 | 241 |
| 245 | Ac-EISIQALSYALGGDINKVLEKLGYSGGDLLGILES-NH2 | 242 |
| 246 | Ac-ISIQALSYALQGDINKVLEKLGYSGGDLLGILESR-NH2 | 243 |
| 247 | Ac-SIQALSYALGGDINKVLEKLGYSGGDLLGILESRG-NH2 | 244 |
| 248 | Ac-IQALSYALGGDINKVLEKLGYSGGDLLGILESRGI-NH2 | 245 |
| 249 | Ac-QALSYALGGDINKVLEKLGYSGGDLLGILESRGIK-NH2 | 246 |
| 250 | Ac-ALSYALGGDINKVLEKLGYSGGDLLGILESRGIKA-NH2 | 247 |
| 251 | Ac-LSYALGGDINKVLEKLGYSGGDLLGILESRGIKAR-NH2 | 248 |
| 252 | Ac-PDAVYLHRIDLGPPISLERLDVGTNLGNAIAKLED-NH2 | 249 |
| 253 | Ac-DAVYLHRIDLGPPISLERLDVGTNLGNAIAKLEDA-NH2 | 250 |
| 254 | Ac-AVYLHRIDLGPPISLERLDVGTNLGNAIAKLEDAK-NH2 | 251 |
| 255 | Ac-VYLHRDLGPPISLERLDVGTNLGNAIAKLEDAKE-NH2 | 252 |
| 256 | Ac-YLHRIDLGPPISLERLDVGTNLGNAIAKLEDAKEL-NH2 | 253 |
| 257 | Ac-LHRIDLGPPISLERLDVGTNLGNAIAKLEDAKELL-NH2 | 254 |
| 258 | Ac-HRIDLGPPISLERLDVGTNLGNAIAKLEDAKELLE-NH2 | 255 |
| 259 | Ac-RIDLGPPISLERLDVGTNLGNAIAKLEDAKELLES-NH2 | 256 |
| 260 | Ac-IDLGPPISLERLDVGTNLGNAIAKLEDAKELLESS-NH2 | 257 |
| 261 | Ac-DLGPPISLERLDVGTNLGNAIAKLEDAKELLESSD-NH2 | 258 |
| 262 | Ac-LGPPISLERLDVGTNLGNAIAKLEDAKELLESSDQ-NH2 | 259 |
| 263 | Ac-GPPISLERLDVGTNLGNAIAKLEDAKELLESSDQI-NH2 | 260 |
| 264 | Ac-PPISLERLDVGTNLGNAIAKLEDAKELLESSDQIL-NH2 | 261 |
| 265 | Ac-PISLERLDVGTNLGNAIAKLEDAKELLESSDQILR-NH2 | 262 |
| 266 | Ac-ISLERLDVGTNLGNAIAKLEDAKELLESSDQIRS-NH2 | 263 |
| 267 | Ac-SLERLDVGTNLGNAIAKLEDAKELLESSDQILRSM-NH2 | 264 |
| 268 | Ac-LERLDVGTNLGNAIAKLEDAKELLESSDQILRSMK-NH2 | 265 |
| 269 | Ac-EWIRRSNQKLDSI-NH2 | 266 |
| 270 | Ac-LELDKWASLANAF-NH2 | 267 |
| 271 | Ac-LELDKWASLENFF-NH2 | 268 |
| 272 | Ac-LELDKWASLANWF-NH2 | 269 |
| 273 | Ac-LELDKWASLWNAF-NH2 | 270 |
| 274 | Ac-ELGNVNNSISNALDKLEESNSKLDKVNVKLTSTSA-NH2 | 271 |
| 275 | Ac-TELGNVNNSISNALDKLEESNSKLDKVNVKLTSTS-NH2 | 282 |
| 276 | Ac-STELGNVNNSISNALDKLEESNSKLDKVNVKLTST-NH2 | 273 |
| 277 | Ac-ISTBLGNVNNSISNALDKLEESNSKLDKVNVKLTS-NH2 | 274 |
| 278 | Ac-DISTELGNVNNSISNALDKLEESNSKLDKVNVKLT-NH2 | 275 |
| 279 | Ac-LDISTELGNVNNSISNALDKLEESNSKLDKVNVKL-NH2 | 276 |
| 280 | Ac-NLDISTELGNVNNSISNALDKLEESNSKLDKVNVK-NH2 | 277 |
| 281 | Ac-GNLDISTELGNVNNSISNALDKLEESNSKLDKVNV-NH2 | 278 |
| 282 | Ac-TGNLDISTELGNVNNSISNALDKLEESNSKLDKVN-NH2 | 279 |
| 283 | Ac-VTGNLDISTELGNVNNSISNALDKLEESNSKLDKV-NH2 | 280 |
| 284 | Ac-IVTGNLDISTELGNVNNSISNALDKLEESNSKLDK-NH2 | 281 |
| 285 | Ac-VIVTGNLDISTELGNVNNSISNALDKLEESNSKLD-NH2 | 282 |
| 286 | Ac-QVIVTGNLDISTELGNVNNSISNALDKLEESNSKL-NH2 | 283 |
| 287 | Ac-SQVIVTGNLDISTELGNVNNSISNALDKLEESNSK-NH2 | 284 |
| 288 | Ac-DSQVIVTGNLDISTELGNVNNSISNALDKLEESNS-NH2 | 285 |
| 289 | Ac-LDSQVIVTGNLDISTELGNVNNSISNALDKLEESN-NH2 | 286 |
| 290 | Ac-ILDSQVIVTGNLDISTELGNVNNSISNALDKLEES-NH2 | 287 |
| 291 | Ac-SILDSQVIVTGNLDISTELGNVNNSISNALDKLEE-NH2 | 288 |
| 292 | Ac-ISILDSQVIVTGNLDISTELGNVNNSISNALDKLE-NH2 | 289 |
| 293 | Ac-NISILDSQVIVTGNLDISTELGNVNNSISNALDKL-NH2 | 290 |
| 294 | Ac-KNISILDSQVIVTGNLDISTELGNVNNSISNALDK-NH2 | 291 |
| 295 | Ac-QKNISILDSQVIVTGNLDISTELGNVNNSISNALD-NH2 | 292 |
| 296 | Ac-YQKNISILDSQVIVTGNLDISTELGNVNNSISNAL-NH2 | 293 |
| 297 | Ac-TYQKNISILDSQVIVTGNLDISTELGNVNNSISNA-NH2 | 294 |
| 298 | Ac-ATYQKNISILDSQVIVTGNLDISTELGNVNNSISN-NH2 | 295 |
| 299 | Ac-DATYQKNISILDSQVTVTGNLDISTELGNVNNSIS-NH2 | 296 |
| 300 | Ac-FDATYQKNISILDSQVIVTGNLDISTELGNVNNSI-NH2 | 297 |
| 301 | Ac-EFDATYQKNISILDSQVIVTGNLDISTELGNVNNS-NH2 | 298 |
| 302 | Ac-GEFDATYQKNISILDSQVIVTGNLDISTELGNVNN-NH2 | 299 |
| 303 | Ac-SGEFDATYQKNISILDSQVIVTGNLDISTELGNVN-NH2 | 300 |
| 304 | Ac-LSGEFDATYQKNISILDSQVIVTGNLDISTELGNV-NH2 | 301 |
| 305 | Ac-RLSGEFDATYQKNISILDSQVIVTGNLDISTELGN-NH2 | 302 |
| 306 | Ac-LRLSGEFDATYQKNISILDSQVIVTGNLDISTELG-NH2 | 303 |
| 307 | Ac-TLRLSGEFDATYQKNISILDSQVIVTGNLDISTEL-NH2 | 304 |
| 308 | Ac-ITLRLSGEFDATYQKNISILDSQVIVTGNLDISTE-NH2 | 305 |
| 309 | Ac-GITLRLSGEFDATYQKNISILDSQVIVTGNLDIST-NH2 | 306 |
| 310 | Ac-TATIEAVHEVTDGLSQLAVAVGKMQQFVNDQFNNT-NH2 | 307 |
| 311 | Ac-ITATIEAVHEVTDGLSQLAVAVGKMQQFVNDQFNN-NH2 | 308 |
| 312 | Ac-SITATIEAVHEVTDGLSQLAVAVGKMQQFVNDQFN-NH2 | 309 |
| 314 | Ac-KESITATIEAVHEVTDGLSQLAVAVGKMQQFVNDQ-NH2 | 310 |
| 315 | Ac-LKESITATIEAVHEVTDGLSQLAVAVGKMQQFVND-NH2 | 311 |
| 316 | Ac-RLKESITATIEAVHEVTDGLSQLAVAVGKMQQFVN-NH2 | 312 |
| 317 | Ac-LRLKESITATIEAVHEVTDGLSQLAVAVGKMQQFV-NH2 | 313 |
| 318 | Ac-ILRLKESITATIEAVHEVTDGLSQLAVAVGKMQQF-NH2 | 314 |
| 319 | Ac-NILRLKESITATIEAVHEVTDGLSQLAVAVGKMQQ-NH2 | 315 |
| 320 | Ac-ANILRLKESITATIEAVHEVTDGLSQLAVAVGKMQ-NH2 | 316 |

TABLE 1-continued

| T No. | Sequence | Seq. ID No. |
|---|---|---|
| 321 | Ac-AANILRLKESITATIEAVHEVTDGLSQLAVAVGKM-NH2 | 317 |
| 322 | Ac-HKCDDECMNSVKNGTYDYPKYEEESKLNRNEIKGV-NH2 | 318 |
| 323 | Ac-KCDDECMNSVKNGTYDYPKYEEESKLNRNEIKGVK-NH2 | 319 |
| 324 | Ac-CDDECMNSVKNGTYDYPKYEEESKLNRNEIKGVKL-NH2 | 320 |
| 325 | Ac-DDECMNSVKNGTYDYPKYEEESKLNRNEIKGVKLS-NH2 | 321 |
| 326 | Ac-DECMNSVKNGTYDYPKYEEESKLNRNEIKGVKLSS-NH2 | 322 |
| 327 | Ac-ECMNSVKNGTYDYPKYEEESKLNRNEIKGVKLSSM-NH2 | 323 |
| 328 | Ac-CMNSVKNGTYDYPKYEEESKLNRNEIKGVKLSSMG-NH2 | 324 |
| 329 | Ac-MNSVKNGTYDYPKYEEESKLNRNEIKGVKLSSMGV-NH2 | 325 |
| 330 | Ac-NSVKNGTYDYPKYEEESKLNRNEIKGVKLSSMGVY-NH2 | 326 |
| 331 | Ac-SVKNGTYDYPKYEEESKLNRNEIKGVKLSSMGVYQ-NH2 | 327 |
| 332 | Ac-VKNGTYDYPKYEEESKLNRNEIKGVKLSSMGVYQI-NH2 | 328 |
| 333 | Ac-KNGTYDYPKYEEESKLNRNEIKGVKLSSMGVYQIL-NH2 | 329 |
| 334 | Ac-AFIRKSDELLHNV-NH2 | 330 |
| 335 | Ac-VVLAGAALGVATAAQITAGIALHQSMLNSQAIDNL-NH2 | 331 |
| 336 | Ac-VLAGAALGVATAAQITAGIALHQSMLNSQAIDNLR-NH2 | 332 |
| 337 | Ac-LAGAALGVATAAQITAGIALHQSMLNSQAIDNLRA-NH2 | 333 |
| 338 | Ac-AGAALGVATAAQITAGIALHQSMLNSQAIDNLRAS-NH2 | 334 |
| 339 | Ac-GAALGVATAAQITAGIALHQSMLNSQAIDNLRASL-NH2 | 335 |
| 340 | Ac-AALGVATAAQITAGIALHQSMLNSQAIDNLRASLE-NH2 | 336 |
| 341 | Ac-ALGVATAAQITAGIALHQSMLNSQAIDNLRASLET-NH2 | 337 |
| 342 | Ac-LGVATAAQITAGIALHQSMLNSQAIDNLRASLETT-NH2 | 338 |
| 343 | Ac-GVATAAQITAGIALHQSMLNSQAIDNLRASLETTN-NH2 | 339 |
| 344 | Ac-VATAAQITAGIALHQSMLNSQAIDNLRASLETTNQ-NH2 | 340 |
| 345 | Ac-ATAAQITAGIALHQSMLNSQAIDNLRASLETTNQA-NH2 | 341 |
| 346 | Ac-TAAQITAGIALHQSMLNSQAIDNLRASLETTNQAI-NH2 | 342 |
| 347 | Ac-AAQITAGIALHQSMLNSQAIDNLRASLETTNQAIE-NH2 | 343 |
| 348 | Ac-AQITAGIALHQSMLNSQAIDNLRASLETTNQAIEA-NH2 | 344 |
| 349 | Ac-QITAGIALHQSMLNSQAIDNLRASLETTNQAIEAI-NH2 | 345 |
| 350 | Ac-ITAGIALHQSMLNSQAIDNLRASLETTNQAIEAIR-NH2 | 346 |
| 351 | Ac-TAGIALHQSMLNSQAIDNLRASLETTNQAIEAIRQ-NH2 | 347 |
| 352 | Ac-AGIALHQSMLNSQAIDNLRASLETTNQAIEAIRQA-NH2 | 348 |
| 353 | Ac-GIALHQSMLNSQAIDNLRASLETTNQAIEAIRQAG-NH2 | 349 |
| 354 | Ac-IALHQSMLNSQAIDNLRASLETTNQAIEAIRQAGQ-NH2 | 350 |
| 355 | Ac-ALHQSMLNSQAIDNLRASLETTNQAIEAIRQAGQE-NH2 | 351 |
| 356 | Ac-LHQSMLNSQAIDNLRASLETTNQAIEAIRQAGQEM-NH2 | 352 |
| 357 | Ac-HQSMLNSQAIDNLRASLETTNQAIEAIRQAGQEMI-NH2 | 353 |
| 358 | Ac-QSMLNSQAIDNLRASLETTNQAIEAIRQAGQEMIL-NH2 | 354 |
| 359 | Ac-SMLNSQAIDNLRASLETTNQAIEAIRQAGQEMILA-NH2 | 355 |
| 360 | Ac-MLNSQAIDNLRASLETTNQAIEAIRQAGQEMILAV-NH2 | 356 |
| 361 | Ac-LNSQAIDNLRASLETTNQAIEAIRQAGQEMILAVQ-NH2 | 357 |
| 362 | Ac-NSQAIDNLRASLETTNQAIEAIRQAGQEMILAVQG-NH2 | 358 |
| 363 | Ac-SQAIDNLRASLETTNQAIEAIRQAGQEMILAVQGV-NH2 | 359 |
| 364 | Ac-QAIDNLRASLETTNQAIEAIRQAGQEMILAVQGVQ-NH2 | 360 |
| 365 | Ac-AIDNLRASLETTNQAIEAIRQAGQEMILAVQGVQD-NH2 | 361 |
| 366 | Ac-IDNLRASLETTNQAIEAIRQAGQEMILAVQGVQDY-NH2 | 362 |
| 367 | Ac-DNLRASLETTNQAIEAIRQAGQEMILAVQGVQDYI-NH2 | 363 |
| 368 | Ac-NLRASLETTNQAIEAIRQAGQEMILAVQGVQDYIN-NH2 | 364 |
| 369 | Ac-LRASLETFNQAIEAIRQAGQEMILAVQGVQDYINN-NH2 | 365 |
| 370 | Ac-RASLETTNQAIEAIRQAGQEMILAVQGVQDYINNE-NH2 | 366 |
| 371 | Ac-YTSVITIELSNIKENKLNGTDAVKLIKQELDKYK-NH2 | 367 |
| 372 | Ac-TSVITIELSNIKENKLNGTDAVKLIKQELDKYKN-NH2 | 368 |
| 373 | Ac-SVITIELSNIKENKLNGTDAVKLIKQELDKYKNA-NH2 | 369 |
| 374 | Ac-SNIKENKLNGTDAKVKLIKQELDKYKNAVTELQLL-NH2 | 370 |
| 375 | Ac-KENKLNGTDAKVKLIKQELDKYKNAVTELQLLMQS-NH2 | 371 |
| 376 | Ac-CLELDKWASLWNWFC-NH2 | 372 |
| 377 | Ac-CLELDKWASLANWFC-NH2 | 373 |
| 378 | Ac-CLELDKWASLFNFFC-NH2 | 374 |
| 379 | Ac-YTSLIHSLIEESQNQQEKNEQELLELDKWASLFNFF-NH2 | 375 |
| 381 | Ac-KMKQLEDKVEELLSKNYHLENELELDKWASLWNWF-NH2 | 376 |
| 382 | Ac-KVEELLSKNYHLENELELDKWASLWNWF-NH2 | 377 |
| 383 | Ac-RMKQLEDKVEELLSKLEWIRRSNQKLDSI-NH2 | 378 |
| 384 | Ac-RMKQLEDkVEELLSKLAFIRKSDELLHNV-NH2 | 379 |
| 385 | Ac-ELEALRGELRALRGELELDKWASLWNWF-NH2 | 380 |
| 386 | Ac-LDPIDISIELNKAKSDLEESKEWIRRSNQKLDSI-NH2 | 381 |
| 387 | Ac-CNEQLSDSFPVEFFQV-NH2 | 382 |
| 388 | Ac-MAEDDPYLGRPEQMFHLDPSL-NH2 | 383 |
| 389 | Ac-EDFSSIADMDFSALLSQISS-NH2 | 384 |
| 390 | Ac-TWQEWERKVDFLEENITALLEEAQIQQEKNMYELQ-NH2 | 385 |
| 391 | Ac-WQEWERKVDFLEENITALLEEAQIQQEKNMYELQK-NH2 | 386 |
| 392 | Ac-QEWERKVDFLEENITALLEEAQIQQEKNMYELQKL-NH2 | 387 |
| 393 | Ac-EWERKVDFLEENITALLEEAQIQQEKNMYELQKLN-NH2 | 388 |
| 394 | Ac-WERKVDFLEENITALLEEAQIQQEKNMYELQKLNS-NH2 | 389 |
| 395 | Ac-ERKVDFLEENITALLEEAQIQQEKNMYELQKLNSW-NH2 | 390 |
| 396 | Ac-RKVDFLEENITALLEEAQIQQEKNMYELQKLNSWD-NH2 | 391 |
| 397 | Ac-KVDFLEENITALLEEAQIQQEKNMYELQKLNSWDV-NH2 | 392 |

TABLE 1-continued

| T No. | Sequence | Seq. ID No. |
|---|---|---|
| 398 | Ac-VDFLEENITALLEEAQIQQEKNMYELQKLNSWDVF-NH2 | 393 |
| 399 | Ac-DFLEENITALLEEAQIQQEKNMYELQKLNSWDVFG-NH2 | 394 |
| 400 | Ac-FLEENITALLEEAQIQQEKNMYELQKLNSWDVFGN-NH2 | 395 |
| 401 | Ac-LEENITALLEEAQIQQEKNMYELQKLNSWDVFGNW-NH2 | 396 |
| 402 | Ac-LEENITALLEEAQIQQEKNMYELQKLNSWDVFGNWF-NH2 | 397 |
| 403 | Ac-NEQSEEKENELYWAKEQLLDLLFNIFNQTVGAWIMQ-NH2 | 398 |
| 405 | Ac-QQQLLDVVKRQQELLRLTVWGTKNLQTRVTAIEKYLKD-NH2 | 400 |
| 406 | Ac-QQLLDVVKRQQELLRLTVWGTKNLQTRVTAIEKYLKLQ-NH2 | 401 |
| 407 | Ac-QQLLDVVKRQQELLRLTVWGPKNLQTRVTAIEKYLKLQ-NH2 | 402 |
| 408 | Ac-DERKQDKVLVVQQTGTLQtTLIQLEKTAKLQWVRLNRY-NH2 | 403 |
| 409 | Ac-QQQLLDVVKRQQELLRLTVWGTKNLQTRVTAIEKY-NH2 | 404 |
| 410 | Ac-QQLLDVVKRQQELLRLTVWGTKNLQTRVTAIEKYL-NH2 | 405 |
| 411 | Ac-QLLDVVKRQQELLRLTVWGTKNLQTRVTAIEKYLK-NH2 | 406 |
| 412 | Ac-LLDVVKRQQELLRLTVWGTKNLQTRVTAIEKYLKL-NH2 | 407 |
| 413 | Ac-LDVVKRQQELLRLTVWGTKNLQTRVTAIEKYLKLQ-NH2 | 408 |
| 414 | Ac-DVKKRQQELLRLTVWGTKNLQTRVTAIEKYLKLQA-NH2 | 409 |
| 415 | Ac-VVKRQQELLRLTVWGTKNLQTRVTAIEKYLKLQAQ-NH2 | 410 |
| 416 | Ac-VKRQQELLRLTVWGTKNLQTRVTAIEKYLKLQAQL-NH2 | 411 |
| 417 | Ac-KRQQELLRLTVWGTKNLQTRVTAIEKYLKDQAQLN-NH2 | 412 |
| 418 | Ac-RQQELLRLTVWGTKNLQTRVTAIEKYLKDQAQLNA-NH2 | 413 |
| 419 | Ac-QQELLRLTVWGTKNLQTRVTAIEKYLKDQAQLNAW-NH2 | 414 |
| 420 | Ac-QELLRLTVWGTKNLQTRVTAIEKYLKDQAQLNAWG-NH2 | 415 |
| 421 | Ac-ELLRLTVWGTKNLQTRVTAIEKYLKDQAQLNAWGC-NH2 | 416 |
| 422 | Ac-NNLLRAIEAQQHLLQLTVWGPKQLQARILAVERYLKDQ-NH2 | 417 |
| 423 | Ac-SELEIKRYKNRVASRKCRAKFKQLLQHYREVAAAK-NH2 | 418 |
| 424 | Ac-ELEIKRYKNRVASRKCRAKFKQLLQHYREVAAAKS-NH2 | 419 |
| 425 | Ac-LEIKRYNNRVASRKCRAKFKQLLQHYREVAAAKSS-NH2 | 420 |
| 426 | Ac-EIKRYKNRVASRKCRAKFKQLLQHYREVAAAKSSE-NH2 | 421 |
| 427 | Ac-IKRYKNRVASRKCRAKFKQLLQHYREVAAAKSSEN-NH2 | 422 |
| 428 | Ac-KRYKNRVASRKCRAKFKQLLQHYREVAAAKSSEND-NH2 | 423 |
| 429 | Ac-RYKNRVASRKCRAKFKQLLQHYREVAAAKSSENDR-NH2 | 424 |
| 430 | Ac-YKNRVASRKCRAKFKQLLQHYREVAAAKSSENDRL-NH2 | 425 |
| 431 | Ac-KNRVASRKCRAKFKQLLQHYREVAAAKSSENDRLR-NH2 | 426 |
| 432 | Ac-NRVASRKCRAKFKQLLQHYREVAAAKSSENDRLRL-NH2 | 427 |
| 433 | Ac-RVASRKCRAKFKQLLQHYREVAAAKSSENDRLRLL-NH2 | 428 |
| 434 | Ac-VASRKCRAKFKQLLQHYREVAAAKSSENDRLRLLL-NH2 | 429 |
| 435 | Ac-ASRKCRAKFKQLLQHYREVAAAKSSENDRLRLLLK-NH2 | 430 |
| 436 | Ac-SRKCRAKFKQLLQHYREVAAAKSSENDRLRLLLKQ-NH2 | 431 |
| 437 | Ac-RKCRAKFKQLLQHYREVAAAKSSENDRLRLLLKQM-NH2 | 432 |
| 438 | Ac-KCRAKFKQLLQHYREVAAAKSSENDRLRLLLKQMC-NH2 | 433 |
| 439 | Ac-CRAKFKQLLQHYREVAAAKSSENDRLRLLLKQMCP-NH2 | 434 |
| 440 | Ac-RAKFKQLLQHYREVAAAKSSENDRLRLLLKQMCPS-NH2 | 435 |
| 441 | Ac-AKFKQLLQHYREVAAAKSSENDRLRLLLKQMCPSL-NH2 | 436 |
| 442 | Ac-KFKQLLQHYREVAAAKSSENDRLRLLLKQMCPSLD-NH2 | 437 |
| 443 | Ac-FKQLLQHYREVAAAKSSENDRLRLLLKQMCPSLDV-NH2 | 438 |
| 444 | Ac-KQLLQHYREVAAAKSSENDRLRLLLKQMCPSLDVD-NH2 | 439 |
| 445 | Ac-QLLQHYREVAAAKSSENDRLRLLLKQMCPSLDVDS-NH2 | 440 |
| 446 | Ac-LLQHYREVAAAKSSENDRLRLLLKQMCPSLDVDSI-NH2 | 441 |
| 447 | Ac-LQHYREVAAAKSSENDRLRLLLKQMCPSLDVDSII-NH2 | 442 |
| 448 | Ac-QHYREVAAAKSSENDRLRLLLKQMCPSLDVDSIIP-NH2 | 443 |
| 449 | Ac-HYREVAAAKSSENDRLRLLLKQMCPSLDVDSIIPR-NH2 | 444 |
| 450 | Ac-YREVAAAKSSENDRLRLLLKQMCPSLDVDSIIPRT-NH2 | 445 |
| 451 | Ac-REVAAAKSSENDRLRLLLKQMCPSLDVDSIIPRTP-NH2 | 446 |
| 452 | Ac-EVAAAKSSENDRLRLLLKQMCPSLDVDSIIPRTPD-NH2 | 447 |
| 453 | Ac-VAAAKSSENDRLRLLLKQMCPSLDVDSIIPRTPDV-NH2 | 448 |
| 454 | Ac-AAAKSSENDRLRLLLKQMCPSLDVDSIIPRTPDVL-NH2 | 449 |
| 455 | Ac-AAKSSENDRLRLLLKQMCPSLDVDSIIPRTPDVLH-NH2 | 450 |
| 456 | Ac-AKSSENDRLRLLLKQMCPSLDVDSIIPRTPDVLHE-NH2 | 451 |
| 457 | Ac-KSSENDRLRLLLKQMCPSLDVDSIIPRTPDVLHED-NH2 | 452 |
| 458 | Ac-SSENDRLRLLLKQMCPSLDVDSIIPRTPDVLHEDL-NH2 | 453 |
| 459 | Ac-SENDRLRLLLKQMCPSLDVDSIIPRTPDVLHEDLL-NH2 | 454 |
| 460 | Ac-ENDRLRLLLKQMCPSLDVDSIIPRTPDVLHEDLLN-NH2 | 455 |
| 461 | Ac-NDRLRLLLKQMCPSLDVDSIIPRTPDVLHEDLLNF-NH2 | 456 |
| 534 | Ac-PGYRWMCLRRFIIFLFILLLCLIFLLVLLDYQGML-NH2 | 458 |
| 535 | Ac-GYRWMCLRRFIIFLFILLLCLIFLLVLLDYQGMLP-NH2 | 459 |
| 536 | Ac-YRWMCLRRFIIFLFILLLCLIFLLVLLDYQGMLPV-NH2 | 460 |
| 537 | Ac-RWMCLRRFIIFLFILLLCLIFLLVLLDYQGMLPVC-NH2 | 461 |
| 538 | Ac-WMCLRRFIIFLFILLLCLIFLLVLLDYQGMLPVCP-NH2 | 462 |
| 539 | Ac-MCLRRFIIFLFILLLCLIFLLVLLDYQGMLPVCPL-NH2 | 463 |
| 540 | Ac-CLRRFIIFLFILLLCLIFLLVLLDYQGMLPVCPLI-NH2 | 464 |
| 541 | Ac-LRRFIIFLFILLLCLIFLLVLLDYQGMLPVCPLIP-NH2 | 465 |
| 542 | Ac-RRFIIFLFILLLCLIFLLVLLDYQGMLPVCPLIPG-NH2 | 466 |
| 543 | Ac-RFIIFLFILLLCLIFLLVLLDYQGMLPVCPLIPGS-NH2 | 467 |
| 544 | Ac-FIIFLFILLLCLIFLLVLLDYQGMLPVCPLIPGSS-NH2 | 468 |
| 545 | Ac-HFLFILLLCLIFLLVLLDYQGMLPVCPLIPGSST-NH2 | 469 |
| 546 | Ac-IFLFILLLCLIFLLVLLDYQGMLPVCPLIPGSSTT-NH2 | 470 |

TABLE 1-continued

| T No. | Sequence | Seq. ID No. |
|---|---|---|
| 547 | Ac-FLFILLLCLIFLLVLLDYQGMLPVCPLIPGSSTTS-NH2 | 471 |
| 548 | Ac-LFILLLCLIFLLVLLDYQGMLPVCPLIPGSSTTST-NH2 | 472 |
| 549 | Ac-FILLLCLIFLLVLLDYQGMLPVCPLIPGSSTTSTG-NH2 | 473 |
| 550 | Ac-ILLLCLIFLLVLLDYQGMLPVCPLIPGSSTTSTGP-NH2 | 474 |
| 551 | Ac-LLLCLIFLLVLLDYQGMLPVCPLIPGSSTTSTGPC-NH2 | 475 |
| 552 | Ac-LLCLIFLLVLLDYQGMLPVCPLIPGSSTTSTGPCR-NH2 | 476 |
| 553 | Ac-LCLIFLLVLLDYQGMLPVCPLIPGSSTTSTGPCRT-NH2 | 477 |
| 554 | Ac-CLIFLLVLLDYQGMLPVCPLIPGSSTTSTGPCRTC-NH2 | 478 |
| 555 | Ac-LIFLLVLLDYQGMLPVCPLIPGSSTTSTGPCRTCM-NH2 | 479 |
| 556 | Ac-IFLLVLLDYQGMLPVCPLIPGSSTTSTGPCRTCMT-NH2 | 480 |
| 557 | Ac-FLLVLLDYQGMLPVCPLIPGSSTTSTGPCRTCMTT-NH2 | 481 |
| 558 | Ac-PPLVLQAGFFLLTMLTIPQSLDSWWTSLNFLGGT-NH2 | 482 |
| 559 | Ac-LLVLQAGFFLLTRILTIPQSLDSWWTSLNFLGGTT-NH2 | 483 |
| 560 | Ac-LVLQAGFFLLTRILTIPQSLDSWWTSLNFLGGTTV-NH2 | 484 |
| 561 | Ac-VLQAGFFLLTMLTIPQSLDSWWTSLNFLGGTTVC-NH2 | 485 |
| 562 | Ac-LQAGFFLLTMLTIPQSLDSWWTSLNFLGGTTVCL-NH2 | 486 |
| 563 | Ac-QAGFFLLTRILTIPQSLDSWWTSLNFLGGTTVCLG-NH2 | 487 |
| 564 | Ac-AGFFLLTMLTIPQSLDSWWTSLNFLGGTTVCLGQ-NH2 | 488 |
| 565 | Ac-GFFLLTRILTIPQSLDSWWTSLNFLGGTTVCLGQN-NH2 | 489 |
| 566 | Ac-FFLLTRILTIPQSLDSWWTSLNFLGGTTVCLGQNS-NH2 | 490 |
| 567 | Ac-FLLTMLTIPQSLDSWWTSLNFLGGTTVCLGQNSQ-NH2 | 491 |
| 568 | Ac-LLTRILTIPQSLDSWWTSLNFLGGTTVCLGQNSQS-NH2 | 492 |
| 569 | Ac-LTMLTIPQSLDSWWTSLNFLGGTTVCLGQNSQSP-NH2 | 493 |
| 570 | Ac-FWNWLSAWKDLELKSLLEEVKDELQKMR-NH2 | 494 |
| 571 | Ac-NNLLRAIEAQQHLLQLTVW-NH2 | 495 |
| 572 | Ac-CGGNNLLRAIEAQQHLLQLTVWGIKQLQAMLAVERYLKDQ-NH2 | 496 |
| 573 | Ac-YTSLIHSLIEESQNQQEKNEQELLELDKWASLWNWF-NH2 | 497 |
| 574 | C13H27CO-YTSLIHSLIEESQNQQEKNEQELLELDKWASLWNWF-NH2 | 498 |
| 575 | Ac-AVSKGYLSALRTGWYTSVITIELSNIKENKLNGTDA-NH2 | 499 |
| 576 | Ac-SISNIETVIEFQQKRRRLLEITREFSVNAGVTTPVS-NH2 | 500 |
| 577 | Ac-DQQIKQYRRLLDRLIIPLYDGLRQKDVWSNQESN-NH2 | 501 |
| 578 | Ac-YSELTNIFGDMGSLQEKGIKLQGIASLYRTNITEI-NH2 | 502 |
| 579 | Ac-TSITLQVRLPLLTRLLNTQIYRVDSISYNIQNREWY-NH2 | 503 |
| 580 | Ac-VEIAEYRRLLRTVLEPIRDALNAMTQNIRPVQSVA-NH2 | 504 |
| 581 | Ac-SYFIVLSIAYPTLSEIKGVIVHRLEGVSYNIGSQEW-NH2 | 505 |
| 582 | Ac-LKEAIRDTKKAVQSVQSSIGNLIVAIKS-NH2 | 506 |
| 583 | NNLLRAIEAQQHLLQLTVWGIKQLQARILAVERYLKDQ-NH2 | 507 |
| 583 | NNLLRAIEAQQHLLQLTVWGIKQLQARILAVERYLKDQ-NH2 | 507 |
| 584 | QKQEPIDKELYPLTSL | 508 |
| 585 | YPKFVKQNTLKLAT | 509 |
| 586 | QYIKANQKFIGITE | 510 |
| 587 | NGQIGNDPNRDILY | 511 |
| 588 | AC-RPDVY-OH | 512 |
| 589 | CLELDKWASLWWWFC-(cyclic) | 513 |
| 590 | CLELDKWASLANWFC-(cyclic) | 514 |
| 591 | CLELDKWASLANFFC-(cyclic) | 515 |
| 594 | Ac-NNLLRAIEAQQQHLLQLTVWGIKQLQARILAVERYLKDQ-NH2 | 516 |
| 595 | Ac-CGGYTSLIHSLIEESQNQQEKNEQELLELDKWASLWNNWF-NH2 | 517 |
| 596 | Ac-PLLVLQAGFFLLTRILTIPQSLDSWWTSLNFLGGT-NH2 | 518 |
| 597 | Ac-LLVLQAGFFLLTRILTIPQSLDSWWTSLNFLGGTT-NH2 | 519 |
| 598 | Ac-LVLQAGFFLLTRILTIPQStDSWWTSLNFLGGTTV-NH2 | 520 |
| 599 | Ac-VLQAGFFLLTRILTIPQSLDSWWTSLNFLGGTTVC-NH2 | 521 |
| 600 | Ac-LQAGFFLLTRILTIPQSLDSWWTSLNFLGGTTVCL-NH2 | 522 |
| 601 | Ac-QAGFFLLTRILTIPQSLDSWWTSLNFLGGTTVCLG-NH2 | 523 |
| 602 | Ac-AGFFLLTRILTIPQSLDSWWTSLNFLGGTTVCLGQ-NH2 | 524 |
| 603 | Ac-GFFLLTRILTIPQSLDSWWTSLNFLGGTTVCLGQN-NH2 | 525 |
| 604 | Ac-FFLLTRILTIPQSLDSWWTSLNFLGGTTVCLGQNS-NH2 | 526 |
| 605 | Ac-FLLTRILTIPQSLDSWWTSLNFLGGTTVCLGQNSQ-NH2 | 527 |
| 606 | Ac-LLTRILTIPQSLDSWWTSLNFLGGTTVCLGQNSQS-NH2 | 528 |
| 607 | Ac-LTRILTIPQSLDSWWTSLNFLGGTTVCLGQNSQSP-NH2 | 529 |
| 608 | Ac-LELDKWASLWNWA-NH2 | 530 |
| 609 | Ac-LELDKWASAWNWF-NH2 | 531 |
| 610 | Ac-LELDKAASLWNWF-NH2 | 532 |
| 611 | Ac-LKLDKWASLWNWF-NH2 | 533 |
| 612 | Ac-LELKKWASLWNWF-NH2 | 534 |
| 613 | Ac-DELLHNVNAGKST-NH2 | 535 |
| 614 | Ac-KSDELLHNVNAGKST-NH2 | 536 |
| 615 | Ac-IRKSDELLHNVNAGKST-NH2 | 537 |
| 616 | Ac-AFIRKSDELLHNVNAGKST-NH2 | 538 |
| 617 | Ac-FDASISQVNEKINQSLAFI-NH2 | 539 |
| 618 | Ac-YAADKESTQKAFDGITNKVNSVIEKMNTQFEAVGKE-NH2 | 540 |
| 619 | Ac-SVIEKMNTQFEAVGKEFGNLERRLENLNKRMEDGFL-NH2 | 541 |
| 620 | Ac-VWTYNAELLVLMENERTLDFHDSNNKNLYDKVRMQL-NH2 | 542 |
| 621 | Ac-EWDREINNYTSLIHSLIEESQNQQEKNEQEGGC-NH2 | 543 |
| 622 | Ac-INNYTSLIHSLIEESQNQQEKNEQELLELDKWASL-NH2 | 544 |
| 623 | Ac-INNYTSLIHSLIEESQNQQEKNEQELLE-NH2 | 545 |

TABLE 1-continued

| T No. | Sequence | Seq. ID No. |
|---|---|---|
| 624 | Ac-WMEWDREINNYTSLIHSLIEESQNQQEKNEQELLE-NH2 | 546 |
| 625 | Ac-MTWMEWDREINNYTSLIHSLIEESQNQQEKNEQELLELDKWASLWNWF-NH2 | 547 |
| 626 | Ac-IDISIELNKAKSDLEESKEWIKKSNQKLDSIGNWH-NH2 | 548 |
| 627 | Ac-NQQEKNEQELLELDKWASLWNWFNITNWLWYIKIFI-NH2 | 549 |
| 627 | Ac-NQQEKNEQELLELDKWASLWNWFNITNWLWYIKIFI-NH2 | 549 |
| 628 | Ac-QNQQEKNEQELLELDKWASLWNWFNITNWLWYIKIF-NH2 | 550 |
| 629 | Ac-SQNQQEKNBQELLELDKWASLWWWFMTNWLWYIKI-NH2 | 551 |
| 630 | Ac-ESQNQQEKNEQELLELDKWASLWNWFNITNWLWYIK-NH2 | 552 |
| 631 | Ac-EESQNQQEKNEQELLELDKWASLWNWFNITNWLWYI-NH2 | 553 |
| 632 | Ac-IEESQNQQEKNEQELLELDKWASLWNWFhTNWLWY-NH2 | 554 |
| 633 | Ac-LIEESQNQQEKNEQELLELDKWASLWNWFMTNWLW-NH2 | 555 |
| 634 | Ac-SLIEESQNQQEKNEQELLELDKWASLWNWFNITNWL-NH2 | 556 |
| 635 | Ac-HSLIEESQNQQEKNEQELLELDKWASLWNWFNITNW-NH2 | 557 |
| 636 | Ac-IHSLIEESQNQQEKNEQELLELDKWASLWNWFNITN-NH2 | 558 |
| 637 | Ac-LIHSLIEESQNQQEKNEQELLELDKWASLWNWFNIT-NH2 | 559 |
| 638 | Ac-SLIHSLIEESQNQQEKNEQELLELDKWASLWNWFNI-NH2 | 560 |
| 639 | Ac-TSLIHSLIEESQNQQEKNEQELLELDKWASLWNWFN-NH2 | 561 |
| 640 | Ac-NYTSLIHSLIEESQNQQEKNEQELLELDKWASLWNW-NH2 | 562 |
| 641 | Ac-NNYTSLIHSLIEESQNQQEKNEQELLELDKWASLWN-NH2 | 563 |
| 642 | Ac-INNYTSLIHSLIEESQNQQEKNEQELLELDKWASLW-NH2 | 564 |
| 643 | Ac-EINNYTSLIHSLIEESQNQQEKNEQELLELDKWASL-NH2 | 565 |
| 644 | Ac-REINNYTSLIHSLIEESQNQQEKNEQELLELDKWAS-NH2 | 566 |
| 645 | Ac-DREINNYTSLIHSLIEESQNQQEKNEQELLELDKWA-NH2 | 567 |
| 646 | Ac-WDKEINNYTSLIHSLIEESQNQQEKNEQELLELDKW-NH2 | 568 |
| 647 | Ac-EWDREINNYTSLIHSLIEESQNQQEKNEQELLELDK-NH2 | 569 |
| 648 | Ac-MEWDREINNYTSLIHSLIEESQNQQEKNEQELLELD-NH | 570 |
| 649 | Ac-WMEWDREINNYTSLIHSLIEESQNQQEKNEQELLEL-NH2 | 572 |
| 650 | Ac-TWMEWDREINNYTSLIHSLIEESQNQQEKNEQELLE-NH2 | 573 |
| 651 | Ac-MTWMEWDREINNYTSLIHSLIEESQNQQEKNEQELL-NH2 | 574 |
| 652 | Ac-NMTWMEWDREINNYTSLIHSLIEESQNQQEKNEQEL-NH2 | 575 |
| 653 | Ac-NNMTWMEWDREINNYTSLIHSLIEESQNQQEKNEQE-NH2 | 576 |
| 654 | Ac-WNNMTWMEWDREINNYTSLIHSLIEESQNQQEKNEQ-NH2 | 577 |
| 655 | Ac-IWNNMTWMEWDREINNYTSLIHSLIEESQNQQEKNE-NH2 | 578 |
| 656 | Ac-QIWNNMTWMEWDREINNYTSLIHSLIEESQNQQEKN-NH2 | 579 |
| 657 | Ac-EQIWNNMTWMEWDREINNYTSLIHSLIEESQNQQEK-NH2 | 580 |
| 658 | Ac-LEQIWNNMTWMEWDREINNYTSLIHSLIEESQNQQE-NH2 | 581 |
| 659 | Ac-SLEQIWNNMTWMEWDREINNYTSLIHSLIEESQNQQ-NH2 | 582 |
| 660 | Ac-KSLEQIWNNMTWMEWDREINNYTSLIHSLIEESQNQ-NH2 | 583 |
| 661 | Ac-NKSLEQIWNNMTWMEWDREINNYTSLIHSLIEESQN-NH2 | 584 |
| 662 | Ac-SLAFIRKSDELLHNVNAGKST-NH2 | 585 |
| 663 | Ac-FDASISQVNEKINQSLAFIRK-NH2 | 586 |
| 664 | Ac-YTSLIHSLIEESQQQQEKQEQELLELDKWASLWNWF-NH2 | 587 |
| 665 | Ac-FDASISQVNEKINQSLAFIRKSDELLHNVNAGK-NH2 | 588 |
| 666 | Ac-FDASISQVNEKINQSLAFIRKSDELLHNVNA-NH2 | 589 |
| 667 | Ac-FDASISQVNEKINQSLAFIRKSDELLHNV-NH2 | 590 |
| 668 | Ac-FDASISQVNEKINQSLAFIRKSDELLH-NH2 | 591 |
| 669 | Ac-FDASISQVNEKINQSLAFIRKSDEL-NH2 | 592 |
| 670 | Ac-FDASISQVNEKINQSLAFIRKSD-NH2 | 593 |
| 671 | Ac-ASISQVNEKINQSLAFIRKSDELLHNVNAGKST-NH2 | 594 |
| 672 | Ac-ISQVNEKINQSLAFIRKSDELLHNVNAGKST-NH2 | 595 |
| 673 | Ac-QVNEKINQSLAFIRKSDELLHNVNAGKST-NH2 | 596 |
| 674 | Ac-NEKINQSLAFIRKSDELLHNVNAGKST-NH2 | 597 |
| 675 | Ac-KINQSLAFIRKSDELLHNVNAGKST-NH2 | 598 |
| 676 | Ac-NQSLAFIRKSDELLHNVNAGKST-NH2 | 599 |
| 677 | Ac-FWNWLSAWKDLELYPGSLELDKWASLWNWF-NH2 | 600 |
| 678 | Ac-CGGNNLLRAIEAQQHLLQLTVWGIKQLQARILAVERYLKDQ-NH2 | 601 |
| 679 | Ac-CGGYTSLIHSLIEESQNQQEKNEQELLELDKWASLWNWF-NH2 | 602 |
| 680 | YTSLIHSLIEESQNQQEKNEQELLELDKWASLWNWF | 603 |
| 681 | NNLLRAIEAQQHLLQLTVWGIKQLQARILAVERYLKDQ | 604 |
| 682 | Ac-EKNMYELQKLNSWDVFTNWLDFTSWVRYIQYIQYGV-NH2 | 605 |
| 683 | Ac-QEKNMYELQKLNSWDVFTNWLDFTSWVRYIQYIQYG-NH2 | 606 |
| 684 | Ac-QQEKNMYELQKLNSWDVFTNWLDFTSWVRYIQYIQY-NH2 | 607 |
| 685 | Ac-IQQEKNMYELQKLNSWDVFTNWLDFTSWVRYIQYIQ-NH2 | 608 |
| 686 | Ac-QIQQEKNMYELQKLNSWDVFTNWLDFTSWVRYIQYI-NH2 | 609 |
| 687 | Ac-AQIQQEKNMYELQKLNSWDVFTNWLDFTSWVRYIQY-NH2 | 610 |
| 688 | Ac-QAQIQQEKNMYELQKLNSWDVFTNWLDFTSWVRYIQ-NH2 | 611 |
| 689 | Ac-EQAQIQQEKNMYELQKLNSWDVFTNWLDFTSWVRYI-NH2 | 612 |
| 690 | Ac-LEQAQIQQEKNMYELQKLNSWDVFTNWLDFTSWVRY-NH2 | 613 |
| 691 | Ac-SLEQAQIQQEKNMYELQKLNSWDVFTNWLDFTSWVR-NH2 | 614 |
| 692 | Ac-QSLEQAQIQQEKNMYELQKLNSWDVFTNWLDFTSWV-NH2 | 615 |
| 693 | Ac-SQSLEQAQIQQEKNMYELQKLNSWDVFTNWLDFTSW-NH2 | 616 |
| 694 | Ac-ISQSLEQAQIQQEKNMYELQKLNSWDVFTNWLDFTS-NH2 | 617 |
| 695 | Ac-NISQSLEQAQIQQEKNMYELQKLNSWDVFTNWLDFT-NH2 | 618 |
| 696 | Ac-ANISQSLEQAQIQQEKNMYELQKLNSWDVFTNWLDF-NH2 | 619 |
| 697 | Ac-EAMSQSLEQAQIQQEKNMYELQKLNSWDVFTMWLD-NH2 | 620 |
| 699 | Ac-YLEAMSQSLEQAQIQQEKNMYELQKLNSWDVFTNW-NH2 | 621 |

TABLE 1-continued

| T No. | Sequence | Seq. ID No. |
|---|---|---|
| 700 | Ac-YTSLIHSLIEESQNQQEKNEQEL-NH2 | 622 |
| 701 | Ac-YTSLIHSLIEESQNLQEKNEQELLELDKWASLWNWF-NH2 | 623 |
| 702 | Ac-YTSLIHSLIEESQNQQEKLEQELLELDKWASLWNWF-NH2 | 624 |
| 703 | Ac-YTSLIHSLIEESQNQQEKNEQELLEFDKWASLWNWF-NH2 | 625 |
| 704 | Ac-YTSLIHSLIEESQNQQEKNEQELLELDKPASLWNWF-NH2 | 626 |
| 705 | Ac-YTSLIHSLIEESQNQQEKNEQELLELDKWASPWNWF-NH2 | 627 |
| 706 | Ac-YTSLIHSLIEESQNQQEKNEQELLELDKWASLWNSF-NH2 | 628 |
| 707 | Biotin NH(CH2)4CO-YTSLIHSLIEESQNQQEKNEQELLELDKWASLWNWF-NH2 | 629 |
| 708 | Biotin NH(CH2)6CO-YTSLIHSLIEESQNQQEKNEQELLELDKWASLWNWF-NH2 | 630 |
| 709 | FMOC-YTSLIHSLIEESQNQQEKNEQELLELDKWASLWNWF | 92 |
| 710 | FMOC-NNLLRAIEAQQHLLQLTVWGIKQLQARILAVERYLKDQ | 16 |
| 711 | Ac-EWDREINNYTSLIHSLIEESQNQQEKNEQE-NH2 | 634 |
| 712 | Ac-LIEESQNQQEKNEQELLELDKWASLWNWF-NH2 | 635 |
| 713 | Ac-FWNWLSAWKDLELGGPGSGPGGLELDKWASLWNWF-NH2 | 636 |
| 714 | Ac-LIHSLIEESQNQQEKNEQELLELDKWASL-NH2 | 637 |
| 715 | Ac-TSLIHSLIEESQNQQEKNEQELLELDKWASLWNWF-NH2 | 638 |
| 716 | Ac-LIHSLIEESQNQQEKNEQELLELDKWASLWNWF-NH2 | 639 |
| 718 | FMOC-GGGGGYTSLIHSLIEESQNQQEKNEQELLELDKWASLWNWF-NH2 | 640 |
| 719 | Ac-HSLIEESQNQQEKNEQELLELDKWASLWNWF-NH2 | 641 |
| 720 | Ac-YTSLIYSLIEESQNQQEKNEQELLELDKWASLWNWF-NH2 | 642 |
| 721 | Ac-YTSLIHSLIEKSQNQQEKNEQELLELDKWASLWNWF-NH2 | 643 |
| 722 | Ac-YTSLIHSSIEESQNQQEKNEQELLELDKWASLWNWF-NH2 | 644 |
| 723 | Ac-LEANISQLLEQAQIQQEKNMYELQKLNSWDVFTNWL-NH2 | 645 |
| 724 | Ac-SLEECDSELEIKRYKNRVASRKCRAKFKQLLQHYR-NH2 | 646 |
| 725 | Ac-LEECDSELEIKRYKNRVASRKCRAKFKQLLQHYRE-NH2 | 647 |
| 726 | Ac-EECDSELEIKRYKNRVASRKCRAKFKQLLQHYREV-NH2 | 648 |
| 727 | Ac-ECDSELEIKRYKNRVASRKCRAKFKQLLQHYREVA-NH2 | 649 |
| 728 | Ac-CDSELEIKRYKNRVASRKCRAKFKQLLQHYREVAA-NH2 | 650 |
| 729 | Ac-DSELEIKRYKNRVASRKCRAKFKQLLQHYREVAAA-NH2 | 651 |
| 730 | Desaminotyrosine-FDASISQVNEKINQSLAFIRKSDELLHNVNAGKST-NH2 | 652 |
| 731 | WASLWNW-NH2 | 653 |
| 732 | Ac-EAQQHLLQLTVWGIKQLQARILAVERYLKDQQLGIWG-NH2 | 654 |
| 733 | Ac-IEAQQHLLQLTVWGIKQLQARILAVERYLKDQQLLGIW-NH2 | 655 |
| 734 | Ac-AIEAQQHLLQLTVWGIKQLQARILAVERYLKDQQLLGI-NH2 | 656 |
| 735 | Ac-RAIEAQQHLLQLTVWGIKQLQARILAVERYLKDQQLLG-NH2 | 657 |
| 736 | Ac-LRAIEAQQHLLQLTVWGIKQLQARILAVERYLKDQQLL-NH2 | 658 |
| 737 | Ac-LLRAIEAQQHLLQLTVWGIKQLQARILAVERYLKDQQL-NH2 | 659 |
| 738 | Ac-NLLRAIEAQQHLLQLTVWGIKQLQARILAVERYLKDQQ-NH2 | 660 |
| 739 | Ac-QNNLLRAIEAQQHLLQLTVWGIKQLQARILAVERYLKD-NH2 | 661 |
| 740 | Ac-QQNNLLRAIEAQQHLLQLTVWGIKQLQARILAVERYLK-NH2 | 662 |
| 741 | Ac-QQQNNLLRAIEAQQHLLQLTVWGIKQLQARILAVERYL-NH2 | 663 |
| 742 | Ac-VQQQNNLLRAIEAQQHLLQLTVWGIKQLQARILAVERY-NH2 | 664 |
| 743 | Ac-IVQQQNNLLRAIEAQQHLLQLTVWGIKQLQARILAVER-NH2 | 665 |
| 744 | Ac-GIVQQQNNLLRAIEAQQHLLQLTVWGIKQLQARILAVE-NH2 | 666 |
| 745 | Ac-SGIVQQQNNLLRAIEAQQHLLQLTVWGIKQLQARILAV-NH2 | 667 |
| 758 | Ac-RSMTLTVQARQLLSGIVQQQNNLLRAIEAQQHLLQLTV-NH2 | 668 |
| 760 | Ac-GARSMTLTVQARQLLSGIVQQQNNLLRAIEAQQHLLQL-NH2 | 669 |
| 764 | Ac-GSTMGARSMTLTVQARQLLSGIVQQQNNLLRAIEAQQH-NH2 | 670 |
| 765 | Ac-GSTMGARSMTLTVQARQLLSGIVQQQNNLLRAIEAQQH-NH2 | 671 |
| 766 | Ac-EGSTMGARSMTLTVQARQLLSGIVQQQNNLLRAIEAQQ-NH2 | 672 |
| 767 | Ac-RAKFKQLLQHYREVAAAKSSENDRLRLL-NH2 | 673 |
| 768 | Ac-AKFKQLLQHYREVAAAKSSENDRLRLLL-NH2 | 674 |
| 769 | Ac-KFKQLLQHYREVAAAKSSENDRLRLLLK-NH2 | 675 |
| 770 | Ac-FKQLLQHYREVAAAKSSENDRLRLLLKQ-NH2 | 676 |
| 771 | Ac-RAKFKQELQHYREVAAAKSSENDRLRLLLKQMCPS-NH2 | 677 |
| 772 | DKWASLWNWF-NH2 | 678 |
| 773 | Biotin-FDASISQVNEKINQSLAFIRKSDELLHNVNAGKST-NH2 | 679 |
| 774 | Ac-YDASISQVNEKINQSLAFIRKSDELLHNVNAGKST-NH2 | 680 |
| 775 | Ac-YDASISQVNEKINQSLAYIRKSDELLHNVNAGKST-NH2 | 681 |
| 776 | Ac-FDASISQVNEKINQSLAYIRKSDELLHNVNAGKST-NH2 | 682 |
| 777 | Ac-FDASISQVQEKIQQSLAFIRKSDELLHQVQAGKST-NH2 | 683 |
| 778 | Ac-FDASISQVNEKINQALAFIRKADELLHNVNAGKST-NH2 | 684 |
| 779 | Ac-FDASISQVNEKINQALAFIRKSDELLHNVNAGKST-NH2 | 685 |
| 780 | Ac-FDASISQVNEKINQSLAFIRKADELLHNVNAGKST-NH2 | 686 |
| 781 | Ac-YDASISQVQEEIQQALAFIRKADELLEQVQAGKST-NH2 | 687 |
| 782 | Ac-FDASISQVNEKINQSLAFIRKSDELLENVNAGKST-NH2 | 688 |
| 783 | Ac-FDASISQVNEEINQSLAFIRKSDELLHNVNAGKST-NH2 | 689 |
| 784 | Ac-VFPSDEFDASISQVNEKINQSLAFIRKSDELLENV-NH2 | 690 |
| 785 | Ac-VFPSDEFDASISQVNEEINQSLAFIRKSDELLENV-NH2 | 691 |
| 786 | Ac-VYPSDEYDASISQVNEEINQALAYIRKADELLENV-NH2 | 692 |
| 787 | Ac-VFPSDEFDASISQVNEEINQSLAFIRKSDELLHNV-NH2 | 693 |
| 788 | Ac-SNKSLEQIWNNMTWMEWDREINNYTSLIHSLIEESQ-NH2 | 694 |
| 789 | Ac-WSNKSLEQIWNNMTWMEWDREINNYTSLIHSLIEES-NH2 | 695 |
| 790 | Ac-SWSNKSLEQIWNNMTWMEWDREINNYTSLIHSLIEE-NH2 | 696 |
| 791 | Ac-ASWSNKSLEQIWNNMTWMEWDREINNYTSLIHSLIE-NH2 | 697 |
| 792 | Ac-NASWSNKSLEQIWNNMTWMEWDREINNYTSLIHSLI-NH2 | 698 |

TABLE 1-continued

| T No. | Sequence | Seq. ID No. |
|---|---|---|
| 793 | Ac-WNASWSNKSLEQIWNNMTWMEWDREINNYTSLIHSL-NH2 | 699 |
| 793 | Ac-WNASWSNKSLEQIWNNMTWMEWDREINNYTSLIHSL-NH2 | 699 |
| 794 | Ac-PWNASWSNKSLEQIWNNMTWMEWDREINNYTSLIHS-NH2 | 700 |
| 795 | Ac-VPWNASWSNKSLEQIWNNMTWMEWDREINNYTSLIH-NH2 | 701 |
| 796 | Ac-AVPWNASWSNKSLEQIWNNMTWMEWDREINNYTSLI-NH2 | 702 |
| 797 | Ac-TAVPWNASWSNKSLEQIWNNMTWMEWDREINNYTSL-NH2 | 703 |
| 798 | Ac-TTAVPWNASWSNKSLEQIWNNMTWMEWDREINNYTS-NH2 | 704 |
| 800 | Ac-AAASDEFDASISQVNEKINQSLAFIRKSDELLHNV-NH2 | 705 |
| 801 | Ac-VFPAAAFDASISQVNEKINQSLAFIRKSDELLHNV-NH2 | 706 |
| 802 | Ac-VFPSDEAAASISQVNEKINQSLAFIRKSDELLHNV-NH2 | 707 |
| 803 | Ac-VFPSDEFDAAAAQVNEKINQSLAFIRKSDELLHNV-NH2 | 708 |
| 804 | Ac-VFPSDEFDASISAAAEKINQSLAFIRKSDBLLHNV-NH2 | 709 |
| 805 | Ac-VFPSDEFDASISQVNAAANQSLAFIRKSDELLHNV-NH2 | 711 |
| 806 | Ac-VFPSDEFDASISQVNEKIAAALAFIRKSDELLHNV-NH2 | 712 |
| 807 | Ac-VFPSDEFDASISQVNEKINQSAAAIRKSDELLHNV-NH2 | 713 |
| 808 | Ac-VFPSDEFDASISQVNEKINQSLAFAAASDELLHNV-NH2 | 714 |
| 809 | Ac-VFPSDEFDASISQVNEKINQSLAFIRKAAALLHNV-NH2 | 715 |
| 810 | Ac-VFPSDEFDASISQVNEKINQSLAFIRKSDEAAANV-NH2 | 716 |
| 811 | Ac-VFPSDEFDASISQVNEKINQSLAFIRKSDELLAAA-NH2 | 717 |
| 812 | Ac-VYPSDEFDASISQVNEKINQSLAFIRKSDELLHNV-NH2 | 718 |
| 813 | Ac-AAAAIHSLIEESQNQQEKNEQELLELDKWASLWNWF-NH2 | 719 |
| 814 | Ac-YTSLIHSLIEESQQQQEKNEQELLELDKWASLWNWF-NH2 | 720 |
| 815 | Ac-YTSLIHSLIEESQNQQEKQEQELLELDKWASLWNWF-NH2 | 721 |
| 816 | Ac-QIWNNMTWMEWDREINNYTSLIHSLIEESQNQQEKQ-NH2 | 722 |
| 817 | Ac-QIWNNMTWMEWDREINNYTSLIHSLIEESQQQQEKN-NH2 | 723 |
| 818 | Ac-QIWNNMTWMEWDREINNYTSLIHSLIEESQQQQEKQ-NH2 | 724 |
| 819 | Ac-NKSLEQIWNNMTWMEWDREINNYTSLIHSLIEESQQ-NH2 | 725 |
| 820 | Ac-FDASISQVNEKINQSLAFIEESDELLHNVNAGKST-NH2 | 726 |
| 821 | Ac-ACIRKSDELCL-NH2 | 727 |
| 823 | Ac-YTSLIHSLIEESQNQQEKDEQELLELDKWASLWNWF-NH2 | 728 |
| 824 | Ac-YTSLIHSLIEESQDQQEKNEQELLELDKWASLWNWF-NH2 | 729 |
| 825 | Ac-YTSLIHSLIEESQDQQEKDEQELLELDKWASLWNWF-NH2 | 730 |
| 826 | Ac-YTSLIHSLIEESQNQQEKNEQELLELDKWASLWDWF-NH2 | 731 |
| 841 | Ac-LEANITQSLEQAQIQQEKNMYELQKLNSWDVFTNWLNH2 | 732 |
| 842 | Ac-LEANISASLEQAQIQQEKNMYELQKLNSWDVFTNWL-NH2 | 733 |
| 843 | Ac-LEANISALLEQAQIQQEKNMYELQKLNSWDVFTNWL-NH2 | 734 |
| 844 | Ac-LEAMTALLEQAQIQQEKNMYELQKLNSWDVFTNWL-NH2 | 735 |
| 845 | Ac-LEAMTASLEQAQIQQEKNMYELQKLNSWDVFTNWL-NH2 | 736 |
| 845 | Ac-LEAMTASLEQAQIQQEKNMYELQKLNSWDVFTNWL-NH2 | 736 |
| 846 | Ac-RAKFKQLLQHYREVAAAKSSENDRLRLLLKQMUPS-NH2 | 737 |
| 847 | Ac-Abu-DDE-Abu-MNSVKNGTYDYPKYEEESKLNRNEIKGVKL-NH2 | 738 |
| 856 | Ac-WQEWEQKVRYLEANISQSLEQAQIQQEKNMYELQKL-NH2 | 739 |
| 860 | Ac-DEYDASISQVNEKiNQSLAFIRKSDELLHNVNAGK-NH2 | 740 |
| 861 | Ac-YTSLIHSLIEESQNQQEKNEQELLELDKWASLWN-NH2 | 741 |
| 862 | Ac-YTSLIHSLIEESQNQQEKNEQELLELDKWASLW-NH2 | 742 |
| 863 | Ac-YTSLIHSLIEESQNQQEKNEQELLELDKWASL-NH2 | 743 |
| 864 | Ac-YTSLIHSLIEESQNQQEKNEQELLELDKWAS-NH2 | 744 |
| 865 | Ac-QARQLLSGWQQQNNLLRAIEAQQHLLQLTVWGIKQLQARILAVERYLKDQ-NH2 | 745 |
| 866 | Ac-DREINNYTSLIHSLIEESQNQQEKNEQELLELDKWASLWNWF-NH2 | 746 |
| 867 | Ac-NNMTWMEWDREINNYTSLIHSLIEESQNQQEKNEQELLELDK-NH2 | 747 |
| 868 | Ac-YTSLIHSLIEESQNQQEKNEQELLELDKWASLWAAA-NH2 | 748 |
| 869 | Ac-YTSLIHSLIEESQN9QEKNEQELLELDKWAAAANWF-NH2 | 749 |
| 870 | Ac-YTSLIHSHEESQNQQEKNEQELLELDAAASLWNWF-NH2 | 750 |
| 871 | Ac-YTSLIHSLIEESQNQQEKNEQELLAAAKWASLWNWF-NH2 | 751 |
| 872 | Ac-YTSLIHSLIEESQNQQEKNEQAAAELDKWASLWNWF-NH2 | 752 |
| 873 | Ac-YTSLIHSLIEESQNQQEKAAAELLELDKWASLWNWF-NH2 | 753 |
| 874 | Ac-YTSLIHSLIEESQNQAAANEQELLELDKWASLWNWF-NH2 | 754 |
| 875 | Ac-YTSLIHSLIEESAAAQEKNEQELLELDKWASLWNWF-NH2 | 755 |
| 876 | Ac-YTSLIHSLIAAAQNQQEKNEQELLELDKWASLWNWF-NH2 | 756 |
| 877 | Ac-YTSLIHAAAEESQNQQEKNEQELLELDKWASLWNWF-NH2 | 757 |
| 878 | Ac-YTSAAASLIEESQNQQEKNEQELLELDKWASLWNWF-NH2 | 758 |
| 879 | Ac-EIWNNMTWMEWDRENEKINQSLAFIRKSDELLHNV-NH2 | 759 |
| 880 | Ac-YISEVNEEINQSLAHRKADELLENVDKWASLWNWF-NH2 | 760 |
| 881 | Ac-TSVITIELSMKENKANGTDAKVKLIKQELDKYKN-NH2 | 761 |
| 882 | YTSLIHSLlEESQNQQEKNEQELLELDKWASLWNWFMG-NH2 | 762 |
| 883 | Ac-NEKINQSLAFIRKSDELLHNV-NH2 | 763 |
| 884 | Biotin-YDPLVFPSDEFDASISQVNEKINQSLAFIRKSDEL-NH2 | 764 |
| 885 | Biotin-PLVFPSDEFDASISQVNEKINQSLAFIRKSDELLH-NH2 | 765 |
| 886 | Biotin-VFPSDEFDASISQVNEKINQSLAFIRKSDELLHNV-NH2 | 766 |
| 887 | Biotin-DEFDASISQVNEKINQSLAFIRKSDELLHNVNAGK-NH2 | 767 |
| 888 | Biotin-VYPSDEFDASISQVNEKINQSLAFIRKSDELLHNV-NH2 | 768 |
| 889 | Biotin-VYPSDEYDASISQVNEEINQALAYIRKADELLENV-NH2 | 769 |
| 890 | Ac-VYPSDEFDASISQVQEEIQQALAFIRKADELLEQV-NH2 | 770 |
| 891 | Ac-NYTSLIHSLIEESQNQQEKNEQELLELDKWASLWNWF-NH2 | 771 |
| 892 | Ac-NNYTSLIHSLIEESQNQQEKNEQELLELDKWASLWNWF-NH2 | 772 |
| 893 | Ac-INNYTSLIHSLIEESQNQQEKNEQELLELDKWASLWNWF-NH2 | 773 |

TABLE 1-continued

| T No. | Sequence | Seq. ID No. |
|---|---|---|
| 894 | Ac-EINNYTSLIHSLIEESQNQQEKNEQELLELDKWASLWWWF-NH2 | 774 |
| 895 | Ac-YTSLIHSLIEESQNQQEKNEQELLELDKWASLWNWFN-NH2 | 775 |
| 896 | Ac-YTSLIHSLIEESQNQQEKNEQELLELDKWASLWNWFM-NH2 | 776 |
| 897 | Ac-YTSLIHSLIEES9NQQEKNEQELLELDKWASLWNWFNIT-NH2 | 777 |
| 898 | Ac-YTSLIHSLIEESQNQQEKNEQELLELDKWASLWNWFNITN-NH2 | 778 |
| 899 | Ac-YDPLVFPSDEFDASISQVNEKINQSLAHRKSDELLHNVNAGK-NH2 | 779 |
| 900 | Ac-NYTSLIHSHEESQNQQEKNEQELLELDKWASLWNWFN-NH2 | 780 |
| 901 | Ac-NNYTSLIHSLIEESQNQQEKNEQELLELDKWASLWNWFNI-NH2 | 781 |
| 905 | Ac-KCRAKFKQLLQHYREVAAAKSSENDRLRLLLKQMCPSLDVDSIIPRTPD-NH2 | 782 |
| 906 | Ac-RAKFKQLLQHYREVAAAKSSENDRLRLLLKQMCPSLDVDSIIPRTPD-NH2 | 783 |
| 907 | Ac-VYPSDEYDASISQVNEEINQALAYIAAADELLENV-NH2 | 784 |
| 909 | Ac-YDASISQVNEEINQALAYIRKADELL-NH2 | 785 |
| 910 | Ac-M-Nle-WMEWDREINNYTSLIHSLIEESQNQQEKNEQELLEL-NH2 | 786 |
| 911 | Ac-KNGTYDYPKYEEESKLNRNEIKGVKLSSMGVYQI-NH2 | 787 |
| 912 | Ac-VTEKIQMASDNINDLIQSGVNTRLLTIQSHVQNYI-NH2 | 788 |
| 913 | QNQQEKNEQELLELDKWASLWNWF-NH2 | 789 |
| 914 | Ac-QNQQEKNEQELLELDKWASLWNWF-NH2 | 790 |
| 915 | LWNWF-NH2 | 791 |
| 916 | ELLELDKWASLWNWF-NH2 | 792 |
| 917 | EKNEQELLELDKWASLWNWF-NH2 | 793 |
| 918 | SLIEESQNQQEKNEQELLELDKWASLWNWF-NH2 | 794 |
| 919 | Ac-YTSLIHSLIEESQNQQEKNEQELLELDKWASLWNW | 795 |
| 920 | Ac-YTSLIHSLIEESQNQQEKNEQELLELDKWASLWN | 796 |
| 921 | Ac-YTSLIHSLIEESQNQQEKNEQELLELDKWASLW | 797 |
| 922 | Ac-YTSLIHSLIEESQNQQEKNEQELLELDKWASL | 798 |
| 923 | TSHHSLIEESQNQQEKNEQELLELDKWASLWNWF-NH2 | 799 |
| 924 | SLIHSLIEESQNQQEKNEQELLELDKWASLWNWF-NH2 | 800 |
| 925 | LIHSLIEESQNQQEKNEQELLELDKWASLWNWF-NH2 | 801 |
| 926 | IHSLIEESQNQQEKNEQELLELDKWASLWNWF-NH2 | 802 |
| 940 | Ac-AAVALLPAVLLALLAPSELEIKRYKNRVASRKCRAKFKQLLQHYREVAAAK-NH2 | 803 |
| 941 | Ac-AAVALLPAVLLALLAPCRAKFKQLLQHYREVAAAKSSENDRLRLLLKQMCP-NH2 | 804 |
| 942 | Ac-YTSLIHSLIEESQNQQEKNNNIERDWEMWTMNNWIQ-NH2 | 805 |
| 944 | VYPSDEYDASISQVNEEINQALAYIRKADELLENV-NH2 | 806 |
| 945 | Ac-LMQLARQLMQLARQMKQLADSLMQLARQVSRLFSA-NH2 | 807 |
| 946 | Ac-WMEWDREINNYTSLIHSLIEESQNQQEKNEQELL-NH2 | 808 |
| 947 | Ac-MEWDREINNYTSLIHSLIEESQNQQEKNEQELLEL-NH2 | 809 |
| 948 | Ac-EWDREINNYTSLIHSLIEESQNQQEKNEQELLEL-NH2 | 810 |
| 949 | Ac-MEWDREINNYTSLIHSLIEESQNQQEKNEQELLE-NH2 | 811 |
| 950 | Biotin-W-Nle-EWDREINNYTSLIHSLIEESQNQQEKNEQELLEL-NH2 | 812 |
| 951 | Ac-YLEYDREINNYTSLIHSLIEESQN9QEKNEQELLEL-NH2 | 813 |
| 952 | Ac-IKQFINMWQEVGKAMYA-NH2 | 814 |
| 953 | Ac-IRKSDELL-NH2 | 815 |
| 954 | Decanoyl-IRKSDELL-NH2 | 815 |
| 955 | Acetyl-Aca-Aca-IRKSDELL-NH2 | 815 |
| 956 | Ac-YDASISQV-NH2 | 816 |
| 957 | Ac-NEKINQSL-NH2 | 817 |
| 958 | Ac-SISQVNEEINQALAYIRKADELL-NH2 | 818 |
| 959 | Ac-QVNEEINQALAYIRKADELL-NH2 | 819 |
| 960 | Ac-EEINQALAYIRKADELL-NH | 820 |
| 961 | Ac-NQALAYIRKADELL-NH2 | 821 |
| 962 | Ac-LAYIRKADELL-NH2 | 822 |
| 963 | FDASISQVNEKINQALAFIRKSDELL-NH2 | 823 |
| 964 | Ac-W-Nle-EWDREINNYTSLIHSLIEESQNQQEKNEQELLEL-NH2 | 824 |
| 965 | Ac-ASRKCRAKFKQLLQHYREVAAAKSSENDRLRLLLKQMCPSLDVDS-NH2 | 825 |
| 967 | Ac-WLEWDREINNYTSLIHSLIEESQNQQEKNEQELLEL-NH2 | 827 |
| 968 | Ac-YVKGEPIINFYDPLVFPSDEFDASISQVNEKINQSL-NH2 | 828 |
| 969 | Ac-VYPSDEYDASISQVNEEINQSLAYIRKADELLHNV-NH2 | 829 |
| 970 | Ac-YDASISQVNEEINQALAYIRKADELLENV-NH2 | 830 |
| 971 | Ac-YDASISQVNEEINQALAYIRKADELLE-NH2 | 831 |
| 972 | Ac-VYPSDEYDASISQVNEEINQALAYIRAAAELLHNV-NH2 | 832 |
| 973 | Ac-VYPSDEYDASISQVNEEINQALAYIRKALELLHNV-NH2 | 833 |
| 974 | Decanoyl-YTSLIHSLIEESQNQQEKNEQELLELDKWASLWNWF-NH2 | 834 |
| 975 | Ac-VYPSDEYDASISQVNEEINQLLAYIRKLDELLENV-NH2 | 835 |
| 976 | Ac-DEYDASISQVNEKINQSLAFIRKSDELL-NH2 | 836 |
| 977 | Ac-SNDQGSGYAADKESTQKAFDGITNKVNSVIEKTNT-NH2 | 837 |
| 978 | Ac-ESTQKAFDGITNKVNSVIEKTNTQFEAVGKEFGNLEKR-NH2 | 838 |
| 979 | Ac-DGITNKVNSVIEKTNTQFEAVGKEFGNLEKRLENLNK-NH2 | 839 |
| 980 | Ac-DSNVKNLYDKVRSQLRDNKKELGNGAFEFYHK-NH2 | 840 |
| 981 | Ac-RDNKKELGNGAFEFYHKADDEALNSVKNGTYDYPKY-NH2 | 841 |
| 982 | Ac-EFYHKADDEALNSVKNGTYDYPKY-NH2 | 842 |
| 983 | Ac-AAVALLPAVLLALLAPAADKESTQKAFDGITNKVNS-NH2 | 843 |
| 984 | Ac-AAVALLPAVLLALLAPAADSNVKNLYDKVRSQLRDN-NH2 | 844 |
| 985 | Ac-KESTQKAFDGITNKVNSV-NH2 | 845 |
| 986 | Ac-IEKTNTQFEAVGKEFGNLER-NH2 | 846 |
| 987 | Ac-RLENLNKRVEDGFLDVWTYNAELLVALEME-NH2 | 847 |
| 988 | Ac-SNVKNLYDKVRSQLRDN-NH2 | 848 |

TABLE 1-continued

| T No. | Sequence | Seq. ID No. |
|---|---|---|
| 989 | Ac-WMEWDREINNYTSLIHSLIEESQNQQEKNEQEL-NH2 | 849 |
| 990 | Ac-WMEWDREINNYTSLIHSLIEESQNQQEKNEQE-NH2 | 850 |
| 991 | Ac-MEWDREINNYTSLIHSLIEESQNQQEKNEQEL-NH2 | 851 |
| 992 | Ac-MEWDREINNYTSuHSLIEESQNQQEKNEQE-NH2 | 852 |
| 993 | Ac-EWDREINNYTSLIHSLIEESQNQQEKNEQELLE-NH2 | 853 |
| 994 | Ac-EWDREINNYTSLIHSLEESQNQQEKNEQELL-NH2 | 854 |
| 995 | Ac-EWDREINNYTSLIHSLIEESQNQQEKNEQEL-NH2 | 855 |
| 996 | Ac-YTKFIYTLLEESQNQQEKNEQELLELDKWASLWNWF-NH2 | 856 |
| 997 | Ac-YMKQLADSLMQLARQVSRLESA-NH2 | 857 |
| 998 | Ac-YLMQLARQMKQLADSLMQLARQVSRLESA-NH2 | 858 |
| 999 | Ac-YQEWERKVDFLEENITALLEEAQIQQEKNMYELQKL-NH2 | 859 |
| 1000 | Ac-WMAWAAAINNYTSLIHSLIEESQNQQEKNEQEEEEE-NH2 | 860 |
| 1001 | Ac-YASLIAALIEESQNQQEKNEQELLELAKWAALWAWF-NH2 | 861 |
| 1002 | [Ac-EWDREINNYTSLIHSLIEESQNQQEKNEQEGGC-NH2]dimer | 862 |
| 1003 | Ac-YDISIELNKAKSDLEESKEWIKKSNQKLDSIGNWH-NH2 | 863 |
| 1004 | Biotinyl-IDISIELNAAKSDLEESKEWIKKSNQKLDSIGNWH-NH2 | 864 |
| 1005 | Ac-YTSLI-OH | 865 |
| 1006 | Fmoc-HSLIEE-OH | 866 |
| 1007 | Fmoc-SQNQQEK-OH | 867 |
| 1008 | Fmoc-NEQELLEL-OH | 868 |
| 1009 | Fmoc-DKWASL-OH | 869 |
| 1010 | Fmoc-WNWF-OH | 870 |
| 1011 | Ac-AKTLERTWDTLNHLLFISSALYKLNLKSVAQITLSI-NH2 | 871 |
| 1012 | Ac-MTLQAKIKQFINMWQEVGKAMYA-NH2 | 872 |
| 1013 | Ac-LENERTLDFHDSNVKNLYDKVRLQLRDN-NH2 | 873 |
| 1014 | Ac-LENERTLDFHDSNVKNLYDKVRLQLRDNVKELGNG-NH2 | 874 |
| 1015 | Ac-TLDFHDSNVKNLYDKVRLQLRDNVKELGNGAFEF-NH2 | 875 |
| 1016 | Ac-IDISIELNKAKSDLEESKEWIKKSNQKLDSIGNWH-NH2 | 876 |
| 1021 | Biotinyl-SISQVNEEINQALAYIRKADELL-NH2 | 877 |
| 1022 | Biotinyl-SISQVNEEINQSLAYIRKSDELL-NH2 | 878 |
| 1023 | Ac-SISQVNEEINQSLAYIRKSDELL-NH2 | 879 |
| 1024 | Ac-IDISIFLNKAKSDLEESKEWIEKSNQELDSIGNWE-NH2 | 39 |
| 1025 | Ac-IDISIELNKAKSDLEESKEWIKKSNQELDSIGNWH-NH2 | 864 |
| 1026 | Ac-IDISIELNKAKSDLEEAKEWIDDANQKLDSIGNWH-NH2 | 79 |
| 1027 | Ac-IDISIELNKAKSDLEESKEWIKKANQKLDSIGNWH-NH2 | 80 |
| 1028 | Ac-IDISIELNKAKSDLEEAKEWIKKSNQKLDSIGNWH-NH2 | 548 |
| 1029 | Biotinyl-NSVALDPIDISIELNKAKSDLEESKEWIKKSNQKL-NH2 | 880 |
| 1030 | Biotinyl-ALDPIDISIELNKAKSDLEESKEWIKKSNQKLDSI-NH2 | 881 |
| 1031 | desAminoTyrosine-NSVALDPIDISIELNKAKSDLEESKEWIKKSNQKL-NH2 | 882 |
| 1032 | desAminoTyrosine-ALDPIDISIELNKAKSDLEESKEWIKKSNQKLDSI-NH2 | 883 |
| 1033 | Ac-YDASISQVNEEINQALAFIRKADEL-NH2 | 984 |
| 1034 | Ac-YDASISQVNEEINQSLAYIRKADELL-NH2 | 985 |
| 1035 | Biotinyl-YDASISQVNEEINQALAYIRKADELL-NH2 | 986 |
| 1036 | Biotinyl-YDASISQVNEEINQSLAFIRKSDELL-NH2 | 987 |
| 1037 | Ac-YDASISQVNEEINQSLAFIRKSDELL-NH2 | 988 |
| 1038 | Ac-WLEWDREINNYTSLIHSLIEESQNQQEKNEQEL-NH2 | 989 |
| 1039 | Biotinyl-IDISIELNKAKSDLEESKEWIRRSNQKLDSIGNWH-NH2 | 916 |
| 1044 | Ac-YESTQKAFDGITNKVNSVIEKTNTQFEAVGKEFGNLEKR-NH2 | 81 |
| 1045 | Biotin-DEYDASISQVNEKINQSLAFIRKSDELL-NH2 | 82 |
| 1046 | Ac-MEWDREINNYTSLIHSLIEESQNQQEKNEQELL-NH2 | 90 |
| 1047 | Ac-WQEWEQKVRYLEANISQSLEQAQIQQEKNMYEL-NH2 | 892 |
| 1048 | Ac-WQEWEQKVRYLEAMSQSLEQAQIQQEKNEYEL-NH2 | 893 |
| 1049 | Ac-WQEWEQKVRYLEANITALLEQAQIQQEKNEYEL-NH2 | 894 |
| 1050 | Ac-WQEWEQKVRYLEANITALLEQAQIQQEKNMYEL-NH2 | 895 |
| 1051 | Ac-WQEWEQKVRYLEANISQSLEQAQIQQEKNEYELQKL-NH2 | 896 |
| 1052 | Ac-WQEWEQKVRYLEANITALLEQAQIQQEKNEYELQKL-NH2 | 897 |
| 1053 | Ac-WQEWEQKVRYLEAMTALLEQAQIQQEKNMYELQKL-NH2 | 898 |
| 1054 | Ac-IDISIELNKAKSDLEESKEWIEKSNQKLDSIGNWH-NH2 | |
| 1055 | Ac-EFGNLEKRLENLNKRVEDGFLDVWTYNAELLVALENE-NH2 | 899 |
| 1056 | Ac-EDGFLDVWTYNAELLVLMENERTLDFHDSNKKNLYDKVRMQL-NH2 | 900 |
| 1057 | Ac-SISQVNEKINQSLAFIRKSDELL-NH2 | 901 |
| 1058 | desaminoTyr-SISQVNEKINQSLAFIRKSDELL-NH2 | 902 |
| 1059 | Ac-SISQVNEKINQSLAYIRKSDELL-NH2 | 903 |
| 1060 | Ac-QQLLDVKKRQQEMLRLTVWGTKNLQARVTAIEKYLKDQ-NH2 | 904 |
| 1061 | YTSLIHSLIEESQNQQEKNEQELLELDKWASLWNWFC | 905 |
| 1062 | Ac-FDASISQVNEKINQSLAYIRKSDELL-NH2 | 906 |
| 1063 | Ac-YTSLIHSHEESQNQQEKNEQELLELDKWA | 907 |
| 1064 | Indole-3-acetyl-DEFDASISQVNEKINQSLAFIRKSDELL-NH2 | 908 |
| 1065 | Indole-3-acetyl-DEFDESISQVNEKINQSLAFIRKSDELL-NH2 | 909 |
| 1066 | Indole-3-acetyl-DEFDESISQVNEKIEQSLAFIRKSDELL-NH2 | 910 |
| 1067 | Indole-3-acetyl-DEFDESISQVNEKIEESLAFIRKSDELL-NH2 | 911 |
| 1068 | Indole-3-acetyl-DEFDESISQVNEKIEESLQFIRKSDELL-NH2 | 912 |
| 1069 | Indole-3-acetyl-GGGGGDEFDASISQVNEKINQSLAFIRKSDELL-NH2 | 913 |
| 1070 | 2-Napthoyl-DEFDASISQVNEKINQSLAFIRKSDELL-NH2 | 914 |
| 1071 | desNH2Tyr-DEFDASISQVNEKINQSLAFIRKSDELL-NH2 | 915 |
| 1072 | biotin-ALDPIDISIELNKAKSDLEESKEWIRRSNQKLDSI-NH2 | 916 |

TABLE 1-continued

| T No. | Sequence | Seq. ID No. |
|---|---|---|
| 1073 | Ac-YDASISQVNEKINQALAYIRKADELLHNvNAGKST-NH2 | 917 |
| 1074 | Ac-VYPSDEYDASISQVNEKINQALAYIRKADELLHNV-NH2 | 918 |
| 1075 | Ac-VYPSDEYDASISQVNEKINQSLAYIPKSDELLHNV-NH2 | 718 |
| 1076 | Ac-WGWGYGYG-NH2 | 919 |
| 1077 | Ac-YGWGWGWGF-NH2 | 920 |
| 1078 | Ac-WQEWEQKVRYLEANITALQEQAQIQAEKAEYELQKL-NH2 | 921 |
| 1079 | Ac-WQEWEQKVRYLEAEITALQEEAQIQAEKAEYELQKL-NH2 | 922 |
| 1081 | Ac-YTSLIHSLIEESQNQQEKNEQELLELDKWAS | 923 |
| 1082 | Ac-VWPSDEFDASISQVNEKINQSLAFIRKSDELLHNV-NH2 | 924 |
| 1083 | Ac-SKNISEQIDQIKKDEQKEGTGWGLGGKWWTSDWGV-NH2 | 925 |
| 1084 | Ac-LSKNISEQIDQIKKDEQKEGTGWGLGGKWWTSDWG-NH2 | 926 |
| 1085 | Ac-DLSKNISEQIDQIKKDEQKEGTGWGLGGKWWTSDW-NH2 | 927 |
| 1086 | Ac-EDLSKNISEQIDQIKKDEQKEGTGWGLGGKWWTSD-NH2 | 928 |
| 1087 | Ac-IEDLSKNISEQIDQIKKDEQKEGTGWGLGGKWWTS-NH2 | 929 |
| 1088 | Ac-GIEDLSKMSEQIDQIKKDEQKEGTGWGLGGKWWT-NH2 | 930 |
| 1089 | Ac-IGIEDLSKNISEQIDQIKKDEQKEGTGWGLGGKWW-NH2 | 931 |
| 1090 | 2-Napthoyl--PSDEFDASISQVNEKINQSLAFIRKSDELLHNVN-NH2 | 932 |
| 1091 | Ac-VYPSDEYDASISQVNEKINQALAYIRKADELLENV-NH2 | 933 |
| 1092 | Ac-VYPSDEFDASISQVNEKINQALAFIRKADELLENV-NH2 | 934 |
| 1093 | Ac-VYPSDEYDASISQVNEKINQALAYIREADELLENV-NH2 | 935 |
| 1094 | Biotinyl-YDASISQVNEKINQSLAFIRESDELL-NH2 | 936 |
| 1095 | Ac-AIGIEDLSKNISEQIDQIKKDEQKEGTGWGLGGKW-NH2 | 937 |
| 1096 | Ac-AAIGIEDLSKNISEQIDQIKKDEQKEGTGWGLGGK-NH2 | 938 |
| 1097 | Ac-DAAIGIEDLSKNISEQIDQIKKDEQKEGTGWGLGG-NH2 | 939 |
| 1098 | Ac-PDAAIGIEDLSKNISEQIDQIKKDEQKEGTGWGLG-NH2 | 940 |
| 1099 | Ac-NITDKIDQIIHDFVDKTLPDQGDNDNWWTGWRQWI-NH2 | 941 |
| 1100 | Ac-KNITDKIDQIIHDFVDKTLPDQGDNDNWWTGWRQW-NH2 | 942 |
| 1101 | Ac-TKNITDKIDQIIHDFVDKTLPDQGDNDNWWTGWRQ-NH2 | 943 |
| 1102 | Ac-WTKNITDKIDQIIHDFVDKTLPDQGDNDNWWTGWR-NH2 | 944 |
| 1103 | Ac-DWTKNITDKIDQIIHDFVDKTLPDQGDNDNWWTGW-NH2 | 945 |
| 1104 | Ac-HDWTKNITDKIDQIIHDFVDKTLPDQGDNDNWWTG-NH2 | 946 |
| 1105 | Ac-PHDWTKNITDKIDQIIHDFVDKTLPDQGDNDNWWT-NH2 | 947 |
| 1106 | Ac-EPHDWTKNITDKIDQIIHDFVDKTLPDQGDNDNWW-NH2 | 948 |
| 1107 | Ac-IEPHDWTKNITDKIDQIIHDFVDKTLPDQGDNDNW-NH2 | 949 |
| 1108 | Ac-AIEPHDWTKNITDKIDQIIHDFVDKTLPDQGDNDN-NH2 | 950 |
| 1109 | Ac-AAIEPHDWTKNITDKIDQIIHDFVDKTLPDQGDND-NH2 | 951 |
| 1110 | Ac-DAAIEPHDWTKNITDKIDQIIHDFVDKTLPDQGDN-NH2 | 952 |
| 1111 | Ac-LSPTVWLSVIWMMWYWGPSLYSILSPFLPLLPIFF-NH2 | 953 |
| 1112 | Ac-GLSPTVWLSVIWMMWYWGPSLYSILSPFLPLLPIF-NH2 | 1345 |
| 1113 | Ac-VGLSPTVWLSVIWMMWYWGPSLYSILSPFLPLLPI-NH2 | 1346 |
| 1114 | Ac-FVGLSPTVWLSVIWMMWYWGPSLYSILSPFLPLLP-NH2 | 1347 |
| 1115 | Ac-WFVGLSPTVWLSVIWMMWYWGPSLYSILSPFLPLL-NH2 | 1348 |
| 1116 | Ac-QWFVFLSPTVWLSVIWMMWYWGPSLYSILSPFLPL-NH2 | 1349 |
| 1117 | Ac-VQWFVGLSPTVWLSVIWMMWYWGPSLYSILSPFLP-NH2 | 1350 |
| 1118 | Ac-FVQWFVGLSPTVWLSVIWMMWYWGPSLYSILSPFL-NH2 | 1351 |
| 1119 | Ac-PFVQWFVGLSPTVWLSVIWMMWYWGPSLYSILSPF-NH2 | 1352 |
| 1120 | Ac-VPFVQWFVGLSPTVWLSVIWMMWYWGPSLYSILSP-NH2 | 1353 |
| 1121 | Ac-LVPFVQWFVGLSPTVWLSVIWMMWYWGPSLYSILS-NH2 | 1354 |
| 1122 | H-NHTTWMEWDEREINNYTSLIHSLIEESQNQQEKNEQELLELDKW-OH | 954 |
| 1123 | H-QARQLLSGIVQQQNNLLRAEIAQQHLLQLTVWGIKQLQARILAVERYLKDQ-OH | 955 |
| 1124 | Ac-VYPSDEFDASISQVNEKINQSLAFIREADELLENV-NH2 | 956 |
| 1125 | AcNFPSDEFDASISQVNEKWQSLAYIREADELLENV-NH2 | 957 |
| 1126 | Ac-DEFDASISQVNEKWQSLAYIREADELL-NH2 | 958 |
| 1127 | Ac-NEQELLELDKWASLWNWFGGGGDEFDASISQVNEKWQSLAFIRKSDELL-NH2 | 959 |
| 1128 | Ac-LELDKWASLWNWFGGGGDEFDASISQVNEKWQSLAFIRKSDELL-NH2 | 960 |
| 1129 | Naphthoyl-EGEGEGEGDEFDASISQVNEKWQSLAFIRKSDELL-NH2 | 961 |
| 1130 | Ac-ASRKCRAKFKQLLQHYREVAAAKSSENDRLRLLLKQMCPSLDV-NH2 | 962 |
| 1131 | Naphthoyl-GDEEDASISQVNEKWQSLAFIRKSDELL-NH2 | 963 |
| 1132 | Naphthoyl-GDEEDASESQVNEKWQSLAFIRKSDELL-NH2 | 964 |
| 1133 | Naphthoyl-GDEEDASESQQNEKWQSLAFIRKSDELL-NH2 | 965 |
| 1134 | Naphthoyl-GDEEDASESQQNEKQNQSLAFIRKSDELL-NH2 | 966 |
| 1135 | Naphthoyl-GDEEDASESQQNEKQNQSEAFIRKSDELL-NH2 | 967 |
| 1136 | Ac-WGDEFDESISQVNEKIEESLAFIRKSDELL-NH2 | 968 |
| 1137 | Ac-YTSLGGDEFDESISQVNEKIEESLAFIRKSDELLGGWNWF-NH2 | 969 |
| 1138 | Ac-YTSLIHSLGGDEFDESISQVNEKIEESLAFIRKSDELLGGWASLWNWF-NH | 970 |
| 1139 | 2-Naphthoyl-GDEFDESISQVNEKIEESLAFIRKSDELL-NH2 | 971 |
| 1140 | 2-Naphthoyl-GDEEDESISQVNEKIEESLAFIRKSDELL-NH2 | 972 |
| 1141 | 2-Naphthoyl-GDEEDESISQVQEKIEESLAFIRKSDELL-NH2 | 973 |
| 1142 | 2-Naphthoyl-GDEEDESISQVQEKIEESLLFIRKSDELL-NH2 | 974 |
| 1143 | Biotin-GDEYDESISQVNEKIEESLAFIRKSDELL-NH2 | 975 |
| 1144 | 2-Naphthoyl-GDEYDESISQVNEKIEESLAFIRKSDELL-NH2 | 976 |
| 1145 | Ac-YTSLIHSLIDEQEKIEELAFIRKSDELLELDKWNWF-NH2 | 977 |
| 1146 | VYPSDEYDASISQVNEEWQALAYIRKADELLENV-NH2 | 978 |
| 1147 | Ac-NNLLRAIEAQQHLLQLTVWGSKQLQARILAVERYLKDQ-NH2 | 979 |
| 1148 | GGGVYPSDEYDASISQVNEEWQALAYIRKADELLENV-NH2 | 980 |
| 1149 | Ac-NNLLRAIEAQQHLLQLTVWGEKQLQARILAVERYLKDQ-NH2 | 981 |

TABLE 1-continued

| T No. | Sequence | Seq. ID No. |
|---|---|---|
| 1150 | Ac-PTRVNYILIIGVLVLAbuEVTGVRADVHLL-NH2 | 982 |
| 1151 | Ac-PTRVNYILIIGVLVLAbuEVTGVRADVHLLEQPGNLW-NH2 | 983 |
| 1152 | Ac-PEKTPLLPTRVNYILIIGVLVLAbuEVTGVRADVHLL-NH2 | 984 |
| 1153 | AhaGGGVYPSDEYDASISQVNEEWQALAYIRAADELLENV-NH2 | 985 |
| 1155 | Ac-YTSLIHSLGGDEFDESISQVNEKIEESLAFIRKSDELL-NH2 | 986 |
| 1156 | Ac-YTSLGGDEFDESISQVNEKIEESLAFIRKSDELL-NH2 | 987 |
| 1157 | Ac-DEFDESISQVNEKIEESLAFIRKSDELLGGWASLWNWF-NH2 | 988 |
| 1158 | Ac-DEFDESISQVNEKIEESLAFIRKSDELLGGWNWF-NH2 | 989 |
| 1159 | Ac-YTSLIHSLIEESQNQQEKNEQELLELDKASLWNWF-NH2 | 990 |
| 1160 | Ac-YTSLIHSLIEESQNQQEKNEQELLELDKSLWNWF-NH2 | 991 |
| 1161 | Ac-YTSLIHSLIEESQNQQEKNEQELLELDKLWNWF-NH2 | 992 |
| 1162 | Ac-YTSLIHSLIEESQNQQEKNEQELLELDKWNWF-NH2 | 993 |
| 1163 | Ac-MTWMEWDREWNYTSLIHSLIEESQNQQEKNEQELLELDKASLWNWF-NH2 | 994 |
| 1164 | Ac-MTWMEWDREWNYTSLIHSLIEESQNQQEKNEQELLELDKSLWNWF-NH2 | 995 |
| 1165 | Ac-MTWMEWDREWNYTSLIHSLIEESQNQQEKNEQELLELDKLWNWF-NH2 | 996 |
| 1166 | Ac-MTWMEWDREWNYTSLIHSLIEESQNQQEKNEQELLELDKWNWF-NH2 | 997 |
| 1167 | Ac-MTWMEWDREWNYTSLIHSLIEESQNQQEKNEQELLELDKWASLWN-NH2 | 998 |
| 1168 | Ac-MTWMEWDREINNYTSLIHSLIEESQNQQEKNEQELLELDKWASL-NH2 | 999 |
| 1169 | (Pyr)HWSY(2-napthyl-D-Ala)LRPG-NH2 | 1000 |
| 1170 | Ac-WNWFDEFDESISQVNEKIEESLAFIRKSDELLWNWF-NH2 | 1001 |
| 1171 | Ac-YTSLIHSLIEESQNQQEKNEQELLELDKYASLYYYF-NH2 | 1002 |
| 1172 | Ac-YTSLIHSLIEESQNQQEKNEQELLELDKYAYLYNYF-NH2 | 1003 |
| 1173 | 2-NaphthoAcaAcaAcaDEFDESISQVNEKIEESLAFIRKSDELLAcaAcaAcaW-NH2 | 1004 |
| 1174 | 2-Naphthoyl-AcaAcaAcaGDEFDESISQVNEKIEESLAFIRKSDELLGAcaAcaAcaW-NH2 | 1005 |
| 1175 | 2-Naphthoyl-GDEFDESISQVNEKIEESLAFIRESDELL-NH2 | 1006 |
| 1176 | 2-Naphthoyl-GDEFDESISQVNEKIEESLAFIEESDELL-NH2 | 1007 |
| 1177 | Ac-WQEWEQKVNYLEANITALLEQAQIQQEKNEYELQKL-NH2 | 1008 |
| 1178 | Ac-WQEWEQKVDYLEANITALLEQAQIQQEKNEYELQKL-NH2 | 1009 |
| 1179 | Ac-WQEWEQKVRWLEAMTALLEQAQIQQEKNEYELQKL-NH2 | 1010 |
| 1180 | Ac-WQEWEKQVRYLEANITALLEQAQIQQEKNEYELQKL-NH2 | 1011 |
| 1181 | Ac-WQEWEHQVRYLEANITALLEQAQIQQEKNEYELQKL-NH2 | 1012 |
| 1182 | Ac-WQEWEHKVRYLEANITALLEQAQIQQEKNEYELQKL-NH2 | 1013 |
| 1183 | Ac-WQEWDREVRYLEAMTALLEQAQIQQEKNEYELQKL-NH2 | 1014 |
| 1184 | Ac-WQEWEREVRYLEANITALLEQAQIQQEKNEYELQKL-NH2 | 1015 |
| 1185 | Ac-WQFWERQVRYLEANITALLEQAQIQQEKNEYELQKL-NH2 | 1016 |
| 1186 | Ac-WQEWEQKVKYLEANITALLEQAQIQQEKNEYELQKL-NH2 | 1017 |
| 1187 | Ac-WQEWEQKVRFLEANITALLEQAQIQQEKNEYELQKL-NH2 | 1018 |
| 1188 | Ac-VNalPSDEYDASISQVNEEINQALAYIRKADELLENV-NH2 | 1019 |
| 1189 | Ac-VNalPSDENalDASISQVNEEINQALAYIRKADELLENV-NH2 | 1020 |
| 1190 | Ac-VNalPSDEYDASISQVNEEINQALANalIRKADELLENV-NH2 | 1021 |
| 1191 | Ac-VYPSDEFDASISQVNEKINQSLAFIREADELLFNFF-NH2 | 1022 |
| 1192 | Ac-VYPSDEYDASISQVNEEINQALAYIRKADELLFNFF-NH2 | 1023 |
| 1193 | Ac-YTSLITALLEQAQIQQEKNEYELQKLDKWASLWNWF-NH2 | 1024 |
| 1194 | Ac-YTSLITALLEQAQIQQEKNEYELQKLDKWASLWEWF-NH2 | 1025 |
| 1195 | Ac-YTSLITALLEQAQIQQEKNEYELQKLDEWASLWEWF-NH2 | 1026 |
| 1196 | Ac-YTSLITALLEQAQIQQEKNEYELQELDEWASLWEWF-NH2 | 1027 |
| 1197 | Ac-YTSLITALLEEAQIQQEKNEYELQELDEWASLWEWF-NH2 | 1028 |
| 1198 | Naphthoyl-Aua-Aua-Aua-TALLEQAQIQQEKNEYELQKLAua-Aua-Aua-W-NH2 | 1029 |
| 1199 | Ac-WAAWEQKVRYLEAMTALLEQAQIQQEKNEYELQKL-NH2 | 1030 |
| 1200 | Ac-WQEAAQKVRYLEANITALLEQAQIQQEKNEYELQKL-NH2 | 1031 |
| 1201 | Ac-WQEWAAKVRYLEANITALLEQAQIQQEKNEYELQKL-NH2 | 1032 |
| 1202 | Ac-WQAAEQKVRYLEANITALLEQAQIQQEKNEYELQKL-NH2 | 1033 |
| 1203 | Ac-WQEWEAAVRYLEAMTALLEQAQIQQEKNEYELQKL-NH2 | 1034 |
| 1204 | Ac-WQEWEQAARYLEAMTALLEQAQIQQEKNEYELQKL-NH2 | 1035 |
| 1205 | Ac-WQEWEQKAAYLEAMTALLEQAQIQQEKNEYELQKL-NH2 | 1036 |
| 1206 | Ac-WQEWEQKVAALEANITALLEQAQIQQEKNEYELQKL-NH2 | 1037 |
| 1207 | Ac-WQEWEQKVRYLEANITALLEQAQIQQEKNEYELQKLGGGGWASLWNF-NH2 | 1038 |
| 1208 | 2-Naphthoyl-GDEFDASISQVNEKINQSLAFIRKSDELT-NH2 | 1039 |
| 1209 | 2-Naphthoyl-GDEFDASISQVNEKINQSLAFTRKSDELT-NH2 | 1040 |
| 1210 | 2-Naphthoyl-GDEFDASISQVNEKTNQSLAFTRKSDELT-NH2 | 971 |
| 1211 | 2-Naphthoyl-GDEFDASISQTNEKTNQSLAFTRKSDELT-NH2 | 1038 |
| 1212 | 2-Naphthoyl-GDEFDASTSQTNEKTNQSLAFTRKSDELT-NH2 | 1039 |
| 1213 | 2-Naphthoyl-GDEYDASTSQTNEKTNQSLAFTRKSDELT-NH2 | 1040 |
| 1214 | 2-Naphthoyl-GDEFDEEISQVNEKIEESLAHRKSDELL-NH2 | 1041 |
| 1215 | 2-Naphthoyl-GDEFDASISQVNEKINQSLAFIRKSDELA-NH2 | 1042 |
| 1216 | 2-Naphthoyl-GDEFDASASQANEKANQSLAFARKSDELA-NH2 | 1043 |
| 1217 | 2-Naphthoyl-GDEFDESISQVNEKIEESLAFTRKSDELL-NH2 | 1044 |
| 1218 | 2-Naphthoyl-GDEFDESISQVNEKTEESLAFIRKSDELL-NH2 | 1045 |
| 1219 | 2-Naphthoyl-GDEFDESISQTNEKIEESLAFIRKSDELL-NH2 | 1046 |
| 1220 | 2-Naphthoyl-GDEFDESTSQVNEKIEESLAFIRKSDELL-NH2 | 1047 |
| 1221 | Ac-WNWFDEFDESTSQVNEKIEESLAFIRKSDELLWNWF-NH2 | 1048 |
| 1222 | Ac-WNWFDEFDESTSQTNEKIEESLAFIRKSDELLWNWF-NH2 | 1049 |
| 1223 | Ac-WNWFDEFDESTSQTNEKTEESLAFIRKSDELLWNWF-NH2 | 1050 |
| 1224 | Ac-LQAGFFLLTRILTIPQSLDSWWTSLNFLGGTTVAL-NH2 | 1355 |
| 1225 | Ac-YTNLIYTLLEESQNQQEKNEQELLELDKWASLWSWF-NH2 | 1051 |
| 1226 | Ac-WQEWEQKVRYLEANITALLEQAQIQQEKNEYELQKLDKWASLWNWF-NH2 | 1052 |

TABLE 1-continued

| T No. | Sequence | Seq. ID No. |
|---|---|---|
| 1227 | Ac-NNMTWQEWEQKVRYLEANITALLEQAQIQQEKNEYELQKLDKWASLWNWF-NH2 | 1053 |
| 1230 | Ac-WWWFIEESDELLWNWF-NH2 | 1054 |
| 1231 | 2-Naphthoyl-GFIEESDELLW-NH2 | 1055 |
| 1232 | Ac-WFIEESDELLW-NH2 | 1056 |
| 1233 | 2-Naphthoyl-GFNFFIEESDELLFNFF-NH2 | 1057 |
| 1234 | 2-Naphthoyl-GESDELW-NH2 | 1058 |
| 1235 | Ac-WNWFGDEFDESISQVQEEIEESLAFIEESDELLGGWNWF-NH2 | 1059 |
| 1236 | Ac-WNWFIHSLIEESQNQQEKNEQELLELDKWASLWNWF-NH2 | 1356 |
| 1237 | Ac-YTSLITALLEQAQIQQEENEYELQALDEWASLWEWF-NH2 | 1025 |
| 1238 | Ac-YTSLIHSLGGDEFDESISQVNEEIEESLAFIEESDELLGGWASLWNWF-NH2 | 1060 |
| 1239 | 2-Naphthoyl-GDEFDESISQVQEEIEESLAFIEESDELL-NH2 | 1061 |
| 1240 | H-QARQLLSSIMQQQNNLLRAIEAQQHLLQLTVWGIKQLQARILAVERYLKDQ-OH | 1062 |
| 1241 | Ac-CPKYVKQNTLKLATGMRNVPEKQTR-NH2 | 1063 |
| 1242 | Ac-GLFGAIAGFIENGWEGMIDGWYGFRHQNSC-NH2 | 1064 |
| 1243 | Ac-LNFLGGT-NH2 | 1065 |
| 1244 | Ac-LDSWWTSLNFLGGT-NH2 | 1066 |
| 1245 | Ac-ILTIPQSLDSWWTSLNFLGGT-NH2 | 1067 |
| 1246 | Ac-GFFLLTRILTIPQSLDSWWTSLNFLGGT-NH2 | 1068 |
| 1247 | Ac-WQEWEQKITALLEQAQIQQEKNEYELQKLDKWASLWNWF-NH2 | 1069 |
| 1248 | Ac-WNWFITALLEQAQIQQEKNEYELQKLDKWASLWNWF-NH2 | 1070 |
| 1249 | Ac-WQEWEQKITALLEQAQIQQEKNEYELQKLDKWASLWEWF-NH2 | 1071 |
| 1250 | Ac-WQEWEQKVRYLEANITALLEQAQIQQEKIEYELQKL-NH2 | 1072 |
| 1251 | Ac-WQEWEQKVRYLEAQITALLEQAQIQQEKIEYELQKL-NH2 | 1073 |
| 1252 | Ac-KENKANGThAKVKLIKQELDKYKNAVTELQLLMQS-NH2 | 1074 |
| 1253 | Ac-NIKENKANGTDAKVKLIKQELDKYKNAVTELQLLM-NH2 | 1075 |
| 1254 | (FS)-YTSLIHSLIEESQNQQEKNEQELLELDKWASLWNWF-NH2 | 1076 |
| 1255 | 2-Naphthoyl-GWNWFAcaDEFDESISQVQEEIEESLAFIEESDELLAcaWNWF-NH2 | 1077 |
| 1256 | Ac-WNWFGDEFDESISQVNEKIEESLAFIEESDELLGWNWF-NH2 | 1078 |
| 1257 | Ac-WNWFGDEFDESISQVNEKIEESLAFIRKSDELLGWNWF-NH2 | 1079 |
| 1258 | Ac-WNWF-Aca-DEFDESISQVNEKIEESLAFIRKSDELL-Aca-WNWF-NH2 | 1080 |
| 1259 | Ac-WNWF-Aca-DEFDESISQVNEKIEESLAFIEESDELL-Aca-WNWF-NH2 | 1081 |
| 1260 | Ac-EESQNQQEKNEQELLELDKWA-NH2 | 1082 |
| 1261 | EESQNQQEKNEQELLELDKWA | 1083 |
| 1262 | Ac-CGTTDRSGAPTYSWGANDTDVFVLNNTRPPLGNWFG-NH2 | 1084 |
| 1263 | Ac-GVEHRLEAACNWTRGERADLEDRDRSELSP-NH2 | 1085 |
| 1264 | Ac-CVREGNASRAWVAVTPTVATRDGKLPT-NH2 | 1086 |
| 1265 | Ac-CFSPRHHWTTQDANASIYPG-NH2 | 1087 |
| 1266 | Ac-LQHYREVAAAKSSENDRLRLLLKQMCPSLDVDS-NH2 | 1088 |
| 1267 | Ac-WQEWDREISNYTSLITALLEQAQIQQEKNEYELQKLDEWASLWEWF-NH2 | 1089 |
| 1268 | Ac-CWQEWDREISNYTSLITALLEQAQIQQEKNEYELQKLDEWASLWEWFC-NH2 | 1090 |
| 1269 | Ac-WQEWDREISNYTSLITALLEQAQIQQEKNEYELQKLDEWEWF-NH2 | 1091 |
| 1270 | Ac-CWQEWDREISNYTSLITALLEQAQIQQEKNEYELQKLDEWEWFC-NH2 | 1092 |
| 1271 | Ac-GQNSQSPTSNHSPTSAPPTAPGYRWA-NH2 | 1093 |
| 1272 | Ac-PGSSTTSTGPARTALTTAQGTSLYPSA-NH2 | 1094 |
| 1273 | Ac-PGSSTTSTGPARTALTTAQGTSLYPSAAATKPSDGNATA-NH2 | 1095 |
| 1275 | Ac-WQEWDREITALLEQAQIQQEKNEYELQKLDKWASLWNWF-NH2 | 1097 |
| 1276 | Ac-WQEWDREITALLEQAQIQQEKNEYELQKLDEWASLWEWF-NH2 | 1098 |
| 1277 | Ac-WQEWDREITALLEQAQIQQEKNEYELQKLDEWEWF-NH2 | 1099 |
| 1278 | Ac-WQEWDREITALLEQAQIQQEKNEYELQKLDEWEWF-NH2 | 1100 |
| 1279 | Ac-WQEWEREITALLEQAQIQQEKNEYELQKLIEWEWF-NH2 | 1101 |
| 1280 | Ac-WQEWEREITALLEQAQIQQEKIEYELQKLDEWEWF-NH2 | 1102 |
| 1281 | Ac-WQEWEITALLEQAQIQQEKNEYELQKLDEWEWF-NH2 | 1103 |
| 1282 | Ac-WQEWEITALLEQAQIQQEKNEYELQKLIEWEWF-NH2 | 1104 |
| 1283 | Ac-WQEWEITALLEQAQIQQEKIEYELQKLDEWEWF-NH2 | 1105 |
| 1284 | Ac-WQEWEITALLEQAQIQQEKIEYELQKLIEWEWF-NH2 | 1106 |
| 1285 | Ac-WQEWDREDEYDASISQVNEKINQALAYIREADELWEWF-NH2 | 1107 |
| 1286 | Ac-WQEWEREIDEYDASISQVNEKINQALAYIREADELWEWF-NH2 | 1108 |
| 1287 | Ac-WQEWEIDEYDASISQVNEKINQALAYIREADELWEWF-NH2 | 1109 |
| 1288 | Ac-WQEWDREIDEYDASISQVNEEINQALAYIREADELWEWF-NH2 | 1110 |
| 1289 | Ac-WQEWEREIDEYDASISQVNEEINQALAYIREADELWEWF-NH2 | 1111 |
| 1290 | Ac-WQEWEIDEYDASISQVNEEINQALAYIREADELWEWF-NH2 | 1112 |
| 1291 | Ac-WQEWDEYDASISQVNEKINQALAYIREADELWEWF-NH2 | 1113 |
| 1292 | Ac-WQEWDEYDASISQVNEEINQALAYIREADELWEWF-NH2 | 1114 |
| 1293 | Ac-WQEWEQKITALLEQAQIQQEKiEYELQKLIEWEWF-NH2 | 1115 |
| 1294 | Ac-WQEWEQKITALLEQAQIQQEKIEYELQKLIEWASLWEWF-NH2 | 1116 |
| 1295 | Ac-WQEWEITALLEQAQIQQEKIEYELQKLIEWASLWEWF-NH2 | 1117 |
| 1298 | VYPSDEYDASISQVNEEINQALAYIRKADELLENV-NH2 | 1160 |
| 1299 | Ac-WVYPSDEYDASISQVNEEINQALAYIRKADELLENVWNWF-NH2 | 1120 |
| 1300 | YTSLIHSLIEESQNQQEKNEQELLELDKWASLWNWF-NH2 | 1121 |
| 1301 | Ac-WQEWDEYDASISQVNEKINQALAYIREADELWAWF-NH2 | 1122 |
| 1302 | Ac-WQAWDEYDASISQVNEKINQALAYIREADELWAWF-NH2 | 1123 |
| 1303 | Ac-WQAWDEYDASISQVNEKINQALAYIREADELWEWF-NH2 | 1124 |
| 1304 | Biotin-YDPLVFPSDEFDASISQVNEKINQSLAFIRKSDEL-NH2 | 1125 |
| 1305 | Biotin-YDPLVFPSDEFDASISQVNEKINQSLAF-NH2 | 1126 |
| 1306 | Biotin-QVNEKINQSLAFIRKSDELLHNVNAGKST-NH2 | 1127 |
| 1307 | Ac-WMEWDREI-NH2 | 1128 |

TABLE 1-continued

| T No. | Sequence | Seq. ID No. |
|---|---|---|
| 1308 | Ac-WQEWEQKI-NH2 | 1129 |
| 1309 | Ac-WQEWEQKITALLEQAQIQQEKIEYELQKLIKWASLWEWF-NH2 | 1130 |
| 1310 | Ac-WQEWEQKITALLEQAQIQQEKiEYELQKLIEWASLWEWF-NH2 | 1131 |
| 1311 | Ac-WQEWEREISAYTSLITALLEQAQIQQEKIEYELQKLIEWEWF-NH2 | 1132 |
| 1312 | Ac-WQEWEREISAYTSLITALLEQAQIQQEKIEYELQKEWEWF-NH2 | 1133 |
| 1313 | Ac-WQEWEREISAYTSLITALLEQAQIQQEKIEYELQKEWEW-NH2 | 1134 |
| 1314 | Ac-WQEWEREISAYTSLITALLEQAQIQQEKIEYELQKLIEWEW-NH2 | 1135 |
| 1315 | Ac-FNLSDHSESIQKKFQLMKKHVNKIGVDSDPIGSWLWNH2 | 1136 |
| 1316 | Ac-DHSESIQKKFQLMKKHVNKIGVDSDPIGSWLRGIF-NH2 | 1137 |
| 1317 | Ac-WSVKQANLTTSLLGDLLDDVTSIRHAVLQNRA-NH2 | 1138 |
| 1318 | Biotin-WMEWDREI-NH2 | 1128 |
| 1319 | Biotin-NNMTWMEWDREINNYTSL-NH2 | 1139 |
| 1320 | Ac-GAASLTLTVQARQLLSGWQQQNNLLRAIEAQQHLL-NH2 | 1140 |
| 1321 | Ac-ASLTLTVQARQLLSG4VQQQNNLLKAIEAQQHLLQL-NH2 | 1141 |
| 1322 | Ac-VSVGNTLYYVNKQEGKSLYVKGEPIINFYDPLVF-NH2 | 1142 |
| 1323 | Ac-QHWSYGLREG-NH2 | 1143 |
| 1324 | Ac-WQEWEQKIQHWSYGLRPGWASLWEWF-NH2 | 1144 |
| 1325 | Ac-WQEWEQKIQHWSYGLRPGWEWF-NH2 | 1145 |
| 1326 | Ac-WNWFQHWSYGLRPGWNWF-NH2 | 1146 |
| 1327 | Ac-FNFFQHWSYGLREGFNFF-NH2 | 1147 |
| 1328 | Ac-GAGAQHWSYGLRPGAGAG-NH2 | 1148 |
| 1329 | PLLVLQAGFFLLTRILTIPQSLDSWWTSLNFLGGT | 482 |
| 1330 | Ac-WQEWEQKITALLEQAQIQQEKIEYELQKLAKWASLWEWF-NH2 | 1149 |
| 1331 | Ac-WQEWEQKITALLEQAQIQQEKIEYELQKLAEWASLWEWF-NH2 | 1150 |
| 1332 | Ac-WQEWEQKITALLEQAQIQQEKAEYELQKLAEWASLWEWF-NH2 | 1151 |
| 1333 | Ac-WQEWEQKITALLEQAQIQQEKAEYELQKLAEWASLWAWF-NH2 | 1152 |
| 1334 | Ac-WQEWEQKITALLEQAQIQQEKAEYELQKLAKWASLWAWF-NH2 | 1153 |
| 1335 | Ac-TNKAVVSLSNGVSVLTSKVLDLKNYIDKQLLPIVNK-NH2 | 1154 |
| 1336 | Ac-KAVVSLSNGVSVLTSKVLDLKNYIDKQLLPIVNKQS-NH2 | 1155 |
| 1337 | Ac-WQEWEQKITALLEQAQIQQEKNEYELQKLIEWEWF-NH2 | 1156 |
| 1338 | Ac-WQEWEQKITALLEQAQIQQEKNEYELQKLIEWEWF-NH2 | 1157 |
| 1339 | Ac-WQEWEQKITALLEQAQIQQEKIEYELQKLDKWEWF-NH2 | 1158 |
| 1340 | Ac-YDPLVFPSDEFDASISQVNEKINQSLAF-NH2 | 1159 |
| 1341 | Fluor--VYPSDEYDASISQVNEEWQALAYIRKADELLENV-NH2 | 1160 |
| 1342 | Fluor-YTSLIHSLIEESQNQQEKNEQELLELDKWASLWNWF-NH2 | 1161 |
| 1344 | Ac-SGIVQQQNNLLRAIEAQQHLLQLTVWGIKQLQARIL-NH2 | 1162 |
| 1345 | Ac-QQQNNLLRAIEAQQHLLQLTVWGIKQLQARILAVERYLKDQ-NH2 | 1163 |
| 1346 | Ac-SGIVQQQNNLLRAIEAQQHLLQLTVWGIKQLQARILAVERYLKDQ-NH2 | 1164 |
| 1347 | Ac-WQEWEQKITALLEQAQIQQEKNEYELQKLAEWASLWAWF-NH2 | 1165 |
| 1348 | Ac-WQEWEQKITALLEQAQIQQEKNEYELQKLAEWASLWAW-NH2 | 1166 |
| 1349 | Ac-WQEWEQKITALLEQAQIQQEKAEYELQKLAEWASLWAW-NH2 | 1167 |
| 1350 | Ac-WQEWEQKITALLEQAQIQQEKNEYELQKLAEWAGLWAWF-NH2 | 1168 |
| 1351 | Ac-WQEWEQKITALLEQAQIQQEKNEYELQKLAEWAGLWAW-NH2 | 1169 |
| 1352 | Ac-WQEWEQKITALLEQAQIQQEKAEYELQKLAEWAGLWAW-NH2 | 1170 |
| 1353 | Ac-WQEWEQKITALLEQAQIQQEKNEYELQKLDKWAGLWEWF-NH2 | 1171 |
| 1354 | Ac-WQEWQHWSYGLRPGWEWF-NH2 | 1172 |
| 1355 | Ac-WQAWQHWSYGLRPGWAWF-NH2 | 1173 |
| 1356 | Biotinyl-WQEWEQKITALLEQAQIQQEKNEYELQKLDKWASLWEWF-NH2 | 1174 |
| 1357 | WQEWEQKITALLEQAQIQQEKNEYELQKLDKWASLWEWF | 1175 |
| 1358 | WQEWEQKITALLEQAQIQQEKIEYELQKLIEWEWF | 1176 |
| 1361 | Ac-AGSTMGARSMTLTVQARQLLSGIVQQQNNLLRAIEAQQ-NH2 | 1179 |
| 1362 | Ac-AGSAMGAASLTLSAQSRTLLAGIVQQQQQLLDVVKRQQ-NH2 | 1180 |
| 1363 | Ac-AGSAMGAASTALTAQSRTLLAGIVQQQQQLLDVVKRQQ-NH2 | 1181 |
| 1364 | Ac-ALTAQSRTLLAGIVQQQQQLLDVVKRQQELLRLTVWGT-NH2 | 1182 |
| 1365 | Ac-TLSAQSRTLLAGIVQQQQQLLDVVKRQQEMLRLTVWGT-NH2 | 1183 |
| 1366 | Ac-TLTVQARQLLSGIVQQQNNLLRAIEAQQHLLQLTVWGI-NH2 | 1184 |
| 1367 | Ac-WQAWIEYEAELSQVKEKiEQSLAYIREADELWAWF-NH2 | 1185 |
| 1368 | Ac-WQAWIEYEASLSQAKEKIEESKAYIREADELWAWF-NH2 | 1186 |
| 1369 | Ac-WQAWIEYERLLVQAKLKlAIAKLYIAKELLEWAWF-NH2 | 1187 |
| 1370 | Ac-WQAWIEYERLLVQVKLKIAIALLYIAKELLEWAWF-NH2 | 1188 |
| 1371 | Ac-WQAWIELERLLVQVKLKLAIAKLEIAKELLEWAWF-NH2 | 1189 |
| 1372 | Ac-GEWTYDDATKTFTVTEGGH-NH2 | 1190 |
| 1373 | Ac-WQEWEQKIGEWTYDDATKTFTVTEGGHWASLWEWF-NH2 | 1191 |
| 1374 | Ac-GEWTYDDATKTFTVTE-NH2 | 1192 |
| 1375 | Ac-WQEWEQKIGEWTYDDATKTFTVTEWASLWEWF-NH2 | 1193 |
| 1376 | Ac-MHRFDYRT-NH2 | 1194 |
| 1377 | Ac-WQEWEQKIMHRFDYRTWASLWEWF-NH2 | 1195 |
| 1378 | Ac-MHRFNWSTGGG-NH2 | 1196 |
| 1379 | Ac-WQEWEQKIMHRFNWSTGGGWASLWEWF-NH2 | 1197 |
| 1380 | Ac-MHRFNWST-NH2 | 1198 |
| 1381 | Ac-WQEWEQKIMHRFNWSTWASLWEWF-NH2 | 1199 |
| 1382 | Ac-LLVPLARlMTMSSVHGGG-NH2 | 1200 |
| 1383 | Ac-WQEWEQKILLVPLARIMTMSSVHGGGWASLWEWF-NH2 | 1201 |
| 1384 | Ac-LLVPLARIMTMSSVH-NH2 | 1202 |
| 1385 | Ac-WQEWEQKILLVPLARIMTMSSVHWASLWEWF-NH2 | 1203 |
| 1386 | TALLEQAQIQQEKNEYELQKLDK | 1204 |

TABLE 1-continued

| T No. | Sequence | Seq. ID No. |
|---|---|---|
| 1387 | Ac-TALLEQAQIQQEKNEYELQKLDK-NH2 | 1205 |
| 1388 | Ac-TALLEQAQIQQEKIEYELQKLIE-NH2 | 1206 |
| 1389 | TALLEQAQIQQEKIEYELQKLIE | 1207 |
| 1390 | Ac-QARQLLSGIVQQQNNLLRAIEAQQHLLQLTVWGIKQLQARILAVERY-NH2 | 1208 |
| 1391 | Rhod-QARQLLSGIVQQQNNLLRAIEAQQHLLQLTVWGIKQLQARILAVERY-NH2 | 1209 |
| 1392 | Ac-GAASLTLSAQSRTLLAGIVQQQQQLLDVVKRQQEML-NH2 | 1210 |
| 1393 | Ac-GSAMGAASLTLSAQSRTLLAGIVQQQQQLLDVVKRQQEML-NH2 | 1211 |
| 1394 | Ac-PALSTGLIHLHQNIVDVQFLFGVGSSIASWAIKWEY-NH2 | 1212 |
| 1395 | Ac-PALSTGLIHLHQNIVDVQFLYGVGSSIASWAIK-NH2 | 1213 |
| 1396 | Ac-LSTTQWQVLPUSFTTLPALSTGLIHLHQMVDVQY-NH2 | 1214 |
| 1397 | Ac-FRKFPEATFSRUGSGPRITPRUMVDFPFRLWHY-NH2 | 1215 |
| 1398 | Ac-DFPFRLWHFPUTINYTIFKVRLFVGGVEHRLEAAUNWTWNH2♂ | 1216 |
| 1399 | Ac-YVGGVEHRLEAAUNWTRGERUDLEDRDRSELSPL-NH2 | 1217 |
| 1400 | MVYPSDEYDASISQVNEEINQALAYIRKADELLENV | 1218 |
| 1402 | Ac-GPLLVLQAGFFLLTRILTIPQSLDSWWTSLNFLGG-NH2 | 1220 |
| 1403 | Ac-LGPLLVLQAGFFLLTRILTIPQSLDSWWTSLNFLG-NH2 | 1221 |
| 1404 | Ac-FLGPLLVLQAGFFLLTRILTIPQSLDSWWTSLNFL-NH2 | 1222 |
| 1405 | Ac-YTNTIYTLLEESQNQQEKNEQELLELDKWASLWNWF-NH2 | 1223 |
| 1406 | YTNTIYTLLEESQNQQEKNEQELLELDKWASLWNWF | 1357 |
| 1407 | Ac-YTGIIYNLLEESQNQQEKNEQELLELDKWANLWNWF-NH2 | 1358 |
| 1408 | YTGIIYNLLEESQNQQEKNEQELLELDKWANLWNWF | 1359 |
| 1409 | Ac-YTSLWSLLEKSQIQQEKNEQELLELDKWASLWNWF-NH2 | 1360 |
| 1410 | YTSLIYSLLEKSQIQQEKNEQELLELDKWASLWNWF | 1361 |
| 1411 | Ac-EKSQIQQEKNEQELLELDKWA-NH2 | 1362 |
| 1412 | EKSQIQQEKNEQELLELDKWA | 1363 |
| 1413 | Ac-EQAQIQQEKNEYELQKLDKWA-NH2 | 1364 |
| 1414 | Ac-YTSLIGSLIEESQIQQERNEQELLELDRWASLWEWF-NH2 | 1365 |
| 1415 | Ac-YTXLIHSLIXESQNQQXKNEQELXELDKWASLWNWF-NH2 | 1366 |
| 1416 | Ac-YTXLIHSLIWESQNQQXKNEQELXELD-NH2 | 1367 |
| 1417 | Ac-YTSLIHSHEESQNQQEKNEQELLELD-NH2 | 1368 |
| 1418 | Ac-WQEQEXKITALLXQAQIQQXKNEYELXKLDKWASLWEWF-NH2 | 1369 |
| 1419 | Ac-XKITALLXQAQIQQXKNEYELXKLDKWASLWEWF-NH2 | 1370 |
| 1420 | Ac-WQEWWXKITALLXQAQIQQXKNEYELXKLD-NH2 | 1371 |
| 1421 | Ac-WEQKITALLEQAQIQQEKNEYELQKLD-NH2 | 1372 |
| 1422 | Ac-WEXKITALLXQAQIQQXKNEYELXKLD-NH2 | 1373 |
| 1423 | Ac-XKITALLXQAQIQQXKNEYELXKLD-NH2 | 1374 |
| 1425 | Ac-QKITALLEQAQIQQEKNEYELQKLD-NH2 | 1375 |
| 1426 | Ac-QKITALLEQAQIQQEKNEYELQKLDKWASLWEWF-NH2 | 1381 |
| 1427 | Ac-WQEWEQKITALLEQAQIQQEKNEYELQKLD-NH2 | 1379 |
| 1428 | Ac-VYPSDEYDASISQVNEEINQALAYIRKADELLEN-OH | 1377 |
| 1429 | Ac-VYPSDEYDASISQVNEEINQALAYIRKADELLE-OH | 1380 |
| 1430 | Ac-VYPSDEYDASISQVNEEINQALAYIRKADELL-OH | 1376 |
| 1431 | Ac-VYPSDEYDASISQVNEEINQALAYIRKADEL-OH | 1378 |
| 1432 | YPSDEYDASISQVNEEINQALAYIRKADELLENV-NH2 | 1227 |
| 1433 | PSDEYDASISQVNEEINQALAYIRKADELLENV-NH2 | 1228 |
| 1434 | SDEYDASISQVNEEINQALAYIRKADELLENV-NH2 | 1229 |
| 1435 | DEYDASISQVNEEINQALAYIRKADELLENV-NH2 | 1230 |
| 1436 | Ac-VYPSDEYDASISQVDEEINQALAYIRKADELLENV-NH2 | 1231 |
| 1437 | Ac-VYPSDEYDASISQVNEEIDQALAYIRKADELLENV-NH2 | 1232 |
| 1438 | Ac-VYPSDEYDASISQVNEEINQALAYIRKADELLEDV-NH2 | 1233 |
| 1439 | Ac-VYPSDEYDASISQVDEEIDQALAYIRKADELLENV-NH2 | 1234 |
| 1440 | Ac-LLSTNKAVVSLNGVSVLTSKVLDLKNYIDKQLLP-NH2 | 1235 |
| 1441 | Ac-LSTNKAVVSLSNGVSVLTSKVLDLKNYIDKQLLPI-NH2 | 1236 |
| 1442 | Ac-STNKAVVSLSNGVSVGTSKVLDLKNYIDKQLLPIV-NH2 | 1382 |
| 1443 | Ac-TNKAVVSLSNGVSVLTSKVLDLKNYIDKQLLPIVN-NH2 | 1383 |
| 1444 | Ac-NKAVVSLSNGVSVLTSKVLDLKNYIDKQLLPIVNK-NH2 | 1384 |
| 1445 | Ac-KAVVSLSNGVSVLTSKVLDLKNYIDKQLLPIVNKQ-NH2 | 1385 |
| 1446 | Ac-AVVSLSNGVSVLTSKVLDLKNYIDKQLLPIVNKQS-NH2 | 1386 |
| 1447 | Ac-VVSLSNGVSVLTSKVLDLKNYIDKQWLLPIVNKQSU-NH2 | 1387 |
| 1448 | Ac-VSLSNGVSVLTSKVLDLKNYIDKQLLPIVNKQSUS-NH2 | 1388 |
| 1449 | Ac-SLSNGVSVLTSKVLDLKNYIDKQLLPIVNKQSUSI-NH2 | 1389 |
| 1450 | Ac-LSNGVSVLTSKVLDLKNYIDKQLLPIVNKQSUSIS-NH2 | 1390 |
| 1451 | Ac-SNGVSVLTSKVLDLKNYIDKQLLPIVNKQSUSISN-NH2 | 1391 |
| 1452 | Ac-NGVSVLTSKVLDLKNYIDKQLLPIVNKQSUSISNI-NH2 | 1392 |
| 1453 | Ac-GVSVLTSKVLDLKNYIDKQLLPIVNKQSUSISNIE-NH2 | 1393 |
| 1454 | Ac-VSVLTSKVLDLKNYIDKQLLPIVNKQSUSISINIET-NH2 | 1394 |
| 1455 | Ac-SVLTSKVLDLKNYIDKQLLPIVNKQSUSISNIETV-NH2 | 1395 |
| 1456 | Ac-VLTSKVLDLKNYIDKQLLPIVNKQSUSISNIETVI-NH2 | 1396 |
| 1457 | Ac-LTSKVLDLKNYIDKQLLPIVNKQSUSISNIETVIE-NH2 | 1397 |
| 1458 | Ac-TSKVLDLKNYIDKQLLPIVKQSUSISNIETVIEF-NH2 | 1398 |
| 1459 | Ac-SKVLDLKNYIDKQLLPIVNKQSUSISNIETVIEFQ-NH2 | 1399 |
| 1460 | Ac-KVLDLKNYIDKQLLPIVNKQSUSISNIETVIEFQQ-NH2 | 1400 |
| 1461 | Ac-VLDLKNYIDKQLLPIVNKQSUSISNIETVIEFQQK-NH2 | 1401 |
| 1462 | Ac-LDLKNYIDKQLLPIVNKQSUSISNIETVIEFQQKN-NH2 | 1402 |
| 1463 | Ac-DLKYNYIDKQLLPIVNKQSUSISNIETVIEFQQKNN-NH2 | 1403 |
| 1464 | Ac-LKNYIDKQLLPIVNKQSUSISNIETVIEFQQKNNR-NH2 | 1404 |

TABLE 1-continued

| T No. | Sequence | Seq. ID No. |
|---|---|---|
| 1465 | Ac-KNYIDKQLLPIVNKQSUSISNIETVIEFQQKNNRL-NH2 | 1405 |
| 1466 | Ac-NYIDKQLLPIVNKQSUSISNIETVIEFQQKNNRLL-NH2 | 1406 |
| 1467 | Ac-YIDKQLLPIVNKQSUSISNIETVIEFQQKNNRLLE-NH2 | 1407 |
| 1468 | Ac-IDKQLLPIVNKQSUSISNIETVIEFQQKNNRLLEI-NH2 | 1408 |
| 1469 | Ac-DKQLLPIVNKQSUSISNIETVIEFQQKNNRLLEIT-NH2 | 1409 |
| 1470 | Ac-KQLLPIVNKQSUSISNIETVIEFQQKNNRLLEITR-NH2 | 1410 |
| 1471 | Ac-QLLPIVNKQSUSISNIETVIEFQQKNNRLLEITRE-NH2 | 1411 |
| 1472 | Ac-VYPSDEYDASISQVNEEINQALA | 1412 |
| 1473 | QVNEEINQALAYIRKADELLENV-NH2 | 1413 |
| 1474 | VYPSDEYDASISQVNEEINQALAYIRKADELLENV | 1414 |
| 1475 | Ac-DEYDASISQVNEEINQALAYIREADEL-NH2 | 1415 |
| 1476 | Ac-DEYDASISQVNEKINQALAYIREADEL-NH2 | 1416 |
| 1477 | Ac-DDECLNSVKNGTYDFPKFEEESKLNRNEIKGVKLS-NH2 | 1417 |
| 1478 | Ac-DDE-Abu-LNSVKNGTYDFPKFEEESKLNRNEIKGVKLS-NH2 | 1718 |
| 1479 | Ac-YHKCDDECLNSVKNGTFDFPKFEEESKLNRNEIKGVKLSS-NH2 | 1719 |
| 1480 | Ac-YHK-Abu-DDE-Abu-LNSVKNGTFDFPKFEEESKLNRNEIKGVKLSS-NH2 | 1420 |
| 1481 | Ac-YTSLIHSLIEESQIQQEKNEQELLELDKWASLWNWF-NH2 | 1344 |
| 1482 | Ac-YTSLIHSLIEESQNQQEKNEYELLELDKWASLWNWF-NH2 | 1345 |
| 1483 | Ac-YTSLIHSLIEESQIQQEKNEYELLELDKWASLWNWF-NH2 | 1346 |
| 1484 | Ac-YTSLIHSLIEESQIQQEKNEYELQKLDKWASLWNWF-NH2 | 1347 |
| 1485 | Ac-YTSLIHSLIEESQNQQEKNEQELQKLDKWASLWNWF-NH2 | 1348 |
| 1486 | Ac-YTSLIHSLIEESQNQQEKNEYELQKLDKWASLWNWF-NH2 | 1421 |
| 1487 | Ac-YTSHHSLIEESQIQQEKNEQELQKLDKWASLWNWF-NH2 | 1422 |
| 1488 | Ac-YTSLIHSLIEESQNQQEKNEQELLELDKWASLWEWF-NH2 | 1423 |
| 1489 | Ac-YTSuHSLIEESQIQQEKNEQELLELDKWASLWEWF-NH2 | 1424 |
| 1490 | Ac-YTSLIHSuEESQNQQEKNEYELLELDKWASLWEWF-NH2 | 1425 |
| 1491 | Ac-YTSHHSLIEESQIQQEKNEYELLELDKWASLWEWF-NH2 | 1426 |
| 1492 | Ac-YTSLIHSLIEESQIQQEKNEYELQKLDKWASLWEWF-NH2 | 1427 |
| 1493 | Ac-YTSLIHSLIEESQNQQEKNEQELQKLDKWASLWEWF-NH2 | 1428 |
| 1494 | Ac-YTSLIHSLIEESQNQQEKNEYELQKLDKWASLWEWF-NH2 | 1429 |
| 1495 | Ac-YTSLIHSLIEESQIQQEKNEQELQKLDKWASLWEWF-NH2 | 1430 |
| 1496 | Ac-WQEQEQKITALLEQAQIQQEKNEYELQKLDKEWWF-NH2 | 1431 |
| 1497 | Ac-WQEWEQKITALLEQAQIQQEKNEYELQKLIEWASLWEWF-NH2 | 1432 |
| 1498 | Ac-WQEWEQKITALLEQAQIQQEKNEYELQKLAKWASLWEWF-NH2 | 1256 |
| 1499 | Ac-WQEWEQKITALLEQAQIQQEKNEYELQKLIKWASLWEWF-NH2 | 1257 |
| 1500 | Ac-WQEWEQKITALLEQAQIQQEKNEYELQKLIEWAGLWEWF-NH2 | 1258 |
| 1501 | Ac-WQEWEQKITALLEQAQIQQEKNEYELQKLAKWAGLWEWF-NH2 | 1259 |
| 1502 | Ac-WQEWEQKITALLEQAQIQQEKNEYELQKLIKWAGLWEWF-NH2 | 1260 |
| 1503 | Ac-WQEWEQKITALLEQAQIQQEKNEYELQKLIEWAGLWAWF-NH2 | 1261 |
| 1504 | Ac-WQEWEQKITALLEQAQIQQEKNEYELQKLAKWAGLWAWF-NH2 | 1262 |
| 1505 | Ac-WQEWEQKITALLEQAQIQQEKNEYELQKLIKWAGLWAWF-NH2 | 1263 |
| 1506 | Ac-WQEWEQKITALLEQAQIQQEKGEYELQKLDKQEQF-NH2 | 1264 |
| 1507 | Ac-WQEWEQKITALLEQAQIQQEKGEYELLELDKWEWF-NH2 | 1265 |
| 1508 | Ac-WQEWEQKITALLEQAQIQQEKGEYELQKLAKWEWF-NH2 | 1266 |
| 1509 | Ac-WQEWEQKITALLEQAQIQQEKGEYELQKLDWQWEF-NH2 | 1267 |
| 1510 | Ac-WQEWEQKITALLEQAQIQQEKGEYELLELAKWEWF-NH2 | 1268 |
| 1511 | Ac-WEQWEQKITALLEQAQIQQEKNEYELLELDKWEWF-NH2 | 1269 |
| 1512 | Ac-WQEWEQKITALLEQAQIQQEKNEYELEEEHEWASLWEWF-NH2 | 1270 |
| 1513 | Ac-WQEWEQKITALLEQAQIQQEKNEYELLEuEWAGLWEWF-NH2 | 1271 |
| 1514 | Ac-WQEWEQKITALLEQAQIQQEKNEYELLELIEWAGLWAWF-NH2 | 1272 |
| 1515 | Ac-WQEWEREITALLEQAQIQQEKNEYELQKLIEWASLWEWF-NH2 | 1273 |
| 1516 | Ac-WQEWEREIQQEKNEYELQKLDKWASLWEWF-NH2 | 1274 |
| 1517 | Ac-WQEWEREIQQEKGEYELQKLIEWEWF-NH2 | 1275 |
| 1518 | Ac-WQEWQAQIQQEKNEYELQKLDKWASLWEWF-NH2 | 1276 |
| 1519 | Ac-WQEWQAQIQQEKGEYELQKLIEWEWF-NH2 | 1277 |

What is claimed is:

1. A hybrid polypeptide comprising an enhancer peptide sequence linked to a core polypeptide, wherein the enhancer peptide comprises an amino-terminal:
WXXWXXXI, WXXWXXX, WXXWXX, WXXWX, WXXW, WXXXWXWX, XXXWXWX, XXWXWX, XWXWX, WXWX, WXXXWXW, WXXXWX WXXXW, IXXXWXXW, XXXWXXW, XXWXXW, XWXXW, XWXWXXXW, XWXWXXX, XWXWXX, XWXWX, XWXW, WXWXXXW, or XWXXXW, and wherein the core polypeptide comprises the following amino acid sequence:
TALLEQAQIQQEKNEYELQKLDK; (SEQ ID NO:1286).

2. The hybrid polypeptide of claim 1, further comprising an enhancer peptide sequence linked to the carboxy-terminal end of the core polypeptide.

3. A hybrid polypeptide comprising an enhancer peptide sequence linked to a core polypeptide, wherein the enhancer peptide sequence comprises WQEWEQKI (SEQ ID NO:1129) or WASLWEWF (SEQ ID NO:1433) and the core polypeptide comprises the following amino acid sequence:
TALLEQAQIQQEKNEYELQKLDK (SEQ ID NO:1286).

4. A method for enhancing the pharmacokinetic properties of a core polypeptide, comprising linking an enhancer peptide sequence to the core polypeptide to produce a hybrid polypeptide, wherein the enhancer peptide sequence comprises:
WXXWXXXI, WXXWXXX, WXXWXX, WXXWX, WXXW, WXXXWXWX, XXXWXWX, XXWXWX, XWXWX, WXWX, WXXXWXW, WXXXWX, WXXXW, IXXXWXXW, XXXWXXW, XXWXXW, XWXXW, XWXWXXXW, XWXWXXX, XWXWXX, XWXWX, XWXW, WXWXXXW, or XWXXXW, and wherein the core polypeptide comprises TALLEQAQIQQEKNEYELQKLDK (SEQ ID NO:1286) such that, when introduced into a living system, the hybrid polypeptide exhibits enhanced pharmacokinetic properties relative to those exhibited by the core polypeptide.

5. A polypeptide comprising the amino acid sequence:
WQEWEQKITALLEQA-QIQQEKNEYELQKLDKWASLWEWF (SEQ ID NO:1310).

6. The polypeptide of claim 5, further comprising an amino terminal acetyl group and a carboxy terminal amido group.

7. A hybrid polypeptide comprising an enhancer peptide sequence linked to a core polypeptide, wherein the enhancer peptide sequence comprises a carboxy-terminal:
WXXWXXXI, WXXWXXX, WXXWXX, WXXWX, WXXW, WXXXWXWX, XXXWXWX, XXWXWX, XWXWX, WXWX, WXXXWXW, WXXXWX, WXXXW, IXXXWXXW, XXXWXXW, XXWXXW, XWXXW, XWXWXXXW, XWXWXXX, XWXWXX, XWXWX, XWXW, WXWXXXW, or XWXXXW, and wherein the core polypeptide comprises the following amino acid sequence:

TALLEQAQIQQEKNEYELQKLDK (SEQ ID NO:1286).

8. The hybrid polypeptide of claim 7, further comprising an enhancer peptide sequence linked to the amino-terminal end of the core polypeptide.

9. The hybrid polypeptide of claims 1, 2, 8, 3, or 7 further comprising an amino terminal acetyl group and a carboxy terminal amido group.

10. A polypeptide comprising TALLEQAQIQQEKNEYELQKLDK (SEQ ID NO:1286).

11. The polypeptide of claim 10, further comprising an amino terminal acetyl group and a carboxy terminal amido group.

12. A pharmaceutical composition comprising the polypeptide:

TALLEQAQIQQEKNEYELQKLDK (SEQ ID NO:1286), and a pharmaceutically acceptable carrier.

13. The pharmaceutical composition of claim 12, wherein the polypeptide further comprises an amino terminal acetyl group and a carboxy terminal amido group.

14. A pharmaceutical composition comprising the polypeptide:

WQEWEQKITALLEQAQIQQEKNEYELQKLDKWASLWEWF (SEQ ID NO:1310), and a pharmaceutically acceptable carrier.

15. The pharmaceutical composition of claim 14, wherein the polypeptide further comprises an amino terminal acetyl group and a carboxy terminal amido group.

* * * * *